United States Patent [19]

Ogawa et al.

[11] Patent Number: 5,753,677
[45] Date of Patent: May 19, 1998

[54] BENZOHETEROCYCLIC COMPOUNDS

[75] Inventors: Hidenori Ogawa, Tokushima-ken; Hisashi Miyamoto, Kyoto-fu; Kazumi Kondo, Tokushima-ken; Hiroshi Yamashita, Tokushima-ken; Kenji Nakaya, Tokushima-ken; Hajime Komatsu, Tokushima-ken; Michinori Tanaka, Tokushima-ken; Shinya Kora, Nagasaki-ken; Michiaki Tominaga; Yoichi Yabuuchi, both of Tokushima-ken, all of Japan

[73] Assignee: Otsuka Pharmaceutical Co., Ltd., Tokyo, Japan

[21] Appl. No.: 474,544

[22] Filed: Jun. 7, 1995

Related U.S. Application Data

[62] Division of Ser. No. 76,804, Jun. 10, 1993, Pat. No. 5,559,230, which is a division of Ser. No. 851,541, Mar. 13, 1992, Pat. No. 5,258,510, which is a continuation-in-part of Ser. No. 762,015, Jun. 19, 1991, abandoned.

[51] Int. Cl.[6] .................... A61K 31/47; A61K 31/55
[52] U.S. Cl. .................... 514/311; 514/183; 514/213; 546/156
[58] Field of Search .................... 514/311, 213, 514/183

[56] References Cited

U.S. PATENT DOCUMENTS

| | | | |
|---|---|---|---|
| 3,035,047 | 5/1962 | Perron et al. | 260/239.1 |
| 4,582,909 | 4/1986 | Butler et al. | 548/486 |
| 4,677,112 | 6/1987 | Butler et al. | 514/312 |
| 4,760,064 | 7/1988 | Tominaga et al. | 514/253 |

OTHER PUBLICATIONS

Yoshitake Yamamura, Hidenori Ogawa, Tomihiko Chihara, Kazumi Kondo, Toshiyuki Onogawa, Shigeki Nakamura Toyoki Mori, Michiaki Tominaga and Youichi Yabucchi, *OPC-21268, An Orally Effective, Nonpeptide Vasopressin V1 Receptor Antagonist*, Science, vol. 252, pp. 572-574 (Apr. 1991).

*Primary Examiner*—Robert T. Bond
*Attorney, Agent, or Firm*—Sughrue, Mion, Zinn, Macpeak & Seas, PLLC

[57] ABSTRACT

Novel benzoheterocyclic compounds of the formula:

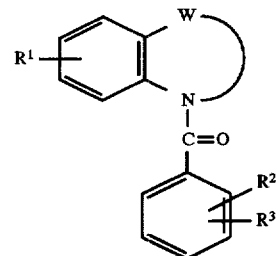

which have excellent vasopressin antagonistic activities and are useful as vasodilator, hypotensive agent, water diuretics, platelet agglutination inhibitor, and a vasopressin antagonistic composition containing the compound as the active ingredient.

78 Claims, 4 Drawing Sheets

BENZOHETEROCYCLIC COMPOUNDS

This is a divisional of application Ser. No. 08/076,804 filed Jun. 10, 1993, now U.S. Pat. No. 5,559,230, which is a divisional of application Ser. No. 07/851,541 filed Mar. 13, 1992, now U.S. Pat. No. 5,258,510, which is a Continuation-In-Part of application Ser. No. 07/762,015 filed Jun. 19, 1991, now abandoned.

TECHNICAL FIELD

This invention relates to novel benzoheterocyclic compounds which have excellent vasopressin antagonistic activities and are useful as vasodilator, hypotensive agent, water diuretics, platelet aggregation inhibitor.

DISCLOSURE OF THE INVENTION

The benzoheterocyclic compounds of this invention have the following formula:

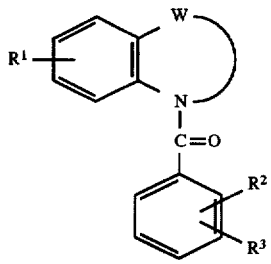
(1)

wherein

- $R^1$ is hydrogen atom, a halogen atom, a lower alkyl, an amino having optionally a lower alkyl substituent, or a lower alkoxy,
- $R^2$ is hydrogen atom, a halogen atom, a lower alkoxy, a phenyl(lower)alkoxy, hydroxy, a lower alkyl, an amino having optionally a lower alkyl substituent, a carbamoyl-substituted lower alkoxy, an amino-substituted lower alkoxy having optionally a lower alkyl substituent, or a benzoyloxy which has optionally a halogen substituent on the phenyl ring,
- $R^3$ is a group of the formula:

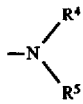

or a group of the formula:

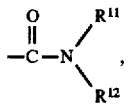

- $R^4$ is hydrogen atom, a benzoyl which has optionally a halogen substituent on the phenyl ring, or a lower alkyl,
- $R^5$ is a group of the formula:

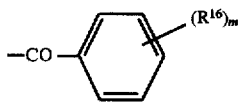

[wherein $R^{16}$ is a halogen atom; a lower alkyl which has optionally a substituent selected from a halogen atom and hydroxy; hydroxy; a lower alkoxy; a lower alkanoyloxy; a lower alkylthio; a lower alkanoyl; carboxy; a lower alkoxycarbonyl; cyano; nitro; an amino which has optionally a substituent selected from a lower alkyl and a lower alkanoyl; phenyl; a cycloalkyl; a lower alkanoyloxy-substituted lower alkoxy; a carboxy-substituted lower alkoxy; a halogen-substituted lower alkoxy; a carbamoyl-substituted lower alkoxy; a hydroxy-substituted lower alkoxy; a lower alkoxycarbonyl-substituted lower alkoxy; a phthalimido-substituted lower alkoxy; an aminocarbonyl-lower alkoxy having a lower alkyl substituent; or a group of the formula:

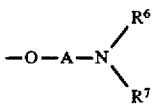

(A is a lower alkylene, and $R^6$ and $R^7$ are the same or different and are each hydrogen atom, a lower alkyl having optionally a hydroxy substituent, a lower alkanoyl, or benzoyl, or $R^6$ and $R^7$ may bind together with nitrogen atom to which they bond to form a 5- or 6-membered saturated heterocyclic group with or without being intervened with nitrogen or oxygen atom wherein the heterocyclic group has optionally a substituent selected from piperidinyl and a lower alkyl); and m is an integer of 0 to 3], a phenyl-lower alkoxycarbonyl, a lower alkanoyl, a phenyl-lower alkanoyl, a cycloalkyl-lower alkanoyl, a cycloalkylcarbonyl, tricyclo[3.3.1.1]-decanylcarbonyl, naphthylcarbonyl, pyridylcarbonyl, furoyl, thenoyl, a phenoxy-lower alkanoyl which phenyl ring has optionally 1 to 3 substituents selected from a lower alkyl, a lower alkoxy and an amino having optionally a lower alkanoyl substituent, a phthalimido-substituted lower alkanoyl, a lower alkoxycarbonyl-lower alkanoyl, a carboxy-lower alkanoyl, a naphthyloxy-lower alkanoyl, a halogen-substituted lower alkanoyl, a group of the formula:

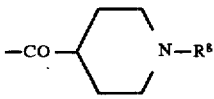

(wherein $R^8$ is hydrogen atom, a lower alkyl, a phenyl-lower alkoxycarbonyl, a carbamoyl-lower alkyl, an amino-lower alkanoyl having optionally a lower alkyl substituent, or a lower alkanoyl), an anilinocarbonyl which has optionally a lower alkyl substituent on the phenyl ring, phenoxycarbonyl, a phenylsulfonyl which has optionally a substituent selected from a halogen atom and a lower alkyl on the phenyl ring, quinolylsulfonyl, or a group of the formula:

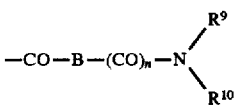

(wherein B is a lower alkylene, n is an integer of 0 or 1, and $R^9$ and $R^{10}$ are the same or different and are each hydrogen atom, a lower alkyl having optionally a hydroxy substituent, a cycloalkyl, a phenyl-lower alkyl, a lower alkanoyl, a lower alkenyl, a phenoxy-lower alkyl, a phenyl which has optionally 1 to 3 substituents selected from an amino-lower alkyl having optionally a lower alkanoyl substituent, a lower alkyl, a lower alkoxy and a halogen atom, a phthalimido-substituted lower alkyl, an amino-lower alkyl having optionally a lower alkanoyl substituent, a lower alkynyl, or an amino-lower alkyl having optionally a lower alkyl substituent, or $R^9$ and $R^{10}$ may bind together with nitrogen atom to which they bond to form a 5- or 6-membered saturated heterocyclic group with or without being intervened with nitrogen or oxygen atom wherein the heterocylic group has optionally a substituent selected from a lower alkyl, a lower alkoxycarboyl and piperidinyl), $R^{11}$ is hydrogen atom or a lower alkyl, $R^{12}$ is a cycloalkyl, or a phenyl which has optionally 1 to 3 substituents selected from a lower alkoxy, a lower alkyl and a halogen atom, W is a group of the formula: —$(CH_2)_p$— (p is an integer of 3 to 5), or a group of the formula: —CH=CH—$(CH_2)_q$— (q is an integer of 1 to 3), the carbon atom of these groups: —$(CH_2)_p$— and —CH=CH—$(CH_2)_q$— being optionally replaced by oxygen atom, sulfur atom, sulfinyl, sulfonyl, or a group of the formula:

$$\begin{array}{c} R^{13} \\ | \\ -N- \end{array}$$

($R^{13}$ is hydrogen atom, a cycloalkyl, or a lower alkyl), and further said —$(CH_2)_p$— and —CH=CH—$(CH_2)_q$— groups having optionally 1 to 3 substituents selected from a lower alkyl having optionally a hydroxy substituent, a lower alkoxycarbonyl, carboxy, hydroxy, oxo, a lower alkanoyloxy having optionally a halogen substituent, an amino-lower alkyl having optionally a substituent selected from a lower alkyl and a lower alkanoyl, a lower alkanoyloxy-substituted lower alkyl, a lower alkyl sulfonyloxy-lower alkyl, an azido-lower alkyl, a group of the formula:

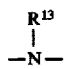

an aminocarbonyloxy having optionally a lower alkyl substituent, a lower alkoxy, a lower alkoxycarbonyl-substituted lower alkoxy, a carboxy-substituted lower alkoxy, an aminocarbonyl-lower alkoxy having optionally a lower alkyl substituent, an amino-lower alkoxy having optionally a substituent selected from a lower alkyl and a lower alkanoyl, a phthalimido-substituted lower alkoxy, hydroxyimino, a lower alkanoyloxy-imino, a lower alkylidene, a halogen atom, azido, sulfoxyimino, a group of the formula:

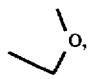

($R^{81}$ is hydrogen atom or a lower alkyl), hydrazino, pyrrolyl, an amino-lower alkanoyloxy having optionally a lower alkyl substituent, a group of the formula:

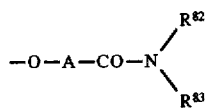

(A is as defined above, and $R^{82}$ and $R^{83}$ are the same or different and are each hydrogen atom, a lower alkyl, a carbamoyl-substituted lower alkyl, a hydroxy-substituted lower alkyl, or a pyridyl-lower alkyl, or $R^{82}$ and $R^{83}$ may bind together with nitrogen atom to which they bond to form a 5- or 6-membered saturated heterocyclic group with or without being intervened with nitrogen, oxygen or sulfur atom wherein the heterocyclic group has optionally a substituent selected from oxo, a lower alkyl, a lower alkanoyl, and carbamoyl), and a group of the formula:

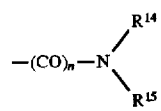

(wherein n is as defined above, and $R^{14}$ and $R^{15}$ are the same or different and are each hydrogen atom, a lower alkyl, a lower alkenyl, a lower alkanoyl, a cycloalkyl, an oxiranyl-substituted lower alkyl, a lower alkyl having optionally 1 to 2 substituents selected from a lower alkoxy, hydroxy and an amino having optionally a lower alkyl substituent, a phenyl-lower alkyl, a pyridyl-lower alkyl, a lower alkylsulfonyl, benzoyl, a lower alkoxycarbonyl, anilinocarbonyl, an aminocarbonyl having optionally a lower alkyl substituent, a cyano-substituted lower alkyl, a lower alkoxycarbonyl-substituted lower alkyl, a carbamoyl-substituted lower alkyl, a carboxy-substituted lower alkyl, a tetrahydropyranyloxy-substituted lower alkyl, a lower alkanoyloxy-substituted lower alkyl, a piperidinyl having optionally a phenyl-lower alkyl substituent on the piperidinyl ring, a halogen-substituted lower alkanoyl, an imidazolyl-substituted lower alkanoyl, an amino-lower alkanoyl having optionally a substituent selected from a lower alkyl and a lower alkoxycarbonyl, an aminocarbonyl-lower alkyl having optionally a lower alkyl substituent, or a phenyl-lower alkoxycarbonyl, or $R^{14}$ and $R^{15}$ may bind together with nitrogen atom to which they bond to form a 5- or 6-membered saturated heterocyclic group with or without being intervened with nitrogen or oxygen, wherein the heterocyclic group may optionally have a substituent selected from a lower alkyl, a phenyl-lower alkyl or a lower alkanoyl).

The benzoheterocyclic compounds of the formula (1) and their salts have excellent vasopressin antagonistic activities and vasodilating activity, hypotensive activity, activity for inhibiting saccharide release in liver, activity for inhibiting growth of mesangium cells, water diuretic activity, platelet agglutination inhibitory activity and are useful as vasodilator, hypotensive agent, water diuretics, platelet agglutination inhibitor and are used for the prophylaxis and treatment of hypertension, edema, ascites, heart failure, renal function disorder, vasopressin parasecretion syndrome (SIADH), hepatocirrhosis, hyponatremia, hypokaliemia, diabetic, circulation disorder, and the like.

Each group in the above formula (1) includes specifically the following groups.

The "lower alkoxy" includes a straight chain or branched chain alkoxy group having 1 to 6 carbon atoms, for example, methoxy, ethoxy, propoxy, isopropoxy, butoxy, tert-butoxy, pentyloxy, hexyloxy, and the like.

The "lower alkyl" includes a straight chain or branched chain alkyl group having 1 to 6 carbon atoms, for example, methyl, ethyl, propyl, isopropyl, butyl, tert-butyl, pentyl, hexyl, and the like.

The "halogen atom" includes fluorine atom, chlorine atom, bromine atom and iodine atome.

The "amino having optionally a lower alkyl substituent" includes an amino having optionally one or two substituents selected from a straight chain or branched chain alkyl group having 1 to 6 carbon atoms, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, and the like.

The "lower alkenyl" includes a straight chain or branched chain alkenyl group having 2 to 6 carbon atoms, for example, vinyl, allyl, 2-butenyl, 3-butenyl, 1-methylallyl, 2-pentenyl, 2-hexenyl, and the like.

The "lower alkyl which has optionally a substituent selected from a halogen atom and hydroxy" includes a straight chain or branched chain alkyl group having 1 to 6 carbon atoms which may optionally have 1 to 3 substituents selected from a halogen atom and hydroxy, for example, in addition to the above-mentioned lower alkyl groups, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, and the like.

The "lower alkylene" includes a straight chain or branched chain alkylene group having 1 to 6 carbon atoms, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, and the like.

The "lower alkanoyloxy" includes a straight chain or branched chain alkanoyloxy group having 1 to 6 carbon atoms, for example, formyloxy, acetyloxy, propionyloxy, butyryloxy, isobutyryloxy, pentanoyloxy, tert-butylcarbonyloxy, hexanoyloxy, and the like.

The "lower alkylthio" includes a straight chain or branched chain alkylthio group having 1 to 6 carbon atoms, for example, methylthio, ethylthio, propylthio, isopropylthio, butylthio, tert-butylthio, pentylthio, hexylthio, and the like.

The "lower alkanoyl" includes a straight chain or branched chain alkanoyl group having 1 to 6 carbon atoms, for example, formyl, acetyl, propionyl, butyryl, isobutyryl, pentanoyl, tert-butylcarbonyl, hexanolyl, and the like.

The "lower alkoxycarbonyl" includes a straight chain or branched chain alkoxycarbonyl group having 1 to 6 carbon atoms in the alkoxy moiety, for example, methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, and the like.

The "amino having optionally a substituent selected from a lower alkyl and a lower alkanoyl" includes an amino having optionally one or two substituents selected from a straight chain or branched chain alkyl group having 1 to 6 carbon atoms and a straight chain or branched chain alkanoyl group having 1 to 6 carbon atoms, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tert-butylcarbonylamino, N-hexanoylamino, N-ethyl-N-acetylamino, and the like.

The "cycloalkyl" includes a cycloalkyl having 3 to 8 carbon atoms, for example, cyclopentyl, cyclobutyl, cyclopentyl, cyclohexyl, cycloheptyl, cyclooctyl, and the like.

The "lower alkanoyloxy-substituted lower alkoxy" includes a straight chain or branched chain alkoxy group having 1 to 6 carbon atoms which is substituted by a straight chain or branched chain alkanoyloxy group having 2 to 6 carbon atoms, for example, acetyloxymethoxy, 2-propionyloxyethoxy, 1-butyryloxyethoxy, 3-acetyloxypropoxy, 4-acetyloxybutoxy, 4-isobutyryloxybutoxy, 5-pentanoyloxypentyloxy, 6-acetyloxyhexyloxy, 6-tert-butylcarbonyloxyhexyloxy, 1,1-dimethyl-2-hexanoyloxyethoxy, 2-methyl-3-acetyloxypropoxy, and the like.

The "carbamoyl-substituted lower alkoxy" includes a carbamoyl-substituted alkoxy group wherein the alkoxy moiety is a straight chain or branched chain alkoxy group having 1 to 6 carbon atoms, for example, carbamoylmethoxy, 2-carbamoylethoxy, 1-carbamoylethoxy, 3-carbamoylpropoxy, 4-carbamoylbutoxy, 5-carbamoylpentyloxy, 6-carbamoylhexyloxy, 1,1-dimethyl-2-carbamoylethoxy, 2-methyl-3-carbamoylpropoxy, and the like.

The "hydroxy-substituted lower alkoxy" includes a straight chain or branched chain alkoxy group having 1 to 6 carbon atoms and having 1 to 3 hydroxy substitutents, for example, hydroxymethoxy, 2-hydroxyethoxy, 1-hydroxyethoxy, 3-hydroxypropoxy, 2,3-dihydroxypropoxy, 4-hydroxybutoxy, 3,4-dihydroxybutoxy, 1,1-dimethyl-2-hydroxyethoxy, 5-hydroxypentyloxy, 6-hydroxyhexyloxy, 2-methyl-3-hydroxypropoxy, 2,3,4-trihydroxybutoxy, and the like.

The "lower alkoxycarbonyl-substituted lower alkoxy" includes an alkoxycarbonyl-substituted straight chain or branched chain alkoxy group having 1 to 6 carbon atoms wherein the alkoxycarbonyl moiety is a straight chain or branched chain alkoxycarbonyl group having 1 to 6 carbon atoms, for example, methoxycarbonylmethoxy, 3-methoxycarbonylpropoxy, ethoxycarboxymethoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-tert-butoxycarbonylpropoxy, 2-pentyloxycarbonylethoxy, hexyloxycarbonylmethoxy, and the like.

The "carboxy-substituted lower alkoxy" includes a carboxy-substituted alkoxy group wherein the alkoxy moiety is a straight chain or branched chain alkoxy group having 1 to 6 carbon atoms, for example, carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, 2-methyl-3-carboxypropoxy, and the like.

The "phthalimido-substituted lower alkoxy" includes a straight chain or branched chain alkoxy group having 1 to 6 carbon atoms which is substituted by phthalimido group, for example, phthalimidomethoxy, 2-phthalimidoethoxy, 1-phthalimidoethoxy, 3-phthalimidopropoxy, 4-phthalimidobutoxy, 5-phthalimidopentyloxy, 6-phthalimidohexyloxy, 1,1-dimethyl-2-phthalimidoethoxy, 2-methyl-3-phthalimidopropoxy, and the like.

The "5- or 6-membered saturated heterocyclic group which is formed by binding the groups $R^6$ and $R^7$ together with the nitrogen atom to which they bond with or without being intervened with nitrogen or oxygen atom" includes, for example, pyrrolidinyl, piperidinyl, piperazinyl, morpholino, and the like.

The "heterocyclic group having a substituent selected from piperidinyl and a lower alkyl" includes a heterocyclic group having 1 to 3 substituents selected from piperidinyl and a straight chain or branched chain alkyl group having 1 to 6 carbon atoms, for example, 4-methylpiperiazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 4-(1-piperidinyl)piperidinyl, 3-(1-piperidinyl)pyrrolidinyl, 3-(1-piperidinyl)-4-methylpiperazinyl, 3-(1-piperidinyl)morpholino, and the like.

The "phenyl(lower)alkanoyl" includes a phenylalkanoyl wherein the alkanoyl moiety is a straight chain or branched chain alkanoyl group having 2 to 6 carbon atoms, for example, phenylacetyl, 3-phenylpropionyl, 2-phenylpropionyl, 4-phenylbutyryl, 2,2-dimethyl-3-phenylpropionyl, 5-phenylpentanoyl, 6-phenylhexanoyl, and the like.

The "cycloalkyl-lower alkanoyl" includes $C_3$–$C_8$ cycloalkyl-alkanoyl group wherein the alkanoyl moiety is a straight chain or branched chain alkanoyl having 2 to 6 carbon atoms, for example, cyclohexylacetyl, 3-cyclopropylpropionyl, 2-cyclopentylpropionyl, 4-cyclohexylbutyryl, 2,2-dimethyl-3-cycloheptylpropionyl, 5-cyclooctylpentanoyl, 6-cyclohexylhexanoyl, and the like.

The "cycloalkylcarbonyl" includes a cycloalkylcarbonyl having 3 to 8 carbon atoms, for example, cyclopropylcarbonyl, cyclobutylcarbonyl, cyclopentylcarbonyl, cyclohexylcarbonyl, cycloheptylcarbonyl, cyclooctylcarbonyl, and the like.

The "amino having optionally a lower alkanoyl substituent" includes an amino having optionally a straight chain or branched chain alkanoyl group having 1 to 6 carbon atoms, for example, amino, formylamino, acetylamino, propionylamino, butyrylamino, isobutyrylamino, pentanoylamino, tert-butylcarbonylamino, hexanoylamino, and the like.

The "phenoxy-lower alkanoyl which phenyl ring has optionally 1 to 3 substituents selected from a lower alkyl, a lower alkoxy and an amino having optionally a lower alkanoyl substituent" includes a phenoxyalkanoyl group wherein the alkanoyl moiety is a straight chain or branched chain alkanoyl having 2 to 6 carbon atoms and the phenyl ring has optionally 1 to 3 substituents selected from a straight chain or branched chain alkyl having 1 to 6 carbon atoms, a straight chain or branched chain alkoxy having 1 to 6 carbon atoms and an amino having optionally a straight chain or branched chain alkanoyl having 1 to 6 carbon atoms, for example, phenoxyacetyl, 3-phenoxypropionyl, 2-phenoxypropionyl, 4-phenoxybutyryl, 2,2-dimethyl-3-phenoxypropionyl, 5-phenoxypentanoyl, 6-phenoxyhexanoyl, (2-aminophenoxy)acetyl, 3-(4-aminophenoxy)propionyl, (2-methylphenoxy)acetyl, (4-methylphenoxy)acetyl, (3-methylphenoxy)acetyl, (3-methoxyphenoxy)acetyl, (3-acetylaminophenoxy)acetyl, 4-(2-propionylaminophenoxy)butyryl, 2,2-dimethyl-3-(4-butyrylaminophenoxy)propionyl, 5-(2-pentanoylaminophenoxy)pentanoyl, 6-(4-hexanoylaminophenoxy)hexanoyl, 3-(2-ethylphenoxy)propionyl, 2-(4-propylphenoxy)propionyl, 4-(4-butylphenoxy)butyryl, 5-(3-pentylphenoxy)pentanoyl, 6-(4-hexylphenoxy)hexanoyl, (2,3-dimethylphenoxy)acetyl, (2,5-dimethylphenoxy)acetyl, (3,4-dimethylphenoxy)acetyl, (3,4,5-trimethylphenoxy)acetyl, 3-(4-ethoxyphenoxy)propionyl, 2-(2-propoxyphenoxy)propionyl, 4-(3-butoxyphenoxy)butyryl, 5-(4-pentyloxyphenoxy)pentanoyl, 6-(4-hexyloxyphenoxy)hexanoyl, (3,4-dimethoxyphenoxy)acetyl, (3,5-dimethoxyphenoxy)acetyl, (2,4-dimethoxyphenoxy)acetyl, (3,4,5-trimethoxyphenoxy)acetyl, (2-acetylamino-4-methylphenoxy)acetyl, (4-acetylamino-3-methoxyphenoxy)acetyl, and the like.

The "phthalimido-substituted lower alkanoyl" includes a straight chain or branched chain alkanoyl group having 2 to 6 carbon atoms which is substituted by phthalimido group, for example, 2-phthalimidoacetyl, 3-phthalimidopropionyl, 2-phthalimidopropionyl, 4-phthalimidobutyryl, 2,2-dimethyl-3-phthalimidopropionyl, 5-phthalimidopentanoyl, 6-phthalimidohexanoyl, 3-methyl-4-phthalimidobutyryl, and the like.

The "lower alkoxycarbonyl-lower alkanoyl" includes an alkoxycarbonyl-alkanoyl group wherein the alkoxy moiety is a straight chain or branched chain alkoxy having 1 to 6 carbon atoms and the alkanoyl moiety is a straight chain or branched chain alkanoyl having 2 to 6 carbon atoms, for example, methoxycarbonylacetyl, 3-methoxycarbonylpropionyl, ethoxycarbonylacetyl, 3-ethoxycarbonylpropionyl, 4-ethoxycarbonylbutyryl, 3-propoxycarbonylpropionyl, 2-methoxycarbonylpropionyl, 6-propoxycarbonylhexanoyl, 5-isopropoxycarbonylpentanoyl, 2,2-dimethyl-3-butoxycarbonylpropionyl, 2-methyl-3-tert-butoxycarbonylpropionyl, pentyloxycarbonylacetyl, hexyloxycarbonylacetyl, and the like.

The "carboxy-lower alkanoyl" includes a carboxyalkanoyl group wherein the alkanoyl moiety is a straight chain or branched chain alkanoyl having 2 to 6 carbon atoms, for example, carboxyacetyl, 3-carboxypropionyl, 2-carboxypropionyl, 4-carboxybutyryl, 2,2-dimethyl-3-carboxypropionyl, 5-carboxypentanoyl, 6-carboxyhexanoyl, and the like.

The "naphthyloxy-lower alkanoyl" includes a naphthyloxy-alkanoyl group wherein the alkanoyl moiety is a straight chain or branched chain alkanoyl having 2 to 6 carbon atoms, for example, naphtyloxyacetyl, 3-naphtyloxypropionyl, 2-naphtyloxypropionyl, 4-naphthyloxybutyryl, 2,2-dimethyl-3-naphthyloxypropionyl, 5-naphthyloxypentanoyl, 6-naphthyloxyhexanoyl, and the like.

The "phenyl-lower alkoxycarbonyl" includes a phenylalkoxycarbonyl wherein the alkoxycarbonyl moiety is a straight chain or branched chain alkoxycarbonyl group having 1 to 6 carbon atoms, for example, benzyloxycarbonyl, 2-phenylethoxycarbonyl, 1-phenylethoxycarbonyl, 3-phenylpropoxycarbonyl, 4-phenylbutoxycarbonyl, 5-phenylpentyloxycarbonyl, 6-phenylhexyloxycarbonyl, 1,1-dimethyl-2-phenylethoxycarbonyl, 2-methyl-3-phenylpropoxycarbonyl, and the like.

The "lower alkyl having optionally a hydroxy substituent" includes a straight chain or branched chain alkyl having 1 to 6 carbon atoms and having optionally 1 to 3 hydroxy substituents, for example, hydroxymethyl, 2-hydroxyethyl, 1-hydroxyethyl, 3-hydroxypropyl, 2,3-dihydroxyethyl, 4-hydroxybutyl, 3,4-dihydroxybutyl, 1,1-dimethyl-2-hydroxyethyl, 5-hydroxypentyl, 6-hydroxyhexyl, 2-methyl-3-hydroxypropyl, 2,3,4-trihydroxybutyl, and the like.

The "phenyl-lower alkyl" includes a phenylalkyl group wherein the alkyl moiety is a straight chain or branched chain alkyl group having 1 to 6 carbon atoms, for example, benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, and the like.

The "phenoxy-lower alkyl" includes a phenoxyalkyl group wherein the alkyl moiety is a straight chain or branched chain alkyl group having 1 to 6 carbon atoms, for example, phenoxymethyl, 1-phenoxyethyl, 2-phenoxyethyl, 3-phenoxypropyl, 4-phenoxybutyl, 5-phenoxypentyl, 6-phenoxyhexyl, 1,1-dimethyl-2-phenoxyethyl, 2-methyl-3-phenoxypropyl, and the like.

The "phenyl which has optionally 1 to 3 substituents selected from a lower alkyl, a lower alkoxy and a halogen atom" includes a phenyl group which has optionally 1 to 3 substituents selected from a straight chain or branched chain alkyl group having 1 to 6 carbon atoms, a straight chain or branched chain alkoxy group having 1 to 6 carbon atoms and a halogen atom, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 3,4,5-trichlorophenyl, 2-methoxy-3-chlorophenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 3-chloro-4-methylphenyl, 3-methoxy-4-methyl-5-iodophenyl, 3,4-dimethoxy-5-bromophenyl, 3,5-diiodo-4-methoxyphenyl, and the like.

The "amino-lower alkyl having optionally a lower alkyl substituent" includes a straight chain or branched chain alkyl group having 1 to 6 carbon atoms which is substituted by an amino group having optionally 1 to 2 substituents of a straight chain or branched chain alkyl group having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, (N-ethyl-N-propylamino)methyl, 2-(N-methyl-N-hexylamino)ethyl, and the like.

The "5- or 6-membered saturated heterocyclic group which is formed by binding the groups $R^9$ and $R^{10}$ together with the nitrogen atom to which they bond with or without being intervened with nitrogen or oxygen atom" includes, for example, pyrrolidinyl, piperidinyl, piperazinyl, morpholino, and the like.

The "heterocyclic group having a substituent selected from a lower alkyl, a lower alkoxycarbonyl and piperidinyl" includes a heterocyclic group having 1 to 3 substituents selected from a straight chain or branched chain alkyl group having 1 to 6 carbon atoms, a straight chain or branched chain alkoxycarbonyl having 1 to 6 carbon atoms and piperidinyl, for example, in addition to the above-mentioned heterocyclic groups having a substituent of a lower alkyl and piperidinyl, 4-methoxycarbonylpiperazinyl, 4-ethoxycarbonylpiperidinyl, 3-propoxycarbonylpyrrolidinyl, 2-pentyloxycarbonylmorpholino, 4-hexyloxycarbonylpiperidinyl, 4-ethoxycarbonyl-3-methylpiperidinyl, 3-methyl-4-ethoxycarbonylpiperazinyl, and the like.

The "5- or 6-membered saturated heterocyclic group which is formed by binding the groups $R^{14}$ and $R^{15}$ together with the nitrogen atom to which they bond with or without being intervened with nitrogen or oxygen atom" includes, for example, pyrrolidinyl, piperidinyl, piperazinyl, morpholino, and the like.

The "heterocyclic group having a lower alkyl substituent" includes a heterocyclic group having 1 to 3 substituents of a straight chain or branched chain alkyl group having 1 to 6 carbon atoms, for example, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, and the like.

The heterocyclic ring in the formula (1) includes tetrahydroquinolyl, 2,3,4,5-tetrahydro-1H-benzazepinyl, 1,2,3,4,5,6-hexahydrobenzazocinyl, 1,2-dihydroquinolyl, 2,3-dihydro-1H-benzazepinyl, 1,2,3,4-tetrahydrobenzazocinyl, and the like.

The heterocyclic ring in the formula (1) wherein the carbon atom in the group of the formula: —(CH$_2$)$_p$— or —CH═CH—(CH$_2$)$_q$— for W is replaced by oxygen atom, sulfur atom, sulfinyl, sulfonyl, or a group of the formula:

($R^{13}$ is hydrogen atom or a lower alkyl) includes a heterocylic group wherein the carbon atom in the group of the formula: —(CH$_2$)$_p$— or —CH═CH—(CH$_2$)$_q$— for W is replaced by oxygen atom, sulfur atom, sulfinyl, sulfonyl, or a group of the formula:

($R^{13}$ is hydrogen atom or a straight chain or branched chain alkyl having 1 to 6 carbon atoms), for example, 3,4-dihydro-2H-1,4-benzoxazinyl, 1,2,3,5-tetrahydro-4,1-benzoxazepinyl, 1,2,3,4-tetrahydroquinoxalinyl, 1,2,3,4,5,6-hexahydro-1,5-benzodiazocinyl, 5-methyl-1,2,3,4,5,6-hexahydro-1,5-benzodiazocinyl, 4-methyl-1,2,3,4-tetrahydroquinoxalinyl, 1,2,3,4-tetrahydro-5,1-benzoxazepinyl, 3,4-dihydro-2H-1,4-benzothiazinyl, 2,3,4,5-tetrahydro-1,5-benzothiazepinyl, 1,2,3,5-tetrahydro-4,1-benzothiazepinyl, 4-ethyl-1,2,3,4-tetrahydroquinoxalinyl, 4-propyl-1,2,3,4-tetrahydroquinoxalinyl, 4-butyl-1,2,3,4-tetrahydroquinoxalinyl, 4-pentyl-1,2,3,4-tetrahydroquinoxalinyl, 4-hexyl-1,2,3,4- tetrahydroquinoxalinyl, 2,3,4,5-tetrahydro-1H-1,4-benzodiazepinyl, 4-methyl-2,3,4,5-tetrahydro-1H-1,4-benzodiazepinyl, 4-ethyl-2,3,4,5-tetrahydro-1H-1,4-benzodiazepinyl, 4-propyl-2,3,4,5-tetrahydro-1H-1,4-benzodiazepinyl, 4-butyl-2,3,4,5-tetrahydro-1H-1,4-benzodiazepinyl, 4-pentyl-2,3,4,5-tetrahydro-1H-1,4-benzodiazepinyl, 4-hexyl-2,3,4,5-tetrahydro-1H-1,4-benzodiazepinyl, 2,3,4,5-tetrahydro-1H-1,5-benzodiazepinyl, 5-methyl-2,3,4,5-tetrahydro-1H-1,5-benzodiazepinyl, 5-ethyl-2,3,4,5-tetrahydro-1H-1,5-benzodiazepinyl, 5-propyl-2,3,4,5-tetrahydro-1H-1,5-benzodiazepinyl, 5-butyl-2,3,4,5-tetrahydro-1H-1,5-benzodiazepinyl, 5-pentyl-2,3,4,5-tetrahydro-1H-1,5-benzodiazepinyl, 5-hexyl-2,3,4,5-tetrahydro-1H-1,5-benzodiazepinyl, 3,4-dihydro-1-oxo-2H-1,4-benzothiazepinyl, 3,4-dihydro-1,1-dioxo-2H-1,4-benzothiazepinyl, 1-oxo-2,3,4,5-tetrahydro-1,5-benzothiazepinyl, 1,1-dioxo-2,3,4,5-tetrahydro-1,5-benzothiazepinyl, 4-oxo-1,2,3,5-tetrahydro-4,1-benzothiazepinyl, 4,4-dioxo-1,2,3,5-tetrahydro-4,1-benzothiazepinyl, and the like.

The "halogen-substituted lower alkoxy" includes a straight chain or branched chain alkoxy group having 1 to 6 carbon atoms which has 1 to 3 substituents of a halogen atom, for example, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 6-bromohexyloxy, 5,6-dichlorohexyloxy, and the like.

The "halogen-substituted lower alkanoyl" includes a straight chain or branched chain alkanoyl group having 1 to 6 carbon atoms which has 1 to 3 substituents of a halogen atom, for example, 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutyryl, 4-fluorobutyryl, 5-chloropentanoyl, 3-chloro-2-methylpropionyl, 6-bromohexanoyl, 5,6-dibromohexanoyl, and the like.

The "aminocarbonyl-lower alkoxy having a lower alkyl substituent" includes a straight chain or branched chain alkoxy group having 1 to 6 carbon atoms which is substituted by an aminocarbonyl group having 1 to 2 substituents of a straight chain or branched chain alkyl group having 1 to 6 carbon atoms, for example, methylaminocarbonylmethoxy, 1-ethylaminocarbonylethoxy, 2-propylaminocarbonylethoxy, 3-isopropylaminocarbonylpropoxy, 4-butylaminocarbonylbutoxy, 5-pentylaminocarbonylpentyloxy, 6-hexylaminocarbonylhexyloxy, dimethylaminocarbonylmethoxy, 3-diethylaminocarbonylpropoxy, diethylaminocarbonylmethoxy, (N-ethyl-N-propylamino)carbonylmethoxy, 2-(N-methyl-N-hexylamino)carbonylethoxy, and the like.

The "carbamoyl-lower alkyl" includes a carbamoyl-substituted alkyl group wherein the alkyl moiety is a straight chain or branched chain alkyl group having 1 to 6 carbon atoms, for example, carbamoylmethyl, 2-carbamoylethyl, 1-carbamoylethyl, 3-carbamoylpropyl, 4-carbamoylbutyl, 5-carbamoylpentyl, 6-carbamoylhexyl, 1,1-dimethyl-2-carbamoylethyl, 2-methyl-3-carbamoylpropyl, and the like.

The "amino-lower alkanoyl having optionally a lower alkyl substituent" includes a straight chain or branched chain alkanoyl having 2 to 6 carbon atoms which is substituted by an amino group having optionally 1 to 2 substituents of a straight chain or branched chain alkyl group having 1 to 6 carbon atoms, for example, 2-aminoacetyl, 3-aminopropionyl, 2-aminopropionyl, 4-aminobutyryl, 5-aminopentanoyl, 6-aminohexanoyl, 2,2-dimethyl-3-aminopropionyl, 2-methyl-3-aminopropionyl, 2-methylaminoacetyl, 2-ethylaminopropionyl, 3-propylaminopropionyl, 3-isopropylaminopropionyl, 4-butylaminobutyryl, 5-pentylaminopentanoyl, 6-hexylaminohexanoyl, 2-dimethylaminoacetyl, 2-diethylaminoacetyl, 2-(N-ethyl-N-propylamino)acetyl, 3-(N-methyl-N-hexylamino)propionyl, and the like.

The "amino-lower alkyl having optionally a lower alkanoyl substituent" includes a straight chain or branched chain alkyl having 1 to 6 carbon atoms which is substituted by an amino group having optionally a substituent of a straight chain or branched chain alkanoyl group having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, acetylaminomethyl, 1-acetylaminoethyl, 2-propionylaminoethyl, 3-isopropionylaminopropyl, 4-butyrylaminobutyl, 5-pentanoylaminopentyl, 6-hexanoylaminohexyl, formylaminomethyl, and the like.

The "anilinocarbonyl having optionally a lower alkyl substituent on the phenyl ring" includes an anilinocarbonyl substituent having optionally 1 to 3 substituents of a straight group or branched chain alkyl group having 1 to 6 carbon atoms on the phenyl ring, for example, anilinocarbonyl, 2-methylanilinocarbonyl, 3-methylanilinocarbonyl, 4-methylanilinocarbonyl, 2-ethylanilinocarbonyl, 3-ethylanilinocarbonyl, 4-ethylanilinocarbonyl, 4-isopropylanilinocarbonyl, 3-butylanilinocarbonyl, 4-pentylanilinocarbonyl, 4-hexylanilinocarbonyl, 3,4-dimethylanilinocarbonyl, 3,4-diethylanilinocarbonyl, 2,4-dimethylanilinocarbonyl, 2,5-dimethylanilinocarbonyl, 2,6-dimethylanilinocarbonyl, 3,4,5-trimethylanilinocarbonyl, and the like.

The "phenylsulfonyl which has optionally a substituent selected from a halogen and a lower alkyl on the phenyl ring" includes a phenylsulfonyl group which has optionally 1 to 3 substitutents selected from a straight chain or branched chain alkyl group having 1 to 6 carbon atoms and a halogen atom, for example, phenylsulfonyl, 2-chlorophenylsulfonyl, 3-chlorophenylsulfonyl, 4-chlorophenylsulfonyl, 2-fluorophenylsulfonyl, 3-fluorophenylsulfonyl, 4-fluorophenylsulfonyl, 2-bromophenylsulfonyl, 3-bromophenylsulfonyl, 4-bromophenylsulfonyl, 2-iodophenylsulfonyl, 3-iodophenylsulfonyl, 4-iodophenylsulfonyl, 3,4-dichlorophenylsulfonyl, 3,5-dichlorophenylsulfonyl, 2,6-dichlorophenylsulfonyl, 2,3-dichlorophenylsulfonyl, 2,4-dichlorophenylsulfonyl, 3,4-difluorophenylsulfonyl, 3,5-dibromophenylsulfonyl, 3,4,5-trichlorophenylsulfonyl, 2-ethyl-3-chlorophenylsulfonyl, 2-methylphenylsulfonyl, 3-methylphenylsulfonyl, 4-methylphenylsulfonyl, 2-ethylphenylsulfonyl, 3-ethylphenylsulfonyl, 4-ethylphenylsulfonyl, 4-isopropylphenylsulfonyl, 3-butylphenylsulfonyl, 4-pentylphenylsulfonyl, 4-hexylphenylsulfonyl, 3,4-dimethylphenylsulfonyl, 3,4-diethylphenylsulfonyl, 2,4-dimethylphenylsulfonyl, 2,5-dimethylphenylsulfonyl, 2,6-dimethylphenylsulfonyl, 3,4,6-trimethylphenylsulfonyl, 3,4,5-trimethylphenylsulfonyl, 3-chloro-4-methylphenylsulfonyl, 4-methyl-5-iodophenylsulfonyl, 3,4-dimethyl-5-bromophenylsulfonyl, 3,5-diiodo-4-methylphenylsulfonyl, and the like.

The "phthalimido-substituted lower alkyl" includes a straight chain or branched chain alkyl group having 1 to 6 carbon atoms which is substituted by phthalimido group, for example, phthalimidomethyl, 2-phthalimidoethyl, 1-phthalimidoethyl, 3-phthalimidopropyl, 4-phthalimidobutyl, 5-phthalimidopentyl, 6-phthalimidohexyl, 1,1-dimethyl-2-phthalimidoethyl, 2-methyl-3-phthalimidopropyl, and the like.

The "lower alkynyl" includes a straight chain or branched chain alkynyl having 2 to 6 carbon atoms, for example, ethynyl, 2-propynyl, 2-butynyl, 3-butynyl, 1-methyl-2-propynyl, 2-pentynyl, 2-hexynyl, and the like.

The "benzoyl which has optionally a halogen substituent on the phenyl ring" includes a benzoyl group which has optionally 1 to 3 substituents of a halogen atom on the phenyl ring, for example, benzoyl, 2-chlorobenzoyl, 3-chlorobenzoyl, 4-chlorobenzoyl, 2-fluorobenzoyl, 3-fluorobenzoyl, 4-fluorobenzoyl, 2-bromobenzoyl, 3-bromobenzoyl, 4-bromobenzoyl, 2-iodobenzoyl, 3-iodobenzoyl, 4-iodobenzoyl, 3,4-dichlorobenzoyl, 3,5-dichlorobenzoyl, 2,6-dichlorobenzoyl, 2,3-dichlorobenzoyl, 2,4-dichlorobenzoyl, 3,4-difluorobenzoyl, 3,5-dibromobenzoyl, 3,4,5-trichlorobenzoyl, and the like.

The "phenyl-lower alkoxy" includes a phenylalkoxy group wherein the alkoxy moiety is a straight chain or branched chain alkoxy group having 1 to 6 carbon atoms, for example, benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, 2-methyl-3-phenylpropoxy, and the like.

The "amino-lower alkoxy having optionally a substituent selected from a lower alkyl and a lower alkanoyl" include a straight chain or branched chain alkoxy group having 1 to 6 carbon atoms which is substituted by an amino group having optionally 1 to 2 substituents selected from a straight chain or branched chain alkyl group having 1 to 6 carbon atoms and a straight chain or branched chain alkanoyl group having 1 to 6 carbon atoms, for example, aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, acetylaminomethoxy, 1-acetylaminoethoxy, 2-propionylaminoethoxy, 3-isopropionylaminopropoxy, 4-butyrylaminobutoxy, 5-pentanoylaminopentyloxy, 6-hexanoylaminohexyloxy, formylaminomethoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, (N-ethyl-N-propylamino)methoxy, 2-(N-methyl-N-hexylamino)ethoxy, and the like.

The "benzoyloxy which has optionally a halogen substituent on the phenyl ring" includes a benzoyloxy group which has optionally 1 to 3 substituents of a halogen atom on the phenyl ring, for example, benzoyloxy, 2-chlorobenzoyloxy, 3-chlorobenzoyloxy, 4-chlorobenzoyloxy, 2-fluorobenzoyloxy, 3-fluorobenzoyloxy, 4-fluorobenzoyloxy, 2-bromobenzoyloxy, 3-bromobenzoyloxy, 4-bromobenzoyloxy, 2-iodobenzoyloxy, 3-iodobenzoyloxy, 4-iodobenzoyloxy, 3,4-dichlorobenzoyloxy, 3,5-dichlorobenzoyloxy, 2,6-dichlorobenzoyloxy, 2,3-dichlorobenzoyloxy, 2,4-dichlorobenzoyloxy, 3,4-difluorobenzoyloxy, 3,5-dibromobenzoyloxy, 3,4,5-trichlorobenzoyloxy, and the like.

The "lower alkanoyloxy-substituted lower alkyl" includes a straight chain or branched chain alkyl group having 1 to 6 carbon atoms which is substituted by a straight chain or branched chain alkanoyloxy group having 2 to 6 carbon atoms, for example, acetyloxymethyl, 2-propionyloxyethyl, 1-butyryloxyethyl, 3-acetyloxypropyl, 4-acetyloxybutyl, 4-isobutyryloxybutyl, 5-pentanoyloxypentyl, 6-acetyloxyhexyl, 6-tert-butylcarbonyloxyhexyl, 1,1-dimethyl-2-hexanoyloxyethyl, 2-methyl-3-acetyloxypropyl, and the like.

The "lower alkylsulfonyloxy-lower alkyl" includes a straight chain or branched chain alkyl group having 1 to 6 carbon atoms which is substituted by a straight chain or branched chain alkylsulfonyloxy group having 1 to 6 carbon atoms, for example, methylsulfonyloxymethyl, 1-ethylsulfonyloxyethyl, 2-propylsulfonyloxyethyl, 3-isopropylsulfonyloxypropyl, 4-butylsulfonyloxybutyl, 5-pentylsulfoyloxypentyl, 6-hexylsulfonyloxyhexyl, 1,1-dimethyl-2-methylsulfoyloxyethyl, 2-methyl-3-ethylsulfonyloxypropyl, and the like.

The "azido-lower alkyl" includes a straight chain or branched chain alkyl group having 1 to 6 carbon atoms which is substituted by an azido group, for example, azidomethyl, 1-azidoethyl, 2-azidoethyl, 3-azidopropyl, 4-azidobutyl, 5-azidopentyl, 6-azidohexyl, 1,1-dimethyl-2-azidoethyl, 2-methyl-3-azidopropyl, and the like.

The "lower alkanoyloxyimino" includes a straight chain or branched chain alkanoyloxyimino group having 1 to 6 carbon atoms, for example, formyloxyimino, acetyloxyimino, propionyloxyimino, butyryloxyimino, isobutyryloxyimino, pentanoyloxyimino, tert-butylcarbonyloxyimino, hexanoyloxyimino, and the like.

The "lower alkylidene" includes a straight chain or branched chain alkylidene group having 1 to 6 carbon atoms, for example, methylidene, ethylidene, propylidene, isopropylidene, butylidene, pentylidene, hexylidene, and the like.

The "oxiranyl-substituted lower alkyl" includes a straight chain or branched chain alkyl group having 1 to 6 carbon atoms which is substituted by oxiranyl group, for example, oxiranylmethyl, 1-oxiranylethyl, 2-oxiranylethyl, 3-oxiranylpropyl, 4-oxiranylbutyl, 5-oxiranylpentyl, 6-oxiranylhexyl, 1,1-dimethyl-2-oxiranylethyl, 2-methyl-3-oxiranylpropyl, and the like.

The "lower alkyl having 1 to 2 substituents selected from a lower alkoxy, hydroxy and an amino having optionally a lower alkyl substituent" includes a straight chain or branched chain alkyl group having 1 to 6 carbon atoms and having 1 to 2 substituents selected from a straight chain or branched chain alkoxy group having 1 to 6 carbon atoms, hydroxy and an amino having optionally a straight chain or branched chain alkyl group having 1 to 6 carbon atoms, for example, methoxymethyl, 1-ethoxyethyl, 2-propoxyethyl, 3-isopropoxypropyl, 4-butoxybutyl, 5-pentyloxypentyl, 6-hexyloxyhexyl, 1,1-dimethyl-2-methoxyethyl, 2-methyl-3-ethoxypropyl, 3-methoxy-2-hydroxypropyl, hydroxymethyl, 2-hydroxyethyl, 1-hydroxyethyl, 3-hydroxypropyl, 2,3-dihydroxyethyl, 4-hydroxybutyl, 3,4-dihydroxybutyl, 1,1-dimethyl-2-hydroxyethyl, 5,6-dihydroxyhexyl, 5-hydroxypentyl, 6-hydroxyhexyl, 6-(N-ethyl-N-methylamino)-5-methoxyhexyl, 2-methyl-3-hydroxypropyl, aminomethyl, 1-aminoethyl, 2-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, ethylaminomethy, propylaminomethyl, isopropylaminomethyl, butylaminomethyl, tert-butylaminomethyl, pentylaminomethyl, hexylaminomethyl, dimethylaminomethyl, diethylaminomethyl, dipropylaminomethyl, dibutylaminomethyl, dipentylaminomethyl, dihexylaminomethyl, N-methyl-N-ethylaminomethyl, N-methyl-N-propylaminomethyl, N-methyl-N-butylaminomethyl, N-methyl-N-hexylaminomethyl, 1-methylaminoethyl, 2-ethylaminoethyl, 3-propylaminopropyl, 4-butylaminobutyl, 1,1-dimethyl-2-pentylaminoethyl, 5-hexylaminopentyl, 6-dimethylaminohexyl, 4-dimethylaminobutyl, 2-diethylaminoethyl, 1-(N-methyl-N-hexylamino)ethyl, 3-dihexylaminopropyl, 6-diethylaminohexyl, 4-dibutylaminobutyl, 2-(N-methyl-N-pentylamino)ethyl, 2-hydroxy-3-diethylaminopropyl, 3-hydroxy-4-methylaminobutyl, 5-hydroxy-6-diethylaminohexyl, 4-hydroxy-5-dimethylaminopentyl, 4-hydroxy-5-methylaminopentyl, 4-hydroxy-5-diethylaminopentyl, 5-hydroxy-6-ethylaminohexyl, 5-hydroxy-6-isopropylaminohexyl, 5-hydroxy-6-aminohexyl, and the like.

The "aminocarbonyloxy having optionally a lower alkyl substituent" includes an aminocarbonyloxy group having optionally 1 to 2 substituents of a straight chain or branched chain alkyl group having 1 to 6 carbon atoms, for example, aminocarbonyloxy, methylaminocarbonyloxy, ethylaminocarbonyloxy, propylaminocarbonyloxy, isopropylaminocarbonyloxy, butylaminocarbonyloxy, tert-butylaminocarbonyloxy, pentylaminocarbonyloxy, hexylaminocarbonyloxy, dimethylaminocarbonyloxy, diethylaminocarbonyloxy, dipropylaminocarbonyloxy, dibutylaminocarbonyloxy, dipentylaminocarbonyloxy, dihexylaminocarbonyloxy, N-methyl-N-ethylaminocarbonyloxy, N-ethyl-N-propylaminocarbonyloxy, N-methyl-N-butylaminocarbonyloxy, N-methyl-N-hexylaminocarbonyloxy, and the like.

The "lower alkanoyloxy having optionally a halogen substituent" includes a straight chain or branched chain alkanoyloxy group having 1 to 6 carbon atoms which has optionally 1 to 3 substituents of a halogen atom, for example, in addition to the above lower alkanoyl group, 2,2,2-trifluoroacetyloxy, 2,2,2-trichloroacetyloxy, 2-chloroacetyloxy, 2-bromoacetyloxy, 2-fluoroacetyloxy, 2-iodoacetyloxy, 2,2-difluoroacetyloxy, 2,2-dibromoacetyloxy, 3,3,3-trifluoropropionyloxy, 3,3,3-trichloropropionyloxy, 3-chloropropionyloxy, 2,3-dichloropropionyloxy, 4,4,4-trichlorobutyryloxy, 4-fluorobutyryloxy, 5-chloropentanoyloxy, 3-chloro-2-methylpropionyloxy, 6-bromohexanoyloxy, 5,6-dibromohexanoyloxy, and the like.

The "amino-lower alkyl having optionally a substituent selected from a lower alkyl and a lower alkanoyl" include a straight chain or branched chain alkyl group having 1 to 6 carbon atoms which is substituted by an amino group having optionally 1 to 2 substituents selected from a straight chain or branched chain alkyl group having 1 to 6 carbon atoms and a straight chain or branched chain alkanoyl group having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, acetylaminomethyl, 1-acetylaminoethyl, 2-propionylaminoethyl, 3-isopropionylaminopropyl, 4-butyrylaminobutyl, 5-pentanoylaminopentyl, 6-hexanoylaminohexyl, formylaminomethyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, (N-ethyl-N-propylamino)methyl, 2-(N-methyl-N-hexylamino)ethyl, and the like.

The "amino-lower alkanoyloxy having optionally a lower alkyl substituent" includes a straight chain or branched chain alkanoyloxy having 2 to 6 carbon atoms which is substituted by an amino group having optionally 1 to 2 substituents of a straight chain or branched chain alkyl group having 1 to 6 carbon atoms, for example, 2-aminoacetyloxy, 3-aminopropionyloxy, 2-aminopropionyloxy, 4-aminobutyryloxy, 5-aminopentanoyloxy, 6-aminohexanoyloxy, 2,2-dimethyl-3-aminopropionyloxy, 2-methyl-3-aminopropionyloxy, 2-methylaminoacetyloxy, 2-ethylaminopropionyloxy, 3-propylaminopropionyloxy, 3-isopropylaminopropionyloxy, 4-butylaminobutyryloxy, 5-pentylaminopentanoyloxy, 6-hexylaminohexanoyloxy, 2-dimethylaminoacetyloxy, 2-diethylaminoacetyloxy, 2-(N-ethyl-N-propylamino)acetyloxy, 3-(N-methyl-N-hexylamino)propionyloxy, and the like.

The "pyridyl-lower alkyl" include a pyridylalkyl group wherein the alkyl moiety is a straight chain or branched chain alkyl group having 1 to 6 carbon atoms, for example, (4-pyridyl)methyl, 1-(3-pyridyl)ethyl, 2-(2-pyridyl)ethyl, 3-(2-pyridyl)propyl, 4-(3-pyridyl)butyl, 5-(4-pyridyl)pentyl, 6-(2-pyridyl)hexyl, 1,1-dimethyl-2-(3-pyridyl)ethyl, 2-methyl-3-(4-pyridyl)propyl, and the like.

The "5- or 6-membered saturated heterocyclic group which is formed by binding the groups $R^{82}$ and $R^{83}$ together with the nitrogen atom to which they bond with or without being intervened with nitrogen, oxygen or sulfur atom" includes, for example, pyrrolidinyl, piperidinyl, piperazinyl, morpholino, thiomorpholino, and the like.

The above heterocyclic group which has a substituent selected from oxo, a lower alkyl, a lower alkanoyl and carbamoyl includes the above heterocyclic groups which have 1 to 3 substituents selected from oxo, a straight chain or branched chain alkyl group having 1 to 6 carbon atoms, a straight chain or branched chain alkanoyl group having 1 to 6 carbon atoms, and carbamoyl group, for example, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 2-methylthiomorpholino, 4-acetylpiperazinyl, 2-propionylmorpholino, 3-butyrylthiomorpholino, 3-pentanoylpyrrolidinyl, 4-hexanoylpiperidinyl, 3-methyl-4-acetylpiperazinyl, 2-carbamoylpyrrolidinyl, 4-carbamoylpiperazinyl, 3-carbamoylthiomorpholino, 2-carbamoylmorpholino, 3-carbamoylpiperidinyl, 1-oxo-thiomorpholino, 1,1-dioxothiomorpholino, and the like.

The "lower alkylsulfonyl" includes a straight chain or branched chain alkylsulfonyl group having 1 to 6 carbon atoms, for example, methylsulfonyl, ethylsulfonyl, propylsulfonyl, isopropylsulfonyl, butylsulfonyl, tert-butylsulfonyl, pentylsulfonyl, hexylsulfonyl, and the like.

The "aminocarbonyl having optionally a lower alkyl substituent" includes an aminocarbonyl group having optionally 1 to 2 substituents of a straight chain or branched chain alkyl group having 1 to 6 carbon atoms, for example, aminocarbonyl, methylaminocarbonyl, ethylaminocarbonyl, propylaminocarbonyl, isopropylaminocarbonyl, butylaminocarbonyl, tert-butylaminocarbonyl, pentylaminocarbonyl, hexylaminocarbonyl, dimethylaminocarbonyl, diethylaminocarbonyl, dipropylaminocarbonyl, dibutylaminocarbonyl, dipentylaminocarbonyl, dihexylaminocarbonyl, N-methyl-N-ethylaminocarbonyl, N-ethyl-N-propylaminocarbonyl, N-methyl-N-butylaminocarbonyl, N-methyl-N-hexylaminocarbonyl, and the like.

The "cyano-substituted lower alkyl" includes a straight chain or branched chain alkyl group having 1 to 6 carbon atoms which is substituted by cyano group, for example, cyanomethyl, 2-cyanoethyl, 1-cyanoethyl, 3-cyanopropyl, 4-cyanobutyl, 5-cyanopentyl, 6-cyanohexyl, 1,1-dimethyl-2-caynoethyl, 2-methyl-3-cyanopropyl, and the like.

The "lower alkoxycarbonyl-substituted lower alkyl" includes an alkoxycarbonyl-substituted straight chain or branched chain alkyl group having 1 to 6 carbon atoms wherein the alkoxycarbonyl moiety is a straight chain or branched chain alkoxycarbonyl group having 1 to 6 carbon atoms, for example, methoxycarbonylmethyl, 3-methoxycarbonylpropyl, ethoxycarbonylmethyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl, hexyloxycarbonylmethyl, and the like.

The "carboxy-substituted lower alkyl" includes a carboxy-substituted alkyl group wherein the alkyl moiety is a straight chain or branched chain alkyl group having 1 to 6 carbon atoms, for example, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl, and the like.

The "tetrahydropyranyloxy-substituted lower alkyl" includes a tetrahydropyranyloxy-substituted straight chain or branched chain alkyl group having 1 to 6 carbon atoms, for example, (2-tetrahydropyranyloxy)methyl, 2-(3-tetrahydropyranyloxy)ethyl, 1-(4-tetrahydropyranyloxy)ethyl, 3-(2-tetrahydropyranyloxy)propyl, 4-(3-tetrahydropyranyloxy)butyl, 5-(4-tetrahydropyranyloxy)pentyl, 6-(2-tetrahydropyranyloxy)hexyl, 1,1-dimethyl-2-(3-tetrahydropyranyloxy)ethyl, 2-methyl-3-(4-tetrahydropyranyloxy)propyl, and the like.

The "piperidinyl having optionally a phenyl-lower alkyl substituent" includes a piperidinyl which has optionally a substituent of a phenylalkyl group wherein the alkyl moiety is a straight chain or branched chain alkyl group having 1 to 6 carbon atoms, for example, piperidinyl, 1-benzyl-4-piperidinyl, 1-(2-phenylethyl)-3-piperidinyl, 1-(1-phenylethyl)-2-piperidinyl, 1-(3-phenylpropyl)-4-piperidinyl, 1-(4-phenylbutyl)-4-piperidinyl, 1-(5-phenylpentyl)-4-piperidinyl, 1-(6-phenylhexyl)-4-piperidinyl, 1-(1,1-dimethyl-2-phenylethyl)-3-piperidinyl, 1-(2-methyl-3-phenylpropyl)-2-piperidinyl, and the like.

The "imidazolyl-substituted lower alkanoyl" includes an imidazolyl-substituted alkanoyl group wherein the alkanoyl moiety is a straight chain or branched chain alkanoyl group having 2 to 6 carbon atoms, for example, (1-imidazolyl)acetyl, 3-(2-imidazolyl)propionyl, 2-(4-imidazolyl)propionyl, 4-(1-imidazolyl)butyryl, 2,2-dimethyl-3-(2-imidazolyl)propionyl, 5-(4-imidazolyl)pentanoyl, 6-(1-imidazolyl)hexanoyl, and the like.

The "amino-lower alkanoyl having optionally a substituent selected from a lower alkyl and a lower alkoxycarbonyl" includes a straight chain or branched chain alkanoyl having 2 to 6 carbon atoms which is substituted by an amino group having optionally 1 to 2 substituents selected from a straight chain or branched chain alkyl group having 1 to 6 carbon atoms and a straight chain or branched chain alkoxycarbonyl group having 1 to 6 carbon atoms, for example, 2-aminoacetyl, 3-aminopropionyl, 2-aminopropionyl, 4-aminobutyryl, 5-aminopentanoyl, 6-aminohexanoyl, 2,2-dimethyl-3-aminopropionyl, 2-methyl-3-aminopropionyl, 2-methylaminoacetyl, 2-ethylaminopropionyl, 3-propylaminopropionyl, 3-isopropylaminopropionyl, 4-butylaminobutyryl, 5-pentylaminopentanoyl, 6-hexylaminohexanoyl, 2-dimethylaminoacetyl, 2-diethylaminoacetyl, 2-(N-ethyl-N-propylamino)acetyl, 3-(N-methyl-N-hexylamino)propionyl, 2-methoxycarbonylaminoacetyl, 2-ethoxycarbonylaminoacetyl, 3-propoxycarbonylaminopropionyl, 4-butoxycarbonylaminobutyryl, 2-tert-butoxycarbonylaminoacetyl, 5-pentyloxycarbonylaminopentanoyl, 6-hexyloxycarbonylaminohexanoyl, 2-(N-methyl-N-tert-butoxycarbonylamino)acetyl, and the like.

The "aminocarbonyl-lower alkyl having a lower alkyl substituent" includes a straight chain or branched chain alkyl group having 1 to 6 carbon atoms which is substituted by an aminocarbonyl group having 1 to 2 substituents of a straight chain or branched chain alkyl group having 1 to 6 carbon atoms, for example, methylaminocarbonylmethyl, 1-ethylaminocarbonylethyl, 2-propylaminocarbonylethyl, 3-isopropylaminocarbonylpropyl, 4-butylaminocarbonylbutyl, 5-pentylaminocarbonylpentyl, 6-hexylaminocarbonylhexyl, dimethylaminocarbonylmethyl, 3-diethylaminocarbonylpropyl, diethylaminocarbonylmethyl, (N-ethyl-N-propylamino)carbonylmethyl, 2-(N-methyl-N-hexylamino)carbonylethyl, and the like.

The "amino-substituted lower alkoxy having optionally a lower alkyl substituent" includes an amino-substituted straight chain or branched chain alkoxy having 1 to 6 carbon atoms which has optionally 1 to 2 substituents of a straight chain or branched chain alkyl having 1 to 6 carbon atoms, such as aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, (N-ethyl-N-propylamino)methoxy, 2-(N-methyl-N-hexylamino)ethoxy, and the like.

The compounds of the present invention can be prepared by various processes, for example, by the processes shown in the following reaction schemes.

[Reaction Scheme-1]

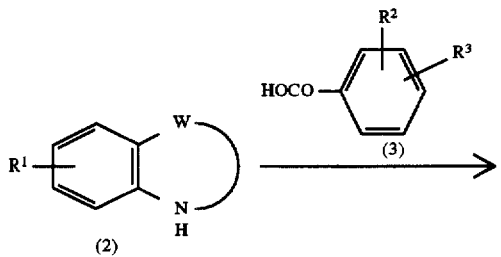

-continued
[Reaction Scheme-1]

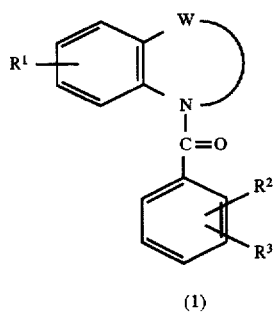

(1)

wherein $R^1$, $R^2$, $R^3$, and W are the same as defined above.

The process of Reaction Scheme-1 is carried out by reacting a benzoheterocyclic compound of the formula (2) and a carboxylic acid compound of the formula (3) by a conventional amido bond forming reaction. The amido bond forming reaction can be carried out under the conditions for the conventional amido bond forming reaction, for example, (a) a mixed acid anhydride process, i.e. a process of reacting the carboxylic acid compound (3) with an alkylhalocarboxylic acid to form a mixed acid anhydride and reacting the resultant with the amine compound (2), (b) an activated ester process, i.e. a process of converting the carboxylic acid compound (3) into an activated ester, such as p-nitrophenyl ester, N-hydroxysuccinimide ester, 1-hydroxybenzotriazole ester, etc., and reacting the resultant with the amine compound (2), (c) a carbodiimide process, i.e. a process of condensing the carboxylic acid compound (3) and the amine compound (2) in the presence of an activating agent such as dicyclohexylcarbodiimide, carbonyldiimidazole, etc., (d) other processes, i.e. a process of converting the carboxylic acid compound (3) into a carboxylic anhydride by treatment with a dehydrating agent such as acetic anhydride, and reacting the resultant with the amine compound (2); a process of reacting an ester of the carboxylic acid compound (3) with a lower alcohol and the amine compound (2) at a high temperature under high pressure; a process of reacting an acid halide compound of the carboxylic acid compound (3), i.e. a carboxylic acid halide, with the amine compound (2), and the like.

The mixed acid anhydride used in the above mixed acid anhydride process (a) is obtained by the known Schötten-Baumann reaction, and the reaction product is used without isolation from the reaction mixture for the reaction with the amine compound (2) to give the desired compound of the formula (1). The Schötten-Baumann reaction is usually carried out in the presence of a basic compound. The basic compound is any conventional compounds used for the Schötten-Baumann reaction and includes, for example, organic basic compounds such as triethylamine, trimethylamine, pyridine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature of from about −20° C. to about 100° C., preferably from about 0° C. to about 50° C., for about 5 minutes to about 10 hours, preferably about 5 minutes to about 2 hours.

The reaction of the thus obtained mixed acid anhydride with the amine compound (2) is usually carried out at a temperature of from about −20° C. to about 150° C., preferably about 10° C. to about 50° C., for about 5 minutes to about 10 hours, preferably about 5 minutes to about 5 hours. The mixed acid anhydride process is usually carried out in an appropriate solvent. The solvent is any conventional solvents which are usually used in the mixed acid anhydride process and includes, for example, halogenated hydrocarbons (e.g. chloroform, dichloromethane dichloroethane, etc.), aromatic hydrocarbons (e.g. benzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The alkylhalocarboxylic acid used in the mixed acid anhydride process includes, for example, methyl chloroformate, methyl bromoformate, ethyl chloroformate, ethyl bromoformate, isobutyl chloroformate, and the like. In said process, the carboxylic acid compound (3), the alkylhalocarboxylic acid and the amine (2) are usually used in each equimolar amount, but preferably, the alkylhalocarboxylic acid and the carboxylic acid compound (3) are used each in an amount of about 1 to 1.5 mole to 1 mole of the amine (2).

Among the above other processes (d), in case of the process of reacting the carboxylic acid halide with the amine compound (2), the reaction is usually carried out in the presence of a basic compound in an appropriate solvent. The basic compound is any conventional compounds and includes, in addition to the basic compounds used for the above-mentioned Schötten-Baumann reaction, sodium hydroxide, potassium hydroxide, sodium hydride, potassium hydride, etc. The solvent includes, in addition to the solvents used for the above-mentioned mixed acid anhydride process, alcohols (e.g. methanol, ethanol, propanol, butanol, 3-methoxy-1-butanol, ethylcellosolve, methylcellosolve, etc.), acetonitrile, pyridine, acetone, water, and the like. The amount of the amine compound (2) and the carboxylic acid halide is not critical, but the carboxylic acid halide is usually used at least in equimolar amount, preferably about 1 to 5 moles to 1 mole of the amine compound (2). The reaction is usually carried out at a temperature of from about −20° C. to about 180° C., preferably from about 0° C. to about 150° C., for about 5 minutes to about 30 hours.

The amido bond forming reaction in the above Reaction Scheme-1 may also be carried out by reacting the carboxylic acid compound (3) and the amine (2) in the presence of a condensation agent, i.e. phosphoric compounds such as triphenylphosphine, diphenylphosphinyl chloride, phenyl-N-phenylphosphoramide chloridate, diethyl chlorophosphate, diethyl phosphorocyanidate, diphenylphosphoric azide, bis(2-oxo-3-oxazolidinyl)phosphinic chloride, etc. The reaction is usually carried out in the presence of the solvent and basic compound as used in the above reaction of the carboxylic acid halide and the amine (2) at a temperature of from about −20° C. to about 150° C., preferably about 0° C. to about 100° C., for about 5 minutes to about 30 hours. The condensation agent and the carboxylic acid compound (3) are used at least in equimolar amount, preferably about 1 to 2 moles, to 1 mole of the amine (2).

[Reaction Scheme-2]

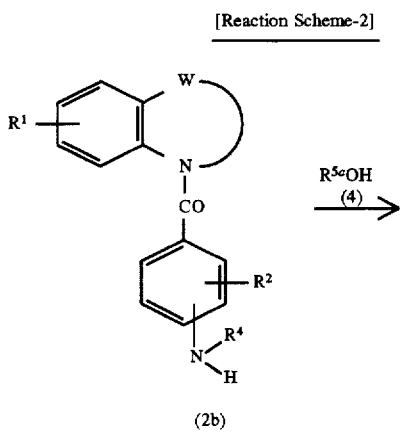

(2b)

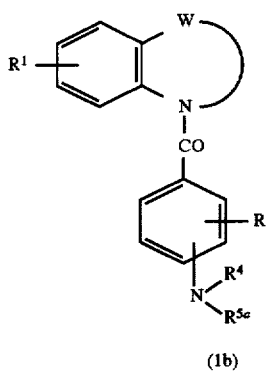

(1b)

wherein $R^1$, $R^2$, $R^4$ and W are as defined above, $R^{5a}$ is the same as $R^5$ as defined above except excluding an anilinocarbonyl having optionally a lower alkyl substituent on the phenyl ring, a phenylsulfonyl having optionally a substituent selected from a halogen atom and a lower alkyl on the phenyl ring and quinolylsulfonyl.

The reaction of the compound (2b) and the compound (4) is carried out in the same manner as in the reaction of the compound (2) and the compound (3) in the above Reaction Scheme-1.

[Reaction Scheme-3]

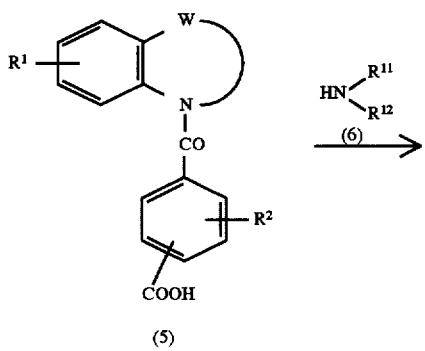

(5)

-continued
[Reaction Scheme-3]

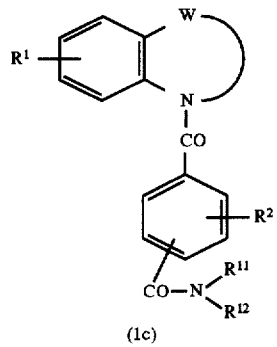

(1c)

wherein $R^1$, $R^2$, $R^{11}$, $R^{12}$ and W are as defined above.

The reaction of the compound (5) and the compound (6) is carried out under the same conditions as used in the reaction of the compound (2) and the compound (3) in the above Reaction Scheme-1.

[Reaction Scheme-4]

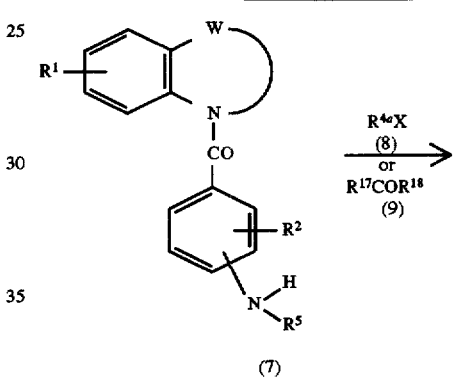

(7)

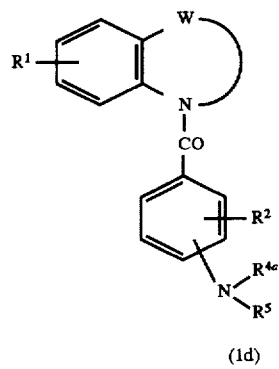

(1d)

wherein $R^1$, $R^2$, $R^5$ and W are as defined above, and $R^{4a}$ is a lower alkyl, $R^{17}$ and $R^{18}$ are each hydrogen atom or a lower alkyl, and X is a halogen atom.

The reaction of the compound (7) and the compound (8) is usually carried out in an inert solvent in the presence or absence of a basic compound. The inert solvent includes, for example, aromatic hydrocarbons (e.g. benzene, toluene, xylene, etc.), ethers (e.g. tetrahydrofuran, dioxane, diethylene glycol dimethyl ether, etc.), halogenated hydrocarbons (e.g. dichloromethane, chloroform, carbon tetrachloride, etc.), lower alcohols (e.g. methanol, ethanol, isopropanol, butanol, tert-butanol, etc.), acetic acid, ethyl acetate, acetone, acetonitrile, pyridine, dimethylsulfoxide, dimethylformamide, hexamethylphosphoric triamide, etc., or a mixture of these solvents. The basic compound includes, for example, carbonates (e.g. sodium carbonate, potassium carbonate, sodium hydrogen carbonate, potassium hydrogen carbonate, etc.), metal hydroxides (e.g. sodium hydroxide, potassium hydroxide, etc.), sodium hydride, potassium, sodium, sodium amide, metal alcoholates (e.g. sodium methoxide, sodium ethoxide, etc.), and organic basic compounds (e.g. pyridine, N-ethyldiisopropylamine, dimethylaminopyridine, triethylamine, 1,5-diazabicyclo [4.3.0]nonene-(5) (DBN), 1,8-diazabicyclo[5.4.0] undecene-7 (DBU), 1,4-diazabicyclo[2.2.2]octane (DABCO), etc.). The amount of the compound (7) and the compound (8) is not critical, but the compound (8) is usually used at least in equivalent amount, preferably 1 to 10 moles, to 1 mole of the compound (7). The reaction is usually carried out at a temperature of from about 0° C. to about 200° C., preferably from about 0° C. to about 170° C., for about 30 minutes to about 30 hours. In the reaction, an alkali metal halide (e.g. sodium iodide, potassium iodide, etc.) may be added to the reaction system.

The reaction of the compound (7) and the compound (9) is carried out in an appropriate solvent or without solvent in the presence of a reducing agent. The solvent includes, for example, water, alcohols (e.g. methanol, ethanol, isopropanol, etc.), acetonitrile, formic acid, acetic acid, ethers (e.g. dioxane, diethyl ether, diglyme, tetrahydrofuran, etc.), aromatic hydrocarbons (e.g. benzene, toluene, xylene, etc.), or a mixture of these solvents. The reducing agent includes, for example, formic acid, fatty acid alkali metal salts (e.g. sodium formate, etc.), hydrogenating reducing agents (e.g. sodium boro hydride, sodium cyanoboro hydride, lithium aluminum hydride, etc.), catalystic reducing agents (e.g. palladium black, palladium-carbon, platinum oxide, platinum black, Raney nickel, etc.).

When formic acid is used as the reducing agent, the reaction is usually carried out at a temperature of from room temperature to about 200° C., preferably about 50° C. to about 150° C., for about 1 to 10 hours. The formic acid is usually used in a large excess amount to the compound (7).

When a hydrogenating reducing agent is used, the reaction is usually carried out at a temperature of about −30° C. to about 100° C., preferably about 0° C. to about 70° C., for about 30 minutes to about 12 hours. The reducing agent is usually used in an amount of 1 to 20 moles, preferably 1 to 6 moles, to 1 mole of the compound (7). When lithium aluminum hydride is used as the reducing agent, it is preferable to use a solvent selected from ethers (e.g. diethyl ether, dioxane, tetrahydrofuran, diglyme, etc.) and aromatic hydrocarbons (e.g. benzene, toluene, xylene, etc.).

When a catalytic reducing agent is used, the reaction is usually carried out under atmospheric pressure to about 20 atm., preferably atmospheric pressure to about 10 atm. under hydrogen atmosphere or in the presence of a hydrogen donor (e.g. formic acid, ammonium formate, cyclohexene, hydrazine hydrate, etc.) at a temperature of about −30° C. to about 100° C., preferably about 0° C. to about 60° C., for about 1 to 12 hours. The catalytic reducing agent is usually used in an amount of about 0.1 to 40% by weight, preferably about 1 to 20% by weight; of the amount of the compound (7). The compound (9) is usually used at least in equivalent amount, preferably equivalent to a large excess amount, to the compound (7).

[Reaction Scheme-5A]

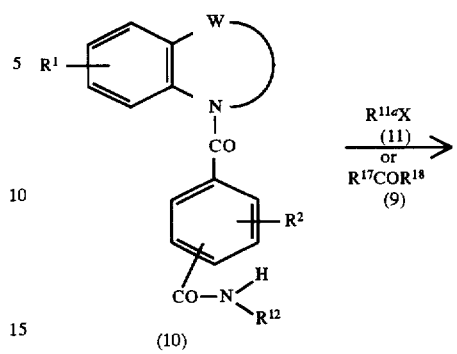

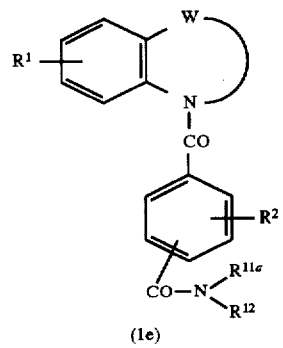

wherein $R^1$, $R^2$, $R^{12}$, $R^{17}$, $R^{18}$, X and W are as defined above, and $R^{11a}$ is a lower alkyl.

[Reaction Scheme-5B]

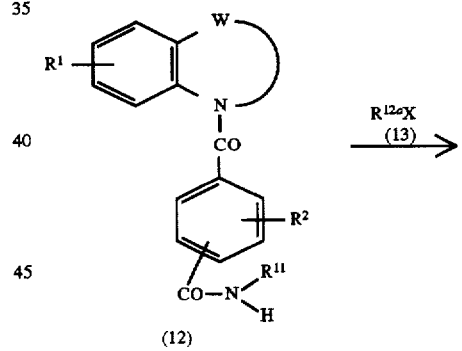

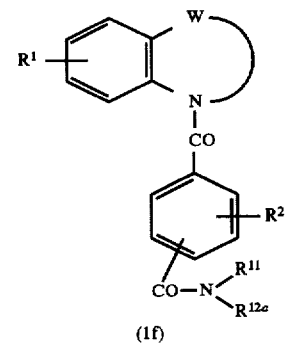

wherein $R^1$, $R^2$, $R^{11}$, X and W are as defined above, and $R^{12a}$ is a cycloalkyl.

The reaction of the compound (10) and the compound (11) in the Reaction Scheme-5A and the reaction of the compound (12) and the compound (13) in the Reaction Scheme-5B are carried out in the same manner as in the reaction of the compound (7) and the compound (8) in the above Reaction Scheme-4.

Besides, the reaction of the compound (10) and the compound (9) in the Reaction Scheme-5A is carried out in the same manner as in the reaction of the compound (7) and the compound (9) in the above Reaction Scheme-4.

[Reaction Scheme-6A]

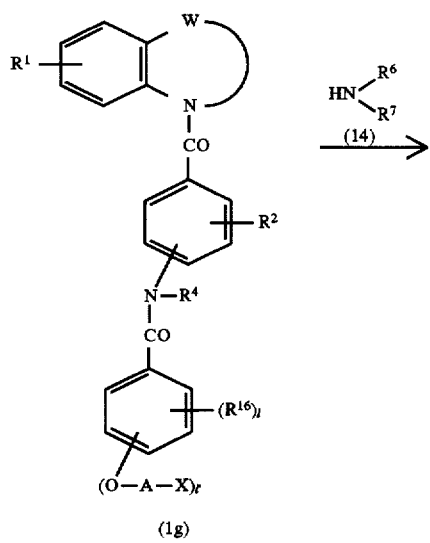

wherein $R^1$, $R^2$, $R^4$, $R^{16}$, $R^6$, $R^7$, X, W, and A are as defined above, l is 0 or an integer of 1 to 3, l' and l" are each an integer of 1 to 3, provided that l+l' and l+l" are each an integer not more than 3.

[Reaction Scheme-6B]

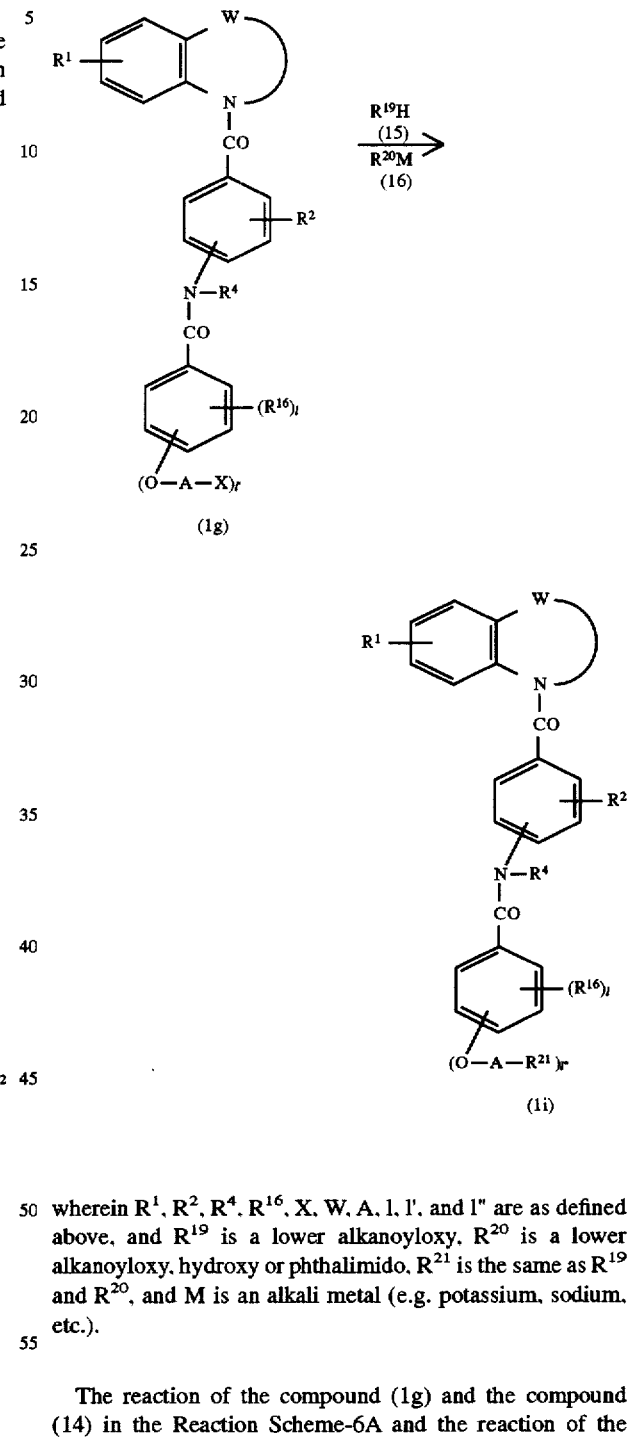

wherein $R^1$, $R^2$, $R^4$, $R^{16}$, X, W, A, l, l', and l" are as defined above, and $R^{19}$ is a lower alkanoyloxy, $R^{20}$ is a lower alkanoyloxy, hydroxy or phthalimido, $R^{21}$ is the same as $R^{19}$ and $R^{20}$, and M is an alkali metal (e.g. potassium, sodium, etc.).

The reaction of the compound (1g) and the compound (14) in the Reaction Scheme-6A and the reaction of the compound (1g) and the compound (15) or (16) in the Reaction Scheme-6B can be carried out under the same conditions as in the reaction of the compound (7) and the compound (8) in the above Reaction Scheme-4. In the reaction, an alkali metal halide (e.g. sodium iodide, potassium iodide, etc.) may be added to the reaction system.

[Reaction Scheme-7]

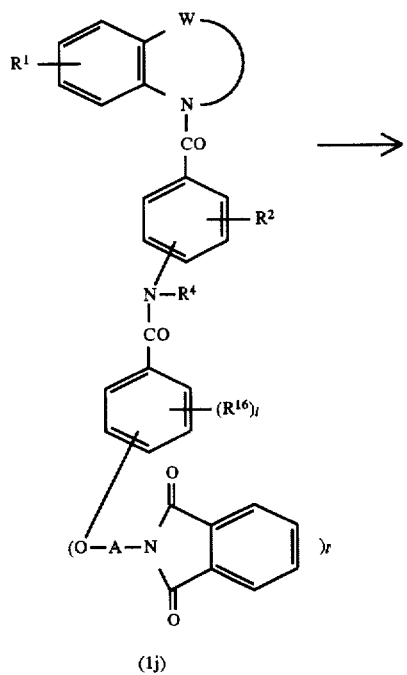

wherein $R^1$, $R^2$, $R^4$, $R^{16}$, W, l, l', l" and A are as defined above.

The reaction of converting the compound (1j) into the compound (1k) can be carried out by reacting the compound (1j) with hydrazine in an appropriate solvent or by hydrolyzing the compound (1j). The solvent used in the reaction with hydrazine includes water and further the same solvent as used in the reaction of the compound (2b) and the compound (4) in the above Reaction Scheme-2. The reaction is usually carried out at a temperature of from room temperature to about 120° C., preferably about 0° C. to about 100° C., for about 0.5 to 5 hours. Hydrazine is usually used in an amount of at least 1 mole, preferably about 1 to 5 moles, to 1 mole of the compound (1j).

The hydrolysis can be carried out in an appropriate solvent or without solvent in the presence of an acid or a basic compound. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.) and organic acids (e.g. formic acid, acetic acid, aromatic sulfonic acids, etc.). The basic compound includes, for example, metal carbonates (e.g. sodium carbonate, potassium carbonate, etc.), metal hydroxides (e.g. sodium hydroxide, potassium hydroxide, calcium hydroxide, etc.), and the like. The reaction is usually carried out at a temperature of from room temperature to about 200° C., preferably from room temperature to about 150° C., for about 10 minutes to 25 hours.

[Reaction Scheme-8]

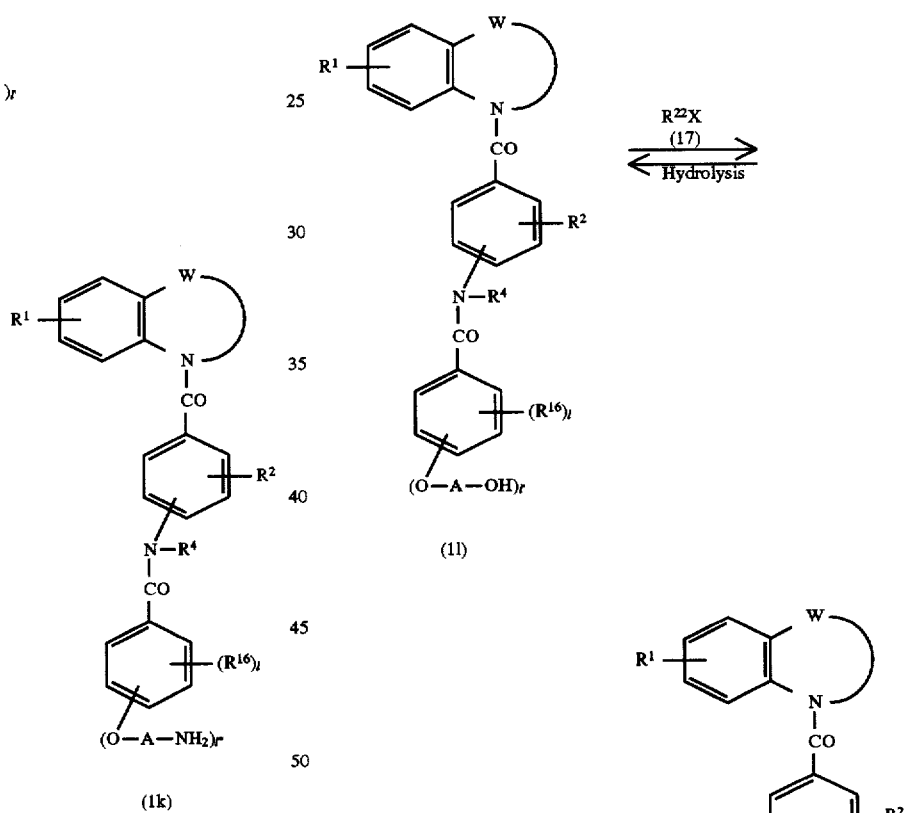

wherein $R^1$, $R^2$, $R^4$, W, $R^{16}$, l, l', l", X, and A are as defined above, and $R^{22}$ is a lower alkanoyl.

The reaction of the compound (1l) and the compound (17) is carried out under the same conditions as in the reaction of the compound (7) and the compound (8) in the Reaction Scheme-4. In the reaction, an alkali metal halide (e.g. sodium iodide, potassium iodide, etc.) may be added to the reaction system.

The reaction of converting the compound (1m) into the compound (1l) can be carried out under the same condition as in the hydrolysis of the compound (1j) in the Reaction Scheme-7.

[Reaction Scheme-9]

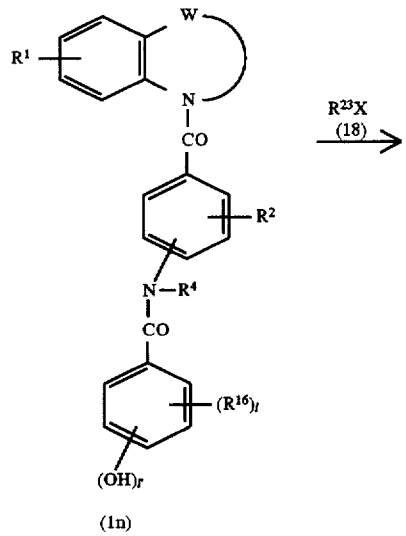

(1n)

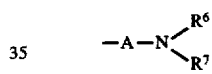

-continued
[Reaction Scheme-9]

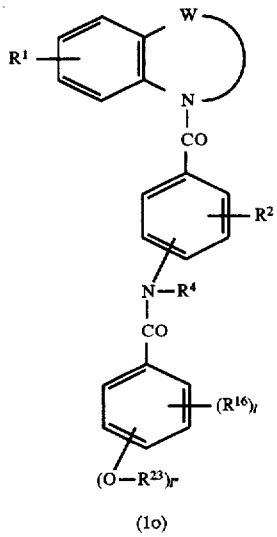

(1o)

wherein $R^1$, $R^2$, $R^4$, W, $R^{16}$, l, l', l", and X are as defined above, and $R^{23}$ is a lower alkyl, a lower alkanoyloxy-substituted lower alkyl, a halogen-substituted lower alkyl, a carboxy-substituted lower alkyl, a carbamoyl-substituted lower alkyl, a hydroxy-substituted lower alkyl, a lower alkoxycarbonyl-substituted lower alkyl, a phthalimido-substituted lower alkyl, an aminocarbonyl-lower alkyl having optionally a lower alkyl substituent, or a group of the formula:

$$-A-N\begin{matrix}R^6\\R^7\end{matrix}$$

(A, $R^6$ and $R^7$ are as defined above).

The reaction of the compound (1n) and the compound (18) can be carried out under the same conditions as in the reaction of the compound (7) and the compound (8) in the above Reaction Scheme-4. In the reaction, an alkali metal halide (e.g. sodium iodide, potassium iodide, etc.) may be added to the reaction system.

[Reaction Scheme-10]

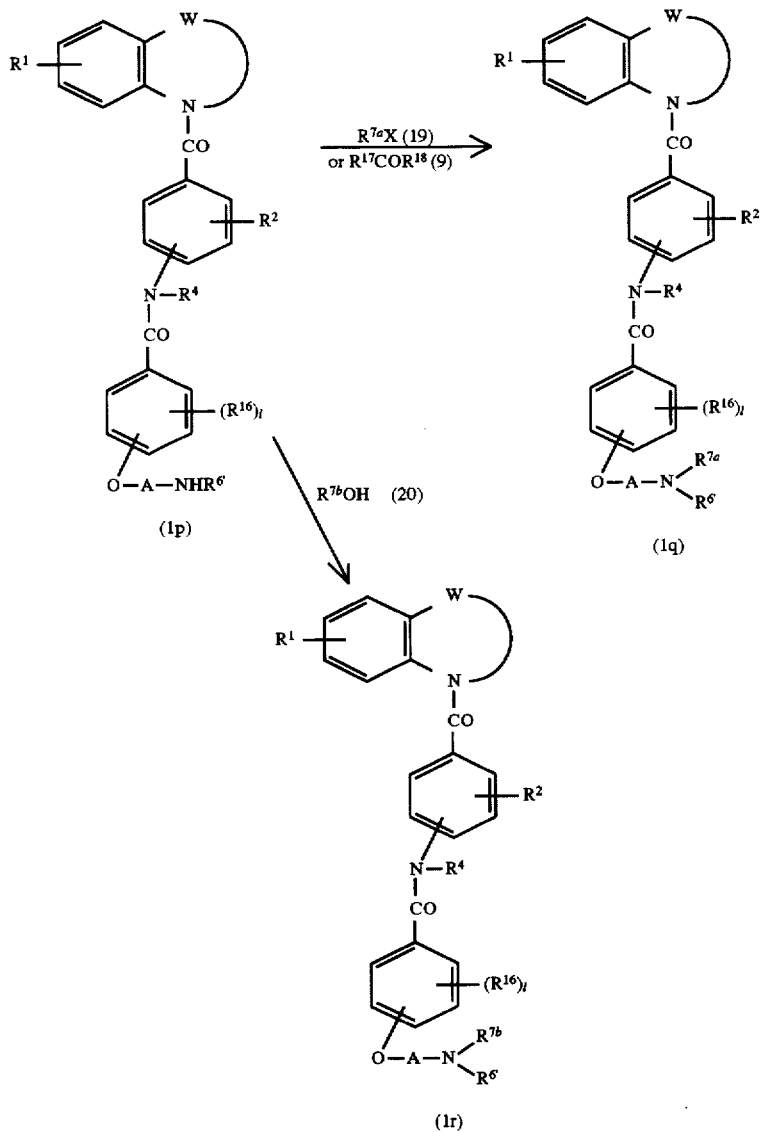

wherein $R^1$, $R^2$, $R^4$, W, $R^{16}$, $R^{17}$, $R^{18}$, l, X, and A are as defined above, and $R^{6'}$ is hydrogen atom, a lower alkyl having optionally a hydroxy substituent, a lower alkanoyl, or benzoyl, $R^{7a}$ is a lower alkyl having optionally a hydroxy substituent, and $R^{7b}$ is a lower alkanoyl or benzoyl.

The reaction of the compound (1p) and the compound (19) or the compound (9) can be carried out under the same conditions as in the reaction of the compound (7) and the compound (8) or the compound (9) in the above Reaction Scheme-4.

The reaction of the compound (1p) and the compound (20) can be carried out under the same conditions as in the reaction of the compound (2) and the compound (3) in the Reaction Scheme-1.

Besides, the compound (1r) can also be obtained by reacting the compound (1p) with a compound of the formula: $(R^{7b})_2O$ ($R^{7b}$ is as defined above). The reaction can be carried out in an appropriate solvent or without solvent in the presence or absence, preferably presence, of a basic compound. The solvent includes, for example, the above-mentioned aromatic hydrocarbons, lower alcohols (e.g. methanol, ethanol, propanol, etc.), dimethylformamide, dimethylsulfoxide, and further halogenated hydrocarbons (e.g. chloroform, methylene chloride, etc.), acetone, pyridine, etc. The basic compound includes, for example, tertiary amines (e.g. triethylamine, pyridine, etc.), sodium hydroxide, potassium hydroxide, sodium hydride, and the like. The above reaction can also be carried out in a solvent such as acetic acid or benzoic acid in the presence of a mineral acid (e.g. sulfuric acid, etc.). The acid anhydride is usually used in an equimolar amount or more, preferably 1 to 10 moles, to 1 mole of the starting compound, and the reaction is usually carried out at a temperature of about 0° C. to about 200° C., preferably from about 0° C. to about 150° C., for about 0.5 to 15 hours.

[Reaction Scheme-11]

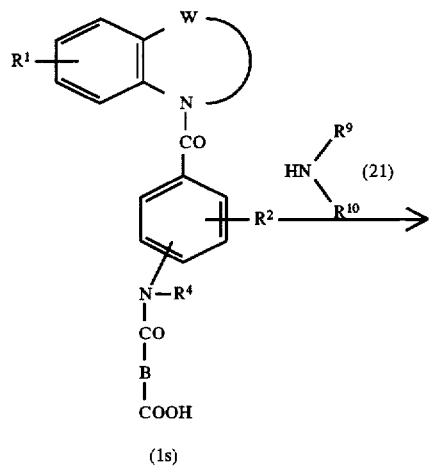

(1s)

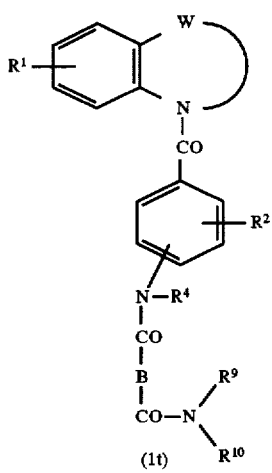

(1t)

wherein $R^1$, $R^2$, $R^4$, $R^9$, $R^{10}$, W, and B are as defined above.

The reaction of the compound (1s) and the compound (21) can be carried out under the same conditions as in the reaction of the compound (2) and the compound (3) in the above Reaction Scheme-1.

Reaction Scheme-12]

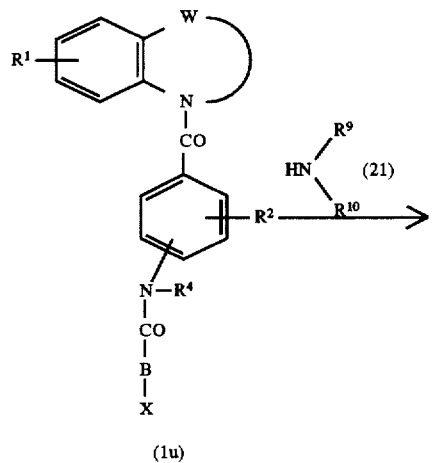

(1u)

-continued
Reaction Scheme-12]

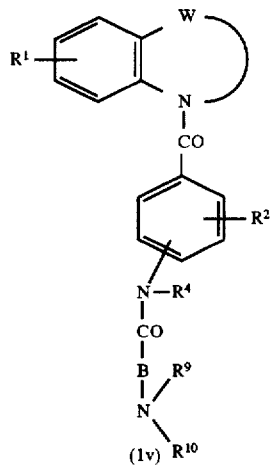

(1v)

wherein $R^1$, $R^2$, $R^4$, W, $R^9$, $R^{10}$, X, and B are as defined above.

The reaction of the compound (1u) and the compound (21) can be carried out under the same conditions as in the reaction of the compound (7) and the compound (8) in the above Reaction Scheme-4. In the reaction, an alkali metal halide (e.g. sodium iodide, potassium iodide, etc.) may be added to the reaction system.

[Reaction Scheme-13]

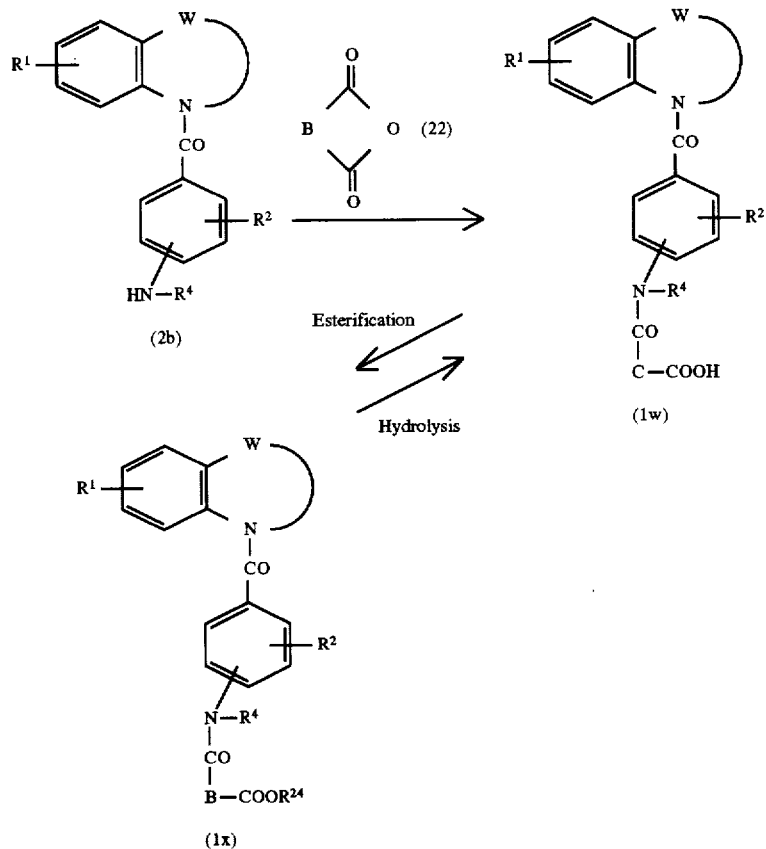

wherein $R^1$, $R^2$, $R^4$, W, and B are as defined above, and $R^{24}$ is a lower alkyl.

The reaction of the compound (2b) and the compound (22) can be carried out in an appropriate inert solvent. The inert solvent includes, for example, aromatic hydrocarbons (e.g. benzene, toluene, xylene, etc.), ethers (e.g. tetrahydrofuran, dioxane, diethylene glycol dimethyl ether, etc.), lower alcohols (e.g. methanol, ethanol, isopropanol, butanol, etc.), halogenated hydrocarbons (e.g. dichloromethane, chloroform, carbon tetrachloride, etc.), acetic acid, ethyl acetate, acetonitrile, dimethylsulfoxide, dimethylformamide, hexamethylphosphoric triamide, and the like. The amount of the compound (2b) and the compound (22) is not critical, but the compound (22) is usually used in an amount of at least one mole, preferably 1 to 2 moles, to 1 mole of the compound (2b). The reaction is usually carried out at a temperature of from about 0° C. to about 150° C., preferably from about 0° C. to about 100° C., for about 30 minutes to about 10 hours.

The esterification of the compound (1w) is usually carried out by reacting the starting compound with an alcohol (e.g. methanol, ethanol, isopropanol, etc.) in the presence of a mineral acid (e.g. hydrochloric acid, sulfuric acid, etc.) and a halogenating agent (e.g. thionyl chloride, phosphorus oxychloride, phosphorus pentachloride, phosphorus trichloride, etc.) at a temperature of 0° C. to 150° C., preferably 50° C. to 100° C., for about 1 to 10 hours.

The hydrolysis of the compound (1x) can be carried out under the same conditions as in the hydrolysis of the compound (1j) in the Reaction Scheme-7.

[Reaction Scheme-14]

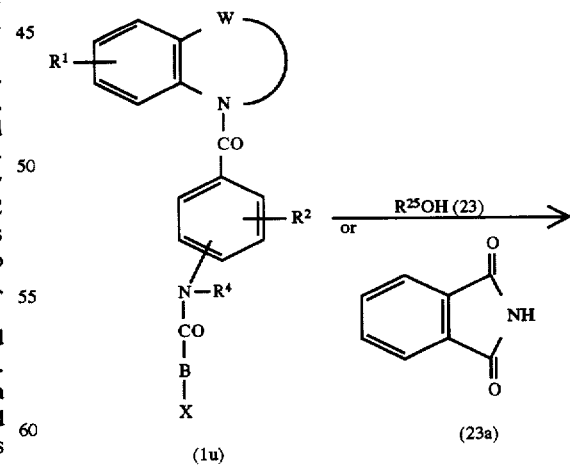

[Reaction Scheme-14]

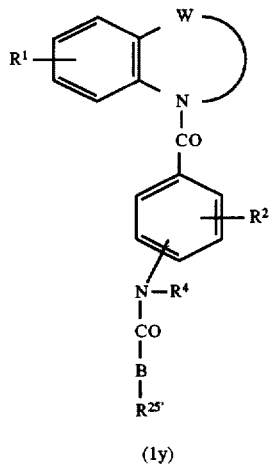

(1y)

wherein $R^1$, $R^2$, $R^4$, W, B, M, and X are as defined above, and $R^{25}$ is a phenyl which has optionally 1 to 3 substituents selected from a lower alkyl, a lower alkoxy and an amino having optionally a lower alkanoyl substituent, or naphthyl, and $R^{25'}$ is a phenoxy which has optionally 1 to 3 substituents selected from a lower alkyl, a lower alkoxy and an amino having optionally a lower alkanoyl substituent, naphthyloxy or phthalimido.

The reaction of the compound (1u) and the compound (23) or (23a) can be carried out under the same conditions as in the reaction of the compound (7) and the compound (8) in the above Reaction Scheme-4.

The compound (1y) wherein $R^{25'}$ is phthalimido can be converted into the compound (1y) wherein $R^{25'}$ is amino under the same conditions as in the reaction of converting the compound (1j) into the compound (1k) in the above Reaction Scheme-7.

[Reaction Scheme-15]

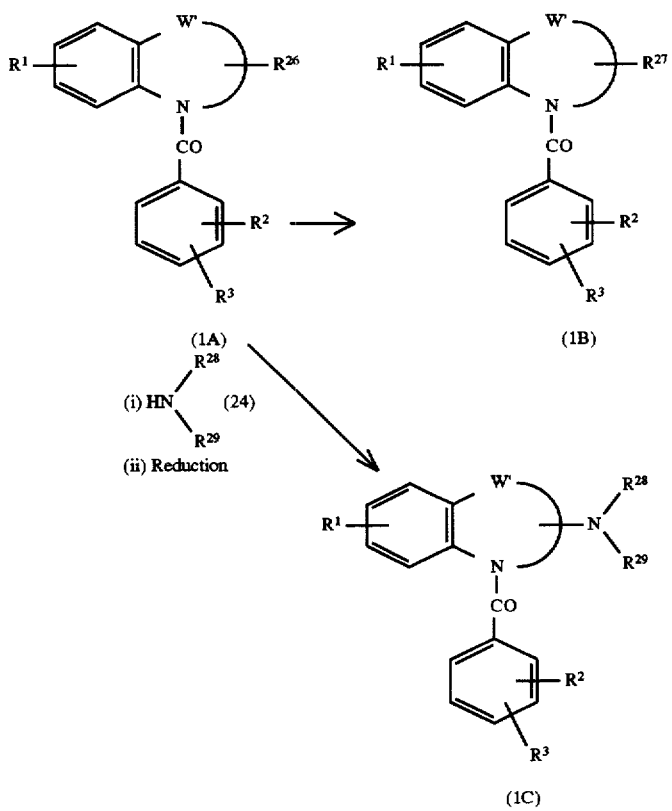

wherein $R^1$, $R^2$ and $R^3$ are as defined above, and $R^{26}$ is oxo, $R^{27}$ is hydroxy, and W' is the same as W, provided that the substituents on the group —$(CH_2)_p$— or —CH=CH—$(CH_2)_q$— are 0 to 2, and $R^{28}$ and $R^{29}$ are the same or different and are each hydrogen atom, a lower alkenyl, a cycloalkyl, an oxiranyl-substituted lower alkyl, a lower alkyl having 1 to 2 substituents selected from a lower alkoxy, hydroxy and an amino having optionally a lower alkyl substituent, a phenyl-lower alkyl, a pyridyl-lower alkyl, a cyano-substituted lower alkyl, a lower alkoxycarbonyl-substituted lower alkyl, a carbamoyl-substituted lower alkyl, a carboxy-substituted lower alkyl, a tetrahydropyranyloxy-substituted lower alkyl, a lower alkanoyloxy-substituted lower alkyl, a piperidinyl which has optionally a phenyl-lower alkyl substituent, an aminocarbonyl-lower alkyl having optionally a lower alkyl substituent, or a lower alkyl, or $R^{28}$ and $R^{29}$ may bind together with the nitrogen atom to which they bond to form a 5- or 6-membered saturated heterocyclic group with or without being intervened with nitrogen or oxygen atom, which heterocyclic ring may optionally have a substituent selected from a lower alkyl, a phenyl-lower alkyl, or a lower alkanoyl.

The conversion of the compound (1A) into the compound (1B) is carried out by reduction thereof. The reducing reaction is preferably carried out by using a hydrogenating reducing agent (e.g. lithium aluminum hydride, sodium boro hydride, diborane, etc.). The reducing agent is usually used in an amount of at least one mole, preferably 1 to 15 moles, to 1 mole of the starting compound. The reducing reaction is usually carried out in an appropriate solvent, for example, water, alcohols (e.g. methanol, ethanol, isopropanol, etc.), ethers (e.g. tetrahydrofuran, diethyl ether, diisopropyl ether, diglyme, etc.), or a mixture of these solvents, at a temperature of from about −60° C. to about 150° C., preferably about −30° C. to about 100° C., for about 10 minutes to 15 hours. When lithium aluminum hydride or diborane is used as the reducing agent, it is preferable to use an anhydrous solvent such as tetrahydrofuran, diethyl ether, diisopropyl ether, diglyme, etc.

The reaction of converting the compound (1A) into the compound (1C) is usually carried out in an appropriate solvent or without solvent in the presence or absence of a dehydrating agent. The solvent includes, for example, lower alcohols (e.g. methanol, ethanol, isopropanol, etc.), aromatic hydrocarbons (e.g. benzene, toluene, xylene, etc.), halogenated hydrocarbons (e.g. dichloromethane, dichloroethane, chloroform, carbon tetrachloride, etc.), aprotic polar solvents (e.g. dimethylformamide, dimethylacetamide, N-methylpyrrolidone, etc.), or a mixture of these solvents. The dehydrating agent includes, for example, conventional drying agent used for dehydrating solvents (e.g. molecular sieves, etc.), mineral acids (e.g. hydrochloric acid, sulfuric acid, borone trifluoride, etc.), organic acids (e.g. p-toluenesulfonic acid, etc.), and the like. The reaction is usually carried out at a temperature of from room temperature to about 250° C., preferably from about 50° C. to about 200° C., for about 1 to 48 hours. The amount of the compound (24) is not critical, but it is usually used at least in an equivalent amount, preferably equimolar to largely excess to the amount of the compound (1A). The dehydrating agent is preferably used in a largely excess amount in case of the drying agent and in a catalytic amount in case of the acid.

The subsequent reducing reaction can be carried out by various methods, for example by catalytically hydrogenating the compound in an appropriate solvent in the presence of a catalyst. The solvent includes, for example, water, acetic acid, alcohols (e.g. methanol, ethanol, isopropanol, etc.), hydrocarbons (e.g. hexane, cyclohexane, etc.), ethers (e.g. diethylene glycol dimethyl ether, dioxane, tetrahydrofuran, diethyl ether, etc.), esters (e.g. ethyl acetate, methyl acetate, etc.), aprotic polar solvents (e.g. dimethylformamide, etc.), or a mixture of these solvents. The catalyst includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of from about −20° C. to about 100° C., preferably about 0° C. to about 70° C., under a hydrogen atmospheric pressure of 1 to 10 atm. for about 0.5 to 20 hours.

Although the reducting reaction can be carried out under the above conditions, it is preferably carried out by using a hydrogenating reducing agent. The hydrogenating reducing agent includes, for example, lithium aluminum hydride, sodium borohydride, diborane, etc., and it is usually used in an amount of at least one mole, preferably 1 to 10 moles, to 1 mole of the compound (1A). The reaction is usually carried out in an appropriate solvent, such as water, lower alcohols (e.g. methanol, ethanol, isopropanol, etc.), ethers (e.g. tetrahydrofuran, diethyl ether, diglyme, etc.), dimethylformamide, or a mixture of these solvents, at a temperature of about −60° C. to about 50° C., preferably about −30° C. to room temperature, for about 10 minutes to about 5 hours. When lithium aluminum hydride or diborane is used as the reducing agent, it is preferable to use an anhydrous solvent such as diethyl ether, tetrahydrofuran, diglyme, etc.

The compound (1C) wherein at least one of $R^{28}$ and $R^{29}$ is hydrogen atom can be converted into the compound (1C) wherein at least one of $R^{28}$ and $R^{29}$ is a lower alkyl by reacting the compound (1C) with the compound (8) or the compound (9) under the same conditions as in the reaction of the compound (7) and the compound (8) or (9) in the above Reaction Scheme-4.

[Reaction Scheme-16]

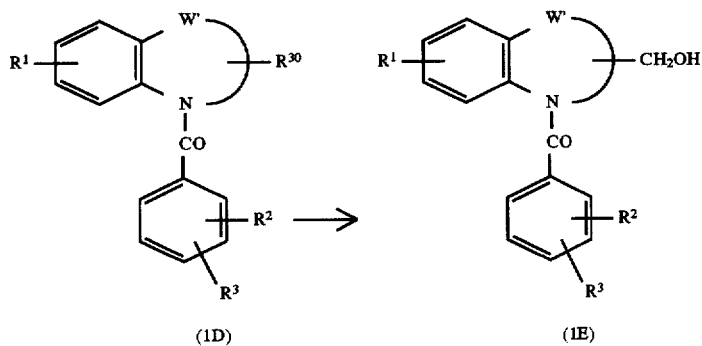

-continued

[Reaction Scheme-16]

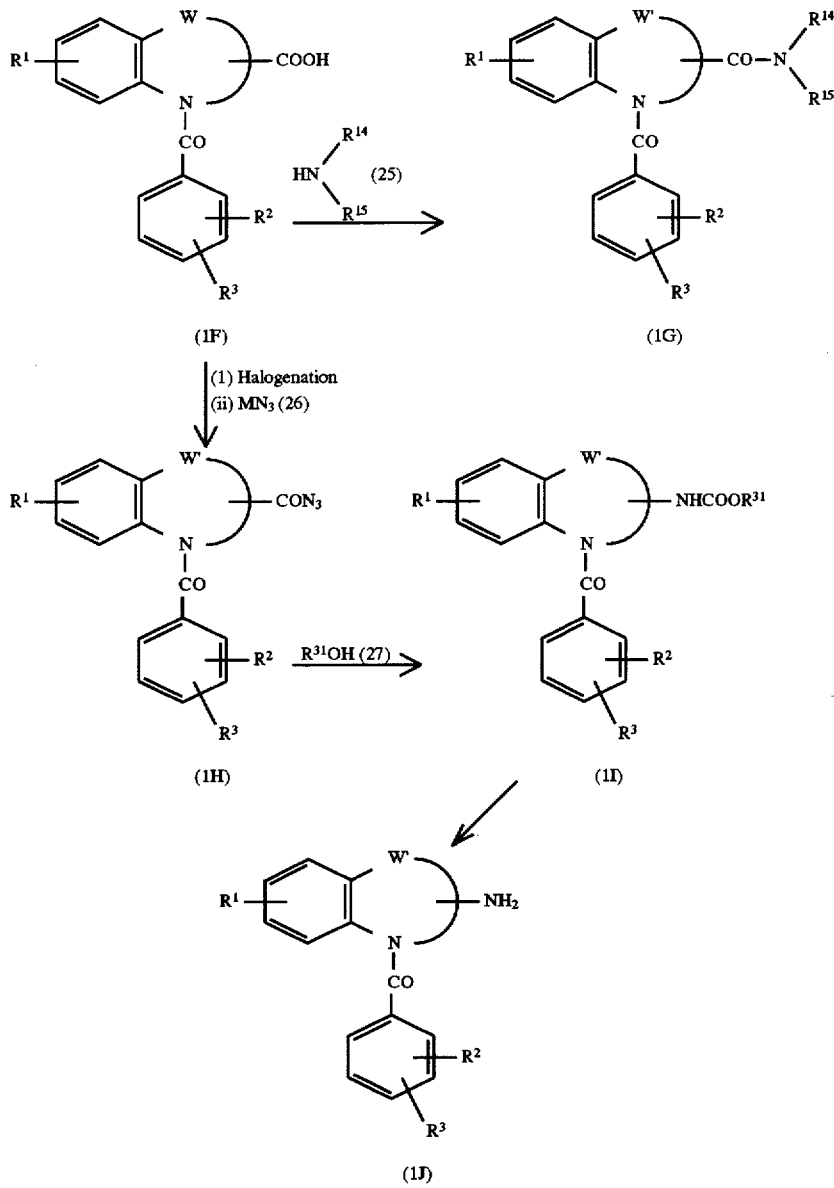

wherein $R^1$, $R^2$, $R^3$, $R^{14}$, $R^{15}$, W', and M are as defined above, and $R^{31}$ is a phenyl-lower alkyl, and $R^{30}$ is a lower alkoxycarbonyl.

The reaction of converting the compound (1D) into the compound (1E) can be carried out under the same conditions as in the reaction of converting the compound (1A) into the compound (1B) in the above Reaction Scheme-15.

The reaction of converting the compound (1D) into the compound (1F) can be carried out under the same conditions as in the hydrolysis reaction of the compound (1j) in the above Reaction Scheme-7.

The reaction of the compound (1F) and the compound (25) can be carried out under the same conditions as in the reaction of the compound (2) and the compound (3) in the above Reaction Scheme-1.

The halogenation of the compound (1F) can be carried out under a conventional condition for halogenation of a carboxylic acid. The reaction of the thus-obtained carboxylic acid halide of the compound (1F) with the compound (26) is carried out in an appropriate solvent in the presence or absence of a basic compound. The solvent includes, for example, halogenated hydrocarbons (e.g. methylene chloride, chloroform, etc.), aromatic hydrocarbons (e.g. benzene, toluene, xylene, etc.), ethers (e.g. diethyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, hexamethylphosphoric triamide, etc.), alcohols (e.g. methanol, ethanol, propanol, butanol, 3-methoxy-1-butanol, ethyl cellosolve, methyl cellosolve, etc.), pyridine, acetone, acetonitrile, water, or a mixture of these solvents. The basic compound includes, for example, organic bases such as triethylamine, trimethylamine, pyridine, dimethylaniline, N-methylmorpholine, DBN, DBU, DABCO, etc., inorganic bases such as potassium carbonate, sodium carbonate, potassium hydroxide, sodium hydroxide, potassium hydride, sodium hydride, silver carbonate, alcoholates (e.g. sodium methylate, sodium ethylate, etc.), and the like. The compound (26) is usually used in an amount of at least 1 mole, preferably 1 to 1.5 mole, to 1 mole of the carboxylic acid halide of the compound (1F). The reaction is usually carried out at a temperature of from −30° C. to about 180° C., preferably from about 0° C. to about 150° C., for about 5 minutes to 30 hours.

The reaction of the compound (1H) and the compound (27) is carried out in an appropriate solvent or without solvent at a temperature of from about 0° C. to about 200° C., preferably from room temperature to about 150° C. The solvent includes the same solvents as used in the above reaction of the carboxylic acid halide of the compound (1F) and the compound (26). The compound (27) is preferably used in an amount largely excess to the compound (1H). The reaction is usually completed in a reaction time of about 1 to 5 hours.

The reaction of converting the compound (1I) into the compound (1J) can be carried out by reducing the compound. The reducing reaction is usually carried out by catalytically hydrogenating the compound in an appropriate solvent in the presence of a catalyst. The solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvents (e.g. N,N-dimethylformamide, etc.), acetic acid, or a mixture of these solvents. The catalyst includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of from about −20° C. to about 100° C., preferably about 0° C. to about 80° C., under a hydrogen atmospheric pressure of 1 to 10 atm. for about 0.5 to 20 hours.

[Reaction Scheme-17]

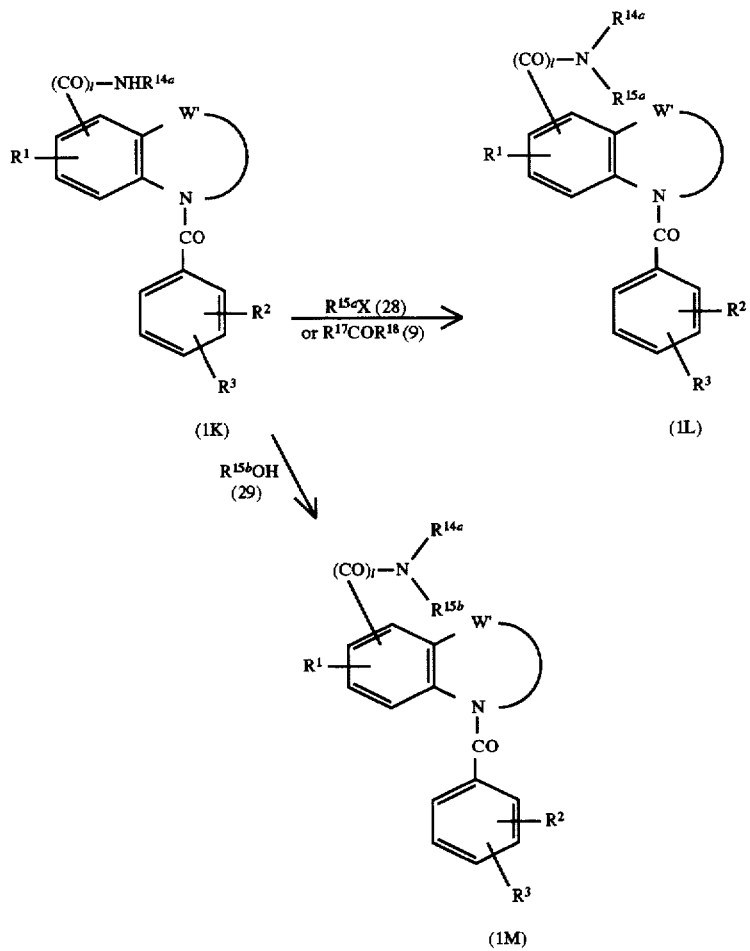

wherein $R^1$, $R^2$, $R^3$, W', l, $R^{17}$, $R^{18}$, and X are as defined above, and $R^{14a}$ is hydrogen atom, a lower alkyl, a lower alkanoyl, a lower alkenyl, a cycloalkyl, an oxiranyl-substituted lower alkyl, a lower alkyl having 1 to 2 substituents selected from a lower alkoxy, hydroxy and an amino having optionally a lower alkyl substituent, a phenyl-lower alkyl, a pyridyl-lower alkyl, a lower alkylsulfonyl, benzoyl, a lower alkoxycarbonyl, anilinocarbonyl, an aminocarbonyl having optionally a lower alkyl substituent, a cyano-substituted lower alkyl, a lower alkoxycarbonyl-substituted lower alkyl, a carbamoyl-substituted lower alkyl, a carboxy-substituted lower alkyl, a tetrahydropyranyloxy-substituted lower alkyl, a lower alkanoyloxy-substituted lower alkyl, a piperidinyl having optionally a phenyl-lower alkyl substituent, a halogen-substituted lower alkanoyl, an imiazolyl-substituted lower alkanoyl, an amino-lower alkanoyl having optionally a substituent selected from a lower alkyl and a lower alkoxycarbonyl, an aminocarbonyl-lower alkyl having optionally a lower alkyl substituent, or a phenyl-lower alkoxycarbonyl. $R^{15a}$ is a lower alkyl, a cycloalkyl, an oxiranyl-substituted lower alkyl, a lower alkyl having 1 to 2 substituents selected from a lower alkoxy, hydroxy and an amino having optionally a lower alkyl substituent, a phenyl-lower alkyl, a pyridyl-lower alkyl, a lower alkylsulfonyl, a cyano-substituted lower alkyl, a lower alkoxycarbonyl-substituted lower alkyl, a carbamoyl-substituted lower alkyl, a carboxy-substituted lower alkyl, a tetrahydropyranyloxy-substituted lower alkyl, a lower alkanoyloxy-substituted lower alkyl, a piperidinyl having optionally a phenyl-lower alkyl substituent, an aminocarbonyl-lower alkyl having optionally a lower alkyl substituent, or a lower alkenyl, and $R^{15b}$ is a lower alkanoyl, a phenyl-lower alkoxycarbonyl, benzoyl, a lower alkoxycarbonyl, a halogen-substituted lower alkanoyl, an imidazolyl-substituted lower alkanoyl, or an amino-lower alkanoyl having optionally a substituent selected from a lower alkyl and a lower alkoxycarbonyl.

The reaction of the compound (1K) and the compound (28) or the compound (9) can be carried out under the same conditions as in the reaction of the compound (7) and the compound (8) or the compound (9) in the above Reaction Scheme-4.

The reaction of the compound (1K) and the compound (29) can be carried out under the same conditions as in the reaction of the compound (2) and the compound (3) in the above Reaction Scheme-1. The compound (1M) can also be obtained by reacting the compound (1K) with a compound of the formula $(R^{15b})_2O$ (wherein $R^{15b}$ is as defined above). The reaction can be carried out under the same conditions as in the reaction of the compound (1p) and the compound of the formula: $(R^{7b})_2O$ as described hereinbefore.

The compound (1M) wherein $R^{15b}$ is formyl can also be prepared by reacting the compound (1K) with a formate of the formula: $HCOCR^{82}$ ($R^{82}$ is a lower alkyl). The reaction is usually carried out in the solvent as used in the reaction of the compound (7) and the compound (8) in the above Reaction Scheme-4 or without solvent, at a temperature of, about 0° C. to about 200° C., preferably about 0° C. to about 170° C., for about 30 minutes to about 30 hours. The formate is preferably used in a largely excess amount to the compound (1K).

[Reaction Scheme-18]

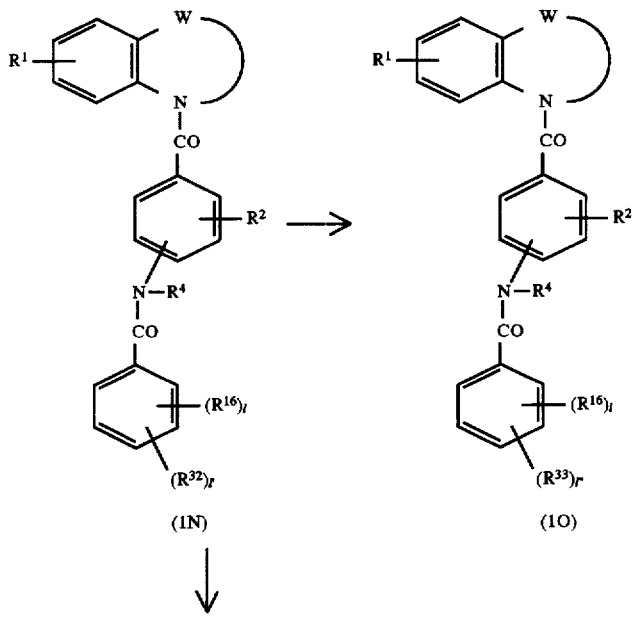

[Reaction Scheme-18]

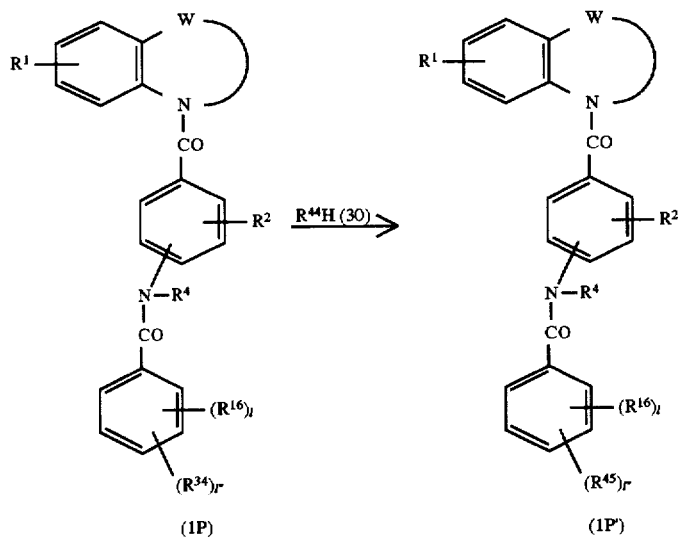

wherein $R^1$, $R^2$, $R^4$, $R^{16}$, W, l, l' and l" are as defined above, and $R^{32}$ is a lower alkoxycarbonyl-substituted lower alkoxy, $R^{33}$ is a carbamoyl-substituted lower alkoxy, $R^{34}$ is a carboxy-substituted lower alkoxy, $R^{44}$ is an amino having optionally a lower alkyl substituent, and $R^{45}$ is an aminocarbonyl-lower alkoxy having optionally a lower alkyl substituent.

The conversion of the compound (1N) into the compound (1O) can be carried out by reacting the compound with aqueous ammonia in an appropriate solvent in an autoclave. The solvent includes the same solvents as used in the reaction of the carboxylic acid halide and the amine (2) in the above Reaction Scheme-1. The aqueous ammonia is used in a largely excess amount to the compound (1N). The reaction proceeds advantageously by adding an ammonium halide (e.g. ammonium chloride, etc.) to the reaction system. The reaction is usually carried out at a temperature of from room temperature to about 200° C., preferably from room temperature to about 150° C., for about 1 to 10 hours.

The reaction of converting the compound (1N) into the compound (1P) can be carried out under the same conditions as in the hydrolysis of the compound (1j) in the above Reaction Scheme-7.

The reaction of the compound (1P) and the compound (30) can be carried out under the same conditions as in the reaction of the compound (2) and the compound (3) in the above Reaction Scheme-1.

[Reaction Scheme-19]

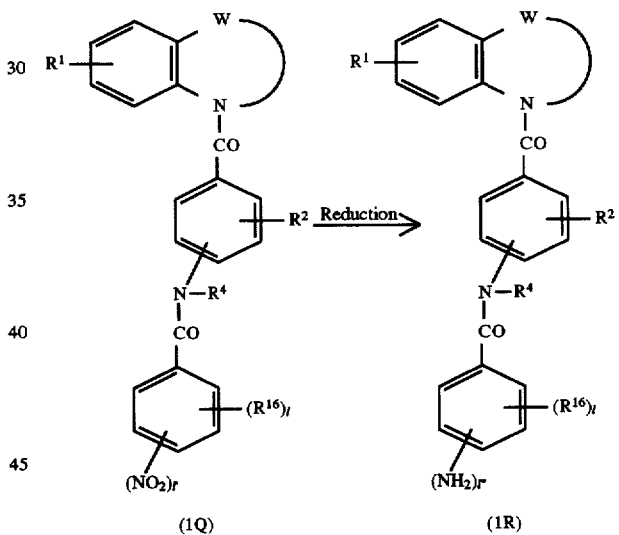

wherein $R^1$, $R^2$, $R^4$, $R^{16}$, W, l, l' and l" are as defined above.

The reducing reaction in the above reaction scheme is usually carried out, for example, (i) with a reducing catalyst in an appropriate solvent or (ii) with a reducing agent such as a mixture of a metal or metal salt with an acid, or a mixture of a metal or metal salt with an alkali metal hydroxide, a sulfide or an ammonium salt in an appropriate inert solvent.

In case of using a reducing catalyst, the solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvents (e.g. N,N-dimethylformamide, etc.), or a mixture of these solvents. The catalyst includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of from about -20° C. to about 150° C., preferably about 0° C. to about 100° C., under a hydrogen pressure of 1 to 10 atm. for about 0.5 to 10 hours. In the reaction, an acid such as hydrochloric acid may optionally added to the reaction system.

In case of the above method (ii), the reducting agent includes a mixture of iron, zinc, tin or stannous chloride and a mineral acid (e.g. hydrochloric acid, sulfuric acid, etc.), or a mixture of iron, ferrous sulfate, zinc or tin and an alkali metal hydroxide (e.g. sodium hydroxide, etc.), a sulfide (e.g. ammonium sulfide, etc.), aqueous ammonia, or an ammonium salt (e.g. ammonium chloride, etc.). The inert solvent includes, for example water, acetic acid, methanol, ethanol, dioxane, and the like. The reducing reaction conditions are determined depending on the kinds of the reducting agent, but in case of using a reducing agent comprising stannous chloride and hydrochloric acid, for example, it is preferably carried out at a temperature of about 0° C. to room temperature for about 0.5 to 10 hours. The reducing agent is usually used in an amount of at least one mole, preferably 1 to 5 moles, to 1 mole of the starting compound.

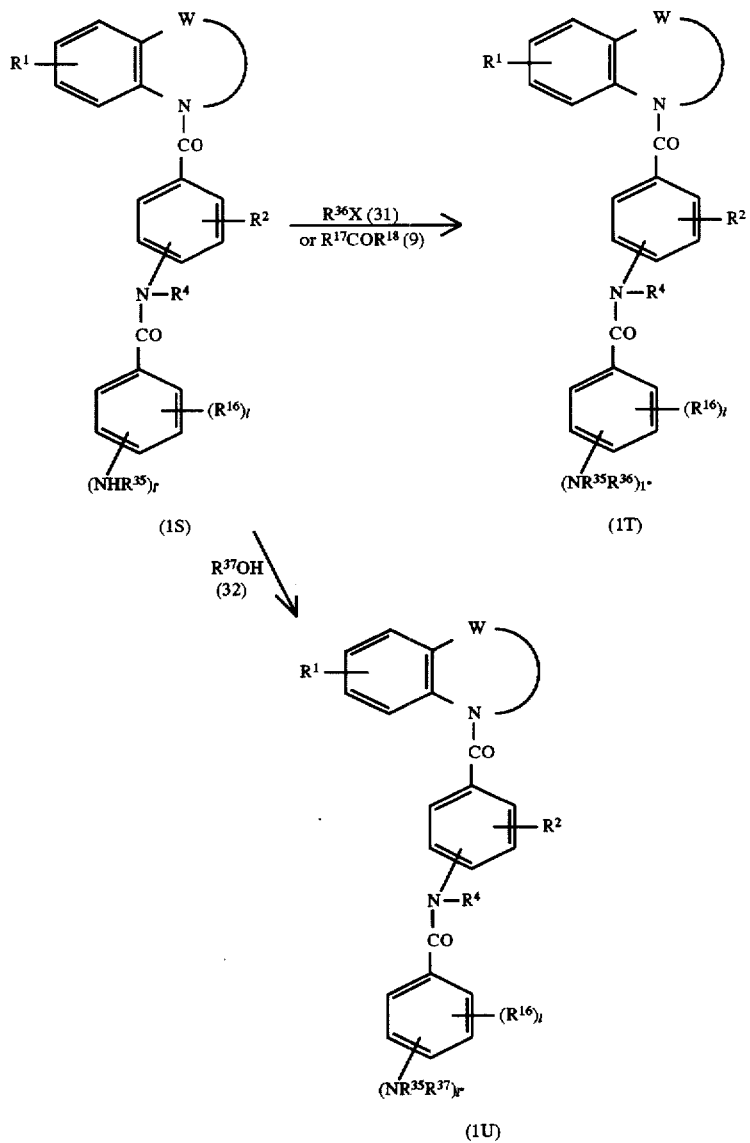

[Reaction Scheme-20]

wherein $R^1$, $R^2$, $R^4$, $R^{16}$, $R^{17}$, $R^{18}$, l, l', l" and W are as defined above, and $R^{36}$ is a lower alkyl, $R^{37}$ is a lower alkanoyl, and $R^{35}$ is hydrogen atom, a lower alkyl or a lower alkanoyl.

The reaction of the compound (1S) and the compound (31) or the compound (9) can be carried out under the same conditions as in the reaction of the compound (7) and the compound (8) or the compound (9) in the above Reaction Scheme-4.

The reaction of the compound (1S) and the compound (32) can be carried out under the same conditions as in the reaction of the compound (2) and the compound (3) in the above Reaction Scheme-1. Besides, the compound (1U) can also be obtained by reacting the compound (1S) with a compound of the formula: $(R^{37})_2O$ ($R^{37}$ is as defined above). The reaction is carried out under the same conditions as in the above reaction of the compound (1p) and a compound of the formula: $(R^{7b})_2O$.

The compound (1) wherein $R^8$ is a phenyl-lower alkoxycarbonyl can be converted into the compound (1) wherein $R^8$ is hydrogen atom in the same manner as in the reaction of converting the compound (1I) into the compound (1J) in the above Reaction Scheme-16.

Other derivatives of the starting compound (2) can be prepared, for example, by the process as shown in the following reaction scheme.

[Reaction Scheme-21]

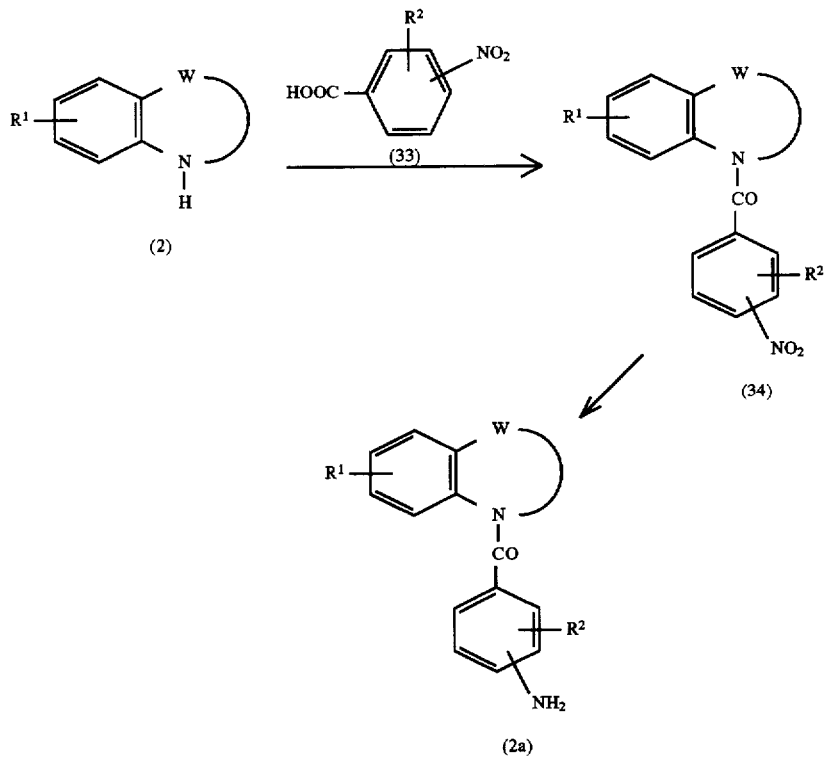

wherein $R^1$, $R^2$, and W are as defined above.

The reaction of the compound (2) and the compound (33) can be carried out under the same conditions as in the reaction of the compound (2) and the compound (3) in the above Reaction Scheme-1.

The reaction of converting the compound (34) into the compound (2a) can be carried out under the same conditions as in the reducing reaction in the above Reaction Scheme-19.

The starting compound (5) can be prepared, for example, by the process of the following reaction scheme.

[Reaction Scheme-22]

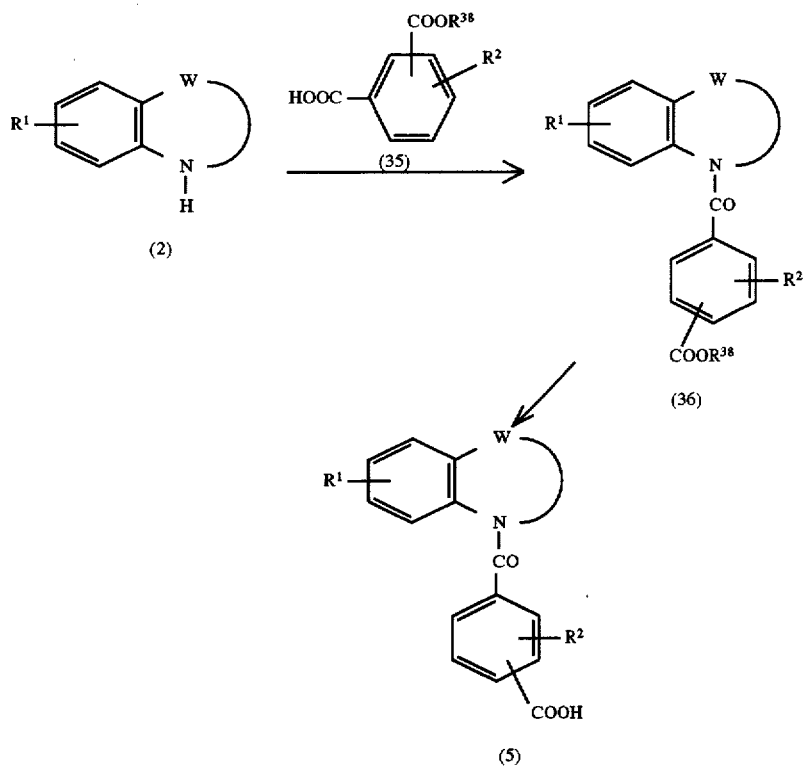

wherein $R^1$, $R^2$, and W are as defined above, and $R^{38}$ is a lower alkyl.

The reaction of the compound (2) and the compound (35) can be carried out under the same conditions as in the reaction of the compound (2) and the compound (3) in the above Reaction Scheme-1.

The reaction of converting the compound (36) into the compound (5) can be carried out under the same conditions as in the hydrolysis reaction in the above Reaction Scheme-7.

[Reaction Scheme-23]

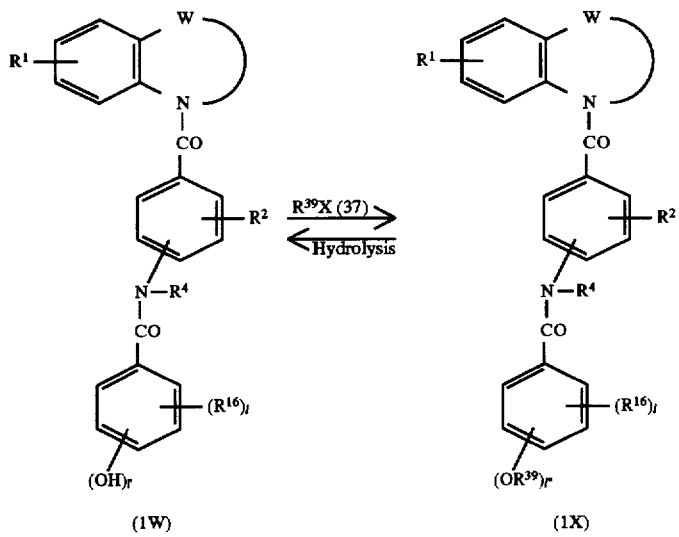

wherein $R^1$, $R^2$, $R^4$, $R^{16}$, 1, 1', 1", X, and W are as defined above, and $R^{39}$ is a lower alkanoyl.

The reaction of the compound (1W) and the compound (37) can be carried out under the same conditions as in the reaction of the compound (1n) and the compound (18) in the above Reaction Scheme-9.

The hydrolysis reaction of the compound (1X) can be carried out under the same conditions as in the hydrolysis of the compound (1j) in the above Reaction Scheme-7.

The reaction of converting the compound (1aa) into the compound (1bb) can be carried out under the same conditions as in the hydrolysis of the compound (1j) in the above Reaction Scheme-7.

The esterification reaction of the compound (1bb) can be carried out under the same conditions as in the esterification of the compound (1w) in the above Reaction Scheme-13.

[Reaction Scheme-24]

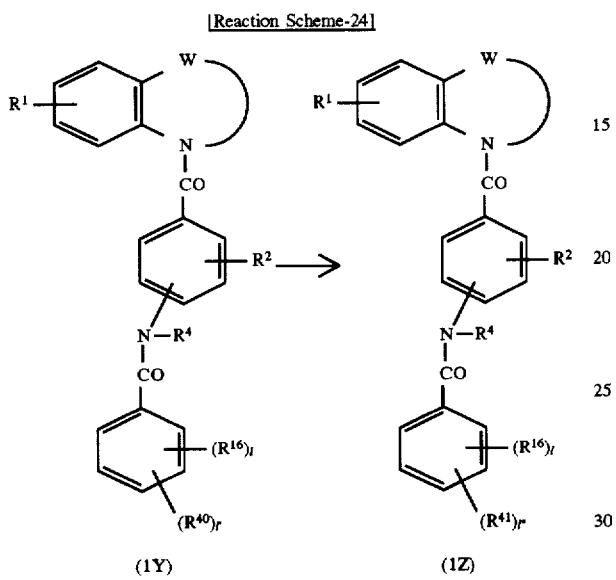

(1Y)    (1Z)

[Reaction Scheme-26]

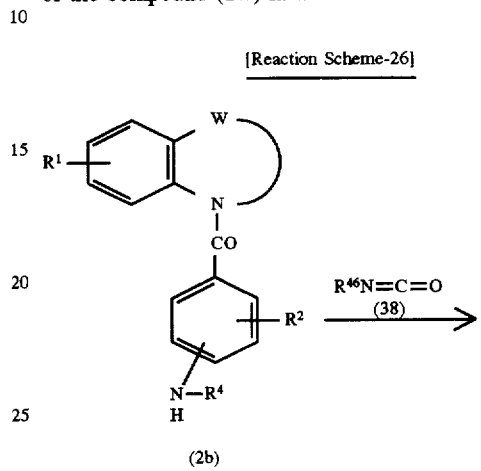

(2b)

wherein $R^1$, $R^2$, $R^4$, $R^{16}$, 1, 1', 1", and W are as defined above, $R^{40}$ is a lower alkanoyl, and $R^{41}$ is a hydroxy-substituted lower alkyl.

The reaction of converting the compound (1Y) into the compound (1Z) can be carried out under the same conditions as in the reaction of converting the compound (1A) into the compound (1B) in the above Reaction Scheme-15.

[Reaction Scheme-25]

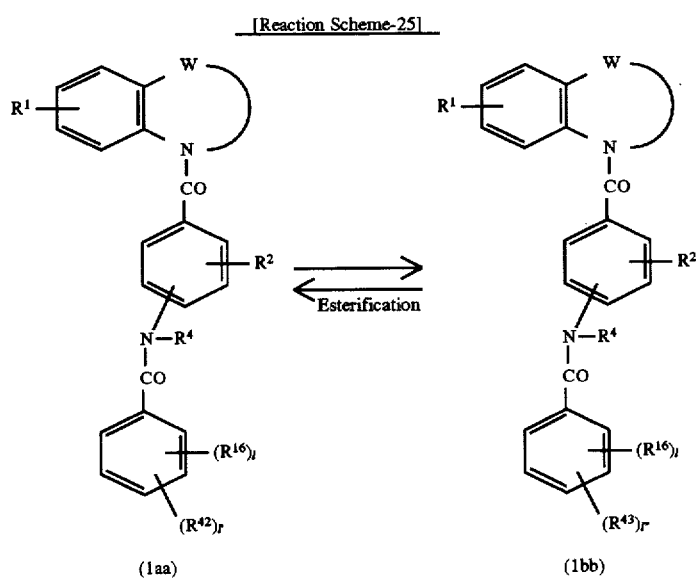

(1aa)    (1bb)

wherein $R^1$, $R^2$, $R^4$, $R^{16}$, 1, 1', 1", and W are as defined above, $R^{42}$ is a lower alkoxycarbonyl and $R^{43}$ is carboxyl.

-continued

[Reaction Scheme-26]

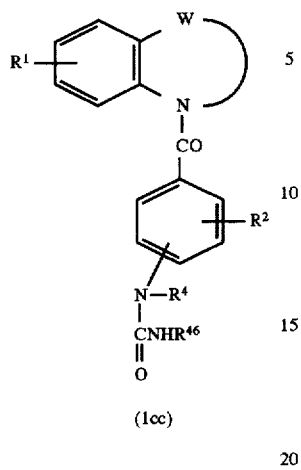

(1cc)

wherein $R^1$, $R^2$, $R^4$, and W are as defined above, and $R^{46}$ is a phenyl having optionally a lower alkyl substituent.

The reaction of the compound (2b) and the compound (38) is usually carried out in an appropriate solvent or without solvent in the presence or absence, preferably in the absence, of a basic compound. The solvent and basic compound are the same as those used in the reaction of the carboxylic acid halide and the amine (2) in the above Reaction Scheme-1.

The compound (38) is usually used in an amount of about 1 to 5 moles, preferably about 1 to 3 moles, to 1 mole of the compound (2b). The reaction is usually carried out at a temperature of from about 0° C. to about 200° C., preferably from room temperature to about 150° C., for about 5 minutes to about 30 hours. In the reaction, a boron compound (e.g. boron trifluoride etherate, etc.) may be added to the reaction system.

[Reaction Scheme-27]

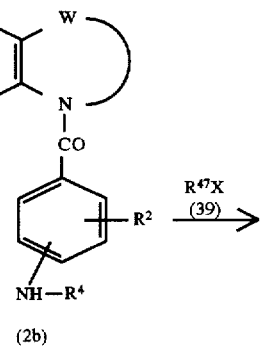

(2b)

(1dd)

wherein $R^1$, $R^2$, $R^4$, W, and X are as defined above, and $R^{47}$ is a phenylsulfonyl which has optionally a substituent selected from a halogen atom and a lower alkyl on the phenyl ring, or quinolylsulfonyl.

The reaction of the compound (2b) and the compound (39) can be carried out under the same conditions as in the reaction of the compound (7) and the compound (8) in the above Reaction Scheme-4.

[Reaction Scheme-28]

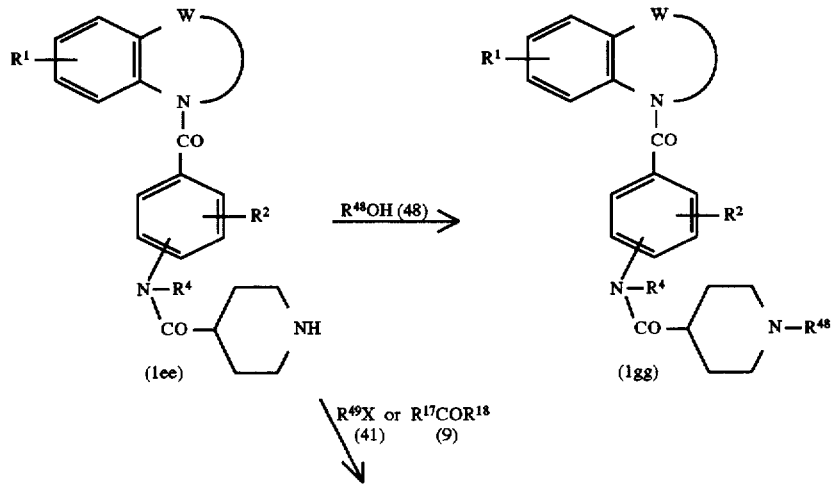

-continued
[Reaction Scheme-28]

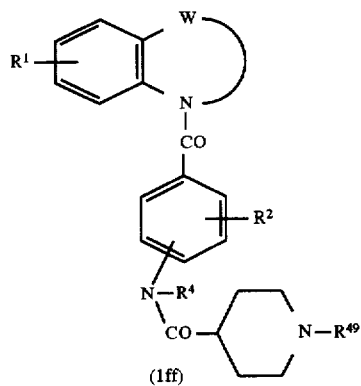

(1ff)

wherein $R^1$, $R^2$, $R^4$, W, $R^{17}$, $R^{18}$, and X are as defined above, $R^{48}$ is a phenyl-lower alkoxycarbonyl, a lower alkanoyl, an amino-lower alkanoyl having optionally a lower alkyl substituent, and $R^{49}$ is a lower alkyl or a carbamoyl-lower alkyl.

The reaction of the compound (1ee) and the compound (40) can be carried out under the same conditions as in the reaction of the compound (2) and the compound (3) in the above Reaction Scheme-1.

The reaction of the compound (1ee) and the compound (41) or the compound (9) can be carried out under the same conditions as in the reaction of the compound (7) and the compound (8) or the compound (9) in the above Reaction Scheme-4, provided that in the reaction product (1ff) produced by the reaction of the compound (1ee) and the compound (9), the group $R^{49}$ is a lower alkyl.

[Reaction Scheme-29]

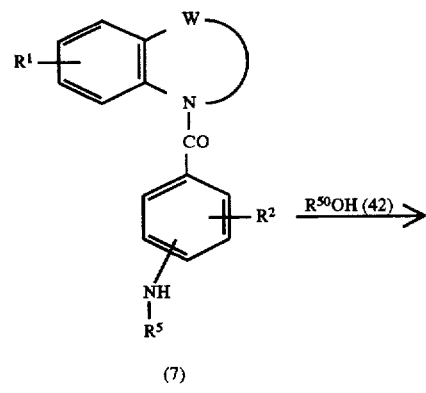

(7)

-continued
[Reaction Scheme-29]

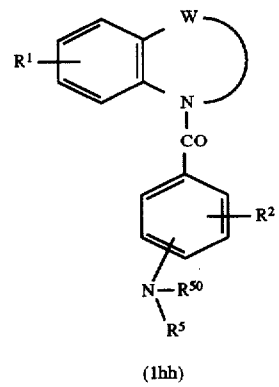

(1hh)

wherein $R^1$, $R^2$, $R^5$, and W are as defined above, and $R^{50}$ is a benzoyl having optionally a halogen substituent on the phenyl ring.

The reaction of the compound (7) and the compound (42) can be carried out under the same conditions as in the reaction of the compound (2) and the compound (3) in the above Reaction Scheme-1.

[Reaction Scheme-30]

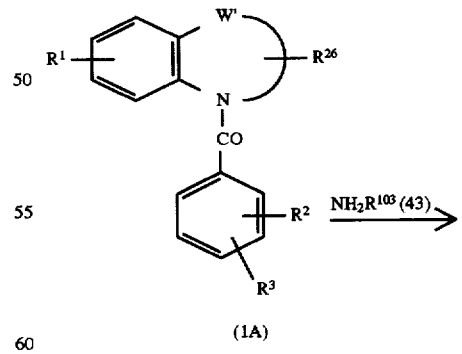

(1A)

-continued
[Reaction Scheme-30]

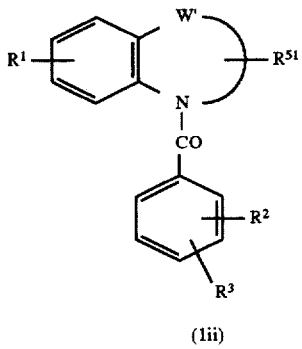

(1ii)

wherein $R^1$, W', $R^{26}$, $R^2$, and $R^3$ are as defined above, $R^{103}$ is hydroxy or sulfoxy, and $R^{51}$ is hydroxyimino or sulfoxyimino.

The reaction of the compound (1A) and the compound (43) is usually carried out in an appropriate inert solvent in the presence or absence of a basic compound. The basic compound includes, for example, inorganic basic compounds such as sodium hydroxide, potassium hydroxide, sodium carbonate, potassium carbonate, etc., and organic basic compounds such as piperidine, pyridine, triethylamine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc. The inert solvent includes, for example, lower alcohols (e.g. methanol, ethanol, isopropanol, etc.), ethers (e.g. dioxane, tetrahydrofuran, diethyl ether, ethylene glycol monomethyl ether, etc.), aromatic hydrocarbons (e.g. benzene, toluene, xylene, etc.), halogenated hydrocarbons (e.g. dichloromethane, dichloroethane, chloroform, carbon tetrachloride, etc.), pyridine, dimethylformamide, dimethylsulfoxide, hexamethylphosphoric triamide, etc., or a mixture of these solvents. The compound (43) is usually used at least in equivalent amount, preferably 1 to 5 moles, to 1 mole of the compound (1A). The reaction is usually carried out at a temperature of from room temperature to about 200° C., preferably from about 50° C. to 150° C., for about 1 to 10 hours.

[Reaction Scheme-31]

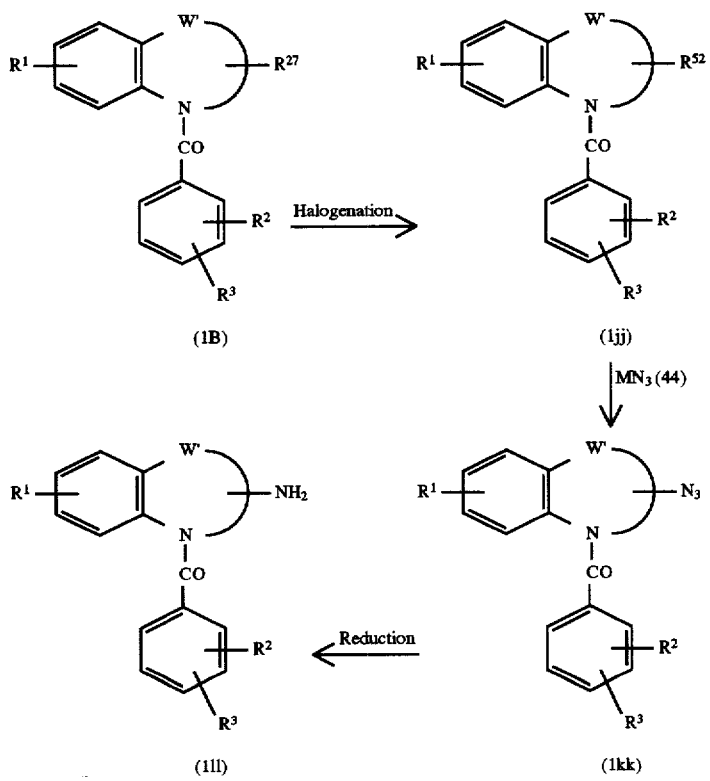

wherein $R^1$, W', $R^{27}$, $R^2$, M, and $R^3$ are as defined above, and $R^{52}$ is a halogen atom.

The halogenation of the compound (1B) is usually carried out in an appropriate solvent or without solvent by reacting the compound (1B) with a halogenating agent.

The halogenating agent includes mineral acids (e.g. hydrochloric acid, hydrobromic acid, etc.), N,N-diethyl-1, 2,2-trichlorovinylamide, phosphorus pentachloride, phosphorus pentabromide, phosphorus oxychloride, thionyl chloride, methanesulfonyl chloride, or a combination of a phenyl-lower alkyl halide (e.g. p-toluenesulfonyl chloride, etc.) and a basic compound. The basic compound includes the same compounds as used in the reaction of the compound (1A) and the compound (43) in the above Reaction Scheme-30. The solvent includes, for example, ethers (e.g. dioxane, tetrahydrofuran, etc.), halogenated hydrocarbons (e.g. chloroform, methylene chloride, carbon tetrachloride, etc.), and the like. The amount of the halogenating agent may vary depending on the kinds of the halogenating agents, and in case of a combination of a phenyl-lower alkyl halide (e.g. p-toluenesulfonyl chloride, etc.) and a basic compound, it is used in an amount of at least 1 mole, preferably 1 to 2 moles, to 1 mole of the compound (1B), and in case of other halogenating agents, it is used at least in an equimolar amount, usually in a largely excess amount, to the compound (1B). The reaction is usually carried out at a temperature of from room temperature to about 150° C., preferably from room temperature to about 80° C., for about 1 to 80 hours.

The reaction of the compound (1jj) and the compound (44) can be carried out under the same conditions as in the reaction of the compound (7) and the compound (8) in the above Reaction Scheme-4.

The reducing reaction of the compound (1kk) can be carried out under the same conditions as in the reducing reaction using a reducing catalyst for converting the compound (1A) into the compound (1C) in the above Reaction Scheme-15.

[Reaction Scheme-32A]

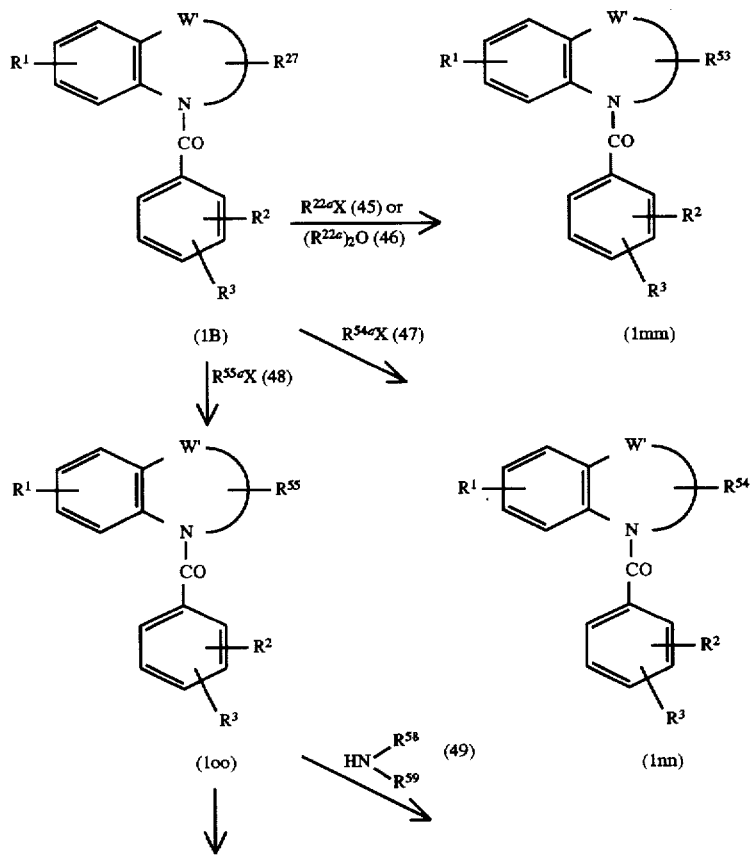

-continued
[Reaction Scheme-32A]

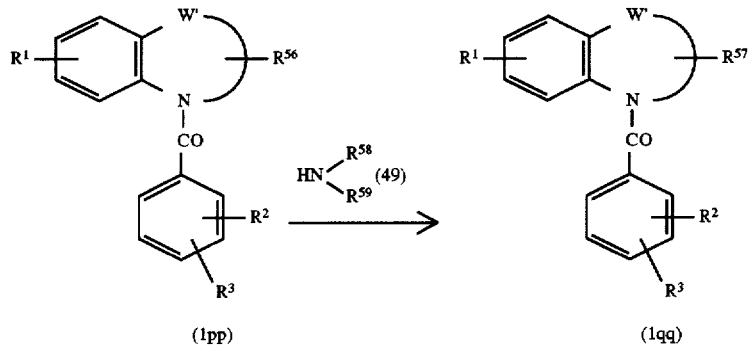

(1pp)    (1qq)

wherein $R^1$, W', $R^2$, $R^3$, $R^{27}$, X, and A are as defined above, $R^{53}$ is a lower alkanoyloxy having optionally a halogen substituent, $R^{54}$ is a lower alkoxy, an amino-lower alkanoyloxy having optionally a lower alkyl substituent, or a group of the formula:

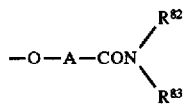

(A, $R^{82}$ and $R^{83}$ are as defined above), $R^{55}$ is a lower alkoxycarbonyl-substituted lower alkoxy, $R^{56}$ is a carboxy-substituted lower alkoxy, $R^{57}$ is an aminocarbonyl-lower alkoxy having optionally a lower alkyl substituent, $R^{54a}$ is a lower alkyl, an amino-lower alkanoyl having optionally a lower alkyl substituent, or a group of the formula:

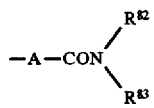

(A, $R^{82}$ and $R^{83}$ are as defined above), $R^{55a}$ is a lower alkoxycarbonyl-substituted lower alkyl, $R^{58}$ and $R^{59}$ are the same or different and are each hydrogen atom or a lower alkyl, and $R^{22a}$ is a lower alkanoyl having optionally a halogen substituent.

[Reaction Scheme-32B]

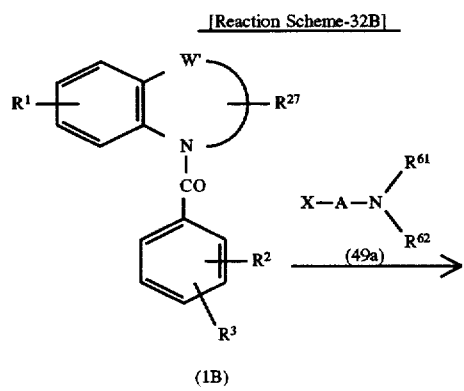

(1B)

-continued
[Reaction Scheme-32B]

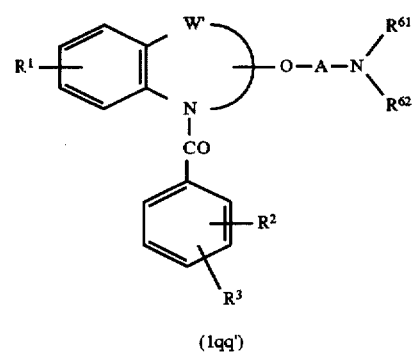

(1qq')

wherein $R^1$, W', $R^2$, $R^3$, X, $R^{27}$, and A are as defined above, and $R^{61}$ and $R^{62}$ are the same or different and are each hydrogen atom, a lower alkyl or a lower alkanoyl.

The reaction of the compound (1B) and the compound (45) or the compound (46) in the Reaction Scheme-32A can be carried out under the same conditions as in the reaction of the compound (1n) and the compound (18) in the above Reaction Scheme-9.

The reaction of the compound (1B) and the compound (47) and the reaction of the compound (1B) and the compound (48) can be carried out under the same conditions as in the reaction of the compound (1n) and the compound (18) in the above Reaction Scheme-9.

The reaction of converting the compound (1oo) into the compound (1pp) can be carried out under the same conditions as in the hydrolysis reaction of the compound (1j) in the above Reaction Scheme-7.

The reaction of the compound (1oo) and the compound (49) and the reaction of the compound (1pp) and the compound (49) can be carried out under the same conditions as in the reaction of the compound (2) and the compound (3) in the above Reaction Scheme-1.

The reaction of the compound (1B) and the compound (49a) in the Reaction Scheme-32B can be carried out under the same conditions as in the reaction of the compound (1n) and the compound (18) in the above Reaction Scheme-9.

[Reaction Scheme-33]

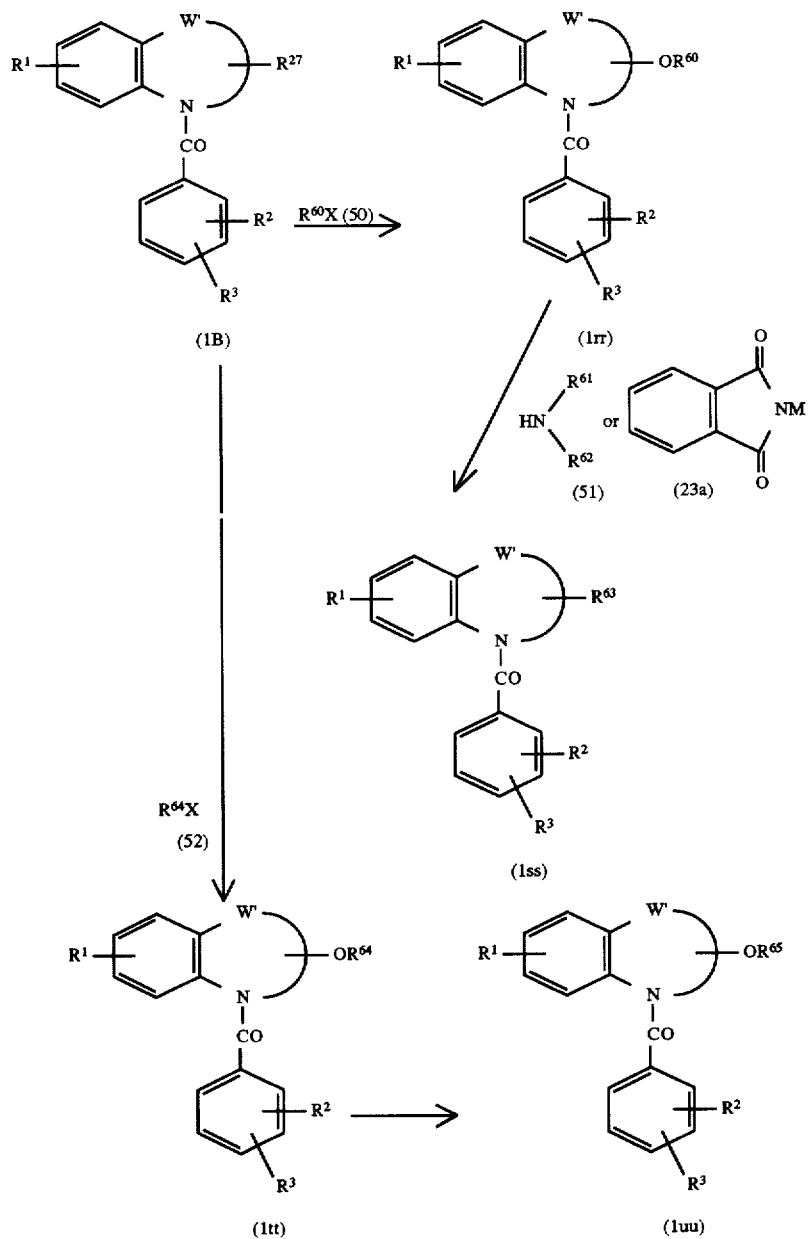

wherein $R^1$, W', $R^2$, $R^3$, $R^{27}$, $R^{61}$, $R^{62}$, M, and X are as defined above, $R^{60}$ is a halogen-substituted lower alkyl, $R^{64}$ is a phthalimido-substituted lower alkyl, $R^{63}$ is an amino-lower alkoxy having optionally a substituent selected from a lower alkyl and a lower alkanoyl, or a phthalimido-substituted lower alkoxy, and $R^{65}$ is an amino-substituted lower alkyl.

The reaction of the compound (1B) and the compound (50) and the reaction of the compound (1B) and the compound (52) can be carried out under the same conditions as in the reaction of the compound (1n) and the compound (18) in the above Reaction Scheme-9.

The reaction of the compound (1rr) and the compound (51) or the compound (23a) can be carried out under the same conditions as in the reaction of the compound (19) and the compound (14) in the above Reaction Scheme-6.

The reaction of converting the compound (1tt) into the compound (1uu) can be carried out under the same conditions as in the reaction of converting the compound (1j) into the compound (1k) in the above Reaction Scheme-7.

[Reaction Scheme-34]

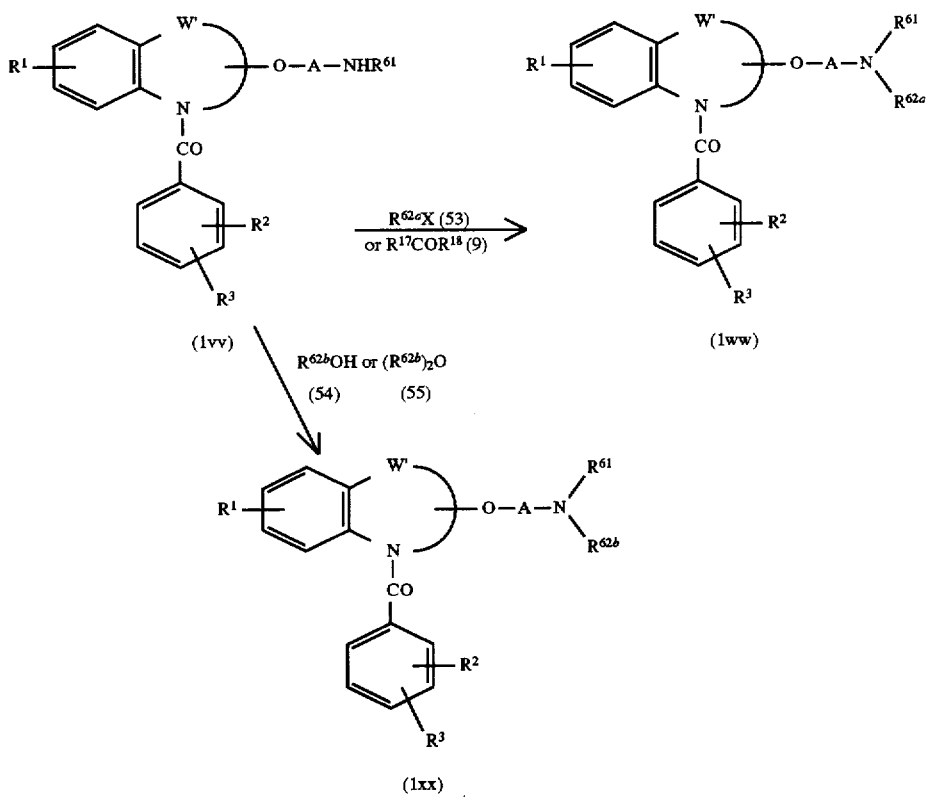

wherein $R^1$, $R^2$, $R^3$, $R^{61}$, W', A, $R^{17}$, $R^{18}$, and X are as defined above, $R^{62a}$ is a lower alkyl, and $R^{62b}$ is a lower alkanoyl.

The reaction of the compound (1vv) and the compound (53) or the compound (9) can be carried out under the same conditions as in the reaction of the compound (7) and the compound (8) or the compound (9) in the above Reaction Scheme-4.

The reaction of the compound (1vv) and the compound (54) can be carried out under the same conditions as in the reaction of the compound (2) and the compound (3) in the above Reaction Scheme-1.

The reaction of the compound (1vv) and the compound (55) can be carried out under the same conditions as in the reaction of the compound (1p) and the compound of the formula: $(R^{7b})_2O$ in the above Reaction Scheme-10.

[Reaction Scheme-35]

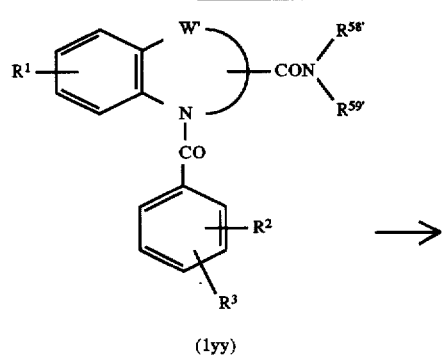

-continued
[Reaction Scheme-35]

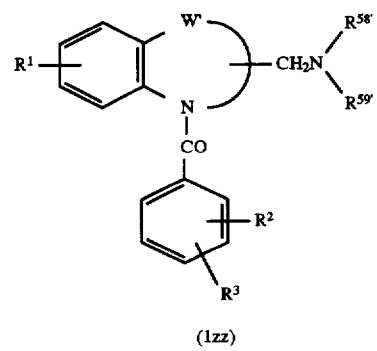

wherein $R^1$, $R^2$, $R^3$, and W' are as defined above, $R^{58'}$ and $R^{59'}$ are the same or different and are each hydrogen atom, a lower alkyl, or a lower alkanoyl.

The reaction of converting the compound (1yy) into the compound (1zz) is usually carried out by reducing the compound (1yy).

The reducting reaction is preferably carried out by using a hydrogenating reducing agent. The hydrogenating reducing agent includes, for example, lithium aluminum hydride, sodium boro hydride, diborane, etc. The reducing agent is usually used in an amount of at least one mole, preferably 1 to 15 moles, to 1 mole of the starting compound. The reducing reaction is usually carried out in an appropriate solvent, such as water, lower alcohols (e.g. methanol, ethanol, isopropanol, etc.), ethers (e.g. tetrahydrofuran, diethyl ether, diisopropyl ether, diglyme, etc.), or a mixture of these solvents, at a temperature of about −60° C. to about 150° C., preferably about −30° C. to 100° C., for about 10 minutes to about 5 hours. When lithium aluminum hydride or diborane is used as the reducing agent, it is preferable to use an anhydrous solvent such as diethyl ether, tetrahydrofuran, diglyme, etc.

The oxidation reaction is carried out in an appropriate solvent in the presence of an oxidizing agent. The solvent includes, for example, water, organic acids (e.g. formic acid, acetic acid, trifluoroacetic acid, etc.), alcohols (e.g. methanol, ethanol, etc.), halogenated hydrocarbons (e.g. chloroform, dichloromethane, etc.), or a mixture of these

[Reaction Scheme-36]

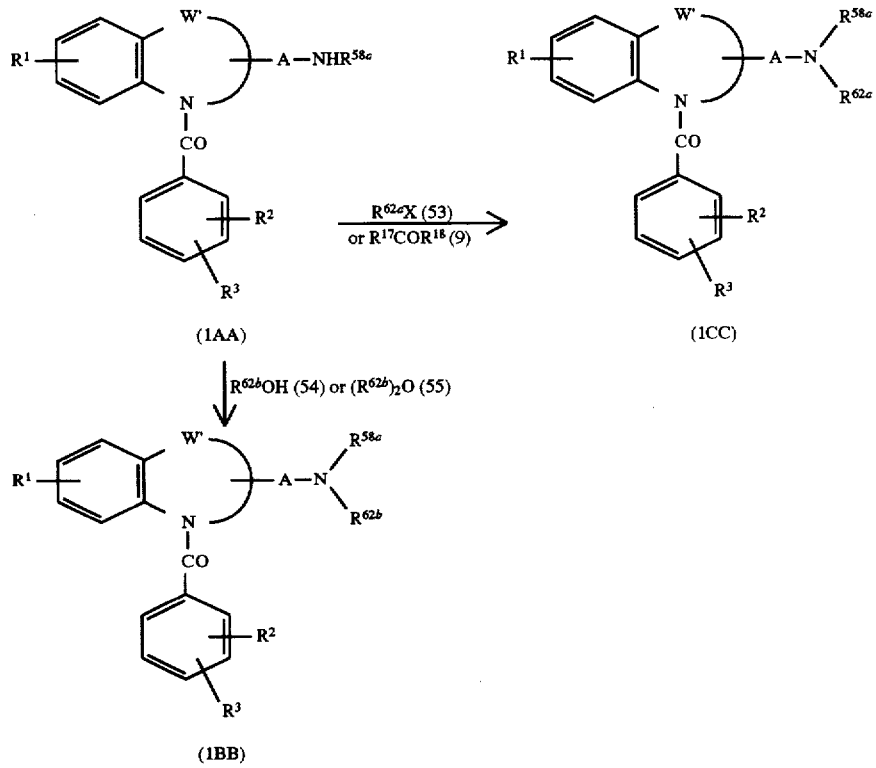

wherein $R^1$, W', $R^2$, $R^3$, $R^{62a}$, $R^{62b}$, X, $R^{17}$, $R^{18}$, and A are as defined above, $R^{58a}$ is hydrogen atom, a lower alkyl or a lower alkanoyl.

The reaction of the compound (1AA) and the compound (53) or the compound (9) can be carried out under the same conditions as in the reaction of the compound (7) and the compound (8) or the compound (9) in the above Reaction Scheme-4.

The reaction of the compound (1AA) and the compound (54) can be carried out under the same conditions as in the reaction of the compound (2) and the compound (3) in the above Reaction Scheme-1.

The reaction of the compound (1AA) and the compound (55) can be carried out under the same conditions as in the reaction of the compound (1p) and the compound of the formula: $(R^{7b})_2O$ in the above Reaction Scheme-10.

The compound (1BB) wherein $R^{62b}$ is formyl can also be prepared by reacting the compound (1AA) with a formate of the formula: $HCOOR^{82}$ under the same conditions as in the reaction of the compound (1K) and the compound of the formula: $HCOOR^{82}$ as described hereinbefore.

The compounds of the formula (1) wherein W is sulfur atom or sulfinyl, or $R^{82}$ and $R^{83}$ bind together with the nitrogen atom to which they bond to form thiomorpholino or 1-oxo-thiomorpholino can be converted into the corresponding compounds of the formula (1) wherein W is sulfinyl or sulfonyl, or $R^{82}$ and $R^{83}$ bind together with the nitrogen atom to which they bond to form 1-oxo-thiomorpholino or 1,1-dioxo-thiomorpholino, respectively, by oxidation thereof.

solvents. The oxidizing agent includes, for example, peracids (e.g. performic acid, peracetic acid, trifluoro-peracetic acid, perbenzoic acid, m-chloroperbenzoic acid, o-carboxyperbenzoic acid, etc.), hydrogen peroxide, sodium metaperiodate, dichromic acid, dichromates (e.g. sodium dichromate, potassium dichromate, etc.), permanganic acid, permanganates (e.g. potassium permanganate, sodium permanganate, etc.), lead salts (e.g. lead tetraacetate, etc.), and the like. The oxidizing agent is usually used in an amount of at least 1 mole, preferably 1 to 2 moles, to 1 mole of the starting compound. Besides, in cases of the oxidation of converting the sulfur atom into sulfonyl group, the oxidizing agent is usually used at least 2 moles, preferably 2 to 4 moles, to 1 mole of the starting compound. The above reaction is usually carried out at a temperature of about −10° C. to about 40° C., preferably from about −10° C. to room temperature, for about 1 to 100 hours.

The compound (1) wherein $R^{16}$ or $R^2$ is a lower alkoxy can be converted into the correspond compound (1) wherein $R^{16}$ or $R^2$ is hydroxy by heating the compound in a mixture of an acid (e.g. hydrobromic acid, hydrochloric acid, etc.) and a solvent (e.g. water, methanol, ethanol, isopropyl alcohol, etc.) at 30° to 150° C., preferably at 50° to 120° C.

Besides, the compound (1) wherein $R^{16}$ or $R^2$ is hydroxy can also be prepared by hydrolysis of the above compound (1) wherein $R^{16}$ or $R^2$ is a lower alkoxy. The hydrolysis can be carried out in an appropriate solvent in the presence of an acid. The solvent includes, for example, water, lower alcohols (e.g. methanol, ethanol, isopropyl alcohol, etc.), ethers (e.g. dioxane, tetrahydrofuran, etc.), halogenated hydrocarbons (e.g. dichloromethane, chloroform, carbon tetrachloride, etc.), polar solvents (e.g. acetonitrile, etc.), or a mixture of these solvents. The acid includes, for example, mineral acids (e.g. hydrochloric acid, hydrobromic acid, etc.), Lewis acids (e.g. boron trifluoride, aluminum chloride, boron tribromide, etc.), iodides (e.g. sodium iodide, potassium iodide, etc.), or a mixture of the above Lewis acid and iodide. The reaction is usually carried out at a temperature of from room temperature to about 150° C., preferably from room temperature to about 100 C., for about 0.5 to 30 hours.

[Reaction Scheme-37]

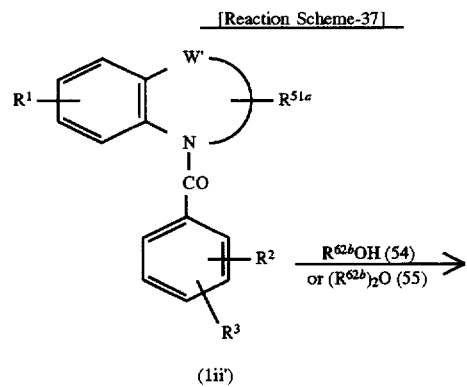

(1ii')

-continued
[Reaction Scheme-37]

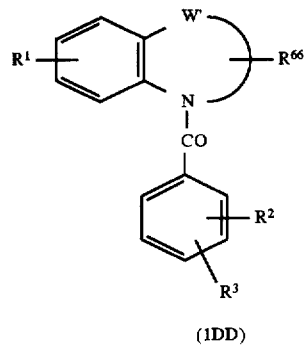

(1DD)

wherein $R^1$, $R^2$, $R^3$, $R^{62b}$, and W' are as defined above, $R^{51a}$ is hydroxyimino, and $R^{66}$ is a lower alkanoyloxyimino.

The reaction of the compound (1ii') and the compound (54) can be carried out under the same conditions as in the reaction of the compound (2) and the compound (3) in the above Reaction Scheme-1.

The reaction of the compound (1ii') and the compound (55) can be carried out under the same conditions as in the reaction of the compound (1p) and the compound of the formula: $(R^{7b})_2O$ in the above Reaction Scheme-10.

[Reaction Scheme-38A]

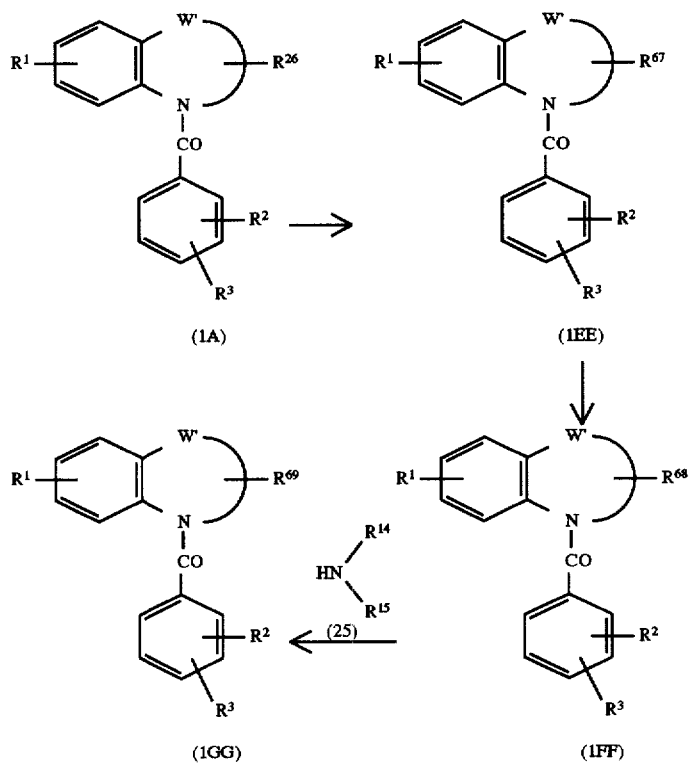

[Reaction Scheme-38B]
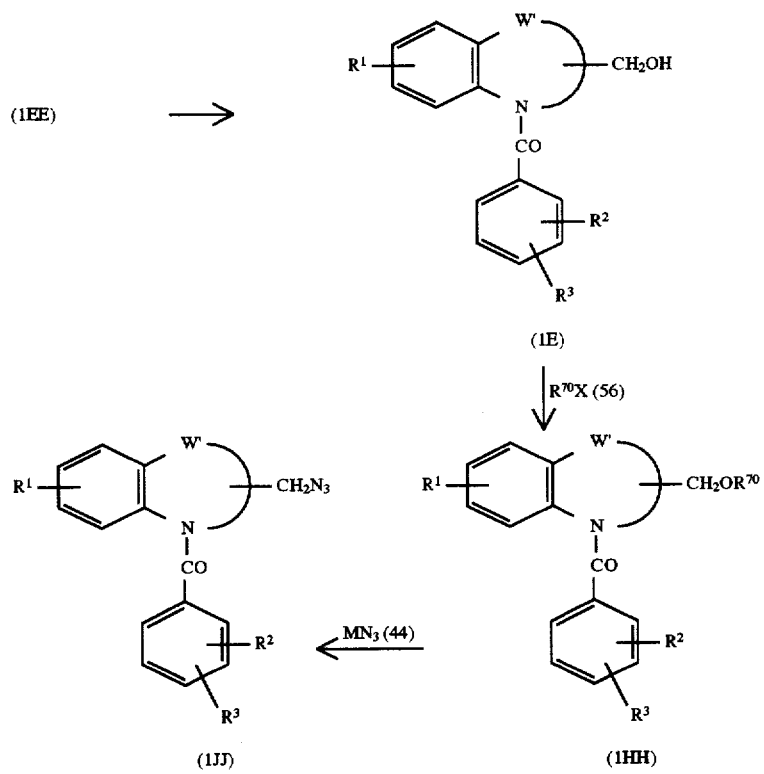
[Reaction Scheme-38C]
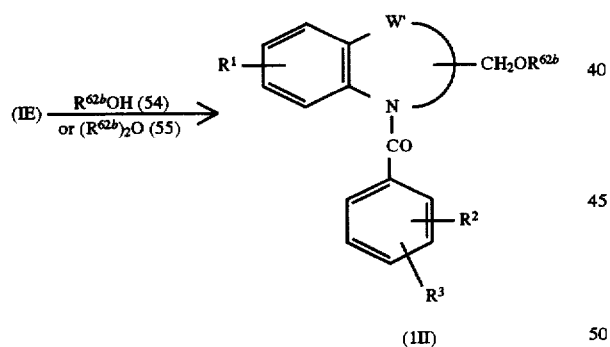
[Reaction Scheme-38D]
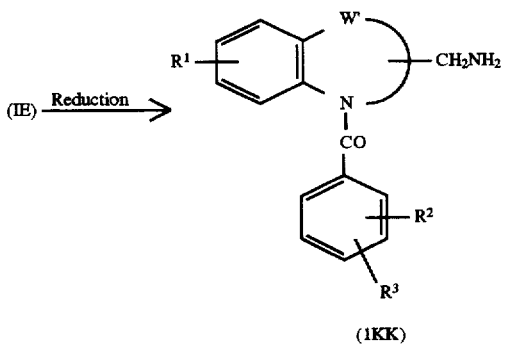

[Reaction Scheme-38E]

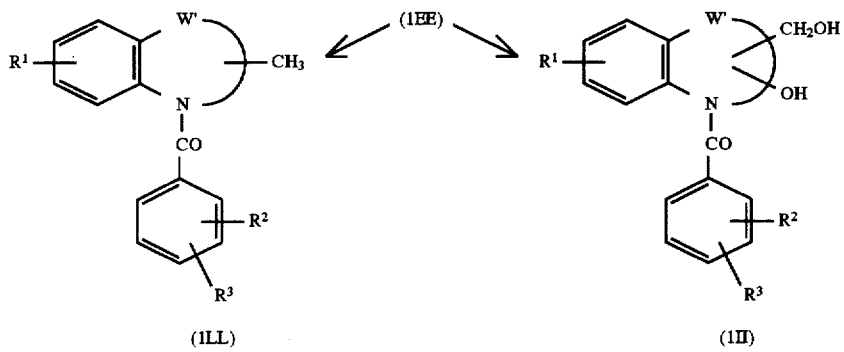

wherein $R^1$, $R^2$, $R^3$, W', $R^{26}$, $R^{14}$, $R^{15}$, $R^{62b}$, X and M are as defined above. $R^{67}$ is methylidene, $R^{68}$ is a group of the formula:

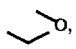

and $R^{69}$ is a group of the formula:

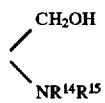

($R^{14}$ and $R^{15}$ are as defined above), or

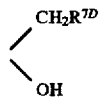

($R^{7D}$ is an amino having optionally a substituent selected from a lower alkyl and a lower alkanoyl, $R^{70}$ is a lower alkylsulfonyl, and W" is the same as the above W, provided that the number of the substituent in the groups —$(CH_2)_p$— and —CH=CH—$(CH_2)_q$— is 0 or 1.

The reaction of converting the compound (1A) into the compound (1EE) is carried out in an appropriate solvent in the presence of a Wittig reagent and a basic compound. The Wittig reagent includes, for example, a phosphoric compound of the formula:

$[(R^{71})_3P^+—CH_2—R^{72}]X^-$     (A)

wherein $R^{71}$ is phenyl, $R^{72}$ is hydrogen atom or a lower alkyl, and X is a halogen atom. The basic compound includes inorganic bases (e.g. metallic sodium, metallic potassium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, potassium t-butoxide, etc.), alkyl or aryl lithiums or lithium amides (e.g. methyl lithium, n-butyl lithium, phenyl lithium, lithium diisopropylamide, etc.), organic bases (e.g. pyridine, piperidine, quinoline, triethylamine, N,N-dimethylaniline, etc.). The solvent includes any solvent which does not affect on the reaction, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc.), aprotic polar solvents (e.g. N,N-dimethylformamide, dimethylsulfoxide, hexamethylphosphoric triamide, etc.), alcohols (e.g. methanol, ethanol, isopropanol, etc.), and the like. The reaction is usually carried out at a temperature of about −80° C. to about 150° C., preferably about −80° C. to about 120° C., for about 0.5 to 15 hours.

The reaction of converting the compound (1EE) into the compound (1LL) can be carried out under the same conditions as in the catalytically hydrogenation reaction for converting the compound (1A) into the compound (1C) in the above Reaction Scheme-15.

The reaction of converting the compound (1EE) into the compound (1FF) is carried out under the same conditions as in the reaction of converting the compound (1) wherein W is sulfur atom or sulfinyl into the corresponding compound (1) wherein W is sulfinyl or sulfonyl respectively as described herebefore.

The reaction of the compound (1FF) and the compound (25) can be carried out under the same conditions as in the reaction of the compound (7) and the compound (8) in the above Reaction Scheme-4.

The reaction of converting the compound (1EE) into the compound (1E) can be carried out by firstly subjecting it to hydroboration reaction and then to oxidation.

The hydroboration reaction is carried out in a solvent such as ethers (e.g. diethyl ether, tetrahydrofuran, dioxane, etc.) in the presence of a hydroborating agent at a temperature of from about 0° C. to about 50° C., preferably about 0° C. to room temperature, for about 1 to 10 hours. The hydroborating agent includes boron hydride compounds, for example, $BH_3$·tetrahydrofuran, $BH_3·S(CH_3)_2$, $BH_2Cl$, $(CH_3)_2CHC(CH_3)_2BH_2$, $(CH_3)_2CHCH(CH_3)BH$,

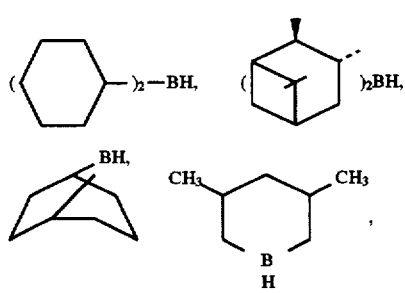

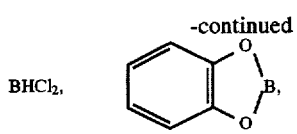

and the like.

The subsequent oxidation is carried out in water in the presence of an oxidizing agent. The oxidizing agent includes, for example, alkaline hydrogen peroxides (e.g. hydrogen peroxide—sodium hydroxide, etc.), and air oxidation is also used. The reaction is usually carried out at a temperature of from room temperature to about 150° C., preferably from room temperature to about 100° C., for 0.5 to 7 hours.

The hydroborating agent and the oxidizing agent are each used in an amount of at least 1 mole, preferably 1 to 2 mole, to 1 mole of the compound (1EE).

The reaction of the compound (1E) and the compound (54) can be carried out under the same conditions as in the reaction of the compound (2) and the compound (3) in the above Reaction Scheme-1.

The reaction of the compound (1E) and the compound (55) can be carried out under the same conditions as in the reaction of the compound (1p) and the compound of the formula: $(R^{7b})_2O$ in the above Reaction Scheme-10.

The reaction of the compound (1E) and the compound (56) can be carried out under the same conditions as in the reaction of the compound (7) and the compound (8) in the above Reaction Scheme-4.

The reaction of the compound (1HH) and the compound (44) can be carried out under the same conditions as in the reaction of the compound (7) and the compound (8) in the above Reaction Scheme-4.

The reducing reaction of the compound (1JJ) can be carried out under the same conditions as in the catalytic hydrogenation reaction for converting the compound (1A) into the compound (1C) in the above Reaction Scheme-15.

The reaction of converting the compound (1EE) into the compound (1MM) can be carried out by reacting with an oxidizing agent in an appropriate solvent in the presence of a co-oxidizing agent.

The solvent used for the reaction with an oxidizing agent includes, for example, pyridine, ethers (e.g. dioxane, tetrahydrofuran, diethyl ether, etc.), aromatic hydrocarbons (e.g. benzene, toluene, xylene, etc.), halogenated hydrocarbons (e.g. dichloromethane, dichloroethane, chloroform, carbon tetrachloride, etc.), esters (e.g. ethyl acetate, etc.), water, alcohols (e.g. methanol, ethanol, isopropanol, t-butanole, etc.), or a mixture of these solvents. The co-oxidizing agent includes, for example, organic amine N-oxides (e.g. pyridine N-oxide, N-ethyldiisopropylamine N-oxide, N-methylmorpholine N-oxide, trimethylamine N-oxide, triethylamine N-oxide, etc.). The oxidizing agent includes, for example, osmium tetraoxide, and the like. The oxidizing agent is usually used in an amount of at least 1 mole, preferably 1 to 5 moles, to 1 mole of the starting compound. The reaction is usually carried out at a temperature of from −20° C. to 150° C., preferably from room temperature to 100° C., for about 1 to 10 hours.

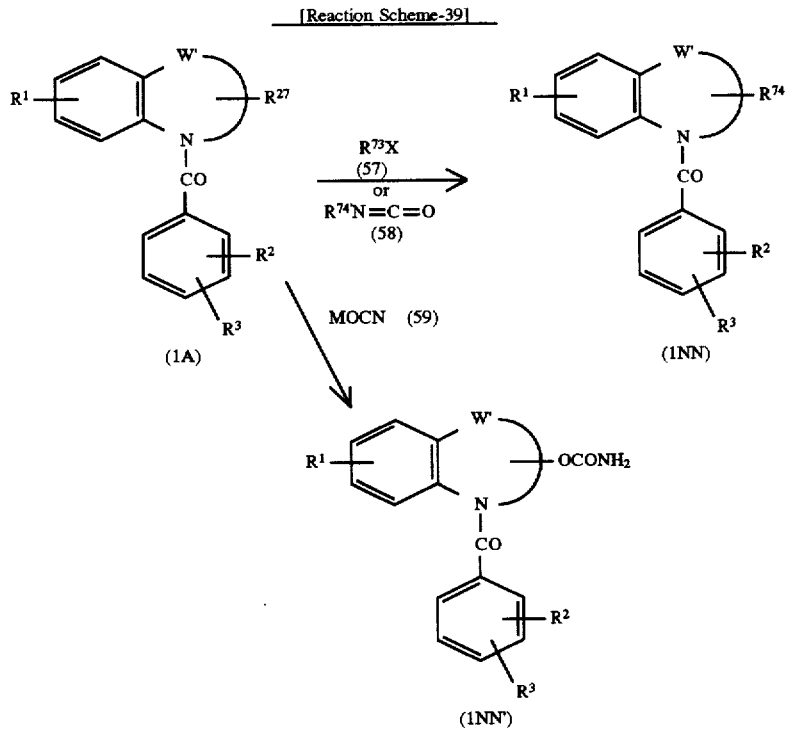

[Reaction Scheme-39]

wherein $R^1$, $R^2$, $R^3$, $R^{27}$, W', M, and X are as defined above, $R^{73}$ is an aminocarbonyl having optionally a lower alkyl substituent, $R^{74}$ is an aminocarbonyloxy having optionally a lower alkyl substituent, $R^{74'}$ is a lower alkyl.

The reaction of the compound (1A) and the compound (57) can be carried out under the same conditions as in the reaction of the compound (7) and the compound (8) in the above Reaction Scheme-4.

The reaction of the compound (1A) and the compound (59) is carried out in an appropriate solvent in the presence of an acid. The solvent includes the same solvent as used in the reaction of the compound (7) and the compound (8) in the above Reaction Scheme-4. The acid includes, for example, mineral acids (e.g. hydrochloride acid, sulfuric acid, etc.), sulfonic acids (e.g. methanesulfonic acid, p-toluenesulfonic acid, etc.), alkanoic acids (e.g. trifluoroacetic acid, etc.), and the like. The compound (59) is used in an amount of at least 1 mole, preferably 1 to 5 moles, to 1 mole of the compound (1A). The reaction is usually carried out at a temperature of from room temperature to about 150° C., preferably from room temperature to about 100° C., for about 1 to 7 hours.

The reaction of the compound (1A) and the compound (58) can be carried out under the same conditions as in the reaction of the compound (2b) and the compound (38) in the above Reaction Scheme-26.

[Reaction Scheme-40]

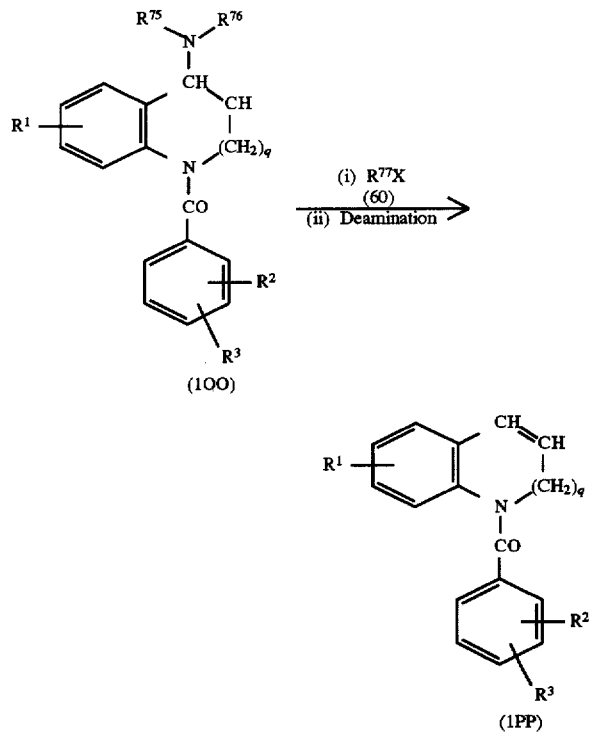

wherein $R^1$, $R^2$, $R^3$, X, and q are as defined above, and $R^{75}$, $R^{76}$ and $R^{77}$ are each a lower alkyl, and the carbon atom in the formula: —$(CH_2)_q$— may be substituted by oxygen atom, sulfur atom, sulfinyl, sulfonyl, or a group of the formula:

$$\begin{array}{c} R^{13} \\ | \\ -N- \end{array}$$

($R^{13}$ is as defined above), and further the group: —$(CH_2)_q$— may optionally have 1 to 3 substituents selected from a lower alkyl having optionally a hydroxy substituent, a lower alkoxycarbonyl, carboxyl, hydroxy, oxo, a lower alkanoyloxy having optionally a halogen substituent, an amino-lower alkyl having optionally a substituent selected from a lower alkyl and a lower alkanoyl, a lower alkanoyloxy-substituted lower alkyl, a lower alkylsulfonyloxy-lower alkyl, an azido-lower alkyl, a group of the formula:

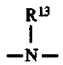

an aminocarbonyloxy having optionally a lower alkyl substituent, a lower alkoxy, a lower alkoxycarbonyl-substituted lower alkoxy, a carboxy-substituted lower alkoxy, an aminocarbonyl-lower alkoxy having optionally a lower alkyl substituent, an amino-lower-alkoxy having optionally a substituent selected from a lower alkyl and a lower alkanoyl, a phthalimido-substituted lower alkoxy, hydroxyimino, a lower alkanoyloxyimino, a lower alkylidene, a halogen atom, azido, sulfoxyimino, a group of the formula:

$$R^{81}-N-CH_2COO-$$

($R^{81}$ is hydrogen atom or a lower alkyl), hydrazino, pyrrolyl, an amino-lower alkanoyloxy having optionally a lower alkyl substituent, a group of the formula:

$$-O-A-CO-N\begin{array}{c}R^{82}\\ \\R^{83}\end{array}$$

(A is as defined above, and $R^{82}$ and $R^{83}$ are the same or different and are each hydrogen atom, a lower alkyl, a carbamoyl-substituted lower alkyl, a hydroxy-substituted lower alkyl, or a pyridyl-lower alkyl, or $R^{82}$ and $R^{83}$ may bind together with nitrogen atom to which they bond to form a 5- or 6-membered saturated heterocyclic group with or without being intervened with nitrogen, oxygen or sulfur atom wherein the heterocyclic group has optionally a substituent selected from oxo, a lower alkyl, a lower alkanoyl, and carbamoyl), and a group of the formula:

$$-(CO)_n-N\begin{array}{c}R^{14}\\ \\R^{15}\end{array}$$

(n is as defined above, and $R^{14}$ and $R^{15}$ are the same or different and are each hydrogen atom, a lower alkyl, a lower alkenyl, a lower alkanoyl, a cycloalkyl, an oxiranyl-substituted lower alkyl, a lower alkyl having 1 to 2 substituents selected from a lower alkoxy, hydroxy and an amino having optionally a lower alkyl substituent, a phenyl-lower alkyl, a pyridyl-lower alkyl, a lower alkylsulfonyl, benzoyl, a lower alkoxycarbonyl, anilinocarbonyl, an aminocarbonyl having optionally a lower alkyl substituent, a cyano-substituted lower alkyl, a lower alkoxycarbonyl-substituted lower alkyl, a carbamoyl-substituted lower alkyl, a carboxy-substituted lower alkyl, a tetrahydropyranyloxy-substituted lower alkyl, a lower alkanoyloxy-substituted lower alkyl, a piperidinyl having optionally a phenyl-lower alkyl substituent on the piperidinyl ring, a halogen-substituted lower alkanoyl, an imidazolyl-substituted lower alkanoyl, an amino-lower alkanoyl having optionally a substituent selected from a lower alkyl and a lower alkoxycarbonyl, an aminocarbonyl-lower alkyl having optionally a lower alkyl substituent, or a phenyl-lower alkoxycarbonyl, or $R^{14}$ and $R^{15}$ may bind together with the nitrogen atom to which they bond to form a 5- or 6-membered saturated heterocyclic group with or without being intervened with nitrogen or oxygen atom, which heterocyclic group may optionally have a substituent selected from a lower alkyl, a phenyl-lower alkyl and a lower alkanoyl.

The reaction of the compound (100) and the compound (60) is carried out in an appropriate solvent in an autoclave. The solvent includes any solvent as used in the reaction of the compound (7) and the compound (8) in the above Reaction Scheme-4. The reaction is usually carried out at a temperature of from room temperature to about 200° C., preferably from room temperature to about 150° C., for about 1 to 7 hours.

The subsequent deamination reaction is carried out in an appropriate solvent in the presence of a basic compound. The solvent includes the same solvent as used in the above reaction of the compound (100) and the compound (60). The basic compound includes any basic compound as used in the reaction of converting the compound (1A) into the compound (1EE) in the above Reaction Scheme-38. The reaction is usually carried out at a temperature of from room temperature to about 150° C., preferably from room temperature to about 100° C., for about 1 to 10 hours.

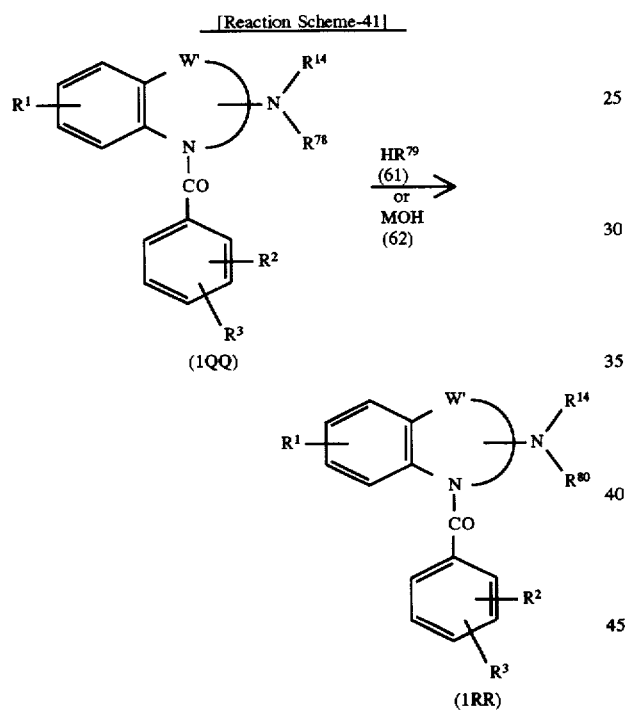

wherein $R^1$, $R^2$, $R^3$, $R^{14}$, M, and W' are as defined above, $R^{78}$ is an oxiranyl-substituted lower alkyl, $R^{79}$ is a lower alkoxy, or an amino having optionally a lower alkyl substituent, and $R^{80}$ is a lower alkyl having 2 substituents selected from hydroxy, a lower alkoxy, and an amino having optionally a lower alkyl substituent.

The reaction of the compound (1QQ) and the compound (61) can be carried out under the same conditions as in the reaction of the compound (7) and the compound (8) in the above Reaction Scheme-4.

The reaction of the compound (1QQ) and the compound (62) can be carried out by firstly reacting them in trifluoroacetic acid at a temperature of about 0° C. to about 100° C., preferably about 0° C. to about 50° C., for about 1 to 7 hours, followed by hydrolysis of the resultant.

The hydrolysis is carried out in an appropriate solvent or without solvent in the presence of an acid or a basic compound. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.), and the like. The basic compound includes, for example, metal carbonates (e.g. sodium carbonate, potassium carbonate, etc.), metal hydroxides (e.g. sodium hydroxide, potassium hydroxide, calcium hydroxide, etc.). The reaction is usually carried out at a temperature of from room temperature to about 200° C., preferably from room temperature to about 150° C., for about 0.5 to 25 hours.

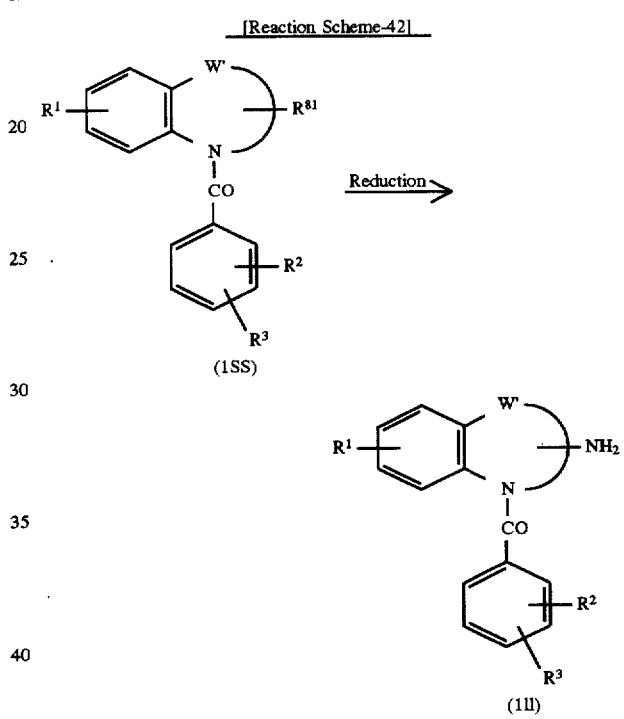

wherein $R^1$, $R^2$, $R^3$, and W' are as defined above, and $R^{81}$ is hydroxyimino or a lower alkanoyloxyimino.

The reaction of converting the compound (1SS) into the compound (1ll) is carried out by catalytically hydrogenating the compound (1SS) in an appropriate solvent in the presence of a catalyst. The solvent includes, for example, water, acetic acid, alcohols (e.g. methanol, ethanol, isopropanol, etc.), hydrocarbons (e.g. hexane, cyclohexane, etc.,), ethers (e.g. diethylene glycol dimethyl ether, dioxane, tetrahydrofuran, diethyl ether, etc.), esters (e.g. ethyl acetate, methyl acetate, etc.), aprotic polar solvents (e.g. dimethylformamide, etc.), or a mixture of these solvents. The catalyst includes, for example, palladium, palladium black, palladium-carbon, platinum, platinum oxide, copper chromate, Raney nickel, and the like. The catalyst is usually used in an amount of 0.02 to 1 part by weight to 1 part by weight of the compound (1SS). The reaction is usually carried out at a temperature of from about −20° C. to about 100° C., preferably about 0° C. to about 70° C., under a hydrogen atmospheric pressure of 1 to 10 atm. for about 0.5 to 20 hours.

Alternatively, the reducing reaction can also be carried out by using a hydrogenating reducing agent. The hydrogenating reducing agent includes, for example, lithium aluminum hydride, sodium boro hydride, diborane, etc. The reducing agent is usually used in an amount of at least one mole, preferably 1 to 10 moles, to 1 mole of the compound (1SS). The reaction is usually carried out in an appropriate solvent, such as water, lower alcohols (e.g. methanol, ethanol, isopropanol, etc.), ethers (e.g. tetrahydrofuran, diethyl ether, diglyme, etc.), acetic acid, and the like, at a temperature of about 0° C. to about 200° C., preferably about 0° C. to 170° C., for about 10 minutes to about 10 hours. When lithium aluminum hydride or diborane is used as the reducing agent, it is preferable to use an anhydrous solvent such as diethyl ether, tetrahydrofuran, diglyme, etc.

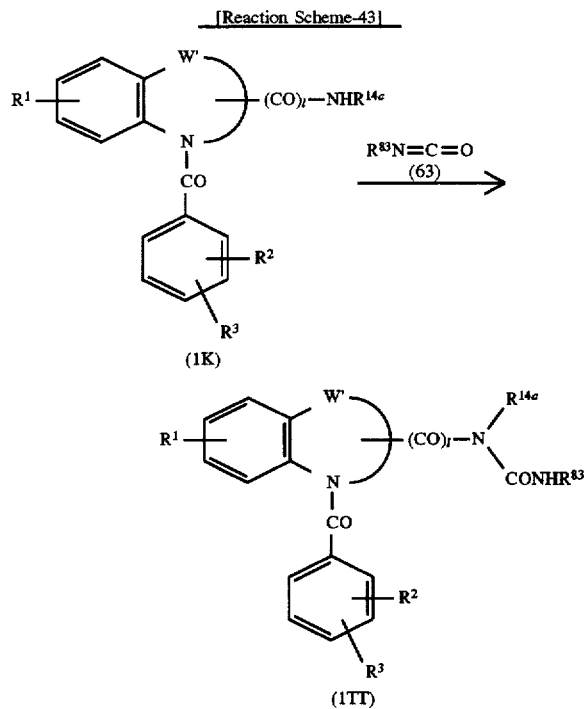

wherein $R^1$, $R^2$, $R^3$, W', 1, $R^{14a}$ are as defined above, and $R^{83}$ is phenyl or a lower alkyl.

The reaction of the compound (1K) and the compound (63) can be carried out under the same conditions as in the reaction of the compound (2b) and the compound (38) in the above Reaction Scheme-26.

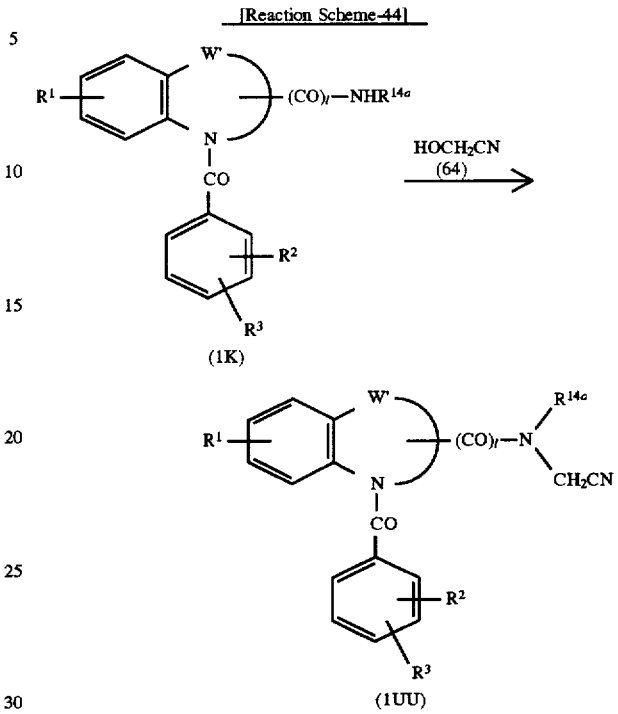

wherein $R^1$, $R^2$, $R^3$, W', 1, $R^{14a}$ are as defined above.

The reaction of the compound (1K) and the glyconitrile (64) can be carried out in an appropriate solvent. The solvent includes the same solvent as used in the reaction of the compound (7) and the compound (8) in the above Reaction Scheme-4. The reaction is usually carried out at a temperature of from about 0° C. to about 150° C., preferably about 0° C. to about 100° C., for about 1 to 10 hours. The glyconitrile (64) is used in an amount of at least 1 mole, preferably 1 to 2 moles, to 1 mole of the compound (1K).

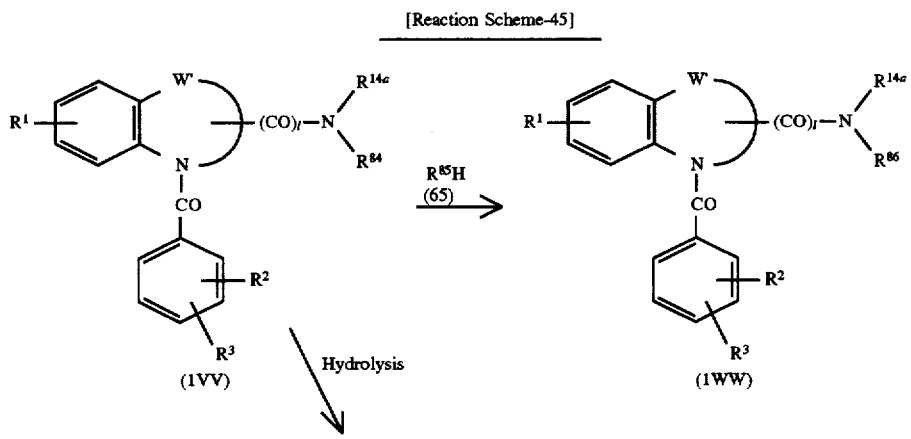

-continued
[Reaction Scheme-45]

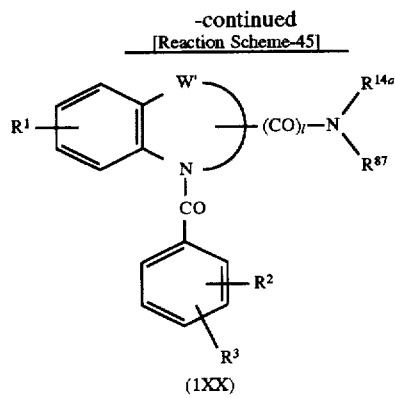

(1XX)

wherein $R^1$, $R^2$, $R^3$, W', l, $R^{14a}$ are as defined above, $R^{84}$ is a lower alkoxycarbonyl-substituted lower alkyl, $R^{85}$ is an amino having optionally a lower alkyl substituent, $R^{86}$ is an aminocarbonyl-lower alkyl having optionally a lower alkyl substituent, and $R^{87}$ is a carboxy-substituted lower alkyl.

The reaction of the compound (1VV) and the compound (65) can be carried out under the same conditions as in the reaction of the compound (2) and the compound (3) in the above Reaction Scheme-1.

The hydrolysis reaction of the compound (1VV) can be carried out under the same conditions as in the hydrolysis reaction of the compound (1QQ) and the compound (62) in the above Reaction Scheme-41.

The reaction of the compound (1YY) and the compound (66) can be carried out in a solvent such as acetic acid at a temperature of about 0° C. to about 200° C., preferably about 0° C. to about 150° C., for about 0.5 to 15 hours.

The hydrolysis reaction of the compound (1YY) can be carried out under the same conditions as in the hydrolysis reaction of the compound (1QQ) and the compound (62) in the above Reaction Scheme-41, wherein a pyridinium salt (e.g. pyridinium p-toluenesulfonate, etc.) may be used as the acid.

[Reaction Scheme-46]

wherein $R^1$, $R^2$, $R^3$, W', l, X, and $R^{14a}$ are as defined above, $R^{88}$ is a tetrahydropyranyloxy-substituted lower alkyl, $R^{89}$ is a lower alkanoyloxy-substituted lower alkyl, $R^{90}$ is a hydroxy-substituted lower alkyl, and $R^{91}$ is a lower alkanoyl.

[Reaction Scheme-47]

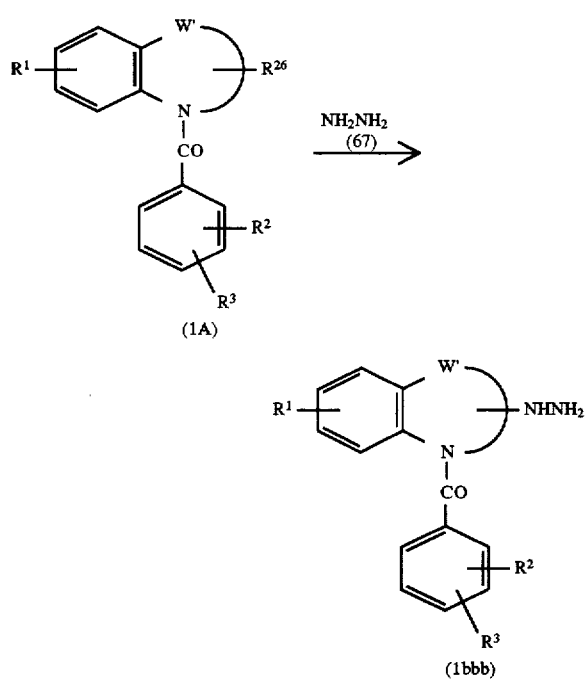

wherein $R^1$, $R^2$, $R^3$, W', and $R^{26}$ are as defined above.

The reaction of converting the compound (1A) into the compound (1bbb) can be carried out under the same conditions as in the reaction of converting the compound (1A) into the compound (1C) in the above Reaction Scheme-15.

[Reaction Scheme-48]

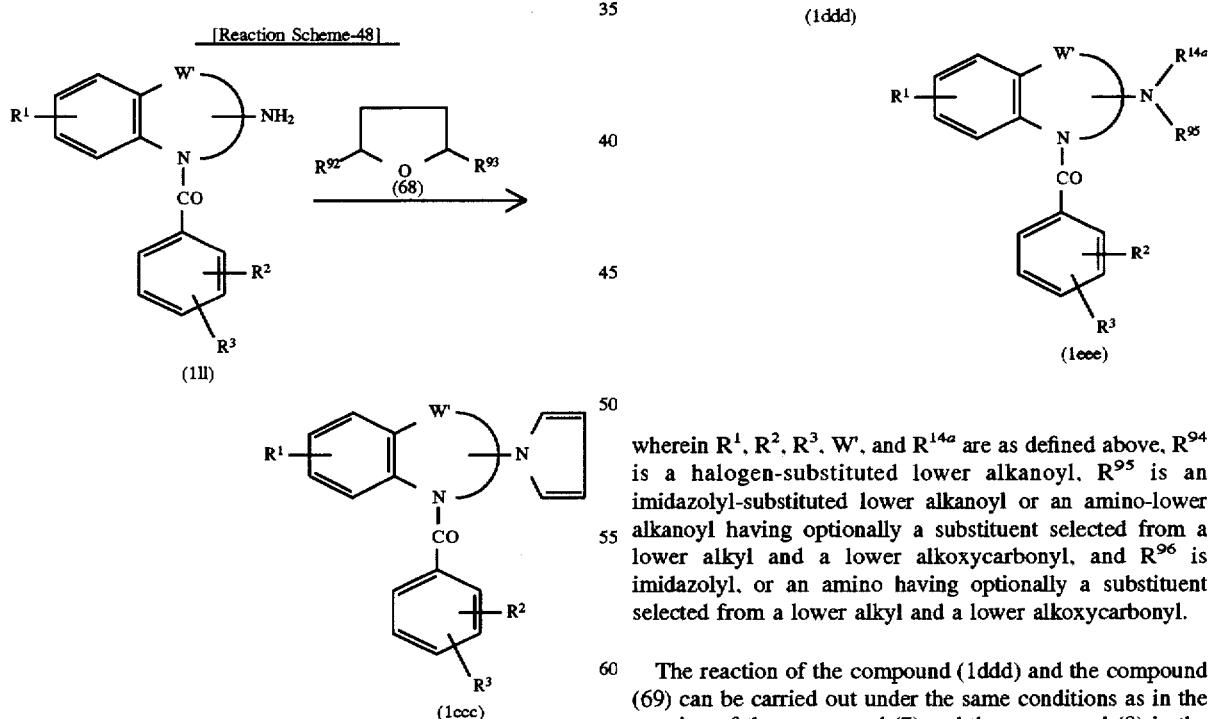

wherein $R^1$, $R^2$, $R^3$ and W' are as defined above, $R^{92}$ and $R^{93}$ are each a lower alkoxy.

The reaction of the compound (1ll) and the compound (68) is carried out in an appropriate solvent in the presence of an acid. The solvent includes, for example, water, alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acids, etc.). The reaction is usually carried out at a temperature of from room temperature to about 200° C., preferably from room temperature to about 150° C., for about 0.5 to 5 hours. The compound (68) is usually used in an amount of at least 1 mole, preferably 1 to 2 moles, to 1 mole of the compound (1ll).

[Reaction Scheme-49]

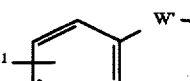

wherein $R^1$, $R^2$, $R^3$, W', and $R^{14a}$ are as defined above, $R^{94}$ is a halogen-substituted lower alkanoyl, $R^{95}$ is an imidazolyl-substituted lower alkanoyl or an amino-lower alkanoyl having optionally a substituent selected from a lower alkyl and a lower alkoxycarbonyl, and $R^{96}$ is imidazolyl, or an amino having optionally a substituent selected from a lower alkyl and a lower alkoxycarbonyl.

The reaction of the compound (1ddd) and the compound (69) can be carried out under the same conditions as in the reaction of the compound (7) and the compound (8) in the above Reaction Scheme-4.

[Reaction Scheme-50]

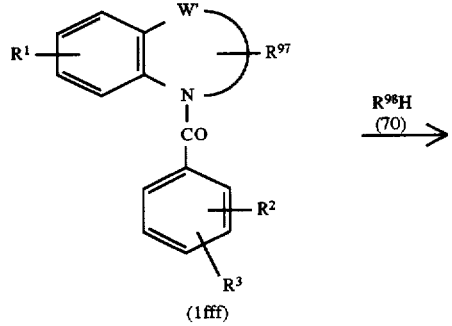

(1fff)

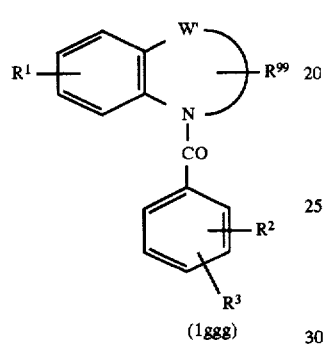

(1ggg)

wherein $R^1$, $R^2$, $R^3$, and W' are as defined above, $R^{97}$ is a lower alkanoyloxy having a halogen substituent, $R^{98}$ is an amino having optionally a lower alkyl substituent, and $R^{99}$ is an amino-lower alkanoyloxy having optionally a lower alkyl substituent.

The reaction of the compound (1fff) and the compound (70) can be carried out under the same conditions as in the reaction of the compound (7) and the compound (8) in the above Reaction Scheme-4.

[Reaction Scheme-51]

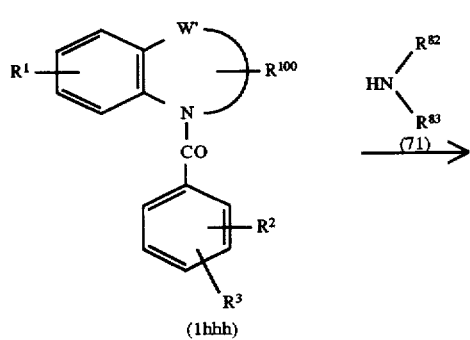

(1hhh)

-continued
[Reaction Scheme-51]

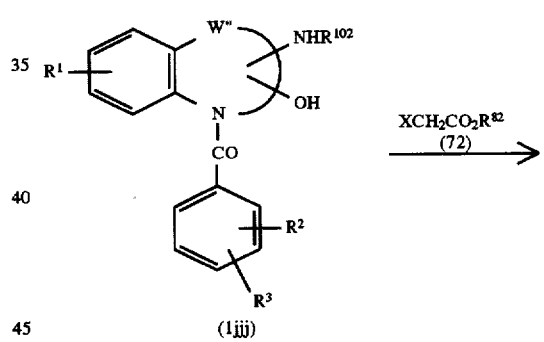

(1iii)

wherein $R^1$, $R^2$, $R^3$, W', $R^{82}$, and $R^{83}$ are as defined above, $R^{100}$ is a carboxy-substituted lower alkoxy, and $R^{101}$ is a group of the formula:

$$-O-A-CON\begin{matrix}R^{82}\\R^{83}\end{matrix}$$

(A, $R^{82}$ and $R^{83}$ are as defined above).

The reaction of the compound (1hhh) and the compound (71) can be carried out under the same conditions as in the reaction of the compound (2) and the compound (3) in the above Reaction Scheme-1.

[Reaction Scheme-52]

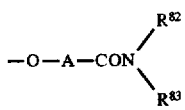

(1jjj)

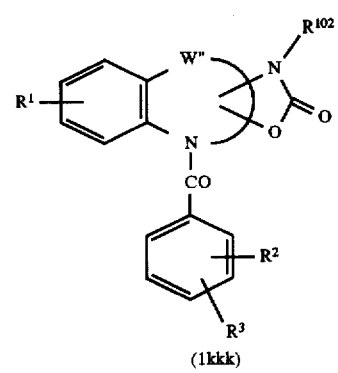

(1kkk)

wherein $R^1$, $R^2$, $R^3$, W", X, and $R^{82}$ are as defined above, and $R^{102}$ is hydrogen atom or a lower alkyl, provided that in the compound (1jjj), the groups of the formulae: —NH—$R^{102}$ and —OH are substituted at the positions adjacent each other.

The reaction of the compound (1jjj) and the compound (72) can be carried out under the same conditions as in the reaction of the compound (7) and the compound (8) in the above Reaction Scheme-4.

[Reaction Scheme-53]

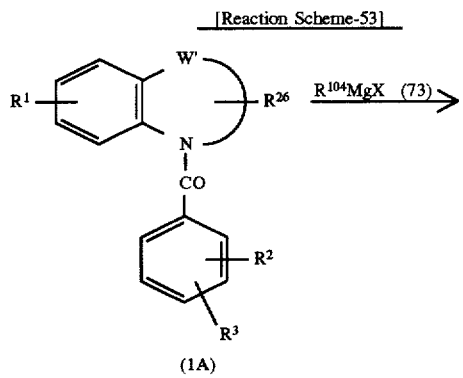

wherein $R^1$, $R^2$, $R^3$, W', $R^{26}$ and X are as defined above, and $R^{104}$ is a lower alkyl.

The reaction of the compound (1A) and the compound (73) can be carried out in an appropriate solvent. The solvent includes, for example, ethers (diethyl ether, dioxane, tetrahydrofuran, etc.), aromatic hydrocarbons (e.g. benzene, toluene, xylene, etc.), saturated hydrocarbons (e.g. pentane, hexane, heptane, cyclohexane, etc.), or a mixture of these solvents. The reaction is usually carried out at a temperature of from about −70° C. to about 50° C., preferably from about −30° C. to room temperature, for about 1 to 6 hours. The compound (73) is used in an amount of at least 1 mole, preferably 1 to 5 moles, to 1 mole of the compound (1A).

[Reaction Scheme-54]

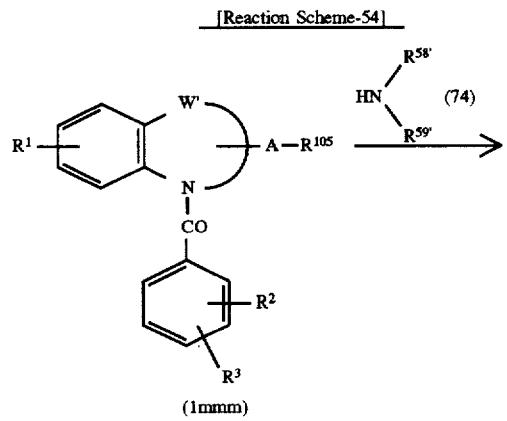

-continued
[Reaction Scheme-54]

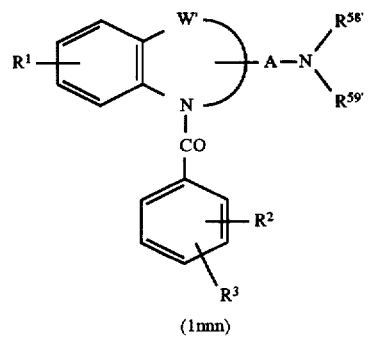

wherein $R^1$, $R^2$, $R^3$, W', $R^{58'}$, $R^{59'}$, and A are as defined above, and $R^{105}$ is a lower alkylsulfonyloxy.

The reaction of the compound (1mmm) and the compound (74) can be carried out under the same conditions as in the reaction of the compound (7) and the compound (8) in the above Reaction Scheme-4.

Among the active compounds (1) of this invention, the compounds having an acidic group can easily be converted into salts by treating with a pharmaceutically acceptable basic compound. The basic compound includes, for example, metal hydroxides such as sodium hydroxide, potassium hydroxide, lithium hydroxide, calcium hydroxide, etc., alkali metal carbonates or hydrogen carbonates such as sodium carbonate, sodium hydrogen carbonate, etc., alkali metal alcoholates such as sodium methylate, potassium ethylate, etc. Besides, among the active compounds (1) of this invention, the compounds having a basic group can easily be converted into acid addition salts thereof by treating with a pharmaceutically acceptable acid. The acid includes, for example, inorganic acids such as sulfuric acid, nitric acid, hydrochloric acid, hydrobromic acid, etc., and organic acids such as acetic acid, p-toluenesulfonic acid, ethanesulfonic acid, oxalic acid, maleic acid, fumaric acid, citric acid, succinic acid, benzoic acid, etc. These salts are useful as an active ingredient as like as the compounds (1) in the free form.

In addition, the compounds (1) of this invention include stereoisomers and optical isomers, and these isomers are also useful as the active ingredient in this invention.

The compounds of this invention thus obtained can easily be isolated and purified by conventional isolation methods. The isolation methods are, for example, distillation method, recrystallization method, column chromatography, ion exchange chromatography, gel chromatography, affinity chromtography, preparative thin layer chromatography, extraction with a solvent, and the like.

The compounds and their salts of this invention are useful as a vasopressin antagonist and are used in the form of a conventional pharmaceutical preparation. The preparation is prepared by using conventional dilutents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carriers into hard gelatin capsules or soft capsules in a usual manner. In the preparation of injections, the solutions, emulsions or suspensions are sterilized and are preferably made isotonic with the blood. In the preparation of these solutions, emulsions and suspensions, there are used conventional diluents, such as water, ethyl alcohol, macrogol (propylene glycol), ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The amount of the active compound of this invention (active ingredient) to be incorporated into the anti-vasopressin preparations is not specified but may be selected from a broad range, but usually, it is preferably in the range of 1 to 70% by weight, more preferably 5 to 50% by weight.

The anti-vasopressin preparation of this invention may be administered in any method, and suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the anti-vasopressin agent of this invention may be selected in accordance with the usage, ages, sexes and other conditions of the patients, the degree of severity of the diseases, and the like, but is usually in the range of about 0.6 to 50 mg of the active compound of this invention per 1 kg of body weight of the patient per day. The active compound is preferably contained in an amount of 10 to 1000 mg per the dosage unit.

BEST MODE FOR CARRYING OUT THE INVENTION

Figure 1:
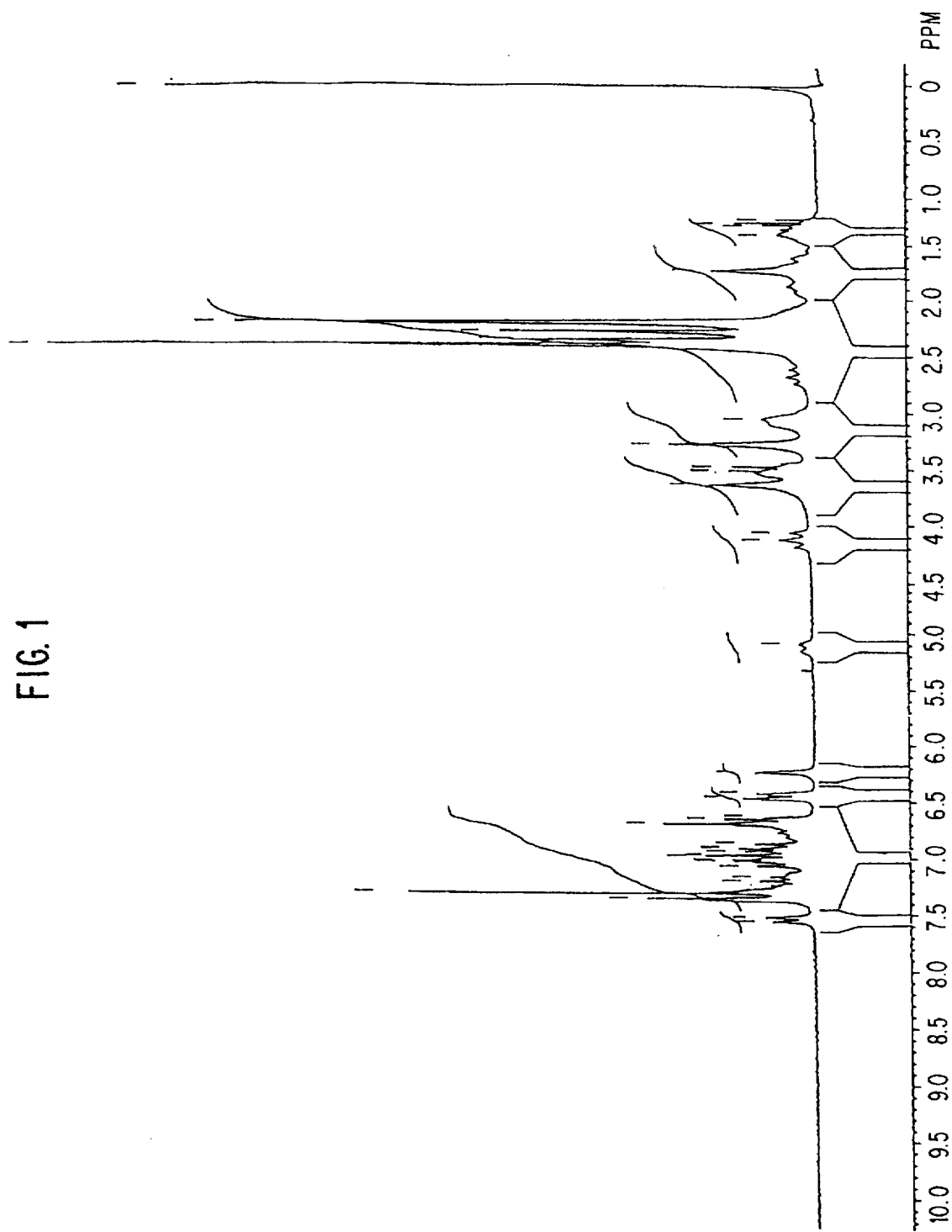
FIG. 1 to FIG. 4 show a chart of NMR ($CDCl_3$) of the compounds in Examples 978 and 979.

The present invention is illustrated by the following Preparations of anti-vasopressin agent, Reference Examples of processes for preparing the starting compounds to be used for preparing the active compounds, Examples of processes for preparing the active compounds, and Experiments of the activities of the active compounds of this invention.

Preparation 1
Film coated tablets are prepared from the following components.

| Components | Amount |
|---|---|
| 4-Methylamino-1-[4-(3,5-dichlorobenzoyl-amino)benzoyl]-1,2,3,4-tetrahydroquinoline | 150 g |
| Avicel (tradename of microcrystalline cellulose, manufactured by Asahi Chemical Industry Co., Ltd., Japan) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active component of this invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2
Tablets are prepared from the following components.

| Components | Amount |
|---|---|
| 1-[4-(N-Butylanilinoacetylamino)benzoyl]-2,3,4,5-tetrahydroy-1H-benzazepine | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of this invention, citric acid, lactose, dicalcium phosphate, Pullonic F-68 and sodium laurylstearate are mixed. The mixture is screened with No. 60 screen and is granulated with an alcohol solution containing polyvinylpyrrolidone, carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 3
An injection preparation is prepared from the following components.

| Components | Amount |
| --- | --- |
| 4-Methyl-1-[4-(2,3-dimethylbenzoyl-amino)benzoyl]-2,3,4,5-tetrahydro-1H-1,4-benzodiazepine | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved in distilled water of half volume of the above with stirring at 80° C. The solution thus obtained is cooled to 40° C., and the active compound of this invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

REFERENCE EXAMPLE 1

To a solution of 1,2,3,4-tetrahydroquinoline (28.7 g) in acetone (400 ml) and water (200 ml) is added potassium carbonate (38.8 g), and thereto is added p-nitrobenzoyl chloride (40 g) under ice-cooling and the mixture is stirred at room temperature overnight. To the reaction mixture is added a suitable amount of water. The precipitated crystal is collected by filtration and dried to give 1-(4-nitrobenzoyl)-1,2,3,4-tetrahydroquinoline (40.8 g) as white powder, m.p. 86°–88° C.

REFERENCE EXAMPLE 2

To a solution of 10% Pd—C (5 g) in ethanol (500 ml) is added 1-(4-nitrobenzoyl)-1,2,3,4-tetrahydroquinoline (53.4 g) and the mixture is subjected to catalytic reduction at ordinary temperature under atmospheric pressure of hydrogen. After the reduction, 10% Pd—C is removed by filtration, and the filtrate is concentrated under reduced pressure to give 1-(4-aminobenzoyl)-1,2,3,4-tetrahydroquinoline (46.7 g) as yellow powder, m.p. 185°–188° C.

REFERENCE EXAMPLE 3

Using the suitable starting materials, the following compounds are obtained in the same manner as in Reference Example 1.

1-(3-Nitrobenzoyl)-1,2,3,4-tetrahydroquinoline, white powder, m.p. 134°–136° C.

1-(2-Nitrobenzoyl)-1,2,3,4-tetrahydroquinoline, yellow powder, m.p. 152°–154° C.

3-Methyl-1-(4-nitrobenzoyl)-1,2,3,4-tetrahydroquinoline, yellow powder, m.p. 109°–110° C.

4-Methyl-1-(4-nitrobenzoyl)-1,2,3,4-tetrahydroquinoline, yellow powder, m.p. 134°–136° C.

2-Methyl-1-(4-nitrobenzoyl)-1,2,3,4-tetrahydroquinoline, yellow powder, m.p. 143°–145° C.

1-(4-Nitrobenzoyl)-2,3,4,5-tetrahydro-1H-benzazepine, yellow powder, m.p. 143°–145° C.

1-(3-Methyl-4-nitrobenzoyl)-2,3,4,5-tetrahydro-1H-benzazepine, white powder, m.p. 100°–102° C.

1-(3-Methoxy-4-nitrobenzoyl)-2,3,4,5-tetrahydro-1H-benzazepine, yellow powder, m.p. 146°–148° C.

1-(4-Nitrobenzoyl)-1,2,3,4,5,6-hexahydrobenzazocine, white powder, m.p. 83°–85° C.

1-(4-Nitrobenzoyl)-3,4-dihydro-2H-1,4-benzoxazine, yellow powder, m.p. 167°–169° C.

1-(4-Nitrobenzoyl)-1,2,3,5-tetrahydro-4,1-benzoxazepine, yellow powder, m.p. 196°–198° C.

1-(4-Nitrobenzoyl)-4-methyl-1,2,3,4-tetrahydroquinoxaline, brown powder $^1$H-NMR (CDCl$_3$) δ: 3.03 (3H, s), 3.54 (2H, t, J=5.7 Hz), 4.06 (2H, t, J=5.7 Hz), 6.2–6.5 (2H, m), 6.70 (1H, d, J=8.2 Hz), 6.9–7.1 (1H, m), 7.54 (2H, d, J=8.8 Hz), 8.13 (2H, d, J=8.8 Hz)

1-(4-Nitrobenzoyl)-5-methyl-2,3,4,5-tetrahydro-1H-1,5-benzodiazepine, yellow oil $^1$H-NMR (CDCl$_3$) δ: 1.7–2.0 (1H, m), 2.0–2.3 (1H, m), 2.8–3.0 (1H, m), 2.98 (3H, s), 3.0–3.2 (1H, m), 3.4–3.6 (1H, m), 4.6–4.8 (1H, m), 6.5–6.7 (2H, m), 6.94 (1H, d, J=8.1 Hz), 7.1–7.2 (1H, m), 7.33 (2H, d, J=8.9 Hz), 7.97 (2H, d, J=8.9 Hz)

1-(4-Nitrobenzoyl)-4-methyl-2,3,4,5-tetrahydro-1H-1,4-benzodiazepine, brown oil $^1$H-NMR (CDCl$_3$) δ: 2.44 (3H, s), 3.0–3.3 (3H, m), 3.77 (1H, d, J=13.7 Hz), 4.06 (1H, d, J=13.6 Hz), 4.9–5.1 (1H, m), 6.59 (1H, d, J=7.7 Hz), 6.97 (1H, t, J=7.6 Hz), 7.15 (1H, t, J=7.4 Hz), 7.2–7.5 (3H, m), 8.03 (2H, d, J=8.8 Hz)

1-(3-Methoxy-4-nitrobenzoyl)-4-methyl-2,3,4,5-tetrahydro-1H-1,4-benzodiazepine, yellow powder, m.p. 146°–148° C.

1-(4-Nitrobenzoyl)-4-n-propyl-2,3,4,5-tetrahydro-1H-1,4-benzodiazepine, yellow powder, m.p. 131°–133° C.

1-(4-Nitrobenzoyl)-5-chloro-1,2,3,4-tetrahydroquinoline, white powder, m.p. 134°–136° C.

1-(4-Nitrobenzoyl)-6-methoxy-1,2,3,4-tetrahydroquinoline, yellow powder, m.p. 149°–151° C.

1-(4-Nitrobenzoyl)-6-methyl-1,2,3,4-tetrahydroquinoline, yellow powder, m.p. 109°–110° C.

1-(4-Nitrobenzoyl)-7-methoxy-1,2,3,4-tetrahydroquinoline, yellow powder, m.p. 139°–141° C.

1-(4-Nitrobenzoyl)-3-(4-methyl-1-piperazinyl)-1,2,3,4-tetrahydroquinoline, yellow amorphous $^1$H-NMR (CDCl$_3$) δ: 2.29 (3H, s), 2.35–3.20 (11H, m), 3.86–4.15 (2H, m), 6.48–6.63 (1H, m), 6.89 (1H, t, J=7.4 Hz), 7.05 (1H, t, J=7.4 Hz), 7.22 (1H, d, J=7.4 Hz), 7.52 (2H, d, J=8.8 Hz), 8.11 (2H, d, J=8.8 Hz)

1-(4-Nitrobenzoyl)-3-(1-pyrrolidinyl)-1,2,3,4-tetrahydroquinoline, yellow amorphous $^1$H-NMR (CDCl$_3$) δ: 1.70–1.95 (4H, m), 2.52–3.30 (7H, m), 3.80–4.22 (2H, m), 6.52 (1H, brs), 6.88 (1H, t, J=7.6 Hz), 6.96–7.11 (1H, m), 7.20 (2H, d, J=7.6 Hz), 7.54 (2H, d, J=8.8 Hz), 8.12 (2H, d, J=8.8 Hz)

1-(4-Nitrobenzoyl)-4-oxo-1,2,3,4-tetrahydroquinoline, yellow powder, m.p. 189°–190° C.

1-(4-Nitrobenzoyl)-3-hydroxymethyl-1,2,3,4-tetrahydroquinoline, yellow powder, m.p. 97°–100° C.

1-(4-Nitrobenzoyl)-3-ethoxycarbonyl-1,2,3,4-tetrahydroquinoline, pale yellow powder, m.p. 162°–163° C.

1-(4-Nitrobenzoyl)-4-dimethylamino-1,2,3,4-tetrahydroquinoline, light brown oil $^1$H-NMR (CDCl$_3$) δ: 1.80–2.02 (1H, m), 2.20–2.50 (7H, m), 3.47 (1H, t, J=4.9 Hz), 3.70–3.88 (1H, m), 4.06–4.25 (1H, m), 6.46 (1H, d, J=7.5 Hz), 6.89 (1H, t, J=7.5 Hz), 7.05 (1H, t, J=7.5 Hz), 7.34 (1H, d, J=7.5 Hz), 7.50 (2H, d, J=7.0 Hz), 8.10 (2H, d, J=7.0 Hz)

REFERENCE EXAMPLE 4

Using the suitable starting materials, the following compounds are obtained in the same manner as in Reference Example 2.

1-(3-Aminobenzoyl)-1,2,3,4-tetrahydroquinoline, white powder, m.p. 128°–130° C.

1-(2-Aminobenzoyl)-1,2,3,4-tetrahydroquinoline, yellow powder $^1$H-NMR (CDCl$_3$) δ: 2.01 (2H, quint, J=6.6 Hz), 2.81 (2H, t, J=6.6 Hz), 3.86 (2H, t, J=6.4 Hz), 4.6–4.8 (2H, m), 6.43 (1H, t, J=7 Hz), 6.66 (1H, d, J=8 Hz), 6.79 (1H, dd, J=1.4 Hz, J=7.6 Hz), 6.8–7.2 (5H, m)

3-Methyl-1-(4-aminobenzoyl)-1,2,3,4-tetrahydroquinoline, yellow powder, m.p. 197°–200° C.

4-Methyl-1-(4-aminobenzoyl)-1,2,3,4-tetrahydroquinoline, yellow powder, m.p. 197°–199° C.

2-Methyl-1-(4-aminobenzoyl)-1,2,3,4-tetrahydroquinoline, yellow powder, m.p. 204°–206° C.

1-(4-Aminobenzoyl)-2,3,4,5-tetrahydro-1H-benzazepine, yellow powder, m.p. 172°–174° C.

1-(3-Methyl-4-aminobenzoyl)-2,3,4,5-tetrahydro-1H-benzazepine, white powder, m.p. 156°–158° C.

1-(3-Methoxy-4-aminobenzoyl)-2,3,4,5-tetrahydro-1H-benzazepine, white powder, m.p. 165°–167° C.

1-(4-Aminobenzoyl)-1,2,3,4,5,6-hexahydrobenzazocine, white powder, m.p. 177°–179° C.

1-(4-Aminobenzoyl)-3,4-dihydro-2H-1,4-benzoxazine, white powder, m.p. 192°–194° C.

1-(4-Aminobenzoyl)-1,2,3,5-tetrahydro-4,1-benzoxazepine, yellow powder, m.p. 196°–198° C.

1-(4-Aminobenzoyl)-4-methyl-1,2,3,4-tetrahydroquinoxaline, yellow powder, m.p. 210°–212° C.

1-(4-Aminobenzoyl)-5-methyl-2,3,4,5-tetrahydro-1H-1,5-benzodiazepine, white powder, m.p. 159°–161° C.

1-(4-Aminobenzoyl)-4-methyl-2,3,4,5-tetrahydro-1H-1,4-benzodiazepine, brown powder, m.p. 169°–171° C.

1-(3-Methoxy-4-aminobenzoyl)-4-methyl-2,3,4,5-tetrahydro-1H-1,4-benzodiazepine, yellow oil $^1$H-NMR (CDCl$_3$) δ: 2.41 (3H, s), 2.9–3.2 (3H, m), 3.61 (3H, s), 3.6–4.2 (4H, m), 4.8–5.2 (1H, m), 6.38 (1H, d, J=8.1 Hz), 6.6–6.8 (3H, m), 6.9–7.2 (2H, m), 7.2–7.4 (1H, m)

1-(4-Aminobenzoyl)-4-n-propyl-2,3,4,5-tetrahydro-1H-1,4-benzazepine, brown powder, m.p. 151°–153° C.

1-(4-Aminobenzoyl)-5-chloro-1,2,3,4-tetrahydroquinoline, white powder, m.p. 174°–175° C.

1-(4-Aminobenzoyl)-6-methoxy-1,2,3,4-tetrahydroquinoline, pale yellow powder, m.p. 159°–160° C.

1-(4-Aminobenzoyl)-6-methyl-1,2,3,4-tetrahydroquinoline, white powder, m.p. 145°–146° C.

1-(4-Aminobenzoyl)-7-methoxy-1,2,3,4-tetrahydroquinoline, pale yellow powder, m.p. 150°–152° C.

1-(4-Aminobenzoyl)-3-(4-methyl-1-piperazinyl)-1,2,3,4-tetrahydroquinoline, light beige powder, m.p. 157°–159° C.

1-(4-Aminobenzoyl)-3-(1-pyrrolidinyl)-1,2,3,4-tetrahydroquinoline, pale yellow powder, m.p. 173°–174.5° C.

1-(4-Aminobenzoyl)-2,3-dihydro-4(1H)-quinolinone, pale yellow powder, m.p. 178°–180° C.

1-(4-Aminobenzoyl)-3-hydroxymethyl-1,2,3,4-tetrahydroquinoline, white powder, m.p. 179°–181° C.

1-(4-Aminobenzoyl)-3-ethoxycarbonyl-1,2,3,4-tetrahydroquinoline, pale yellow amorphous $^1$H-NMR (CDCl$_3$) δ: 1.21 (3H, t, J=7.1 Hz), 3.00–3.24 (3H, m), 3.70–4.30 (6H, m), 6.48 (2H, d, J=8.5 Hz), 6.69 (1H, d, J=7.9 Hz), 6.77–7.30 (5H, m)

1-(4-Aminobenzoyl)-4-dimethylamino-1,2,3,4-tetrahydroquinoline, brown oil $^1$H-NMR (CDCl$_3$) δ: 1.83–2.05 (1H, m), 2.13–2.30 (1H, m), 2.34 (6H, m), 3.55–3.83 (2H, m), 3.89 (1H, brs), 3.97–4.18 (1H, m), 6.47 (2H, d, J=7.0 Hz), 6.68 (1H, d, J=7.9 Hz), 6.85–7.05 (2H, m), 7.20 (2H, d, J=7.0 Hz), 7.37 (1H, d, J=7.4 Hz)

REFERENCE EXAMPLE 5

To terephthalic acid monomethyl ester (15 g) is added thionyl chloride (100 ml) and the mixture is refluxed for 2 hours. The thionyl chloride is distilled off under reduced pressure to give terephthalic acid chloride monomethyl ester. Separately, to a solution of 1,2,3,4-tetrahydroquinoline (14.4 g) in dichloromethane (200 ml) is added triethylamine (16.9 g) and further thereto is added slowly terephthalic acid chloride monomethyl ester obtained above under ice-cooling. Then, the mixture is stirred at room temperature for 1 hour. After completion of the reaction, water is added to the reaction mixture. The mixture is extracted with dichloromethane and dried over magnesium sulfate. The solvent is distilled off under reduced pressure and the resulting residue is purified by silica gel column chromatography (eluent; dichloromethane) to give 1-(4-methoxycarbonylbenzoyl)-1,2,3,4-tetrahydroquinoline (22.7 g) as white powder, m.p. 72°–74° C.

REFERENCE EXAMPLE 6

To a solution of 1-(4-methoxycarbonylbenzoyl)-1,2,3,4-tetrahydroquinoline (22.7 g) in methanol (300 ml) is added 5% aqueous sodium hydroxide solution (150 ml) and the mixture is refluxed for 2 hours. Methanol is distilled off under reduced pressure and the resulting residue is acidified with diluted hydrochloric acid, extracted with diethyl ether, and dried over magnesium sulfate. The solvent is distilled off under reduced pressure and the resulting crystal is collected by filtration to give 1-(4-carboxybenzoyl)-1,2,3,4-tetrahydroquinoline (13.2 g) as white powder, m.p. 181°–183° C.

REFERENCE EXAMPLE 7

Using the suitable starting materials, the following compounds are obtained in the same manner as in Reference Example 1.

5-Dimethylamino-1-(4-nitrobenzoyl)-2,3,4,5-tetrahydro-1H-benzazepine, pale yellow powder, m.p. 139°–142° C.

5-Dimethylamino-1-(3-methoxy-4-nitrobenzoyl)-2,3,4,5-tetrahydro-1H-benzazepine, white powder, m.p. 139°–141° C.

4-(N-Methyl-N-ethylamino)-1-(4-nitrobenzoyl)-1,2,3,4-tetrahydroquinoline, pale yellow oil $^1$H-NMR (CDCl$_3$) δ: 1.11 (3H, t, J=7.1 Hz), 1.90–2.25 (2H, m), 2.30 (3H, s), 2.57 (2H, q, J=7.1 Hz), 3.55–3.85 (2H, m), 4.00–4.21 (1H, m), 6.35–6.60 (1H, m), 6.80–6.98 (1H, t, J=7.9 Hz), 7.00–7.15 (1H, m), 7.33–7.60 (3H, m), 8.10 (2H, d, J=8.8 Hz)

4-Dimethylamino-1-(3-methoxy-4-nitrobenzoyl)-1,2,3,4-tetrahydroquinoline, brown oil $^1$H-NMR (CDCl$_3$) δ: 1.80–2.05 (1H, m), 2.33 (6H, s), 2.30–2.50 (1H, m), 3.40–3.52 (1H, m), 3.78 (3H, s), 3.70–3.88 (1H, m), 4.04–4.24 (1H, m), 6.52 (1H, d, J=8.2 Hz), 6.85–7.13 (4H, m), 7.28–7.38 (1H, m), 7.71 (1H, d, J=8.2 Hz)

1-(4-Nitrobenzoyl)-4-ethyl-2,3,4,5-tetrahydro-1H-1,4-benzodiazepine, yellow oil $^1$H-NMR (CDCl$_3$) δ: 1.16 (3H, t, J=7.1 Hz), 2.5–2.7 (2H, m), 3.0–3.3 (3H, m), 3.98 (2H, q, J=14 Hz), 4.8–5.0 (1H, m), 6.59 (1H, d, J=7.7 Hz), 6.96 (1H, t, J=7.7 Hz), 7.14 (1H, t, J=7.4 Hz), 7.2–7.4 (3H, m), 8.02 (2H, d, J=8.8 Hz)

1-(4-Nitrobenzoyl)-4-isopropyl-2,3,4,5-tetrahydro-1H-1,4-benzodiazepine, yellow powder, m.p. 222°–223° C.

1-(4-Nitrobenzoyl)-4-cyclohexyl-2,3,4,5-tetrahydro-1H-1,4-benzodiazepine, brown oil $^1$H-NMR (CDCl$_3$) δ: 1.0–1.5 (5H, m), 1.5–2.1 (5H, m), 2.4–2.7 (1H, m), 2.9–3.3 (3H, m), 3.94 (2H, s), 4.9–5.1 (1H, m), 6.57 (1H, d, J=7.7 Hz), 6.8–7.0 (1H, m), 7.0–7.2 (1H, m), 7.2–7.4 (3H, m), 8.01 (2H, d, J=8.8 Hz)

1-(4-Nitrobenzoyl)-5-methyl-1,2,3,4,5,6-hexahydro-1,5-benzodiazocine, yellow oil $^1$H-NMR (CDCl$_3$) δ: 1.5–2.1 (2H, m), 2.40 (3H, s), 2.3–2.6 (1H, m), 2.8–3.2 (2H, m), 3.50 (1H, d, J=13.4 Hz), 3.84 (1H, d, J=13.4 Hz), 4.8–5.0 (1H, m), 7.0–7.3 (4H, m), 7.41 (2H, d, J=8.9 Hz), 8.00 (2H, d, J=8.9 Hz)

1-(4-Nitrobenzoyl)-1,2,3,4-tetrahydro-5,1-benzoxazepine, white powder, m.p. 144.5°–145.5° C.

1-(2-Nitrobenzoyl)-4-methyl-2,3,4,5-tetrahydro-1H-1,4-benzodiazepine, yellow powder, m.p. 177°–180° C.

1-(3-Nitrobenzoyl)-4-methyl-2,3,4,5-tetrahydro-1H-1,4-benzodiazepine, yellow powder, m.p. 145°–146° C.

6-Fluoro-1-(4-nitrobenzoyl)-1,2,3,4-tetrahydroquinoline, yellow needles, m.p. 145°–146° C.

REFERENCE EXAMPLE 8

Using the suitable starting materials, the following compounds are obtained in the same manner as in Reference Example 2.

5-Dimethylamino-1-(4-aminobenzoyl)-2,3,4,5-tetrahydro-1H-benzazepine, white powder, m.p. 120°–122° C.

5-Dimethylamino-1-(3-methoxy-4-amino)-2,3,4,5-tetrahydro-1H-benzazepine, white powder, m.p. 121°–123° C.

4-(N-Methyl-N-ethylamino)-1-(4-aminobenzoyl)-1,2,3,4-tetrahydroquinoline, orange amorphous $^1$H-NMR (CDCl$_3$) δ: 1.11 (3H, t, J=7.1 Hz), 1.90–2.20 (2H, m), 2.28 (3H, s), 2.26 (2H, q, J=7.1 Hz), 3.60–4.25 (5H, m), 6.48 (2H, d, J=8.5 Hz), 6.69 (1H, d, J=7.9 Hz), 6.80–7.05 (2H, m), 7.24 (2H, d, J=8.5 Hz), 7.46 (1H, d, J=6.2 Hz)

4-Dimethylamino-1-(3-methoxy-4-aminobenzoyl)-1,2,3,4-tetrahydroquinoline, pale yellow amorphous $^1$H-NMR (CDCl$_3$) δ: 1.83–2.04 (1H, m), 2.15–2.32 (1H, m), 2.33 (6H, s), 3.50–3.82 (2H, m), 3.64 (3H, s), 3.95–4.18 (3H, m), 6.50 (1H, d, J=7.9 Hz), 6.65 (1H, dd, J=7.9 Hz, 1.1 Hz), 6.78–7.03 (4H, m), 7.34 (1H, dd, J=7.5 Hz, 1.5 Hz)

1-(4-Aminobenzoyl)-4-ethyl-2,3,4,5-tetrahydro-1H-1,4-benzodiazepine, white powder, m.p. 186°–188° C.

1-(4-Aminobenzoyl)-4-isopropyl-2,3,4,5-tetrahydro-1H-1,4-benzodiazepine, white powder, m.p. 191°–192° C.

1-(4-Aminobenzoyl)-4-cyclohexyl-2,3,4,5-tetrahydro-1H-1,4-benzodiazepine, white powder, m.p. 149.5°–150.5° C.

1-(4-Aminobenzoyl)-5-methyl-1,2,3,4,5,6-hexahydro-1,5-benzodiazocine, yellow powder, m.p. 143°–145° C.

1-(4-Aminobenzoyl)-1,2,3,4-tetrahydro-5,1-benzoxazepine, yellow powder, m.p. 163.5°–164.5° C.

1-(2-Aminobenzoyl)-4-methyl-2,3,4,5-tetrahydro-1H-1,4-benzodiazepine, yellow powder, m.p. 144°–146° C.

1-(3-Aminobenzoyl)-4-methyl-2,3,4,5-tetrahydro-1H-1,4-benzodiazepine, white powder, mp. 153°–155° C.

6-Fluoro-1-(4-aminobenzoyl)-1,2,3,4-tetrahydroquinoline, white powder, m.p. 160.5°–161.5° C.

REFERENCE EXAMPLE 9

Using the suitable starting materials, the following compounds are obtained in the same manner as in Reference Example 1.

1-(2-Chloro-4-nitrobenzoyl)-4-methyl-2,3,4,5-tetrahydro-1H-1,4-benzodiazepine $^1$H-NMR (CDCl$_3$) δ: 2.40 (3H, s), 2.96–3.33 (3H, m), 3.60–3.79 (1H, m), 3.96–4.23 (1H, m), 4.70–4.91 (1H, m), 6.80–7.43 (5H, m), 7.80–7.99 (1H, m), 8.08–8.21 (1H, m)

1-(3-Methyl-4-nitrobenzoyl)-4-methyl-2,3,4,5-tetrahydro-1H-1,4-benzodiazepine $^1$H-NMR (CDCl$_3$) δ: 2.43 (3H, s), 2.48 (3H, s), 2.92–3.28 (3H, m), 3.91 (2H, AB-q, J=13.9 Hz, 45.5 Hz), 4.77–5.01 (1H, m), 6.54–6.70 (1H, m), 6.88–7.37 (5H, m), 7.62–7.78 (1H, m)

5-Dimethylamino-1-(2-chloro-4-nitrobenzoyl)- 2,3,4,5-tetrahydro-1H-benzazepine $^1$H-NMR (CDCl$_3$) δ: 1.23–2.57 (10H, m), 2.68–5.15 (3H, m), 6.79–7.45 (4H, m), 7.49–8.39 (3H, m)

5-Oxo-1-(4-nitrobenzoyl)-2,3,4,5-tetrahydro-1H-benzazepine, white powder (ethyl acetate/n-hexane), m.p. 147°–148° C.

5-Hydroxy-1-(4-nitrobenzoyl)-2,3,4,5-tetrahydro-1H-benzazepine, white powder (ethyl acetate/n-hexane), m.p. 148°–150° C.

5-Methoxy-1-(4-nitrobenzoyl)-2,3,4,5-tetrahydro-1H-benzazepine, colorless amorphous $^1$H-NMR (CDCl$_3$) δ: 1.47–2.48 (4H, m), 2.70–3.10 (1H, m), 3.26–3.64 (3H, m), 4.29–5.12 (2H, m), 6.60 (1H, d, J=7.7 Hz), 6.88–7.67 (5H, m), 7.92–8.12 (2H, m)

5-Ethoxycarbonylmethoxy-1-(4-nitrobenzoyl)-2,3,4,5-tetrahydro-1H-benzazepine, white powder, m.p. 107°–108° C. (recrystallized from ethyl acetate/n-hexane)

5-(4-Bromobutoxy)-1-(4-nitrobenzoyl)-2,3,4,5-tetrahydro-1H-benzazepine, colorless oil $^1$H-NMR (CDCl$_3$) δ: 1.49–2.55 (8H, m), 2.72–3.07 (1H, m), 3.24–3.77 (4H, m), 4.40–5.15 (2H, m), 6.53–6.66 (1H, m), 6.91–7.06 (1H, m), 7.07–7.80 (4H, m), 7.94–8.13 (2H, m)

5-(4-Dimethylaminobutoxy)-1-(4-nitrobenzoyl)-2,3,4,5-tetrahydro-1H-benzazepine, colorless oil $^1$H-NMR (CDCl$_3$) δ: 1.51–1.88 (6H, m), 2.23–2.61 (4H, m), 2.27 (3H, s), 2.35 (3H, s), 2.74–3.14 (1H, m), 3.55–3.77 (2H, m), 4.48–5.11 (2H, m), 6.54–6.66 (1H, m), 6.91–7.04 (1H, m), 7.06–7.80 (4H, m), 7.93–8.11 (2H, m)

5-[4-(Phthalimid-1-yl)propoxy-1-(4-nitrobenzoyl)-2,3,4,5-tetrahydro-1H-benzazepine, colorless amorphous $^1$H-NMR (CDCl$_3$) δ: 1.48–2.56 (6H, m), 2.71–3.05 (1H, m), 3.40–4.05 (4H, m), 4.47–5.11 (2H, m), 6.50–6.64 (1H, m), 6.84–7.03 (1H, m), 7.03–7.20 (1H, m), 7.20–7.57 (2H, m), 7.57–7.93 (5H, m), 7.97–8.20 (2H, m)

5-Chloro-1-(4-nitrobenzoyl)-2,3,4,5-tetrahydro-1H-benzazepine, light brown powder $^1$H-NMR (CDCl$_3$) δ: 1.75–3.3 (4H, m), 4.6–6.25 (3H, m), 6.45–6.7 (1H, m), 6.8–7.5 (4H, m), 7.55–7.7 (1H, m), 7.9–8.1 (2H, m)

5-Oxo-1-(2-chloro-4-nitrobenzoyl)-2,3,4,5-tetrahydro-1H-benzazepine, pale yellow amorphous $^1$H-NMR (CDCl$_3$) δ: 1.95–2.45 (2H, m), 2.94 (1H, t, J=6 Hz), 3.05–5.3 (2H, m), 6.96–7.1 (1H, m), 7.12–7.5 (3H, m), 7.75–7.85 (1H, m), 7.95–8.1 (1H, m), 8.14 (1H, s)

4-Dimethylaminomethyl-1-(4-nitrobenzoyl)-1,2,3,4-tetrahydroquinoline, white powder, m.p. 117°–119° C.

3-Dimethylamino-1-(4-nitrobenzoyl)-2,3,4,5-tetrahydro-1H-benzazepine, yellow oil $^1$H-NMR (CDCl$_3$) δ: 1.5–1.7 (1H, m), 2.1–2.4 (1H, m), 2.42 (6H, s), 2.6–2.7 (1H, m), 2.8–3.0 (3H, m), 5.1–5.3 (1H, m), 6.62 (1H, d, J=7.8 Hz), 6.95 (1H, t, J=7.7 Hz), 7.14 (1H, t, J=7.5 Hz), 7.2–7.4 (3H, m), 8.00 (2H, d, J=8.9 Hz)

3-Dimethylamino-1-(3-methoxy-4-nitrobenzoyl)-2,3,4,5-tetrahydro-1H-benzazepine, yellow oil $^1$H-NMR (CDCl$_3$) δ: 1.5–1.7 (1H, m), 2.0–2.3 (1H, m), 2.41 (6H, s), 2.5–2.8 (1H, m), 2.8–3.0 (3H, m), 3.75 (3H, s), 5.1–5.3 (1H, m), 6.6–6.8 (2H, m), 6.9–7.3 (4H, m), 7.59 (1H, d, J=8.3 Hz)

4-(4-Nitrobenzoyl)-3,4-dihydro-2H-1,4-benzothiazine, yellow powder, m.p. 180°–182° C.

5-(4-Nitrobenzoyl)-2,3,4,5-tetrahydro-1,5-benzothiazepine, yellow powder, m.p. 162°–163° C.

REFERENCE EXAMPLE 10

Using the suitable starting materials, the following compounds are obtained in the same manner as in Reference Example 2.

1-(2-Chloro-4-aminobenzoyl)-4-methyl-2,3,4,5-tetrahydro-1H-1,4-benzodiazepine, white powder (recrystallized from methanol/diethyl ether), m.p. 194.5°–195.5° C.

1-(3-Methyl-4-aminobenzoyl)-4-methyl-2,3,4,5-tetrahydro-1H-1,4-benzodiazepine $^1$H-NMR (CDCl$_3$) δ: 2.01 (3H, s), 2.41 (3H, s), 2.82–3.21 (3H, m), 3.50–4.21 (4H, m), 4.78–5.14 (1H, m), 6.24–6.40 (1H, m), 6.59–6.82 (2H, m), 6.90–7.18 (3H, m), 7.19–7.34 (1H, m)

5-Dimethylamino-1-(2-chloro-4-aminobenzoyl)-2,3,4,5-tetrahydro-1H-benzazepine, white powder (recrystallized from dichloromethane/diethyl ether), m.p. 162°–164° C.

5-Dimethylamino-1-(2-methoxy-4-aminobenzoyl)-2,3,4,5-tetrahydro-1H-benzazepine (recrystallized from methanol/diethyl ether)

$^1$H-NMR (CDCl$_3$) δ: 1.23–2.80 (11H, m), 2.90–3.38 (1H, m), 3.50–5.19 (6H, m), 5.87–6.41 (2H, m), 6.65–7.56 (5H, m)

5-Methoxy-1-(4-aminobenzoyl)-2,3,4,5-tetrahydro-1H-benzazepine, white powder (recrystallized from ethyl acetate/n-hexane), m.p. 154°–155° C.

5-Ethoxycarbonylmethoxy-1-(4-aminobenzoyl)-2,3,4,5-tetrahydro-1H-benzazepine, white-powder (recrystallized from ethyl acetate/n-hexane), m.p. 231°–232° C.

5-(4-Dimethylaminobutoxy)-1-(4-aminobenzoyl)-2,3,4,5-tetrahydro-1H-benzazepine, colorless oil $^1$H-NMR (CDCl$_3$) δ: 1.47–1.83 (6H, m), 1.83–2.54 (4H, m), 2.29 (6H, s), 2.61–3.00 (1H, m), 3.36–3.76 (2H, m), 4.35–5.20 (2H, m), 6.27–6.48 (2H, m), 6.57–6.76 (1H, m), 6.90–7.61 (5H, m)

5-[4-(Phthalimid-1-yl)propoxy]-1-(4-aminobenzoyl)-2,3,4,5-tetrahydro-1H-benzazepine, colorless amorphous $^1$H-NMR (CDCl$_3$) δ: 1.30–2.47 (6H, m), 2.57–3.01 (1H, m), 3.30–4.06 (4H, m), 4.34–5.20 (2H, m), 6.30–6.53 (2H, m), 6.57–6.78 (1H, m), 6.87–7.57 (5H, m), 7.62–7.76 (2H, m), 7.76–7.97 (2H, m)

5-Chloro-1-(4-aminobenzoyl)-2,3,4,5-tetrahydro-1H-benzazepine, pale yellow amorphous $^1$H-NMR (CDCl$_3$) δ: 1.35–4.3 (7H, m), 4.55–6.7 (2H, m), 6.3–6.55 (2H, m), 6.6–6.8 (1H, m), 6.85–7.45 (5H, m)

5-Oxo-1-(4-aminobenzoyl)-2,3,4,5-tetrahydro-1H-benzazepine, pale yellow amorphous $^1$H-NMR (CDCl$_3$) δ: 1.95–2.35 (2H, m), 2.89 (2H, t, J=6.3 Hz), 3.0–5.3 (4H, m), 6.35–6.47 (2H, m), 6.72–6.83 (1H, m), 7.0–7.15 (2H, m), 7.18–7.32 (2H, m), 7.81–7.93 (1H, m)

5-Oxo-1-(2-chloro-4-aminobenzoyl)-2,3,4,5-tetrahydro-1H-benzazepine, white powder $^1$H-NMR (CDCl$_3$) δ: 1.85–2.3 (2H, m), 2.87 (2H, t, J=6.2 Hz), 3.1–4.75 (4H, m), 6.15–7.5 (6H, m), 7.65–7.9 (1H, m)

4-Dimethylaminomethyl-1-(4-aminobenzoyl)-1,2,3,4-tetrahydroquinoline, white powder, m.p. 123°–125° C.

3-Dimethylamino-1-(4-aminobenzoyl)-2,3,4,5-tetrahydro-1H-benzazepine, white powder, m.p. 175°–177° C.

3-Dimethylamino-1-(3-methoxy-4-aminobenzoyl)-2,3,4,5-tetrahydro-1H-benzazepine, yellow oil $^1$H-NMR (CDCl$_3$) δ: 1.5–1.7 (1H, m), 2.1–2.3 (1H, m), 2.3–2.6 (1H, m), 2.40 (6H, s), 2.7–3.0 (3H, m), 3.60 (3H, s), 3.8–4.0 (2H, br), 5.2–5.4 (1H, m), 6.37 (1H, d, J=8.2 Hz), 6.5–6.8 (3H, m), 6.9–7.4 (3H, m)

4-(4-Aminobenzoyl)-3,4-dihydro-2H-1,4-benzothiazine, yellow powder, m.p. 207°–210° C.

5-(4-Aminobenzoyl)-2,3,4,5-tetrahydro-1,5-benzothiazepine, yellow powder, m.p. 193°–195° C.

REFERENCE EXAMPLE 11

Using the suitable starting materials, the following compounds are obtained in the same manner as in Reference Example 1.

5-Carbamoyloxy-1-(4-nitrobenzoyl)-2,3,4,5-tetrahydro-1H-benzazepine, white powder, m.p. 243°–244° C. (recrystallized from ethyl acetate/diisopropyl ether)

5-Methylaminocarbonyloxy-1-(4-nitrobenzoyl)-2,3,4,5-tetrahydro-1H-benzazepine, white powder, m.p. 207°–208° C. (recrystallized from ethyl acetate/n-hexane)

5-Dimethylaminocarbonyloxy-1-(4-nitrobenzoyl)-2,3,4,5-tetrahydro-1H-benzazepine, white powder, m.p. 155°–156° C. (recrystallized from ethyl acetate/diisopropyl ether/n-hexane)

5-Methylidenyl-1-(4-nitrobenzoyl)-2,3,4,5-tetrahydro-1H-benzazepine, colorless prisms, m.p. 133.5°–134° C. (recrystallized from ethyl acetate/diisopropyl ether)

5-Oxo-6-methyl-1-(2-chloro-4-nitrobenzoyl)-2,3,4,5-tetrahydro-1H-benzazepine, colorless prisms, m.p. 90°–92° C. (recrystallized from ethanol)

1-(4-Nitrobenzoyl)-1,2,3,5-tetrahydro-4,1-benzothiazepine, yellow powder, m.p. 185°–187° C. (recrystallized from dichloromethane/diethyl ether)

5-Dimethylamino-1-(2-dimethylamino-4-nitrobenzoyl)-2,3,4,5-tetrahydro-1H-benzazepine, yellow powder, m.p. 123°–125° C. (recrystallized from diethyl ether/dichloromethane)

5-Oxo-1-(4-nitrobenzoyl)-2,3,4,5-tetrahydro-1H-1,4-benzodiazepine, white powder, m.p. 201.5°–202.5° C. (recrystallized from diethyl ether/dichloromethane)

5-Oxo-4-methyl-1-(4-nitrobenzoyl)-2,3,4,5-tetrahydro-1H-1,4-benzodiazepine, white powder, m.p. 136°–138° C. (recrystallized from diethyl ether/dichloromethane)

5-Dimethylamino-1-(3-methyl-4-nitrobenzoyl)-2,3,4,5-tetrahydro-1H-benzazepine, yellow oil
$^1$H-NMR (CDCl$_3$) δ: 1.16–3.18 (11H, m), 2.18 (3H, s), 3.40–5.15 (2H, m), 6.50–7.68 (6H, m), 7.70–7.84 (1H, m)

5-Dimethylamino-1-(2-methyl-4-nitrobenzoyl)-2,3,4,5-tetrahydro-1H-benzazepine, colorless amorphous
$^1$H-NMR (CDCl$_3$) δ: 1.19–2.86 (11H, m), 2.20 (3H, s), 2.94–3.24 (1H, m), 3.36–5.18 (1H, m), 6.49–8.20 (7H, m)

5-Dimethylamino-1-(2-fluoro-4-nitrobenzoyl)-2,3,4,5-tetrahydro-1H-benzazepine, yellow oil
$^1$H-NMR (CDCl$_3$) δ: 1.21–2.66 (10H, m), 2.66–5.11 (3H, m), 6.63–8.25 (7H, m)

5-Dimethylamino-1-(3-fluoro-4-nitrobenzoyl)-2,3,4,5-tetrahydro-1H-benzazepine, white powder, m.p. 152°–152.5° C. (recrystallized from chloroform/diethyl ether)

REFERENCE EXAMPLE 12

Using the suitable starting materials, the following compounds are obtained in the same manner as in Reference Example 2.

5-Carbamoyloxy-1-(4-aminobenzoyl)-2,3,4,5-tetrahydro-1H-benzazepine, white powder, m.p. 215°–216° C. (recrystallized from ethyl acetate/n-hexane)

5-Methylaminocarbonyloxy-1-(4-aminobenzoyl)-2,3,4,5-tetrahydro-1H-benzazepine, white powder, m.p. 192°–195° C. (recrystallized from ethyl acetate/n-hexane)

5-Dimethylaminocarbonyloxy-1-(4-aminobenzoyl)-2,3,4,5-tetrahydro-1H-benzazepine, white powder, m.p. 228°–230° C. (recrystallized from ethyl acetate/diisopropyl ether)

5-Methyl-1-(4-aminobenzoyl)-2,3,4,5-tetrahydro-1H-benzazepine, white powder, m.p. 155°–156° C. (recrystallized from ethyl acetate/n-hexane)

5-Oxo-6-methyl-1-(2-chloro-4-aminobenzoyl)-2,3,4,5-tetrahydro-1H-benzazepine, white powder, m.p. 193°–195° C. (recrystallized from ethanol)

1-(4-Aminobenzoyl)-1,2,3,5-tetrahydro-4,1-benzothiazepine, white powder, m.p. 179°–180° C. (recrystallized from dichloromethane/diethyl ether)

5-Dimethylamino-1-(2-dimethylamino-4-aminobenzoyl)-2,3,4,5-tetrahydro-1H-benzazepine, white powder, m.p. 163°–165° C. (recrystallized from diethyl ether/dichloromethane)

5-Oxo-1-(4-aminobenzoyl)-2,3,4,5-tetrahydro-1H-benzazepine, yellow powder, m.p. 195°–197° C. (recrystallized from diethyl ether/dichloromethane)

5-Oxo-4-methyl-1-(4-aminobenzoyl)-2,3,4,5-tetrahydro-1H-1,4-benzazepine, yellow powder, m.p. 190°–192° C. (recrystallized from diethyl ether/dichloromethane)

5-Dimethylamino-1-(2-ethoxy-4-aminobenzoyl)-2,3,4,5-tetrahydro-1H-benzazepine, white powder, m.p. 111°–114° C. (recrystallized from diethyl ether)

5-Dimethylamino-1-(3-methyl-4-aminobenzoyl)-2,3,4,5-tetrahydro-1H-benzazepine, yellow oil
$^1$H-NMR (CDCl$_3$) δ: 0.66–2.56 (14H, m), 2.93–5.22 (4H, m), 6.23–7.80 (7H, m)

5-Dimethylamino-1-(2-methyl-4-aminobenzoyl)-2,3,4,5-tetrahydro-1H-benzazepine, white powder, m.p. 154°–156° C. (recrystallized from methanol/diethyl ether)

5-Dimethylamino-1-(2-fluoro-4-aminobenzoyl)-2,3,4,5-tetrahydro-1H-benzazepine, white powder, m.p. 161°–163° C. (recrystallized from dichloromethane/diethyl ether)

5-Dimethylamino-1-(3-fluoro-4-aminobenzoyl)-2,3,4,5-tetrahydro-1H-benzazepine, white powder, m.p. 156°–157° C. (recrystallized from methanol/diethyl ether)

5-Oxo-1-(2-methoxy-4-aminobenzoyl)-2,3,4,5-tetrahydro-1H-benzazepine, colorless prisms, m.p. 160°–160.5° C. (recrystallized from methanol/diethyl ether)

Example 1

To a solution of 1,2,3,4-tetrahydroquinoline (28.7 g) in acetone (400 ml) and water (200 ml) is added potassium carbonate (38.8 g) and further thereto is added 4-benzoylaminobenzoyl chloride (56 g) under ice-cooling. The mixture is stirred at room temperature overnight. Water is added to the reaction mixture, and the mixture is extracted with dichloromethane. The extract is dried over magnesium sulfate, and the solvent is distilled off under reduced pressure. The resulting residue is purified by silica gel column chromatography and recrystallized from methanol to give 1-[4-(benzoylamino)benzoyl]-1,2,3,4-tetrahydroquinoline (57 g) as white powder, m.p. 202.5°–203.5° C.

Using the suitable starting materials, the compounds as shown in the following Table 1 are obtained in the same manner as in Example 1.

TABLE 1
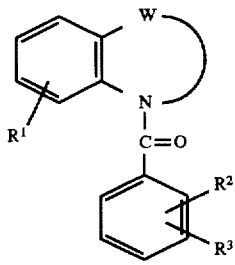
Example 2
Structure
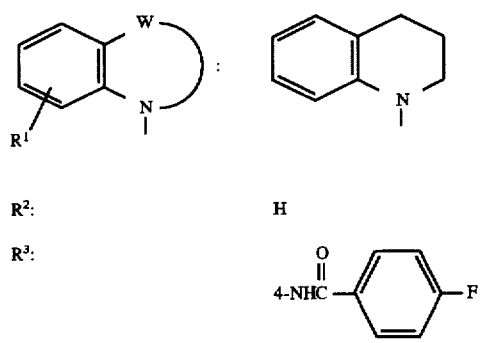
R²: H
R³: 4-NHC(=O)-C₆H₄-F (4-position)
Crystalline form: Light yellow powder
Recrystallization solvent: Methanol
Melting Point: 198.5–199.5° C.
Form: Free
Example 3
Structure
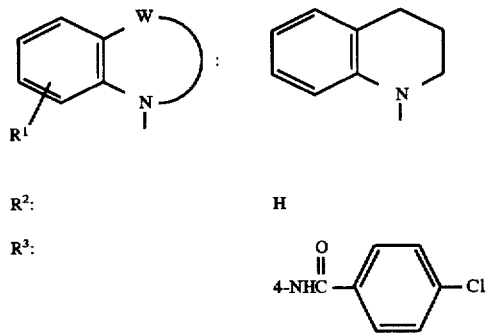
R²: H
R³: 4-NHC(=O)-C₆H₄-Cl (4-position)
Crystalline form: White powder
Recrystallization solvent: Methanol
Melting Point: 200.5–201.5° C.
Form: Free
Example 4
Structure
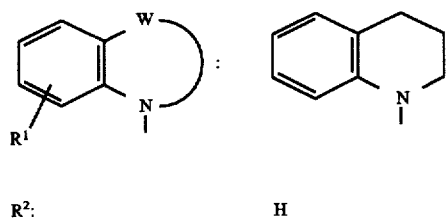
R²: H TABLE 1-continued

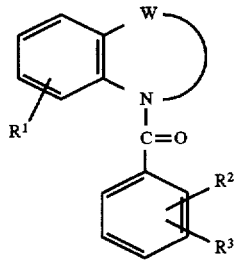

R³:

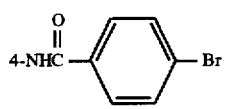
4-NHC—⟨benzene⟩—Br

Crystalline form: Yellow powder
Recrystallization solvent: Methanol
Melting Point: 206–207° C.
Form: Free Example 5

Structure

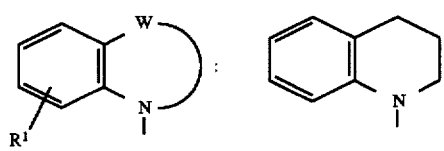

R²: H

R³:

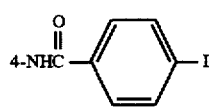
4-NHC—⟨benzene⟩—I

Crystalline form: Yellow powder
Recrystallization solvent: Methanol
Melting Point: 216–217° C.
Form: Free Example 6

Structure

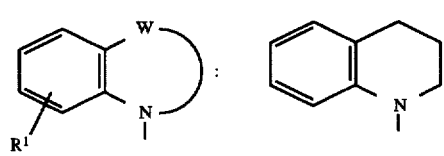

R²: H

R³:

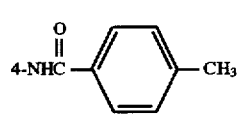
4-NHC—⟨benzene⟩—CH₃

Crystalline form: White powder
Recrystallization solvent: Methanol
Melting Point: 202–203° C.
Form: Free TABLE 1-continued
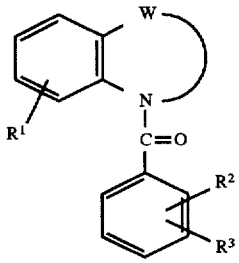
Example 7
Structure
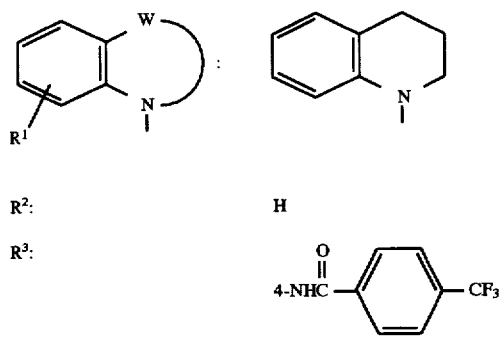
R²: H
R³: 
4-NHC(=O)—C₆H₄—CF₃
Crystalline form: White powder
Recrystallization solvent: Methanol
Melting Point: 212–213° C.
Form: Free
Example 8
Structure
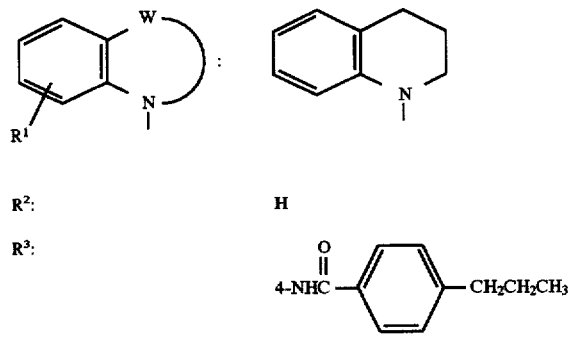
R²: H
R³:
4-NHC(=O)—C₆H₄—CH₂CH₂CH₃
Crystalline form: White powder
Recrystallization solvent: Methanol
Melting Point: 167.5–168.5° C.
Form: Free
Example 9
Structure
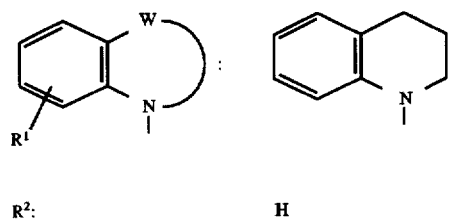
R²: H TABLE 1-continued

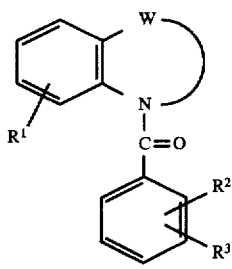

R³:

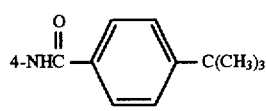

Crystalline form: White powder
Recrystallization solvent: Methanol
Melting Point: 205–206° C.
Form: Free Example 10

Structure

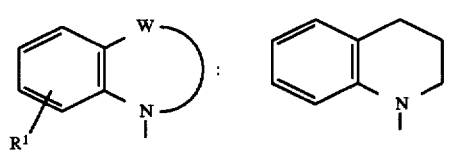

R²: H

R³:

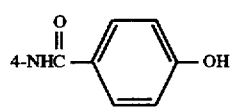

Crystalline form: White powder
Recrystallization solvent: Methanol
Melting Point: >300° C.
NMR analysis: 1)
Form: Free Example 11

Structure

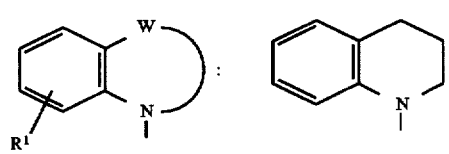

R²: H

R³:

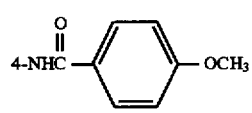

Crystalline form: Yellow powder
Recrystallization solvent: Methanol
Melting Point: 176–177° C.
Form: Free

TABLE 1-continued
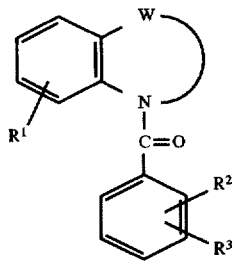
Example 12
Structure
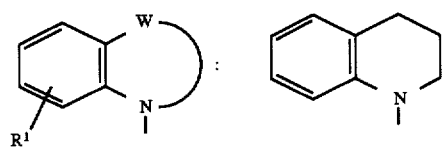
R²: H
R³:
Crystalline form: White powder
Recrystallization solvent: Methanol
Melting Point: 219–220° C.
Form: Free
Example 13
Structure
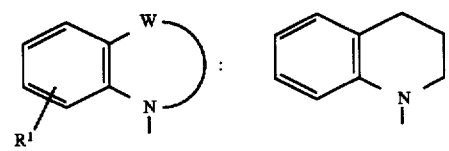
R²: H
R³:
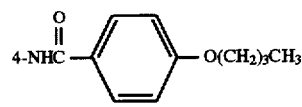
Crystalline form: White powder
Recrystallization solvent: Methanol
Melting Point: 193–194° C.
Form: Free
Example 14
Structure
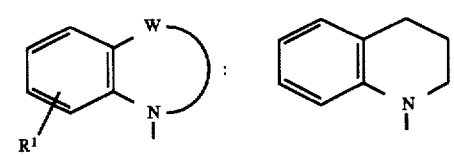
R²: H TABLE 1-continued
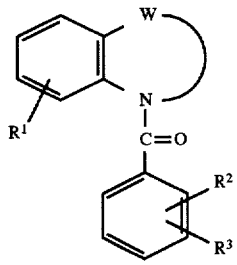
R³:
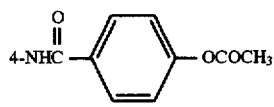
Crystalline form: White powder
Recrystallization solvent: Methanol
Melting Point: 232–233° C.
Form: Free
Example 15
Structure
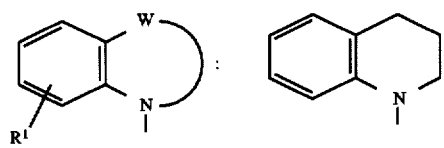
R²: H
R³:
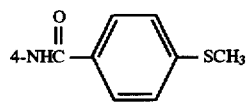
Crystalline form: White powder
Recrystallization solvent: Methanol
Melting Point: 209–210° C.
Form: Free
Example 16
Structure
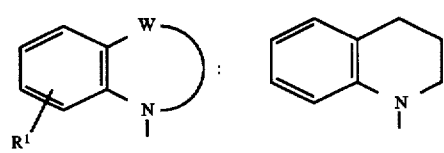
R²: H
R³:
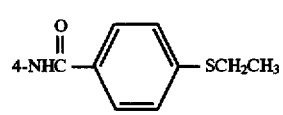
Crystalline form: White powder
Recrystallization solvent: Methanol
Melting Point: 184.5–185.5° C.
Form: Free TABLE 1-continued
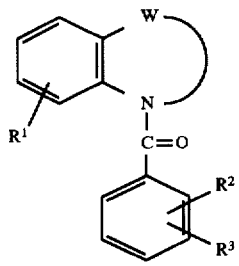
Example 17
Structure
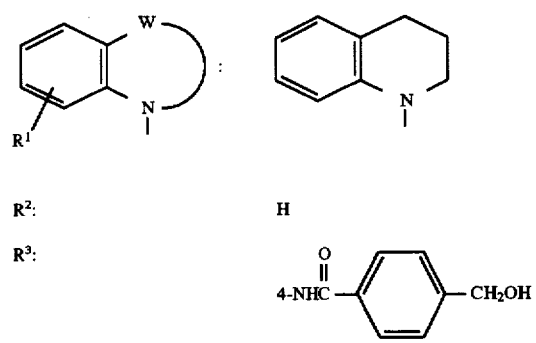
R²: H
R³: 4-NHC(=O)—C₆H₄—CH₂OH
Crystalline form: White powder
Recrystallization solvent: Methanol
Melting Point: 224.5–225.5° C.
Form: Free
Example 18
Structure
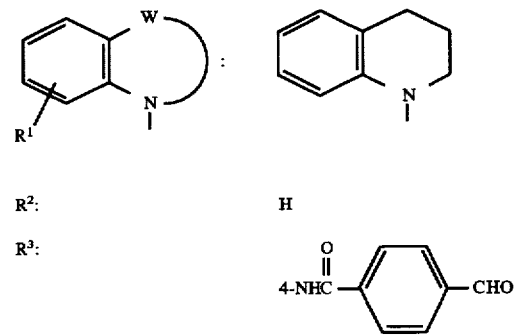
R²: H
R³: 4-NHC(=O)—C₆H₄—CHO
Crystalline form: White powder
Recrystallization solvent: Methanol
Melting Point: 220.5–221.5° C.
Form: Free
Example 19
Structure
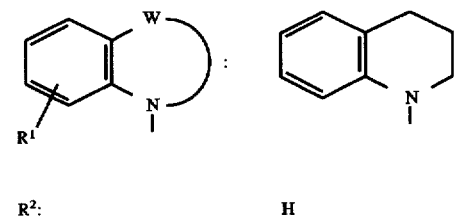
R²: H TABLE 1-continued

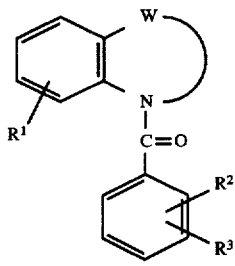

R³:

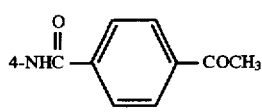

Crystalline form: Yellow powder
Recrystallization solvent: Methanol
Melting Point: 231–232° C.
Form: Free Example 20

Structure

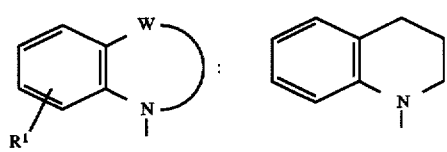

R²: H

R³:

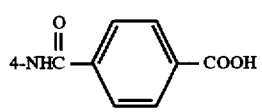

Crystalline form: White powder
Recrystallization solvent: Methanol
Melting Point: >300° C.
NMR analysis: 2)
Form: Free Example 21

Structure

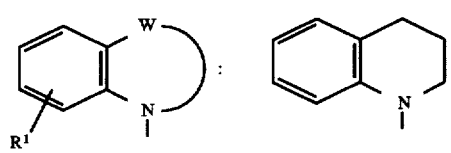

R²: H

R³:

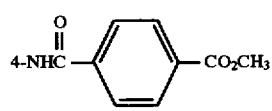

Crystalline form: White powder
Recrystallization solvent: Methanol
Melting Point: 208–209° C.
Form: Free TABLE 1-continued
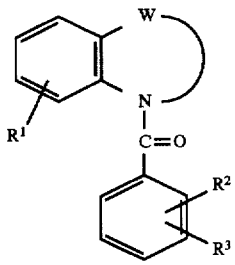
Example 22
Structure
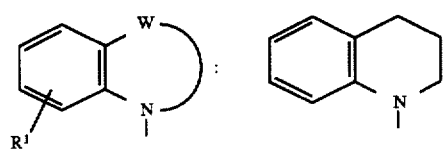
R²: H
R³:
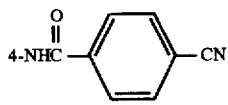
Crystalline form: White powder
Recrystallization solvent: Methanol
Melting Point: 234.5–235.5° C.
Form: Free
Example 23
Structure
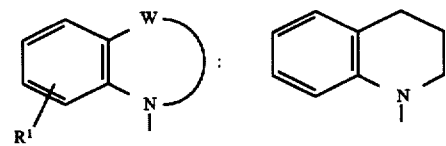
R²: H
R³:
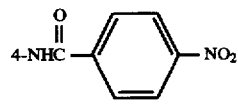
Crystalline form: Yellow powder
Recrystallization solvent: Methanol
Melting Point: 263.5–264.5° C.
Form: Free
Example 24
Structure
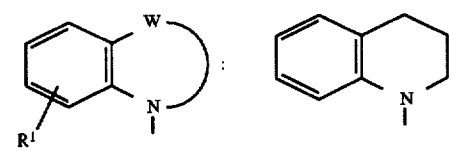
R²: H TABLE 1-continued
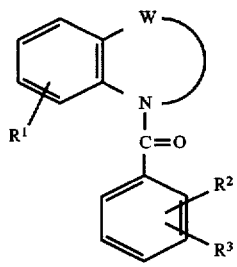
R³:
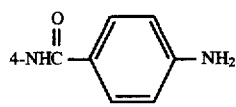
Crystalline form: White powder
Recrystallization solvent: Methanol
Melting Point: 237–238° C.
Form: Free
Example 25
Structure
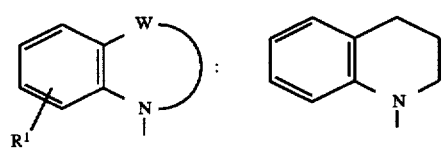
R²: H
R³:
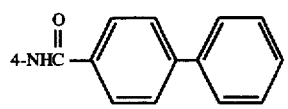
Crystalline form: White powder
Recrystallization solvent: Methanol
Melting Point: 234–235° C.
Form: Free
Example 26
Structure
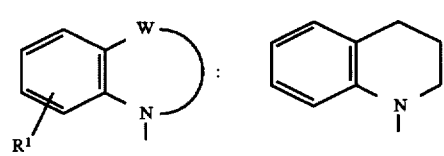
R²: H
R³:
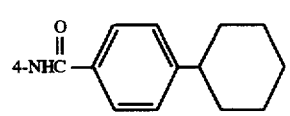
Crystalline form: White powder
Recrystallization solvent: Methanol
Melting Point: 236.5–237.5° C.
Form: Free TABLE 1-continued
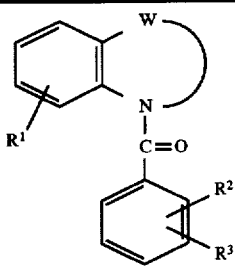
Example 27
Structure
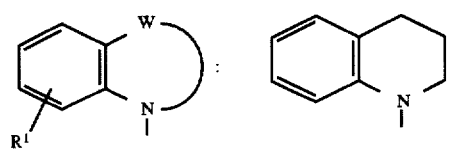
R²: H
R³: 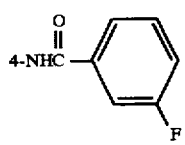
Crystalline form: White powder
Recrystallization solvent: Methanol
Melting Point: 206.5–207.5° C.
Form: Free
Example 28
Structure
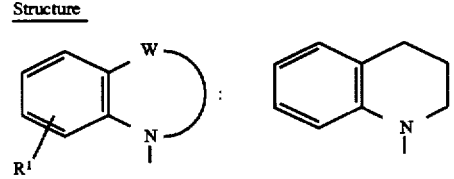
R²: H
R³: 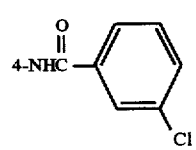
Crystalline form: White powder
Recrystallization solvent: Methanol
Melting Point: 210–211° C.
Form: Free
Example 29
Structure
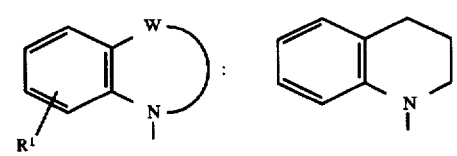
R²: H

TABLE 1-continued
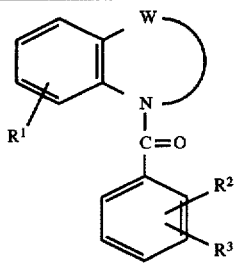
R³:
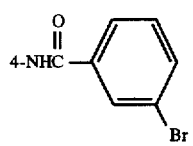
Crystalline form: White powder
Recrystallization solvent: Methanol
Melting Point: 210.5–211.5° C.
Form: Free
Example 30
Structure
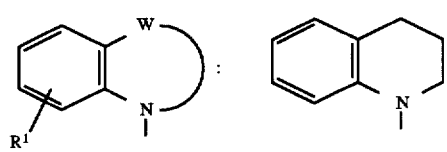
R²: H
R³:
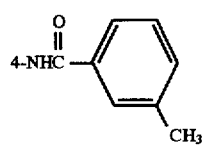
Crystalline form: White powder
Recrystallization solvent: Methanol
Melting Point: 178–179° C.
Form: Free
Example 31
Structure
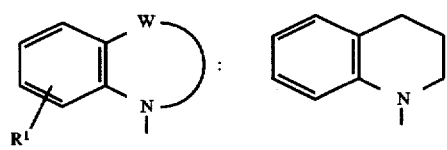
R²: H
R³:
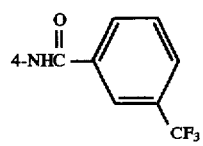
Crystalline form: White powder
Recrystallization solvent: Methanol
Melting Point: 192–193° C.
Form: Free

TABLE 1-continued
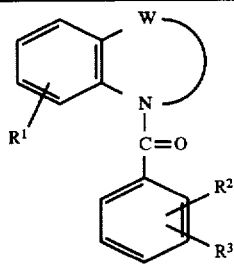
Example 32
Structure
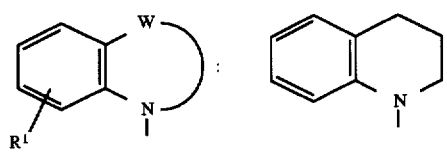
R²: H
R³: 
Crystalline form: White powder
Recrystallization solvent: Methanol
Melting Point: 217–218° C.
Form: Free
Example 33
Structure
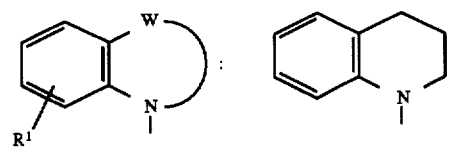
R²: H
R³: 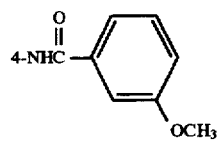
Crystalline form: White powder
Recrystallization solvent: Methanol
Melting Point: 143–144° C.
Form: Free
Example 34
Structure
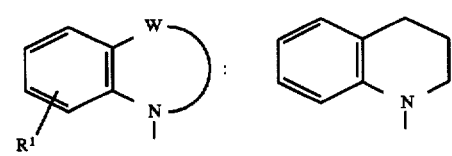
R²: H TABLE 1-continued
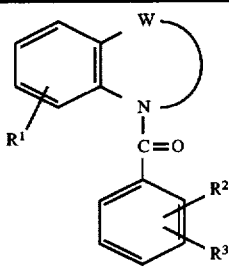
R³:
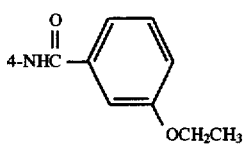
Crystalline form: White powder
Recrystallization solvent: Methanol
Melting Point: 170.5–171.5° C.
Form: Free
Example 35
Structure
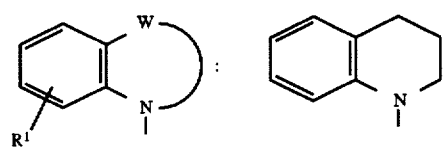
R²: H
R³:
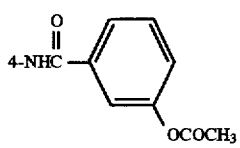
Crystalline form: White powder
Recrystallization solvent: Methanol
Melting Point: 169.5–170.5° C.
Form: Free
Example 36
Structure
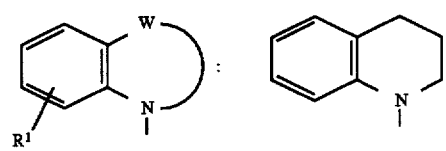
R²: H
R³:
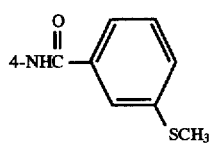
Crystalline form: White powder
Recrystallization solvent: Methanol
Melting Point: 174.5–175.5° C.
Form: Free TABLE 1-continued
Example 37
Structure
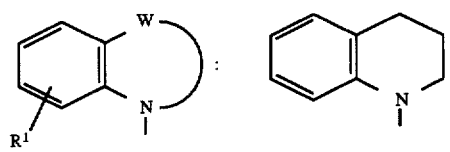
R²: H
R³:
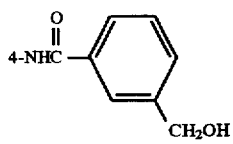
Crystalline form: White powder
Recrystallization solvent: Methanol
Melting Point: 148.5–149.5° C.
Form: Free
Example 38
Structure
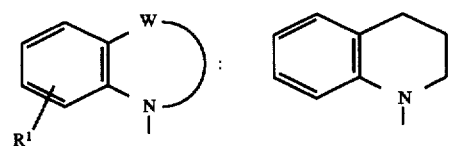
R²: H
R³:
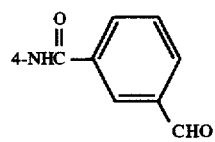
Crystalline form: White powder
Recrystallization solvent: Methanol
Melting Point: 165–166° C.
Form: Free
Example 39
Structure
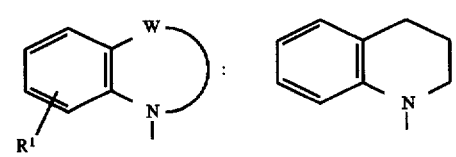
R²: H

TABLE 1-continued
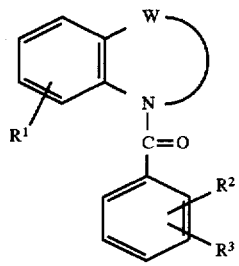
R³:
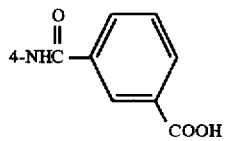
Crystalline form: White powder
Recrystallization solvent: Methanol
Melting Point: 243–244° C.
Form: Free
Example 40
Structure
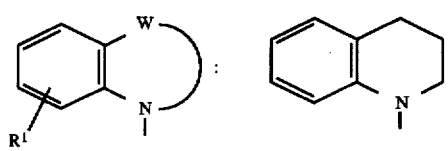
R²: H
R³:
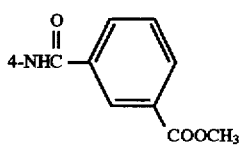
Crystalline form: White powder
Recrystallization solvent: Methanol
Melting Point: 199–200° C.
Form: Free
Example 41
Structure
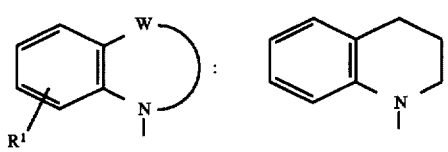
R²: H
R³:
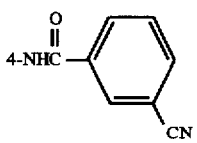
Crystalline form: White powder
Recrystallization solvent: Methanol
Melting Point: 232.5–233.5° C.
Form: Free TABLE 1-continued
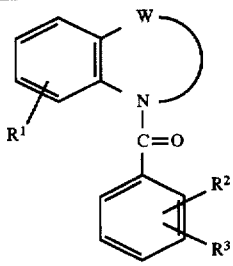
Example 42
Structure
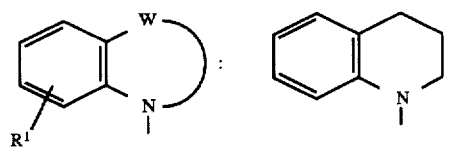
R²: H
R³:
4-NHC(=O)—C₆H₄—NO₂
Crystalline form: White powder
Recrystallization solvent: Methanol
Melting Point: 178.5–179.5° C.
Form: Free
Example 43
Structure
R²: H
R³:
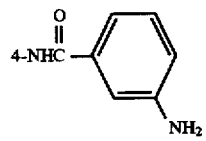
4-NHC(=O)—C₆H₄—NH₂
Crystalline form: White powder
Recrystallization solvent: Methanol
Melting Point: 205.5–206.5° C.
Form: Free
Example 44
Structure
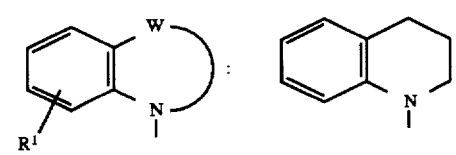
R²: H TABLE 1-continued
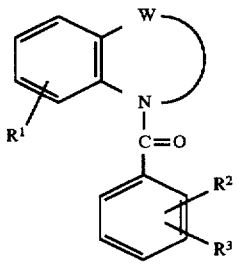
R³:
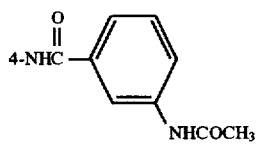
Crystalline form: White powder
Recrystallization solvent: Methanol
Melting Point: 234–235° C.
Form: Free
Example 45
Structure
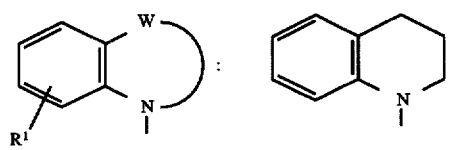
R²: H
R³:
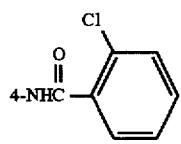
Crystalline form: White powder
Recrystallization solvent: Methanol
Melting Point: 225–226° C.
Form: Free
Example 46
Structure
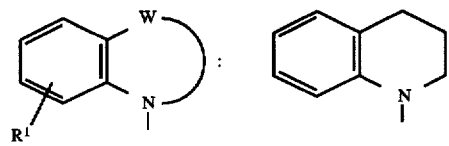
R²: H
R³:
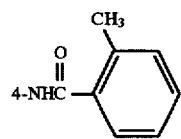
Crystalline form: White powder
Recrystallization solvent: Methanol
Melting Point: 224–225° C.
Form: Free TABLE 1-continued
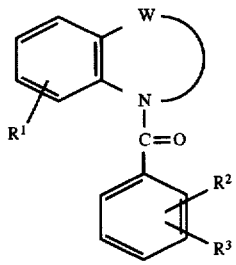
Example 47
Structure
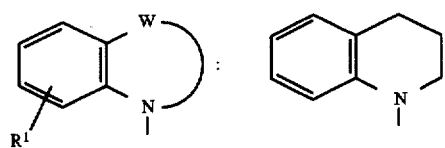
R²: H
R³: 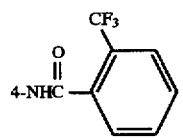
Crystalline form: White powder
Recrystallization solvent: Methanol
Melting Point: 236–237° C.
Form: Free
Example 48
Structure
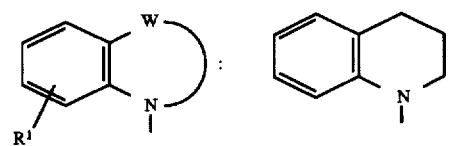
R²: H
R³: 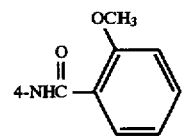
Crystalline form: Yellow powder
Recrystallization solvent: Methanol
Melting Point: 175.5–176.5° C.
Form: Free
Example 49
Structure
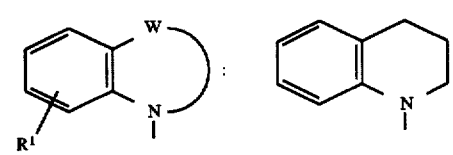
R²: H TABLE 1-continued
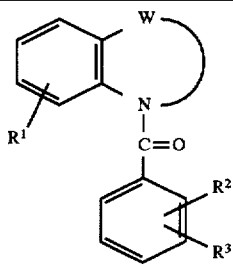
R³:
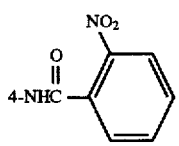
Crystalline form: White powder
Recrystallization solvent: Methanol
Melting Point: 231–232° C.
Form: Free
Example 50
Structure
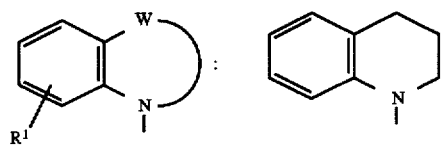
R²: H
R³:
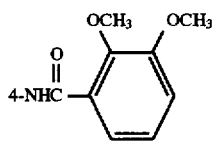
Crystalline form: Yellow powder
Recrystallization solvent: Methanol
Melting Point: 204–205° C.
Form: Free
Example 51
Structure
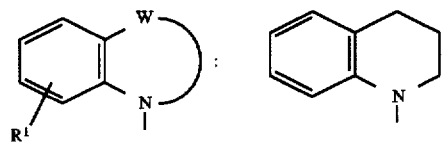
R²: H
R³:
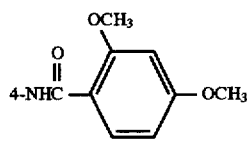
Crystalline form: White powder
Recrystallization solvent: Methanol
Melting Point: 190–191° C.
Form: Free TABLE 1-continued
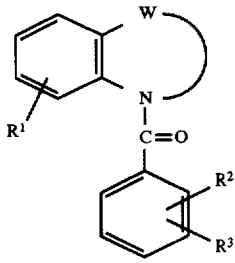
Example 52
Structure
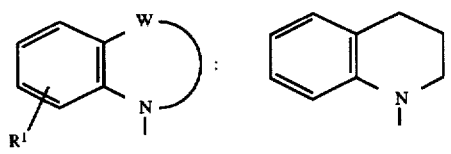
R²: H
R³: 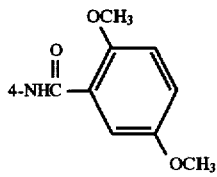
Crystalline form: White powder
Recrystallization solvent: Methanol
Melting Point: 156–157° C.
Form: Free
Example 53
Structure
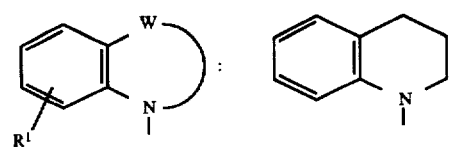
R²: H
R³: 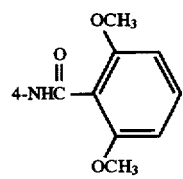
Crystalline form: White powder
Recrystallization solvent: Methanol
Melting Point: 200–201° C.
Form: Free TABLE 1-continued
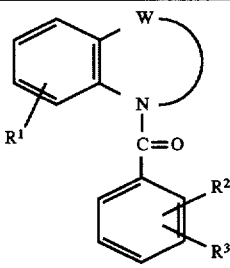
Example 54
Structure
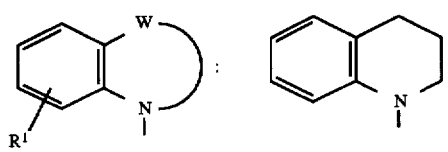
R²: H
R³:
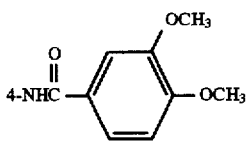
Crystalline form: White powder
Recrystallization solvent: Methanol
Melting Point: 206–207° C.
Form: Free
Example 55
Structure
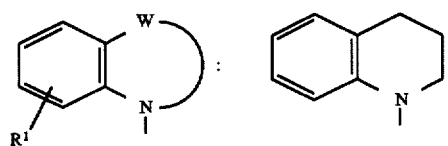
R²: H
R³:
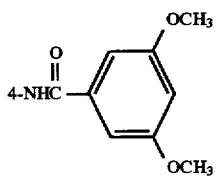
Crystalline form: Colorless amorphous
NMR analysis: 3)
Form: Free
Example 56
Structure
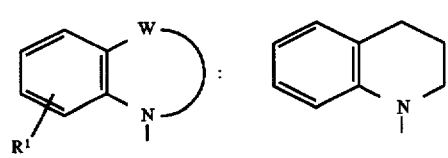

TABLE 1-continued
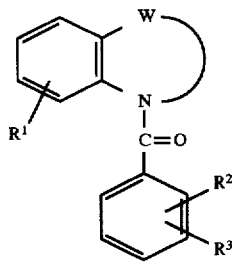
| R²: | H |
|---|---|
| R³: | 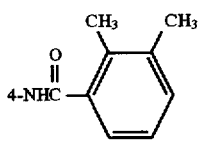 |
Crystalline form: White powder
Recrystallization solvent: Methanol
Melting Point: 215.5–216.5° C.
Form: Free
Example 57
Structure
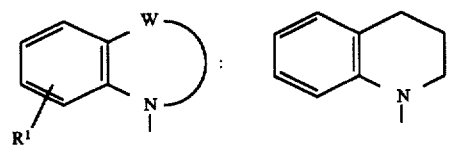
| R²: | H |
|---|---|
| R³: | 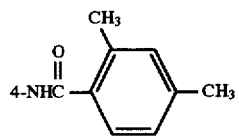 |
Crystalline form: White powder
Recrystallization solvent: Methanol
Melting Point: 189–190° C.
Form: Free
Example 58
Structure
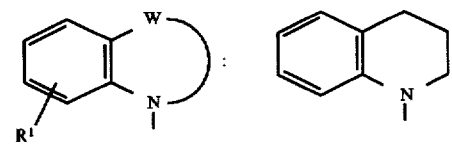
| R²: | H |
|---|---|
| R³: | 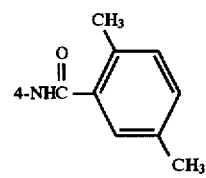 |
Crystalline form: White powder
Recrystallization solvent: Methanol
Melting Point: 203.5–204.5° C.

TABLE 1-continued
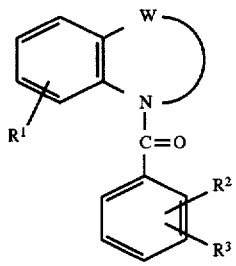
Form: Free
Example 59
Structure
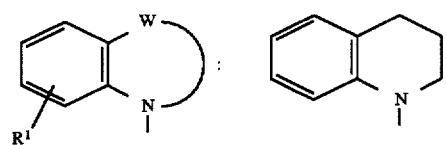
R²: H
R³:
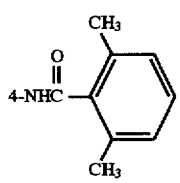
Crystalline form: Yellow powder
Recrystallization solvent: Methanol
Melting Point: 254.5–255.5° C.
Form: Free
Example 60
Structure
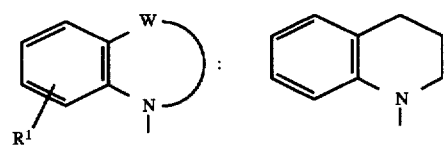
R²: H
R³:
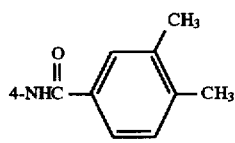
Crystalline form: Brown powder
Recrystallization solvent: Methanol
Melting Point: 182.5–183.5° C.
Form: Free TABLE 1-continued
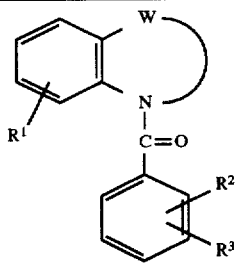
Example 61
Structure
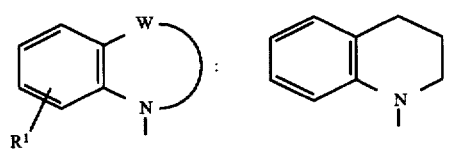
R²: H
R³:
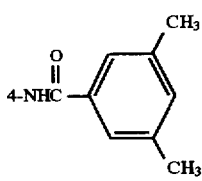
Crystalline form: Colorless amorphous
NMR analysis: 4)
Form: Free
Example 62
Structure
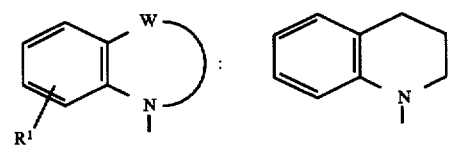
R²: H
R³:
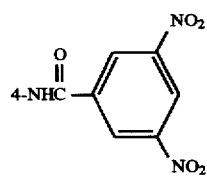
Crystalline form: White powder
Recrystallization solvent: Methanol
Melting Point: 263–264° C.
Form: Free
Example 63
Structure
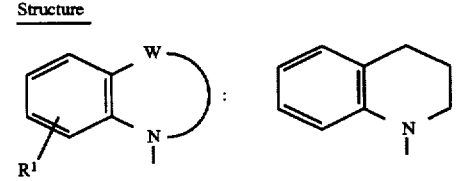

TABLE 1-continued

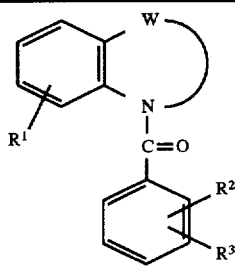

R²:   H

R³:
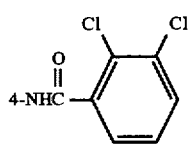

Crystalline form: White powder
Recrystallization solvent: Dichloromethane/ethanol
Melting Point: 217–218° C.
Form: Free Example 64

Structure

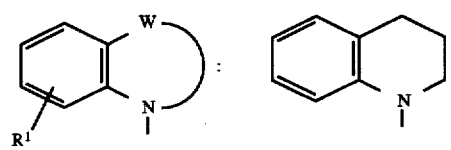

R²:   H

R³:
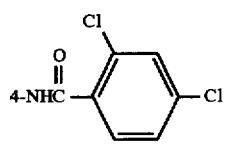

Crystalline form: White powder
Recrystallization solvent: Dichloromethane/ethanol
Melting Point: 183–184° C.
Form: Free Example 65

Structure

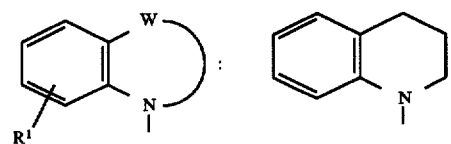

R²:   H

R³:
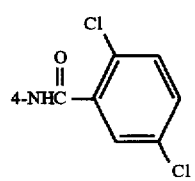

Crystalline form: Yellow powder
Recrystallization solvent: Dichloromethane/ethanol TABLE 1-continued
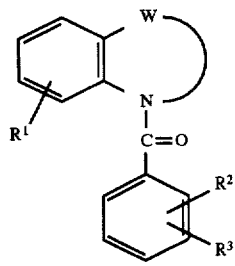
Melting Point: 207.5–208.5° C.
Form: Free
Example 66
Structure
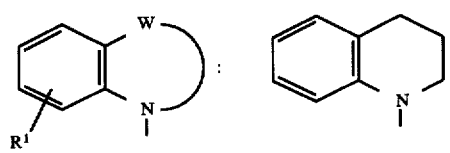
R²: H
R³:
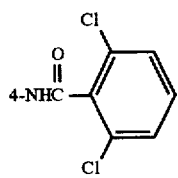
Crystalline form: Yellow powder
Recrystallization solvent: Dichloromethane/ethanol
Melting Point: 251–252° C.
Form: Free
Example 67
Structure
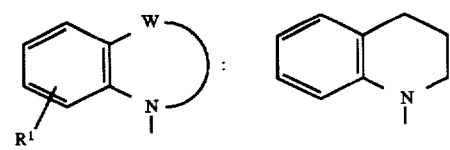
R²: H
R³:
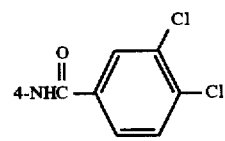
Crystalline form: White powder
Recrystallization solvent: Dichloromethane/ethanol
Melting Point: 208.5–209.5° C.
Form: Free TABLE 1-continued
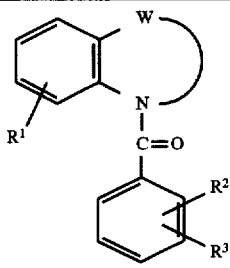
Example 68
Structure
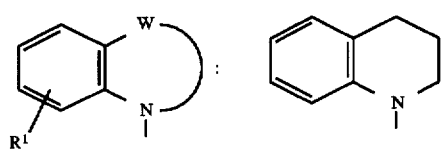
R²: H
R³:
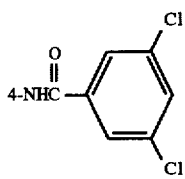
Crystalline form: White powder
Recrystallization solvent: Dichloromethane/ethanol
Melting Point: 231–232° C.
Form: Free
Example 69
Structure
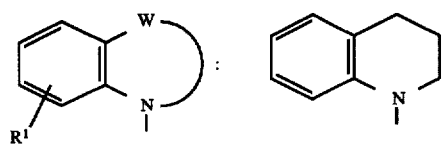
R²: H
R³:
Crystalline form: Colorless amorphous
NMR analysis: 5)
Form: Free
Example 70
Structure
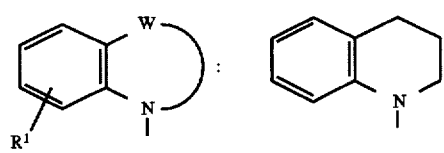
R²: H TABLE 1-continued

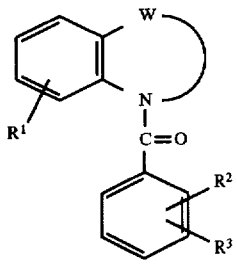

R³: 
$$\underset{4\text{-NHC(CH}_2)_2\text{CH}_3}{\overset{O}{\|}}$$

Crystalline form: White powder
Recrystallization solvent: Methanol
Melting Point: 134–135° C.
Form: Free Example 71

Structure

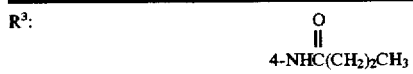

R²: H

R³: 
$$\underset{4\text{-NHC(CH}_2)_4\text{CH}_3}{\overset{O}{\|}}$$

Crystalline form: Yellow powder
Recrystallization solvent: Methanol
Melting Point: 115–116° C.
Form: Free Example 72

Structure

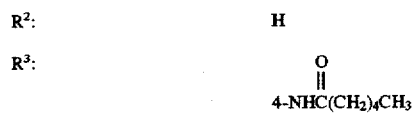

R²: H

R³: 
$$\underset{4\text{-NHCCH}_2\text{C(CH}_3)_3}{\overset{O}{\|}}$$

Crystalline form: White powder
Recrystallization solvent: Methanol
Melting Point: 178.5–179.5° C.
Form: Free Example 73

Structure

TABLE 1-continued

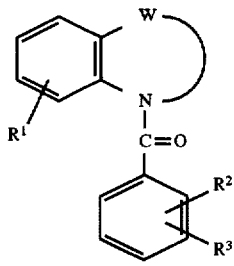

R²: H

R³:  4-NHCCH(CH₃)₂
       ‖
       O

Crystalline form: White powder
Recrystallization solvent: Methanol
Melting Point: 182.5–183.5° C.
Form: Free

Example 74

Structure

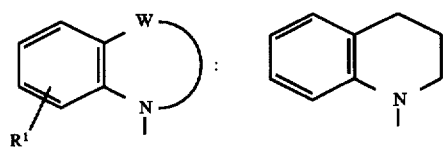

R²: H

R³:  4-NHCC(CH₃)₃
       ‖
       O

Crystalline form: White powder
Recrystallization solvent: Methanol
Melting Point: 164–165° C.
Form: Free

Example 75

Structure

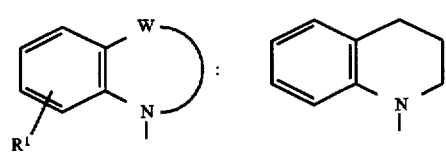

R²: H

R³:  4-NHCCH₂—⟨cyclohexyl⟩
       ‖
       O

Crystalline form: Colorless amorphous
NMR analysis: 6)
Form: Free

TABLE 1-continued
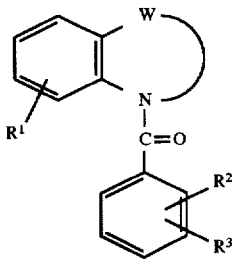
Example 76
Structure
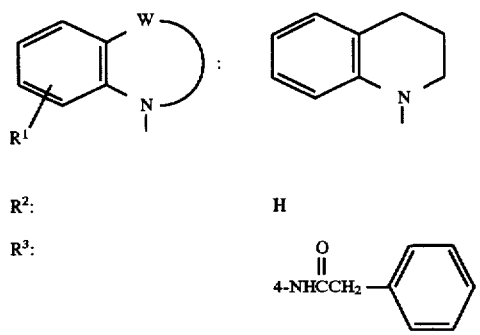
R²: H
R³: 4-NHCCH₂—⌬  (with C=O)
Crystalline form: Yellow amorphous
NMR analysis: 7)
Form: Free
Example 77
Structure
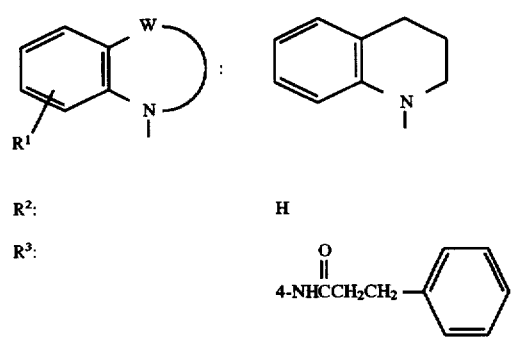
R²: H
R³: 4-NHCCH₂CH₂—⌬  (with C=O)
Crystalline form: White powder
Recrystallization solvent: Methanol
Melting Point: 155–156° C.
Form: Free
Example 78
Structure
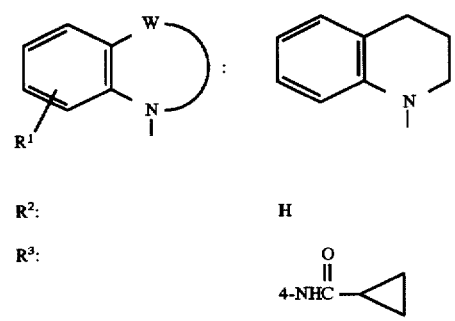
R²: H
R³: 4-NHC—▷ (with C=O)

TABLE 1-continued

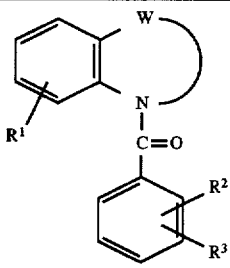

Crystalline form: White powder
Recrystallization solvent: Methanol
Melting Point: 182.5–183.5° C.
Form: Free Example 79

Structure

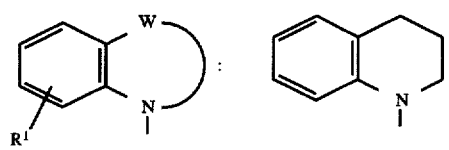

R²:  H

R³:

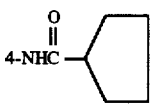

Crystalline form: White powder
Recrystallization solvent: Methanol
Melting Point: 164.5–165.5° C.
Form: Free Example 80

Structure

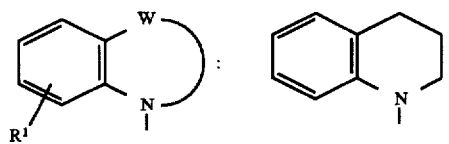

R²:  H

R³:

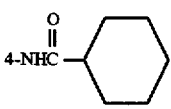

Crystalline form: White powder
Recrystallization solvent: Methanol
Melting Point: 165–167° C.
Form: Free Example 81

Structure

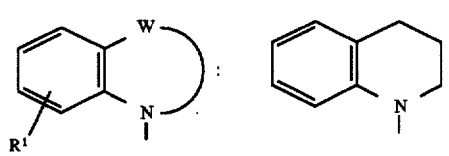

TABLE 1-continued
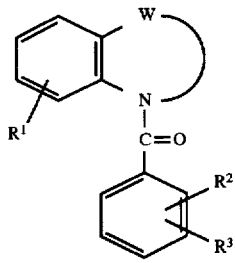
R²: H
R³: 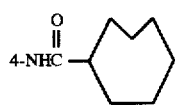
Crystalline form: White powder
Recrystallization solvent: Methanol
Melting Point: 124–125° C.
Form: Free
Example 82
Structure
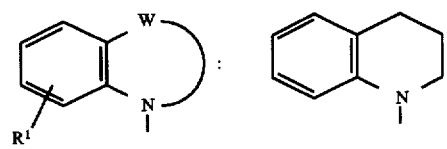
R²: H
R³: 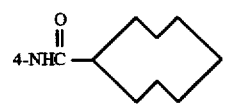
Crystalline form: White powder
Recrystallization solvent: Methanol
Melting Point: 140.5–141.5° C.
Form: Free
Example 83
Structure
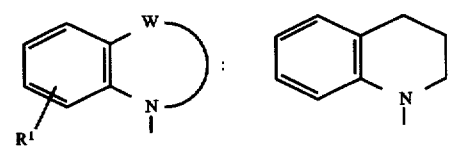
R²: H
R³: 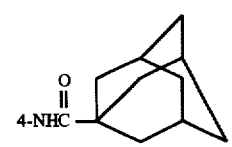
Crystalline form: Colorless amorphous
NMR analysis: 8)
Form: Free TABLE 1-continued
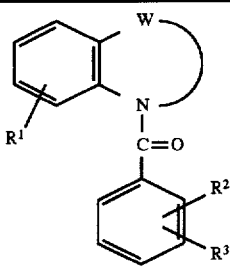
Example 84
Structure
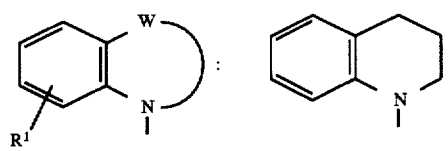
R²: H
R³:
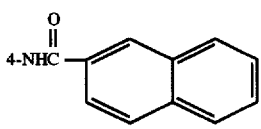
Crystalline form: White powder
Recrystallization solvent: Methanol
Melting Point: 211–212° C.
Form: Free
Example 85
Structure
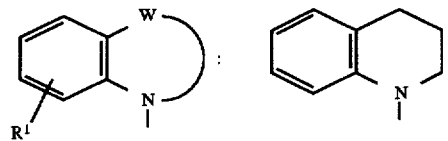
R²: H
R³:
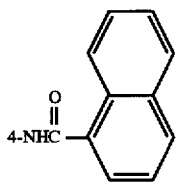
Crystalline form: White powder
Recrystallization solvent: Methanol
Melting Point: 178–179° C.
Form: Free
Example 86
Structure
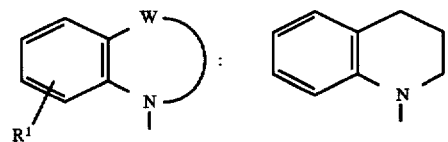

TABLE 1-continued

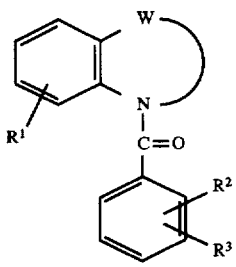

R²: H

R³: 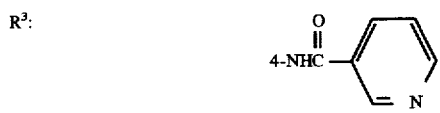

Crystalline form: White powder
Recrystallization solvent: Methanol
Melting Point: 212.5–213.5° C.
Form: Free Example 87

Structure

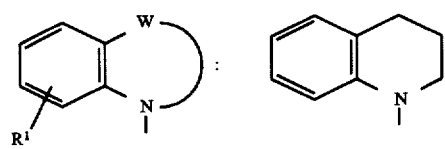

R²: H

R³: 

Crystalline form: White powder
Recrystallization solvent: Methanol
Melting Point: 193–194° C.
Form: Free Example 88

Structure

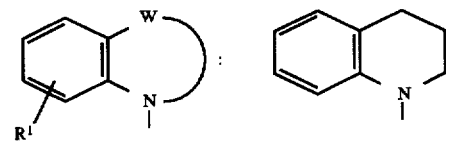

R²: H

R³: 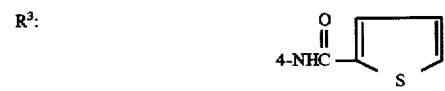

Crystalline form: White powder
Recrystallization solvent: Methanol
Melting Point: 203–204° C.
Form: Free TABLE 1-continued
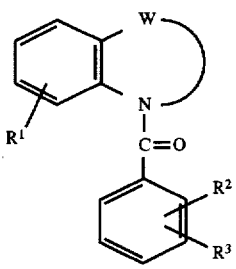
Example 89
Structure
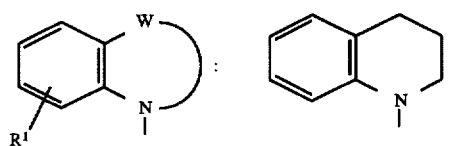
R²: H
R³: 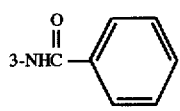
Crystalline form: Colorless amorphous
NMR analysis: 9)
Form: Free
Example 90
Structure
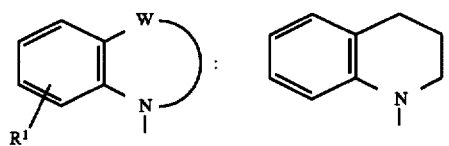
R²: H
R³: 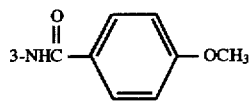
Crystalline form: Colorless amorphous
NMR analysis: 10)
Form: Free
Example 91
Structure
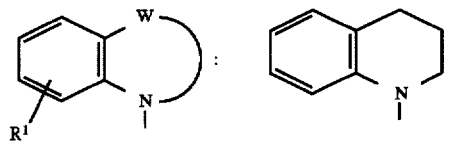
R²: H TABLE 1-continued
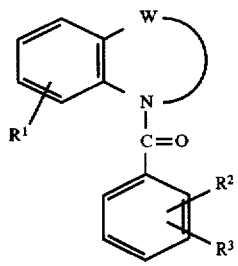
R³:
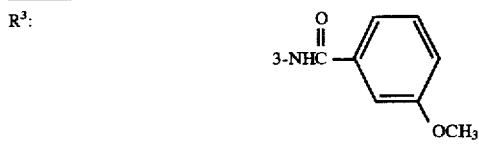
Crystalline form: Colorless amorphous
NMR analysis: 11)
Form: Free
Example 92
Structure
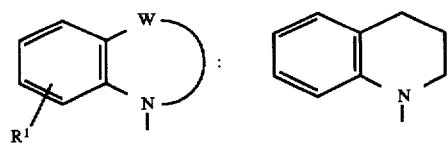
R²: H
R³:
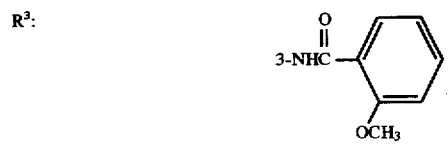
Crystalline form: White powder
Recrystallization solvent: Methanol
Melting Point: 156.5–157.5° C.
Form: Free
Example 93
Structure
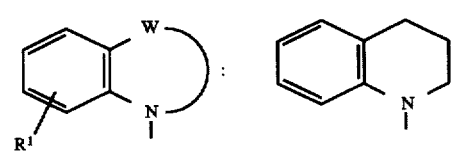
R²: H
R³:
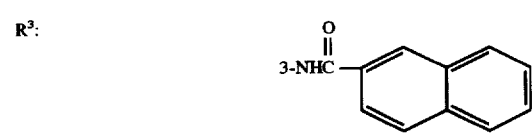
Crystalline form: Colorless amorphous
NMR analysis: 12)
Form: Free TABLE 1-continued
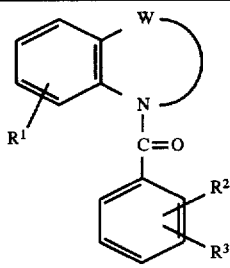
Example 94
Structure
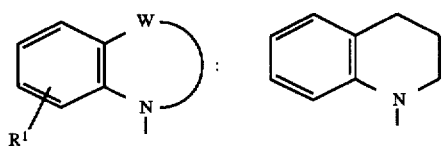
R²: H
R³:
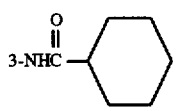
Crystalline form: White powder
Recrystallization solvent: Methanol
Melting Point: 203.5–204.5° C.
Form: Free
Example 95
Structure
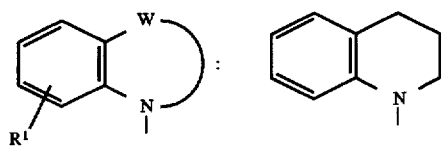
R²: H
R³:
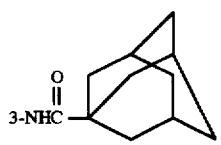
Crystalline form: Colorless amorphous
NMR analysis: 13)
Form: Free
Example 96
Structure
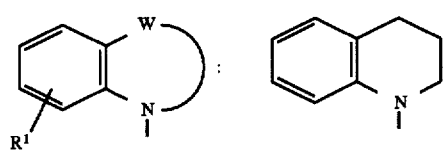
R²: H TABLE 1-continued

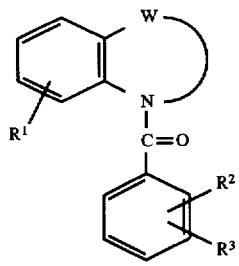

| $R^3$: | 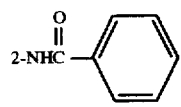 |

Crystalline form: Yellow powder
Recrystallization solvent: Methanol
Melting Point: 126–127° C.
Form: Free Example 97

Structure

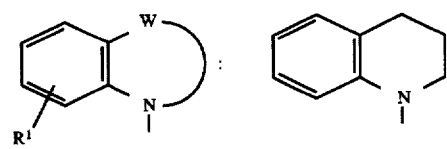

$R^2$:  H $R^3$: 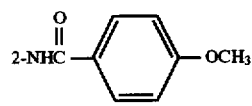

Crystalline form: White powder
Recrystallization solvent: Methanol
Melting Point: 158.5–159.5° C.
Form: Free Example 98

Structure

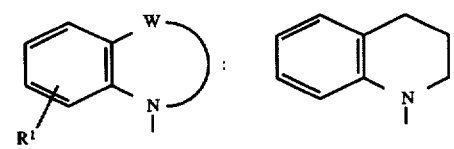

$R^2$:  H $R^3$: 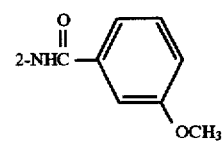

Crystalline form: White powder
Recrystallization solvent: Methanol
Melting Point: 129–130° C.
Form: Free TABLE 1-continued
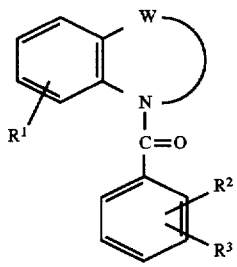
Example 99
Structure
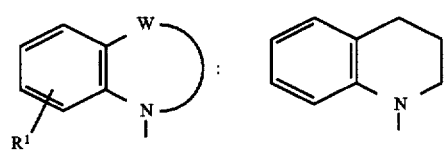
R²: H
R³:
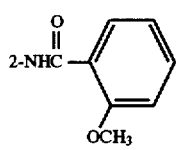
2-NHC(=O)—C₆H₃—OCH₃ (drawn structure)
Crystalline form: White powder
Recrystallization solvent: Methanol
Melting Point: 131.5–132.5° C.
Form: Free
Example 100
Structure
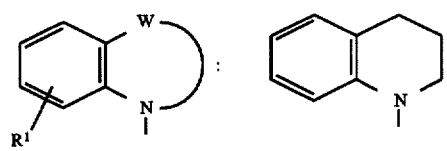
R²: H
R³:
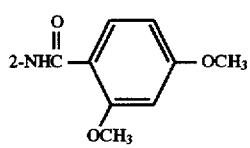
Crystalline form: White powder
Recrystallization solvent: Methanol
Melting Point: 140–141° C.
Form: Free
Example 101
Structure
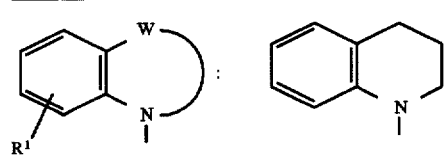
R²: H TABLE 1-continued
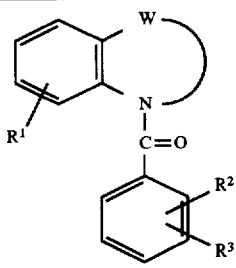
R³:
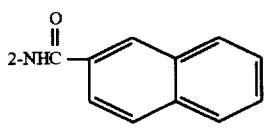
Crystalline form: White powder
Recrystallization solvent: Methanol
Melting Point: 138.5–139.5° C.
Form: Free
Example 102
Structure
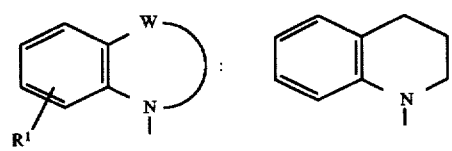
R²: H
R³:
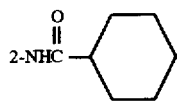
Crystalline form: White powder
Recrystallization solvent: Methanol
Melting Point: 128–129° C.
Form: Free
Example 103
Structure
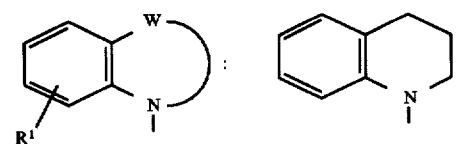
R²: H
R³:
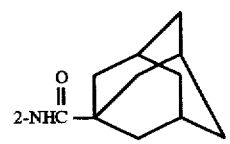
Crystalline form: White powder
Recrystallization solvent: Methanol
Melting Point: 160–161° C.
Form: Free TABLE 1-continued
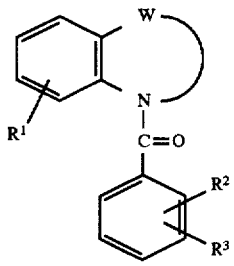
Example 104
Structure
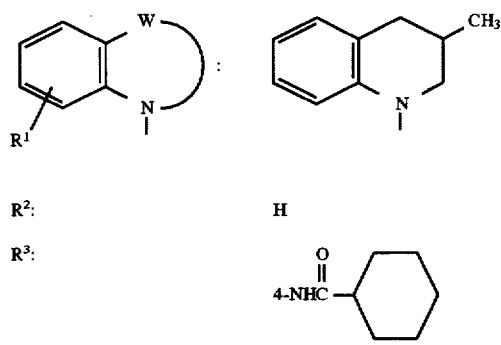
R²: H
R³: 4-NHC(=O)-cyclohexyl
Crystalline form: White powder
Recrystallization solvent: Methanol
Melting Point: 175–176° C.
Form: Free
Example 105
Structure
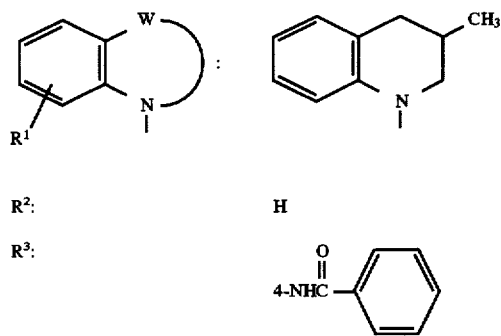
R²: H
R³: 4-NHC(=O)-phenyl
Crystalline form: White powder
Recrystallization solvent: Methanol
Melting Point: 197–198° C.
Form: Free
Example 106
Structure
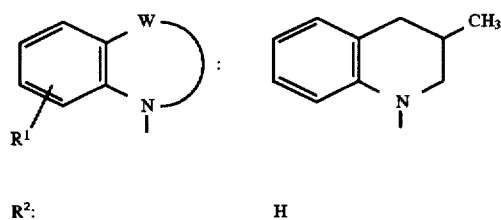
R²: H TABLE 1-continued
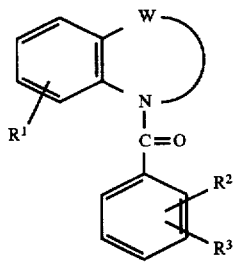
R³:
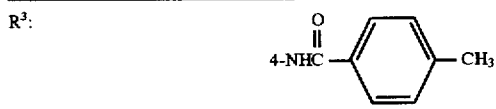
Crystalline form: White powder
Recrystallization solvent: Methanol
Melting Point: 204–205° C.
Form: Free
Example 107
Structure
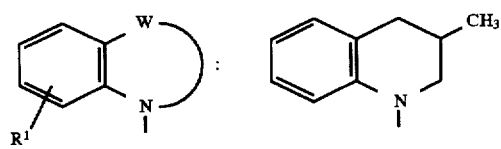
R²: H
R³:
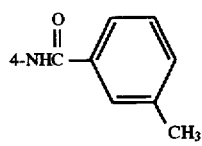
Crystalline form: White powder
Recrystallization solvent: Methanol
Melting Point: 174–175° C.
Form: Free
Example 108
Structure
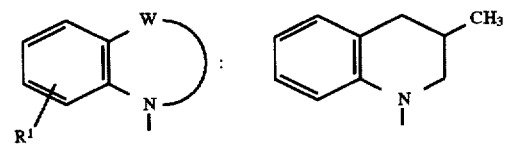
R²: H
R³:
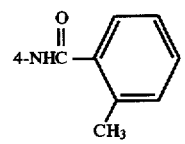
Crystalline form: Yellow powder
Recrystallization solvent: Methanol
Melting Point: 202–203° C.
Form: Free TABLE 1-continued
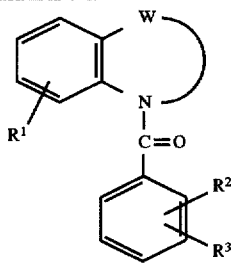
Example 109
Structure
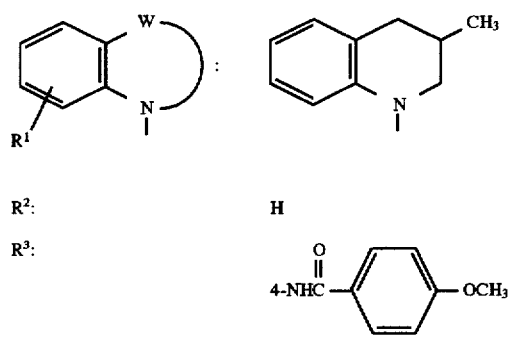
R²: H
R³: 4-NHC(=O)-C₆H₄-OCH₃ (para)
Crystalline form: White powder
Recrystallization solvent: Methanol
Melting Point: 203–204° C.
Form: Free
Example 110
Structure
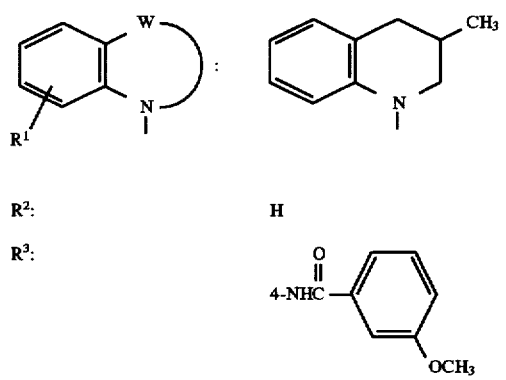
R²: H
R³: 4-NHC(=O)-C₆H₄-OCH₃ (meta)
Crystalline form: White powder
Recrystallization solvent: Methanol
Melting Point: 170.5–171.5° C.
Form: Free
Example 111
Structure
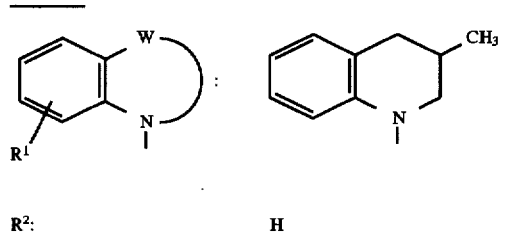
R²: H TABLE 1-continued

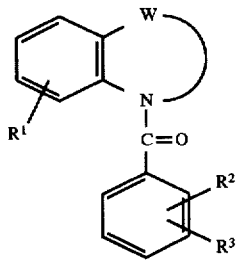

R³:

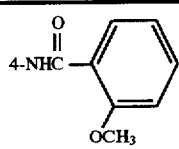

Crystalline form: White powder
Recrystallization solvent: Methanol
Melting Point: 149–150° C.
Form: Free Example 112

Structure

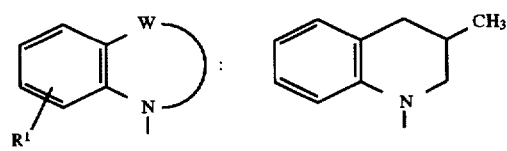

R²: H

R³:

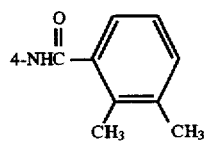

Crystalline form: White powder
Recrystallization solvent: Methanol
Melting Point: 185–186° C.
Form: Free Example 113

Structure

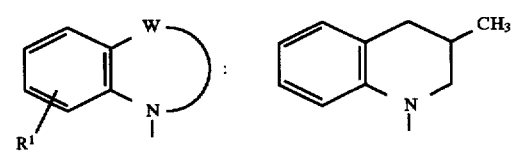

R²: H

R³:

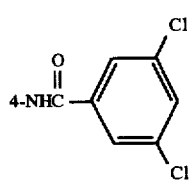

Crystalline form: White powder
Recrystallization solvent: Dichloromethane/ethanol
Melting Point: 225–226° C.
Form: Free TABLE 1-continued
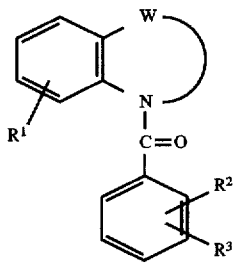
Example 114
Structure
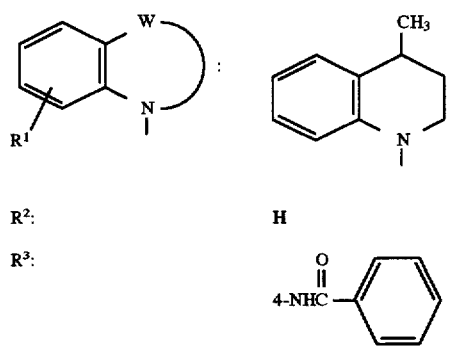
R²: H
R³: 4-NHC(=O)-phenyl
Crystalline form: White powder
Recrystallization solvent: Methanol
Melting Point: 234–235° C.
Form: Free
Example 115
Structure
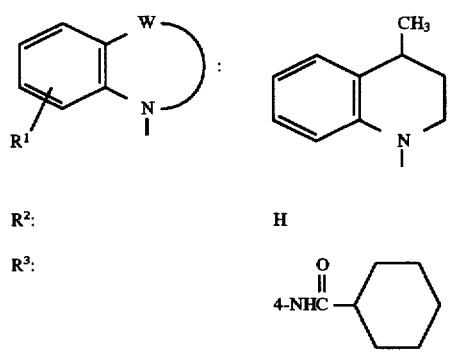
R²: H
R³: 4-NHC(=O)-cyclohexyl
Crystalline form: White powder
Recrystallization solvent: Methanol
Melting Point: 149.5–150.5° C.
Form: Free
Example 116
Structure
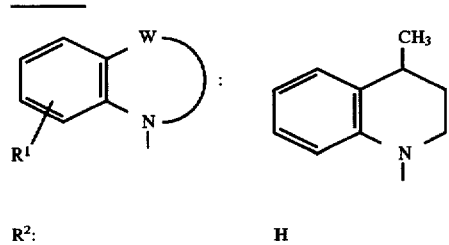
R²: H TABLE 1-continued

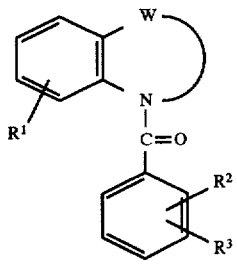

R³:

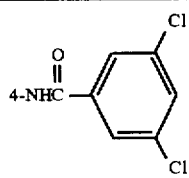

Crystalline form: White powder
Recrystallization solvent: Dichloromethane/ethanol
Melting Point: 197–198° C.
Form: Free Example 117

Structure

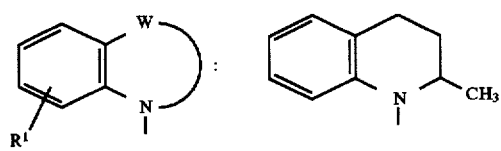

R²: H

R³:

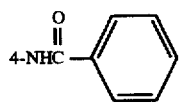

Crystalline form: White powder
Recrystallization solvent: Methanol
Melting Point: 204–205° C.
Form: Free Example 118

Structure

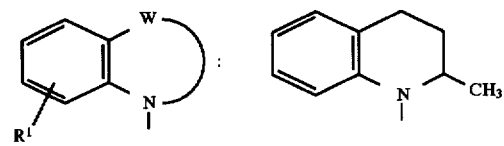

R²: H

R³:

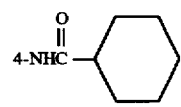

Crystalline form: White powder
Recrystallization solvent: Methanol
Melting Point: 224.5–225.5° C.
Form: Free TABLE 1-continued
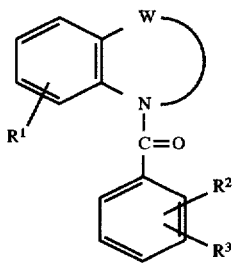
Example 119
Structure
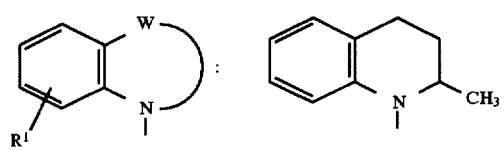
R²: H
R³:
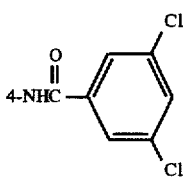
Crystalline form: White powder
Recrystallization solvent: Dichloromethane/ethanol
Melting Point: 189.5–190.5° C.
Form: Free
Example 120
Structure
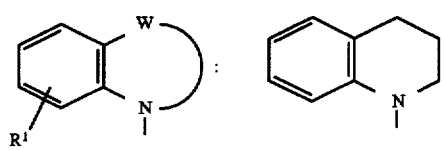
R²: H
R³:
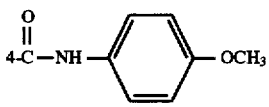
Crystalline form: White powder
Recrystallization solvent: Methanol
Melting Point: 221.5–222.5° C.
Form: Free
Example 121
Structure
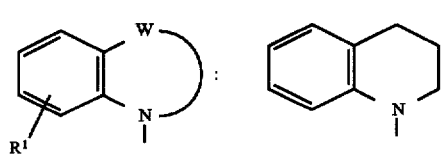
R²: H TABLE 1-continued

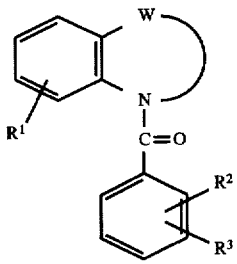

R³:

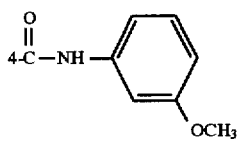

Crystalline form: Colorless needles
Recrystallization solvent: Methanol
Melting Point: 154–155° C.
Form: Free Example 122

Structure

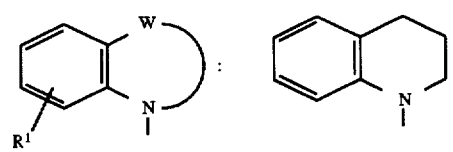

R²: H

R³:

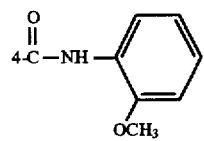

Crystalline form: White powder
Recrystallization solvent: Methanol
Melting Point: 165–166° C.
Form: Free Example 123

Structure

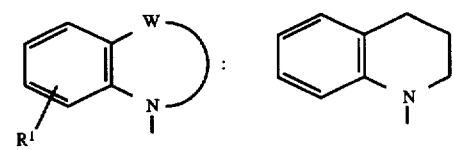

R²: H

R³:

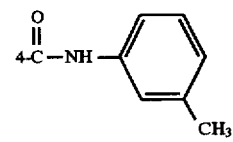

Crystalline form: Colorless needles
Recrystallization solvent: Methanol
Melting Point: 141–142° C.
Form: Free TABLE 1-continued
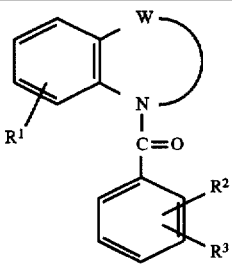
Example 124
Structure
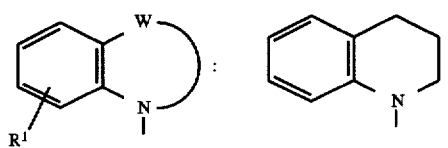
R²: H
R³: 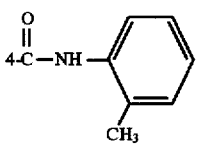
Crystalline form: White powder
Recrystallization solvent: Methanol
Melting Point: 165.5–166.5° C.
Form: Free
Example 125
Structure
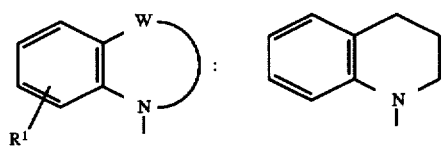
R²: H
R³: 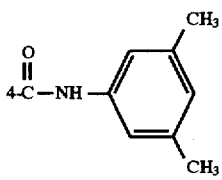
Crystalline form: Colorless needles
Recrystallization solvent: Methanol
Melting Point: 164–165° C.
Form: Free
Example 126
Structure
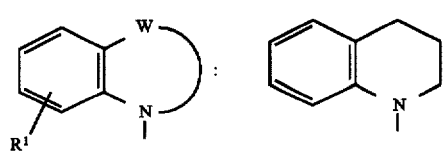

TABLE 1-continued

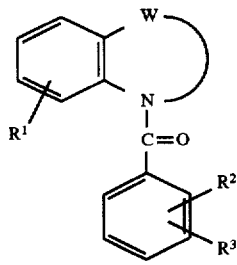

R²: H

R³: 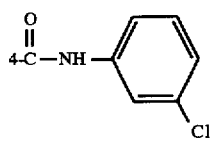

Crystalline form: White powder
Recrystallization solvent: Methanol
Melting Point: 203.5–204.5° C.
Form: Free Example 127

Structure

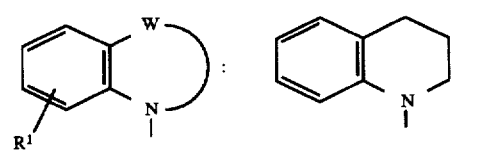

R²: H

R³: 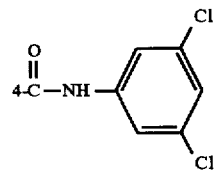

Crystalline form: White powder
Recrystallization solvent: Dichloromethane/ethanol
Melting Point: 236.5–237.5° C.
Form: Free Example 128

Structure

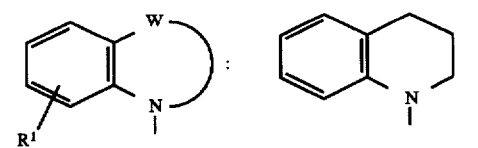

R²: H

R³: 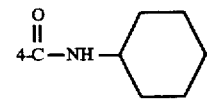

Crystalline form: White powder
Recrystallization solvent: Methanol
Melting Point: 206.5–207.5° C.
Form: Free TABLE 1-continued
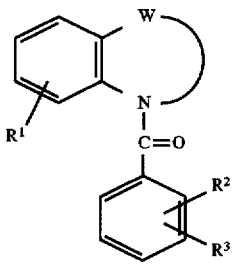
Example 129
Structure
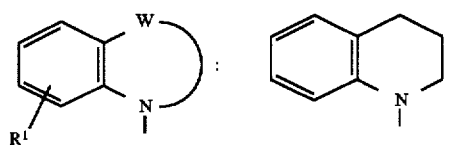
R²: H
R³:
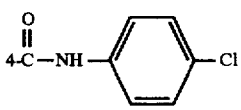
Crystalline form: White powder
Recrystallization solvent: Methanol
Melting Point: 271–272° C.
Form: Free
Example 130
Structure
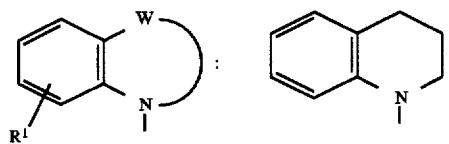
R²: H
R³:
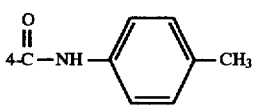
Crystalline form: White powder
Recrystallization solvent: Methanol
Melting Point: 246–247° C.
Form: Free
Example 131
Structure
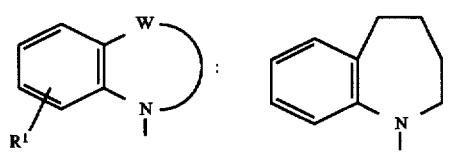
R²: H TABLE 1-continued

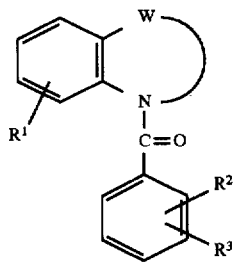

R³: 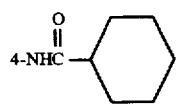

Crystalline form: White powder
Recrystallization solvent: Ethanol/diethyl ether
Melting Point: 210–211° C.
Form: Free Example 132

Structure

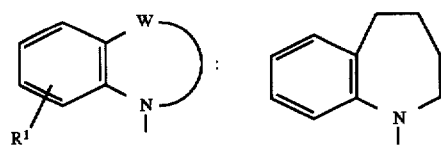

R²: H

R³: 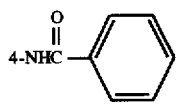

Crystalline form: White powder
Recrystallization solvent: Ethanol/diethyl ether
Melting Point: 230.5–231.5° C.
Form: Free Example 133

Structure

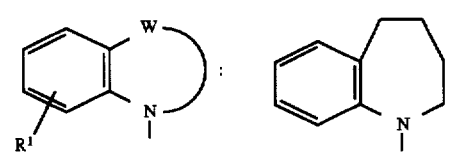

R²: H

R³: 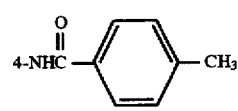

Crystalline form: White powder
Recrystallization solvent: Ethanol/diethyl ether
Melting Point: 203–204° C.
Form: Free TABLE 1-continued
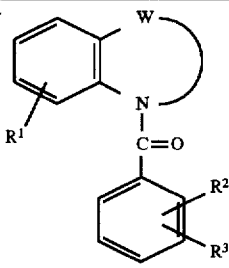
Example 134
Structure
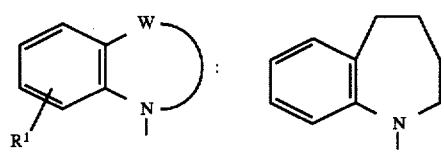
R²: H
R³:
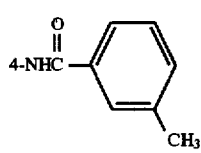
Crystalline form: White powder
Recrystallization solvent: Ethanol/diethyl ether
Melting Point: 170–171° C.
Form: Free
Example 135
Structure
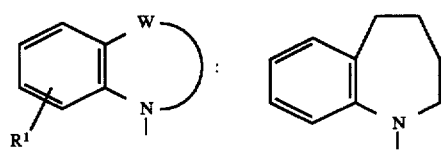
R²: H
R³:
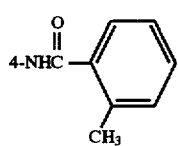
Crystalline form: White powder
Recrystallization solvent: Ethanol/diethyl ether
Melting Point: 225.5–226.5° C.
Form: Free
Example 136
Structure
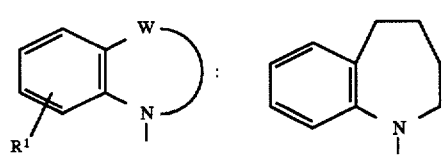
R²: H TABLE 1-continued

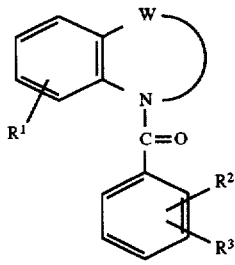

R³:
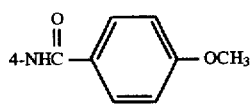

Crystalline form: White powder
Recrystallization solvent: Ethanol/diethyl ether
Melting Point: 210.5–211.5° C.
Form: Free Example 137

Structure

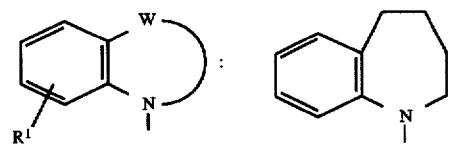

R²: H

R³:
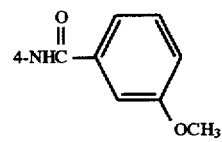

Crystalline form: White powder
Recrystallization solvent: Ethanol/diethyl ether
Melting Point: 183–184° C.
Form: Free Example 138

Structure

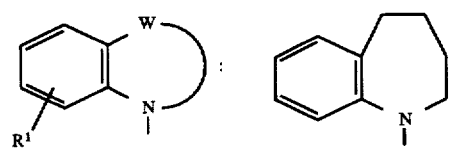

R²: H

R³:
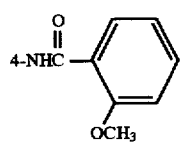

Crystalline form: White powder
Recrystallization solvent: Ethanol/diethyl ether
Melting Point: 191.5–192.5° C.
Form: Free TABLE 1-continued
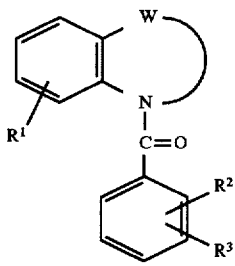
Example 139
Structure
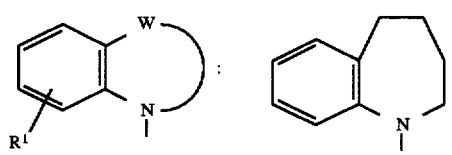
R²: H
R³: 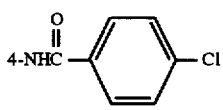
Crystalline form: White powder
Recrystallization solvent: Ethanol/diethyl ether
Melting Point: 203.5–204.5° C.
Form: Free
Example 140
Structure
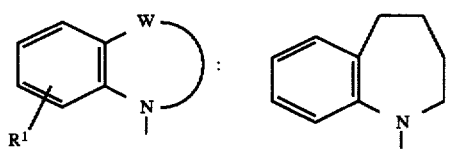
R²: H
R³: 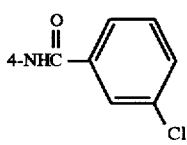
Crystalline form: White powder
Recrystallization solvent: Ethanol/diethyl ether
Melting Point: 215.5–216.5° C.
Form: Free
Example 141
Structure
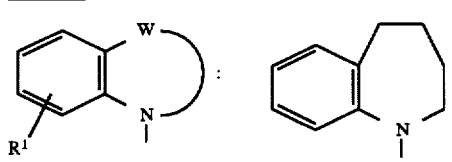
R²: H

TABLE 1-continued

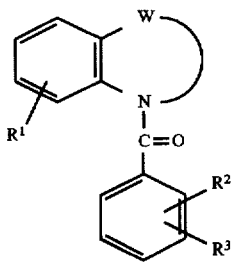

R³:

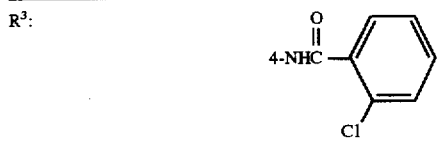

Crystalline form: White powder
Recrystallization solvent: Ethanol/diethyl ether
Melting Point: 211.5–212.5° C.
Form: Free

Example 142

Structure

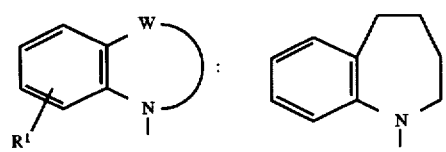

R²: H

R³:

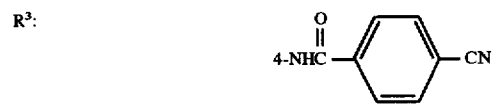

Crystalline form: White powder
Recrystallization solvent: Ethanol/diethyl ether
Melting Point: 280.5–281.5° C.
Form: Free

Example 143

Structure

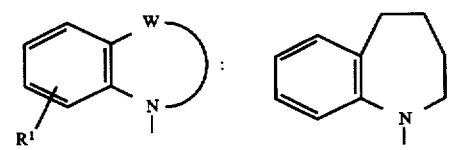

R²: H

R³:

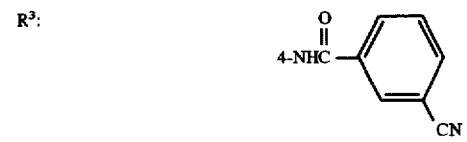

Crystalline form: White powder
Recrystallization solvent: Ethanol/diethyl ether
Melting Point: 235.5–236.5° C.
Form: Free TABLE 1-continued
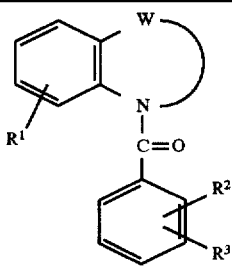
Example 144
Structure
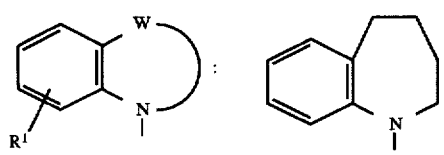
R²: H
R³:
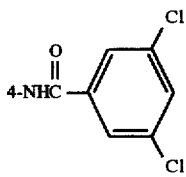
Crystalline form: White powder
Recrystallization solvent: Ethanol/dichloromethane
Melting Point: 249.5–250.5° C.
Form: Free
Example 145
Structure
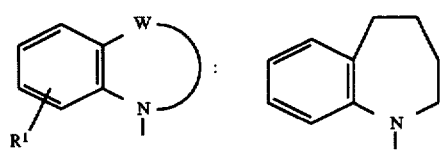
R²: H
R³:
Crystalline form: White powder
Recrystallization solvent: Ethanol/diethyl ether
Melting Point: 217–218° C.
Form: Free
Example 146
Structure
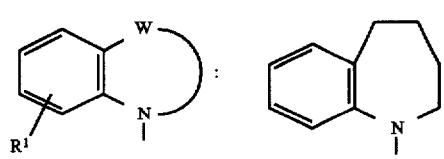

TABLE 1-continued

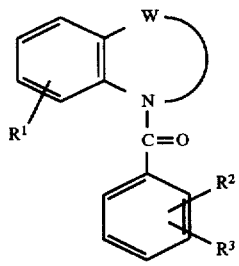

R²: 3-CH₃

R³: 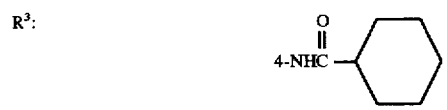

Crystalline form: White powder
Recrystallization solvent: Ethanol/diethyl ether
Melting Point: 201.5–203° C.
Form: Free Example 147

Structure

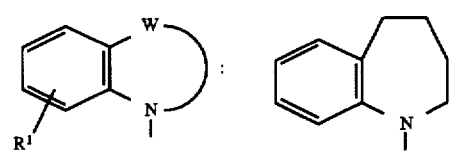

R²: 3-CH₃

R³: 

Crystalline form: White powder
Recrystallization solvent: Ethanol/diethyl ether
Melting Point: 221–222° C.
Form: Free Example 148

Structure

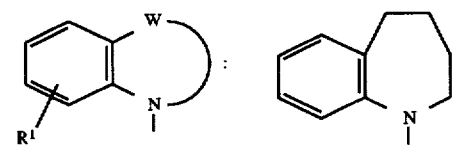

R²: 3-CH₃

R³: 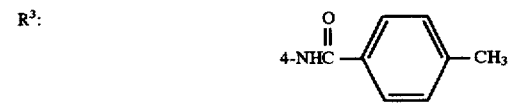

Crystalline form: White powder
Recrystallization solvent: Ethanol/diethyl ether
Melting Point: 193–194° C.
Form: Free TABLE 1-continued
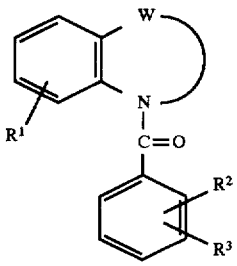
Example 149
Structure
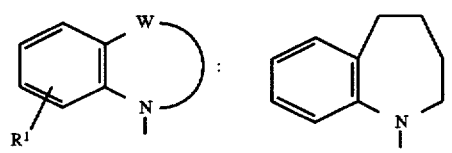
R²: 3-CH₃
R³:
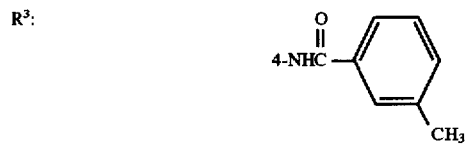
Crystalline form: White powder
Recrystallization solvent: Ethanol/diethyl ether
Melting Point: 176–177° C.
Form: Free
Example 150
Structure
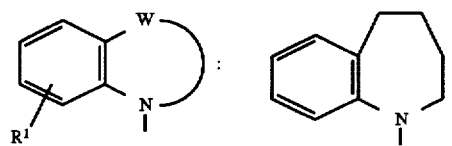
R²: 3-CH₃
R³:
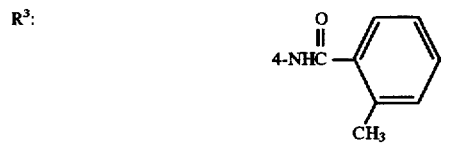
Crystalline form: White powder
Recrystallization solvent: Ethanol/diethyl ether
Melting Point: 188–189.5° C.
Form: Free
Example 151
Structure
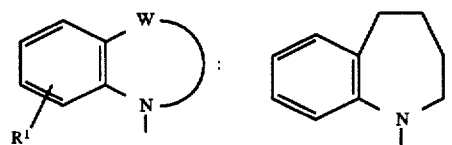
R²: 3-CH₃

TABLE 1-continued

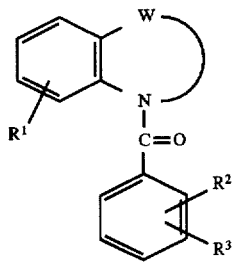

R³:

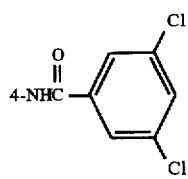

Crystalline form: White powder
Recrystallization solvent: Ethanol/diethyl ether
Melting Point: 227–228° C.
Form: Free Example 152

Structure

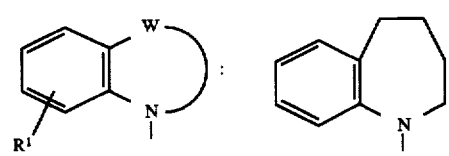

R²: 3-CH₃

R³:

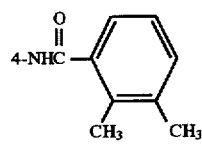

Crystalline form: White powder
Recrystallization solvent: Ethanol/diethyl ether
Melting Point: 186–187° C.
Form: Free Example 153

Structure

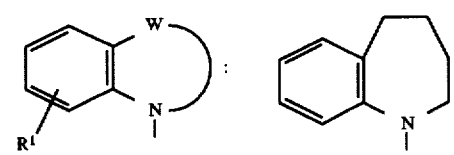

R²: 3-OCH₃

R³:

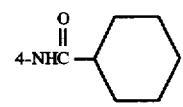

Crystalline form: White powder
Recrystallization solvent: Ethanol/diethyl ether
Melting Point: 135–136° C.
Form: Free TABLE 1-continued
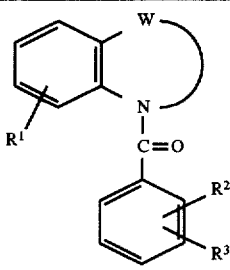
Example 154
Structure
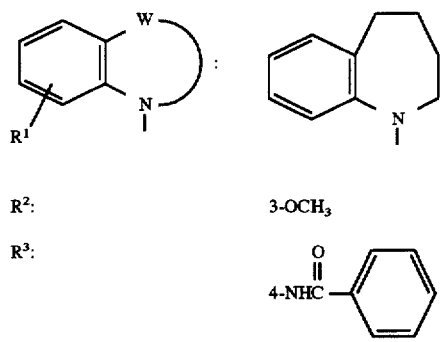
R²:     3-OCH₃
R³:
4-NHC(=O)–phenyl
Crystalline form: White powder
Recrystallization solvent: Ethanol/diethyl ether
Melting Point: 173–174° C.
Form: Free
Example 155
Structure
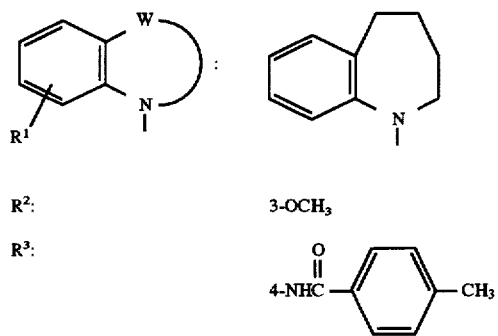
R²:     3-OCH₃
R³:
4-NHC(=O)–(4-CH₃-phenyl)
Crystalline form: White powder
Recrystallization solvent: Ethanol/diethyl ether
Melting Point: 174.5–175.5° C.
Form: Free
Example 156
Structure
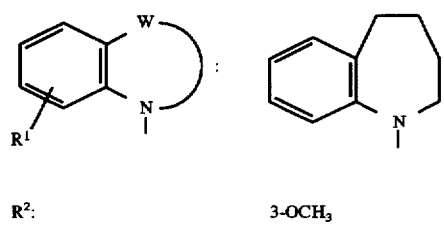
R²:     3-OCH₃

TABLE 1-continued

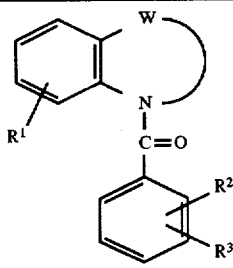

R³:

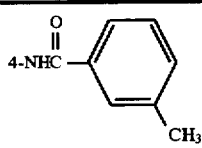

Crystalline form: White powder
Recrystallization solvent: Ethanol/diethyl ether
Melting Point: 156–157° C.
Form: Free Example 157

Structure

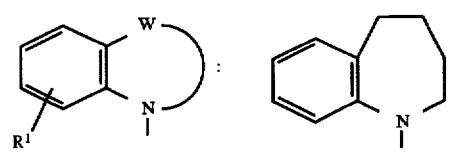

R²: 3-OCH₃

R³:

Crystalline form: White powder
Recrystallization solvent: Ethanol/diethyl ether
Melting Point: 153–154° C.
Form: Free Example 158

Structure

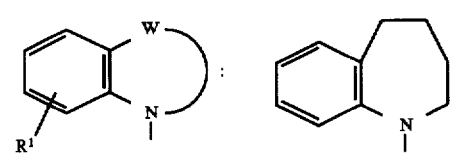

R²: 3-OCH₃

R³:

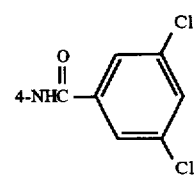

Crystalline form: White powder
Recrystallization solvent: Ethanol/diethyl ether
Melting Point: 169–170° C.
Form: Free

TABLE 1-continued
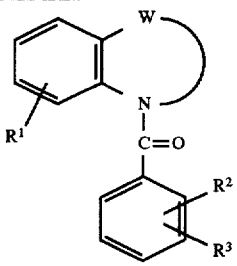
Example 159
Structure
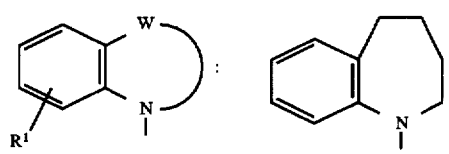
R²: 3-OCH₃
R³:
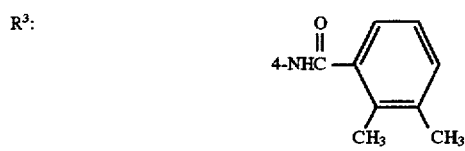
Crystalline form: White powder
Recrystallization solvent: Ethanol/diethyl ether
Melting Point: 185–186° C.
Form: Free
Example 160
Structure
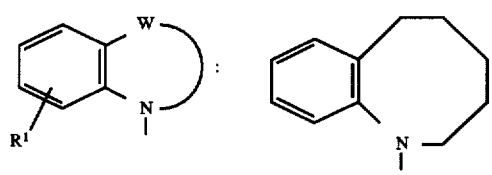
R²: H
R³:
Crystalline form: White powder
Recrystallization solvent: Ethanol/diethyl ether
Melting Point: 213–214° C.
Form: Free
Example 161
Structure
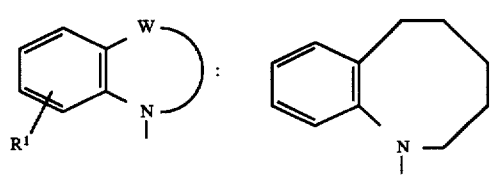
R²: H TABLE 1-continued

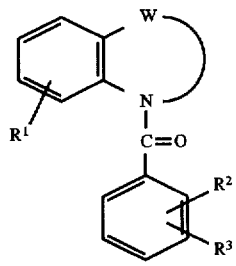

R³: 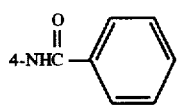

Crystalline form: White powder
Recrystallization solvent: Ethanol/diethyl ether
Melting Point: 240–241° C.
Form: Free Example 162

Structure

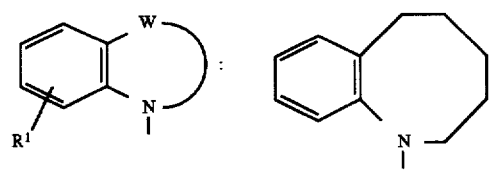

R²: H

R³: 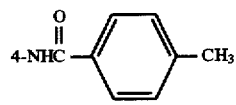

Crystalline form: White powder
Recrystallization solvent: Ethanol/diethyl ether
Melting Point: 225–226° C.
Form: Free Example 163

Structure

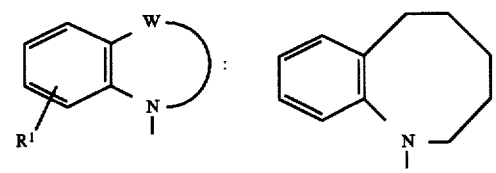

R²: H

R³: 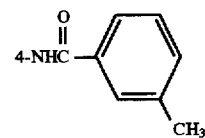

Crystalline form: White powder
Recrystallization solvent: Ethanol/diethyl ether
Melting Point: 209.5–210.5° C.
Form: Free TABLE 1-continued
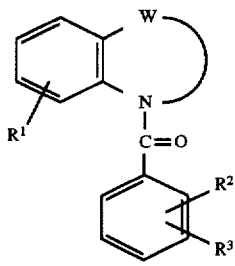
Example 164
Structure
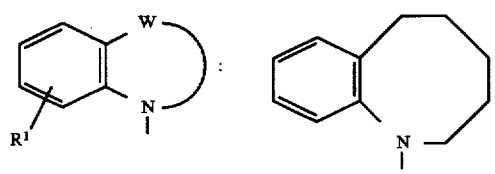
R²: H
R³:
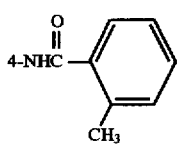
Crystalline form: White powder
Recrystallization solvent: Ethanol/diethyl ether
Melting Point: 198–199° C.
Form: Free
Example 165
Structure
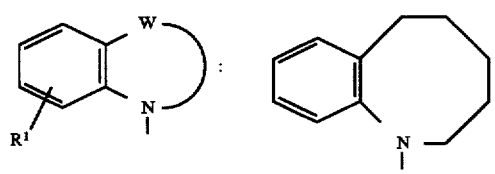
R²: H
R³:
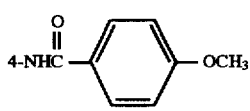
Crystalline form: White powder
Recrystallization solvent: Ethanol/diethyl ether
Melting Point: 214.5–215.5° C.
Form: Free
Example 166
Structure
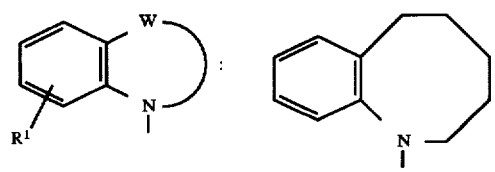
R²: H TABLE 1-continued

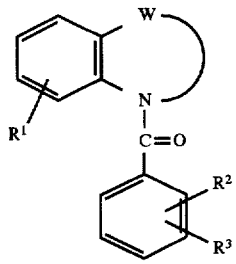

R³:

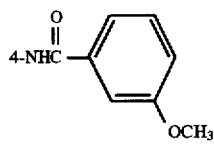

Crystalline form: White powder
Recrystallization solvent: Ethanol/diethyl ether
Melting Point: 196.5–197.5° C.
Form: Free Example 167

Structure

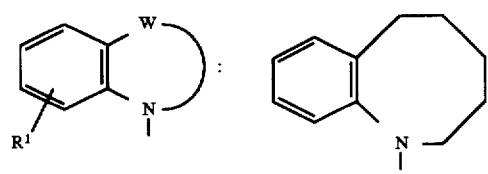

R²: H

R³:

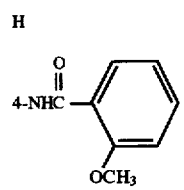

Crystalline form: White powder
Recrystallization solvent: Ethanol/diethyl ether
Melting Point: 194–195° C.
Form: Free Example 168

Structure

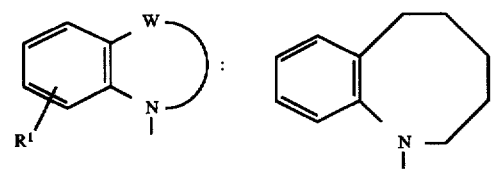

R²: H

R³:

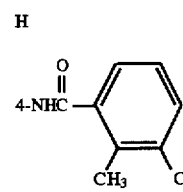

Crystalline form: White powder
Recrystallization solvent: Ethanol/diethyl ether
Melting Point: 191–192° C.
Form: Free TABLE 1-continued
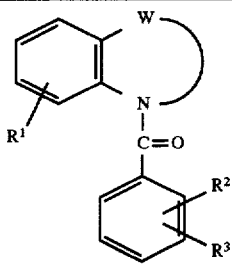
Example 169
Structure
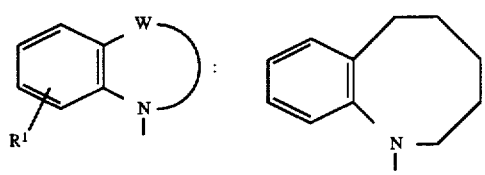
R²: H
R³:
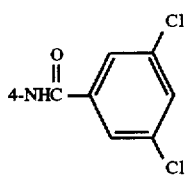
Crystalline form: White powder
Recrystallization solvent: Dichloromethane/ethanol
Melting Point: 227–228° C.
Form: Free
Example 170
Structure
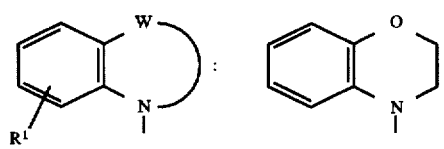
R²: H
R³:
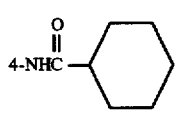
Crystalline form: White powder
Recrystallization solvent: Dichloromethane/diethyl ether
Melting Point: 182–183° C.
Form: Free
Example 171
Structure
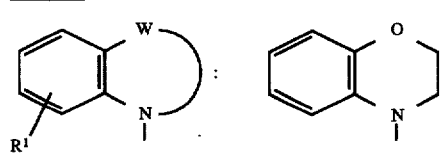

TABLE 1-continued

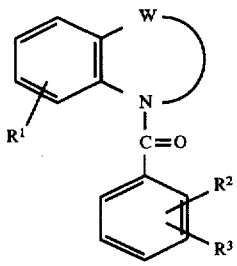

R²: H

R³: 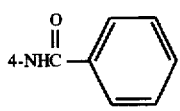

Crystalline form: White powder
Recrystallization solvent: Dichloromethane/diethyl ether
Melting Point: 222–223° C.
Form: Free Example 172

Structure

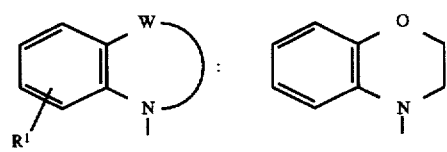

R²: H

R³: 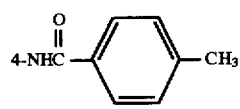

Crystalline form: White powder
Recrystallization solvent: Dichloromethane/diethyl ether
Melting Point: 204–205° C.
Form: Free Example 173

Structure

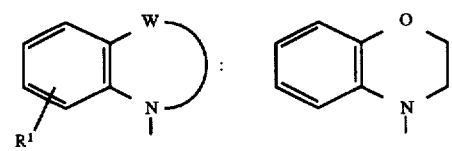

R²: H

R³: 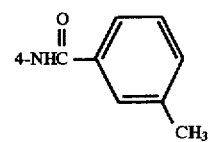

Crystalline form: White powder
Recrystallization solvent: Dichloromethane/diethyl ether
Melting Point: 194–195° C.
Form: Free

TABLE 1-continued
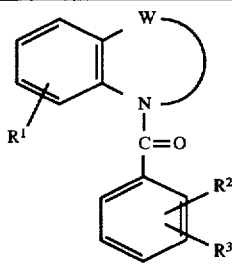
Example 174
Structure
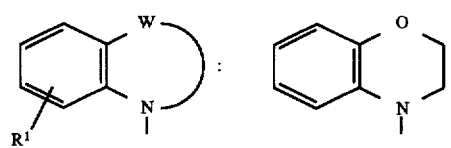
R²: H
R³: 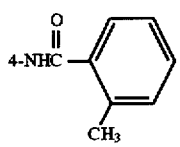
Crystalline form: White powder
Recrystallization solvent: Dichloromethane/diethyl ether
Melting Point: 213–214° C.
Form: Free
Example 175
Structure
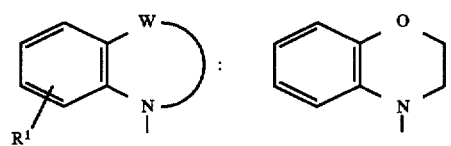
R²: H
R³: 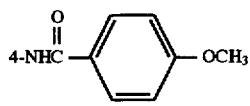
Crystalline form: White powder
Recrystallization solvent: Dichloromethane/diethyl ether
Melting Point: 201–202° C.
Form: Free
Example 176
Structure
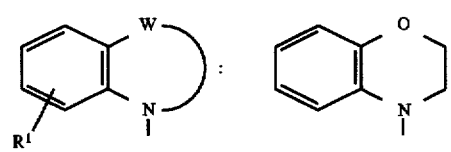
R²: H TABLE 1-continued

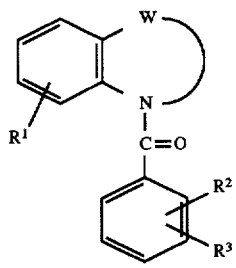

R³: 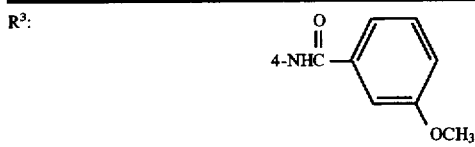

Crystalline form: Colorless needles
Recrystallization solvent: Dichloromethane/diethyl ether
Melting Point: 173–174° C.
Form: Free Example 177

Structure

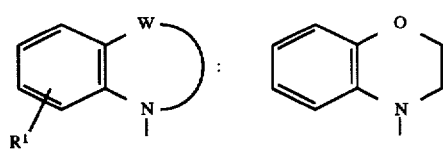

R²: H

R³: 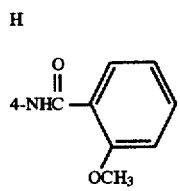

Crystalline form: White powder
Recrystallization solvent: Dichloromethane/diethyl ether
Melting Point: 150.5–151.5° C.
Form: Free Example 178

Structure

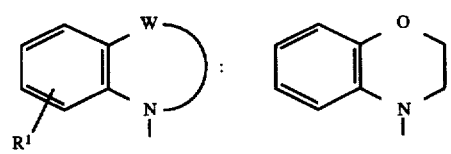

R²: H

R³: 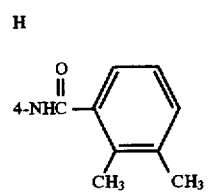

Crystalline form: White powder
Recrystallization solvent: Dichloromethane/diethyl ether
Melting Point: 207.5–208.5° C.
Form: Free TABLE 1-continued
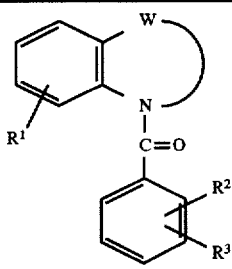
Example 179
Structure
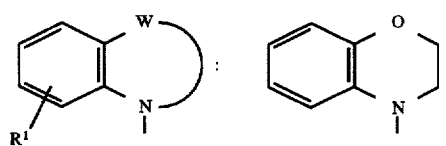
R²: H
R³:
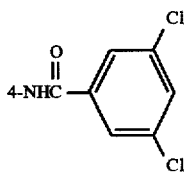
Crystalline form: White powder
Recrystallization solvent: Dichloromethane/diethyl ether
Melting Point: 256.5–257.5° C.
Form: Free
Example 180
Structure
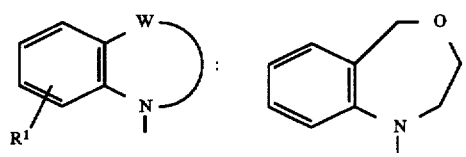
R²: H
R³:
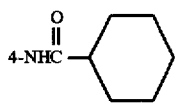
Crystalline form: White powder
Recrystallization solvent: Ethanol/diethyl ether
Melting Point: 199.5–200.5° C.
Form: Free
Example 181
Structure
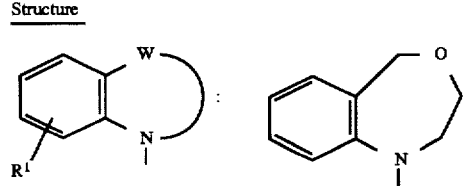
R²: H TABLE 1-continued

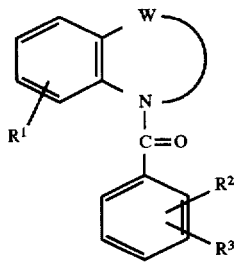

R³:
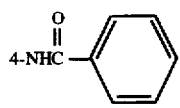

Crystalline form: White powder
Recrystallization solvent: Ethanol/diethyl ether
Melting Point: 211–212° C.
Form: Free Example 182

Structure

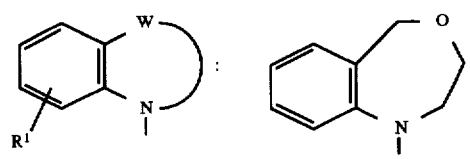

R²: H

R³:
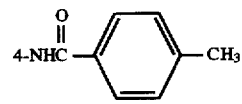

Crystalline form: White powder
Recrystallization solvent: Ethanol/diethyl ether
Melting Point: 189.5–190.5° C.
Form: Free Example 183

Structure

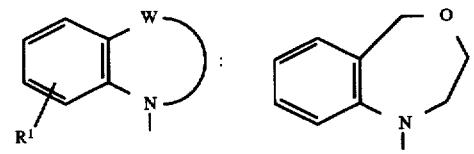

R²: H

R³:
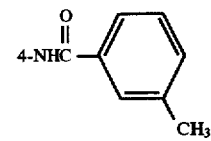

Crystalline form: White powder
Recrystallization solvent: Ethanol/diethyl ether
Melting Point: 176.5–177.5° C.
Form: Free TABLE 1-continued
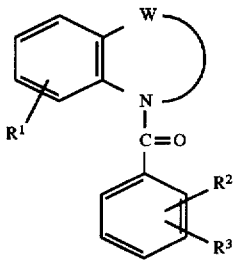
Example 184
Structure
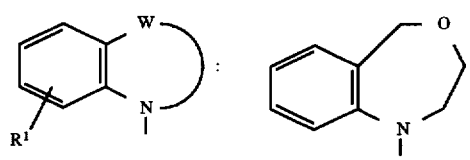
R²: H
R³: 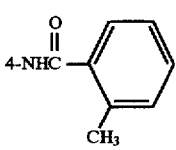
Crystalline form: Yellow powder
Recrystallization solvent: Ethanol/diethyl ether
Melting Point: 202–203° C.
Form: Free
Example 185
Structure
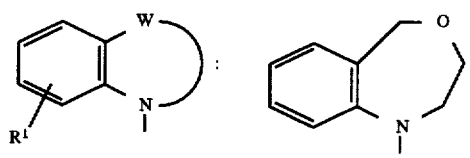
R²: H
R³: 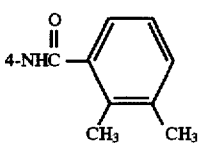
Crystalline form: White powder
Recrystallization solvent: Ethanol/diethyl ether
Melting Point: 219–220° C.
Form: Free
Example 186
Structure
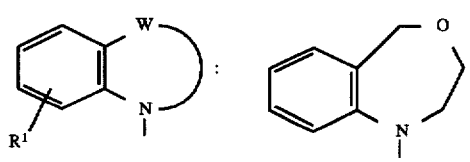
R²: H TABLE 1-continued

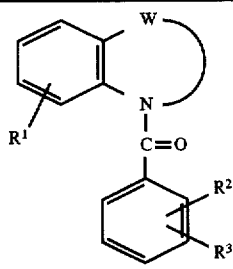

R³:

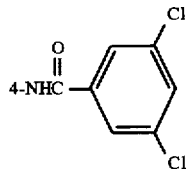

Crystalline form: White powder
Recrystallization solvent: Ethanol/diethyl ether
Melting Point: 272-273° C.
Form: Free Example 187

Structure

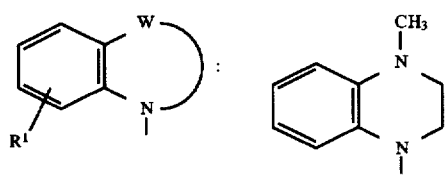

R²: H

R³:

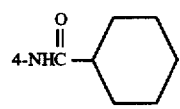

Crystalline form: Yellow powder
Recrystallization solvent: Ethanol/diethyl ether
Melting Point: 146-147° C.
Form: Free Example 188

Structure

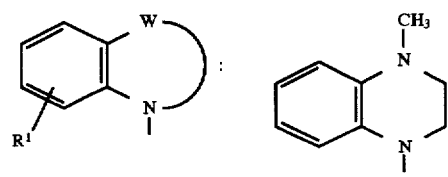

R²: H

R³:

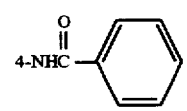

Crystalline form: Yellow powder
Recrystallization solvent: Ethanol/diethyl ether
Melting Point: 229.5-230.5° C.
Form: Free TABLE 1-continued
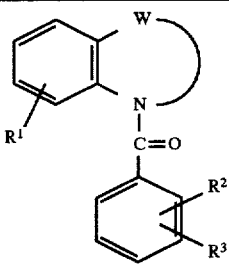
Example 189
Structure
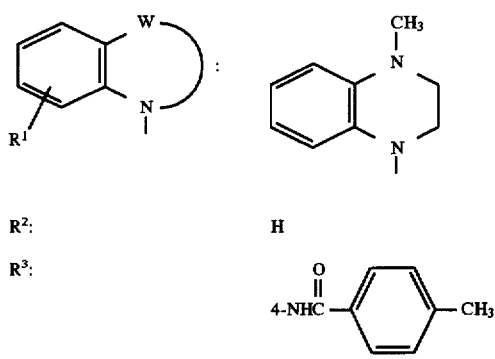
R²: H
R³:
Crystalline form: Yellow powder
Recrystallization solvent: Ethanol/diethyl ether
Melting Point: 119.5–120.5° C.
Form: Free
Example 190
Structure
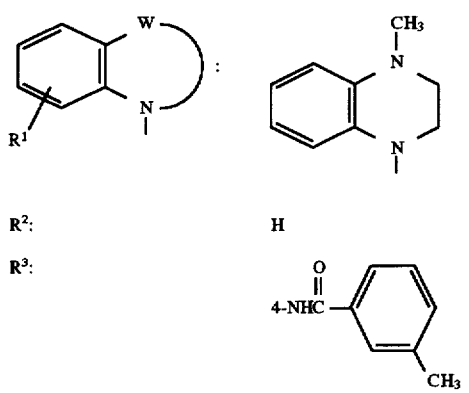
R²: H
R³:
Crystalline form: Yellow powder
Recrystallization solvent: Ethanol/diethyl ether
Melting Point: 189–190° C.
Form: Free
Example 191
Structure
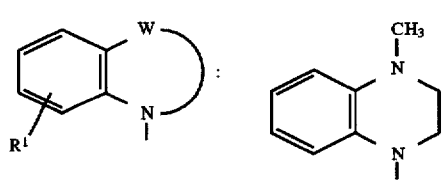

TABLE 1-continued

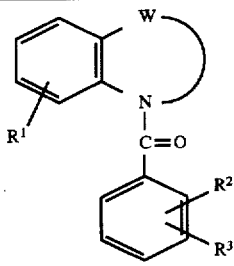

| R²: | H |
|---|---|
| R³: | 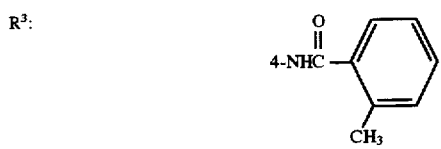 |

Crystalline form: Yellow powder
Recrystallization solvent: Ethanol/diethyl ether
Melting Point: 207–208° C.
Form: Free

Example 192

Structure

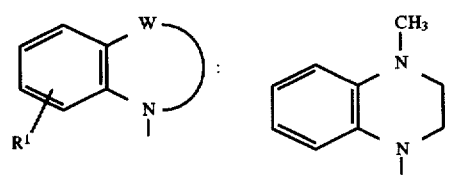

| R²: | H |
|---|---|
| R³: | 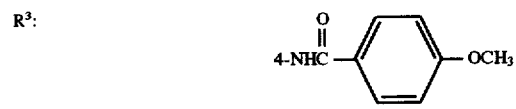 |

Crystalline form: Yellow powder
Recrystallization solvent: Ethanol/diethyl ether
Melting Point: 196.5–197.5° C.
Form: Free

Example 193

Structure

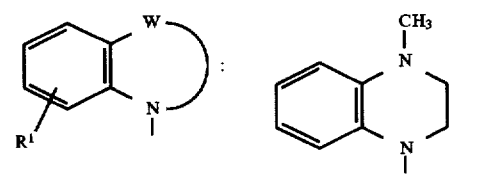

| R²: | H |
|---|---|
| R³: | 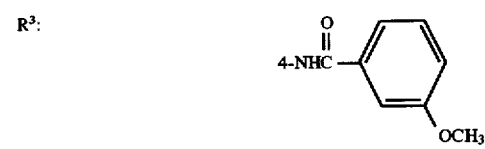 |

Crystalline form: Yellow powder
Recrystallization solvent: Ethanol/diethyl ether
Melting Point: 182–183° C.
Form: Free TABLE 1-continued
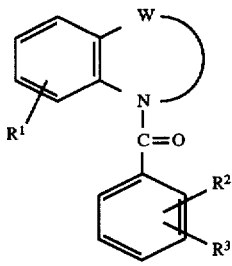
Example 194
Structure
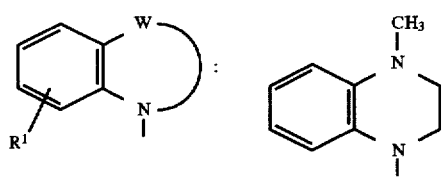
R²: H
R³:
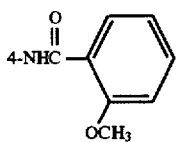
Crystalline form: Yellow powder
Recrystallization solvent: Ethanol/diethyl ether
Melting Point: 172–173° C.
Form: Free
Example 195
Structure
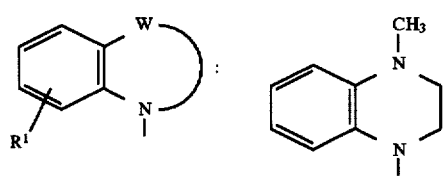
R²: H
R³:
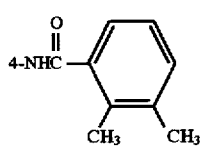
Crystalline form: Yellow powder
Recrystallization solvent: Ethanol/diethyl ether
Melting Point: 197.5–198.5° C.
Form: Free TABLE 1-continued
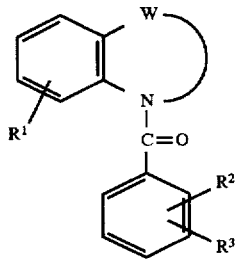
Example 196
Structure
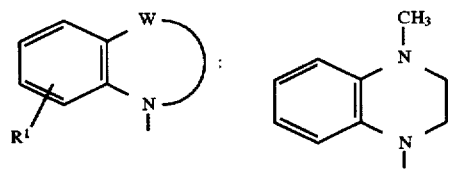
R²: H
R³:
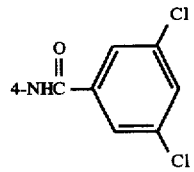
Crystalline form: Yellow powder
Recrystallization solvent: Ethanol/diethyl ether
Melting Point: 227–228° C.
Form: Free
Example 197
Structure
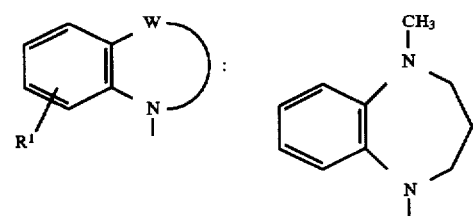
R²: H
R³:
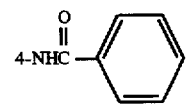
Crystalline form: White powder
Recrystallization solvent: Ethanol/diethyl ether
Melting Point: 216.5–217.5° C.
Form: Free TABLE 1-continued
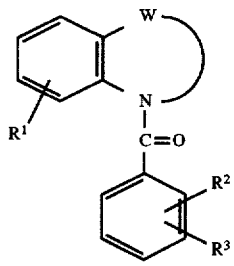
Example 198
Structure
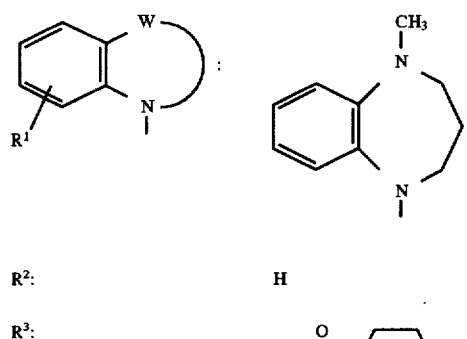
R²: H
R³:
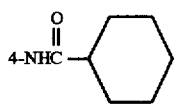
Crystalline form: White powder
Recrystallization solvent: Ethanol/diethyl ether
Melting Point: 207–208° C.
Form: Free
Example 199
Structure
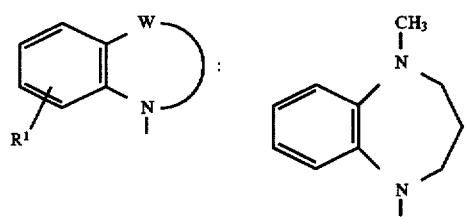
R²: H
R³:
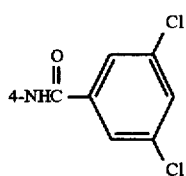
Crystalline form: White powder
Recrystallization solvent: Ethanol/diethyl ether
Melting Point: 236–237° C.
Form: Free TABLE 1-continued
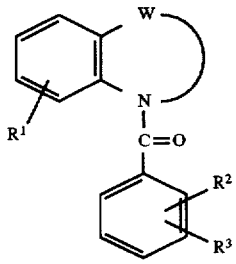
Example 200
Structure
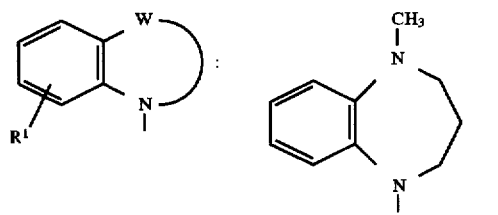
R²: H
R³:
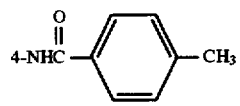
Crystalline form: White powder
Recrystallization solvent: Ethanol/diethyl ether
Melting Point: 199.5–200.5° C.
Form: Free
Example 201
Structure
R²: H
R³:
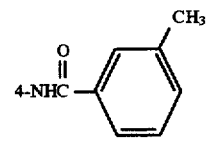
Crystalline form: White powder
Recrystallization solvent: Ethanol/diethyl ether
Melting Point: 171.5–172.5° C.
Form: Free TABLE 1-continued
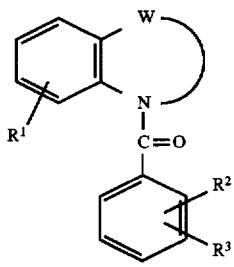
Example 202
Structure
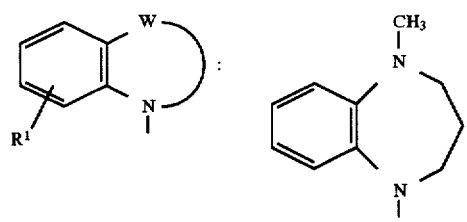
R²: H
R³:
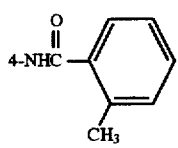
Crystalline form: White powder
Recrystallization solvent: Ethanol/diethyl ether
Melting Point: 222.5–223.5° C.
Form: Free
Example 203
Structure
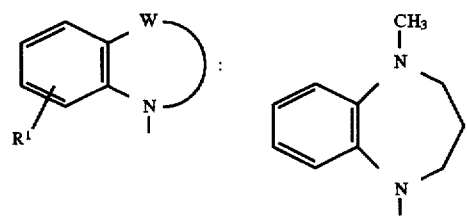
R²: H
R³:
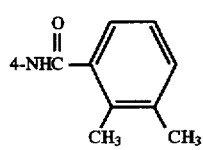
Crystalline form: White powder
Recrystallization solvent: Ethanol/diethyl ether
Melting Point: 209.5–210.5° C.
Form: Free TABLE 1-continued
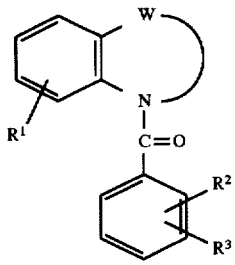
Example 204
Structure
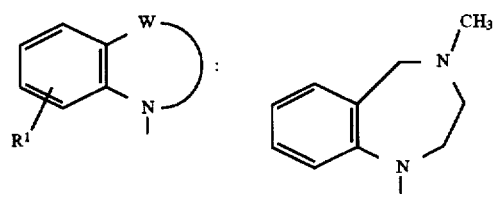
R²: H
R³: 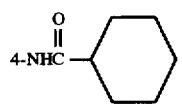
4-NHC(=O)—cyclohexyl
Crystalline form: White powder
Recrystallization solvent: Ethanol/water
NMR analysis: 14)
Form: Hydrochloride
Example 205
Structure
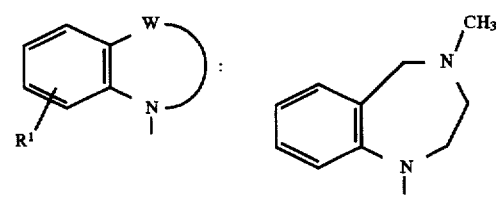
R²: H
R³: 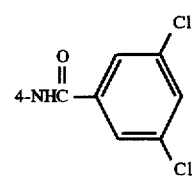
4-NHC(=O)—2,5-dichlorophenyl
Crystalline form: White powder
Recrystallization solvent: Ethanol/water
NMR analysis: 15)
Form: Hydrochloride TABLE 1-continued
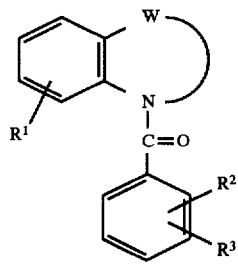
Example 206
Structure
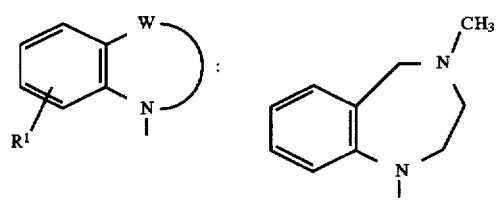
R²: H
R³:
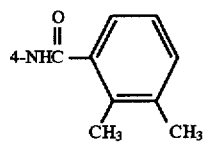
Crystalline form: White powder
Recrystallization solvent: Ethanol/water
NMR analysis: 16)
Form: Hydrochloride
Example 207
Structure
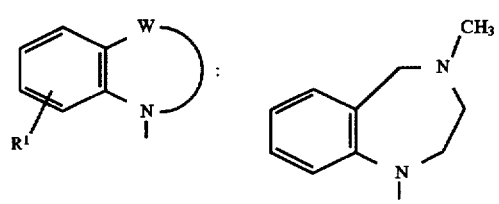
R²: H
R³:
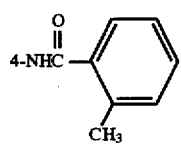
Crystalline form: White powder
Recrystallization solvent: Ethanol/water
NMR analysis: 17)
Form: Hydrochloride

TABLE 1-continued
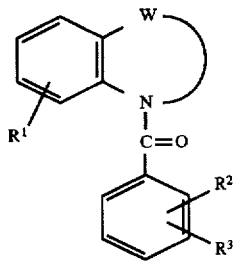
Example 208
Structure
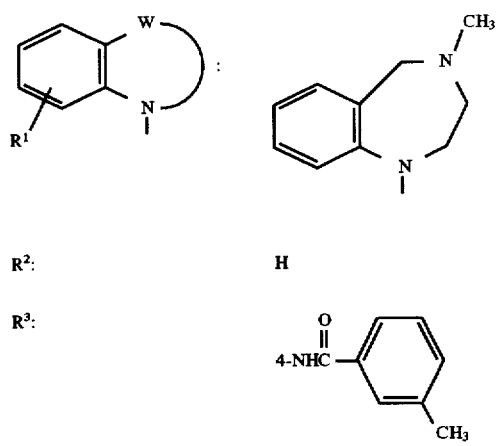
R²: H
R³:
Crystalline form: White powder
Recrystallization solvent: Ethanol/water
NMR analysis: 18)
Form: Hydrochloride
Example 209
Structure
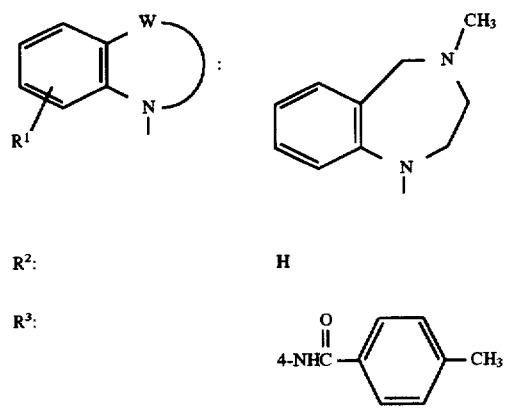
R²: H
R³:
Crystalline form: Yellow powder
Recrystallization solvent: Ethanol/water
NMR analysis: 19)
Form: Hydrochloride TABLE 1-continued
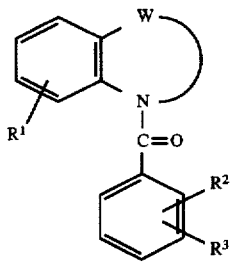
Example 210
Structure
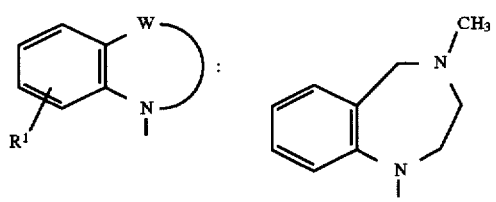
R²: H
R³:
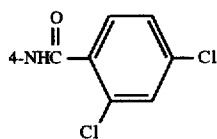
Crystalline form: White powder
Recrystallization solvent: Ethanol/water
NMR analysis: 20)
Form: Hydrochloride
Example 211
Structure
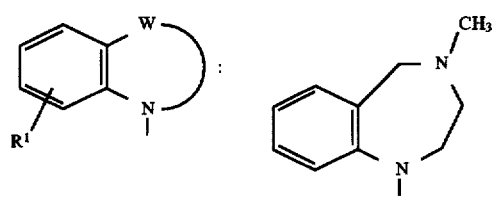
R²: H
R³:
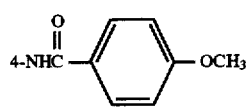
Crystalline form: White powder
Recrystallization solvent: Ethanol/diethyl ether
Melting Point: 159.5–160.5° C.
Form: Free TABLE 1-continued
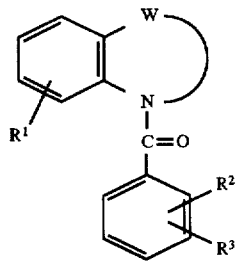
Example 212
Structure
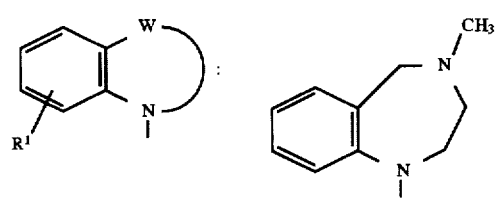
R²: H
R³: 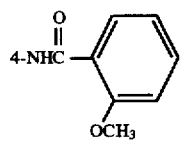
Crystalline form: White powder
Recrystallization solvent: Ethanol/diethyl ether
Melting Point: 189.5–190.5° C.
Form: Free
Example 213
Structure
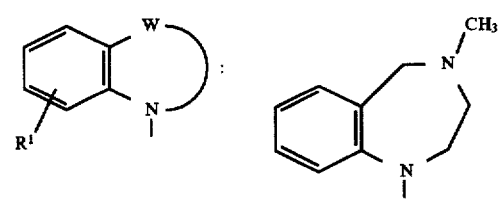
R²: H
R³: 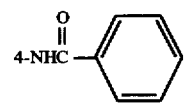
Crystalline form: White powder
Recrystallization solvent: Ethanol/diethyl ether
Melting Point: 170.5–171.5° C.
Form: Free

TABLE 1-continued
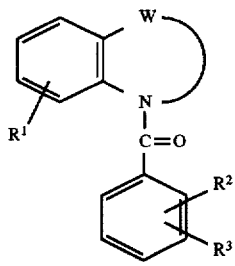
Example 214
Structure
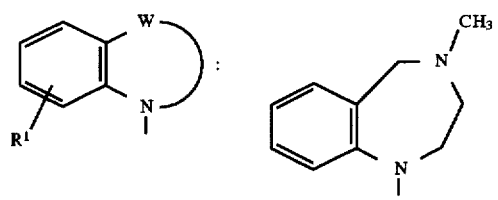
R²: H
R³:
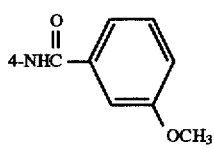
Crystalline form: White powder
Recrystallization solvent: Ethanol/diethyl ether
Melting Point: 165–166° C.
Form: Free
Example 215
Structure
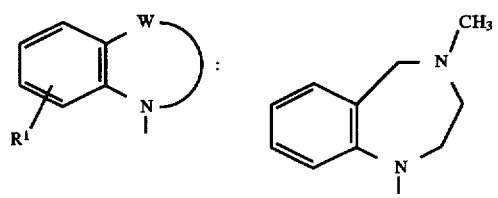
R²: H
R³:
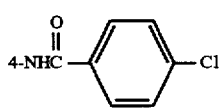
Crystalline form: White powder
Recrystallization solvent: Ethanol/diethyl ether
Melting Point: 173.5–174.5° C.
Form: Free TABLE 1-continued
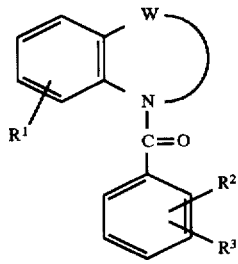
Example 216
Structure
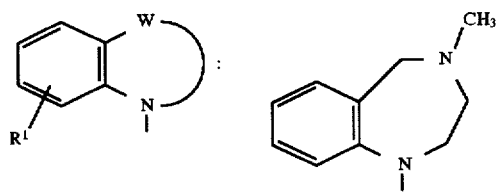
R²: H
R³:
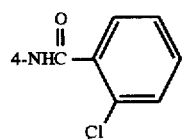
Crystalline form: White powder
Recrystallization solvent: Ethanol/diethyl ether
Melting Point: 182–183° C.
Form: Free
Example 217
Structure
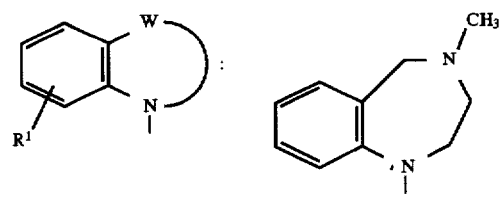
R²: H
R³:
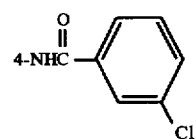
Crystalline form: White powder
Recrystallization solvent: Ethanol/diethyl ether
Melting Point: 225.5–226.5° C.
Form: Free TABLE 1-continued
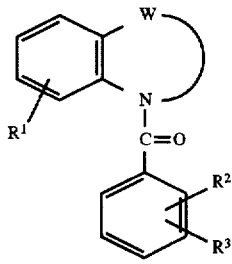
Example 219
Structure
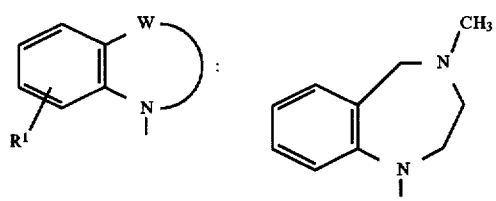
R²:  3-OCH₃
R³:
Crystalline form: White powder
Recrystallization solvent: Ethanol/water
NMR analysis: 21)
Form: Hydrochloride
Example 220
Structure
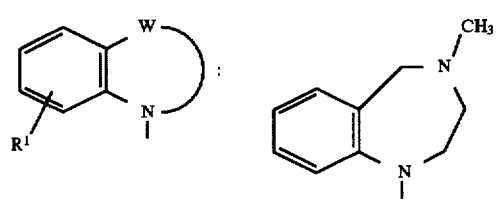
R²:  3-OCH₃
R³:
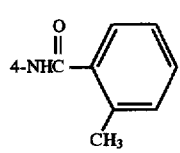
Crystalline form: White powder
Recrystallization solvent: Ethanol/diethyl ether
Melting Point: 147.5–148.5° C.
Form: Free TABLE 1-continued
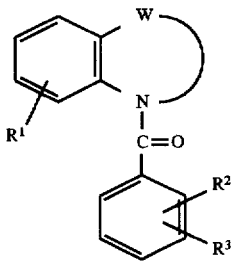
Example 221
Structure
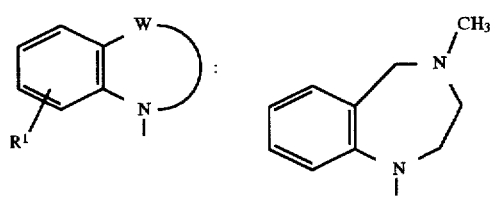
R²: 3-OCH₃
R³:
Crystalline form: White powder
Recrystallization solvent: Ethanol/diethyl ether
Melting Point: 136–137° C.
Form: Free
Example 222
Structure
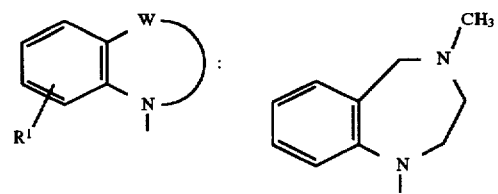
R²: 3-OCH₃
R³:
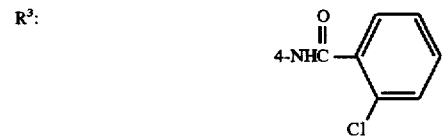
Crystalline form: White powder
Recrystallization solvent: Ethanol/diethyl ether
Melting Point: 191.5–192.5° C.
Form: Free

TABLE 1-continued
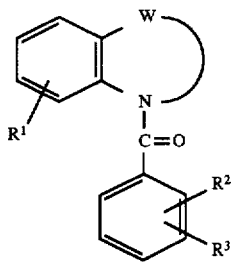
---
Example 223
Structure
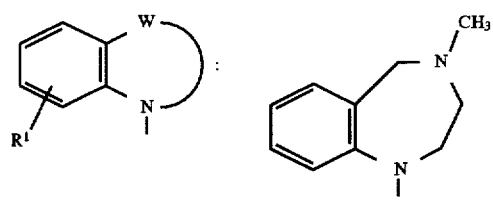
R²: 3-OCH₃
R³:
4-NHC(=O)— [phenyl with 2-CH₃, 3-CH₃]
Crystalline form: White powder
Recrystallization solvent: Ethanol/diethyl ether
Melting Point: 145–146° C.
Form: Free
Example 224
Structure
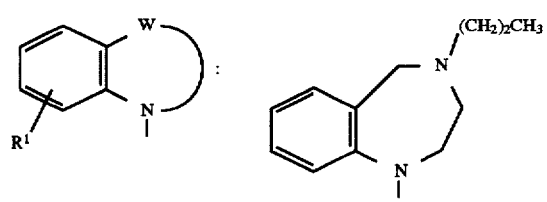
R²: H
R³:
4-NHC(=O)— [phenyl with 2-Cl, 5-Cl]
Crystalline form: White powder
Recrystallization solvent: Ethanol/water
NMR analysis: 22)
Form: Hydrochloride TABLE 1-continued
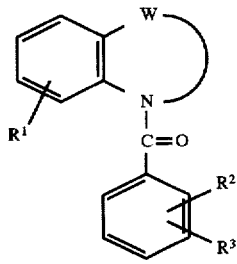
Example 225
Structure
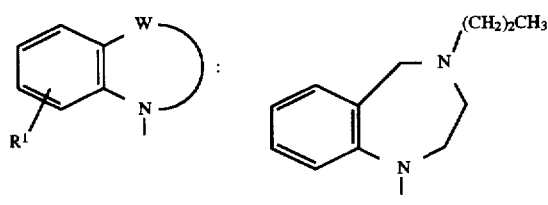
R²: H
R³:
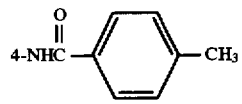
Crystalline form: White powder
Recrystallization solvent: Ethanol/water
NMR analysis: 23)
Form: Hydrochloride
Example 226
Structure
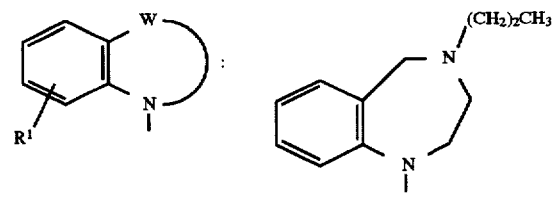
R²: H
R³:
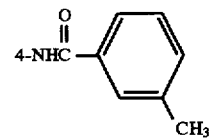
Crystalline form: White powder
Recrystallization solvent: Ethanol/water
NMR analysis: 24)
Form: Hydrochloride TABLE 1-continued
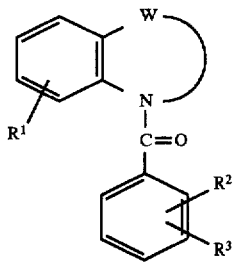
Example 227
Structure
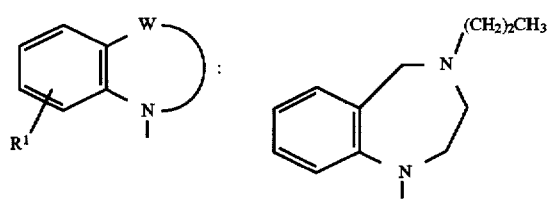
R²: H
R³:
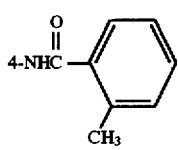
Crystalline form: White powder
Recrystallization solvent: Ethanol/water
NMR analysis: 25)
Form: Hydrochloride
Example 228
Structure
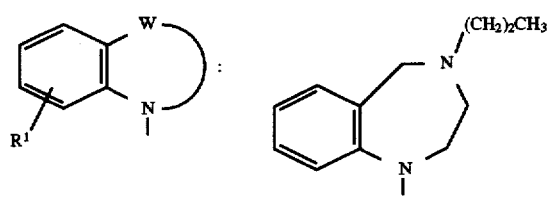
R²: H
R³:
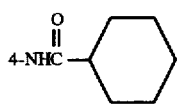
Crystalline form: White powder
Recrystallization solvent: Ethanol/water
NMR analysis: 26)
Form: Hydrochloride TABLE 1-continued
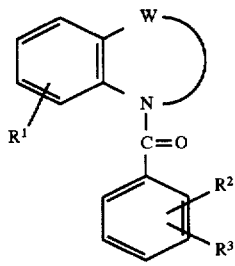
Example 229
Structure
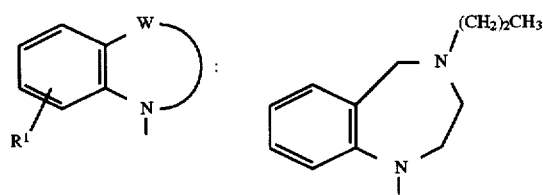
R²: H
R³:
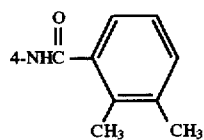
Crystalline form: White powder
Recrystallization solvent: Ethanol/water
NMR analysis: 27)
Form: Hydrochloride
Example 230
Structure
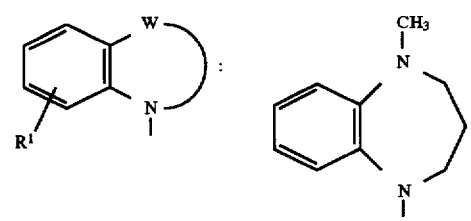
R²: H
R³:
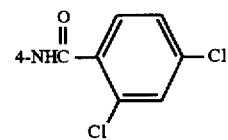
Crystalline form: White powder
Recrystallization solvent: Ethanol/diethyl ether
Melting Point: 206–207° C.
Form: Free TABLE 1-continued
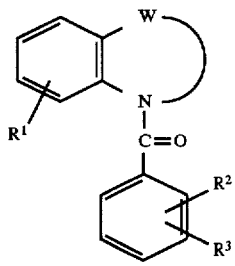
Example 231
Structure
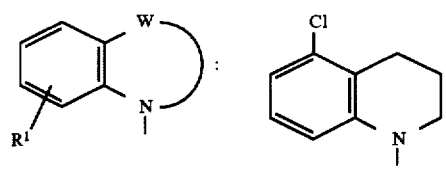
R²:  H
R³:
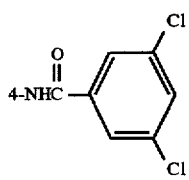
Crystalline form: White powder
Recrystallization solvent: Chloroform/methanol
Melting Point: 211–213° C.
Form: Free
Example 232
Structure
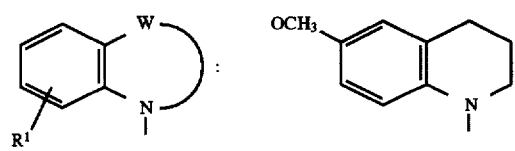
R²:  H
R³:
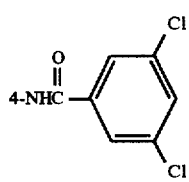
Crystalline form: White powder
Recrystallization solvent: Chloroform/methanol
Melting Point: 228.5–229.5° C.
Form: Free TABLE 1-continued
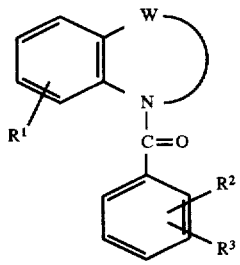
Example 233
Structure
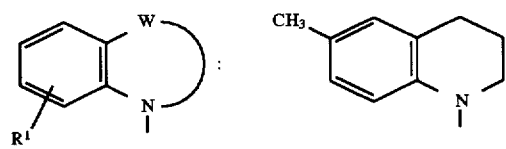
R²:  H
R³:
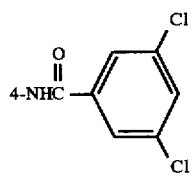
Crystalline form: White powder
Recrystallization solvent: Chloroform/methanol
Melting Point: 237–238° C.
Form: Free
Example 234
Structure
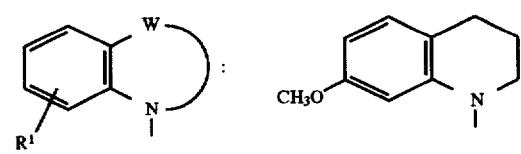
R²:  H
R³:
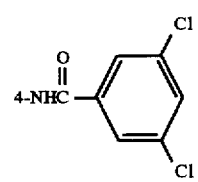
Crystalline form: White powder
Recrystallization solvent: Chloroform/methanol
Melting Point: 226–228° C.
Form: Free TABLE 1-continued
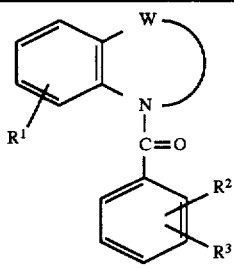
Example 235
Structure
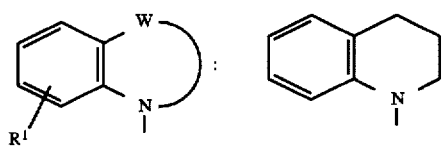
R²: H
R³:
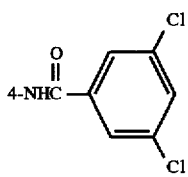
Crystalline form: White powder
Recrystallization solvent: Chloroform/methanol
Melting Point: 220–222° C.
Form: Free
Example 236
Structure
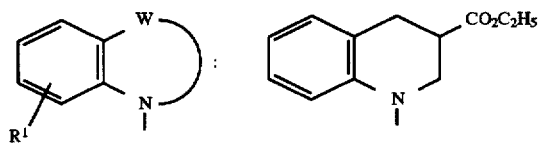
R²: H
R³:
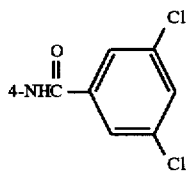
Crystalline form: Colorless amorphous
NMR analysis: 28)
Form: Free
Example 237
Structure
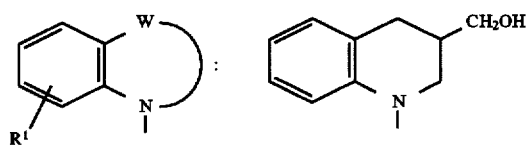

TABLE 1-continued
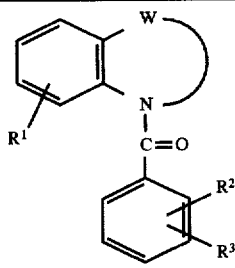
R²: H
R³:
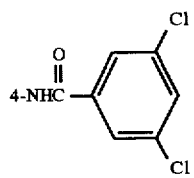
Crystalline form: White powder
Recrystallization solvent: Ethanol
Melting Point: 162–165° C.
Form: Free
Example 238
Structure
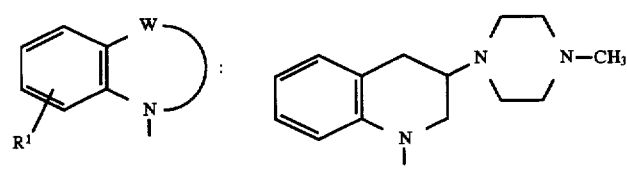
R²: H
R³:
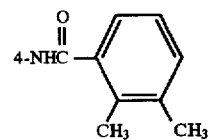
Crystalline form: Light brown amorphous
NMR analysis: 29)
Form: Free
Example 239
Structure
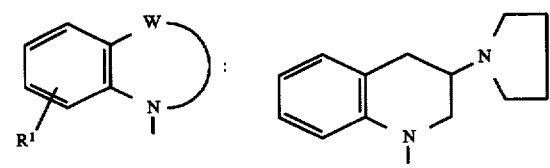
R²: H
R³:
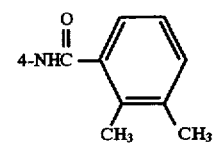
Crystalline form: Light brown amorphous
NMR analysis: 30)

TABLE 1-continued
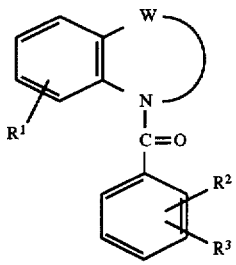
Form: Free
Example 240
Structure
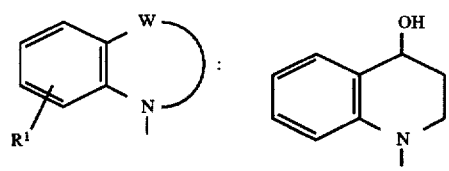
R²: H
R³:
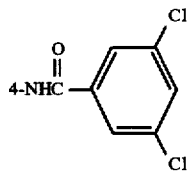
Crystalline form: White powder
Recrystallization solvent: Ethanol
Melting Point: 215–217° C.
Form: Free
Example 241
Structure
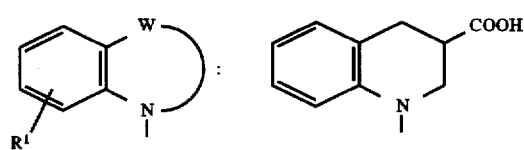
R²: H
R³:
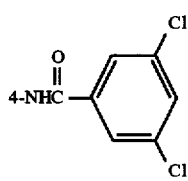
Crystalline form: White powder
Recrystallization solvent: Ethanol
Melting Point: 221–223° C.
Form: Free

TABLE 1-continued
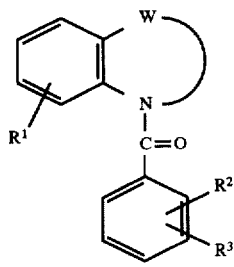
Example 242
Structure
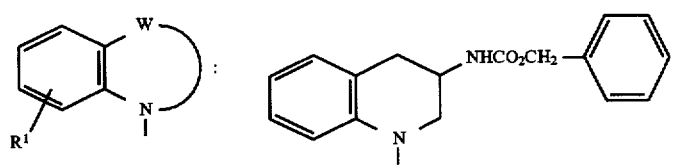
R²:  H
R³:
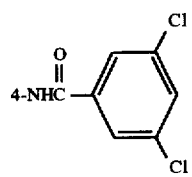
Crystalline form: Colorless amorphous
NMR analysis: 31)
Form: Free
Example 243
Structure
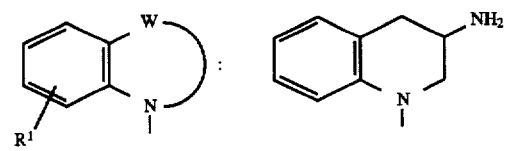
R²:  H
R³:
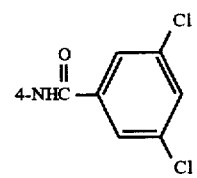
Crystalline form: White powder
Recrystallization solvent: Ethanol
Melting Point: 207–210° C.
Form: Free TABLE 1-continued
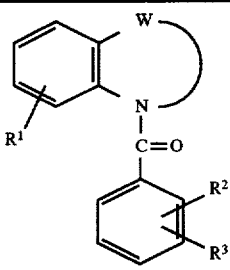
Example 244
Structure
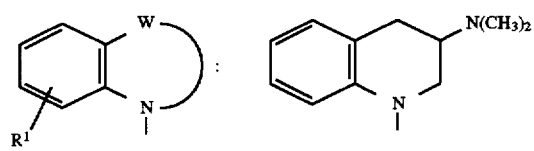
R²: H
R³:
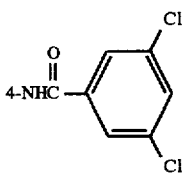
Crystalline form: Colorless amorphous
NMR analysis: 32)
Form: Free
Example 245
Structure
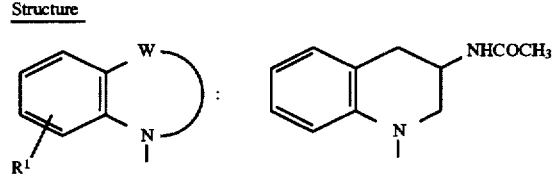
R²: H
R³:
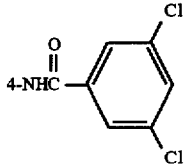
Crystalline form: Colorless amorphous
NMR analysis: 33)
Form: Free
Example 246
Structure

TABLE 1-continued
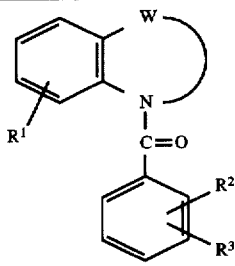
R²: H
R³: 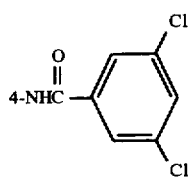
Crystalline form: Colorless amorphous
NMR analysis: 34)
Form: Free
Example 247
Structure
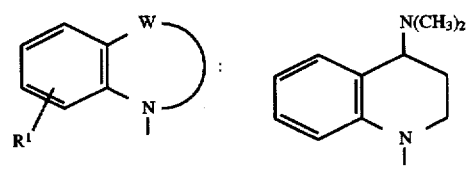
R²: H
R³: 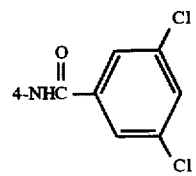
Crystalline form: Colorless amorphous
NMR analysis: 35)
Form: Free
Example 248
Structure
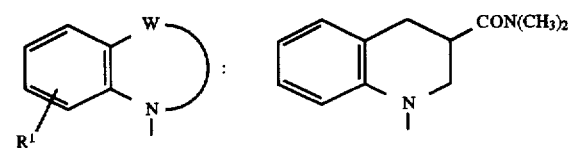
R²: H
R³: 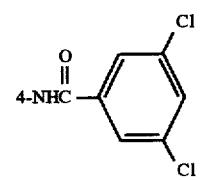

TABLE 1-continued

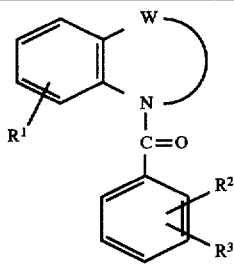

Crystalline form: Light yellow powder
Recrystallization solvent: Ethanol
Melting Point: 186–187° C.
Form: Free Example 249

Structure

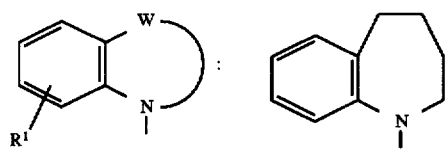

R²: H

R³:
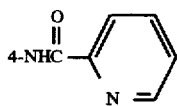
4-NHC

Crystalline form: Colorless needles
Recrystallization solvent: Ethanol
Melting Point: 190–191° C.
Form: Free Example 250

Structure

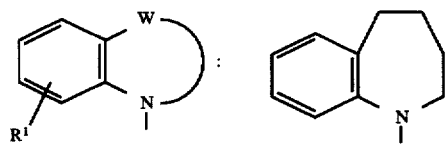

R²: H

R³:
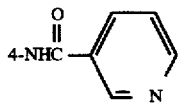
4-NHC

Crystalline form: Light yellow scales
Recrystallization solvent: Ethanol/water
Melting Point: 230–231° C.
Form: Free Example 251

Structure

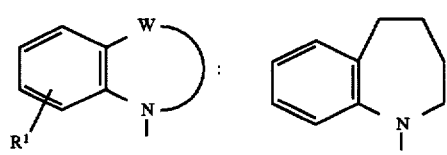

TABLE 1-continued

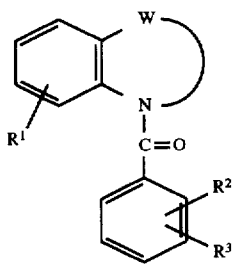

R²: H

R³:
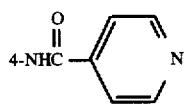
4-NHC(=O)-pyridin-4-yl

Crystalline form: Light yellow needles
Recrystallization solvent: Ethanol
Melting Point: 227–228° C.
Form: Free Example 252

Structure

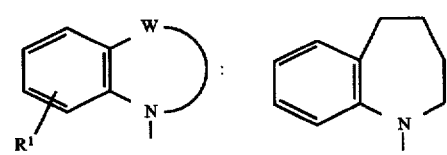

R²: H

R³:
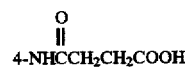
4-NHCCH₂CH₂COOH

Crystalline form: Colorless needles
Recrystallization solvent: Ethyl acetate
Melting Point: 192° C.
Form: Free Example 253

Structure

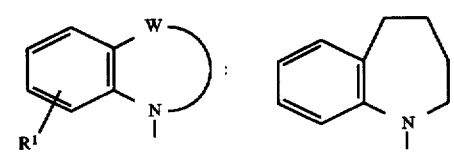

R²: H

R³:
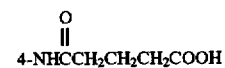
4-NHCCH₂CH₂CH₂COOH

Crystalline form: White powder
Recrystallization solvent: Ethyl acetate
Melting Point: 186.5–189° C.
Form: Free TABLE 1-continued

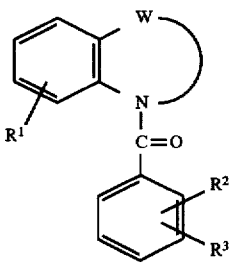

Example 254

Structure

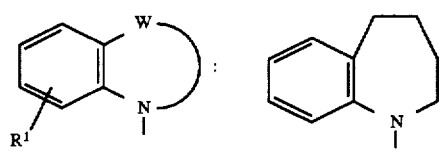

R²: H

R³:

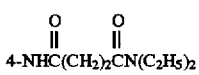

4-NHC(CH₂)₂CN(C₂H₅)₂

Crystalline form: Light yellow scales
Recrystallization solvent: n-Hexane/ethyl acetate
Melting Point: 165–167° C.
Form: Free Example 255

Structure

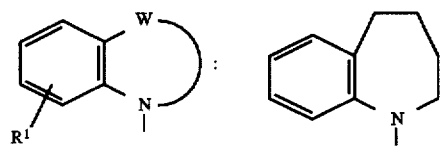

R²: H

R³:

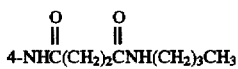

4-NHC(CH₂)₂CNH(CH₂)₃CH₃

Crystalline form: White powder
Recrystallization solvent: Ethyl acetate
Melting Point: 169–170° C.
Form: Free Example 256

Structure

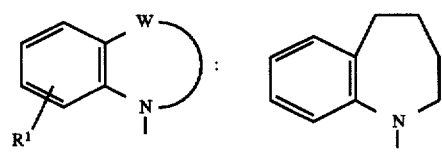

R²: H

R³:

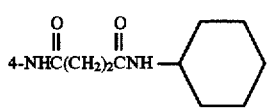

4-NHC(CH₂)₂CNH—

TABLE 1-continued

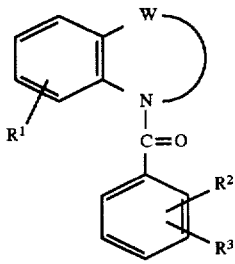

Crystalline form: Colorless scales
Recrystallization solvent: n-Hexane/ethyl acetate
Melting Point: 174–177° C.
Form: Free Example 257

Structure

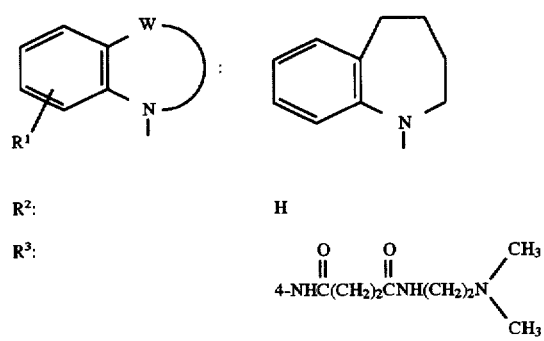

R²: H

R³: 4-NHC(CH₂)₂CNH(CH₂)₂N(CH₃)₂ (with two C=O groups)

(structural formula: 4-NHC(=O)(CH₂)₂C(=O)NH(CH₂)₂N(CH₃)₂)

Crystalline form: White powder
Recrystallization solvent: Ethyl acetate
Melting Point: 114–118° C.
Form: Free Example 258

Structure

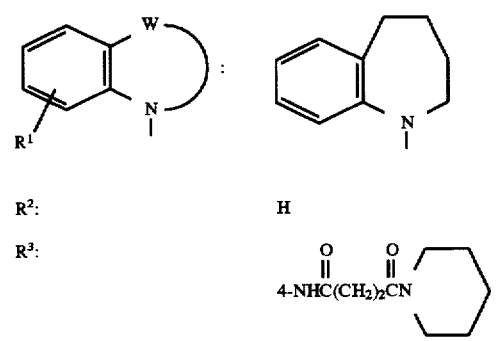

R²: H

R³: 4-NHC(=O)(CH₂)₂C(=O)N-piperidinyl

Crystalline form: White powder
Recrystallization solvent: Ethyl acetate
Melting Point: 170–172° C.
Form: Free Example 259

Structure

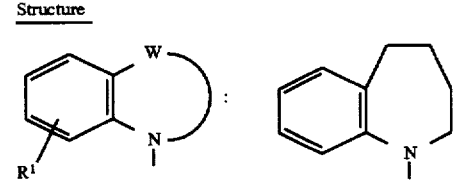

TABLE 1-continued

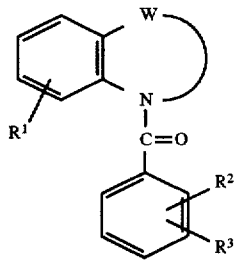

R²: H

R³: 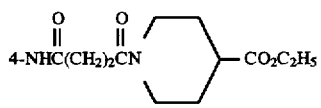

Crystalline form: White powder
Recrystallization solvent: n-Hexane/ethyl acetate
Melting Point: 179–181° C.
Form: Free Example 260

Structure

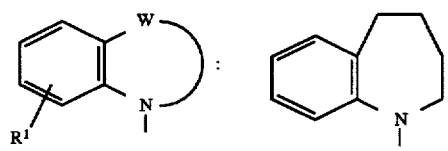

R²: H

R³: 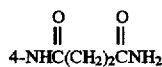

Crystalline form: White powder
Recrystallization solvent: Ethyl acetate
Melting Point: 118–121° C.
Form: Free Example 261

Structure

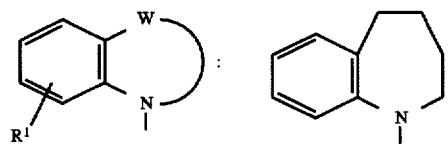

R²: H

R³: 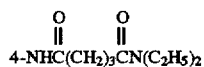

Crystalline form: White powder
Recrystallization solvent: Ethyl acetate
Melting Point: 144–148° C.
Form: Free TABLE 1-continued
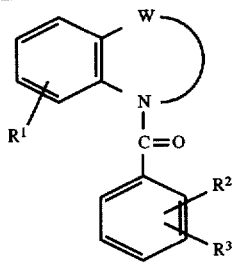
Example 262
Structure
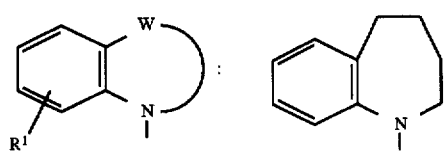
R²: H
R³: 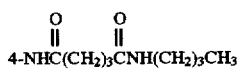
4-NHC(CH₂)₃CNH(CH₂)₃CH₃
Crystalline form: Colorless scales
Recrystallization solvent: Ethyl acetate
Melting Point: 156–157° C.
Form: Free
Example 263
Structure
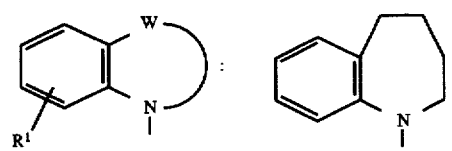
R²: H
R³: 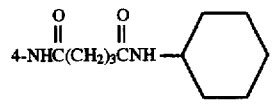
4-NHC(CH₂)₃CNH—
Crystalline form: White powder
Recrystallization solvent: Ethyl acetate
Melting Point: 204–206° C.
Form: Free
Example 264
Structure
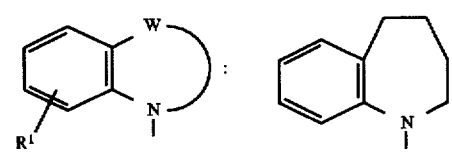
R²: H
R³: 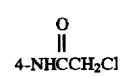
4-NHCCH₂Cl TABLE 1-continued

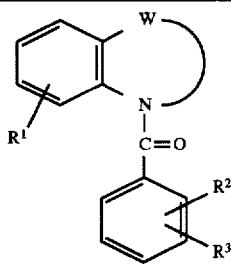

Crystalline form: Light yellow powder
Recrystallization solvent: n-Hexane/ethyl acetate
Melting Point: 165–167° C.
Form: Free Example 265

Structure

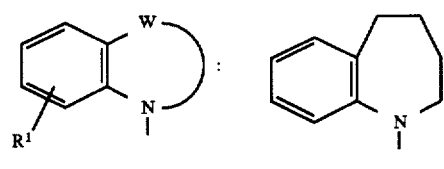

R²: H

R³: 
$$4\text{-NH}\overset{\text{O}}{\overset{\|}{\text{C}}}\text{CH}_2\text{CH}_2\text{Cl}$$

Crystalline form: Light yellow amorphous
NMR analysis: 36)
Form: Free

Example 266

Structure

R²: H

R³: 
$$4\text{-NH}\overset{\text{O}}{\overset{\|}{\text{C}}}(\text{CH}_2)_3\text{Cl}$$

Crystalline form: White powder
Recrystallization solvent: n-Hexane/ethyl acetate
Melting Point: 122–124° C.
Form: Free Example 267

Structure

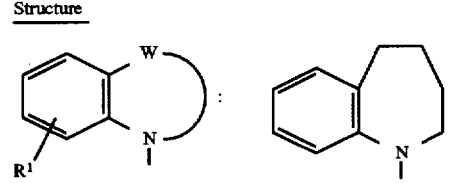

R²: H

R³: 
$$4\text{-NH}\overset{\text{O}}{\overset{\|}{\text{C}}}\text{CH}_2\text{CO}_2\text{C}_2\text{H}_5$$

TABLE 1-continued

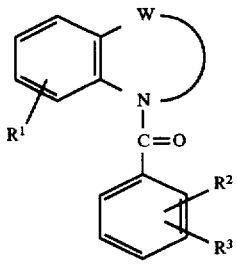

Crystalline form: Light yellow powder
Recrystallization solvent: n-Hexane/ethyl acetate
Melting Point: 116–117° C.
Form: Free Example 268

Structure

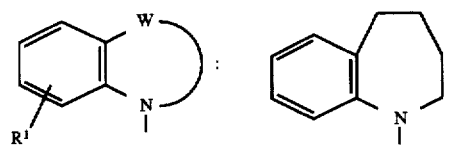

R²: H

R³:
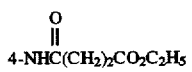
4-NHC(CH₂)₂CO₂C₂H₅

Crystalline form: White powder
Recrystallization solvent: n-Hexane/ethyl acetate
Melting Point: 121–123° C.
Form: Free Example 269

Structure

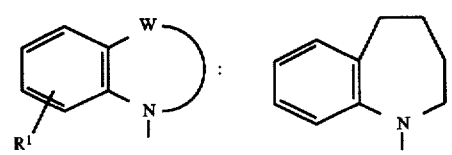

R²: H

R³:
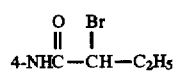
4-NHC—CH—C₂H₅

Crystalline form: Colorless needles
Recrystallization solvent: Ethyl acetate
Melting Point: 186–187° C.
Form: Free Example 270

Structure

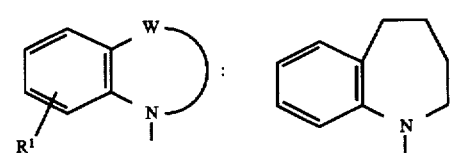

R²: H

TABLE 1-continued
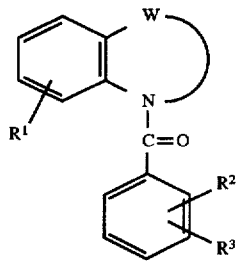
| R³: | 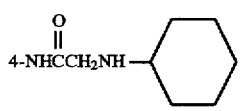 |
|---|---|
Crystalline form: White powder
Recrystallization solvent: n-Hexane/ethyl acetate
Melting Point: 139–142° C.
Form: Free
Example 271
Structure
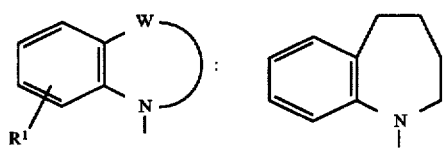
R²: H
| R³: | 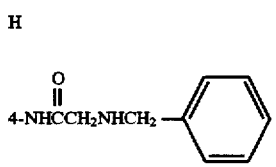 |
|---|---|
Crystalline form: Light yellow amorphous
NMR analysis: 37)
Form: Free
Example 272
Structure
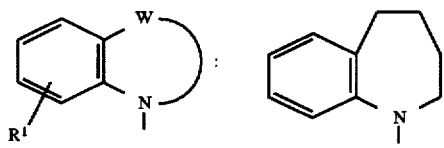
R²: H
R³:
Crystalline form: White powder
Recrystallization solvent: Ethyl acetate
Melting Point: 149.5–152.5° C.
Form: Free TABLE 1-continued

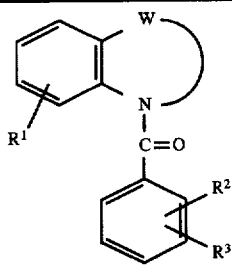

Example 273

Structure

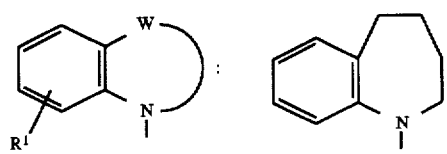

R²: H

R³:
4-NHCCH₂NHC(CH₃)₃

Crystalline form: Colorless needles
Recrystallization solvent: Ethanol
Melting Point: 150–152.5° C.
Form: Free Example 274

Structure

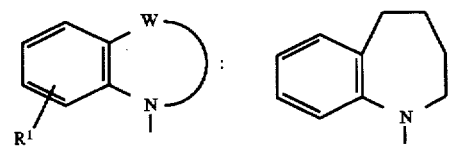

R²: H

R³:
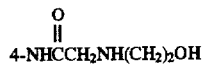
4-NHCCH₂NH(CH₂)₂OH

Crystalline form: White powder
Recrystallization solvent: Ethyl acetate
Melting Point: 150° C.
Form: Free Example 275

Structure

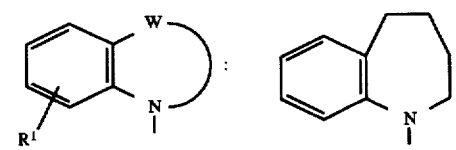

R²: H

R³:
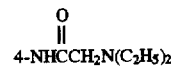
4-NHCCH₂N(C₂H₅)₂

Crystalline form: Colorless needles
Recrystallization solvent: n-Hexane/ethyl acetate TABLE 1-continued
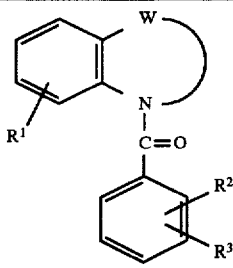
Melting Point: 101–104° C.
Form: Free
Example 276
Structure
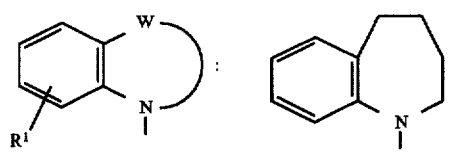
R²: H
R³:
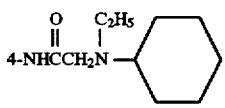
Crystalline form: White powder
Recrystallization solvent: n-Hexane/ethyl acetate
Melting Point: 120–122° C.
Form: Free
Example 277
Structure
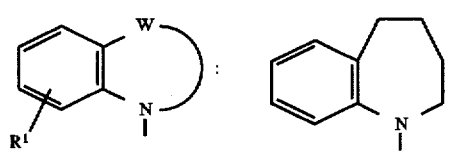
R²: H
R³:
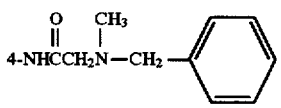
Crystalline form: Light yellow amorphous
NMR analysis: 38)
Form: Free
Example 278
Structure
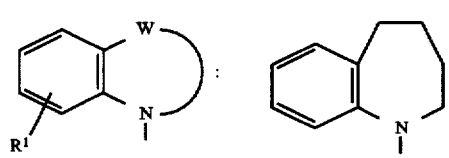
R²: H TABLE 1-continued

R³:

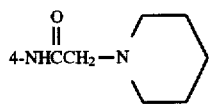
4-NHCCH₂—N (piperidine)

Crystalline form: Colorless needles
Recrystallization solvent: Ethanol
Melting Point: 183–186° C.
Form: Free Example 279

Structure

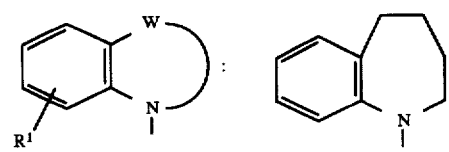

R²: H

R³:

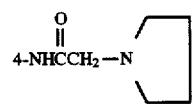
4-NHCCH₂—N (pyrrolidine)

Crystalline form: Light brown powder
Recrystallization solvent: n-Hexane/ethyl acetate
Melting Point: 139–142° C.
Form: Free Example 280

Structure

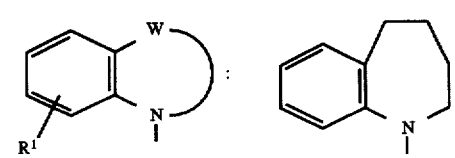

R²: H

R³:

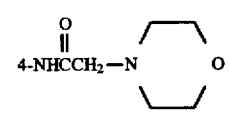
4-NHCCH₂—N (morpholine)

Crystalline form: Light yellow powder
Recrystallization solvent: Ethanol
Melting Point: 162–165° C.
Form: Free TABLE 1-continued
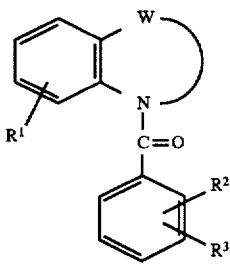
Example 281
Structure
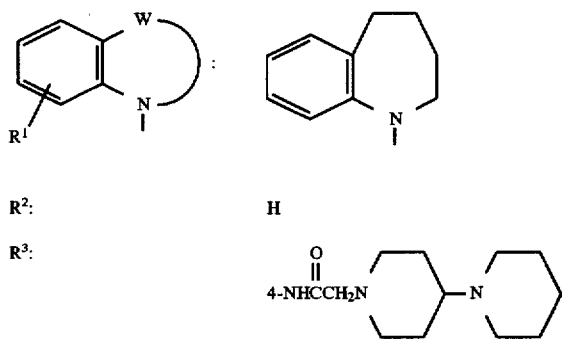
R²: H
R³:
4-NHCCH₂N—[piperidine]—N[piperidine]
  ‖
  O
Crystalline form: Light yellow scales
Recrystallization solvent: Ethyl acetate
Melting Point: 224–227° C.
Form: Free
Example 282
Structure
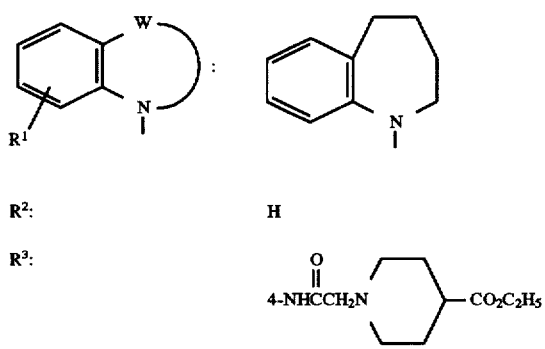
R²: H
R³:
4-NHCCH₂N—[piperidine]—CO₂C₂H₅
  ‖
  O
Crystalline form: Light yellow amorphous
NMR analysis: 39)
Form: Free
Example 283
Structure
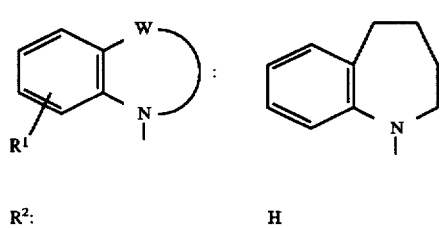
R²: H TABLE 1-continued

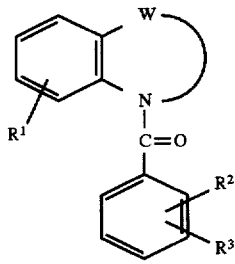

R³:

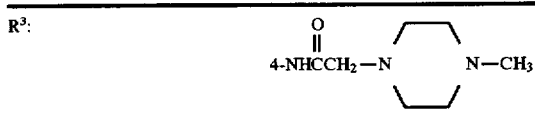

Crystalline form: Light yellow powder
Recrystallization solvent: Ethanol/water
Melting Point: 162–164° C.
Form: Free Example 284

Structure

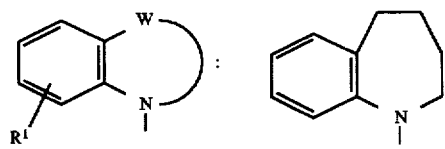 

R²: H

R³:
$$\text{4-NHCCH}_2\text{NH}_2$$
(with C=O)

Crystalline form: Light yellow powder
Recrystallization solvent: Ethanol
Melting Point: 238–241° C. (decomposed)
Form: Hydrochloride Example 285

Structure

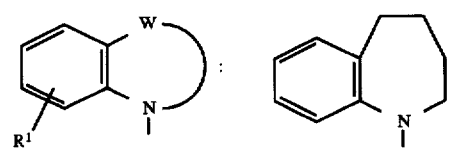 

R²: H

R³:
$$\text{4-NHCCH}_2\text{NHCCH}_3$$
(with two C=O)

Crystalline form: Light yellow amorphous
NMR analysis: 40)
Form: Free

Example 286

Structure

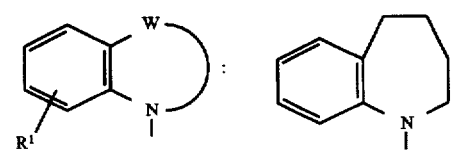

TABLE 1-continued
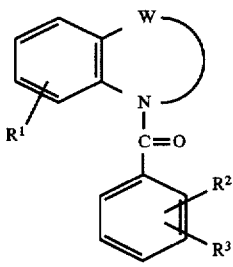
R²: H
R³: 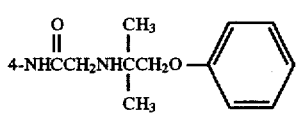
Crystalline form: Colorless amorphous
NMR analysis: 41)
Form: Free
Example 287
Structure
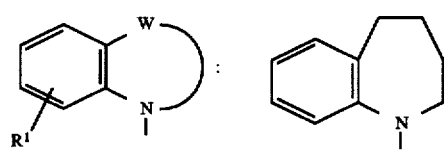
R²: H
R³: 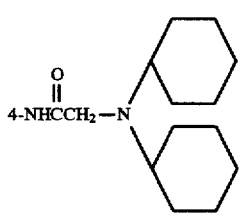
Crystalline form: Colorless needles
Recrystallization solvent: n-Hexane/ethyl acetate
Melting Point: 168–169° C.
Form: Free
Example 288
Structure
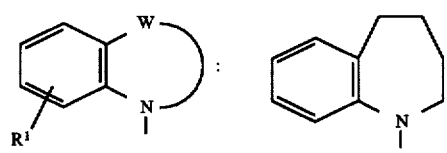
R²: H
R³: 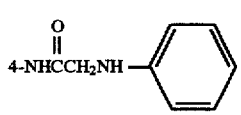
Crystalline form: Light brown powder
Recrystallization solvent: Ethanol
Melting Point: 189–191° C.
Form: Free TABLE 1-continued

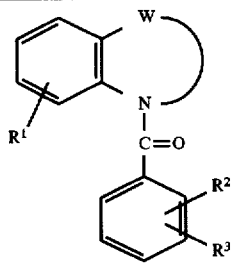

Example 289

Structure

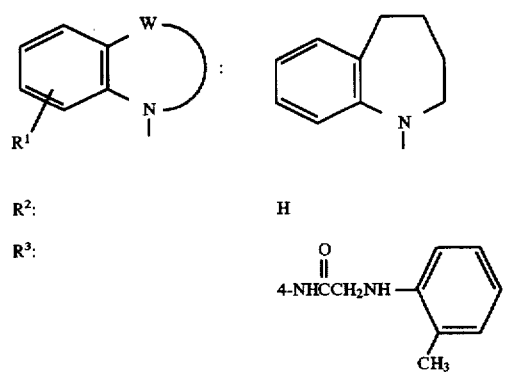

R²: H

R³: 4-NHCCH₂NH—(2-methylphenyl), with structure:

$$\text{4-NHCCH}_2\text{NH} \underset{\text{CH}_3}{\overset{\text{O}}{\|}}$$

Crystalline form: White powder
Recrystallization solvent: n-Hexane/ethyl acetate
Melting Point: 200–202° C.
Form: Free

Example 290

Structure

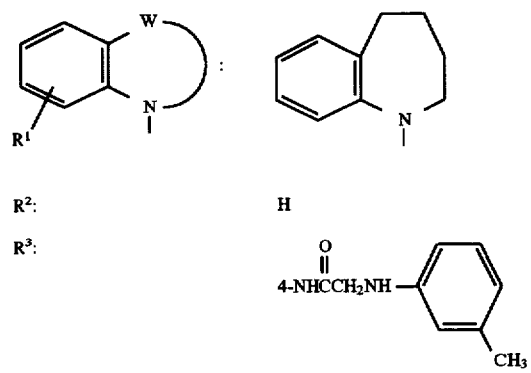

R²: H

R³:

$$\text{4-NHCCH}_2\text{NH} \underset{\text{CH}_3}{\overset{\text{O}}{\|}}$$

Crystalline form: Colorless scales
Recrystallization solvent: n-Hexane/ethyl acetate
Melting Point: 143–146° C.
Form: Free

Example 291

Structure

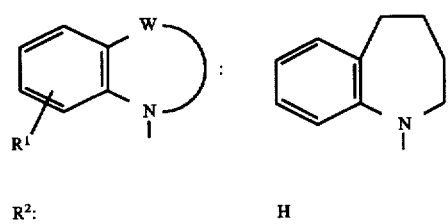

R²: H

TABLE 1-continued

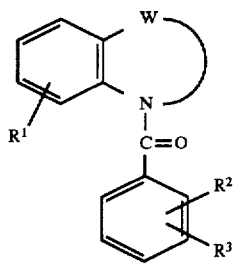

R³:

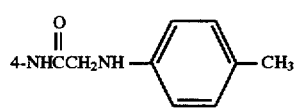

Crystalline form: White powder
Recrystallization solvent: n-Hexane/ethyl acetate
Melting Point: 117–117.5° C.
Form: Free Example 292

Structure

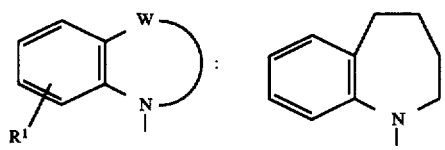

R²: H

R³:

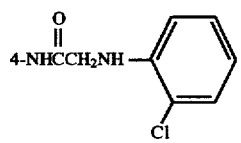

Crystalline form: Light brown powder
Recrystallization solvent: Diethyl ether/ethyl acetate
Melting Point: 225–226° C.
Form: Free Example 293

Structure

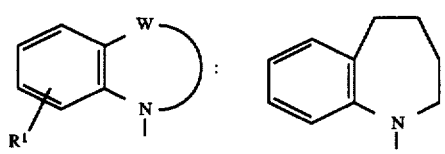

R²: H

R³:

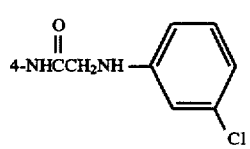

Crystalline form: White powder
Recrystallization solvent: n-Hexane/ethanol
Melting Point: 175–176.5° C.
Form: Free TABLE 1-continued
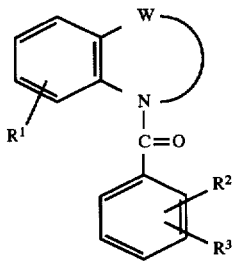
Example 294
Structure
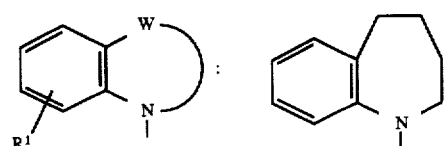
R²: H
R³:
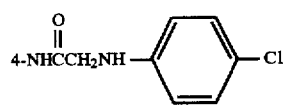
Crystalline form: White powder
Recrystallization solvent: Ethyl acetate
Melting Point: 234–236° C.
Form: Free
Example 295
Structure
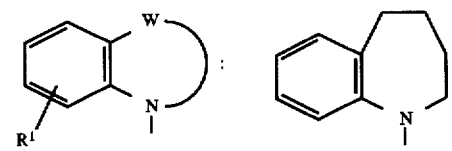
R²: H
R³:
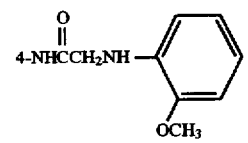
Crystalline form: Colorless scales
Recrystallization solvent: Ethyl acetate
Melting Point: 172–174° C.
Form: Free
Example 296
Structure
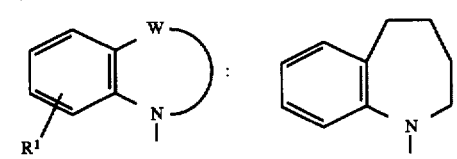
R²: H TABLE 1-continued

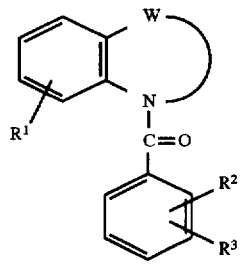

R³:

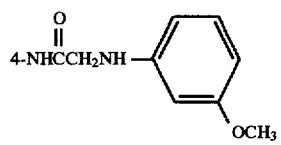

Crystalline form: White powder
Recrystallization solvent: Ethyl acetate
Melting Point: 154–155° C.
Form: Free Example 297

Structure

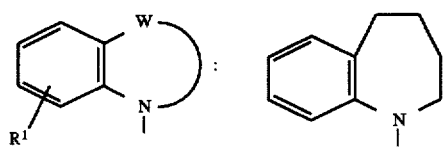

R²: H

R³:

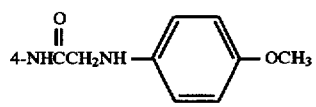

Crystalline form: Light yellow needles
Recrystallization solvent: n-Hexane/ethyl acetate
Melting Point: 181.5–183.5° C.
Form: Free Example 298

Structure

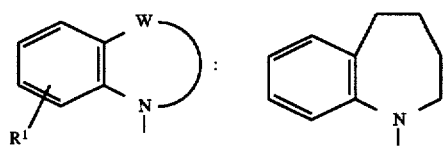

R²: H

R³:

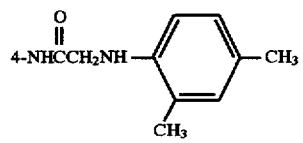

Crystalline form: White powder
Recrystallization solvent: n-Hexane/ethyl acetate
Melting Point: 173–175° C.
Form: Free TABLE 1-continued
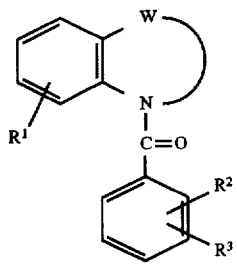
Example 299
Structure
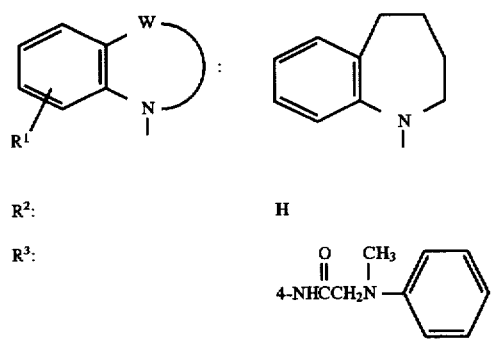
R²: H
R³: 4-NHCCH₂N— (with O=C, CH₃, phenyl)
$R^3$: 4-NHC(=O)CH$_2$N(CH$_3$)(phenyl)-
Crystalline form: White powder
Recrystallization solvent: n-Hexane/ethyl acetate
Melting Point: 137–138° C.
Form: Free
Example 300
Structure
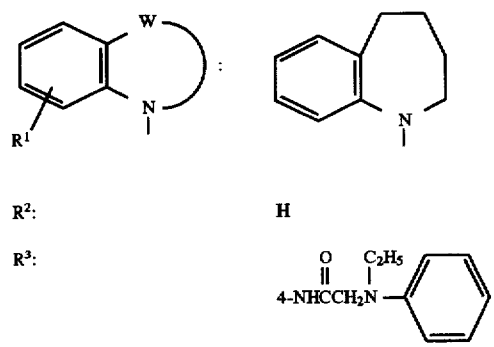
R²: H
$R^3$: 4-NHC(=O)CH$_2$N(C$_2$H$_5$)(phenyl)-
Crystalline form: Light yellow amorphous
NMR analysis: 42)
Form: Free
Example 301
Structure
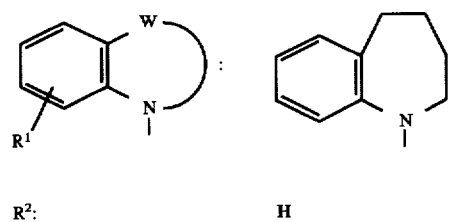
R²: H TABLE 1-continued

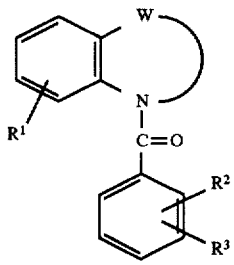

R³:

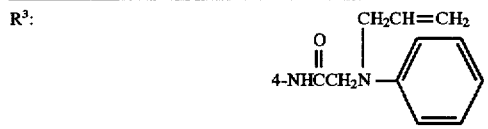

Crystalline form: Colorless needles
Recrystallization solvent: Diethyl ether/ethyl acetate
Melting Point: 129–130° C.
Form: Free Example 302

Structure

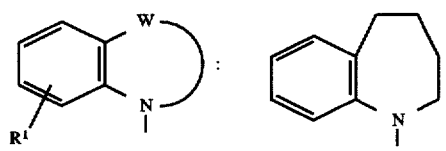

R²: H

R³:

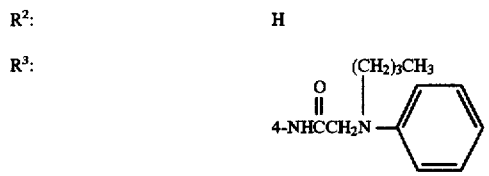

Crystalline form: Colorless needles
Recrystallization solvent: n-Hexane/ethyl acetate
Melting Point: 181–183° C.
Form: Free Example 303

Structure

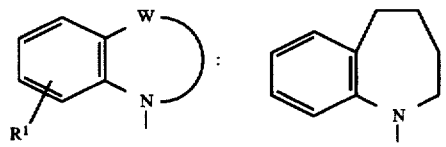

R²: H

R³:

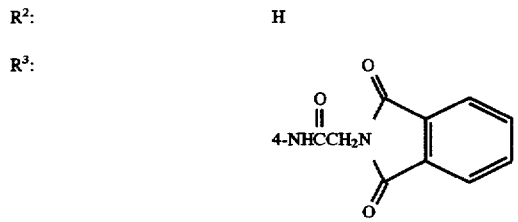

Crystalline form: White powder
Recrystallization solvent: Ethyl acetate
Melting Point: 248–249° C.
Form: Free TABLE 1-continued

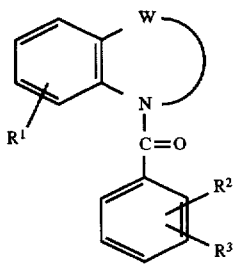

Example 304

Structure

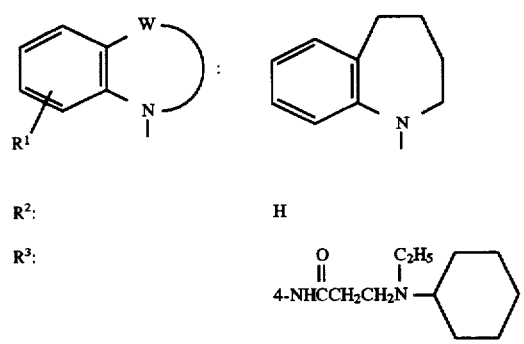

R²: H

R³: 
$$4\text{-NHCCH}_2\text{CH}_2\text{N}\begin{array}{c}\text{O}\\\|\end{array}\begin{array}{c}\text{C}_2\text{H}_5\\|\end{array}-\text{cyclohexyl}$$

Crystalline form: Light yellow amorphous
NMR analysis: 43)
Form: Free

Example 305

Structure

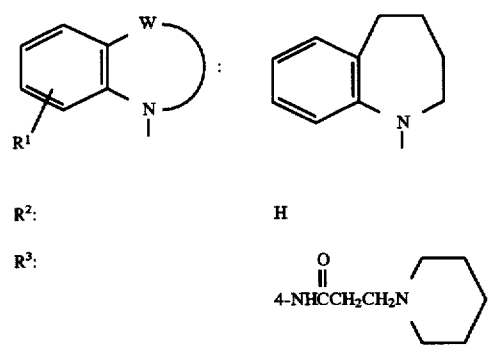

R²: H

R³: 
$$4\text{-NHCCH}_2\text{CH}_2\text{N}-\text{piperidyl}$$

Crystalline form: Light yellow needles
Recrystallization solvent: Ethanol
Melting Point: 94–96° C.
Form: Free

Example 306

Structure

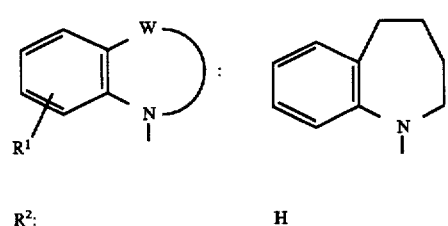

R²: H

TABLE 1-continued

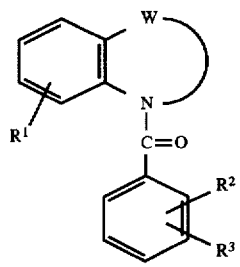

| R³: | 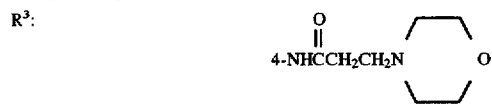 |

Crystalline form: Light brown powder
Recrystallization solvent: Ethyl acetate
Melting Point: 159–161° C.
Form: Free Example 307

Structure

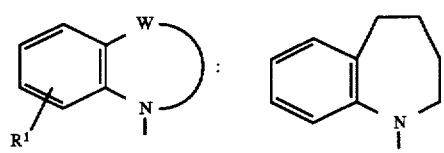

R²: H

R³: 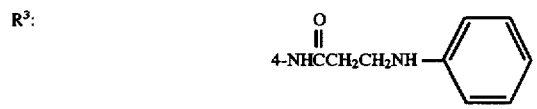

Crystalline form: White powder
Recrystallization solvent: Ethyl acetate
Melting Point: 180–183° C.
Form: Free Example 308

Structure

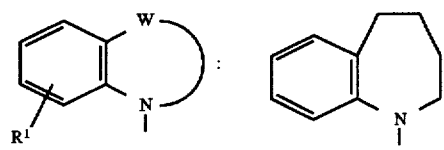

R²: H

R³: 

Crystalline form: Light brown powder
Recrystallization solvent: Ethanol
Melting Point: 177–180° C.
Form: Free TABLE 1-continued
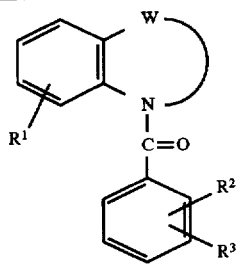
Example 309
Structure
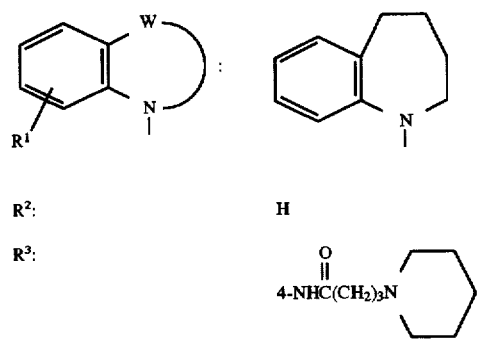
R²: H
R³:
4-NHC(CH₂)₃N⟨piperidine⟩
   ‖
   O
Crystalline form: White powder
Recrystallization solvent: Ethyl acetate
Melting Point: 91–93° C.
Form: Free
Example 310
Structure
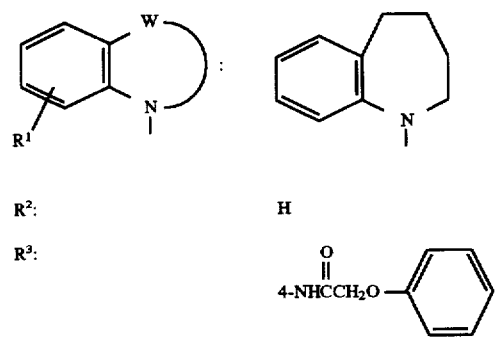
R²: H
R³:
4-NHCCH₂O—⟨phenyl⟩
   ‖
   O
Crystalline form: Light brown scales
Recrystallization solvent: Ethanol
Melting Point: 155–156.5° C.
Form: Free
Example 311
Structure
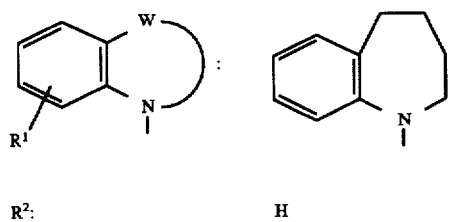
R²: H TABLE 1-continued

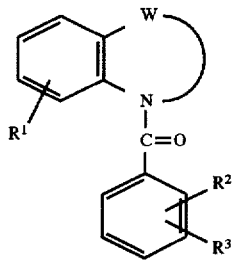

R³:

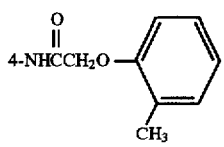

Crystalline form: Colorless scales
Recrystallization solvent: Ethyl acetate
Melting Point: 172.5–175° C.
Form: Free Example 312

Structure

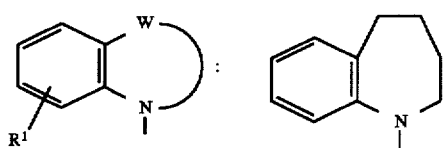

R²: H

R³:

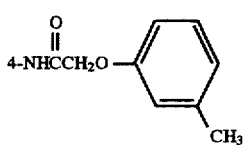

Crystalline form: White powder
Recrystallization solvent: Ethanol
Melting Point: 148–150.5° C.
Form: Free Example 313

Structure

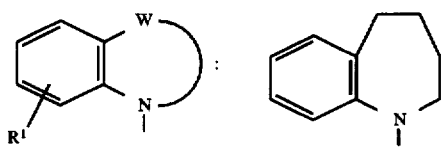

R²: H

R³:

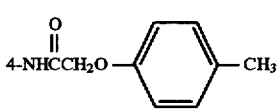

Crystalline form: White powder
Recrystallization solvent: Ethyl acetate
Melting Point: 172–173° C.
Form: Free TABLE 1-continued
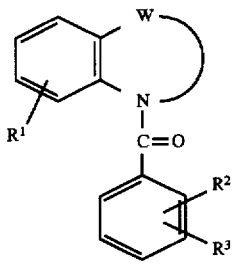
Example 314
Structure
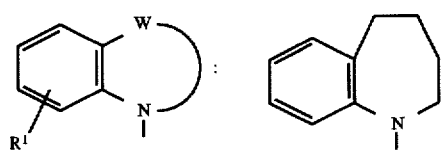
R²: H
R³:
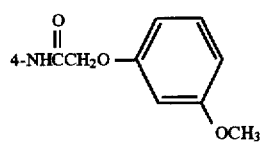
Crystalline form: Colorless scales
Recrystallization solvent: n-Hexane/ethyl acetate
Melting Point: 133–135° C.
Form: Free
Example 315
Structure
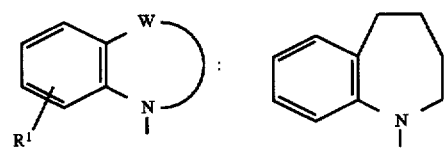
R²: H
R³:
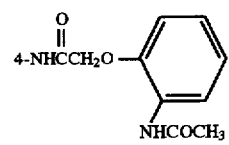
Crystalline form: White powder
Recrystallization solvent: Ethyl acetate
Melting Point: 217–219° C.
Form: Free
Example 316
Structure
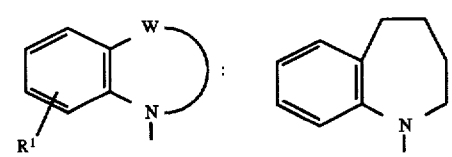
R²: H TABLE 1-continued
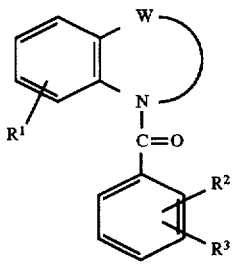
R³:
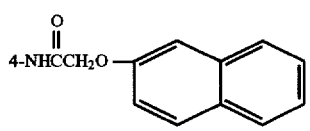
Crystalline form: Colorless needles
Recrystallization solvent: Ethyl acetate
Melting Point: 226–227.5° C.
Form: Free
Example 317
Structure
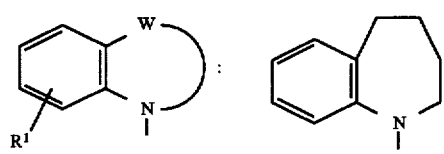
R²: H
R³:
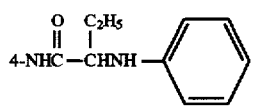
Crystalline form: Colorless amorphous
NMR analysis: 44)
Form: Free
Example 318
Structure
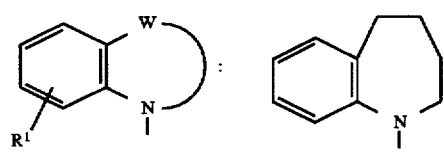
R²: H
R³:
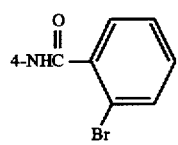
Crystalline form: White powder
Recrystallization solvent: Dichloromethane
Melting Point: 234–235° C.
Form: Free TABLE 1-continued
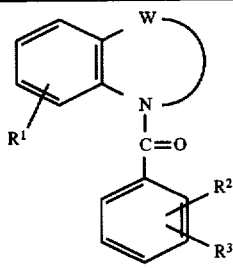
Example 319
Structure
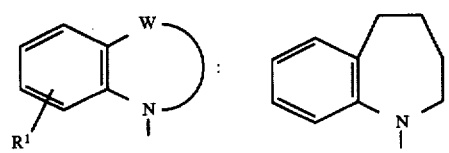
R²: H
R³:
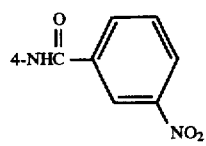
Crystalline form: Colorless prisms
Recrystallization solvent: Methanol
Melting Point: 218–218.5° C.
Form: Free
Example 320
Structure
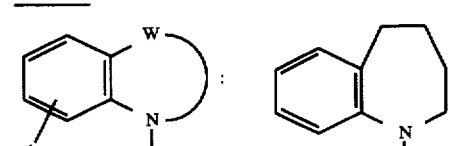
R²: H
R³:
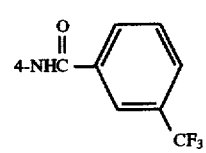
Crystalline form: Colorless prisms
Recrystallization solvent: Ethanol
Melting Point: 202.5–206° C.
Form: Free
Example 321
Structure
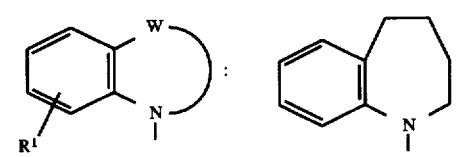
R²: H TABLE 1-continued
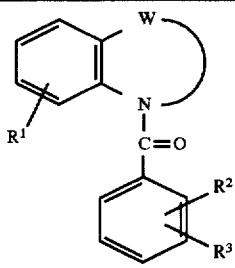
R³:
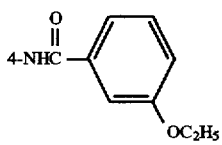
Crystalline form: White powder
Recrystallization solvent: Ethanol
Melting Point: 174–176° C.
Form: Free
Example 322
Structure
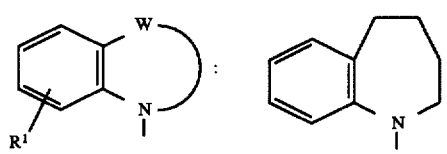
R²: H
R³:
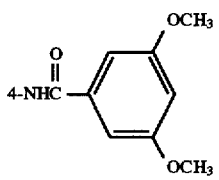
Crystalline form: Colorless prisms
Recrystallization solvent: Ethanol
Melting Point: 216–218° C.
Form: Free
Example 323
Structure
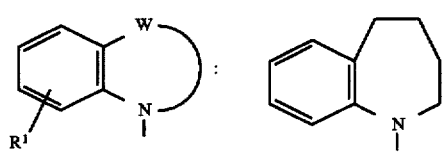
R²: H
R³:
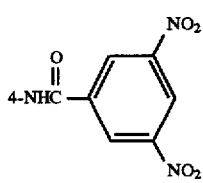
Crystalline form: White powder
Melting Point: >300° C.

TABLE 1-continued
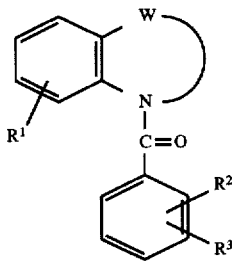
NMR analysis: 45)
Form: Free
Example 324
Structure
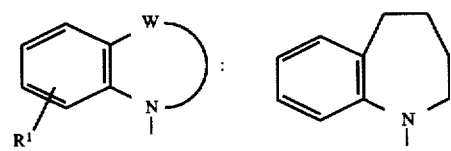
R²: H
R³:
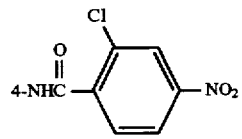
Crystalline form: Colorless prisms
Recrystallization solvent: Ethanol
Melting Point: 250.5–251° C.
Form: Free
Example 325
Structure
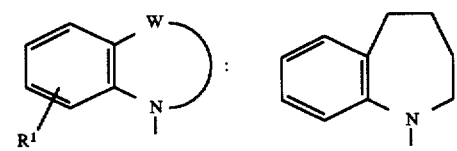
R²: H
R³:
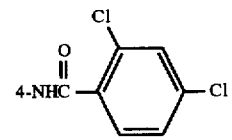
Crystalline form: Colorless prisms
Recrystallization solvent: Ethanol
Melting Point: 223–225° C.
Form: Free
Example 326
Structure
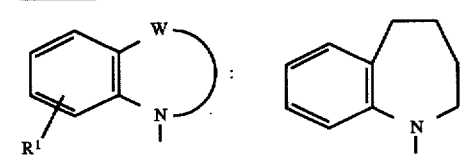

TABLE 1-continued
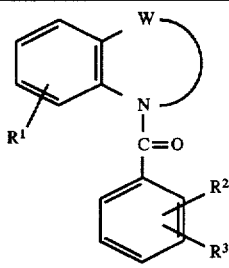
R²: H
R³: 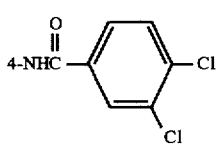
Crystalline form: Colorless prismsr
Recrystallization solvent: Methanol
Melting Point: 213–214° C.
Form: Free
Example 327
Structure
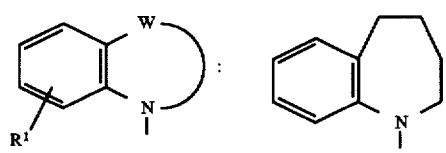
R²: H
R³: 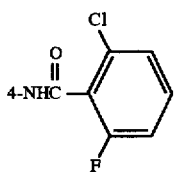
Crystalline form: Colorless prisms
Recrystallization solvent: Ethanol
Melting Point: 246–247° C.
Form: Free
Example 328
Structure
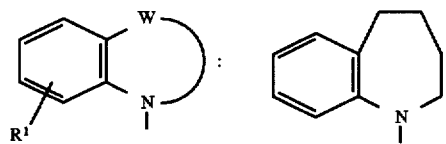
R²: H
R³: 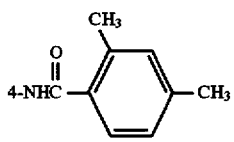
Crystalline form: Colorless prisms
Recrystallization solvent: Methanol

TABLE 1-continued
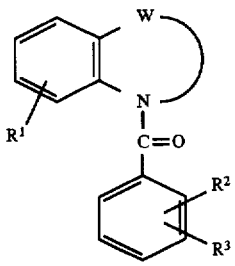
Melting Point: 248–251° C.
Form: Free
Example 329
Structure
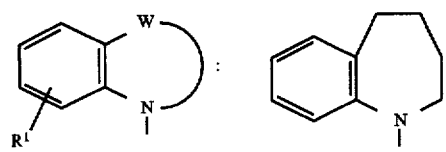
R²: H
R³:
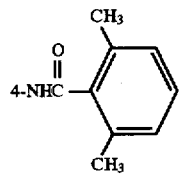
Crystalline form: Colorless prisms
Recrystallization solvent: Ethanol
Melting Point: 268.5–270.5° C.
Form: Free
Example 330
Structure
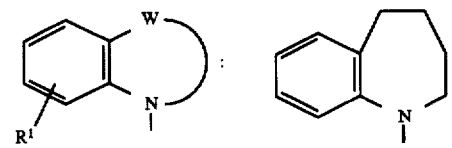
R²: H
R³:
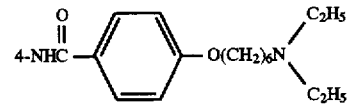
Crystalline form: White powder
Recrystallization solvent: Methanol/diethyl ether
Melting Point: 174–176° C.
Form: Hydrochloride
Example 331
Structure
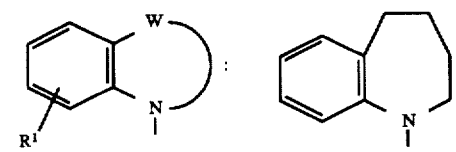

TABLE 1-continued

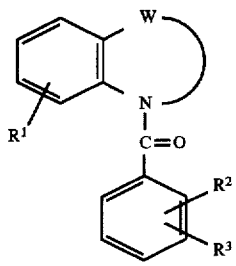

R²: H

R³:
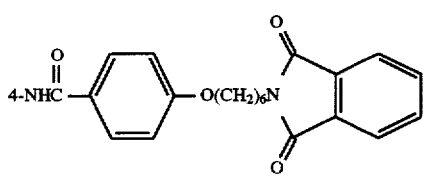

Crystalline form: White powder
Recrystallization solvent: Ethanol
Melting Point: 130–134° C.
Form: Free Example 332

Structure

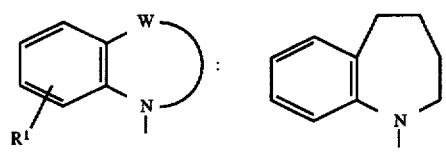

R²: H

R³:
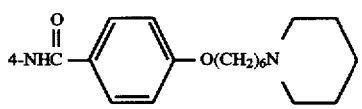

Crystalline form: White powder
Recrystallization solvent: Methanol/diethyl ether
Melting Point: 214–217° C.
Form: Hydrochloride Example 333

Structure

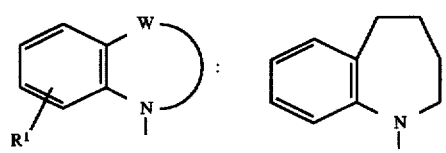

R²: H

R³:
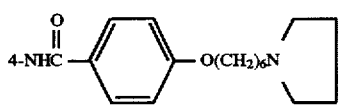

Crystalline form: White powder
Recrystallization solvent: Methanol/diethyl ether
Melting Point: 218–220° C.
Form: Hydrochloride TABLE 1-continued

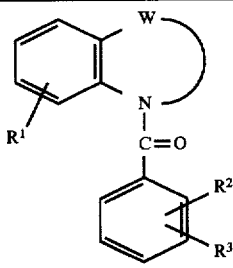

Example 334

Structure

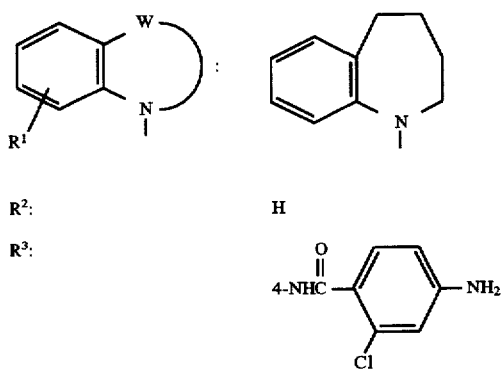

R²: H

R³: 4-NHC(=O)—C₆H₃(Cl)—NH₂ (with Cl and NH₂ substituents)

Crystalline form: White powder
Recrystallization solvent: Ethyl acetate
Melting Point: 222–225° C.
Form: Free

Example 335

Structure

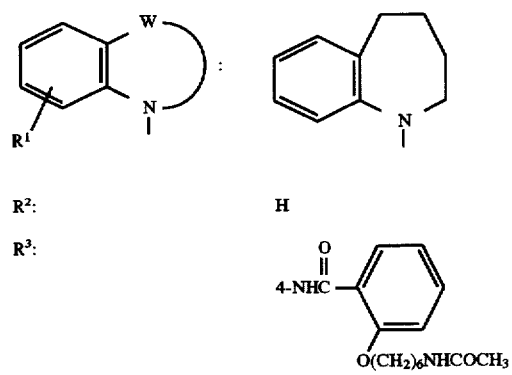

R²: H

R³: 4-NHC(=O)—C₆H₄—O(CH₂)₆NHCOCH₃

Crystalline form: Colorless needles
Recrystallization solvent: Methanol/diethyl ether
Melting Point: 171–172° C.
Form: Free

Example 336

Structure

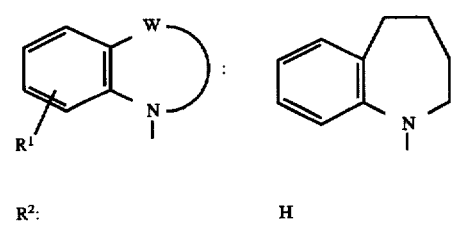

R²: H

TABLE 1-continued

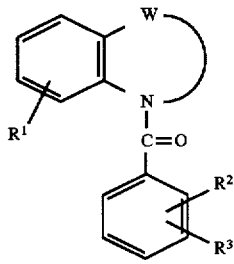

R³: 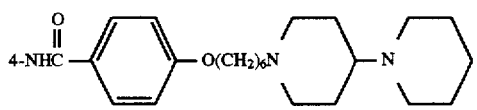

Crystalline form: White powder
Recrystallization solvent: Methanol/diethyl ether
Melting Point: 235.5–236° C.
Form: Dihydrochloride Example 337

Structure

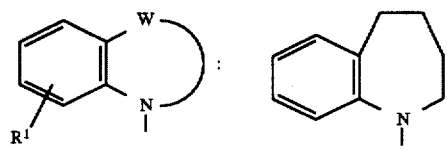

R²: H

R³: 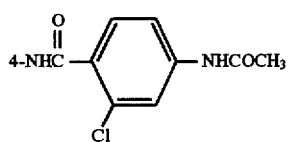

Crystalline form: White powder
Recrystallization solvent: Methanol/diethyl ether
Melting Point: 241–243° C.
Form: Free Example 338

Structure

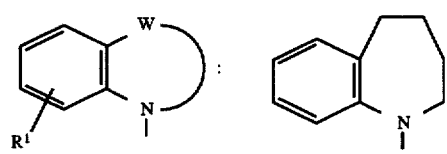

R²: H

R³: 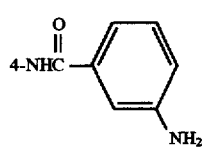

Crystalline form: White powder
Recrystallization solvent: Methanol/diethyl ether
Melting Point: 187–191° C.
Form: Free TABLE 1-continued
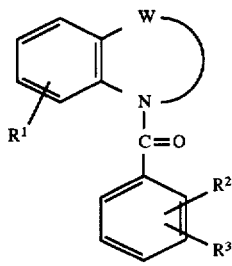
Example 339
Structure
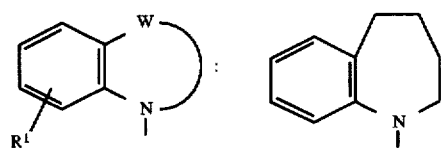
R²: H
R³:
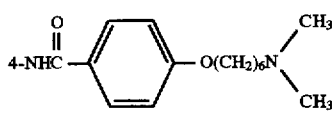
Crystalline form: White powder
Recrystallization solvent: Methanol/diethyl ether
Melting Point: 240–244° C.
Form: Hydrochloride
Example 340
Structure
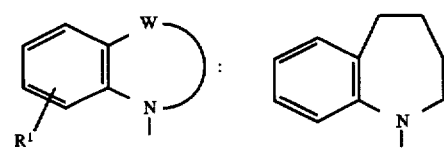
R²: H
R³:
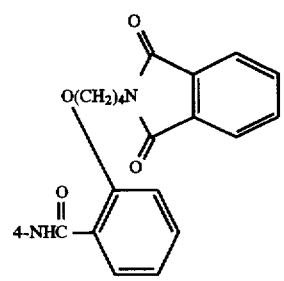
Crystalline form: Colorless prisms
Recrystallization solvent: Methanol/diethyl ether
Melting Point: 181–182° C.
Form: Free TABLE 1-continued
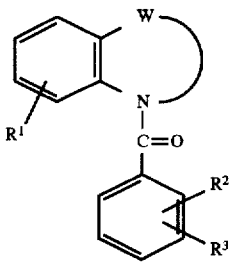
Example 341
Structure
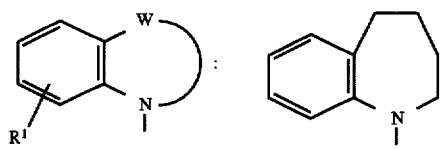
R²: H
R³:
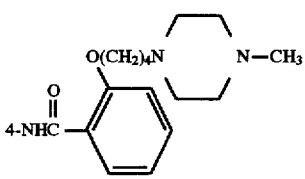
Crystalline form: Colorless prisms
Recrystallization solvent: Methanol/diethyl ether
Melting Point: 188–190° C.
Form: Dihydrochloride
Example 342
Structure
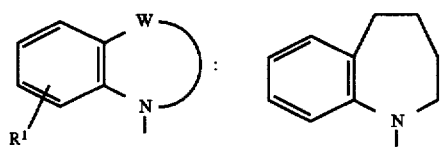
R²: H
R³:
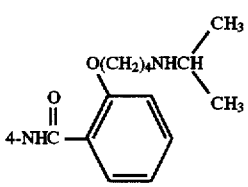
Crystalline form: White powder
Recrystallization solvent: Isopropyl alcohol
Melting Point: 218–218.5° C.
Form: Hydrochloride TABLE 1-continued
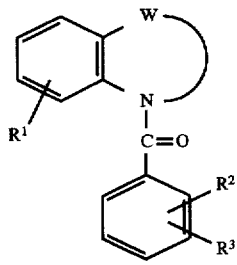
Example 343
Structure
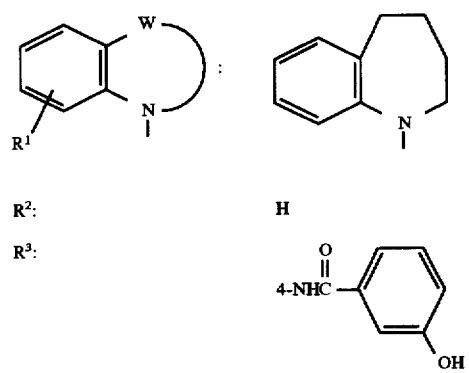
R²: H
R³:
4-NHC(=O)—C₆H₄—OH (3-position)
Crystalline form: White powder
Recrystallization solvent: Methanol/diethyl ether
Melting Point: 243–245.5° C.
Form: Free
Example 344
Structure
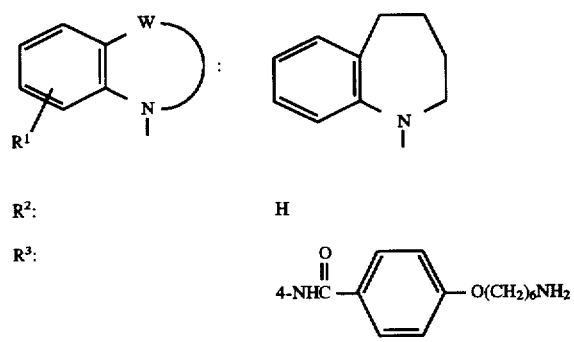
R²: H
R³:
4-NHC(=O)—C₆H₄—O(CH₂)₆NH₂
Crystalline form: White powder
Recrystallization solvent: Methanol/diethyl ether
Melting Point: 130–133° C.
Form: Free
Example 345
Structure
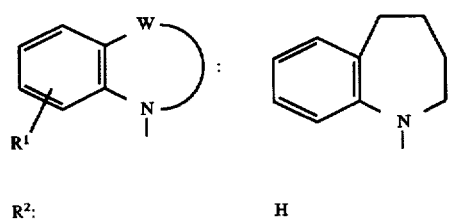
R²: H TABLE 1-continued

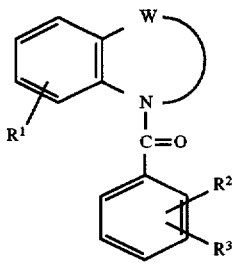

R³:
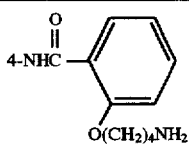

Crystalline form: White powder
Recrystallization solvent: Methanol/diethyl ether
Melting Point: 155–158° C.
Form: Free Example 346

Structure

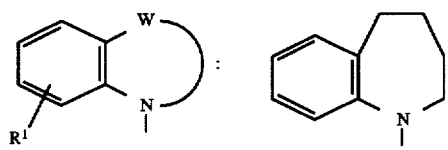

R²: H

R³:
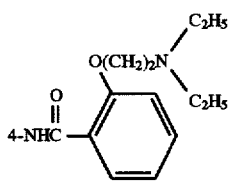

Crystalline form: White powder
Recrystallization solvent: Methanol/diethyl powder
Melting Point: 208–210° C.
Form: Hydrochloride Example 347

Structure

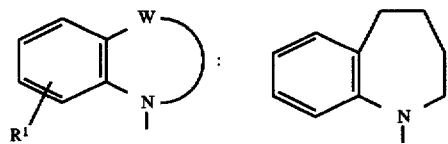

R²: H

R³:
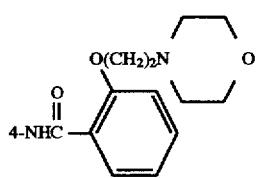

Crystalline form: Colorless prisms
Recrystallization solvent: Methanol/diethyl ether
Melting Point: 154–155° C.

TABLE 1-continued

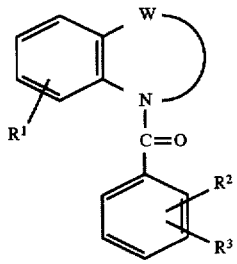

Form: Hydrochloride

Example 348

Structure

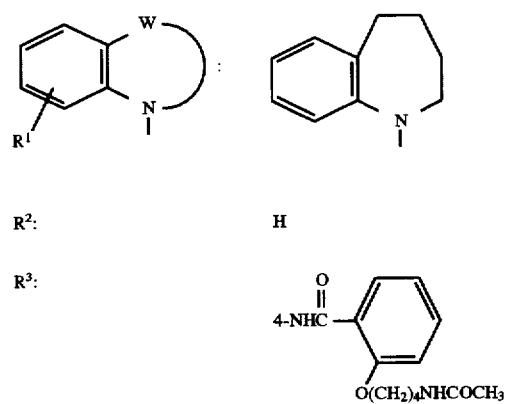

R²: H

R³: 4-NHC(=O)—C₆H₄—O(CH₂)₄NHCOCH₃ (ortho)

Crystalline form: White powder
Recrystallization solvent: Methanol/diethyl ether
Melting Point: 142–143° C.
Form: Free

Example 349

Structure

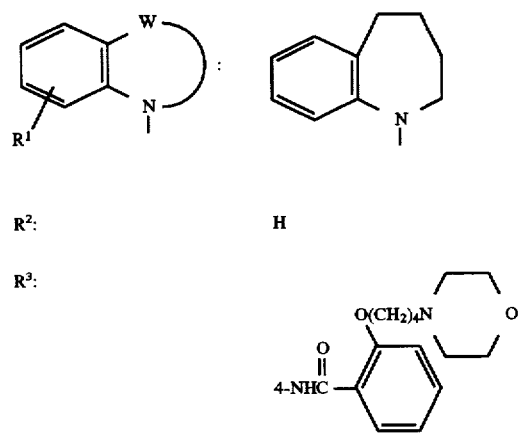

R²: H

R³: 4-NHC(=O)—C₆H₄—O(CH₂)₄N(morpholino) (ortho)

Crystalline form: White powder
Recrystallization solvent: Methanol/diethyl ether
Melting Point: 120–125° C.
Form: Hydrochloride TABLE 1-continued
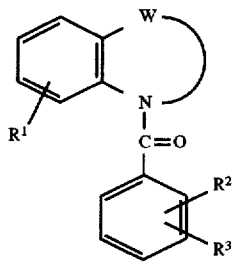
Example 350
Structure
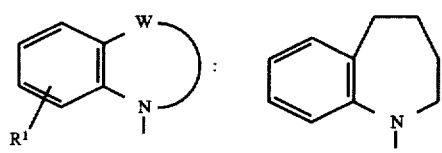
R²: H
R³:
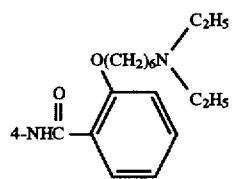
Crystalline form: White powder
Recrystallization solvent: Methanol/diethyl ether
Melting Point: 91–95° C.
Form: Hydrochloride
Example 351
Structure
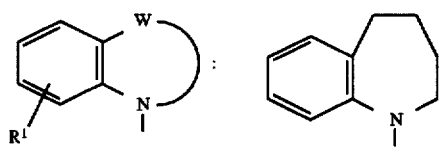
R²: H
R³:
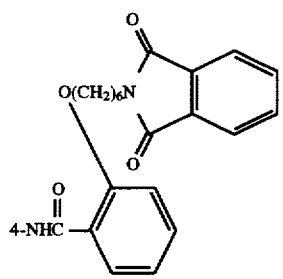
Crystalline form: White powder
Recrystallization solvent: Methanol/diethyl ether
Melting Point: 145–146.5° C.
Form: Free TABLE 1-continued
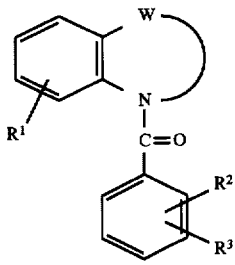
Example 352
Structure
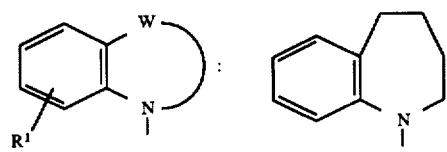
$R^2$: H
$R^3$:
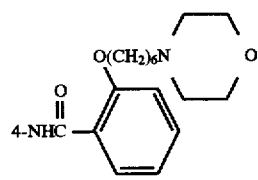
Crystalline form: White powder
Recrystallization solvent: Methanol/diethyl ether
Melting Point: 105–105.5° C.
Form: Free
Example 353
Structure
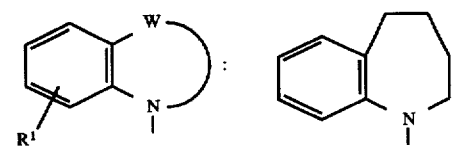
$R^2$: H
$R^3$:
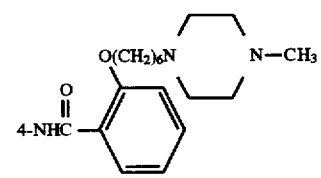
Crystalline form: White powder
Recrystallization solvent: Methanol/diethyl ether
Melting Point: 151–155° C.
Form: Dihydrochloride TABLE 1-continued
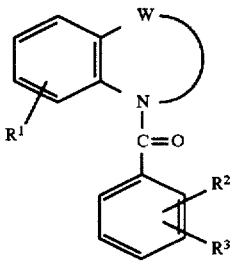
Example 354
Structure
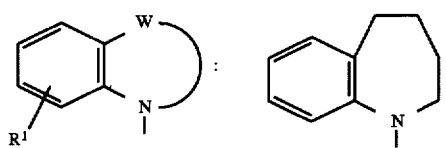
R²: H
R³:
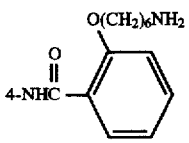
Crystalline form: White powder
Recrystallization solvent: Methanol/diethyl ether
Melting Point: 135.5–137.5° C.
Form: Free
Example 355
Structure
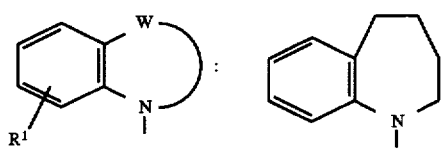
R²: H
R³:
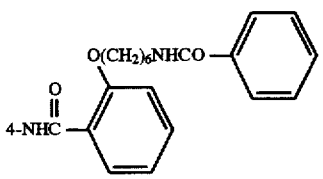
Crystalline form: White powder
Recrystallization solvent: Ethanol
Melting Point: 178–178.5° C.
Form: Free
Example 356
Structure
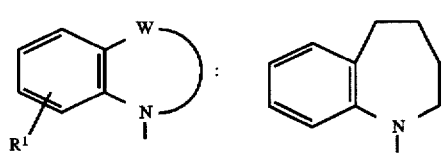

TABLE 1-continued

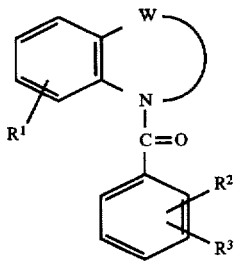

R²: H

R³:
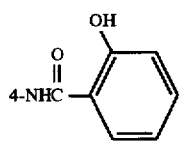

Crystalline form: White powder
Recrystallization solvent: Dichloromethane
Melting Point: 266.5–268° C.
Form: Free Example 357

Structure

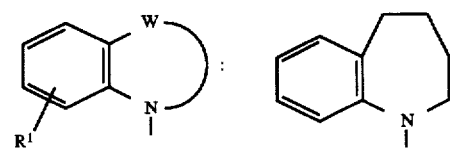

R²: H

R³:
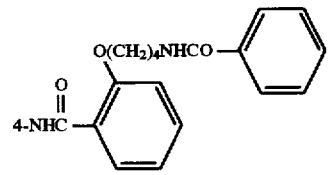

Crystalline form: White powder
Recrystallization solvent: Methanol/diethyl ether
Melting Point: 123–124° C.
Form: Free Example 358

Structure

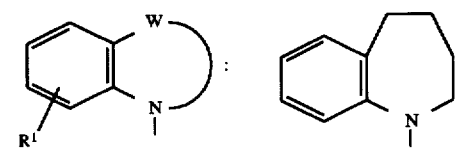

R²: H

R³:
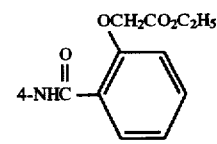

Crystalline form: White powder
Recrystallization solvent: Ethyl acetate

TABLE 1-continued
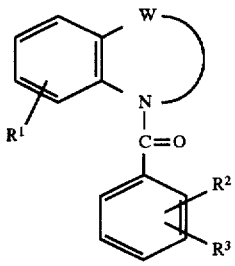
Melting Point: 212–213.5° C.
Form: Free
Example 359
Structure
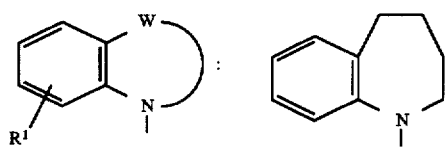
R²: H
R³: 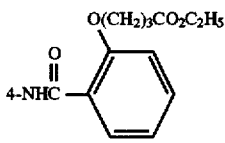
Crystalline form: Colorless scales
Recrystallization solvent: Ethyl acetate
Melting Point: 160.5–162° C.
Form: Free
Example 360
Structure
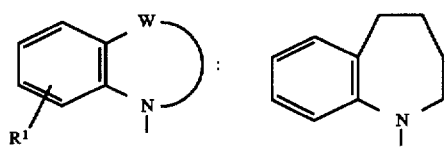
R²: H
R³: 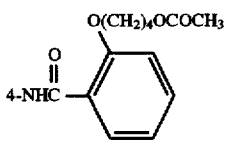
Crystalline form: Colorless needles
Recrystallization solvent: Ethanol
Melting Point: 103–105° C.
Form: Free
Example 361
Structure
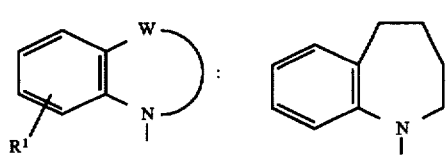

TABLE 1-continued

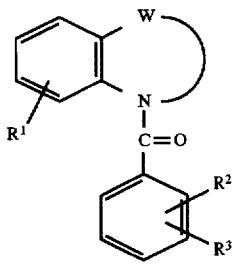

R²: H

R³: 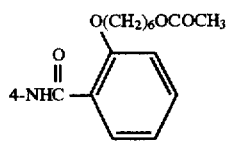
O(CH₂)₆OCOCH₃

Crystalline form: White powder
Recrystallization solvent: Ethanol
Melting Point: 145–146° C.
Form: Free Example 362

Structure

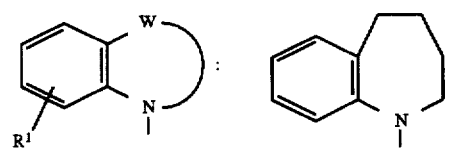

R²: H

R³: 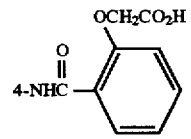
OCH₂CO₂H

Crystalline form: White powder
Recrystallization solvent: Methanol/diethyl ether
Melting Point: 247–250° C.
Form: Free Example 363

Structure

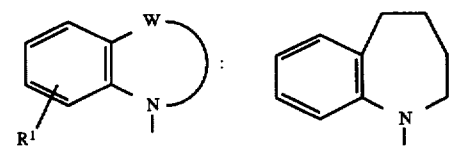

R²: H

R³: 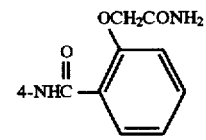
OCH₂CONH₂

Crystalline form: White powder
Recrystallization solvent: Methanol/diethyl ether
Melting Point: 198–199° C.
Form: Free TABLE 1-continued
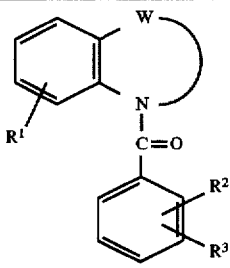
Example 364
Structure
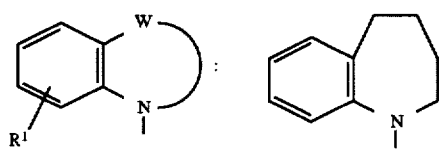
R²: H
R³: 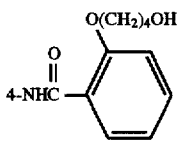
Crystalline form: White powder
Recrystallization solvent: Methanol/diethyl ether
Melting Point: 181.5–182.5° C.
Form: Free
Example 365
Structure
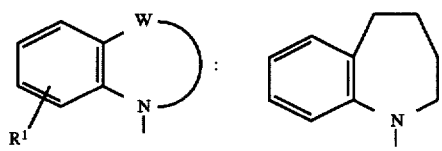
R²: H
R³: 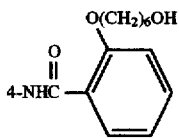
Crystalline form: White powder
Recrystallization solvent: Methanol/diethyl ether
Melting Point: 170–170.5° C.
Form: Free
Example 366
Structure
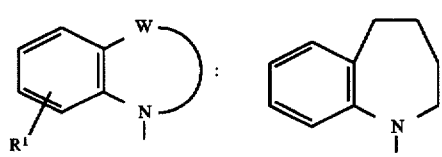
R²: H TABLE 1-continued

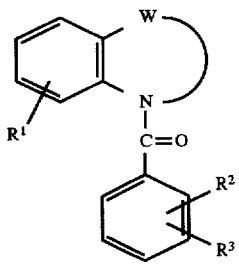

R³:

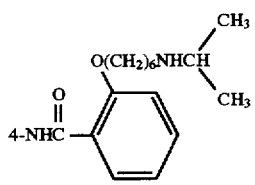

Crystalline form: White powder
Recrystallization solvent: Methanol/diethyl ether
Melting Point: 156–158° C.
Form: Free Example 367

Structure

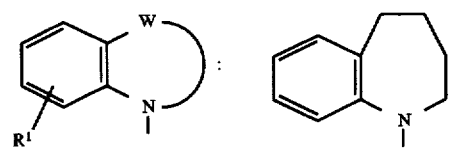

R²: H

R³:

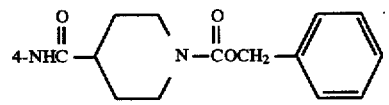

Crystalline form: White powder
Recrystallization solvent: Diethyl ether
Melting Point: 168.5–170.5° C.
Form: Free Example 368

Structure

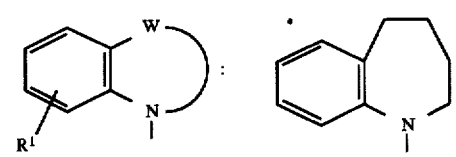

R²: H

R³:

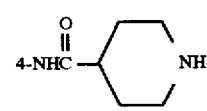

Crystalline form: White powder
Recrystallization solvent: Methanol/diethyl ether
Melting Point: 177–181.5° C.
Form: Hydrochloride TABLE 1-continued
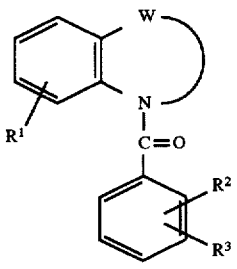
Example 369
Structure
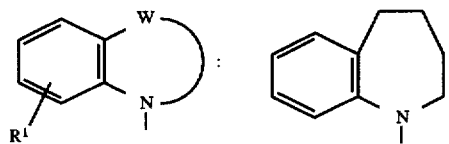
R²: H
R³:
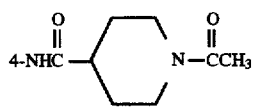
Crystalline form: White powder
Recrystallization solvent: Methanol/diethyl ether
Melting Point: 211–213° C.
Form: Free
Example 370
Structure
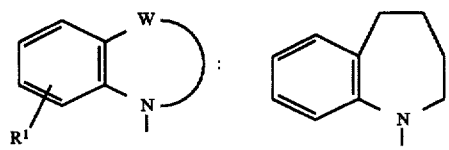
R²: H
R³:
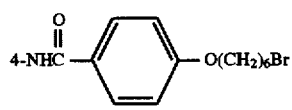
Crystalline form: White powder
NMR analysis: 46)
Form: Free
Example 371
Structure
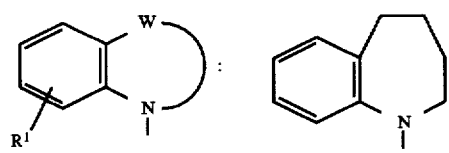
R²: H TABLE 1-continued

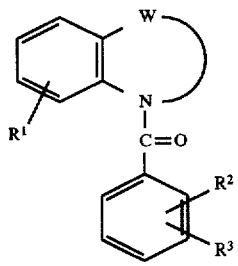

R³:

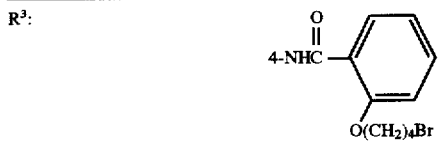

Crystalline form: White powder
Recrystallization solvent: Methanol/ethyl acetate
Melting Point: 166–167° C.
Form: Free Example 372

Structure

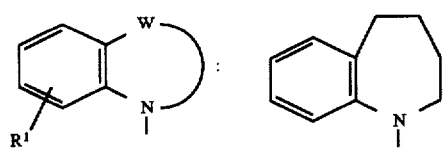

R²: H

R³:

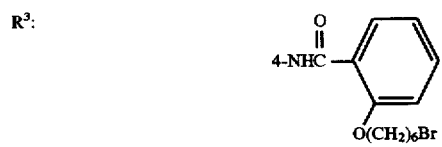

Crystalline form: White powder
Recrystallization solvent: Methanol/diethyl ether
Melting Point: 127–131° C.
Form: Free Example 373

Structure

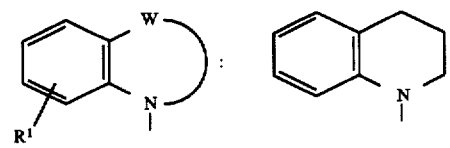

R²: H

R³:

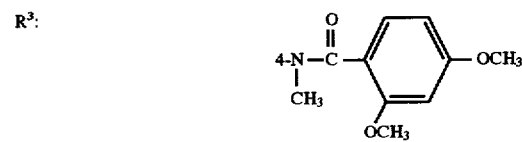

Crystalline form: White powder
Recrystallization solvent: Methanol
Melting Point: 170–171° C.
Form: Free TABLE 1-continued
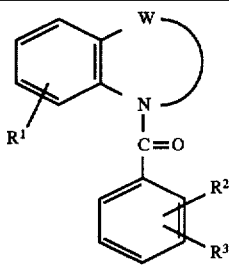
Example 374
Structure
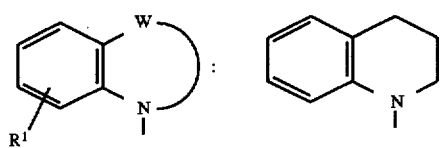
R²: H
R³:
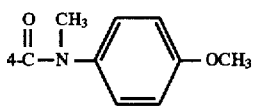
Crystalline form: White powder
Recrystallization solvent: Methanol
Melting Point: 125–126° C.
Form: Free
Example 375
Structure
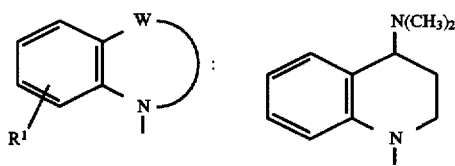
R²: H
R³:
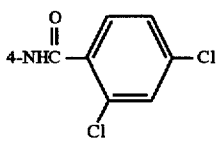
Crystalline form: Light yellow amorphous
NMR analysis: 47)
Form: Hydrochloride
Example 376
Structure
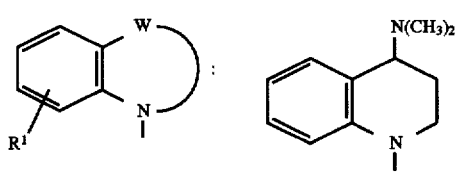
R²: H TABLE 1-continued

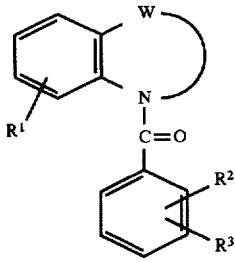

R³:

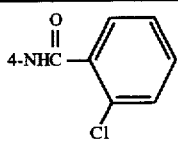

Crystalline form: Colorless amorphous
NMR analysis: 48)
Form: Hydrochloride

1) ¹H-NMR (CDCl₃) δ: 1.92 (1H, t, J=6.2 Hz), 1.98 (1H, t, J=6.4 Hz), 2.8 (2H, t, J=6.4 Hz), 3.76 (2H, t, J=6.2 Hz), 6.75 (1H, d, J=7.6 Hz), 6.86 (2H, d, J=8.6 Hz), 6.8–7.1 (2H, m), 7.20 (1H, d, J=7 Hz), 7.30 (2H, d, J=8.6 Hz), 7.72 (2H, d, J=8.6 Hz), 7.84 (2H, d, J=8.6 Hz), 10.13 (1H, s)

2) ¹H-NMR (DMSO-d₆) δ: 2.05 (2H, quint, J=6.4 Hz), 2.91 (2H, t, J=6.4 Hz), 3.86 (2H, t, J=6.4 Hz), 6.85 (1H, d, J=7.6 Hz), 6.9–7.2 (2H, m), 7.30 (1H, d, J=7.2 Hz), 7.44 (2H, d, J=8.5 Hz), 7.85 (2H, d, J=8.5 Hz), 8.1–8.2 (4H, m), 10.65 (1H, s), 13.2–13.4 (1H, br)

3) ¹H-NMR (CDCl₃) δ: 1.9–2.1 (2H, m), 2.84 (2H, t, J=6.5 Hz), 3.82 (6H, s), 3.90 (2H, t, J=6.6 Hz), 6.5–7.2 (7H, m), 7.35 (2H, d, J=8.7 Hz), 7.55 (2H, d, J=8.7 Hz), 8.05 (1H, s)

4) ¹H-NMR (CDCl₃) δ: 1.9–2.1 (2H, m), 2.37 (6H, s), 2.84 (2H, t, J=6.6 Hz), 3.90 (2H, t, J=6.6 Hz), 6.71 (1H, d, J=7.9 Hz), 6.8–7.2 (4H, m), 7.35 (2H, d, J=8.6 Hz), 7.44 (2H, s), 7.56 (2H, d, J=8.6 Hz), 8.00 (1H, s)

5) ¹H-NMR (CDCl₃) δ: 1.9–2.2 (2H, m), 2.12 (3H, s), 2.84 (2H, t, J=6.6 Hz), 3.89 (2H, t, J=6.5 Hz), 6.71 (1H, d, J=7.8 Hz), 6.87 (1H, t, J=7 Hz), 6.99 (1H, t, J=7.3 Hz), 7.15 (1H, d, J=6.5 Hz), 7.28 (2H, d, J=8.6 Hz), 7.41 (2H, d, J=8.6 Hz), 8.03 (1H, s)

6) ¹H-NMR (CDCl₃) δ: 0.8–1.3 (6H, m), 1.6–2.3 (9H, m), 2.83 (2H, t, J=6.6 Hz), 3.89 (2H, t, J=6.5 Hz), 6.72 (1H, d, J=7.9 Hz), 6.8–7.1 (2H, m), 7.15 (1H, d, J=7.4 Hz), 7.28 (2H, d, J=8.3 Hz), 7.44 (2H, d, J=8.4 Hz), 7.9–8.1 (1H, m)

7) ¹H-NMR (CDCl₃) δ: 2.02 (2H, quint, J=6.5 Hz), 2.81 (2H, t, J=6.6 Hz), 3.69 (2H, s), 3.87 (2H, t, J=6.6 Hz), 6.66 (1H, d, J=8.2 Hz), 6.8–7.0 (2H, m), 7.13 (1H, d, J=7.3 Hz), 7.2–7.4 (9H, m), 7.59 (1H, s)

8) ¹H-NMR (CDCl₃) δ: 1.7–2.1 (17H, m), 2.83 (2H, t, J=6.7 Hz), 3.90 (2H, t, J=6.6 Hz), 6.68 (1H, d, J=8.1 Hz), 6.8–7.1 (2H, m), 7.14 (1H, d, J=7 Hz), 7.32 (2H, d, J=8.7 Hz), 7.39 (1H, s), 7.46 (2H, d, J=8.7 Hz)

9) ¹H-NMR (CDCl₃) δ: 1.99 (2H, quint, J=6.5 Hz), 2.82 (2H, t, J=6.6 Hz), 3.82 (2H, t, J=6.5 Hz), 6.8–7.1 (4H, m), 7.1–7.3 (2H, m), 7.4–7.6 (3H, m), 7.67 (1H, S), 7.8–8.0 (3H, m), 8.42 (1H, s)

10) ¹H-NMR (CDCl₃) δ: 2.00 (2H, quint, J=6.5 Hz), 2.83 (2H, t, J=6.6 Hz), 3.85 (2H, t, J=6.6 Hz), 3.86 (3H, s), 6.8–7.1 (6H, m), 7.1–7.3 (2H, m), 7.64 (1H, s), 7.8–8.0 (3H, m), 8.22 (1H, s)

11) ¹H-NMR (CDCl₃) δ: 1.98 (2H, quint, J=6.5 Hz), 2.82 (2H, t, J=6.5 Hz), 3.81 (2H, t, J=6.5 Hz), 3.84 (3H, s), 6.8–7.5 (10H, m), 7.68 (1H, s), 7.95 (1H, d, J=8.2 Hz), 8.52 (1H, s)

12) ¹H-NMR (CDCl₃) δ: 1.7–1.9 (2H, m), 2.70 (2H, t, J=6.6 Hz), 3.70 (2H, t, J=6.4 Hz), 6.8–7.3 (6H, m), 7.4–7.7 (2H, m), 7.8–7.9 (5H, m), 8.04 (1H, d, J=8 Hz), 8.33 (1H, s), 8.90 (1H, s)

13) ¹H-NMR (CDCl₃) δ: 1.7–2.1 (17H, m), 2.84 (2H, t, J=6.5 Hz), 3.89 (2H, t, J=6.4 Hz), 6.8–7.2 (6H, m), 7.42 (1H, s), 7.56 (1H, s), 7.81 (1H, d, J=8.1 Hz)

14) ¹H-NMR (DMSO-d₆) δ: 1.0–1.5 (5H, m), 1.5–2.0 (5H, m), 2.2–3.8 (8H, m), 4.2–5.2 (3H, m), 6.77 (1H, d, J=7.2 Hz), 7.1–7.4 (4H, m), 7.47 (2H, d, J=8.6 Hz), 7.58 (1H, d, J=6.2 Hz), 10.06 (1H, s), 10.9–12.1 (1H, br)

15) ¹H-NMR (DMSO-d₆) δ: 2.5–3.8 (6H, m), 4.2–5.2 (3H, m), 6.81 (1H, d, J=6.8 Hz), 7.1–7.3 (4H, m), 7.5–7.7 (3H, m), 7.8–8.0 (1H, m), 7.97 (2H, d, J=1.8 Hz), 10.66 (1H, s), 11.1–12.3 (1H, br)

16) ¹H-NMR (DMSO-d₆) δ: 2.20 (3H, s), 2.27 (3H, s), 2.5–3.8 (6H, m), 4.3–5.3 (3H, m), 6.82 (1H, d, J=7.2 Hz), 7.1–7.4 (7H, m), 7.5–7.8 (3H, m), 10.43 (1H, s), 11.0–12.2 (1H, br)

17) ¹H-NMR (DMSO-d₆) δ: 2.34 (3H, s), 2.5–3.7 (6H, m), 4.3–5.2 (3H, m), 6.82 (1H, d, J=6.8 Hz), 7.2–7.7 (11H, m), 10.41 (1H, s), 10.8–12.3 (1H, br)

18) ¹H-NMR (DMSO-d₆) δ: 2.38 (3H, s), 2.5–3.8 (6H, m), 4.3–5.3 (3H, m), 6.81 (1H, d, J=7.0 Hz), 7.1–7.5 (6H, m), 7.5–7.8 (5H, m), 10.35 (1H, s), 10.9–12.2 (1H, br)

19) ¹H-NMR (DMSO-d₆) δ: 2.37 (3H, s), 2.5–3.7 (6H, m), 4.3–5.2 (3H, m), 6.81 (1H, d, J=7.2 Hz), 7.2–7.4 (6H, m), 7.5–7.7 (3H, m), 7.84 (2H, d, J=8.0 Hz), 10.31 (1H, S), 10.9–12.2 (1H, br)

20) ¹H-NMR (DMSO-d₆) δ: 2.5–3.8 (6H, m), 4.3–5.2 (3H, m), 6.82 (1H, d, J=7.4 Hz), 7.2–7.3 (4H, m), 7.5–7.8 (5H, m), 7.75 (1H, d, J=1.8 Hz), 10.70 (1H, s), 10.8–12.2 (1H, br)

21) ¹H-NMR (DMSO-d₆) δ: 2.5–3.8 (9H, m), 4.3–4.7 (1H, m), 4.7–5.1 (2H, m), 6.8–7.1 (3H, m), 7.1–7.4 (2H, m), 7.5–7.7 (2H, m), 7.8–8.0 (3H, m), 9.79 (1H, s), 10.8–12.2 (1H, br)

22) ¹H-NMR (DMSO-d₆) δ: 0.8–1.2 (3H, m), 1.7–2.2 (2H, m), 2.5–3.8 (5H, m), 4.3–5.2 (3H, m), 6.80 (1H, d,

J=7.2 Hz), 7.1–7.3 (4H, m), 7.6–7.7 (3H, m), 7.85 (1H, s), 7.96 (2H, d, J=1.8 Hz), 10.62 (1H, s), 10.8–12.0 (1H, br)

23) ¹H-NMR (DMSO-d₆) δ: 0.8–1.1 (3H, m), 1.7–2.1 (2H, m), 2.37 (3H, s), 2.7–3.8 (5H, m), 4.4–5.2 (3H, m), 6.81 (1H, d, J=7.6 Hz), 7.2–7.4 (6H, m), 7.6–7.7 (3H, m), 7.84 (2H, d, J=8.2 Hz), 10.29 (1H, s), 10.5–11.8 (1H, br)

24) ¹H-NMR (DMSO-d₆) δ: 0.8–1.2 (3H, m), 1.7–2.1 (2H, m), 2.38 (3H, s), 2.6–3.8 (5H, m), 4.3–5.2 (3H, m), 6.81 (1H, d, J=7.0 Hz), 7.2–7.5 (6H, m), 7.6–7.8 (5H, m), 10.33 (1H, s), 10.5–11.7 (1H, br)

25) ¹H-NMR (DMSO-d₆) δ: 0.8–1.2 (3H, m), 1.7–2.1 (2H, m), 2.6–3.8 (5H, m), 3.8–5.2 (3H, m), 6.82 (1H, d, J=7.2 Hz), 7.1–7.5 (8H, m), 7.5–7.7 (3H, m), 10.42 (1H, s), 10.7–12.0 (1H, br)

26) ¹H-NMR (DMSO-d₆) δ: 0.8–2.0 (15H, m), 2.2–2.5 (1H, m), 2.6–3.7 (5H, m), 4.3–5.2 (3H, m), 6.76 (1H, d, J=7.0 Hz), 7.1–7.4 (4H, m), 7.46 (2H, d, J=8.6 Hz), 7.61 (1H, d, J=6.4 Hz), 10.03 (1H, s), 10.5–11.8 (1H, br)

27) ¹H-NMR (DMSO-d₆) δ: 0.8–1.1 (3H, m), 1.7–2.0 (2H, m), 2.20 (3H, s), 2.29 (3H, s), 2.6–3.7 (5H, m), 4.3–5.2 (3H, m), 6.82 (1H, d, J=7.0 Hz), 7.2–7.4 (7H, m), 7.5–7.7 (3H, m), 10.41 (1H, s), 10.6–12.0 (1H, br)

28) ¹H-NMR (CDCl₃) δ: 1.21 (3H, t, J=7.1 Hz), 3.00–3.25 (3H, m), 4.00–4.30 (4H, m), 6.63 (1H, d, J=7.8 Hz), 6.86 (1H, t, J=7.3 Hz), 7.00 (1H, t, J=6.3 Hz), 7.10–7.31 (3H, m), 7.40–7.57 (3H, m), 7.77 (2H, d, J=1.9 Hz), 8.76 (1H, brs)

29) ¹H-NMR (CDCl₃) δ: 2.29 (3H, s), 2.32 (3H, s), 2.34 (3H, s), 2.50–3.15 (11H, m), 3.79 (1H, dd, J=13.2 Hz, 7.3 Hz), 4.05 (1H, dd, J=13.2 Hz, 5.7 Hz), 6.62 (1H, d, J=7.7 Hz), 6.82–7.48 (8H, m), 7.53 (2H, d, J=8.4 Hz), 8.05 (1H, brs)

30) ¹H-NMR (CDCl₃) δ: 1.65–2.01 (4H, m), 2.31 (3H, s), 2.35 (3H, s), 2.55–3.02 (6H, m), 3.09 (1H, dd, J=15 Hz, 5 Hz), 3.70 (1H, dd, J=12.5 Hz, 8.0 Hz), 4.22 (1H, dd, J=12.5 Hz, 5 Hz), 6.67 (1H, d, J=7.8 Hz), 6.80–7.32 (7H, m), 7.37 (2H, d, J=8.6 Hz), 7.53 (1H, d, J=8.3 Hz), 7.66 (1H, brs)

31) ¹H-NMR (CDCl₃) δ: 2.80 (1H, dd, J=16.1 Hz, 5.3 Hz), 3.16 (1H, dd, J=15.8 Hz, 5.3 Hz), 3.75–4.50 (3H, m), 4.87–5.10 (3H, m), 6.80–7.60 (14H, m), 7.74 (2H, d, J=1.9 Hz), 8.47 (1H, brs)

32) ¹H-NMR (CDCl₃) δ: 2.35 (6H, s), 2.72–3.10 (3H, m), 3.65–3.78 (1H, m), 4.06–4.18 (1H, m), 6.60–7.62 (9H, m), 7.74 (2H, d, J=1.8 Hz), 8.52 (1H, brs)

33) ¹H-NMR (CDCl₃) δ: 1.87 t, 3H, s), 2.68 (1H, dd, J=5.6 Hz, 16 Hz), 3.14 (1H, dd, J=5.6 Hz, 16 Hz), 3.70–3.95 (2H, m), 4.32–4.50 (1H, m), 6.29 (1H, d, J=7.6 Hz), 6.90–7.80 (11H, m), 9.16 (1H, brs)

34) ¹H-NMR (CDCl₃) δ: 1.62 (1H, brs), 1.90–2.25 (2H, m), 2.55 (3H, s), 3.78 (1H, t, J=5.1 Hz), 3.95 (2H, t, J=6.7 Hz), 6.69 (1H, t, J=7.9 Hz), 6.90–7.13 (2H, m), 7.23–7.40 (3H, m), 7.42–7.56 (3H, m), 7.77 (2H, d, J=1.9 Hz), 8.53 (1H, brs)

35) ¹H-NMR (CDCl₃) δ: 1.80–2.02 (1H, m), 2.20–2.35 (1H, m), 2.31 (6H, s), 3.52 (1H, t, J=5.4 Hz), 3.68–3.83 (1H, m), 3.95–4.15 (1H, m), 6.59 (1H, d, J=7.8 Hz), 6.81–7.10 (2H, m), 7.16–7.50 (6H, m), 7.80 (2H, d, J=1.8 Hz), 9.13 (1H, brs)

36) ¹H-NMR (CDCl₃) δ: 1.35–1.60 (1H, m), 1.65–2.20 (3H, m), 2.65–3.20 (5H, m), 3.81 (2H, d, J=6.5 Hz), 4.90–5.10 (1H, m), 6.60 (1H, d, J=8.0 Hz), 6.90 (1H, t, J=8.0 Hz), 7.00–7.50 (6H, m)

37) ¹H-NMR (CDCl₃) δ: 1.30–2.25 (4H, m), 2.55–3.20 (3H, m), 3.35 (2H, s), 3.80 (2H, s), 4.90–5.10 (1H, m), 6.62 (1H, d, J=8.0 Hz), 6.85–7.45 (12H, m), 9.27 (1H, brs)

38) ¹H-NMR (CDCl₃) δ: 1.35–2.25 (4H, m), 2.33 (3H, s), 2.60–3.20 (3H, m), 3.12 (2H, s), 3.61 (2H, s), 5.00 (1H, brs), 6.50–7.60 (13H, m), 9.14 (1H, brs)

39) ¹H-NMR (CDCl₃) δ: 1.27 (3H, t, J=7.1 Hz), 1.25–2.50 (12H, m), 2.70–3.10 (4H, m), 3.05 (2H, s), 4.15 (2H, q, J=7.0 Hz), 4.90–5.10 (1H, m), 6.63 (1H, d, J=7.5 Hz), 6.91 (1H, t, J=7.5 Hz), 7.00–7.50 (6H, m), 9.14 (1H, brs)

40) ¹H-NMR (CDCl₃) δ: 1.30–1.65 (1H, m), 1.80–2.25 (5H, m), 2.70–3.20 (3H, m), 4.01 (2H, d, J=5.0 Hz), 4.90–5.10 (1H, m), 6.61 (1H, d, J=7.7 Hz), 6.89 (1H, t, J=7.0 Hz), 7.00–7.45 (6H, m), 9.05 (1H, brs)

41) ¹H-NMR (CDCl₃) δ: 1.18 (6H, s), 1.30–2.20 (4H, m), 2.60–3.20 (3H, m), 3.30 (2H, s), 3.73 (2H, s), 4.90–5.10 (1H, m), 6.61 (1H, d, J=7.3 Hz), 6.70–7.45 (12H, m), 9.50 (1H, brs)

42) ¹H-NMR (CDCl₃) δ: 1.19 (3H, t, J=7.0 Hz), 1.30–1.70 (1H, m), 1.75–2.20 (3H, m), 2.65–3.15 (3H, m), 3.46 (2H, q, J=7.0 Hz), 3.88 (2H, s), 4.90–5.10 (1H, m), 6.55–7.45 (13H, m), 8.36 (1H, brs)

43) ¹H-NMR (CDCl₃) δ: 1.08 (3H, t, J=7.2 Hz), 1.05–2.25 (14H, m), 2.25–3.25 (10H, m), 4.90–5.10 (1H, m), 6.64 (1H, d, J=7.6 Hz), 6.90 (1H, t, J=7.2 Hz), 6.94–7.50 (6H, m), 11.50 (1H, brs)

44) ¹H-NMR (CDCl₃) δ: 1.06 (3H, t, J=7.5 Hz), 1.30–2.20 (6H, m), 2.60–3.20 (3H, m), 3.65 (1H, m), 3.95 (1H, brs), 4.90–5.10 (1H, m), 6.50–6.75 (3H, m), 6.75–7.05 (2H, m), 7.05–7.55 (8H, m), 8.67 (1H, brs)

45) ¹H-NMR (DMSO-d₆) δ: 1.28–1.57 (1H, m), 1.69–2.20 (3H, m), 2.59–3.15 (3H, m), 4.74–4.98 (1H, m), 6.62–6.80 (1H, m), 6.86–7.37 (5H, m), 7.50–7.70 (2H, m), 8.95–9.02 (1H, m), 9.03–9.15 (2H, m), 10.85 (1H, s)

46) ¹H-NMR (CDCl₃) δ: 1.40–1.66 (5H, m), 1.72–2.20 (7H, m), 2.63–3.18 (3H, m), 3.42 (2H, t, J=6.7 Hz), 4.00 (2H, t, J=6.3 Hz), 4.91–5.13 (1H, m), 6.58–6.72 (1H, m), 6.82–7.00 (3H, m), 7.02–7.30 (4H, m), 7.36–7.51 (2H, m), 7.70–7.88 (2H, m), 7.91 (1H, s)

47) ¹H-NMR (DMSO-d₆) δ: 2.05–2.95 (8H, m), 3.43–3.70 (1H, m), 4.08–4.30 (1H, m), 4.72–5.00 (1H, m), 6.70–8.08 (11H, m), 10.8 (1H, s), 11.1 (1H, brs)

48) ¹H-NMR (DMSO-d₆) δ: 2.10–3.00 (8H, m), 3.47–3.70 (1H, m), 4.07–4.33 (1H, m), 4.75–4.98 (1H, m), 6.78–6.91 (1H, m), 7.05–7.22 (2H, m), 7.30–7.97 (9H, m), 10.75 (1H, s), 10.94 (1H, brs)

Example 377

To a solution of 1-[4-(4-formylbenzoylamino)benzoyl]-1,2,3,4-tetrahydroquinoline (0.3 g) in methanol (10 ml) is added gradually sodium borohydride (59 mg) under ice-cooling and the mixture is stirred at room temperature for 2 hours. Water is added to the mixture and the solvent is distilled off under reduced pressure. The resulting residue is extracted with dichloromethane, washed with water, and dried over magnesium sulfate. The solvent is distilled off under reduced pressure and the resulting residue is purified by silica gel column chromatography (eluent; dichloromethane:methanol=50:1), and recrystallized from methanol to give 1-[4-(4-hydroxymethylbenzoylamino)benzoyl]-1,2,3,4-tetrahydroquinoline (165 mg) as white powder, m.p. 224.5°–225.5° C.

Using the suitable starting materials, the compound of the above Example 37 is obtained in the same manner as in Example 377.

Example 378

To a solution of 1-[4-(4-methoxycarbonylbenzoylamino)benzoyl]-1,2,3,4-tetrahydroquinoline (0.5 g) in methanol (20 ml) is added 5% aqueous sodium hydroxide solution (10 ml) and the mixture is stirred at room temperature overnight. Methanol is distilled off under reduced pressure and the resulting residue is acidified with diluted aqueous hydrochloric acid solution. The precipitated crystal is collected by filtration to give 1-[4-(4-carboxybenzoylamino)benzoyl]-1, 2,3,4-tetrahydroquinoline (0.4 g) as white powder, m.p. >300° C.

$^1$H-NMR (DMSO-d$_6$) δ: 2.05 (2H, quint, J=6.4 Hz), 2.91 (2H, t, J=6.4 Hz), 3.86 (2H, t, J=6.4 Hz), 6.85 (1H, d, J=7.6 Hz), 6.9–7.2 (2H, m), 7.30 (1H, d, J=7.2 Hz), 7.44 (2H, d, J=8.5 Hz), 7.85 (2H, d, J=8.5 Hz), 8.1–8.2 (4H, m), 10.65 (1H, s), 13.2–13.4 (1H, br)

Using the suitable starting materials, the compounds of the above Examples 39, 241, 252, 253 and 362 are obtained in the same manner as in Example 378.

Example 379

To a solution of 1-[4-(3-acetyloxybenzoylamino)benzoyl]-1,2,3,4-tetrahydroquinoline (1.5 g) in methanol (20 ml) is added 5% aqueous sodium hydroxide solution (10 ml) and the mixture is stirred at room temperature overnight. Methanol is distilled off under reduced pressure and the resulting residue is acidified with diluted aqueous hydrochloric acid solution. The precipitated crystal is collected by filtration and recrystallized from methanol to give 1-[4-(3-hydroxybenzoylamino)benzoyl]-1,2,3,4-tetrahydroquinoline (1.22 g) as white powder, m.p. 217°–218° C.

Using the suitable starting materials, the compounds of the above Examples 10, 343, 356, 364 and 365 are obtained in the same manner as in Example 379.

Example 380

To a solution of 1-[4-(3-hydroxybenzoylamino)benzoyl]-1,2,3,4-tetrahydroquinoline (0.4 g) in acetone (5 ml) are added potassium carbonate (0.22 g) and ethyl iodide (0.34 g), and the mixture is refluxed for 5 hours. Then, acetone is distilled off under reduced pressure and water is added to the residue. The precipitated crystal is collected by filtration, and recrystallized from methanol to give 1-[4-(3-ethoxybenzoylamino)benzoyl]-1,2,3,4-tetrahydroquinoline (0.36 g) as white powder, m.p. 170.5°–171.5° C.

Using the suitable starting materials, the compounds of the above Examples 11, 12, 13, 14, 33, 35, 48, 50–55, 90–92, 97–100, 109–111, 120–122, 136–138, 165–167, 175–177, 192–194, 211, 212, 214, 321, 322, 330–333, 335, 336, 339–342, 344–355, 357–366 and 370–374 are obtained in the same manner as in Example 380.

Example 381

Ethanol (50 ml) is added to 10% Pd—C (0.1 g) and thereto is added 1-[4-(3-nitrobenzoylamino)benzoyl]-1,2,3, 4-tetrahydroquinoline (0.73 g). The mixture is subjected to catalytic reduction at ordinary temperature under atmospheric pressure of hydrogen. After completion of the reduction, 10% Pd—C is removed by filtration and the filtrate is concentrated under reduced pressure. The residue is extracted with dichloromethane and the extract is dried over magnesium sulfate. The solvent is distilled off under reduced pressure and recrystallized from methanol to give 1-[4-(3-aminobenzoylamino)benzoyl]-1,2,3,4-tetrahydroquinoline (0.54 g) as white powder, m.p. 205.5°–206.5° C.

Using the suitable starting materials, the compounds of the above Examples 24, 334 and 338 are obtained in the same manner as in Example 381.

Example 382

To a solution of 1-(4-aminobenzoyl)-1,2,3,4-tetrahydroquinoline (0.5 g) in dichloromethane (20 ml) is added triethylamine (0.3 g), and thereto is added benzoyl chloride (0.28 g) under ice-cooling. The mixture is stirred at room temperature for 1 hour. To the reaction mixture is added water and extracted with dichloromethane. The extract is dried over magnesium sulfate and the solvent is distilled off under reduced pressure. The resulting residue is purified by silica gel column chromatography (eluent; dichloromethane:methanol=50:1) and recrystallized from methanol to give 1-[4-(benzoylamino)benzoyl]-1,2,3,4-tetrahydroquinoline (245 mg) as white powder, m.p. 202.5°–203.5° C.

Using the suitable starting materials, the compounds of the above Examples 2–119, 131–373, 375 and 376 are obtained in the same manner as in Example 382.

Example 383

Thionyl chloride (10 ml) is added to 1-(4-carboxybenzoyl)-1,2,3,4-tetrahydroquinoline (0.5 g) and the mixture is refluxed for 1 hour. Thionyl chloride is distilled off under reduced pressure to give 4-[1-(1,2,3,4-tetrahydroquinolyl)carbonyl]benzoyl chloride. Separately, to a solution of m-anisidine (0.27 g) in dichloromethane (20 ml) is added triethylamine (0.34 g), and thereto is added gradually the above obtained 4-[1-(1,2,3,4-tetrahydroquinolyl)carbonyl]benzoyl chloride under ice-cooling and the mixture is stirred at room temperature for 1 hour. Water is added to the reaction mixture and the mixture is extracted with dichloromethane. The extract is dried over magnesium sulfate. The solvent is distilled off under reduced pressure and the resulting residue is purified by silica gel column chromatography (eluent; dichloromethane:methanol=50:1), and recrystallized from methanol to give 1-[4-(3-methoxyanilinocarbonyl)benzoyl]-1,2,3,4-tetrahydroquinoline (203 mg) as colorless needles, m.p. 154°–155° C.

Using the suitable starting materials, the compounds of the above Examples 120, 122–130 and 374 are obtained in the same manner as in Example 383.

Example 384

To 4-oxo-1-[4-(3,5-dichlorobenzoylamino)benzoyl]-1,2, 3,4-tetrahydroquinoline (0.7 g) are added tetrahyrdofuran (10 ml) and methanol (10 ml). To the mixture is added sodium borohydride (0.1 g) in portions and the mixture is stirred at room temperature for 1 hour. Water is added to the reaction mixture and the mixture is extracted with dichloromethane. The solvent is concentrated and the resulting residue is purified by silica gel column chromatography (eluent; dichloromethane→dichloromethane:methanol= 20:1), and recrystallized from ethanol to give 4-hydroxy-1-[4-(3,5-dichlorobenzoylamino)benzoyl]-1,2,3,4-tetrahydroquinoline (0.4 g) as white powder, m.p. 215°–217° C.

Example 385

To 3-ethoxycarbonyl-1-[4-(3,5-dichlorobenzoylamino) benzoyl]-1,2,3,4-tetrahydroquinoline (0.6 g) are added an aqueous solution of sodium hydroxide (0.1 g) in water (1 ml) and ethanol (5 ml). The mixture is stirred at room temperature for 15 minutes, and acidified with diluted hydrochloric acid, extracted with dichloromethane. The solvent is distilled off and the resulting residue is purified by silica gel column chromatography (eluent; dichloromethane→dichloromethane:methanol=50:1), and recrystallized from ethanol to give 3-carboxy-1-[4-(3,5-dichlorobenzoylamino)benzoyl]-1,2,3,4-tetrahydroquinoline (0.4 g) as white powder. m.p. 221°–223° C.

Example 386

To 3-carboxy-1-[4-(3,5-dichlorobenzoylamino)benzoyl]-1,2,3,4-tetrahydroquinoline (3.7 g) are added tetrahydrofuran (50 ml) and thionyl chloride (5 ml). The mixture is reacted at 60° C. for 1 hour. The reaction mixture is concentrated and to the residue is added acetone (20 ml). To the mixture is added dropwise a solution of sodium azide (1.0 g) in water (5 ml) under ice-cooling. The reaction mixture is stirred at the same temperature for 30 minutes and extracted with dichloromethane, dried over magnesium sulfate. The solvent is concentrated and to the resulting residue are added anhydrous toluene (30 ml) and benzyl alcohol (1.7 g). The mixture is refluxed for 1 hour. The reaction mixture is concentrated and the resulting residue is purified by silica gel column chromatography (eluent; dichloromethane→dichloromethane:methanol=50:1) to give 3-benzyloxycarbonylamino-1-[4-(3,5-dichlorobenzoylamino)benzoyl]-1,2,3,4-tetrahydroquinoline (3.7 g) as colorless amorphous.

$^1$H-NMR (CDCl$_3$) δ: 2.80 (1H, dd, J=16.1 Hz, 5.3 Hz), 3.16 (1H, dd, J=15.8 Hz, 5.3 Hz), 3.75–4.50 (3H, m), 4.87–5.10 (3H, m), 6.80–7.60 (14H, m), 7.74 (2H, d, J=1.9 Hz), 8.47 (1H, brs)

Example 387

To 3-benzyloxycarbonylamino-1-[4-(3,5-dichlorobenzoylamino)benzoyl]-1,2,3,4-tetrahydroquinoline (3.3 g) are added acetic acid (40 ml) and 10% Pd—C (0.4 g) and the reaction mixture is subjected to catalytic reduction at ordinary temperature under atmospheric pressure of hydrogen. One hour thereafter, the catalyst is removed by filtration and the filtrate is concentrated. The resulting residue is purified by silica gel column chromatography (eluent; dichloromethane:methanol=20:1), and recrystallized from ethanol to give 3-amino-1-[4-(3,5-dichlorobenzoylamino)benzoyl]-1,2,3,4-tetrahydroquinoline (1.6 g) as white powder. m.p. 207°–210° C.

Example 388

To 3-amino-1-[4-(3,5-dichlorobenzoylamino)benzoyl]-1,2,3,4-tetrahydroquinoline (0.5 g) are added methanol (10 ml), 37% formaline (0.8 ml) and sodium cyanoborohydride (0.16 g). To the mixture is added acetic acid (0.5 ml) under ice-cooling and the mixture is stirred at room temperature for 1 hour. Water is added to the reaction mixture and the mixture is basified with potassium carbonate and extracted with dichloromethane. The solvent is concentrated and the resulting residue is purified by silica gel column chromatography (eluent; dichloromethane→dichloromethane:methanol=20:1) to give 3-dimethylamino-1-[4-(3,5-dichlorobenzoylamino)benzoyl]-1,2,3,4-tetrahydroquinoline (0.3 g) as colorless amorphous.

$^1$H-NMR (CDCl$_3$) δ: 2.35 (6H, s), 2.72–3.10 (3H, m), 3.65–3.78 (1H, m), 4.06–4.18 (1H, m), 6.60–7.62 (9H, m), 7.74 (2H, d, J=1.8 Hz), 8.52 (1H, brs)

Using the suitable starting materials, the compounds of the above Examples 246, 247, 375 and 376 are obtained in the same manner as in Example 388.

Example 389

To 3-amino-1-[4-(3,5-dichlorobenzoylamino)benzoyl]-1,2,3,4-tetrahydroquinoline (0.44 g) are added dichloromethane (5 ml) and acetic anhydride (0.12 g) and the mixture is stirred for 1 hour. The reaction mixture is concentrated and the resulting residue is purified by silica gel column chromatography (eluent; dichloromethane→dichloromethane:methanol=50:1) to give 3-acetylamino-1-[4-(3,5-dichlorobenzoylamino)benzoyl]-1,2,3,4-tetrahydroquinoline (0.3 g) as colorless amorphous.

$^1$H-NMR (CDCl$_3$) δ: 1.87 (3H, s), 2.68 (1H, dd, J=5.6 Hz, 16 Hz), 3.14 (1H, dd, J=5.6 Hz, 16 Hz), 3.70–3.95 (2H, m), 4.32–4.50 (1H, m), 6.29 (1H, d, J=7.6 Hz), 6.90–7.80 (11H, m), 9.16 (1H, brs)

Using the suitable starting materials, the compound of the above Example 242 is obtained in the same manner as in Example 389.

Example 390

To 4-oxo-1-[4-(3,5-dichlorobenzoylamino)benzoyl]-1,2,3,4-tetrahydroquinoline (0.5 g) are added 40% solution of methylamine in methanol (5 ml), molecular sieves 4A (1 g) and dimethylformamide (6 ml), and the mixture is refluxed for 4 hours. After cooling, the reaction mixture is filtered and to the filtrate is added sodium borohydride (80 mg), and the mixture is stirred at room temperature for 1 hour. The reaction mixture is concentrated and water is added to the resulting residue, and extracted with ethyl acetate. The solvent is concentrated and the resulting residue is purified by silica gel column chromatography (eluent; dichloromethane:methanol=20:1) to give 4-methylamino-1-[4-(3,5-dichlorobenzoylamino)benzoyl]-1,2,3,4-tetrahydroquinoline (0.2 g) as colorless amorphous.

$^1$H-NMR (CDCl$_3$) δ; 1.62 (1H, brs), 1.90–2.25 (2H, m), 2.55 (3H, s), 3.78 (1H, t, J=5.1 Hz), 3.95 (2H, t, J=6.7 Hz), 6.99 (1H, d, J=7.9 Hz), 6.90–7.13 (2H, m)

Using the suitable starting materials, the compounds of the above Examples 238, 239, 244, 247, 375 and 376 are obtained in the same manner as in Example 390.

Example 391

To 3-carboxy-1-[4-(3,5-dichlorobenzoylamino)benzoyl]-1,2,3,4-tetrahydroquinoline (0.7 g) are added dimethylformamide (7 ml), diethyl cyanophosphate (0.3 ml) and dimethylamine hydrochloride (0.15 g). Further thereto is added triethylamine (0.8 ml) and the mixture is stirred at room temperature for 1 hour. Water is added to the reaction mixture and extracted with ethyl acetate. The solvent is concentrated and to the resulting residue is added diethyl ether. The precipitated crystal is collected by filtration to give 3-dimethylamido-1-[4-(3,5-dichlorobenzoylamino)benzoyl]-1,2,3,4-tetrahydroquinoline (0.5 g) as light yellow powder. m.p. 186°–187° C.

Example 392

To a solution of 1-(4-aminobenzoyl)-2,3,4,5-tetrahydro-1H-benzazepine (3.0 g) in dichloromethane (50 ml) is added succinic anhydride (1.4 g) and the mixture is stirred at room temperature for 4.5 hours. The reaction mixture is evaporated under reduced pressure in order to remove the solvent therefrom, and the resulting crystal is recrystallized from ethyl acetate to give 1-[4-(3-carboxypropionylamino)benzoyl]-2,3,4,5-tetrahydro-1H-benzazepine (3.61 g) as colorless needles, m.p. 192° C.

Using the suitable starting materials, the compound of the above Example 253 is obtained in the same manner as in Example 392.

Example 393

1-[4-(3-Carboxypropionylamino)benzoyl]-2,3,4,5-tetrahydro-1H-benzazepine (0.5 g) is dissolved in dimethylformamide (1 ml) and thereto is added dropwise diethyl cyanophosphate (0.25 g) under ice-cooling. The mixture is stirred at room temperature for 30 minutes and then cooled again with ice. Thereto are added dropwise a solution of diethylamine (0.11 g) in dimethylformamide (1 ml) and triethylamine (0.34 g). The mixture is stirred at room temperature for 16 hours. The solvent is distilled off under reduced pressure and water is added to the resulting residue. The mixture is extracted with dichloromethane. The organic layer is washed successively with diluted hydrochloric acid, water, saturated sodium hydrogen carbonate solution, water and saturated saline solution, and dried over magnesium sulfate. The solvent is distilled off under reduced pressure and the resulting residue is purified by silica gel column chromatography (eluent; ethyl acetate), and recrystallized from n-hexane/ethyl acetate to give 1-[4-(3-diethylaminocarbonylpropionylamino)benzoyl]-2,3,4,5-tetrahydro-1H-benzazepine (0.42 g) as colorless scales, m.p. 165°–167° C.

Using the suitable starting materials, the compounds of the above Examples 255–263 are obtained in the same manner as in Example 393.

Example 394

To a solution of 1-[4-(2-chloroacetylamino)benzoyl]-2,3,4,5-tetrahydro-1H-benzazepine (2.06 g) in dimethylformamide (5 ml) are added sodium iodide (0.90 g), potassium carbonate (1.1 g) and cyclohexylamine (0.89 g), and the mixture is stirred at room temperature for 2 hours. Dimethylformamide is distilled off under reduced pressure and water is added to the resulting residue. The mixture is extracted with dichloromethane. The organic layer is washed successively with water and saturated saline solution, and dried over magnesium sulfate. The solvent is distilled off under reduced pressure and the resulting residue is purified by silica gel column chromatography (eluent; ethyl acetate), and recrystallized from n-hexane/ethyl acetate to give 1-[4-(2-cyclohexylaminoacetylamino)benzoyl]-2,3,4,5-tetrahydro-1H-benzazepine (2.03 g) as white powder, m.p. 139°–142° C.

Using the suitable starting materials, the compounds of the above Examples 271–309 and 317 are obtained in the same manner as in Example 394.

Example 395 o-Cresol (0.36 g) is dissolved in dimethylsulfoxide (4 ml) containing sodium hydroxide powder (0.18 g) and thereto is added 1-[4-(2-chloroacetylamino)benzoyl]-2,3,4,5-tetrahydro-1H-benzazepine (1.03 g). The mixture is stirred at 90° C. for 7.5 hours. The reaction mixture is poured into ice-water (300 ml) and the precipitated crystal is collected by filtration, washed with water, and purified by silica gel column chromatography (eluent; n-hexane:ethyl acetate= 2:1), and recrystallized from ethyl acetate to give 1-{4-[2-(2-methylphenoxy)acetylamino]benzoyl}-2,3,4,5-tetrahydro-1H-benzazepine (546 mg) as colorless scales, m.p. 172.5°–175° C.

Using the suitable starting materials, the compounds of the above Examples 310 and 312–316 are obtained in the same manner as in Example 395.

Example 396

A mixture of 1-{4-[2-(6-bromohexyloxy)benzoylamino]benzoyl}-2,3,4,5-tetrahydro-1H-benzazepine (2.00 g), sodium acetate (0.36 g), sodium iodide (0.55 g) and acetic acid (20 ml) is refluxed for 1 day. The solvent is distilled off and the resulting residue is extracted with ethyl acetate. The organic layer is washed successively with 2N aqueous sodium hydroxide solution and saturated saline solution, and dried over magnesium sulfate. The solvent is concentrated and the resulting residue is purified by silica gel column chromatography (eluent; chloroform:methanol=500:1), and recrystallized from ethanol to give 1-{4-[2-(6-acetyloxyhexyloxy)benzoylamino]benzoyl}-2,3,4,5-tetrahydro-1H-benzazepine (1.07 g) as white powder, m.p. 145°–146° C.

Using the suitable starting materials, the compound of the above Example 360 is obtained in the same manner as in Example 396.

Example 397

A mixture of 1-{4-[2-(6-bromohexyloxy)benzoylamino]benzoyl}-2,3,4,5-tetrahydro-1H-benzazepine (0.70 g), diethylamine (0.16 ml), triethylamine (0.21 ml) and acetonitrile (20 ml) is refluxed overnight. The solvent is distilled off and the resulting residue is dissolved in chloroform, washed successively with water and saturated saline solution, and dried over magnesium sulfate. The solvent is distilled off and the resulting residue is purified by silica gel column chromatography (eluent; chloroform:methanol= 200:1→50:1) and converted into the hydrochloride thereof in methanol. The product is recrystallized from methanol/diethyl ether to give 1-{4-[2-(6-diethylaminohexyloxy)benzoylamino]benzoyl}-2,3,4,5-tetrahydro-1H-benzazepine hydrochloride (0.42 g) as white powder, m.p. 91°–95° C.

Using the suitable starting materials, the compounds of the above Examples 330, 332, 333, 335, 336, 339, 341, 342, 344–349, 352–355, 357 and 366 are obtained in the same manner as in Example 397.

Example 398

A mixture of 1-{4-[2-(6-bromohexyloxy)benzoylamino]benzoyl}-2,3,4,5-tetrahydro-1H-benzazepine (4.00 g), potassium phthalimide (2.02 g) and dimethylformamide (100 ml) is stirred at 100° C. for 5 hours. The reaction mixture is filtered and the filtrate is distilled off. The resulting residue is extracted with ethyl acetate and the organic layer is washed successively with water and saturated saline solution, and dried over magnesium sulfate. The solvent is distilled off and the resulting residue is purified by silica gel column chromatography (eluent; dichloromethane), and recrystallized from methanol/diethyl ether to give 1-{4-[2-(6-phthalimidohexyloxy)benzoylamino]benzoyl}-2,3,4,5-tetrahydro-1H-benzazepine (4.06 g) as white powder, m.p. 145°–146.5° C.

Using the suitable starting materials, the compounds of the above Examples 331, 340, 364 and 365 are obtained in the same manner as in Example 398.

Example 399

A mixture of 1-{4-[2-[6-phthalimidohexyloxy)benzoylamino]benzoyl}-2,3,4,5-tetrahydro-1H-benzazepine (3.75 g), hydrazine hydrate (0.44 ml) and ethanol (30 ml) is refluxed for 3.5 hours. The precipitated crystal is collected by filtration, dried and purified by silica gel column chromatography (eluent; chloroform:methanol:aqueous ammonia=100:10:1), and recrystallized from methanol/diethyl ether to give 1-{4-[2-(6-aminohexyloxy)benzoylamino]benzoyl}-2,3,4,5-tetrahydro-1H-benzazepine (2.52 g) as white powder, m.p. 135.5°–137.5° C.

Using the suitable starting materials, the compounds of the above Examples 284, 344 and 345 are obtained in the same manner as in Example 399.

Example 400

A mixture of 1-{4-[2-(6-aminohexyloxy)benzoylamino]benzoyl}-2,3,4,5-tetrahydro-1H-benzazepine (0.70 g), acetic anhydride (20 ml) and two drops of conc. sulfuric acid is stirred at room temperature for 3 hours. To the reaction mixture is added aqueous 2N aqueous sodium hydroxide solution under ice-cooling and the mixture is extracted with chloroform. The organic layer is washed successively with water and saturated saline solution, and dried over magnesium sulfate. The solvent is distilled off and the resulting residue is purified by silica gel column chromatography (eluent; chloroform:methanol=200:1), and recrystallized from methanol/diethyl ether to give 1-{4-[2-(6-acetylaminohexyloxy)benzoylamino]benzoyl}-2,3,4,5-tetrahydro-1H-benzazepine (0.60 g) as colorless needles, m.p. 171°–172° C.

Example 401

A mixture of 1-{4-[2-(6-aminohexyloxy)benzoylamino]benzoyl}-2,3,4,5-tetrahydro-1H-benzazepine (0.70 g), benzoyl chloride (0.20 ml), triethylamine and dichloromethane (20 ml) is stirred at room temperature for 1 hour. The reaction mixture is washed successively with water and saturated saline solution, and dried over magnesium sulfate. The solvent is concentrated and the resulting residue is recrystallized from ethanol to give 1-{4-[2-(6-benzoylaminohexyloxy)benzoylamino]benzoyl)-2,3,4,5-tetrahydro-1H-benzazepine (0.71 g) as white powder, m.p. 178°–178.5° C.

Using the suitable starting materials, the compounds of the above Examples 348 and 357 are obtained in the same manner as in Examples 400 and 401.

Example 402

A mixture of 1-[4-(2-ethoxycarbonylmethoxybenzoylamino)benzoyl]-2,3,4,5-tetrahydro-1H-benzazepine (1.00 g), aqueous ammonia (100 ml), ammonium chloride (0.3 g) and methanol (150 ml) is heated at 100° C. for 4 hours in a sealed tube. The solvent is distilled off and the resulting residue is extracted with chloroform, washed successively with water and saturated saline solution, and dried over magnesium sulfate. The solvent is concentrated and the resulting residue is purified by silica gel column chromatography (eluent; chloroform:methanol=50:1), and recrystallized from methanol/diethyl ether to give 1-[4-(2-carbamoylmethoxybenzoylamino)benzoyl]-2,3,4,5-tetrahydro-1H-benzazepine (0.43 g) as white powder, m.p. 198°–199° C.

Example 403

A mixture of 1-[4-(2-chloro-4-aminobenzoylamino)benzoyl]-2,3,4,5-tetrahydro-1H-benzazepine (0.55 g), acetic anhydride (15 ml), acetic acid (5 ml) and a drop of sulfuric acid is stirred at room temperature for 1 hour. To the reaction mixture is added aqueous 2N aqueous sodium hydroxide solution and the mixture is extracted with chloroform. The extract is washed with saturated saline solution and dried over magnesium sulfate. The solvent is concentrated and the resulting residue is recrystallized from methanol/diethyl ether to give 1-[4-(2-chloro-4-acetylaminobenzoylamino)benzoyl]-2,3,4,5-tetrahydro-1H-benzazepine (0.28 g) as white powder, m.p. 214°–243° C.

Using the suitable starting materials, the compound of the above Example 44 is obtained in the same manner as in Example 403.

Example 404

A mixture of 1-[4-(1-benzyloxycarbonyl-4-piperidinylcarbonylamino)benzoyl]-2,3,4,5-tetrahydro-1H-benzazepine (8.00 g), 10% Pd—C (0.8 g) and ethanol (250 ml) is subjected to catalytic hydrogenation at 50° C. under 4 atm. of hydrogen pressure for 6 hours. The catalyst is removed by filtration and the filtrate is evaporated under reduced pressure. The resulting residue is extracted with ethyl acetate and washed successively with water and saturated saline solution, and dried over magnesium sulfate. The solvent is distilled off and the resulting residue is purified by silica gel column chromatography (eluent; chloroform:methanol:ammonium hydroxide=50:10:1) to give 1-{4-[4-(4-piperidinyl)benzoylamino)benzoyl]-2,3,4,5-tetrahydro-1H-benzazepine (4.80 g), and a part (0.5 g) thereof is converted into the hydrochloride thereof in methanol. The hydrochloride is recrystallized from methanol/diethyl ether to give 1-{4-[4-(4-piperidinyl)benzoylamino]benzoyl}-2,3,4,5-tetrahydro-1H-benzazepine hydrochloride (0.42 g) as white powder, m.p. 177°–181.5° C.

Example 405

Using the suitable starting materials, the following compound is obtained in the same manner as in the above Examples 1, 382 and 388.

1-[4-(4-Dimethylaminobenzoylamino)benzoyl]-1,2,3,4-tetrahydroquinoline, colorless amorphous $^1$H-NMR (DMSO-$d_6$) δ: 1.90–2.00 (2H, m), 2.82 (2H, t, J=6.5 Hz), 2.98 (6H, s), 3.77 (2H, t, J=6.5 Hz), 6.70–7.30 (6H, m), 7.32 (2H, d, J=8.6 Hz), 7.73 (2H, d, J=8.6 Hz), 8.00–8.20 (1H, m), 8.39 (1H, d, J=2.2 Hz), 10.37 (1H, s)

Using the suitable starting materials, the following compounds are obtained in the same manner as in Example 1.

TABLE 2
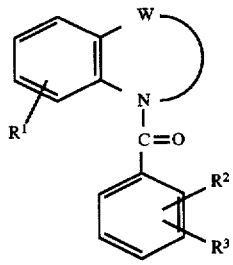
Example 406
Structure
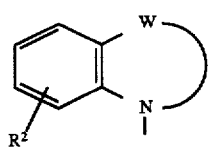 : 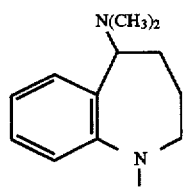
R²: H
R³:
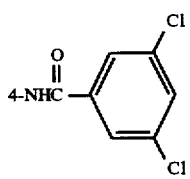
Crystalline form: White powder
Recrystallization solvent: Ethanol
Melting Point: 216–218° C.
Form: Free
Example 407
Structure
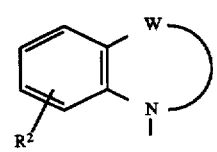 : 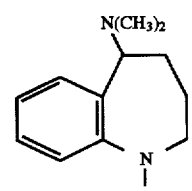
R²: H
R³:
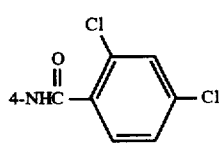
Crystalline form: White powder
Recrystallization solvent: Ethanol
Melting Point: 181–183° C.
Form: Free TABLE 2-continued
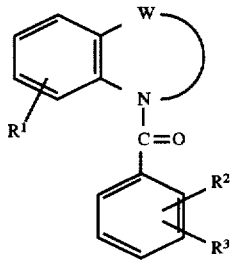
Example 408
Structure
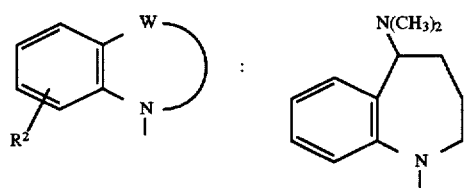
R²: H
R³: 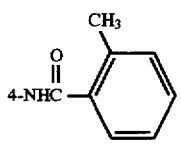
Crystalline form: White powder
Recrystallization solvent: Ethanol
Melting Point: 207–208° C.
Form: Free
Example 409
Structure
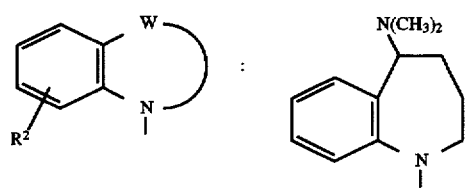
R²: H
R³: 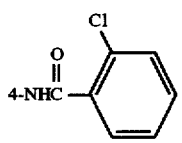
Crystalline form: White powder
Recrystallization solvent: Ethanol
Melting Point: 213–214° C.
Form: Free TABLE 2-continued
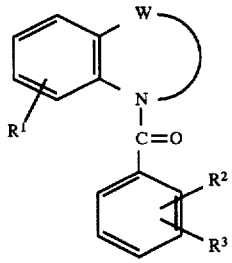
Example 410
Structure
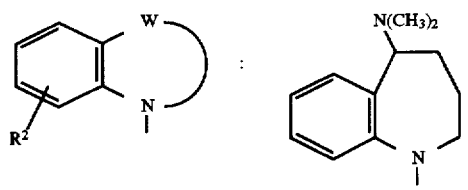
R²: 3-OCH₃
R³: 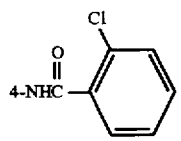
4-NHC(=O)-(2-Cl-phenyl)
Crystalline form: White powder
Recrystallization solvent: Ethanol
Melting Point: 136–138° C.
Form: Free
Example 411
Structure
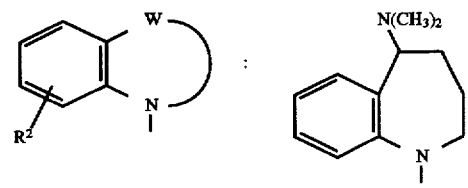
R²: 3-OCH₃
R³: 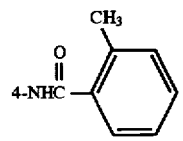
4-NHC(=O)-(2-CH₃-phenyl)
Crystalline form: White powder
Recrystallization solvent: Ethanol
Melting Point: 130–132° C.
Form: Free TABLE 2-continued
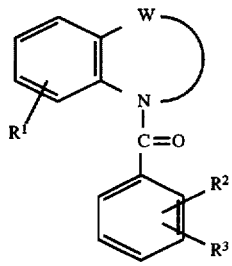
Example 412
Structure
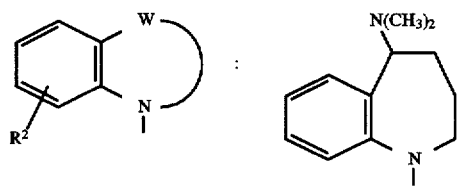
R²:  3-OCH₃
R³:
4-NHC(O)- 2,4-dichlorophenyl
Crystalline form: White powder
Recrystallization solvent: Ethanol
Melting Point: 143–145° C.
Form: Free
Example 413
Structure
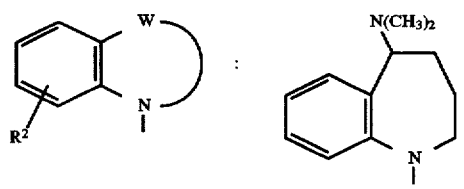
R²:  3-OCH₃
R³:
4-NHC(O)- 2,5-dichlorophenyl
Crystalline form: White powder
Recrystallization solvent: Ethanol
Melting Point: 171–173° C.
Form: Free TABLE 2-continued
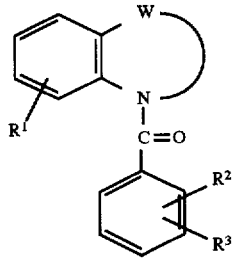
Example 414
Structure
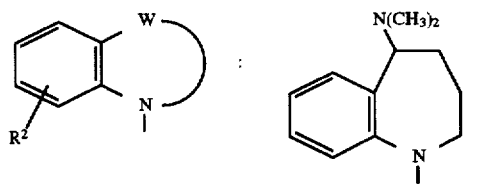
R²:  3-OCH₃
R³:
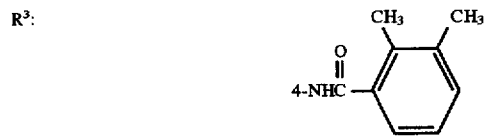
Crystalline form: White powder
Recrystallization solvent: Ethanol
Melting Point: 162–164° C.
Form: Free
Example 415
Structure
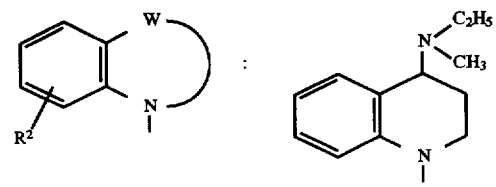
R²:  H
R³:
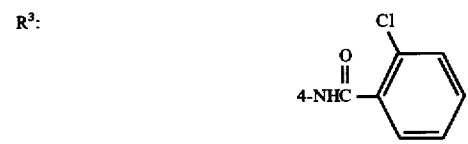
Crystalline form: Colorless amorphous
NMR analysis: 49)
Form: Free TABLE 2-continued
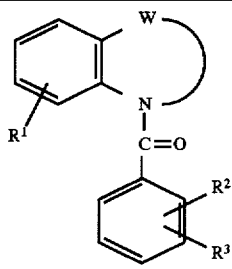
Example 416
Structure
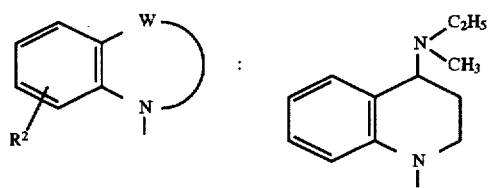
R²:  H
R³:
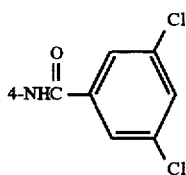
Crystalline form: Colorless amorphous
NMR analysis: 50)
Form: Free
Example 417
Structure
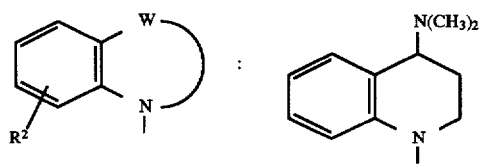
R²:  3-OCH₃
R³:
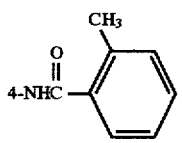
Crystalline form: Colorless amorphous
NMR analysis: 51)
Form: Free
Example 418
Structure
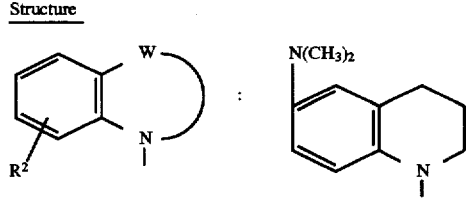

TABLE 2-continued
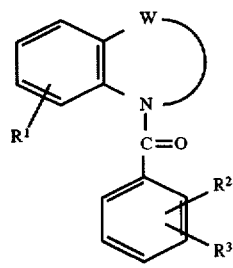
| R²: | H |
| --- | --- |
| R³: | 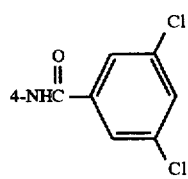 |
Crystalline form: Colorless needles
Recrystallization solvent: Ethyl acetate/n-hexane
Melting Point: 228.5–230° C.
Form: Free
Example 419
Structure
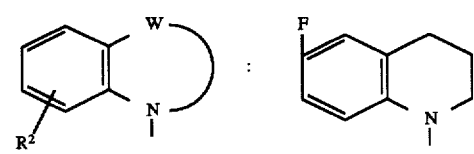
| R²: | H |
| --- | --- |
| R³: | 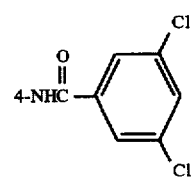 |
Crystalline form: White powder
Recrystallization solvent: Ethyl acetate/n-hexane
Melting Point: 205.5–206.5° C.
Form: Free
Example 420
Structure
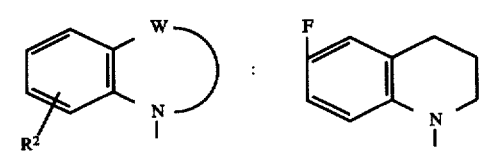
R²: H TABLE 2-continued
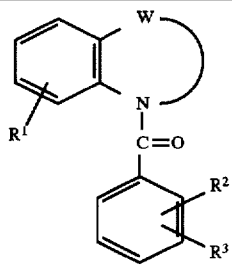
R³:
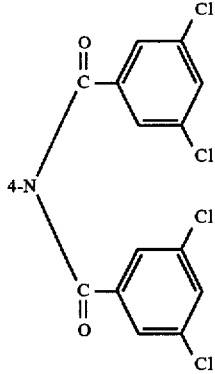
Crystalline form: White powder
Recrystallization solvent: Ethyl acetate/n-hexane
Melting Point: 210–212° C.
Form: Free
Example 421
Structure
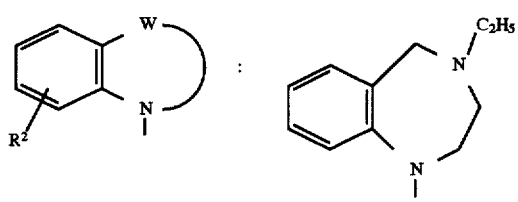
R²: H
R³:
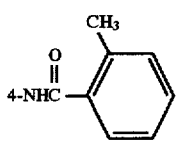
Crystalline form: White powder
Recrystallization solvent: Ethanol
Melting Point: 166–167° C.
Form: Free
Example 422
Structure
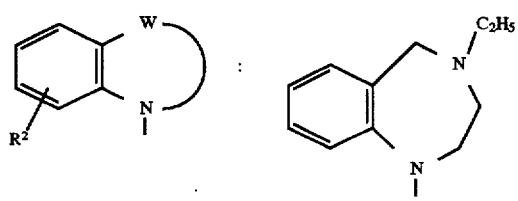
R²: H TABLE 2-continued
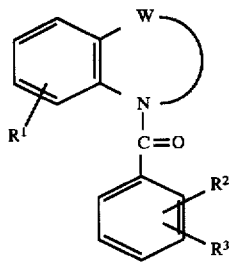
R³:
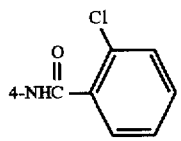
Crystalline form: White powder
Recrystallization solvent: Ethanol
Melting Point: 191.5–192.5° C.
Form: Free
Example 423
Structure
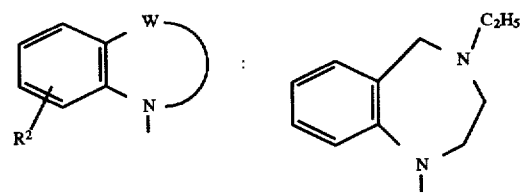
R²: H
R³:
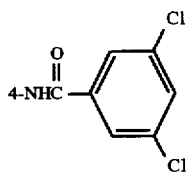
Crystalline form: White powder
Recrystallization solvent: Ethanol
Melting Point: 209–210° C.
Form: Free
Example 424
Structure
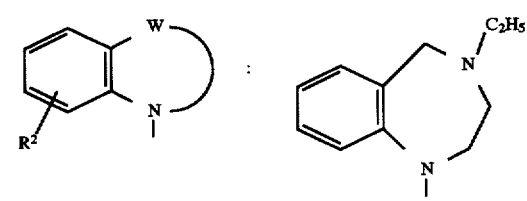
R²: H
R³:
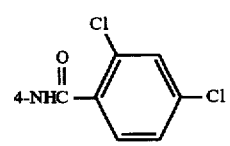

TABLE 2-continued
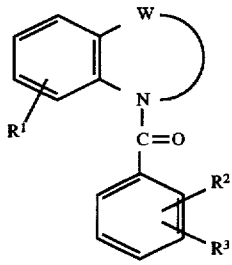
Crystalline form: Colorless amorphous
NMR analysis: 52)
Form: Free
Example 425
Structure
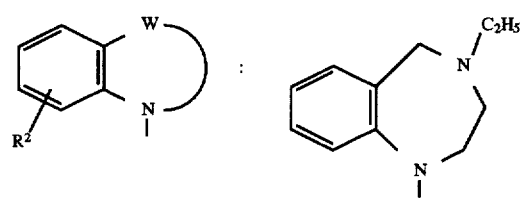
R²: H
R³:
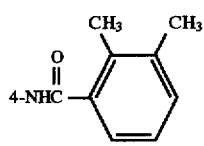
Crystalline form: White powder
Recrystallization solvent: Ethanol
Melting Point: 148–149° C.
Form: Free
Example 426
Structure
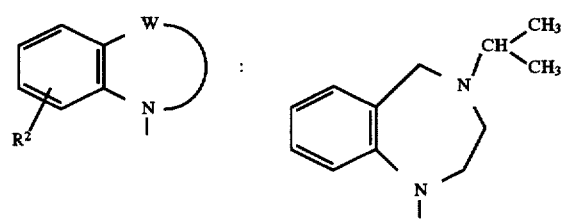
R²: H
R³:
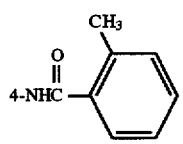
Crystalline form: White powder
Recrystallization solvent: Ethanol
Melting Point: 157–158° C.
Form: Free TABLE 2-continued
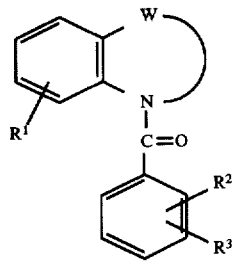
Example 427
Structure
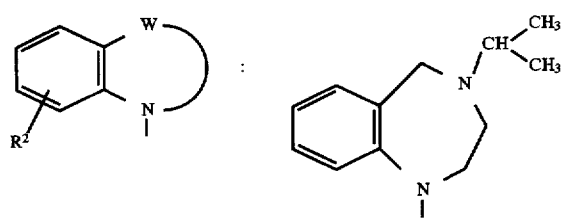
R²: H
R³:
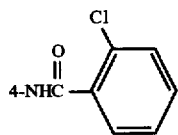
Crystalline form: White powder
Recrystallization solvent: Ethanol
Melting Point: 194.5–195.5° C.
Form: Free
Example 428
Structure
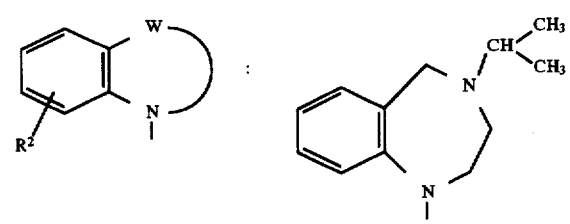
R²: H
R³:
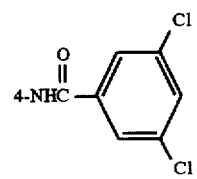
Crystalline form: White powder
Recrystallization solvent: Ethanol
Melting Point: 179.5–180.5° C.
Form: Free TABLE 2-continued
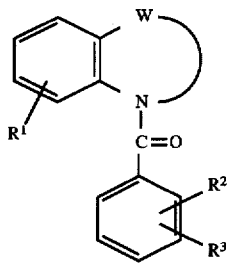
Example 429
Structure
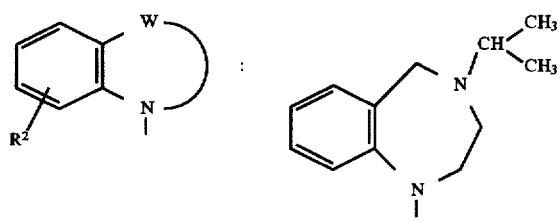
R²: H
R³: 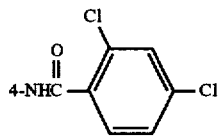
Crystalline form: White powder
Recrystallization solvent: Ethanol
Melting Point: 190–191° C.
Form: Free
Example 430
Structure
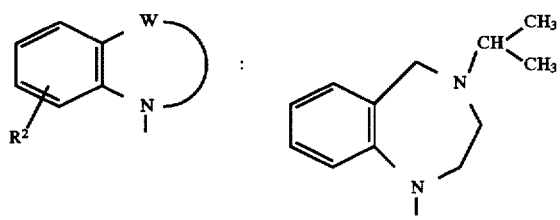
R²: H
R³: 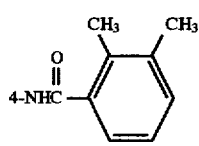
Crystalline form: White powder
Recrystallization solvent: Ethanol
Melting Point: 159–160° C.
Form: Free TABLE 2-continued
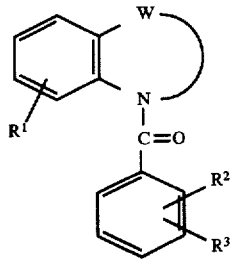
Example 431
Structure
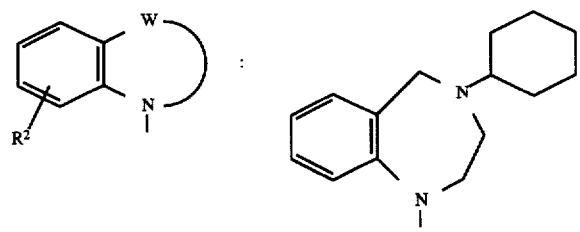
R²:  H
R³:  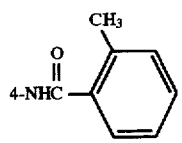
Crystalline form: Colorless amorphous
NMR analysis: 53)
Form: Hydrochloride
Example 432
Structure
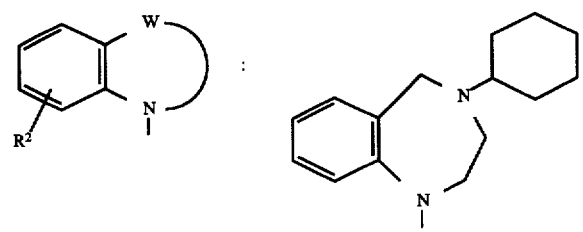
R²:  H
R³:  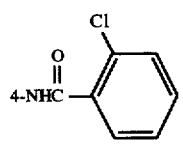
Crystalline form: White powder
Recrystallization solvent: Ethanol
Melting Point: 155–156° C.
Form: Free TABLE 2-continued
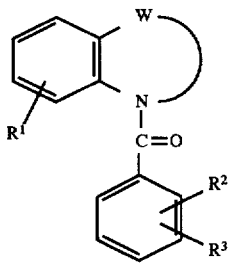
Example 433
Structure
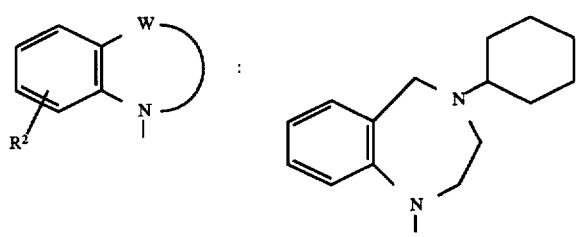
R²:  H
R³:
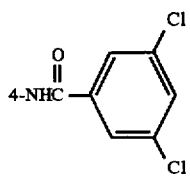
Crystalline form: Colorless amorphous
NMR analysis: 54)
Form: Free
Example 434
Structure
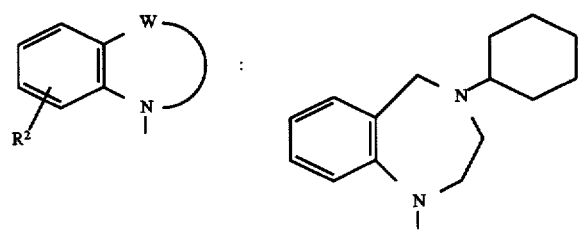
R²:  H
R³:
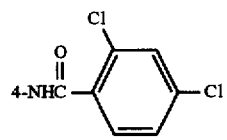
Crystalline form: Colorless amorphous
NMR analysis: 55)
Form: Free

TABLE 2-continued
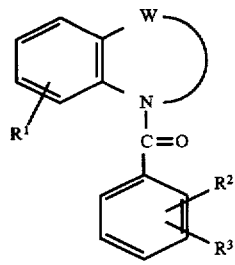
Example 435
Structure
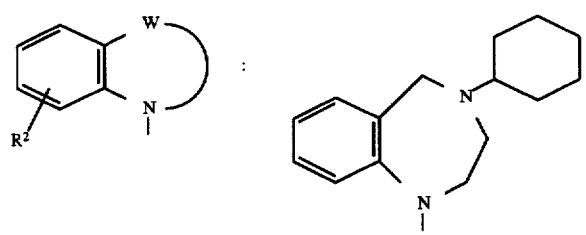
R²: H
R³:
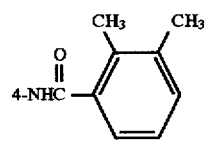
Crystalline form: White powder
Recrystallization solvent: Ethanol
Melting Point: 175–177° C.
Form: Free
Example 436
Structure
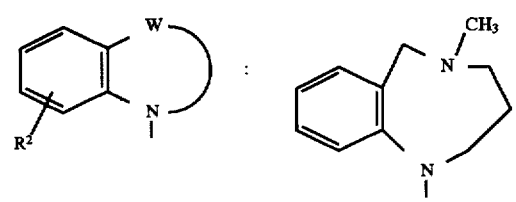
R²: H
R³:
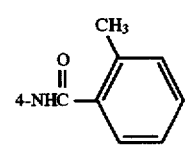
Crystalline form: Colorless amorphous
NMR analysis: 56)
Form: Free TABLE 2-continued
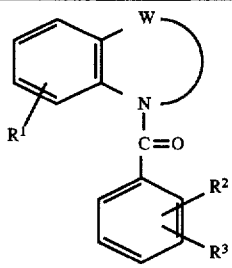
Example 437
Structure
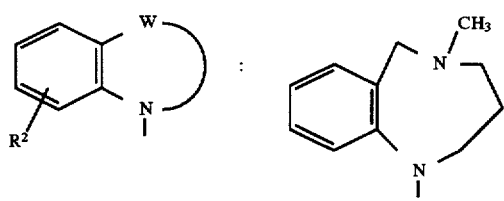
R²: H
R³:
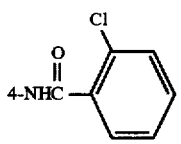
Crystalline form: Colorless amorphous
NMR analysis: 57)
Form: Free
Example 438
Structure
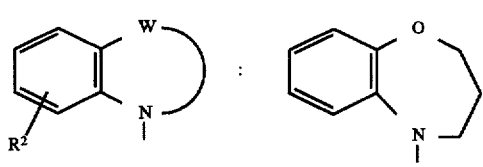
R²: H
R³:
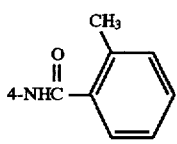
Crystalline form: White powder
Recrystallization solvent: Dichloromethane/diethyl ether
Melting Point: 219–220° C.
Form: Free
Example 439
Structure
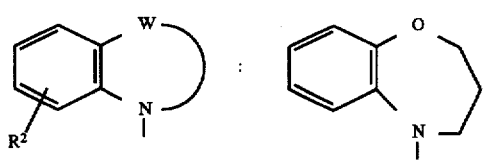

TABLE 2-continued
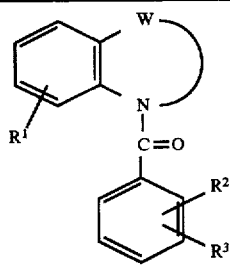
R²: H
R³:
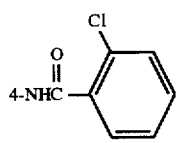
Crystalline form: White powder
Recrystallization solvent: Dichloromethane/diethyl ether
Melting Point: 215–218° C.
Form: Free
Example 440
Structure
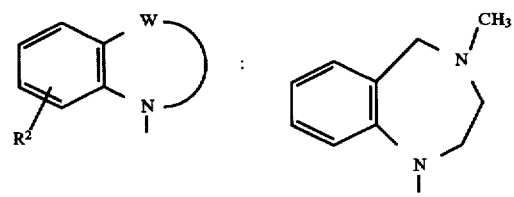
R²: H
R³:
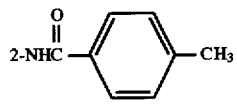
Crystalline form: White powder
Recrystallization solvent: Ethanol
Melting Point: 128.5–129.5° C.
Form: Free
Example 441
Structure
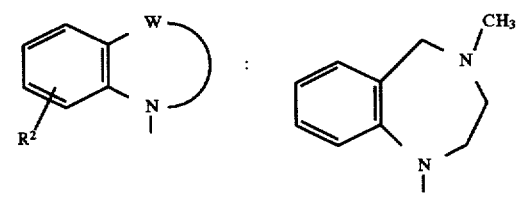
R²: H
R³:
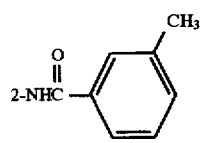
Crystalline form: Colorless amorphous
NMR analysis: 58)
Form: Free TABLE 2-continued
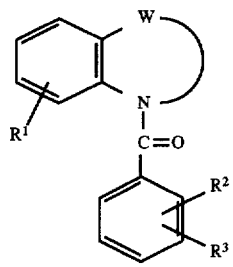
Example 442
Structure
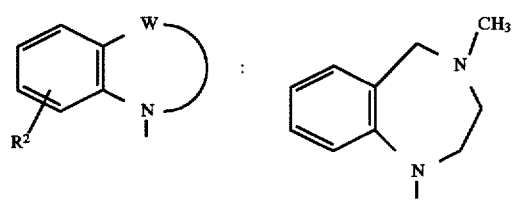
R²: H
R³: 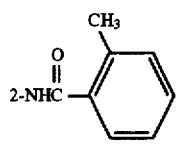
Crystalline form: White powder
Recrystallization solvent: Ethanol
Melting Point: 153–154° C.
Form: Free
Example 443
Structure
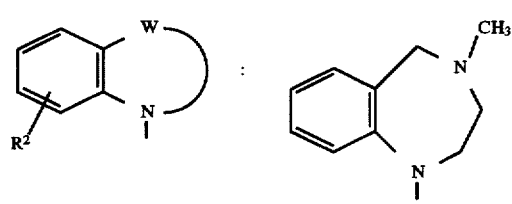
R²: H
R³: 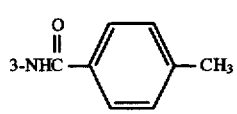
Crystalline form: White powder
Recrystallization solvent: Ethanol
Melting Point: 150–153° C.
Form: Free TABLE 2-continued
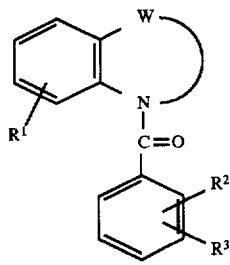
Example 444
Structure
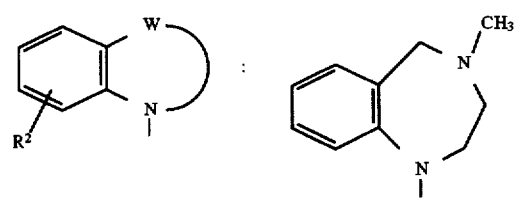
R²:  H
R³:
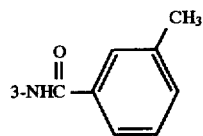
Crystalline form: White powder
Recrystallization solvent: Ethanol
Melting Point: 139–141° C.
Form: Free
Example 445
Structure
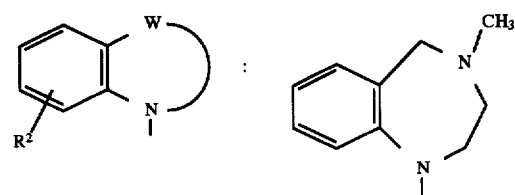
R²:  H
R³:
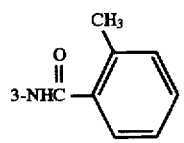
Crystalline form: Colorless amorphous
NMR analysis: 59)
Form: Free TABLE 2-continued
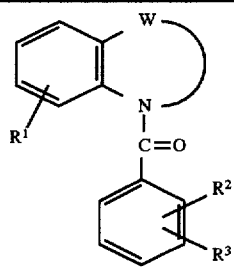
Example 446
Structure
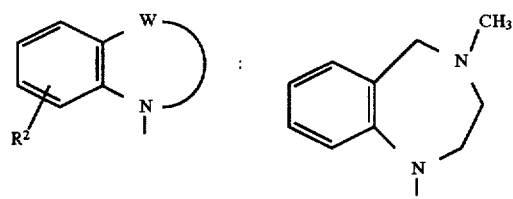
R²: H
R³:
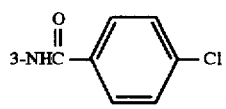
Crystalline form: Colorless amorphous
NMR analysis: 60)
Form: Free
Example 447
Structure
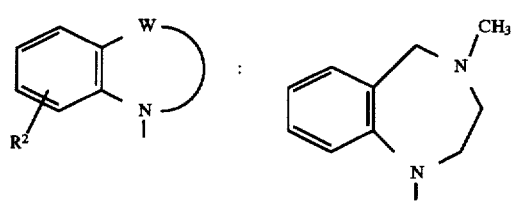
R²: H
R³:
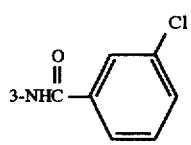
Crystalline form: Colorless amorphous
NMR analysis: 61)
Form: Free
Example 448
Structure
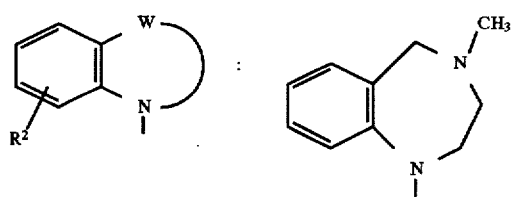

TABLE 2-continued
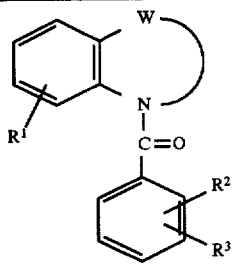
R²: H
R³: 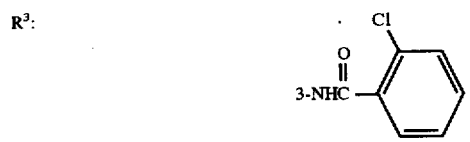
Crystalline form: Colorless amorphous
NMR analysis: 62)
Form: Free
Example 449
Structure
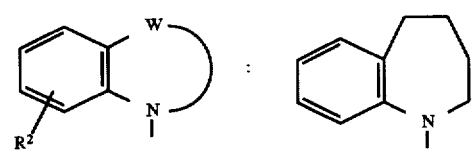
R²: 3-OCH₃
R³: 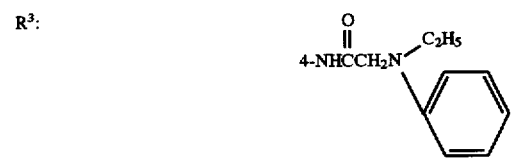
Crystalline form: Colorless amorphous
NMR analysis: 63)
Form: Free
Example 450
Structure
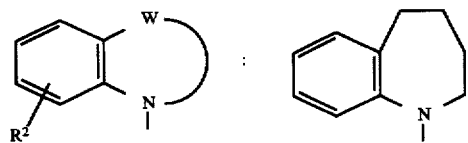
R²: H
R³: 
Crystalline form: White powder
Recrystallization solvent: Methanol/diethyl ether
Melting Point: 172.5–173.5° C.
Form: Free TABLE 2-continued

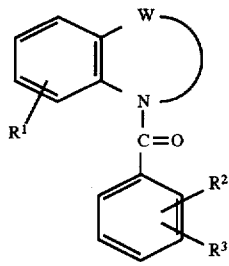

Example 451

Structure

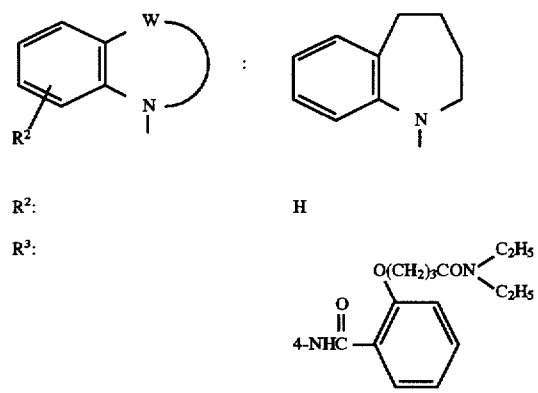

R²: H

R³:

4-NHC(=O)—[phenyl with 2-O(CH₂)₃CON(C₂H₅)₂]

Crystalline form: Colorless prisms
Recrystallization solvent: Methanol/diethyl ether
Melting Point: 122.5–123° C.
Form: Free

Example 452

Structure

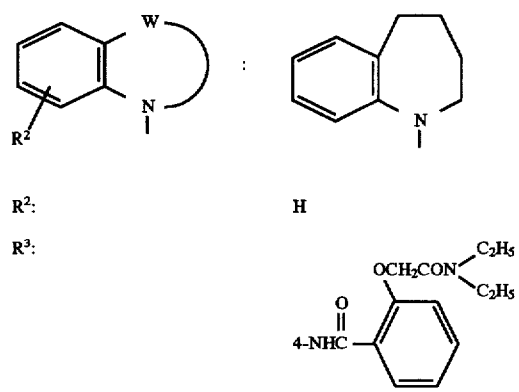

R²: H

R³:

4-NHC(=O)—[phenyl with 2-OCH₂CON(C₂H₅)₂]

Crystalline form: White powder
Recrystallization solvent: Methanol/diethyl ether
Melting Point: 198–199.5° C.
Form: Free

Example 453

Structure

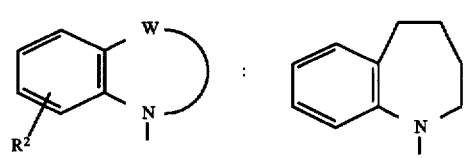

TABLE 2-continued
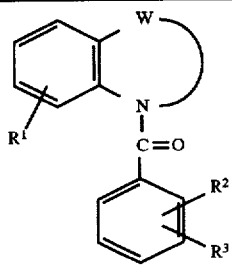
R²: H
R³:
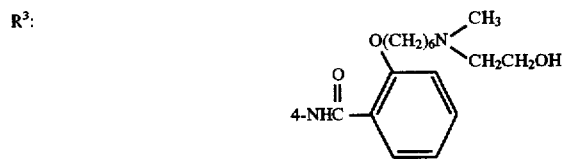
Crystalline form: White powder
Recrystallization solvent: Methanol/diethyl ether
Melting Point: 118–119.5° C.
Form: Hydrochloride
Example 454
Structure
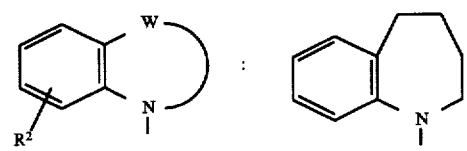
R²: H
R³:
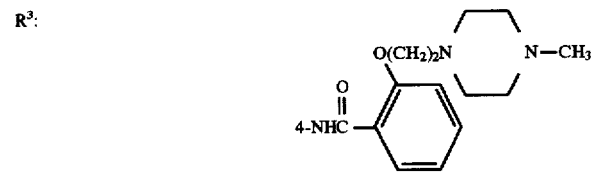
Crystalline form: White powder
Recrystallization solvent: Ethanol
Melting Point: 163–165° C.
Form: Hydrochloride
Example 455
Structure
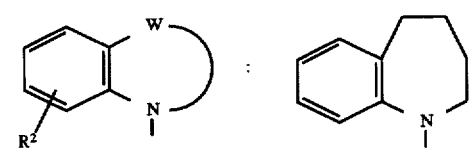
R²: H
R³:
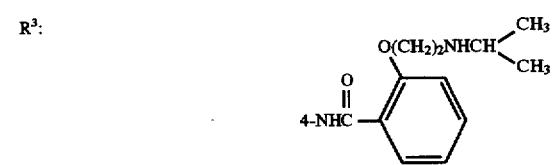

TABLE 2-continued

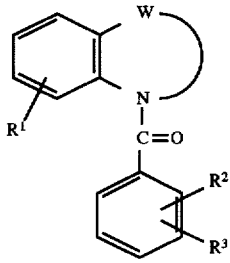

Crystalline form: White powder
Recrystallization solvent: Methanol/diethyl ether
Melting Point: 246–248° C.
Form: Hydrochloride Example 456

Structure

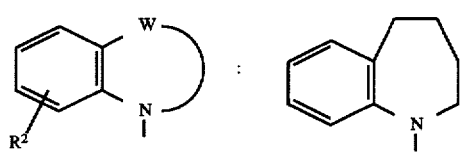

$R^2$: H $R^3$:

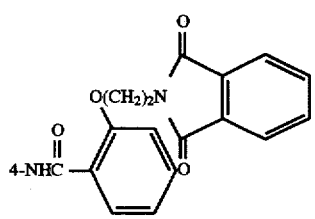

Crystalline form: White powder
Recrystallization solvent: Chloroform/ethanol
Melting Point: 204–205° C.
Form: Free Example 457

Structure

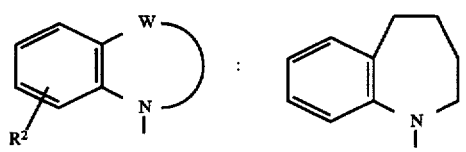

$R^2$: H $R^3$:

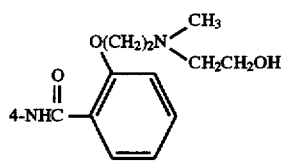

Crystalline form: Colorless prisms
Recrystallization solvent: Methanol/diethyl ether
Melting Point: 127–128° C.
Form: Hydrochloride TABLE 2-continued
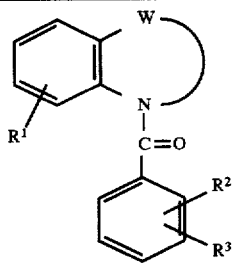
Example 458
Structure
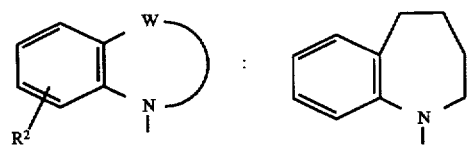
R²: H
R³:
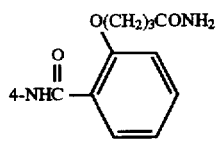
Crystalline form: White powder
Recrystallization solvent: Methanol/diethyl ether
Melting Point: 220–221° C.
Form: Free
Example 459
Structure
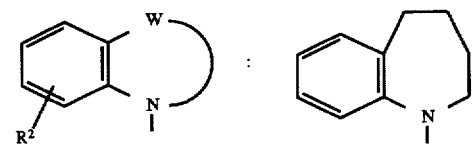
R²: H
R³:
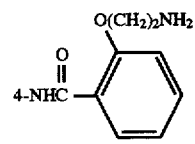
Crystalline form: Colorless needles
Recrystallization solvent: Ethanol
Melting Point: 190–192° C.
Form: Free
Example 460
Structure
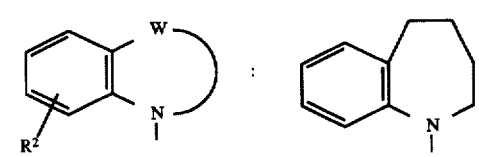
R²: H TABLE 2-continued

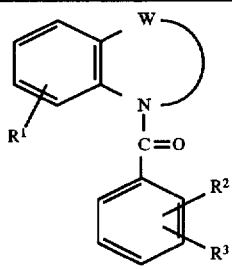

R³:

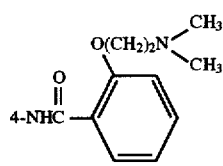

Crystalline form: White powder
Recrystallization solvent: Methanol/diethyl ether
Melting Point: 189–191° C.
Form: Hydrochloride Example 461

Structure

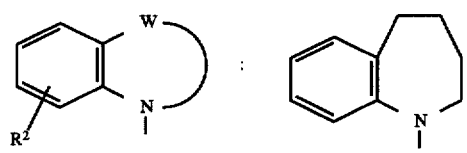

R²: H

R³:

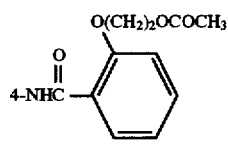

Crystalline form: Colorless needles
Recrystallization solvent: Ethanol
Melting Point: 173–174° C.
Form: Free Example 462

Structure

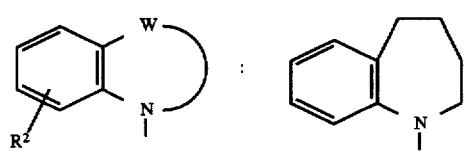

R²: H

R³:

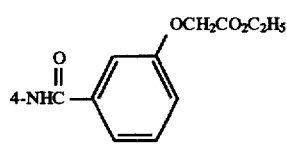

Crystalline form: White powder
Recrystallization solvent: Dichloromethane/ethanol
Melting Point: 129–130° C.
Form: Free TABLE 2-continued
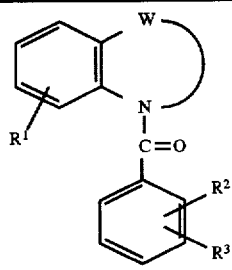
Example 463
Structure
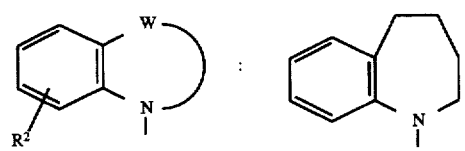
R²: H
R³:
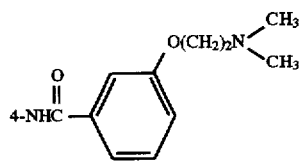
Crystalline form: White powder
Recrystallization solvent: Methanol/diethyl ether
Melting Point: 130–133° C.
Form: Hydrochloride
Example 464
Structure
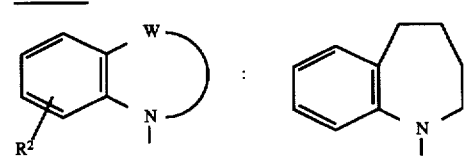
R²: H
R³:
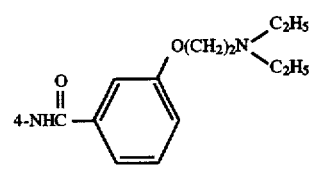
Crystalline form: Light yellow powder
Recrystallization solvent: Methanol/diethyl ether
Melting Point: 170.5–172° C.
Form: Hydrochloride
Example 465
Structure
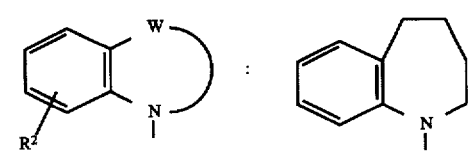

TABLE 2-continued
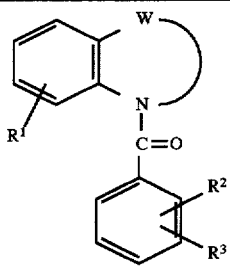
R²: H
R³: 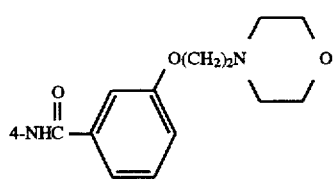
Crystalline form: White powder
Recrystallization solvent: Methanol/diethyl ether
Melting Point: 126–131° C.
Form: Hydrochloride
Example 466
Structure
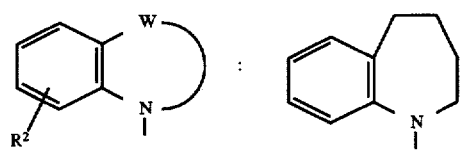
R²: H
R³: 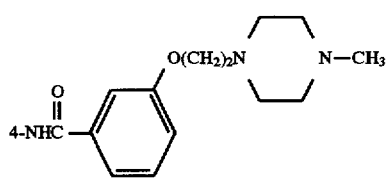
Crystalline form: White powder
Recrystallization solvent: Ethanol
Melting Point: 182–185° C.
Form: Dihydrochloride
Example 467
Structure
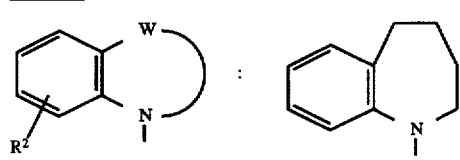
R²: H
R³: 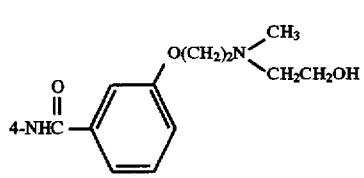

TABLE 2-continued

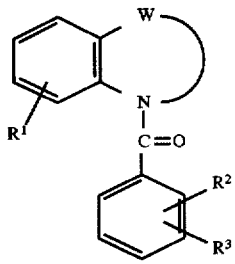

Crystalline form: White powder
Recrystallization solvent: Methanol/diethyl ether
Melting Point: 116–121° C.
Form: Hydrochloride Example 468

Structure

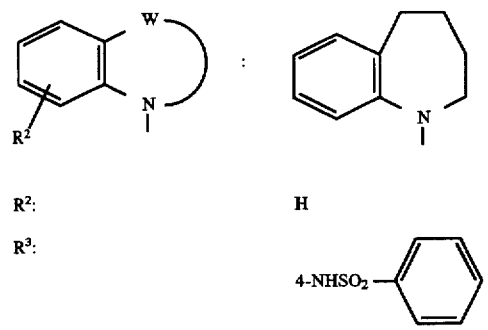

R²: H

R³: 4-NHSO₂—⟨phenyl⟩

Crystalline form: Colorless prisms
Recrystallization solvent: Methanol/diethyl ether
Melting Point: 178–182.5° C.
Form: Free Example 469

Structure

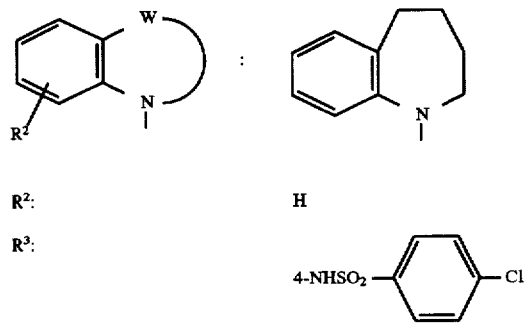

R²: H

R³: 4-NHSO₂—⟨phenyl⟩—Cl

Crystalline form: Colorless particles
Recrystallization solvent: Methanol/diethyl ether
Melting Point: 185–187° C.
Form: Free Example 470

Structure

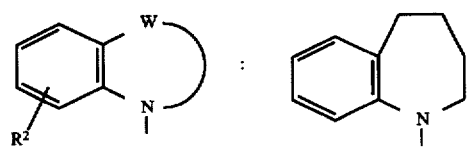

TABLE 2-continued

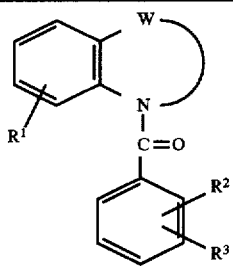

| R²: | H |
|---|---|
| R³: | 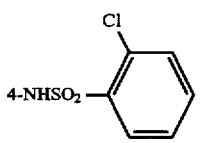 |

Crystalline form: White powder
Recrystallization solvent: Methanol/diethyl ether
Melting Point: 215–217° C.
Form: Free Example 471

Structure

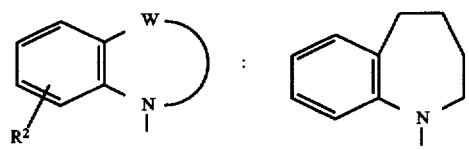

| R²: | H |
|---|---|
| R³: | 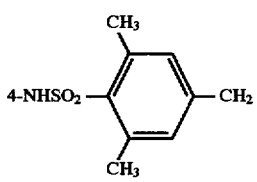 |

Crystalline form: White powder
Recrystallization solvent: Methanol/diethyl ether
Melting Point: 176–178° C.
Form: Free Example 472

Structure

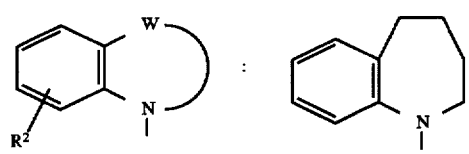

| R²: | H |
|---|---|
| R³: | 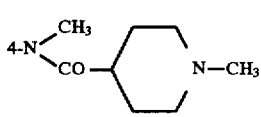 |

Crystalline form: Light yellow powder
Recrystallization solvent: Methanol/n-hexane
Melting Point: 194.5–197° C.
Form: Free TABLE 2-continued
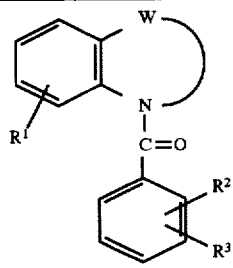
Example 473
Structure
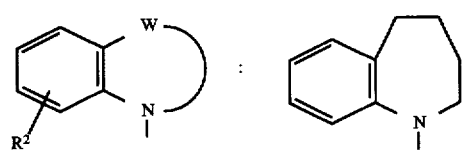
R²: H
R³:
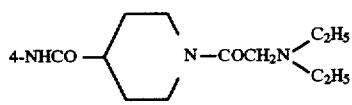
Crystalline form: White powder
Recrystallization solvent: Methanol/diethyl ether
Melting Point: 161.5–165.5° C.
Form: Hydrochloride
Example 474
Structure
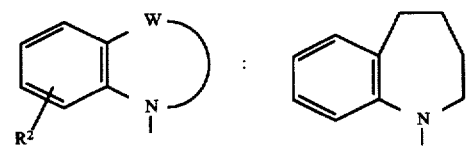
R²: H
R³:
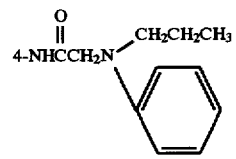
Crystalline form: White powder
Recrystallization solvent: Ethyl acetate
Melting Point: 152–153° C.
Form: Free
Example 475
Structure
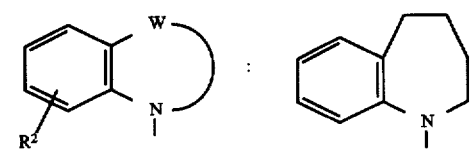
R²: H TABLE 2-continued
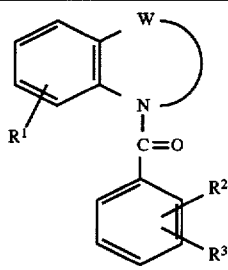
R³:
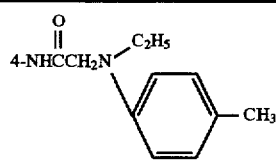
Crystalline form: Colorless needles
Recrystallization solvent: n-Hexane/ethyl acetate
Melting Point: 147–148° C.
Form: Free
Example 476
Structure
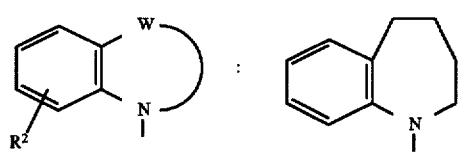
R²: H
R³:
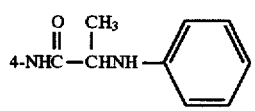
Crystalline form: Light yellow powder
Recrystallization solvent: Ethyl acetate
Melting Point: 215–217° C.
Form: Free
Example 477
Structure
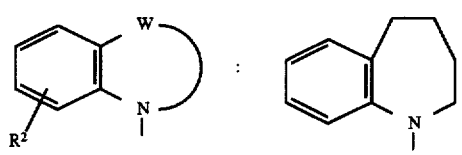
R²: H
R³:
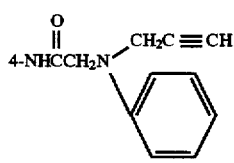
Crystalline form: Colorless amorphous
NMR analysis: 64)
Form: Free TABLE 2-continued
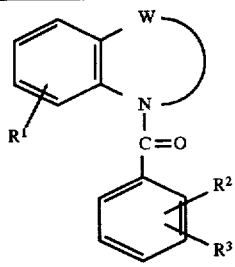
Example 478
Structure
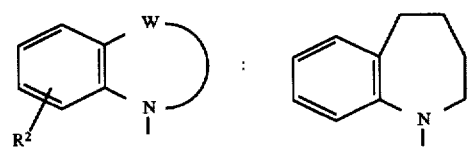
R²: H
R³: 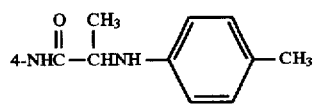
Crystalline form: White powder
Recrystallization solvent: Ethyl acetate
Melting Point: 180–181° C.
Form: Free
Example 479
Structure
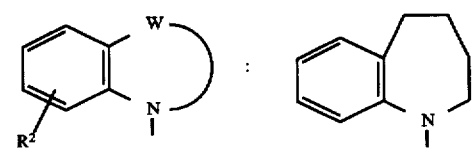
R²: H
R³: 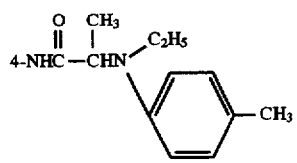
Crystalline form: Colorless amorphous
NMR analysis: 65)
Form: Free
Example 480
Structure
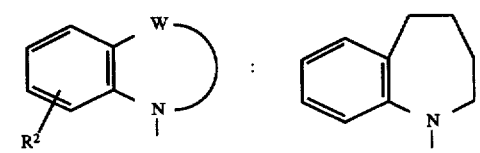
R²: H TABLE 2-continued
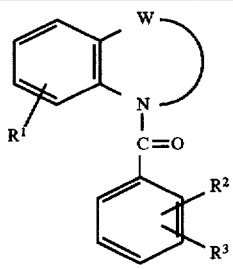
R³:
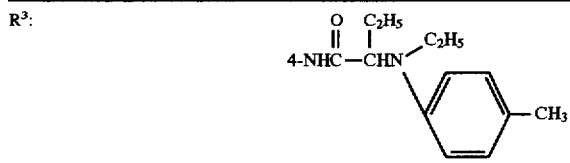
Crystalline form: Colorless amorphous
NMR analysis: 66)
Form: Free
Example 481
Structure
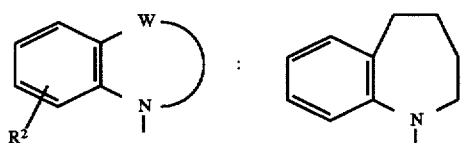 :  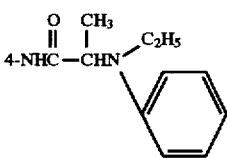
R²: H
R³:
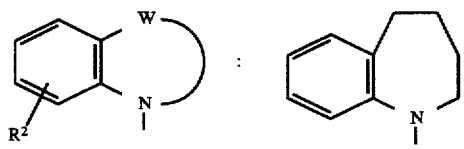
Crystalline form: Colorless amorphous
NMR analysis: 67)
Form: Free
Example 482
Structure
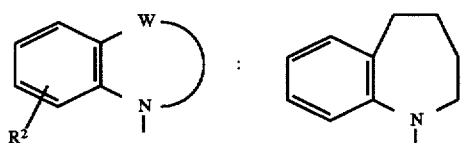 :  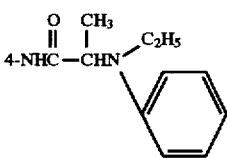
R²: H
R³:
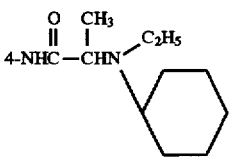
Crystalline form: Colorless scales
Recrystallization solvent: n-Hexane/ethyl acetate
Melting Point: 165–167° C.
Form: Free TABLE 2-continued
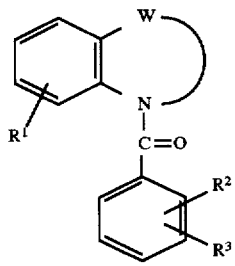
Example 483
Structure
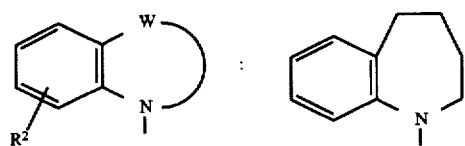
R²: H
R³: 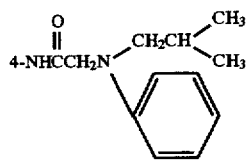
Crystalline form: Colorless amorphous
NMR analysis: 68)
Form: Free
Example 484
Structure
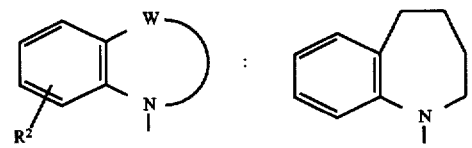
R²: H
R³: 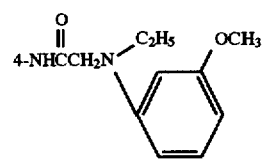
Crystalline form: Colorless amorphous
NMR analsysi: 69)
Form: Free
Example 485
Structure
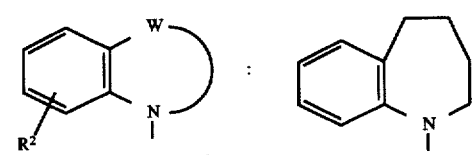
R²: H TABLE 2-continued
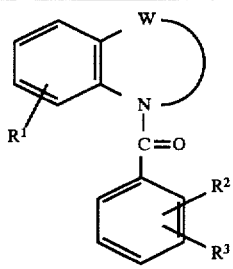
R³:
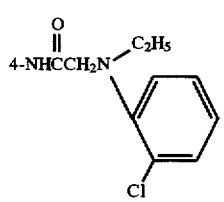
Crystalline form: Colorless amorphous
NMR analysis: 70)
Form: Free
Example 486
Structure
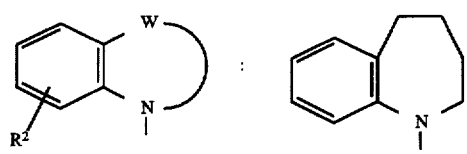
R²: H
R³:
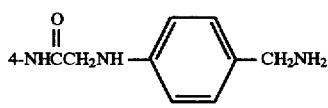
Crystalline form: Colorless amorphous
NMR analysis: 71)
Form: Free
Example 487
Structure
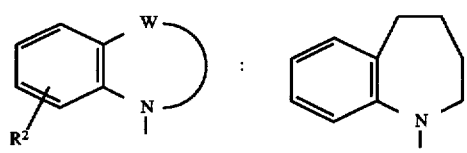
R²: H
R³:
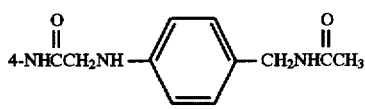
Crystalline form: Colorless amorphous
NMR analysis: 72)
Form: Free TABLE 2-continued
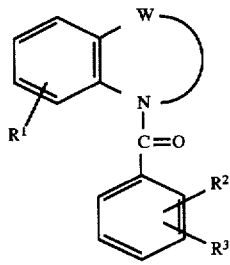
Example 488
Structure
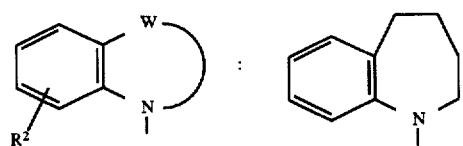
R²: H
R³:
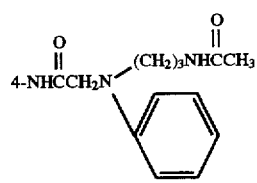
Crystalline form: Colorless amorphous
NMR analysis: 73)
Form: Free
Example 489
Structure
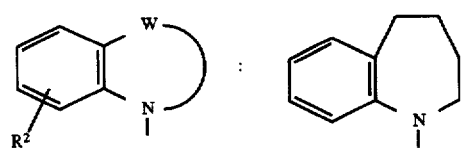
R²: H
R³:
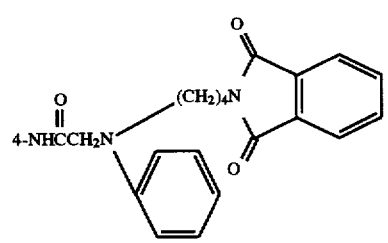
Crystalline form: Light yellow amorphous
NMR analysis: 74)
Form: Free TABLE 2-continued
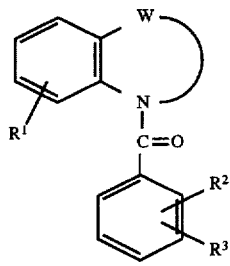
Example 490
Structure
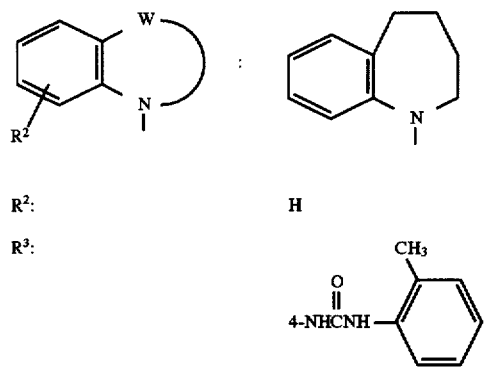
R²: H
R³:
(structure: 4-NHCNH— phenyl with o-CH₃, C=O)
Crystalline form: White powder
Recrystallization solvent: Ethyl acetate
Melting Point: 182–182.5° C.
Form: Free
Example 491
Structure
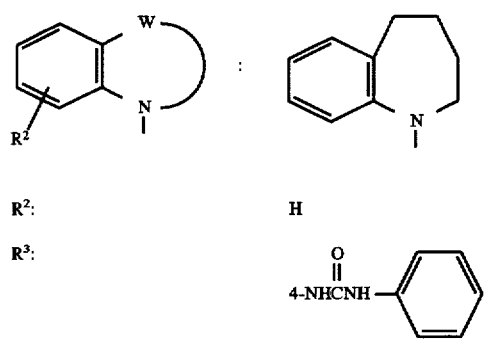
R²: H
R³:
(structure: 4-NHCNH—phenyl, C=O)
Crystalline form: White powder
Recrystallization solvent: Ethyl acetate
Melting Point: 244–245° C.
Form: Free
Example 492
Structure
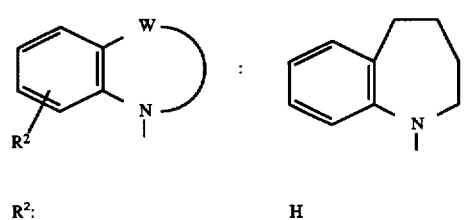
R²: H TABLE 2-continued
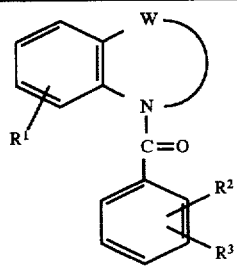
| R³: | 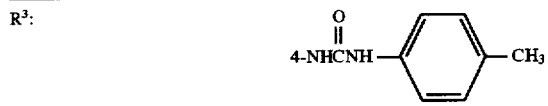 |
|---|---|
Crystalline form: White powder
Recrystallization solvent: Ethyl acetate
Melting Point: 220–221.5° C.
Form: Free
Example 493
Structure
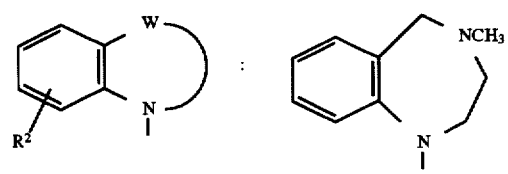
| R²: | H |
|---|---|
| R³: | 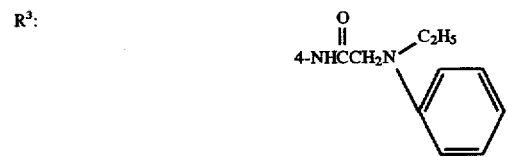 |
Crystalline form: Light yellow amorphous
NMR analysis: 75)
Form: Free
Example 494
Structure
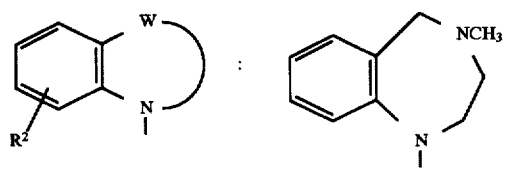
| R²: | 3-OCH₃ |
|---|---|
| R³: | 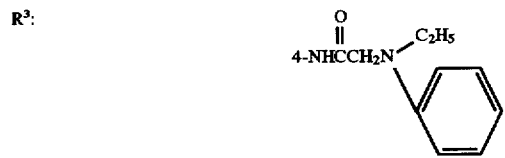 |
Crystalline form: Light yellow amorphous
NMR analysis: 76)
Form: Free TABLE 2-continued
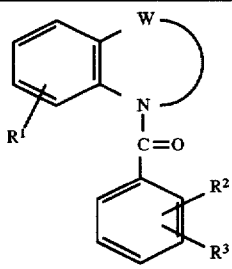
Example 495
Structure
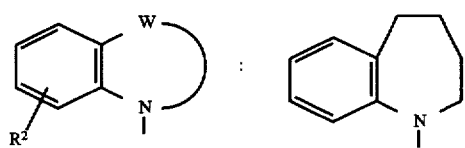
R²: H
R³:
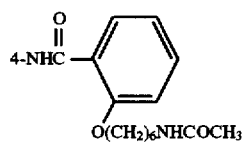
Crystalline form: Colorless needles
Recrystallization solvent: Methanol/diethyl ether
Melting Point: 171–172° C.
Form: Free
Example 496
Structure
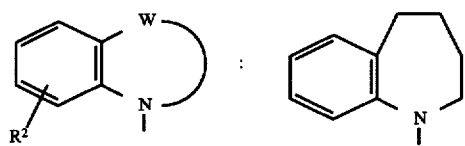
R²: H
R³:
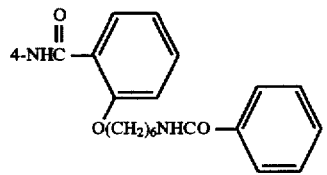
Crystalline form: White powder
Recrystallization solvent: Ethanol
Melting Point: 178–178.5° C.
Form: Free
Example 497
Structure
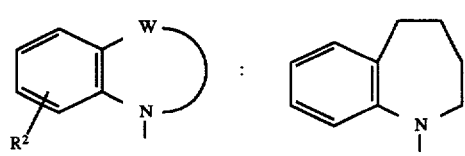

TABLE 2-continued
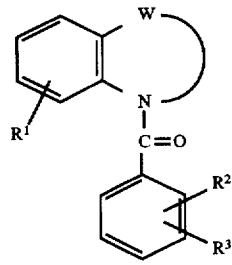
| R²: | H |
| --- | --- |
| R³: | 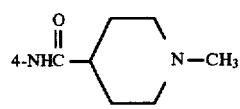 |
Example 498
Structure
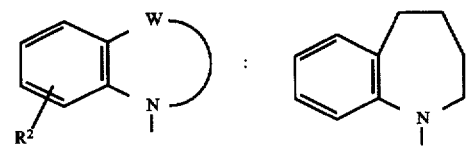
| R²: | H |
| --- | --- |
| R³: | 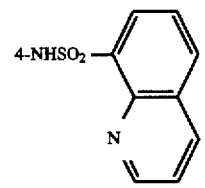 |
Example 499
Structure
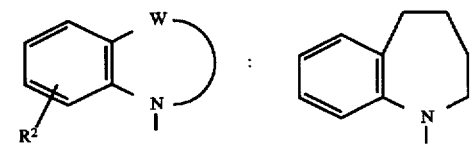
| R²: | H |
| --- | --- |
| R³: | 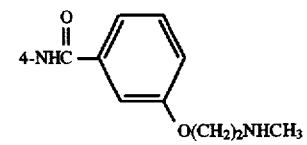 |

TABLE 2-continued
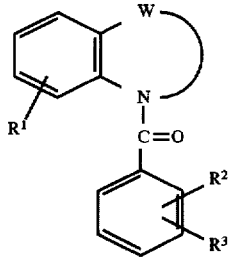
Example 500
Structure
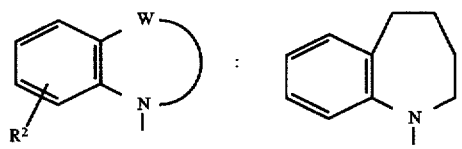
R²: H
R³: 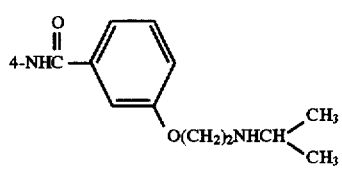
Example 501
Structure
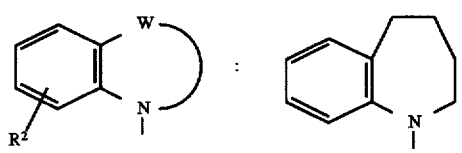
R²: H
R³: 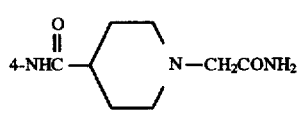
Example 502
Structure
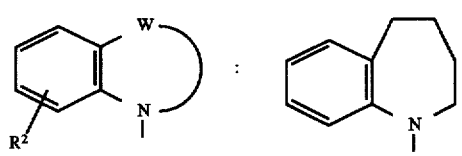
R²: H
R³: 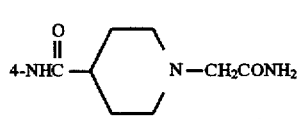

TABLE 2-continued
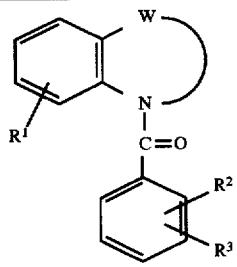
Example 502
Structure
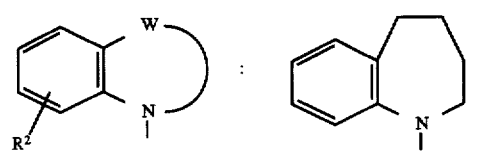
R²: H
R³:
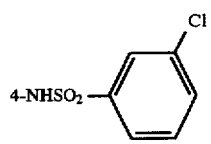
4-NHSO₂―[3-Cl phenyl]
Example 503
Structure
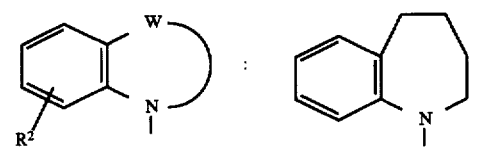
R²: H
R³:
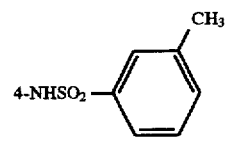
4-NHSO₂―[3-CH₃ phenyl]
Example 504
Structure
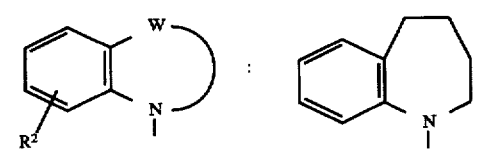
R²: H
R³:
4-NHCCH₂COOH (C=O)
Crystalline form: Light yellow scales
Recrystallization solvent: Ethanol/water
Melting Point: 129–131° C.

TABLE 2-continued
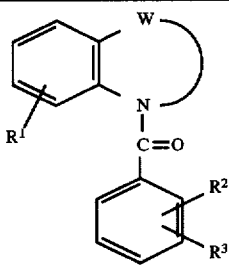
Form: Free
Example 505
Structure
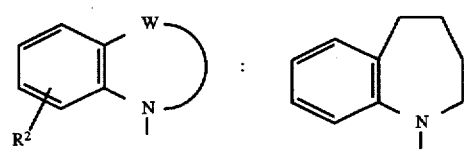
R²: H
R³:
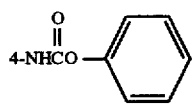
4-NHCO—Ph (phenyl amide)
Crystalline form: White powder
Recrystallization solvent: Ethyl acetate
Melting Point: 199–201° C.
Form: Free
Example 506
Structure
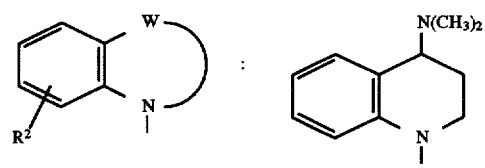
R²: H
R³:
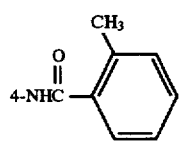
4-NHC(=O)—(2-methylphenyl)
Crystalline form: Colorless amorphous
NMR analysis: 77)
Form: Free
Example 507
Structure
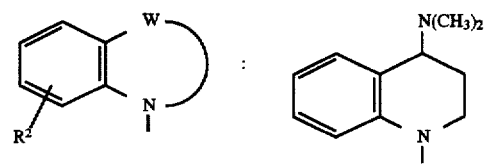
R²: H TABLE 2-continued

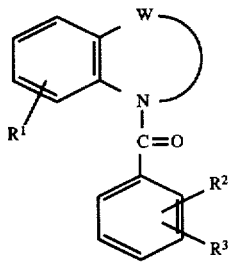

Crystalline form: White powder
Recrystallization solvent: n-Hexane/ethyl acetate
Melting Point: 187.5–189° C.
Form: Free Example 508

Structure

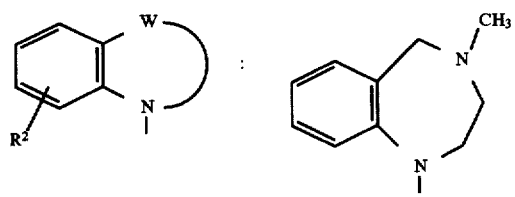

R²: 2-Cl

R³:

Crystalline form: White powder
Recrystallization solvent: Methanol/diethyl ether
Melting Point: 161–164° C.
Form: Free Example 509

Structure

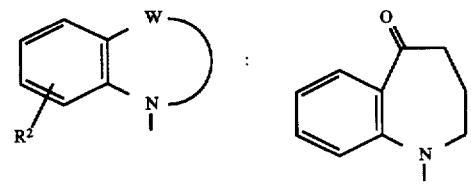

R²: H

R³:

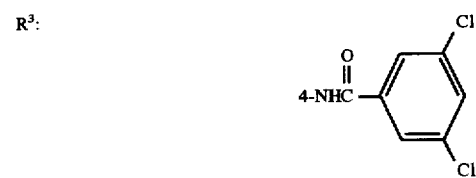

Crystalline form: Colorless prisms
Recrystallization solvent: Ethanol

TABLE 2-continued
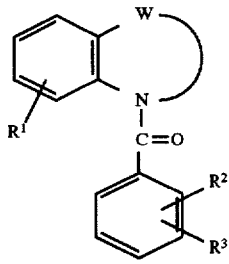
Melting Point: 242–243° C.
Form: Free
Example 510
Structure
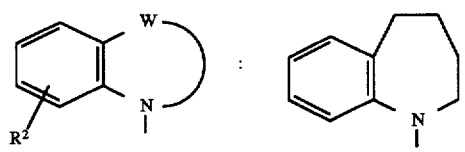
R²:  3-OCH₃
R³:  4-NHCOCH₂Cl
Crystalline form: White powder
Recrystallization solvent: Dichloroethane/diethyl ether
Melting Point: 186–188° C.
Form: Free
Example 511
Structure
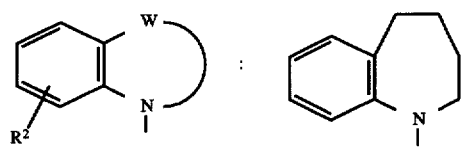
R²:  H
R³:
4-NHC(=O)—C₆H₄—O(CH₂)₂Cl
Crystalline form: Colorless amorphous
NMR analysis: 78)
Form: Free
Example 512
Structure
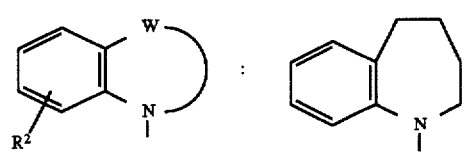
R²:  H TABLE 2-continued

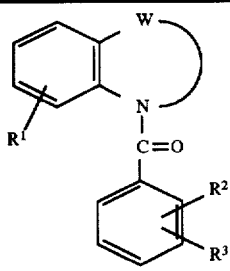

| R³: | 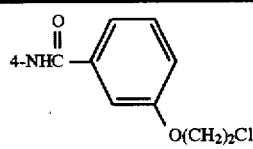 |
|---|---|

Crystalline form: Colorless amorphous
NMR analysis: 79)
Form: Free

49) ¹H-NMR(CDCl₃) δ; 1.11 (3H, t, J=7.1 Hz), 1.90–2.25 (2H, m), 2.29 (3H, s), 2.55 (2H, q, J=7.1 Hz), 3.62–3.90 (2H, m), 4.00–4.20 (1H, m), 6.63 (1H, d, J=7.9 Hz), 6.85–7.10 (2H, m), 7.25–7.80 (9H, m), 8.25 (1H, brs)

50) ¹H-NMR(CDCl₃) δ; 1.10 (3H, t, J=7.1 Hz), 1.90–2.20 (2H, m), 2.28 (3H, s), 3.60–3.90 (2H, m), 3.95–4.20 (1H, m), 6.62 (1H, d, J=7.9 Hz), 6.80–7.10 (2H, m), 7.20 (2H, d, J=8.6 Hz), 7.31–7.55 (4H, m), 7.80 (2H, d, J=1.9 Hz), 9.05 (1H, brs)

51) ¹H-NMR(CDCl₃) δ; 1.80–2.05 (1H, m), 2.15–2.50 (1H, m), 2.34 (6H, s), 2.51 (3H, s), 3.48–3.62 (1H, m), 3.72 (3H, s), 3.70–3.85 (1H, m), 4.00–4.22 (1H, m), 6.64 (1H, d, J=7.8 Hz), 6.84–7.58 (9H, m), 8.16 (1H, brs), 8.40 (1H, d, J=8.7 Hz)

52) ¹H-NMR(CDCl₃) δ; 1.16 (3H, t, J=7.1 Hz), 2.40–2.70 (2H, m), 2.90–3.30 (3H, m), 3.80–4.20 (2H, m), 4.80–5.00 (1H, m), 6.60–6.80 (1H, m), 7.00–7.70 (10H, m), 8.24 (1H, s)

53) ¹H-NMR(DMSO-d₆) δ; 1.0–2.5 (10H, m), 2.34 (3H, s), 3.30–3.80 (4H, m), 4.50–5.30 (3H, m), 6.70–7.00 (1H, m), 7.10–7.80 (11H, m), 10.43 (1H, s), 10.5–12.0 (1H, br)

54) ¹H-NMR(CDCl₃) δ; 1.10–2.10 (10H, m), 2.40–2.70 (1H, m), 2.80–3.20 (3H, m), 3.92 (2H, s), 4.90–5.20 (1H, m), 6.50–6.70 (1H, m), 6.80–7.60 (8H, m), 7.75 (2H, s), 8.73 (1H, s)

55) ¹H-NMR(CDCl₃) δ; 1.10–2.20 (10H, m), 2.40–2.70 (1H, m), 2.90–3.30 (3H, m), 3.93 (2H, s), 4.90–5.20 (1H, m), 6.62 (1H, d, J=7.6 Hz), 6.90–7.70 (10H, m), 8.29 (1H, s)

56) ¹H-NMR(CDCl₃) δ; 1.50–2.10 (2H, m), 2.38 (6H, s), 2.30–2.70 (1H, m), 2.70–3.00 (2H, m), 3.45 (1H, d, J=13 Hz), 3.81 (1H, d, J=14 Hz), 4.70–5.00 (1H, m), 7.0–7.50 (12H, m), 8.23 (1H, s)

57) ¹H-NMR(CDCl₃) δ; 1.50–2.10 (2H, m), 2.42 (3H, s), 2.40–2.70 (1H, m), 2.80–3.00 (2H, m), 3.52 (1H, d, J=13 Hz), 3.85 (1H, d, J=13 Hz), 4.70–5.00 (1H, m), 7.00–7.70 (12H, m), 8.54 (1H, s)

58) ¹H-NMR(CDCl₃) δ; 2.43 (3H, s), 2.47 (3H, s), 3.00–3.30 (3H, m), 3.76 (1H, d, J=14 Hz), 4.06 (1H, d, J=14 Hz), 4.90–5.20 (1H, m), 6.50–6.80 (3H, m), 6.90–7.50 (6H, m), 7.70–8.00 (2H, m), 8.48 (1H, d, J=8 Hz), 10.58 (1H, s)

59) ¹H-NMR(CDCl₃) δ; 2.41 (3H, s), 2.44 (3H, s), 2.90–3.20 (3H, m), 3.74 (1H, d, J=13 Hz), 4.07 (1H, d, J=14 Hz), 4.80–5.00 (1H, m), 6.67 (1H, d, J=7 Hz), 6.76 (1H, d, J=7 Hz), 7.00–7.50 (8H, m), 7.55 (1H, s), 7.70–7.90 (2H, m)

60) ¹H-NMR(CDCl₃) δ; 2.41 (3H, s), 2.80–3.20 (3H, m), 3.73 (1H, d, J=13 Hz), 4.03 (1H, d, J=14 Hz), 6.66 (2H, d, J=7.6 Hz), 6.90–8.00 (10H, m), 8.57 (1H, s)

61) ¹H-NMR(CDCl₃) δ; 2.40 (3H, s), 2.90–3.20 (3H, m), 3.73 (1H, d, J=13 Hz), 4.07 (1H, d, J=13 Hz), 4.70–5.00 (1H, m), 6.60–6.80 (2H, m), 6.90–8.00 (10H, m), 8.54 (1H, s)

62) ¹H-NMR(CDCl₃) δ; 2.41 (3H, s), 2.90–3.20 (3H, m), 3.75 (1H, d, J=14 Hz), 4.08 (1H, d, J=14 Hz), 4.80–5.00 (1H, m), 6.67 (1H, d, J=7.6 Hz), 6.82 (1H, d, J=7.6 Hz), 6.90–7.90 (10H, m), 8.08 (1H, s)

63) ¹H-NMR(CDCl₃) δ; 1.23 (3H, t, J=7 Hz), 1.40–1.70 (1H, m), 1.90–2.20 (3H, m), 2.70–3.30 (3H, m), 3.40–3.60 (5H, m), 3.91 (2H, s), 5.00–5.20 (1H, m), 6.60–7.40 (11H, m), 8.12 (1H, d, J=8 Hz), 8.99 (1H, s)

64) ¹H-NMR(CDCl₃) δ; 1.35–1.70 (1H, m), 1.80–2.20 (3H, m), 2.25–2.35 (1H, m), 2.65–3.20 (3H, m), 4.01 (2H, s), 4.05–4.17 (2H, m), 4.90–5.10 (1H, m), 6.61 (1H, d, J=7.5 Hz), 6.75–7.50 (12H, m), 8.44 (1H, brs)

65) ¹H-NMR(CDCl₃) δ; 1.13 (3H, t, J=7.0 Hz), 1.30–1.65 (4H, m), 1.80–2.20 (3H, m), 2.28 (3H, s), 2.65–3.40 (5H, m), 4.90–5.10 (1H, m), 6.63 (1H, d, J=7.8 Hz), 6.75–7.00 (3H, m), 7.00–7.45 (8H, m), 8.85 (1H, brs)

66) ¹H-NMR(CDCl₃) δ; 0.88 (3H, t, J=7.4 Hz), 1.16 (3H, t, J=7.0 Hz), 1.35–2.20 (6H, m), 2.27 (3H, s), 2.60–3.20 (3H, m), 3.20–3.45 (2H, m), 3.85–4.10 (1H, m), 4.90–5.10 (1H, m), 6.63 (1H, d, J=7.4 Hz), 6.77 (2H, d, J=8.5 Hz), 6.92 (1H, t, J=8.0 Hz), 7.00–7.45 (8H, m), 8.85 (1H, brs)

67) ¹H-NMR(CDCl₃) δ; 1.17 (3H, t, J=7.0 Hz), 1.35–1.65 (4H, m), 2.60–3.45 (5H, m), 4.20 (2H, q, J=7.0 Hz), 4.90–5.10 (1H, m), 6.63 (1H, d, J=7.6 Hz), 6.80–7.45 (12H, m), 8.66 (1H, brs)

68) ¹H-NMR(CDCl₃) δ; 0.96 (6H, d, J=6.6 Hz), 1.35–1.65 (1H, m), 1.80–2.25 (4H, m), 2.65–3.15 (3H, m), 3.19 (2H, d, J=7.3 Hz), 3.99 (2H, s), 4.90–5.10 (1H, m), 6.60 (1H, d, J=7.8 Hz), 6.75–7.05 (4H, m), 7.05–7.40 (8H, m), 8.15 (1H, brs)

69) ¹H-NMR(CDCl₃) δ; 1.19 (3H, t, J=7.0 Hz), 1.35–1.65 (1H, m), 1.80–2.25 (3H, m), 2.70–3.20 (3H, m), 3.44 (2H, q, J=7.0 Hz), 3.77 (3H, s), 3.87 (2H, s), 4.90–5.10 (1H, m), 6.25–6.50 (3H, m), 6.67 (1H, d, J=7.5 Hz), 6.85–7.45 (8H, m), 8.29 (1H, brs)

70) ¹H-NMR(CDCl₃) δ; 1.05 (3H, t, J=7.1 Hz), 1.35–1.65 (1H, m), 1.85–2.25 (3H, m), 2.65–3.30 (5H, m), 3.74 (2H, s), 4.95–5.15 (1H, m), 6.63 (1H, d, J=7.5 Hz), 6.80–7.55 (11H, m), 9.51 (1H, brs)

71) ¹H-NMR(CDCl₃) δ; 1.30–1.65 (1H, m), 1.80–2.30 (3H, m), 2.65–3.15 (3H, m), 3.75 (2H, s), 3.74 (2H, s), 4.95–5.10 (1H, m), 6.45–6.70 (3H, m), 6.88 (1H, t, J=6.8 Hz), 7.00–7.45 (8H, m), 8.74 (1H, brs)

72) ¹H-NMR(CDCl₃) δ; 1.30–1.70 (1H, m), 1.75–2.25 (6H, m), 2.65–3.15 (3H, m), 3.78 (2H, d, J=5.4 Hz), 4.28 (2H, d, J=5.5 Hz), 4.53 (1H, brs), 4.90–5.10 (1H, m), 5.89 (1H, brs), 6.50–6.70 (3H, m), 6.89 (1H, t, J=7.5 Hz), 7.00–7.40 (8H, m), 8.61 (1H, brs)

73) ¹H-NMR(CDCl₃) δ; 1.35–1.65 (1H, m), 1.70–2.20 (8H, m), 2.65–3.20 (3H, m), 3.25–3.55 (4H, m), 3.88 (2H, s), 4.90–5.10 (1H, m), 5.79 (1H, brs), 6.55–7.40 (13H, m), 8.37 (1H, brs)

74) ¹H-NMR(CDCl₃) δ; 1.35–2.00 (8H, m), 2.65–3.20 (3H, m), 3.30–3.35 (2H, m), 3.60–3.85 (2H, m), 3.90 (2H, s), 4.95–5.15 (1H, m), 6.55–7.00 (5H, m), 7.00–7.40 (8H, m), 7.65–7.90 (4H, m), 8.22 (1H, brs)

75) ¹H-NMR(CDCl₃) δ; 1.16 (3H, t, J=7.0 Hz), 2.39 (3H, s), 2.80–3.20 (3H, m), 3.44 (2H, q, J=7.0 Hz), 3.65–4.20 (4H, m), 4.80–5.05 (1H, m), 6.50–7.45 (13H, m), 8.50 (1H, brs)

76) ¹H-NMR(CDCl₃) δ; 1.23 (3H, t, J=7.0 Hz), 2.41 (3H, s), 2.75–3.20 (3H, m), 3.40–3.60 (5H, m), 3.65–3.90 (1H, m), 3.92 (2H, s), 3.90–4.20 (1H, m), 4.85–5.10 (1H, m), 6.65–7.45 (11H, m), 8.13 (1H, d, J=8.4 Hz), 9.01 (1H, brs)

77) ¹H-NMR(CDCl₃) δ; 1.80–1.95 (1H, m), 2.20–2.70 (10H, m), 3.50–3.60 (1H, m), 3.63–3.80 (1H, m), 4.00–4.15 (1H, m), 6.60 (1H, d, J=7.6 Hz), 6.92 (1H, t, J=7.6 Hz), 7.02 (1H, t, J=6.3 Hz), 7.20–7.65 (9H, m), 7.87 (1H, brs)

78) ¹H-NMR(CDCl₃) δ; 1.40–1.62 (1H, m), 1.84–2.22 (3H, m), 2.65–3.19 (3H, m), 3.97 (2H, t, J=4.9 Hz), 4.43 (2H, t, J=4.9 Hz), 4.95–5.18 (1H, m), 6.60–6.77 (1H, m), 6.85–7.02 (2H, m), 7.02–7.30 (5H, m), 7.40–7.68 (3H, m), 8.20–8.32 (1H, m), 9.62–9.81 (1H, m)

79) ¹H-NMR(CDCl₃) δ; 1.38–1.65 (1H, m), 1.84–2.21 (3H, m), 2.64–3.15 (3H, m), 3.81 (2H, t, J=5.7 Hz), 4.25 (2H, t, J=5.7 Hz), 4.90–5.13 (1H, m), 6.58–6.71 (1H, m), 6.82–7.00 (1H, m), 7.00–7.52 (10H, m), 8.11 (1H, brs)

Example 513

To a solution of 1-(4-aminobenzoyl)-2,3,4,5-tetrahydro-1H-benzazepine (1.06 g) in dichloromethane (80 ml) is added o-methylphenyl isocyanate (0.66 g) under ice-cooling. The mixture is stirred at room temperature for 4 hours. After completion of the reaction, the solvent is concentrated under reduced pressure and the resulting residue is purified by silica gel column chromatography (eluent; n-hexane:ethyl acetate=1:1), and recrystallized from ethyl acetate to give 1-[4-(2-methylanilinocarbonylamino) benzoyl]-2,3,4,5-tetrahydro-1H-benzazepine (0.97 g) as white powder, m.p. 182°–182.5° C.

Using the suitable starting materials, the compounds of the above Examples 491–492 are obtained in the same manner as in Example 513.

Example 514

A mixture of 1-(4-aminobenzoyl)-2,3,4,5-tetrahydro-1H-benzazepine (0.50 g), phenylsulfonyl chloride (0.29 ml), triethylamine (0.32 ml) and dichloromethane (30 ml) is stirred at room temperature overnight. The reaction mixture is washed successively with water and saturated saline solution, and dried over magnesium sulfate. The solvent is distilled off and the resulting residue is purified by silica gel column chromatography (eluent; chloroform), and recrystallized from methanol/diethyl ether to give 1-(4-phenylsulfonylaminobenzoyl)-2,3,4,5-tetrahydro-1H-benzazepine (0.27 g) as colorless prisms, m.p. 178°–182.5° C.

Using the suitable starting materials, the compounds of the above Examples 469–471, 498, 502 and 503 are obtained in the same manner as in Example 514.

Example 515

To a solution of 1-[4-(4-piperidinylcarbonylamino) benzoyl]-2,3,4,5-tetrahydro-1H-benzazepine (0.70 g) in dimethylformamide (20 ml) is added 60% sodium hydride dispersion in mineral oil (82 mg) and the mixture is stirred at room temperature for 30 minutes. Thereto is added methyl iodide (0.14 ml) and the mixture is stirred at room temperature overnight. The solvent is distilled off and the resulting residue is extracted with chloroform, and washed successively with water and saturated saline solution, and dried over magnesium sulfate. The solvent is distilled off and the resulting residue is purified by silica gel column chromatography (eluent; chloroform:methanol=10:1), and recrystallized from methanol/n-hexane to give 1-{4-[N-(1-methyl-4-piperidinylcarbonyl)-N-methylamino]benzoyl}-2,3,4,5-tetrahydro-1H-benzazepine (0.03 g) as light yellow powder, m.p. 194.5°–197° C.

Using the suitable starting materials, the compounds of the above Examples 497 and 501 are obtained in the same manner as in Example 515.

Example 516

6-Fluoro-1-(4-aminobenzoyl)-1,2,3,4-tetrahydroquinoline (0.15 g) is dissolved in dichloromethane (10 ml) and thereto is added triethylamine (0.31 ml). To the mixture is added dropwise a solution of 3,5-dichlorobenzoyl chloride (0.14 g) in dichloromethane (2.0 ml) under ice-cooling, and the mixture is stirred for 30 minutes under ice-cooling, and further, at room temperature for 1 hour. To the mixture are added triethylamine (0.31 ml) and 3,5-dichlorobenzoyl chloride (0.14 ml). The mixture is stirred at room temperature for 4 hours. The reaction mixture is washed with water, and dried over magnesium sulfate. The solvent is distilled off and the resulting residue is purified by silica gel column chromatography (eluent; ethyl acetate:n-hexane=1:5→1:4), and recrystallized from ethyl acetate/n-hexane to give 6-fluoro-1-[4-(3,5-dichlorobenzoylamino) benzoyl]-1,2,3,4-tetrahydroquinoline (0.12 g) and 6-fluoro-1-{4-[bis-(3,5-dichlorobenzoyl)amino]benzoyl}-1,2,3,4-tetrahydroquinoline.

The former: White powder, m.p. 205.5°–206.5° C.
The latter: White powder, m.p. 210.5°–212° C.

Example 517

Using the suitable starting materials, the compounds of the above Examples 450 and 504 are obtained in the same manner as in Example 378.

Example 518

Using the suitable starting materials, the compounds of the above Examples 450–467, 495, 496, 499, 500, 511 and 512 are obtained in the same manner as in Example 380.

Example 519

Using the suitable starting materials, the compounds of the above Examples 449, 474–489, 493 and 494 are obtained in the same manner as in Example 394.

Example 520

Using the suitable starting materials, the compounds of the above Examples 453, 455, 457, 459, 460, 463–467, 495, 496 and 499 are obtained in the same manner as in Example 397.

Example 521

Using the suitable starting materials, the compound of the above Example 461 is obtained in the same manner as in Example 396.

Example 522

Using the suitable starting materials, the compound of the above Example 456 is obtained in the same manner as in Example 398.

Example 523

Using the suitable starting materials, the compound of the above Example 459 is obtained in the same manner as in Example 399.

Example 524

Using the suitable starting materials, the compounds of the above Examples 495 and 496 are obtained in the same manner as in Examples 400 and 401.

Example 525

Using the suitable starting materials, the compound of the above Example 458 is obtained in the same manner as in Example 402.

Using the suitable starting materials, the compounds of the following Table 3 are obtained in the same manner as in Examples 1 and 382.

TABLE 3

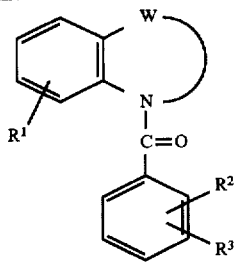

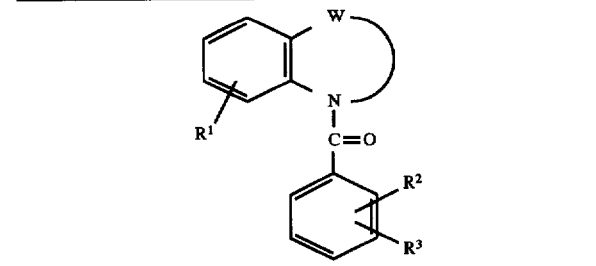

R$^2$: 2-Cl

TABLE 3-continued

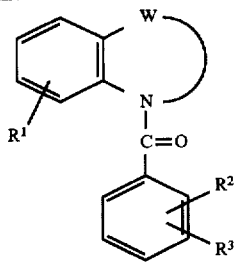

R$^3$:

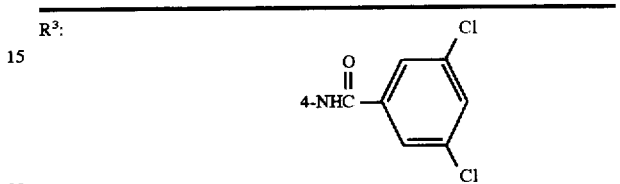

Crystalline form: White powder
Recrystallization solvent: Methanol/diethyl ether
Melting Point: 225–226° C.
Form: Free

Example 528

Structure

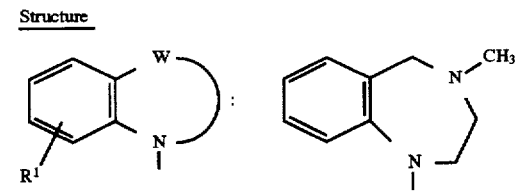

R$^2$: 2-Cl

R$^3$:

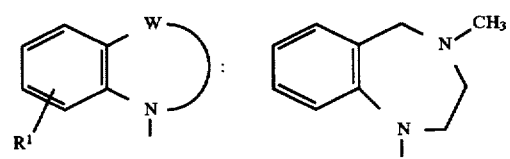

Crystalline form: White powder
Recrystallization solvent: Methanol/diethyl ether
Melting Point: 142.5–145° C.
Form: Free

Example 529

Structure

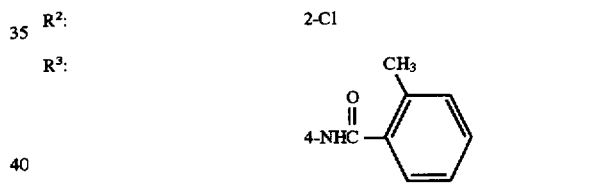

R$^2$: 2-Cl

R$^3$:

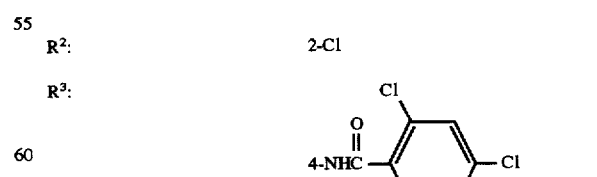

Crystalline form: White powder
Recrystallization solvent: Methanol/diethyl ether
Melting Point: 213–215° C.
Form: Free

TABLE 3-continued

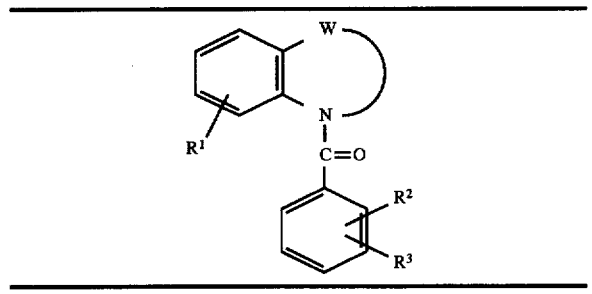

Example 530

Structure

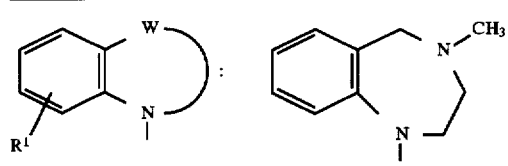

R²: 3-CH₃

R³:

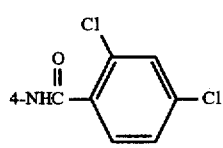

Crystalline form: White powder
Recrystallization solvent: Methanol/diethyl ether
Melting Point: 167–167.5° C.
Form: Free

Example 531

Structure

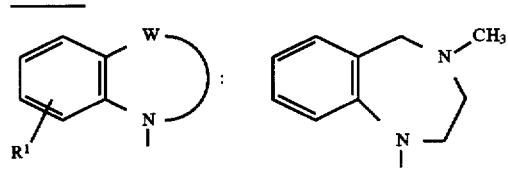

R²: 3-CH₃

R³:

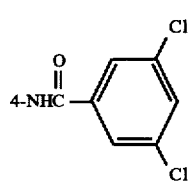

Crystalline form: Colorless scales
Recrystallization solvent: Methanol/diethyl ether
Melting Point: 217–221° C.
Form: Free

Example 532

Structure

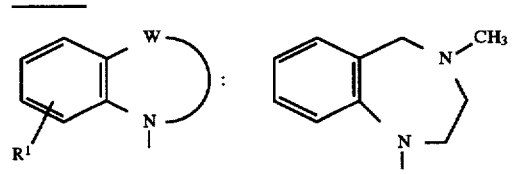

TABLE 3-continued

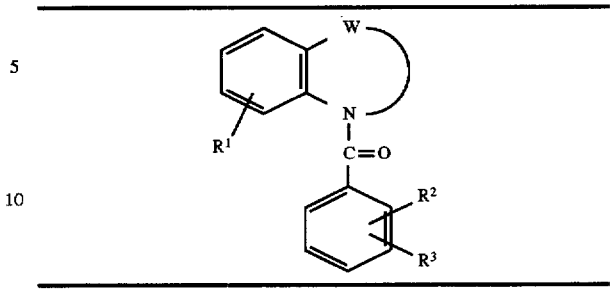

R²: 3-CH₃

R³:

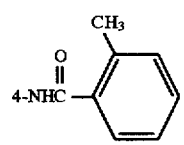

Crystalline form: White powder
Recrystallization solvent: Methanol/diethyl ether
Melting Point: 182–184° C.
Form: Free

Example 533

Structure

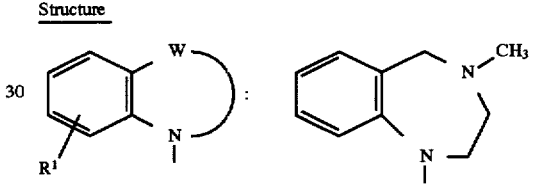

R²: 3-CH₃

R³:

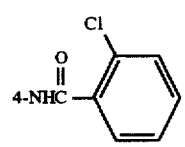

Crystalline form: White powder
Recrystallization solvent: Methanol/diethyl ether
Melting Point: 209–210° C.
Form: Free

Example 534

Structure

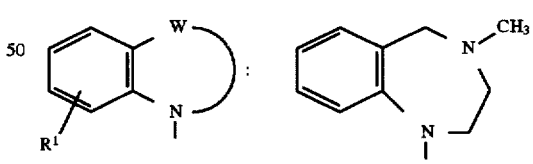

R²: 3-OCH₃

R³:

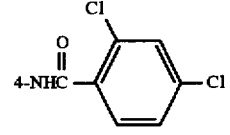

Crystalline form: White powder
Recrystallization solvent: Methanol/diethyl ether
Melting Point: 148–149° C.
Form: Free

TABLE 3-continued

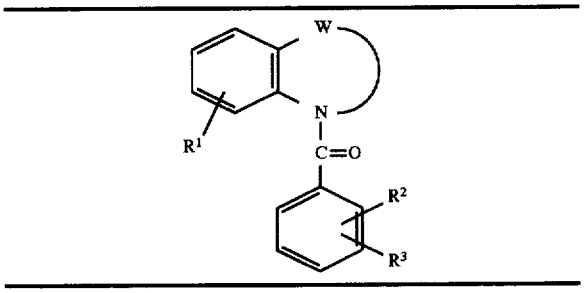

Example 535

Structure

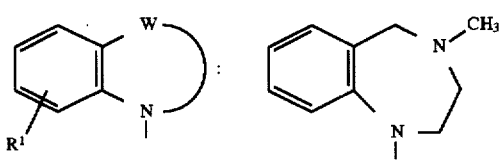

R²: H

R³:

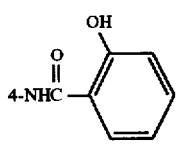

Crystalline form: White powder
Recrystallization solvent: Methanol/diethyl ether
Melting Point: 202–203° C.
Form: Free

Example 536

Structure

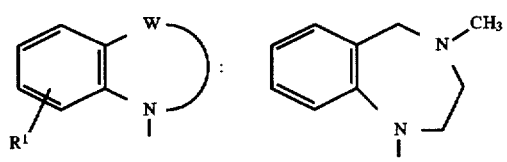

R²: 3-CH₃

R³:

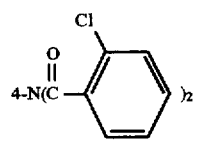

Crystalline form: White powder
Recrystallization solvent: Methanol/diethyl ether
Melting Point: 218–219° C.
Form: Free

Example 537

Structure

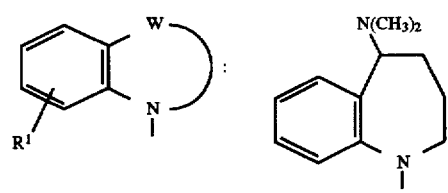

TABLE 3-continued

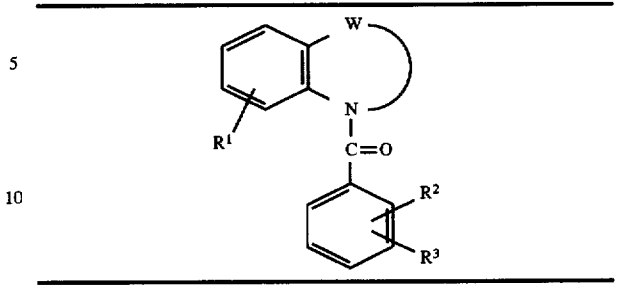

R²: 2-Cl

R³:

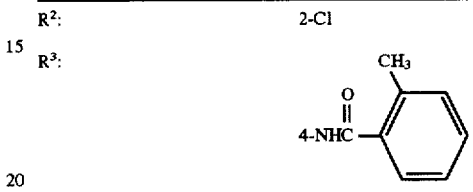

Crystalline form: White powder
Recrystallization solvent: Methanol/n-hexane
Melting Point: 159–160° C.
Form: Free

Example 538

Structure

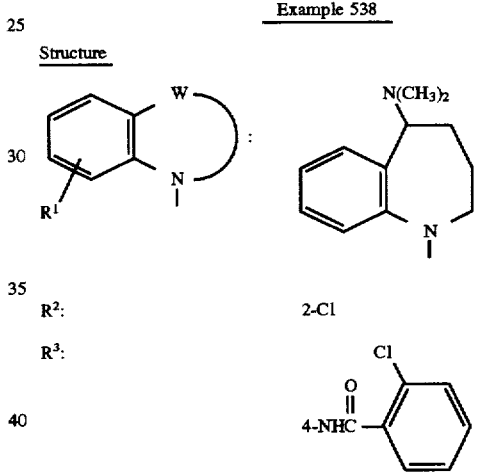

R²: 2-Cl

R³:

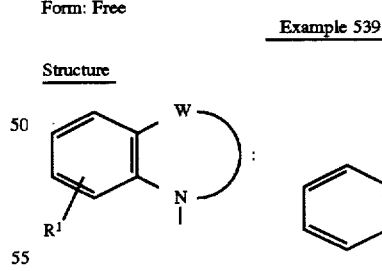

Crystalline form: White powder
Recrystallization solvent: Methanol/n-hexane
Melting Point: 201–202° C.
Form: Free

Example 539

Structure

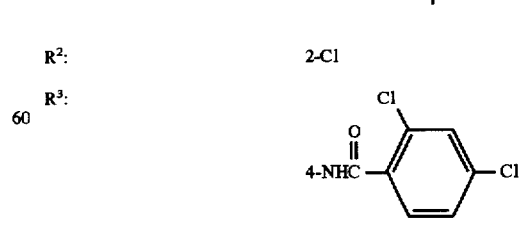

R²: 2-Cl

R³:

Crystalline form: White powder
Recrystallization solvent: Methanol/n-hexane

TABLE 3-continued

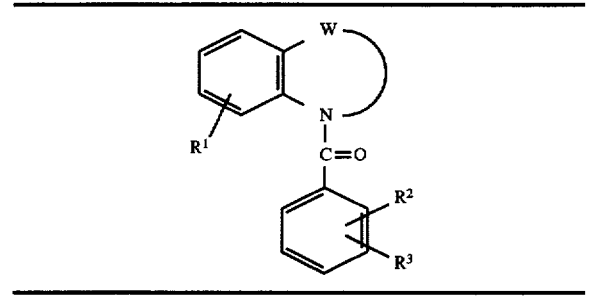

Melting Point: 205–207° C.
Form: Free

Example 540

Structure

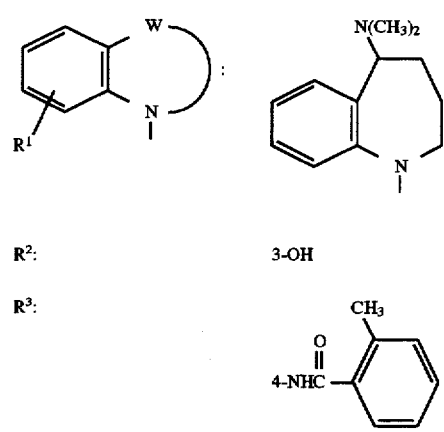

R²:  3-OH

R³:

CH₃
‖
4-NHC—⟨phenyl⟩

O

Crystalline form: White powder
Recrystallization solvent: Methanol/diethyl ether
Melting Point: 201.5–202.5° C.
Form: Free

Example 541

Structure

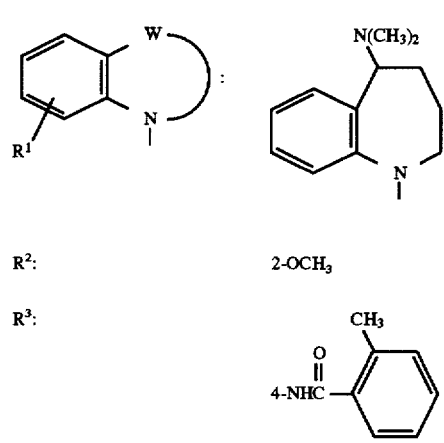

R²:  2-OCH₃

R³:

CH₃
‖
4-NHC—⟨phenyl⟩

O

Crystalline form: White powder
Recrystallization solvent: Methanol/diethyl ether
Melting Point: 226–228° C.
Form: Free

TABLE 3-continued

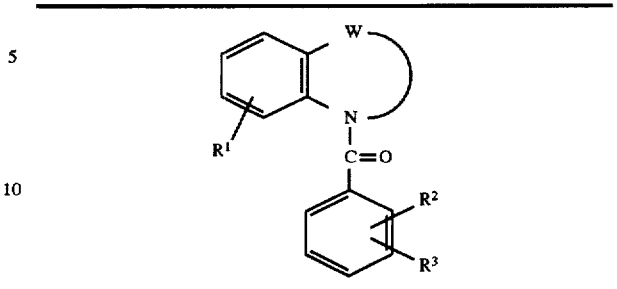

Example 542

Structure

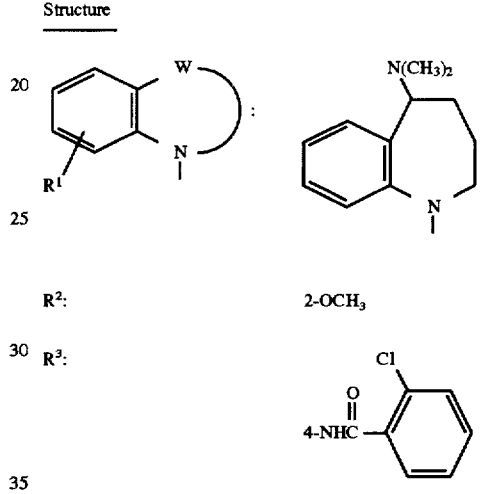

R²:  2-OCH₃

R³:

Cl
‖
4-NHC—⟨phenyl⟩

O

Crystalline form: White powder
Recrystallization solvent: Methanol/diethyl ether
Melting Point: 218–221° C.
Form: Free

Example 543

Structure

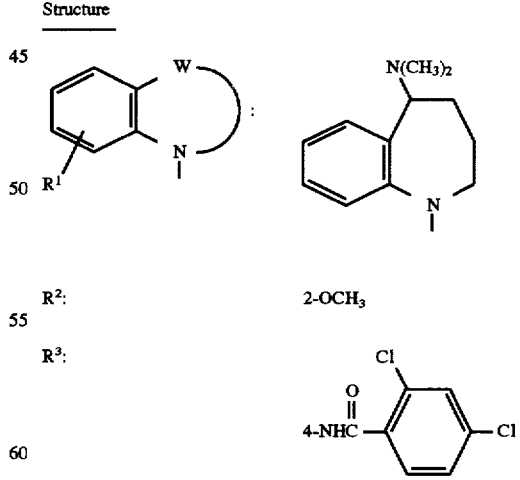

R²:  2-OCH₃

R³:

Cl
‖
4-NHC—⟨phenyl-Cl⟩

O

Crystalline form: White powder
Recrystallization solvent: Methanol/diethyl ether
Melting Point: 156–157° C.
Form: Free TABLE 3-continued

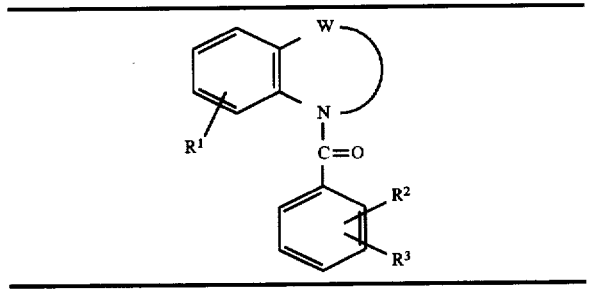

Example 544

Structure

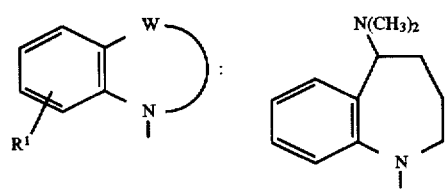

R²: 2-OCH₃

R³:
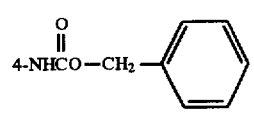
4-NHCO—CH₂—phenyl

Crystalline form: White powder
NMR analysis: 80)
Form: Free

Example 545

Structure

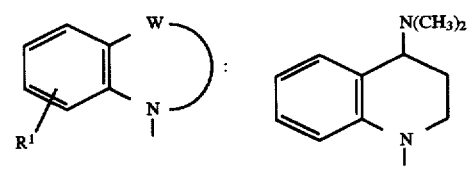

R²: 3-OCH₃

R³:
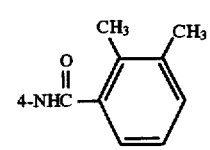
4-NHC(=O)-(2,3-diCH₃-phenyl)

Crystalline form: Colorless amorphous
NMR analysis: 81)
Form: Free

Example 546

Structure

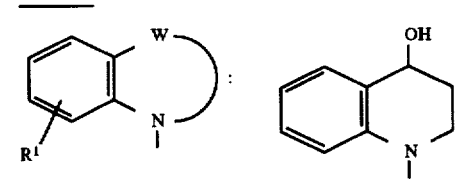

R²: H

TABLE 3-continued

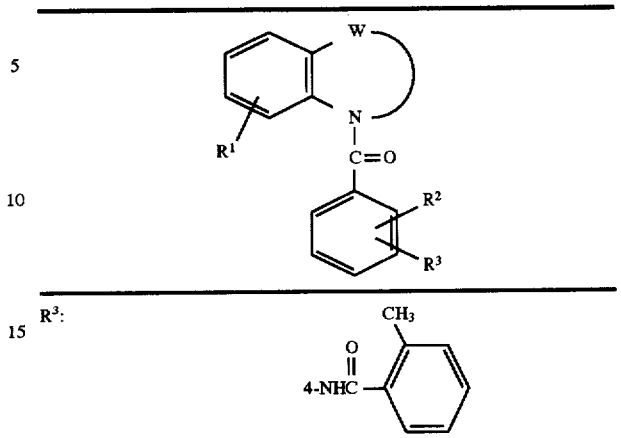

R³:
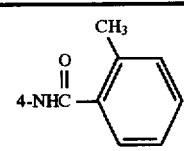
4-NHC(=O)-(2-CH₃-phenyl)

Crystalline form: Colorless amorphous
NMR analysis: 82)
Form: Free

Example 547

Structure

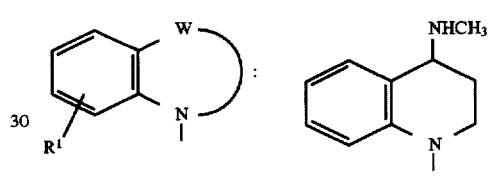

R²: H

R³:
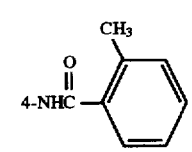
4-NHC(=O)-(2-CH₃-phenyl)

Crystalline form: Light yellow amorphous
NMR analysis: 83)
Form: Free

Example 548

Structure

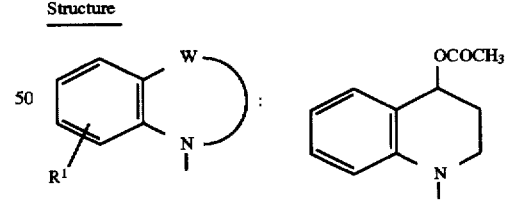

R²: H

R³:
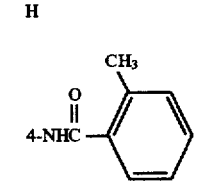
4-NHC(=O)-(2-CH₃-phenyl)

Crystalline form: Colorless amorphous
NMR analysis: 84)
Form: Free

TABLE 3-continued

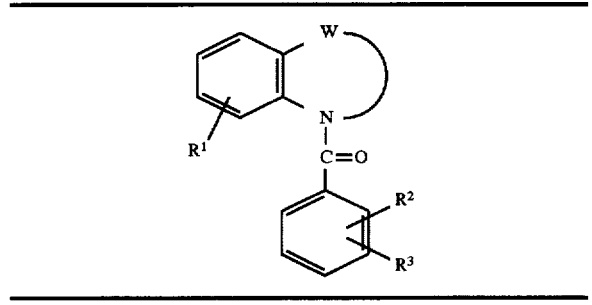

Example 549

Structure

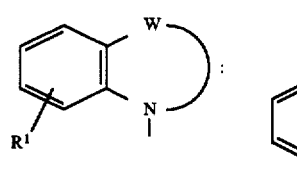

R²: H

R³: 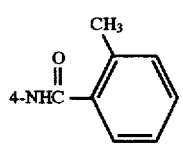

Crystalline form: Colorless amorphous
NMR analysis: 85)
Form: Free

Example 550

Structure

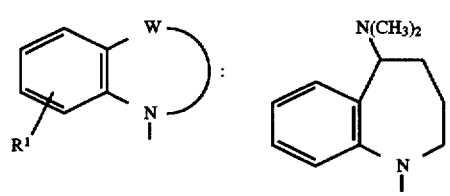

R²: 3-OCH₂CH₃

R³: 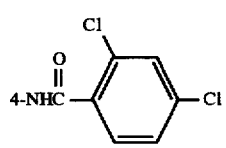

Crystalline form: White powder
Recrystallization solvent: n-Hexane/ethyl acetate
Melting Point: 135–136° C.
Form: Free TABLE 3-continued

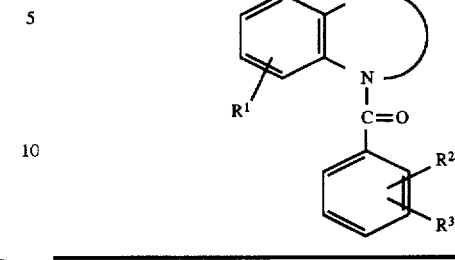

Example 551

Structure

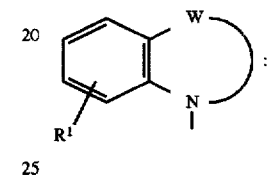

R²: 3-OCH₂CH₃

R³: 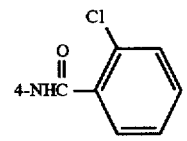

Crystalline form: Colorless prisms
Recrystallization solvent: n-Hexane/ethyl acetate
Melting Point: 122–123° C.
Form: Free Example 552

Structure

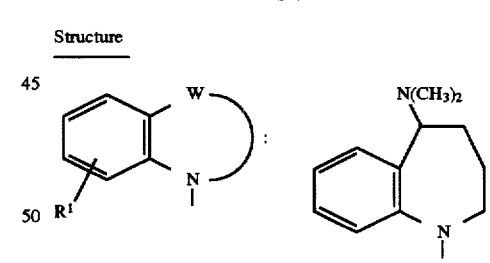

R²: 3-OCH₂CH₃

R³: 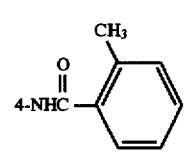

Crystalline form: Colorless prisms
Recrystallization solvent: n-Hexane/ethyl acetate
Melting Point: 118–119° C.
Form: Free TABLE 3-continued

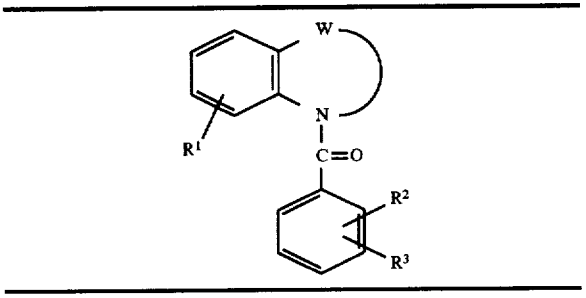

Example 553

Structure

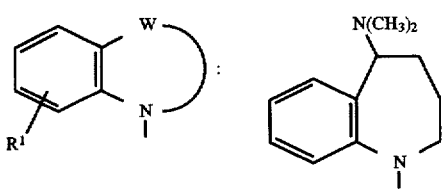

R²:

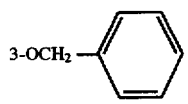 3-OCH₂—

R³:

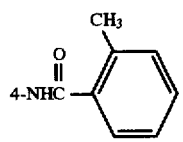

Crystalline form: Colorless prisms
Recrystallization solvent: n-Hexane/ethyl acetate
Melting Point: 145–147° C.
Form: Free Example 554

Structure

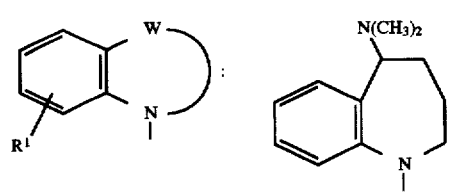

R²:

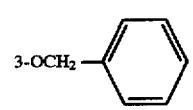 3-OCH₂—

R³:

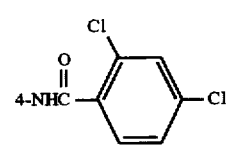

Crystalline form: Light yellow needles
Recrystallization solvent: n-Hexane/ethyl acetate
Melting Point: 169.5–170.5° C.
Form: Free TABLE 3-continued

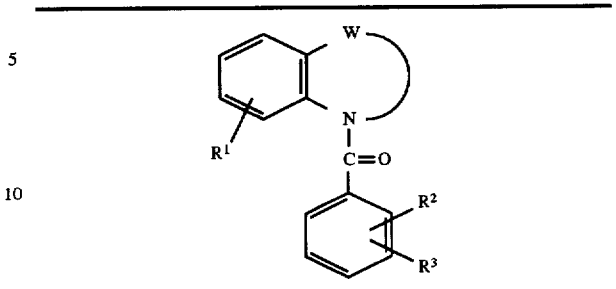

Example 555

Structure

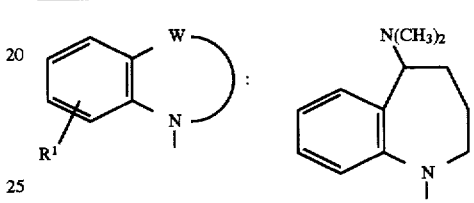

R²: 3-OH

R³:

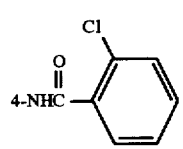

Crystalline form: Colorless prisms
Recrystallization solvent: n-Hexane/ethyl acetate
Melting Point: 194–195° C.
Form: Free Example 556

Structure

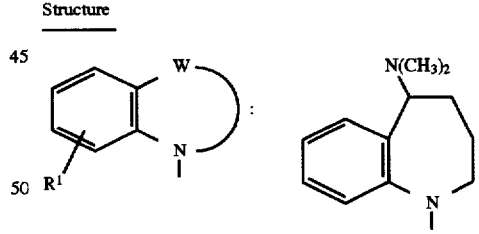

R²: 3-OH

R³:

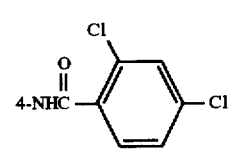

Crystalline form: Colorless needles
Recrystallization solvent: n-Hexane/ethyl acetate
Melting Point: 202–204° C.
Form: Free

TABLE 3-continued

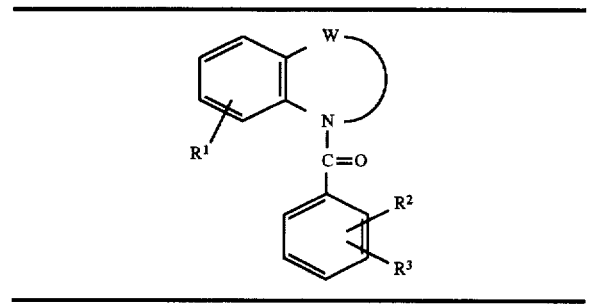

Example 557

Structure

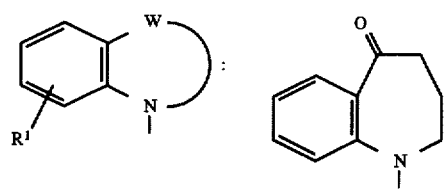

R²: H

R³:
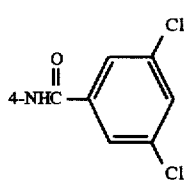

Crystalline form: Colorless prisms
Recrystallization solvent: Ethanol
Melting Point: 242–243° C.
Form: Free

Example 558

Structure

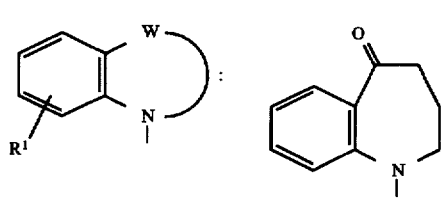

R²: H

R³:
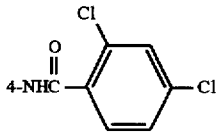

Crystalline form: Light yellow powder
NMR analysis: 86)
Form: Free

TABLE 3-continued

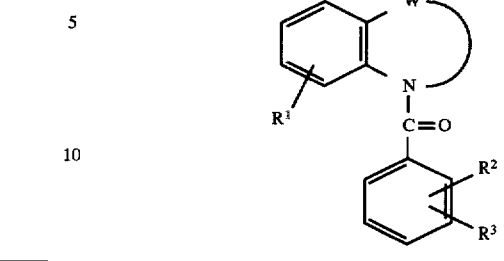

Example 559

Structure

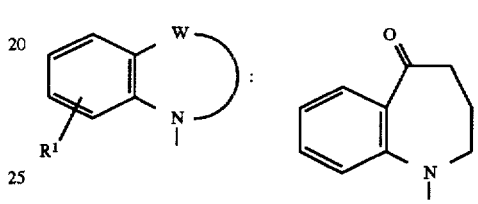

R²: H

R³:
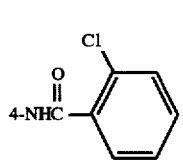

Crystalline form: Light yellow powder
NMR analysis: 87)
Form: Free

Example 560

Structure

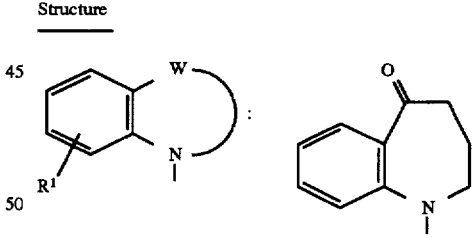

R²: H

R³:
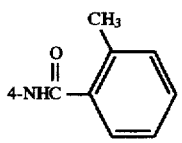

Crystalline form: Colorless needles
Recrystallization solvent: Ethanol
Melting Point: 237–238° C.
Form: Free

TABLE 3-continued

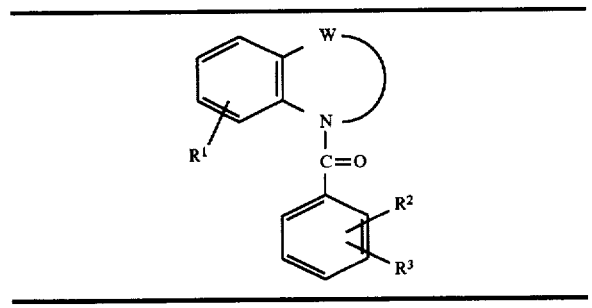

Example 561

Structure

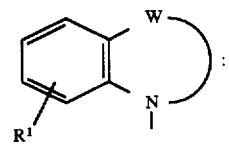

R²: H

R³:
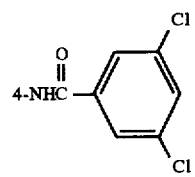

Crystalline form: Colorless prisms
Recrystallization solvent: Dioxane
Melting Point: 258–259° C.
Form: Free

Example 562

Structure

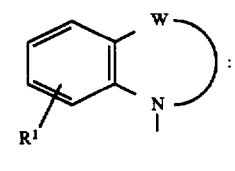

R²: H

R³:
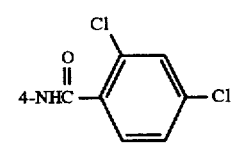

Crystalline form: Colorless prisms
Recrystallization solvent: Ethanol
Melting Point: 182.5–183.5° C.
Form: Free

TABLE 3-continued

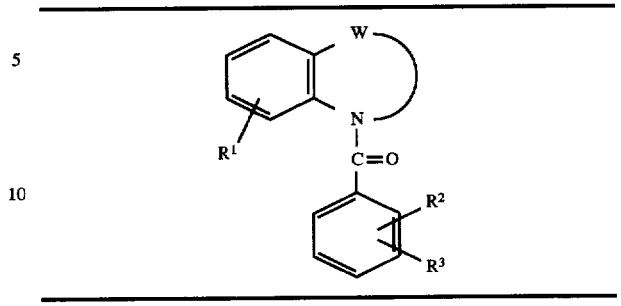

Example 563

Structure

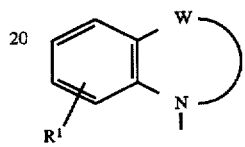

R²: H

R³:
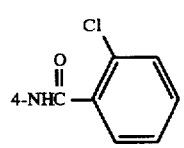

Crystalline form: Colorless prisms
Recrystallization solvent: Ethanol
Melting Point: 209–211° C.
Form: Free

Example 564

Structure

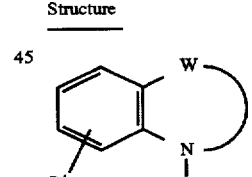

R²: H

R³:
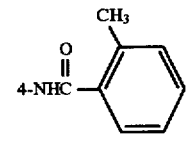

Crystalline form: Colorless prisms
Recrystallization solvent: Dioxane
Melting Point: 210–211° C.
Form: Free TABLE 3-continued

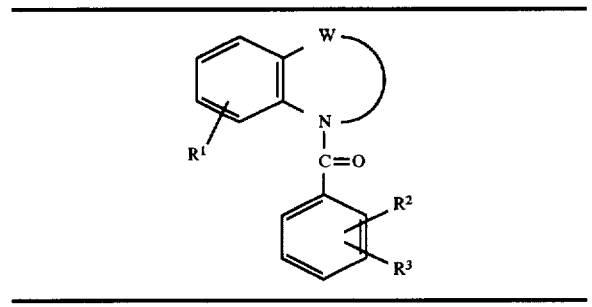

Example 565

Structure

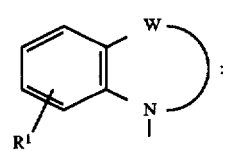 :

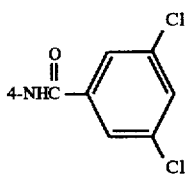

R²:  H

R³:

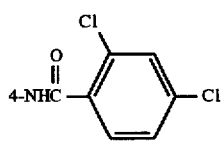

Crystalline form: Colorless needles
Recrystallization solvent: Ethyl acetate/n-hexane
Melting Point: 176–178° C.
Form: Free Example 566

Structure

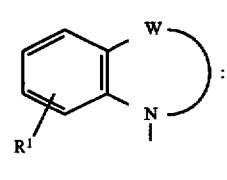 :

R²:  H

R³:

Crystalline form: Light yellow amorphous
NMR analysis: 88)
Form: Free

TABLE 3-continued

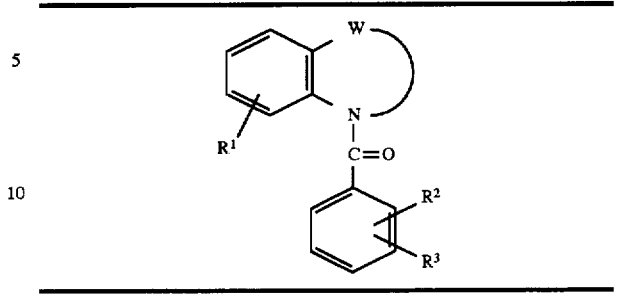

Example 567

Structure

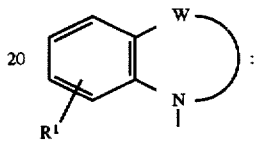 :

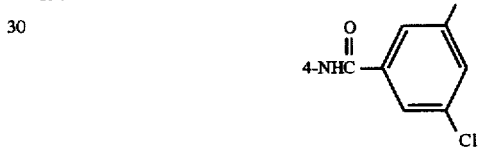

R²:  H

R³:

Crystalline form: White powder
Recrystallization solvent: Dioxane/water
Melting Point: 272–273° C.
Form: Free Example 568

Structure

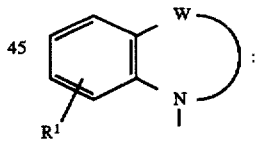 :

R²:  H

R³:

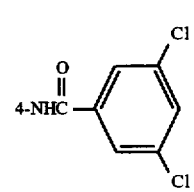

Crystalline form: Colorless prisms
Recrystallization solvent: Dioxane
Melting Point: 253–254° C.
Form: Free

TABLE 3-continued

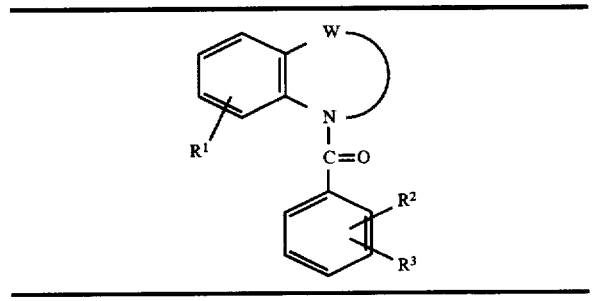

Example 569

Structure

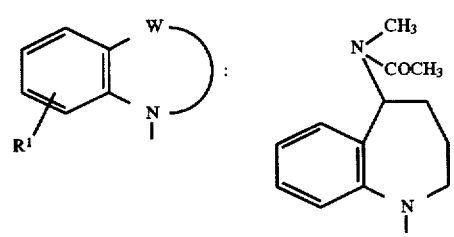

R²: H

R³: 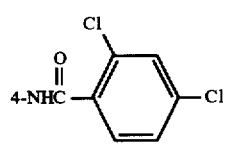

Crystalline form: Colorless prisms
Recrystallization solvent: Ethanol
Melting Point: 248.5–249.5° C.
Form: Free

Example 570

Structure

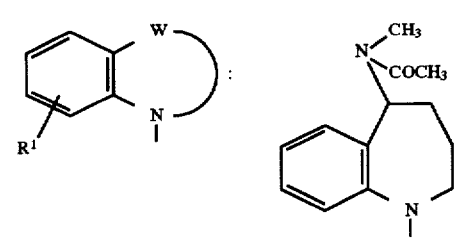

R²: H

R³: 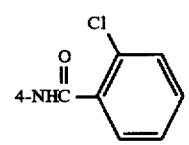

Crystalline form: Colorless needles
Recrystallization solvent: Ethanol
Melting Point: 266.5–267.5° C.
Form: Free

TABLE 3-continued

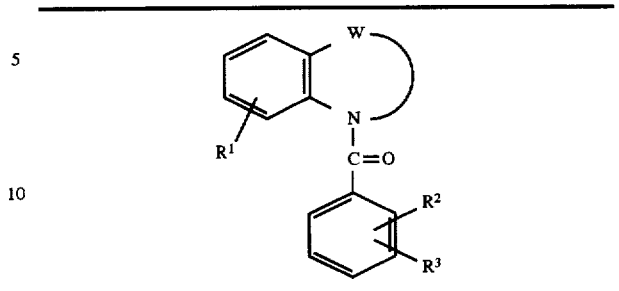

Example 571

Structure

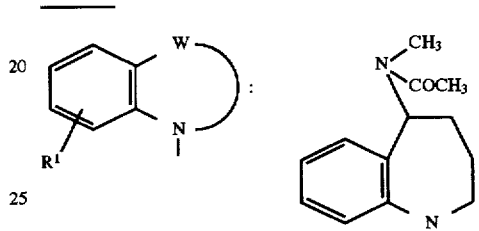

R²: H

R³: 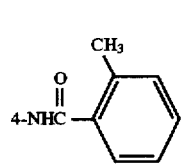

Crystalline form: Colorless needles
Recrystallization solvent: Ethanol
Melting Point: 252–253° C.
Form: Free

Example 572

Structure

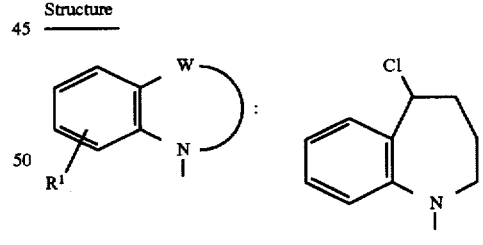

R²: H

R³: 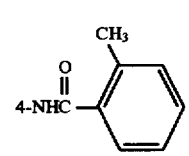

Crystalline form: Light yellow powder
NMR analysis: 89)
Form: Free

TABLE 3-continued

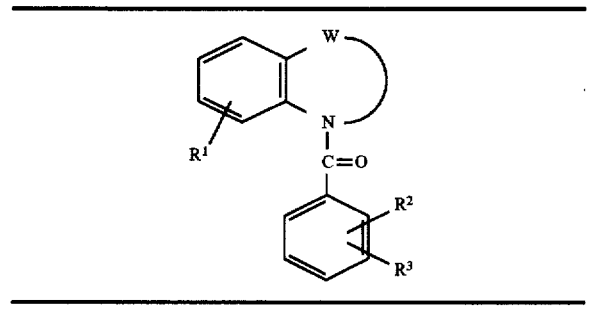

Example 573

Structure

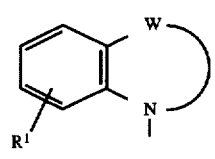 : 

R²: H

R³: 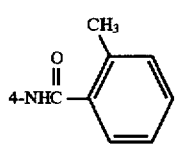

Crystalline form: Light brown powder
NMR analysis: 90)
Form: Free

Example 574

Structure

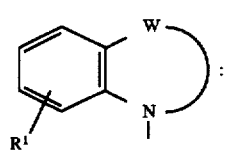 : 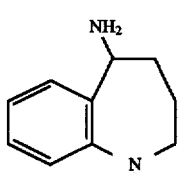

R²: H

R³: 

Crystalline form: White powder
Recrystallization solvent: Diethyl ether
Melting Point: 198.5–199.5° C.
Form: Free TABLE 3-continued

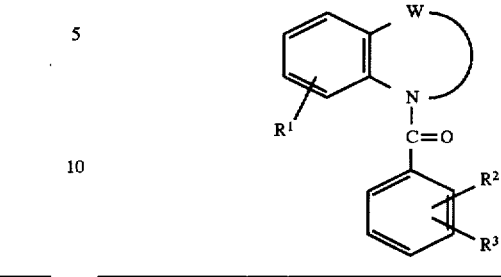

Example 575

Structure

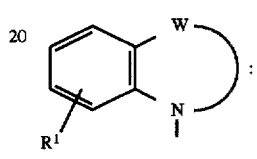 : 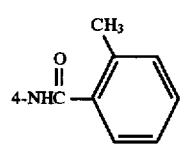

R²: H

R³: 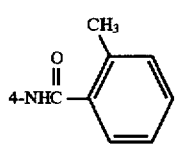

Crystalline form: Colorless needles
Recrystallization solvent: Ethanol
Melting Point: 297–299° C.
Form: Free Example 576

Structure

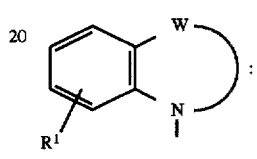 : 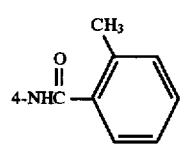

R²: 2-Cl

R³: 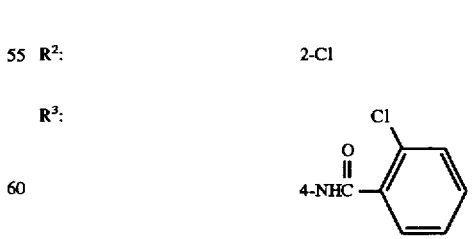

Crystalline form: Colorless amorphous
NMR analysis: 91)
Form: Free

TABLE 3-continued

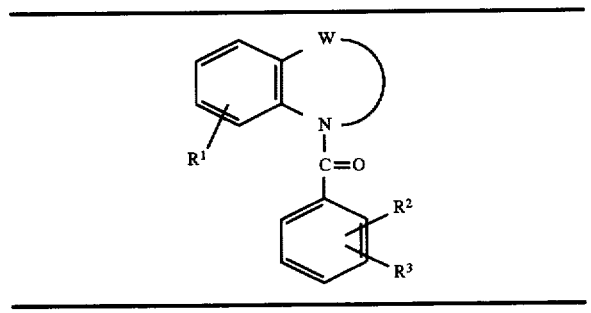

Example 577

Structure

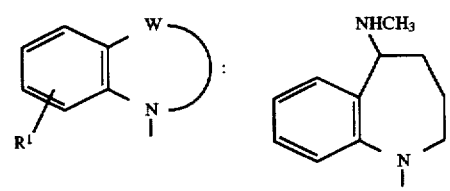

R²: 2-Cl

R³:
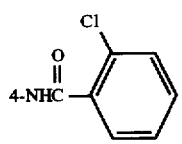

Crystalline form: White powder
Recrystallization solvent: Ethanol/petroleum ether
Melting Point: 202–203° C.
Form: Free Example 578

Structure

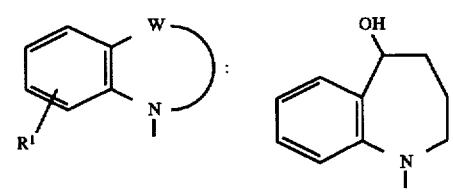

R²: H

R³:
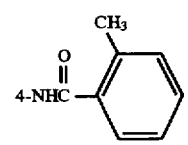

Crystalline form: Colorless amorphous
NMR analysis 92)
Form: Free

TABLE 3-continued

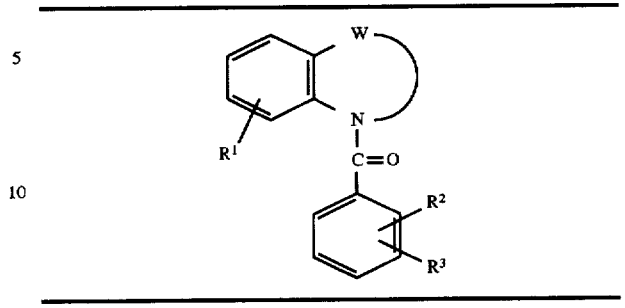

Example 579

Structure

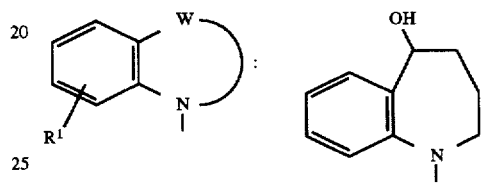

R²: H

R³:
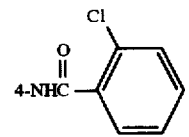

Crystalline form: White powder
Recrystallization solvent: Ethyl acetate/n-hexane
Melting Point: 232–233° C.
Form: Free Example 580

Structure

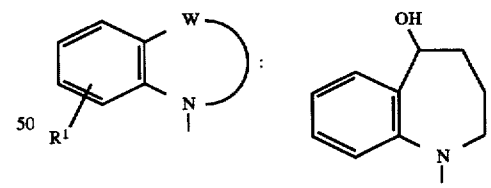

R²: H

R³:
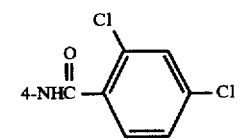

Crystalline form: Colorless amorphous
NMR analysis: 93)
Form: Free

TABLE 3-continued

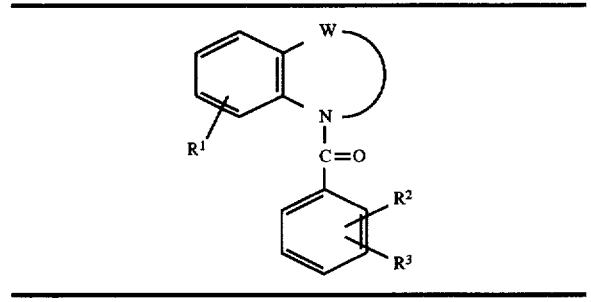

Example 581

Structure

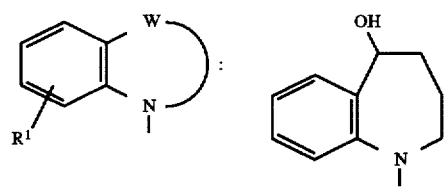

R²: H

R³:

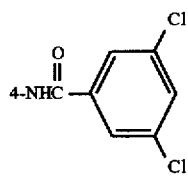

Crystalline form: White powder
Recrystallization solvent: Ethyl acetate/n-hexane
Melting Point: 256.5–257° C.
Form: Free Example 582

Structure

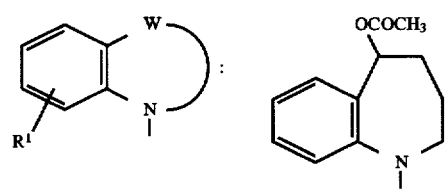

R²: H

R³:

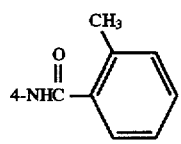

Crystalline form: White powder
Recrystallization solvent: Ethyl acetate/n-hexane
Melting Point: 193–194° C.
Form: Free TABLE 3-continued

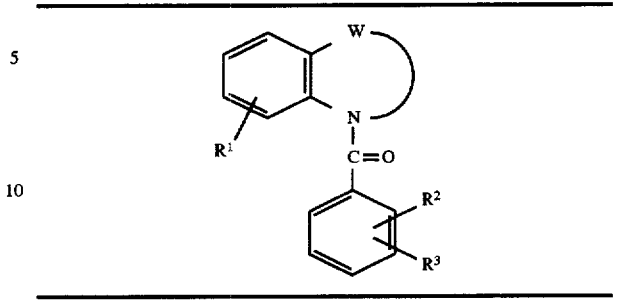

Example 583

Structure

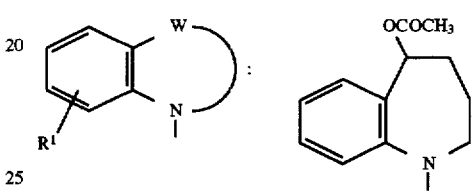

R²: H

R³:

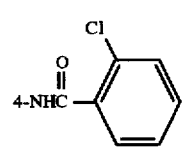

Crystalline form: White powder
Recrystallization solvent: Ethyl acetate/n-hexane
Melting Point: 227–230° C.
Form: Free Example 584

Structure

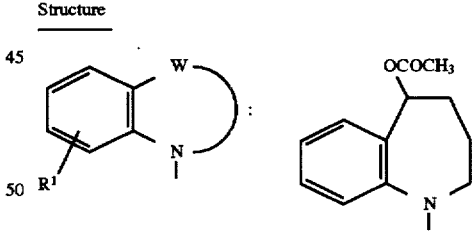

R²: H

R³:

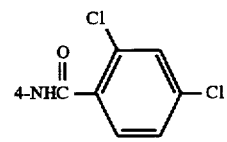

Crystalline form: White powder
Recrystallization solvent: Ethyl acetate/n-hexane
Melting Point: 199.5–202° C.
Form: Free TABLE 3-continued

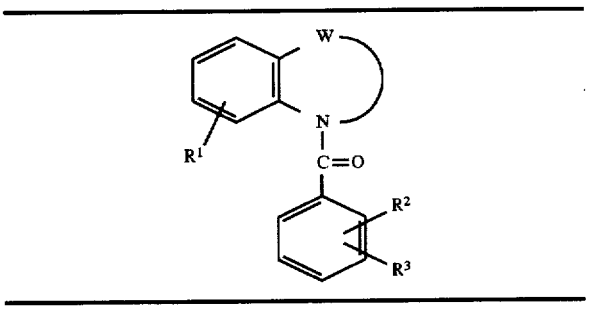

Example 585

Structure

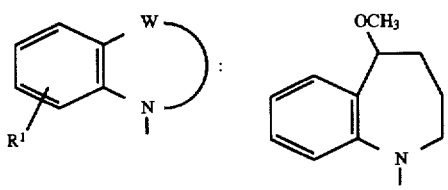

R²: H

R³: 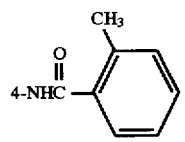

Crystalline form: White powder
Recrystallization solvent: Ethyl acetate/n-hexane
Melting Point: 219–220° C.
Form: Free Example 586

Structure

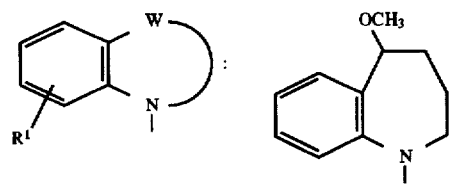

R²: H

R³: 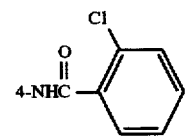

Crystalline form: White powder
Recrystallization solvent: Ethyl acetate/n-hexane
Melting Point: 190–191.5° C.
Form: Free TABLE 3-continued

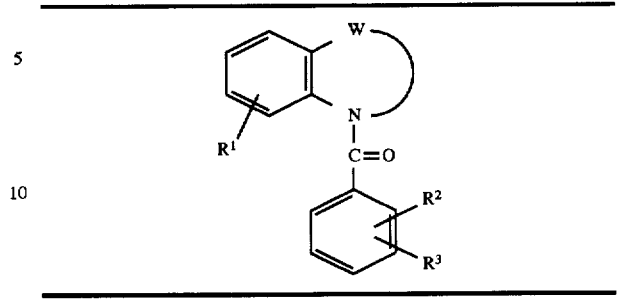

Example 587

Structure

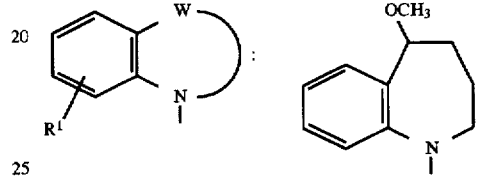

R²: H

R³: 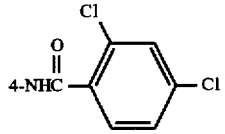

Crystalline form: White powder
Recrystallization solvent: Ethyl acetate/n-hexane
Melting Point: 184–185° C.
Form: Free Example 588

Structure

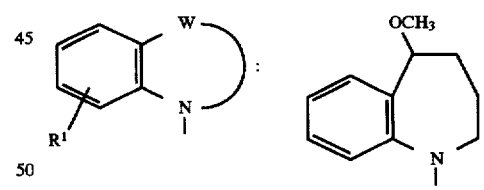

R²: H

R³: 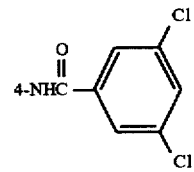

Crystalline form: White powder
Recrystallization solvent: Ethyl acetate/n-hexane
Melting Point: 223–224° C.
Form: Free

TABLE 3-continued

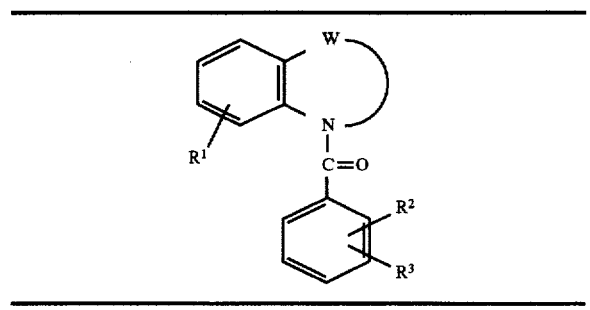

Example 589

Structure

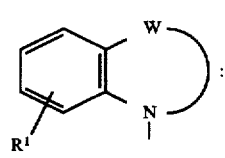

R²: H

R³:

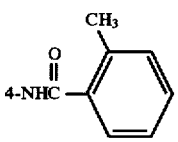

Crystalline form: White powder
Recrystallization solvent: Ethyl acetate/n-hexane
Melting Point: 178–181° C.
Form: Free

Example 590

Structure

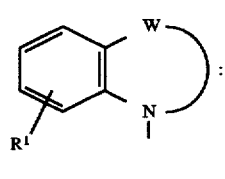

R²: H

R³:

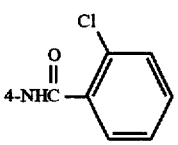

Crystalline form: Colorless needles
Recrystallization solvent: Ethyl acetate/n-hexane
Melting Point: 168–168.5° C.
Form: Free

TABLE 3-continued

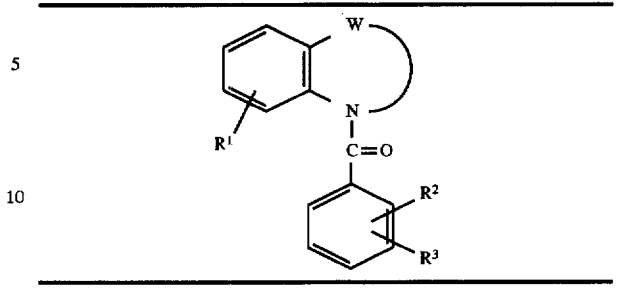

Example 591

Structure

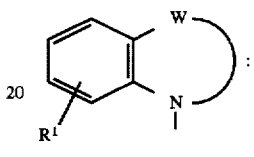

R²: H

R³:

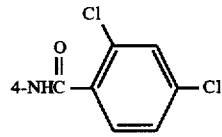

Crystalline form: Colorless amorphous
NMR analysis: 94)
Form: Free

Example 592

Structure

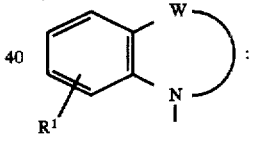

R²: H

R³:

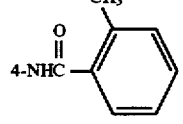

Crystalline form: Colorless amorphous
NMR analysis: 95)
Form: Free

Example 593

Structure

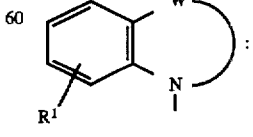

TABLE 3-continued

[Structure: N-benzoyl aniline derivative with W bridge, R¹, R², R³ substituents]

R²: H

R³: 4-NHC(O)-(2-Cl-phenyl)

Crystalline form: White powder
Recrystallization solvent: Ethyl acetate/n-hexane
Melting Point: 196–197° C.
Form: Free

Example 594

Structure

[Structure with OCH₂CONH₂ substituent on tetrahydrobenzazepine]

R²: H

R³: 4-NHC(O)-(2,4-diCl-phenyl)

Crystalline form: Colorless amorphous
NMR analysis: 96)
Form: Free

Example 595

Structure

[Structure with OCH₂COOH substituent on tetrahydrobenzazepine]

R²: H

R³: 4-NHC(O)-(2-CH₃-phenyl)

Crystalline form: White powder
Recrystallization solvent: Ethanol/water

TABLE 3-continued

[Structure: N-benzoyl aniline derivative with W bridge, R¹, R², R³ substituents]

Melting Point: 188–199° C.
Form: Free

Example 596

Structure

[Structure with OCH₂COOH substituent on tetrahydrobenzazepine]

R²: H

R³: 4-NHC(O)-(2-Cl-phenyl)

Crystalline form: Colorless amorphous
NMR analysis: 97)
Form: Free

Example 597

Structure

[Structure with OCH₂COOH substituent on tetrahydrobenzazepine]

R²: H

R³: 4-NHC(O)-(2,4-diCl-phenyl)

Crystalline form: Colorless amorphous
NMR analysis: 98)
Form: Free

TABLE 3-continued

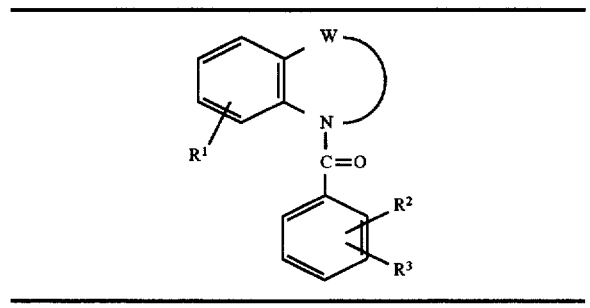

Example 598

Structure

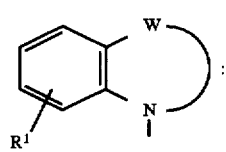 : 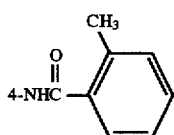

R²: H

R³:

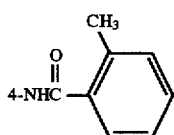

Crystalline form: Colorless prisms
Recrystallization solvent: Ethyl acetate/n-hexane
Melting Point: 203–204° C.
Form: Free Example 599

Structure

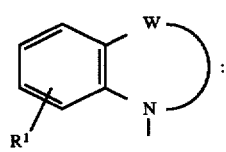 : 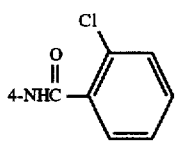

R²: H

R³:

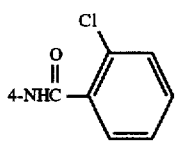

Crystalline form: White powder
Recrystallization solvent: Ethyl acetate/n-hexane
Melting Point: 196–197° C.
Form: Free TABLE 3-continued

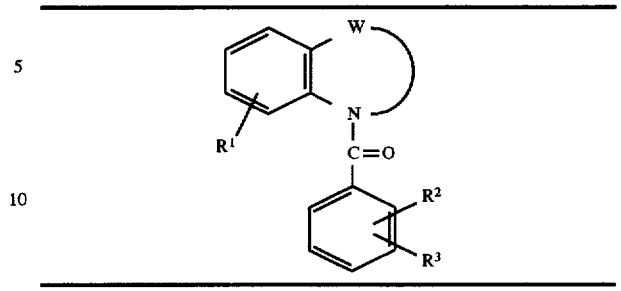

Example 600

Structure

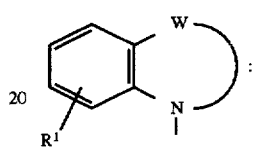 : 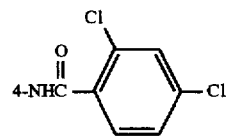

R²: H

R³:

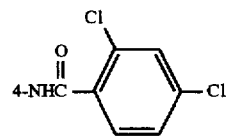

Crystalline form: Colorless amorphous
NMR analysis: 99)
Form: Free

Example 601

Structure

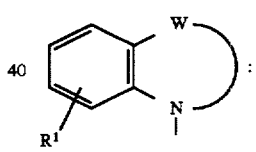 : 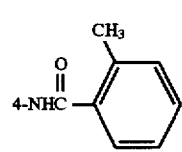

R²: H

R³:

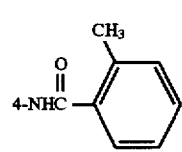

Crystalline form: Colorless amorphous
NMR analysis: 100)
Form: Free

Example 602

Structure

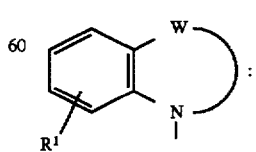 : 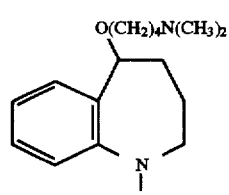

TABLE 3-continued

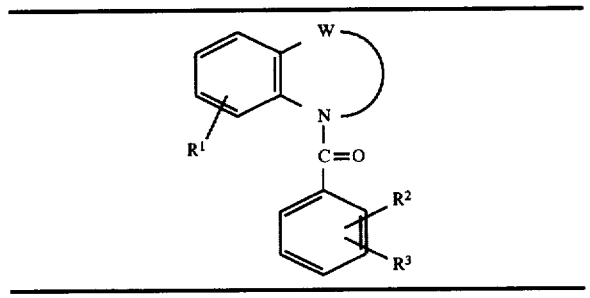

R²: H

R³: 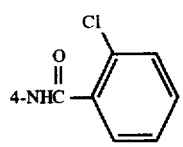

Crystalline form: Colorless amorphous
NMR analysis: 101)
Form: Free

Example 603

Structure

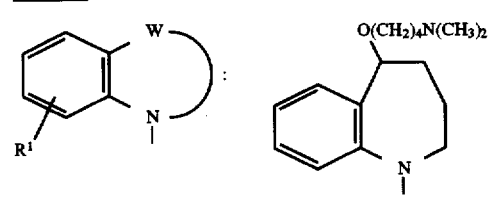

R²: H

R³: 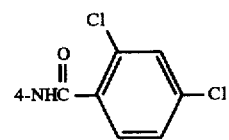

Crystalline form: Colorless amorphous
NMR analysis: 102)
Form: Free

Example 604

Structure

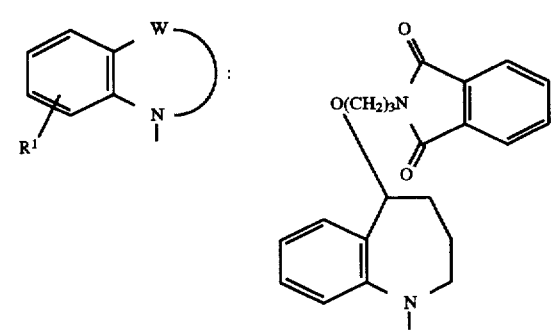

R²: H

TABLE 3-continued

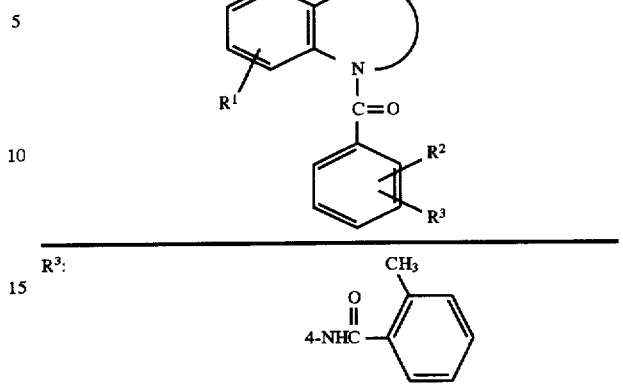

R³: 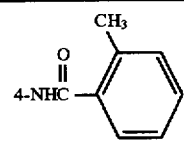

Crystalline form: Colorless amorphous
NMR analysis: 103)
Form: Free

Example 605

Structure

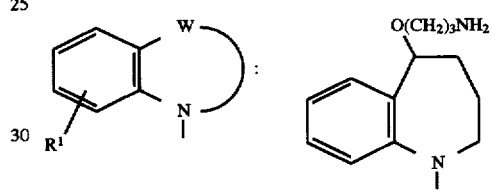

R²: H

R³: 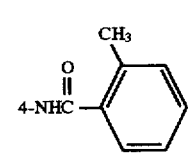

Crystalline form: Colorless amorphous
NMR analysis: 104)
Form: Free

Example 606

Structure

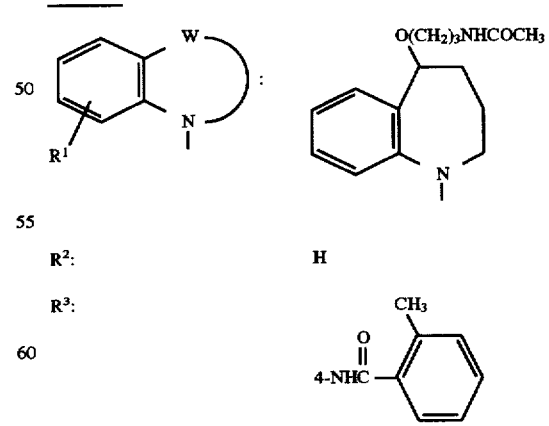

R²: H

R³:

Crystalline form: Colorless amorphous
NMR analysis: 105)
Form: Free

TABLE 3-continued

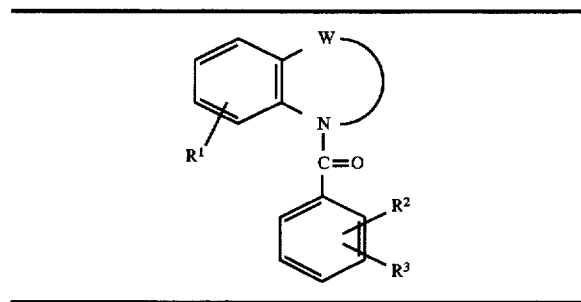

Example 607

Structure

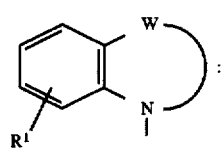 : 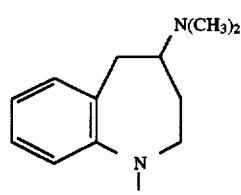

R²:  H

R³:

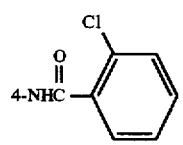

Crystalline form: Colorless needles
Recrystallization solvent: Ethanol
Melting Point: 169–171° C.
Form: Free Example 608

Structure

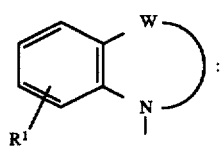 : 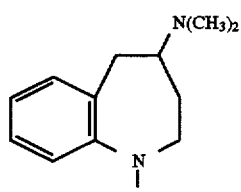

R²:  H

R³:

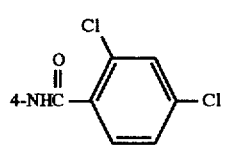

Crystalline form: Colorless needles
Recrystallization solvent: Ethanol/diethyl ether
Melting Point: 178–181° C.
Form: Free TABLE 3-continued

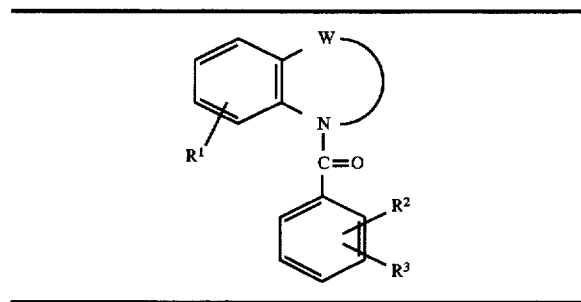

Example 609

Structure

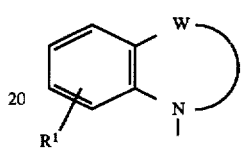 : 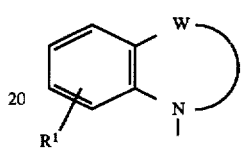

R²:  H

R³:

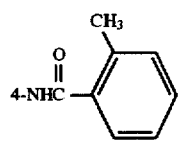

Crystalline form: White powder
Recrystallization solvent: Ethanol
Melting Point: 187–188° C.
Form: Free Example 610

Structure

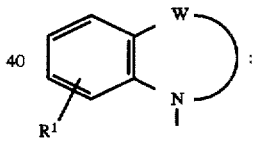 : 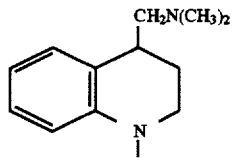

R²:  H

R³:

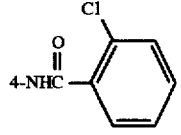

Crystalline form: White powder
Recrystallization solvent: Ethanol
Melting Point: 181–183° C.
Form: Free Example 611

Structure

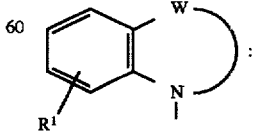 : 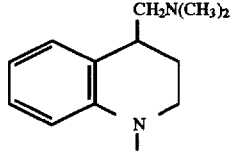

TABLE 3-continued

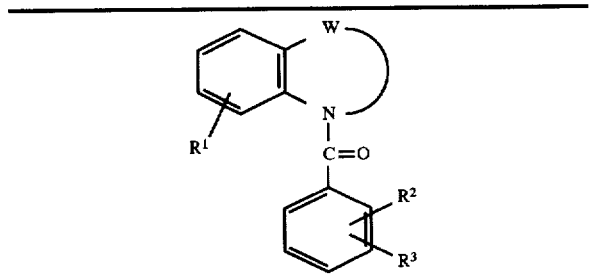

| R²: | H |

R³:

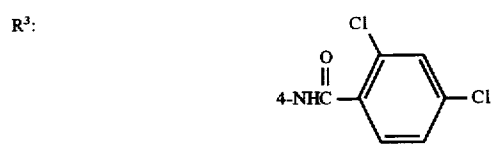

Crystalline form: White powder
Recrystallization solvent: Ethanol
Melting Point: 124–127° C.
Form: Free Example 612

Structure

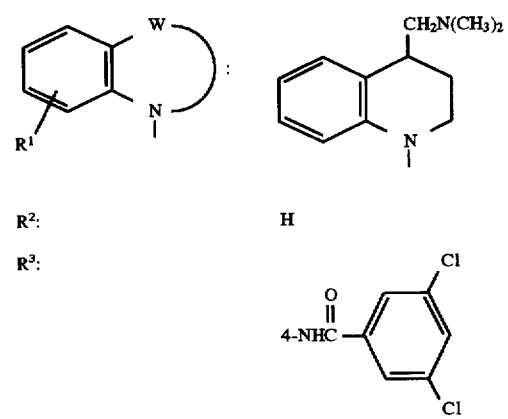

| R²: | H |

R³:

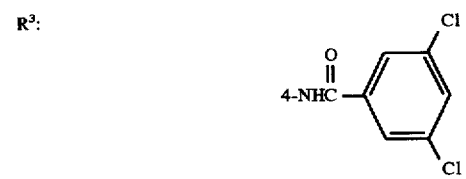

Crystalline form: White powder
Recrystallization solvent: Ethanol
Melting Point: 179–181° C.
Form: Free Example 613

Structure

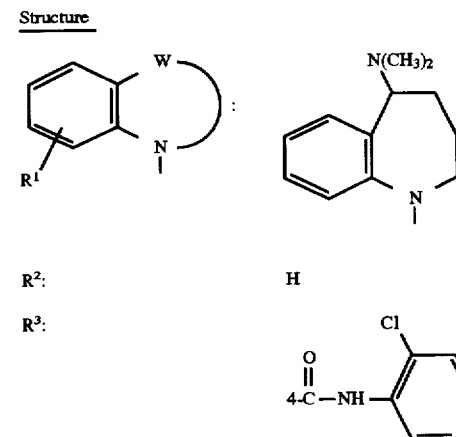

| R²: | H |

R³:

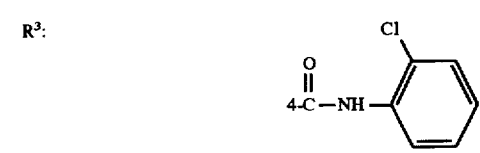

Crystalline form: White powder

TABLE 3-continued

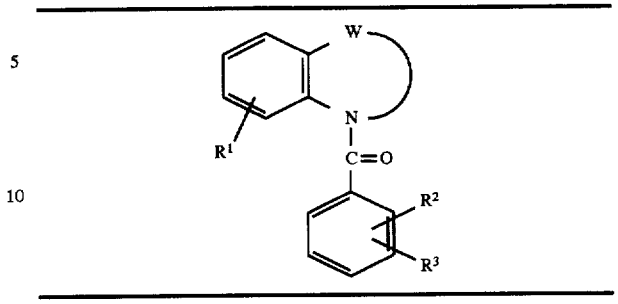

Recrystallization solvent: Ethanol
Melting Point: 148–150° C.
Form: Free

Example 614

Structure

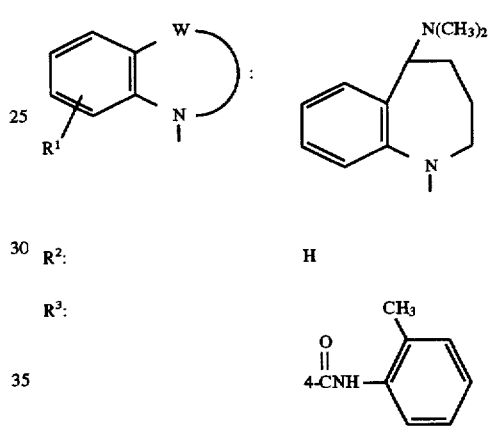

| R²: | H |

R³:

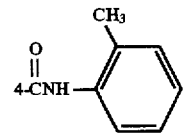

Crystalline form: Colorless amorphous
NMR analysis: 106)
Form: Free

Example 615

Structure

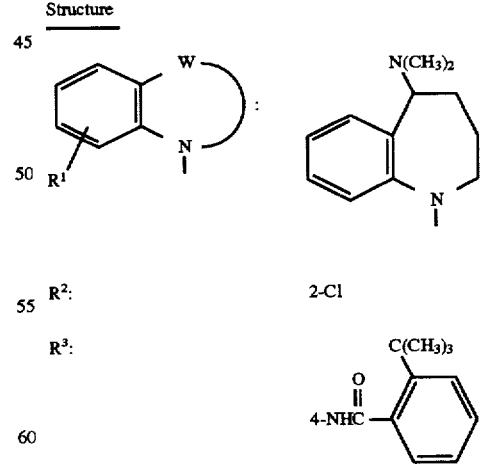

| R²: | 2-Cl |

R³:

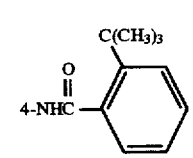

Crystalline form: White powder
Recrystallization solvent: Ethanol
Melting Point: 219–220° C.
Form: Free

TABLE 3-continued

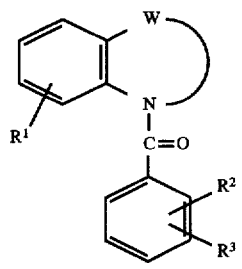

Example 616

Structure

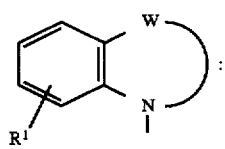  :  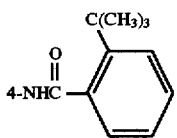

R²: H

R³: 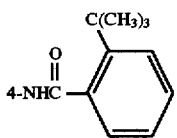

Crystalline form: White powder
Recrystallization solvent: Ethanol
Melting Point: 226–228° C.
Form: Free

Example 617

Structure

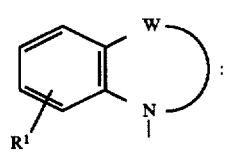  :  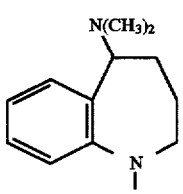

R²: 3-OCH₃

R³: 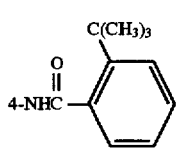

Crystalline form: Colorless amorphous
NMR analysis: 107)
Form: Free

TABLE 3-continued

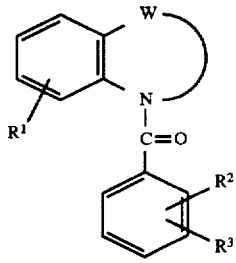

Example 618

Structure

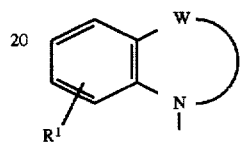  :  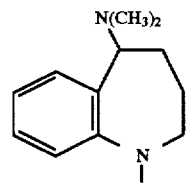

R²: 3-OCH₃

R³: 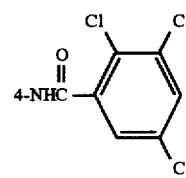

Crystalline form: Colorless amorphous
NMR analysis: 108)
Form: Free

Example 619

Structure

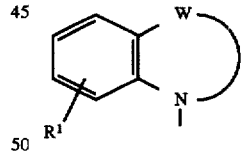  :  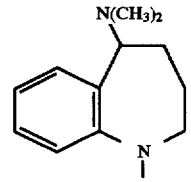

R²: 3-OCH₃

R³: 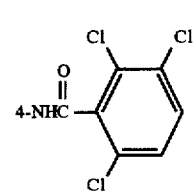

Crystalline form: Colorless amorphous
NMR analysis: 109)
Form: Free

TABLE 3-continued

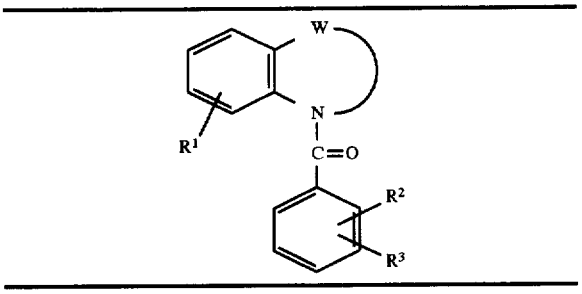

Example 620

Structure

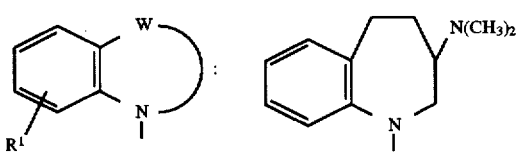

R²: H

R³:
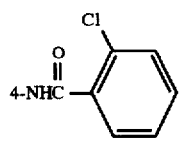

Crystalline form: Colorless amorphous
NMR analysis: 110)
Form: Free

Example 621

Structure

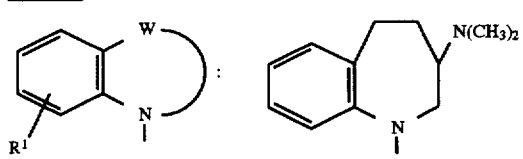

R²: H

R³:
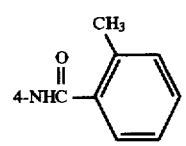

Crystalline form: Colorless amorphous
NMR analysis: 111)
Form: Free

Example 622

Structure

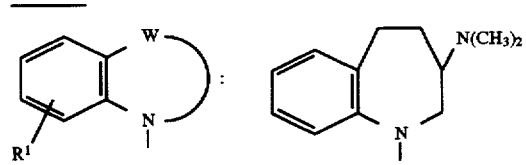

R²: H

TABLE 3-continued

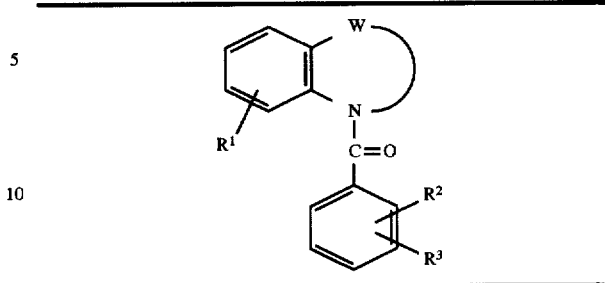

R³:
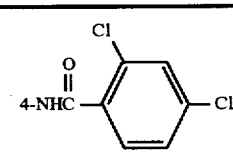

Crystalline form: Colorless amorphous
NMR analysis: 112)
Form: Free

Example 623

Structure

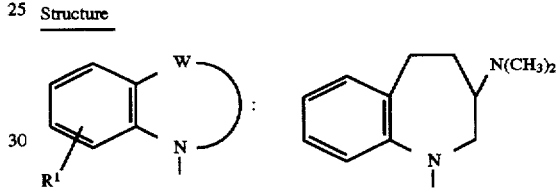

R²: 3-OCH₃

R³:
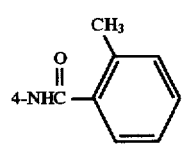

Crystalline form: Colorless amorphous
NMR analysis: 113)
Form: Free

Example 624

Structure

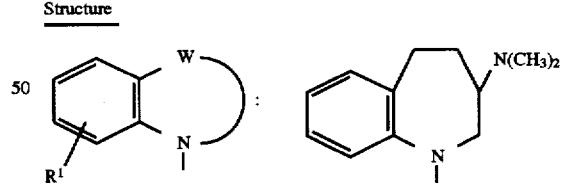

R²: 3-OCH₃

R³:
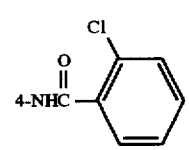

Crystalline form: Colorless amorphous
NMR analysis: 114)
Form: Free

TABLE 3-continued

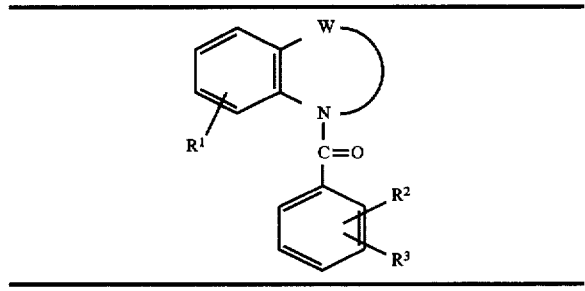

Example 625

Structure

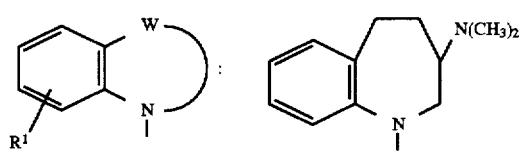

R²: 3-OCH₃

R³:

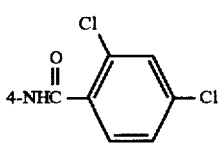

Crystalline form: Colorless amorphous
NMR analysis: 115)
Form: Free

Example 626

Structure

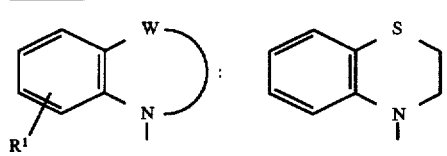

R²: H

R³:

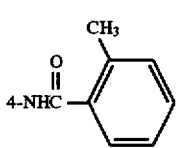

Crystalline form: White powder
Recrystallization solvent: Diethyl ether/dichloromethane
Melting Point: 183–184° C.
Form: Free Example 627

Structure

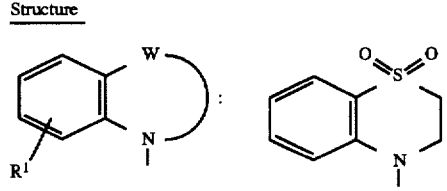

R²: H

TABLE 3-continued

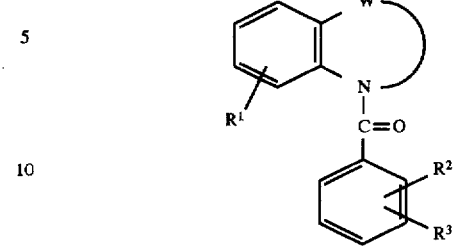

R³:

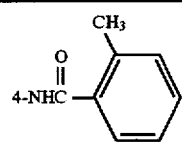

Crystalline form: White powder
Recrystallization solvent: Diethyl ether/dichloromethane
Melting Point: 219–220° C.
Form: Free Example 628

Structure

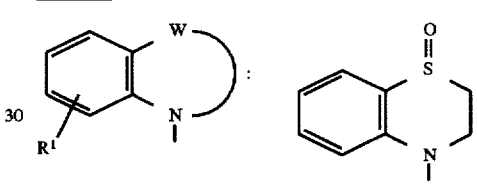

R²: H

R³:

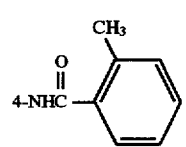

Crystalline form: White powder
Recrystallization solvent: Diethyl ether/dichloromethane
Melting Point: 240–241° C.
Form: Free Example 629

Structure

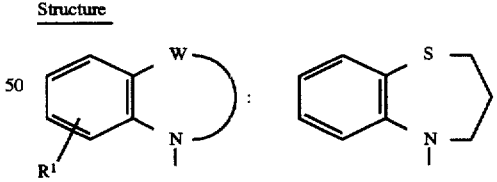

R²: H

R³:

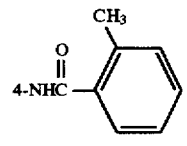

Crystalline form: White powder
Recrystallization solvent: Diethyl ether/dichloromethane
Melting Point: 205–206° C.
Form: Free TABLE 3-continued

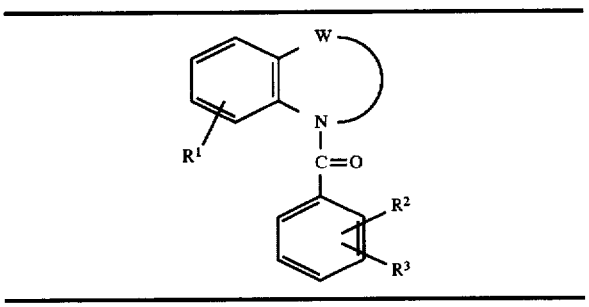

Example 630

Structure

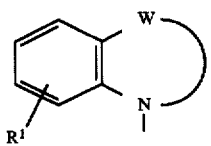 : 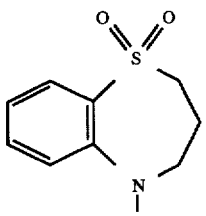

R²: H

R³: 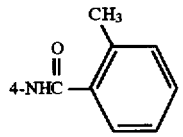

Crystalline form: White powder
Recrystallization solvent: Diethyl ether/dichloromethane
Melting Point: 238–239° C.
Form: Free Example 631

Structure

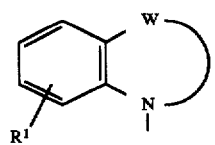 : 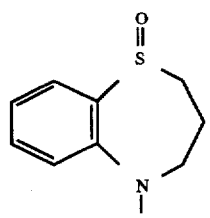

R²: H

R³: 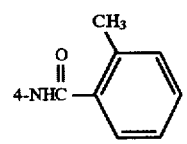

Crystalline form: White powder
Recrystallization solvent: Diethyl ether/dichloromethane
Melting Point: 233–234° C.
Form: Free TABLE 3-continued

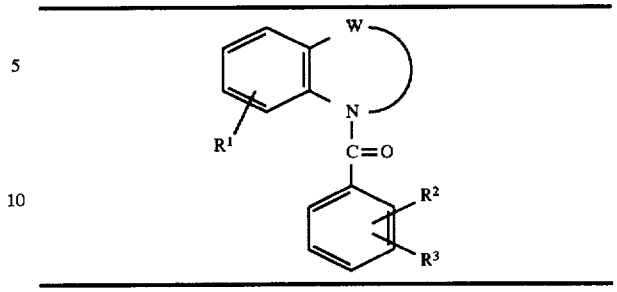

Example 632

Structure

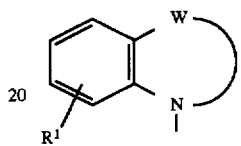 : 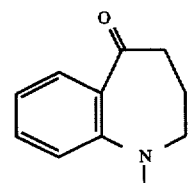

R²: 2-Cl

R³: 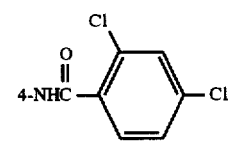

Crystalline form: Colorless amorphous
NMR analysis: 116)
Form: Free

Example 633

Structure

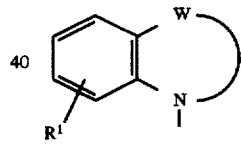 : 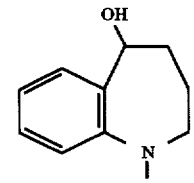

R²: 2-Cl

R³: 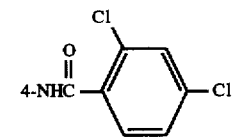

Crystalline form: White powder
Recrystallization solvent: Diethyl ether/dichloromethane
Melting Point: 259.5–260.5° C.
Form: Free 80) $^1$H-NMR(CDCl$_3$) δ; 1.24–5.26 (18H, m), 6.39–7.59 (13H, m)

81) $^1$H-NMR(CDCl$_3$) δ; 1.70–2.10 (m, 2H), 2.15–2.60 (m, 12H), 3.56 (t, J=5.8 Hz, 1H), 3.65–3.95 (m, 4H) 4.05–4.25 (m, 1H), 6.64 (d, J=7.7 Hz, 1H), 6.85–7.50 (m, 9H), 8.11 (brs, 1H), 8.42 (d, J=8.8 Hz, 1H)

82) $^1$H-NMR(CDCl$_3$) δ; 2.00–2.90 (m, 3H), 2.49 (s, 3H), 3.70–3.90 (m, 1H), 4.00–4.20 (m, 1H), 4.80–5.00 (m, 1H), 6.89 (d, J=6.3 Hz, 1H), 6.95–7.65 (m, 11H), 7.70 (brs, 1H)

83) ¹H-NMR(CDCl₃) δ; 1.95–2.90 (m, 2H), 2.48 (s, 3H), 2.55 (s, 3H), 3.77 (t, J=5.1 Hz, 1H), 3.92 (t, J=6.7 Hz, 2H), 6.72 (d, J=8.0 Hz, 1H), 6.90–7.15 (m, 2H), 7.15–7.70 (m, 9H), 7.81 (brs, 1H)

84) ¹H-NMR(CDCl₃) δ; 2.11 (s, 3H), 2.20–2.40 (m, 2H), 2.50 (s, 3H), 3.80–4.10 (m, 1H), 4.12–4.25 (m, 1H), 6.03 (t, J=4.3 Hz, 1H), 6.80–7.65 (m, 12H), 7.80 (brs, 1H)

85) ¹H-NMR(CDCl₃) δ; 1.80–2.40 (m, 5H), 2.45 (s, 3H), 2.81 (s, 3H), 3.55–3.82 (m, 1H), 4.15–4.40 (m, 1H), 5.90–6.10 (m, 1H), 6.80–7.80 (m, 12H), 8.67 (brs, 1H)

86) ¹H-NMR(CDCl₃) δ; 1.95–2.35 (2H, m), 2.75–3.0 (2H, m), 3.0–5.4 (2H, m), 6.55–7.95 (11H, m), 8.09 (1H, s)

87) ¹H-NMR(DMSO-d₆) δ; 1.85–2.2 (2H, m), 2.7–2.95 (2H, m), 3.5–5.0 (2H, m), 6.8–7.8 (12H, m), 10.60 (1H, s)

88) ¹H-NMR(CDCl₃) δ; 0.8–1.1 (3H, m), 1.2–2.35 (6H, m), 2.35–5.25 (6H, m), 6.63 (1H, d, J=7.7 Hz), 6.8–7.6 (9H, m), 7.67 (1H, d, J=8.2 Hz), 7.9–8.15 (1H, m)

89) ¹H-NMR(CDCl₃) δ; 1.7–2.9 (7H, m), 4.5–6.5 (3H, m), 6.55–6.75 (1H, m), 6.85–7.6 (12H, m)

90) ¹H-NMR(CDCl₃) δ; 1.65–3.1 (7H, m), 4.7–6.6 (3H, m), 6.6–6.8 (1H, m), 6.85–7.65 (12H, m)

91) ¹H-NMR(CDCl₃) δ; 1.8–2.4 (2H, m), 2.86 (2H, t, J=6 Hz), 3.1–5.15 (2H, m), 6.85–7.5 (8H, m), 7.5–7.85 (3H, m), 8.19 (1H, s)

92) ¹H-NMR(CDCl₃) δ; 1.46–2.28 (4H, m), 2.37 (3H, s), 2.58–2.90 (1H, m), 4.57–5.10 (2H, m), 6.59 (1H, d, J=7.6 Hz), 6.91–7.52 (11H, m), 7.62 (1H, d, J=7.6 Hz), 8.10–8.40 (1H, m)

93) ¹H-NMR(CDCl₃) δ; 1.45–1.91 (2H, m), 1.91–2.65 (2H, m), 2.65–2.90 (1H, m), 4.63–5.22 (2H, m), 6.63 (1H, d, J=7.4 Hz), 7.34–8.03 (11H, m), 10.16–10.44 (1H, m)

94) ¹H-NMR(CDCl₃) δ; 1.08–1.47 (3H, m), 1.50–1.97 (2H, m), 1.97–2.48 (2H, m), 2.65–3.02 (1H, m), 4.00–4.43 (4H, m), 4.52–5.15 (2H, m), 6.50–6.79 (1H, m), 6.90–7.70 (10H, m), 8.26–8.60 (1H, m)

95) ¹H-NMR(CDCl₃) δ; 1.56–2.67 (4H, m), 2.46 (3H, s), 2.67–3.03 (1H, m), 3.82–4.32 (2H, m), 4.45–5.15 (2H, m), 5.43–5.83 (1H, m), 6.20–6.45 (1H, m), 6.50–6.86 (2H, m), 6.86–7.70 (10H, m), 7.76–8.10 (1H, m)

96) ¹H-NMR(CDCl₃) δ; 1.52–1.90 (2H, m), 1.90–2.54 (2H, m), 2.67–3.05 (1H, m), 3.74–4.32 (2H, m), 4.38–5.17 (2H, m), 5.52–5.98 (1H, brs), 6.20–6.48 (1H, brs), 6.55–6.84 (1H, m), 6.89–7.55 (9H, m), 7.55–7.77 (1H, m), 8.15–8.86 (1H, brs)

97) ¹H-NMR(DMSO-d₆) δ; 1.26–2.49 (4H, m), 2.57–2.93 (1H, m), 4.07–4.43 (2H, m), 4.44–4.98 (2H, m), 6.62–6.87 (1H, m), 6.92–7.80 (11H, m), 10.57 (1H, s), 12.74 (1H, s)

98) ¹H-NMR(CDCl₃) δ; 1.52–1.89 (2H, m), 1.89–2.56 (2H, m), 2.65–3.02 (1H, m), 3.90–4.40 (2H, m), 4.40–5.07 (2H, m), 6.58–6.78 (1H, m), 6.90–7.70 (10H, m), 8.57–8.81 (1H, brs)

99) ¹H-NMR(CDCl₃) δ; 1.49–1.89 (2H, m), 1.89–2.60 (2H, m), 2.63–3.23 (7H, m), 4.04–4.49 (2H, m), 4.52–5.21 (2H, m), 6.52–6.80 (1H, m), 6.89–7.84 (10H, m), 8.08–8.52 (1H, m)

100) ¹H-NMR(CDCl₃) δ; 1.41–1.86 (6H, m), 1.86–2.53 (4H, m), 2.25 (3H, s), 2.29 (3H, s), 2.43 (3H, s), 2.60–2.97 (1H, m), 3.36–3.77 (2H, m), 4.40–5.10 (2H, m), 6.54–6.72 (1H, m), 6.88–7.67 (11H, m), 8.27–8.58 (1H, m)

101) ¹H-NMR(CDCl₃) δ; 1.44–1.85 (6H, m), 1.85–2.61 (4H, m), 2.32 (3H, s), 2.35 (3H, s), 2.61–3.00 (1H, m), 3.33–3.76 (2H, m), 4.40–5.20 (2H, m), 6.57–6.75 (1H, m), 6.90–7.70 (11H, m), 8.50–8.93 (1H, m)

102) ¹H-NMR(CDCl₃) δ; 1.49–2.04 (6H, m), 2.10–3.02 (5H, m), 2.47 (6H, s), 3.40–3.88 (2H, m), 4.30–5.17 (2H, m), 6.59–6.78 (1H, m), 6.93–7.76 (10H, m), 8.75–9.40 (1H, m)

103) ¹H-NMR(CDCl₃) δ; 1.47–2.47 (6H, m), 2.44 (3H, s), 2.62–3.03 (1H, m), 3.47–4.03 (4H, m), 4.48–5.17 (2H, m), 6.51–6.74 (1H, m), 6.87–7.62 (11H, m), 7.62–7.77 (2H, m), 7.77–8.03 (3H, m)

104) ¹H-NMR(CDCl₃) δ; 1.42–2.32 (6H, m), 2.44 (3H, s), 2.57–2.97 (1H, m), 3.12–3.83 (4H, m), 4.39–5.13 (2H, m), 6.50–6.71 (1H, m), 6.90–7.73 (12H, m)

105) ¹H-NMR(CDCl₃) δ; 1.50–2.63 (9H, m), 2.47 (3H, s), 2.66–3.07 (1H, m), 3.10–3.88 (4H, m), 4.40 . 5.17 (2H, m), 5.87–6.23 (1H, brs), 6.60–6.79 (1H, m), 6.94–7.60 (11H, m), 7.67 (1H, s)

106) ¹H-NMR(CDCl₃) δ; 1.20–2.53 (13H, m), 2.63–2.82, 3.00–3.13, 3.50–3.67, 4.05–4.23 (total 3H, m), 6.55–8.00 (13H, m)

107) ¹H-NMR(CDCl₃) δ; 1.41 (9H, s), 1.20–2.55 (10H, m), 3.42–4.20 (5.8H, m), 5.00–5.20 (0.2H, m), 6.60–7.67 (10H, m), 7.99 (1H, brs), 8.26 (1H, d, J=8.4 Hz)

108) ¹H-NMR(CDCl₃) δ; 1.2–3.0 (10H, m), 3.0–5.2 (6H, m), 6.5–7.7 (8H, m), 8.22 (1H, d, J=8.4 Hz), 8.36 (1H, s)

109) ¹H-NMR(CDCl₃) δ; 1.2–3.0 (10H, m), 3.0–5.2(6H, m), 6.3–7.7 (10H, m)

110) ¹H-NMR(CDCl₃) δ; 1.5–1.7 (1H, m), 2.2–2.7 (2H, m), 2.40 (6H, s), 2.7–3.0 (3H, m), 5.1–5.3 (1H, m), 6.67 (1H, d, J=7.7 Hz), 6.9–7.5 (10H, m), 7.69 (1H, d, J=6 Hz), 8.06 (1H, s)

111) ¹H-NMR(CDCl₃) δ; 1.4–1.7 (1H, m), 2.1–2.7 (2H, m), 2.40 (6H, s), 2.44 (3H, s), 2.7–3.0 (3H, m), 5.1–5.3 (1H, m), 6.68 (1H, d, J=7.8 Hz), 6.9–7.5 (11H, m), 7.66 (1H, s)

112) ¹H-NMR(CDCl₃) δ; 1.5–1.8 (1H, m), 2.1–2.7 (2H, m), 2.38 (6H, s), 2.7–3.0 (3H, m), 5.1–5.3 (1H, m), 6.66 (1H, d, J=7.7 Hz), 6.9–7.0 (9H, m), 7.57 (1H, d, J=8.3 Hz), 8.42 (1H, s)

113) ¹H-NMR(CDCl₃) δ; 1.5–1.8 (1H, m), 2.1–2.7 (2H, m), 2.41 (6H, s), 2.48 (3H, s), 2.7–3.0 (3H, m), 3.68 (3H, s), 5.2–5.4 (1H, m), 6.6–6.8 (2H, m), 6.9–7.5 (8H, m), 8.09 (1H, s), 8.26 (1H, d, J=8.1 Hz)

114) ¹H-NMR(CDCl₃) δ; 1.5–1.7 (1H, m), 2.1–2.3 (1H, m), 2.41 (6H, s), 2.4–2.6 (1H, m), 2.8–3.0 (3H, m), 3.71 (3H, s), 5.2–5.4 (1H, m), 6.6–6.8 (2H, m), 6.9–7.5 (7H, m), 7.7–7.8 (1H, m), 8.27 (1H, d, J=8.4 Hz), 8.57 (1H, s)

115) ¹H-NMR(CDCl₃) δ; 1.5–1.7 (1H, m), 2.1–2.7 (2H, m), 2.41 (6H, s), 2.7–3.0 (3H, m), 3.71 (3H, s), 5.2–5.4 (1H, m), 6.6–7.6 (8H, m), 7.70 (1H, d, J=8.3 Hz), 8.24 (1H, d, J=8.5 Hz), 8.59 (1H, s)

116) ¹H-NMR(CDCl₃) δ; 1.8–2.3 (3H, m), 2.7–2.9 (2H, m), 3.5–3.7 (1H, m), 6.8–8.0 (10H, m), 8.7–9.1 (1H, br)

Example 634

To a mixture of 5-oxo-1-[4-(3,5-dichlorobenzoylamino)benzoyl]-2,3,4,5-tetrahydro-1H-benzazepine (4 g) and pyridine (50 ml) is added hydroxylamine hydrochloride (1.84 g) and the mixture is refluxed for 2.5 hours. The reaction solution is concentrated and water is added to the resulting residue. The precipitated crystal is collected by filtration, and recrystallized from dioxane/water to give 5-hydroxyimino-1-[4-(3,5-dichlorobenzoylamino)benzoyl]-2,3,4,5-tetrahydro-1H-benzazepine (2 g) as white powder, m.p. 272°–273° C.

Example 635

5-Chloro-1-[4-(2-methylbenzoylamino)benzoyl]-2,3,4,5-tetrahydro-1H-benzazepine (0.8 g) is dissolved in dimethylformamide and thereto is added sodium azide (0.18 g) at room temperature. The mixture is stirred at room temperature overnight, and further reacted with heating at 50° C. for 5 hours. Water is added to the reaction mixture and the precipitated crystal is collected by filtration to give 5-azido-1-[4-(2-methylbenzoylamino)benzoyl)-2,3,4,5-tetrahydro-1H-benzazepine (0.68 g) as light brown powder.

¹H-NMR(CDCl₃) δ; 1.65–3.1 (8H, m), 4.7–6.6 (3H, m), 6.6–6.8 (1H, m), 6.85–7.65 (12H, m)

Example 636

5-Azido-1-[4-(2-methylbenzoylamino)benzoyl]-2,3,4,5-tetrahydro-1H-benzazepine (0.63 g) is dissolved in ethanol and thereto is added 10% Pd—C (0.1 g). The mixture is subjected to catalytic hydrogenation at room temperature under 1 atm. of hydrogen. Pd—C is removed by filtration and the filtrate is evaporated. The resulting residue is purified by silica gel column chromatography (eluent; dichloromethane:methanol=50:1), and recrystallized from diethyl ether to give 5-amino-1-[4-(2-methylbenzoylamino) benzoyl]-2,3,4,5-tetrahydro-1H-benzazepine (0.34 g) as white powder, m.p. 198.5°–199.5° C.

Example 637

To 5-hydroxy-1-[4-(2-methylbenzoylamino)benzoyl]-2,3,4,5-tetrahydro-1H-benzazepine (0.58 g) are added acetic anhydride (8.0 ml) and pyridine (2.0 ml). The mixture is stirred at room temperature for 1 hour. Water is added to the reaction mixture and the precipitated crystal is collected by filtration, and recrystallized from ethyl acetate/n-hexane to give 5-acetyloxy-1-[4-(2-methylbenzoylamino)benzoyl]-2,3,4,5-tetrahydro-1H-benzazepine (0.56 g) as white powder, m.p. 193°–194° C.

Example 638

5-Ethoxycarbonylmethoxy-1-[4-(2-methylbenzoylamino) benzoyl]-2,3,4,5-tetrahydro-1H-benzazepine (1.00 g) is dissolved in methanol (35 ml) and thereto are added aqueous ammonia (20 ml) and ammonium chloride (0.50 g). The mixture is heated at 100° C. for 3.5 hours in a sealed tube. After cooling, the reaction solution is concentrated under reduced pressure and acidified with hydrochloric acid, and extracted with dichloromethane. The extract is dried over magnesium sulfate and the solvent is distilled off. The resulting residue is purified by silica gel column chromatography (eluent; dichloromethane:methanol=15:1) to give 5-carbamoylmethoxy-1-[4-(2-methylbenzoylamino) benzoyl]-2,3,4,5-tetrahydro-1H-benzazepine (0.68 g) as colorless amorphous.

¹H-NMR(CDCl₃) δ; 1.56–2.67 (4H, m), 2.46 (3H, s), 2.67–3.03 (1H, m), 3.82–4.32 (2H, m), 4.45–5.15 (2H, m), 5.43–5.83 (1H, m), 6.20–6.45 (1H, m), 6.50–6.86 (2H, m), 6.86–7.70 (10H, m), 7.76–8.10 (1H, m)

Using the suitable starting materials, the compounds of the above Examples 593 and 594 are obtained in the same manner as in Example 638.

Example 639

5-Ethoxycarbonylmethoxy-1-[4-(2,4-dichlorobenzoylamino)benzoyl]-2,3,4,5-tetrahydro-1H-benzazepine (0.94 g) is dissolved in ethanol (100 ml) and thereto is added 5N aqueous sodium hydroxide solution (0.50 ml). The mixture is stirred at room temperature for 2 hours. The reaction solution is concentrated under reduced pressure and to the resulting residue is added diluted hydrochloric acid and then extracted with dichloromethane. The extract is dried over magnesium sulfate and the solvent is distilled off. The resulting residue is washed with n-hexane and collected by filtration to give 5-carboxymethoxy-1-[4-(2,4-dichlorobenzoylamino)benzoyl]-2,3,4,5-tetrahydro-1H-benzazepine (0.79 g) as colorless amorphous.

¹H-NMR(CDCl₃) δ; 1.52–1.89 (2H, m), 1.89–2.56 (2H, m), 2.65–3.02 (1H, m), 3.90–4.40 (2H, m), 4.40–5.07 (2H, m), 6.58–6.78 (1H, m), 6.90–7.70 (10H, m), 8.57–8.81 (1H, brs)

Using the suitable starting materials, the compounds of the above Examples 595 and 596 are obtained in the same manner as in Example 639.

Example 640

5-Carboxymethoxy-1-[4-(2-methylbenzoylamino) benzoyl]-2,3,4,5-tetrahydro-1H-benzazepine (0.55 g) is dissolved in dimethylformamide (20 ml) and thereto are added dimethylamine hydrochloride (0.20 g) and diethyl chlorophosphate (0.33 g). To the mixture is added triethylamine (1.0 ml) under ice-cooling, and the mixture is stirred under ice-cooling for 30 minutes, and at room temperature for more 2 hours. Water is added to the reaction solution and the precipitated crystal is collected by filtration and recrystallized from ethyl acetate/n-hexane to give 5-dimethylaminocarbonylmethoxy- 1-[4-(2-methylbenzoylamino)benzoyl]-2,3,4,5-tetrahydro-1H-benzazepine (0.50 g) as colorless prisms, m.p. 203°–204° C.

Using the suitable starting materials, the compounds of the above Examples 599 and 600 are obtained in the same manner as in Example 640.

Example 641

5-[3-(Phthalimid-1-yl)propoxy]-1-[4-(2-methylbenzoylamino)benzoyl]-2,3,4,5-tetrahydro-1H-benzazepine (1.26 g) is dissolved in ethanol (100 ml) and thereto is added hydrazine hydrate (1.0 ml). The mixture is refluxed with stirring for 1 hour. The reaction solution is evaporated under reduced pressure and to the resulting residue is added dichloromethane. The insoluble materials are removed by filtration. The filtrate is purified by silica gel column chromatography (eluent; dichloromethane:methanol:aqueous ammonia=70:10:1) to give 5-(3-aminopropoxy)-1-[4-(2-methylbenzoylamino)benzoyl]-2,3,4,5-tetrahydro-1H-benzazepine (0.70 g) as colorless amorphous.

¹H-NMR(CDCl₃) δ; 1.42–2.32 (6H, m), 2.44 (3H, s), 2.57–2.97 (1H, m), 3.12–3.83 (4H, m), 4.39–5.13 (2H, m), 6.50–6.71 (1H, m), 6.90–7.73 (12H, m)

Example 642

A solution of 5-dimethylamino-1-[3-methoxy-4-(2-methylbenzoylamino)benzoyl]-2,3,4,5-tetrahydro-1H-benzazepine (0.50 g) in dichloromethane (30 ml) is added dropwise to a solution of 1M boron tribromide in dichloromethane (5.46 ml) at −45° C. After completion of the dropping, the mixture is stirred for 1 day while the temperature of the reaction mixture is gradually raised to room temperature. To the reaction solution is added water and the mixture is neutralized with sodium hydrogen carbonate, and extracted with dichloromethane. The extract is washed with saturated saline solution and dried over magnesium sulfate. The solvent is distilled off and the resulting residue is purified by silica gel column chromatography (eluent; chloroform:methanol=500:1), and recrystallized from methanol/diethyl ether to give 5-dimethylamino-1-[3-hydroxy-4-(2-methylbenzoylamino)benzoyl]-2,3,4,5-tetrahydro-1H-benzazepine (0.33 g) as white powder, m.p. 201.5°–202.5° C.

Using the suitable starting materials, the compounds of the above Examples 10, 32, 343, 356, 535, 555 and 556 are obtained in the same manner as in Example 642.

Example 643

To a solution of 4-[4-(2-methylbenzoylamino)benzoyl]-3,4-dihydro-2H-1,4-benzazepine (0.5 g) in dichloromethane (10 ml) is added m-chloroperbenzoic acid (0.58 g) under ice-cooling, and the mixture is stirred at room temperature for 6 hours. The above reaction solution is poured into an aqueous solution of sodium carbonate (0.6 g) in water (10 ml) and the mixture is extracted with dichloromethane. The extract is washed with water, and dried over magnesium sulfate. The solvent is distilled off under reduced pressure and the resulting residue is purified by silica gel column chromatography (eluent; dichloromethane:methanol= 100:1), and recrystallized from diethyl ether/dichloromethane to give 4-[4-(2-methylbenzoylamino)benzoyl]-3,4-dihydro-2H-1,4-benzothiazine-1,1-dioxide (0.49 g) as white powder, m.p. 219°–220° C.

Using the suitable starting materials, the compound of the above Example 630 is obtained in the same manner as in Example 643.

Example 644

To a suspension of 4-[4-(2-methylbenzoylamino)benzoyl]-3,4-dihydro-2H-1,4-benzothiazine (0.5 g) in methanol (15 ml) is added an aqueous solution of sodium metaperiodate (0.28 g) in water (2.5 ml) and the mixture is stirred at room temperature for 72 hours. Water is added to the reaction solution and extracted with dichloromethane. The extract is dried over magnesium sulfate and the solvent is distilled off under reduced pressure. The resulting residue is purified by silica gel column chromatography (eluent; dichloromethane:methanol=100:1), and recrystallized from dichloromethane/diethyl ether to give 4-[4-(2-methylbenzoylamino)benzoyl]-3,4-dihydro-2H-1,4-benzothiazin-1-oxide (0.34 g) as white powder, m.p. 240°–241° C.

Using the suitable starting materials, the compound of the above Example 631 is obtained in the same manner as in Example 644.

Example 645

5-Hydroxy-1-[4-(2-methylbenzoylamino)benzoyl]-2,3,4,5-tetrahydro-1H-benzazepine (3.57 g) is dissolved in dichloromethane (30 ml) and pyridine (1.1 ml), and thereto is added dropwise methanesulfonyl chloride (0.9 ml) in small portions at 0° C. Then, the mixture is stirred at room temperature for 3 days. The solvent is distilled off and the resulting residue is poured into ice-water. The precipitated crystal is collected by filtration, washed with water, and dried to give 5-chloro-1-[4-(2-methylbenzoylamino)benzoyl]-2,3,4,5-tetrahydro-1H-benzazepine (3.10 g) as light yellow powder.

$^1$H-NMR(CDCl$_3$) δ; 1.7–2.9 (8H, m), 4.5–6.5 (3H, m), 6.55–6.75 (1H, m), 6.85–7.6 (12H, m)

Example 646

5-Hydroxy-1-[4-(2-methylbenzoylamino)benzoyl]-2,3,4,5-tetrahydro-1H-benzazepine (2.69 g) is dissolved in dimethylformamide (30 ml) and thereto are added 60% sodium hydride dispersion in mineral oil (0.44 g) and ethyl bromoacetate (1.00 ml) under ice-cooling, and the mixture is stirred at room temperature for 4 hours. The reaction solution is poured into an aqueous ammonium chloride solution under ice-cooling, and extracted with ethyl acetate. The extract is dried over magnesium sulfate and the solvent is distilled off. The resulting residue is purified by silica gel column chromatography (eluent; ethyl acetate:n-hexane= 1:2), and recrystallized from ethyl acetate/n-hexane to give 5-ethoxycarbonylmethoxy-1-[4-(2-methylbenzoylamino)benzoyl-2,3,4,5-tetrahydro-1H-benzazepine (2.10 g) as white powder, m.p. 178°–181° C.

Using the suitable starting materials, the compounds of the above Examples 585–588 and 590–606 are obtained in the same manner as in Example 646.

Example 647

Using the suitable starting materials, the compounds of the above Examples 546 and 578–581 are obtained in the same manner as in Example 384.

Example 648

Using the suitable starting materials, the compounds of the above Examples 537–545, 547, 549–556, 561–564, 566, 568–571, 577, 601–603 and 607–625 are obtained in the same manner as in Example 388.

Example 649

Using the suitable starting materials, the compounds of the above Examples 549, 568–571, 575 and 606 are obtained in the same manner as in Example 389.

Example 650

Using the suitable starting materials, the compounds of the above Examples 537–545, 547, 549–556, 561–566, 568–571, 575, 577, 607, 608 and 613–625 are obtained in the same manner as in Example 390.

Example 651

Using the suitable starting materials, the compounds of the above Examples 601–603, 605 and 606 are obtained in the same manner as in Example 397.

Example 652

Using the suitable starting materials, the compound of the above Example 604 is obtained in the same manner as in Example 398.

Example 653

Using the suitable starting materials, the following compound is obtained in the same manner as in Examples 1, 382, 388 and 390.

5-Methylamino-1-[2-chloro-4-(2-methylbenzoylamino)benzoyl]-2,3,4,5-tetrahydro-1H-benzazepine, white powder, m.p. 184.5°–185.5° C. (recrystallized from ethanol)

Using the suitable starting materials, the compounds of the following Table 4 are obtained in the same manner as in Examples 1 and 382.

TABLE 4
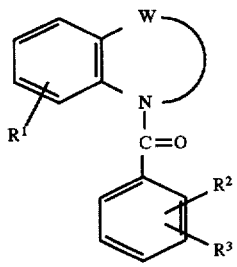
Example 654
Structure
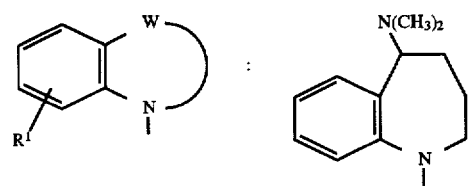
R²:  2-OH
R³:
Crystalline form:         White powder
Recrystallization solvent: Methanol/n-hexane
Melting Point:            193.5–196° C.
Form:                     Free
Example 655
Structure
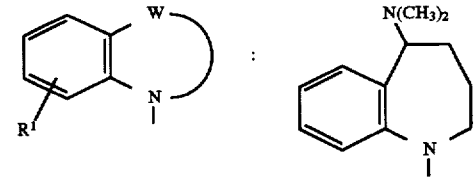
R²:  2-OH
R³:
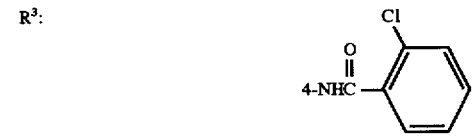
Crystalline form:         White powder
Recrystallization solvent: Methanol/n-hexane
Melting Point:            195–198° C.
Form:                     Free

TABLE 4-continued
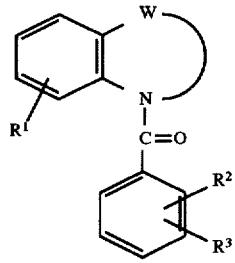
Example 656
Structure
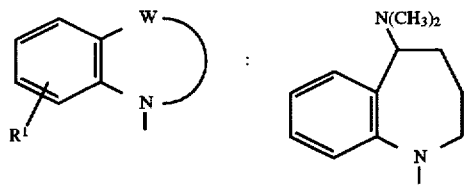
R²: 2-OC₂H₅
R³:
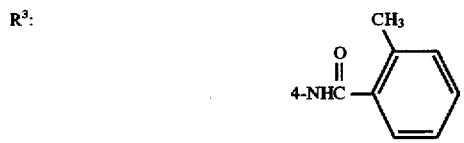
| | |
|---|---|
| Crystalline form: | White powder |
| Recrystallization solvent: | Methanol |
| Melting Point: | 230.5–231.5° C. |
| Form: | Free |
Example 657
Structure
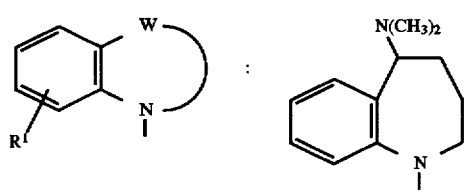
R²: 2-OC₂H₅
R³:
| | |
|---|---|
| Crystalline form: | White powder |
| Recrystallization solvent: | Methanol/diethyl ether |
| Melting Point: | 223–224.5° C. |
| Form: | Free |

TABLE 4-continued
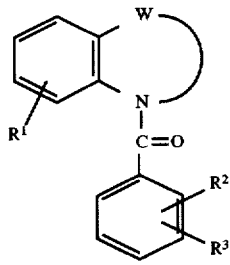
Example 658
Structure
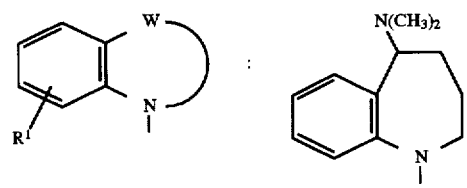
R²:  2-OC₂H₅
R³:
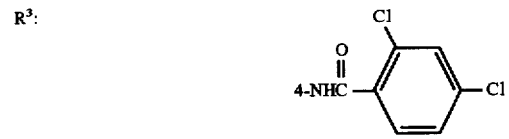
| Crystalline form: | White powder |
|---|---|
| Recrystallization solvent: | Methanol/diethyl ether |
| Melting Point: | 173–174° C. |
| Form: | Free |
Example 659
Structure
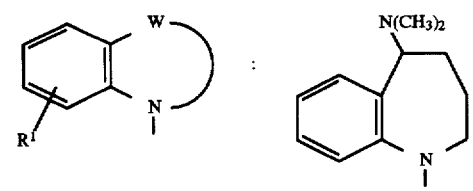
R²:  3-CH₃
R³:
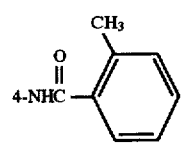
| Crystalline form: | White powder |
|---|---|
| Recrystallization solvent: | Methanol/diethyl ether |
| Melting Point: | 174–175° C. |
| Form: | Free |

TABLE 4-continued
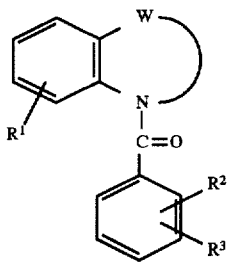
Example 660
Structure
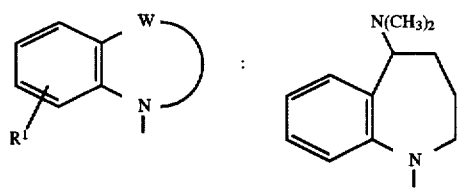
R²:  3-CH₃
R³:
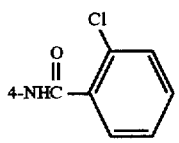
| Crystalline form: | White powder |
|---|---|
| Recrystallization solvent: | Methanol/diethyl ether |
| Melting Point: | 198–200° C. |
| Form: | Free |
Example 661
Structure
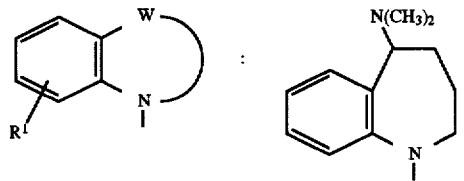
R²:  3-CH₃
R³:
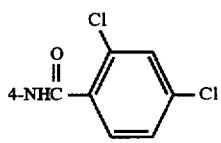
| Crystalline form: | White powder |
|---|---|
| Recrystallization solvent: | Methanol/n-hexane |
| Melting Point: | 149–150.5° C. |
| Form: | Free |

TABLE 4-continued
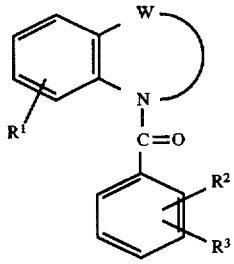
Example 662
Structure
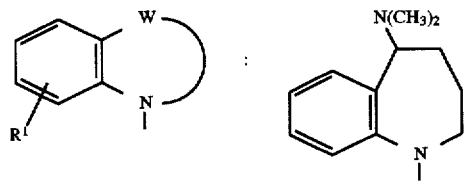
R²:  2-CH₃
R³:
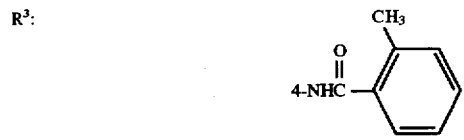
Crystalline form: White powder
Recrystallization solvent: Methanol/diethyl ether
Melting Point: 183–185° C.
Form: Free
Example 663
Structure
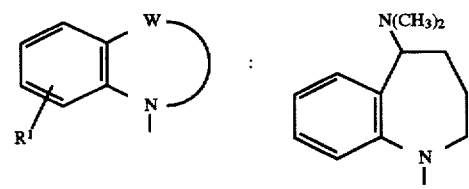
R²:  2-CH₃
R³:
Crystalline form: White powder
Recrystallization solvent: Methanol/diethyl ether
Melting Point: 203–207° C.
Form: Free TABLE 4-continued
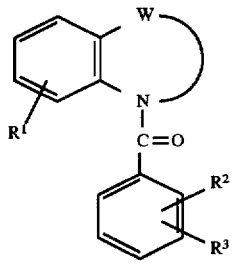
Example 664
Structure
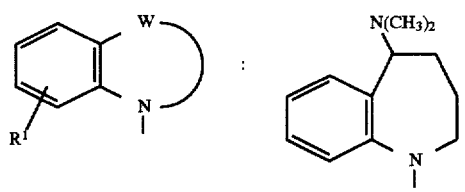
R²: 2-CH₃
R³:
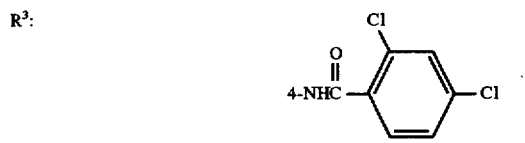
| Crystalline form: | White powder |
|---|---|
| Recrystallization solvent: | Methanol/diethyl ether |
| Melting Point: | 221–222° C. |
| Form: | Free |
Example 665
Structure
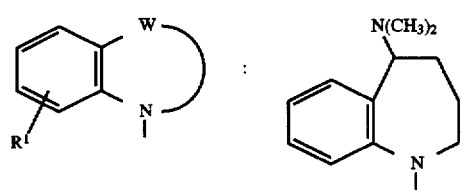
R²: 2-F
R³:
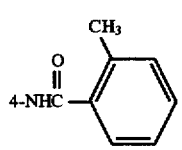
| Crystalline form: | White powder |
|---|---|
| Recrystallization solvent: | Methanol/diethyl ether |
| Melting Point: | 189–191° C. |
| Form: | Free |

TABLE 4-continued
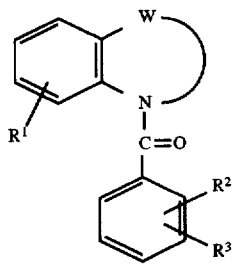
Example 666
Structure
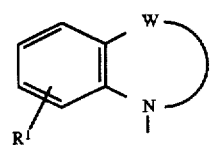 : 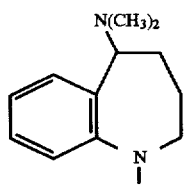
R²:     2-F
R³: 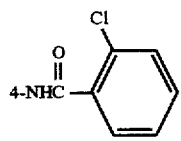
| | |
|---|---|
| Crystalline form: | White powder |
| Recrystallization solvent: | Methanol/diethyl ether |
| Melting Point: | 215.5–217° C. |
| Form: | Free |
Example 667
Structure
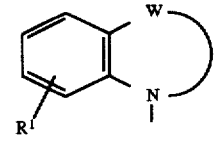 : 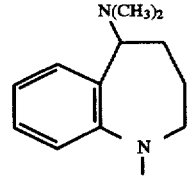
R²:     2-F
R³: 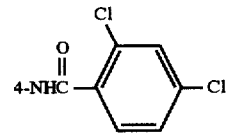
| | |
|---|---|
| Crystalline form: | White powder |
| Recrystallization solvent: | Methanol/n-hexane |
| Melting Point: | 192–194° C. |
| Form: | Free |

TABLE 4-continued
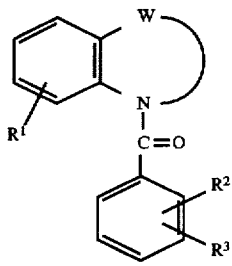
Example 668
Structure
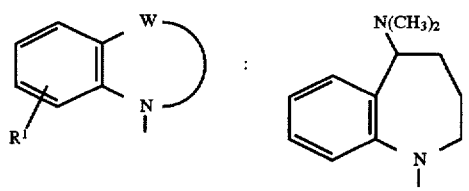
R²: 3-F
R³:
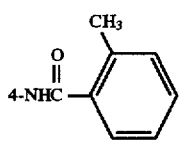
| Crystalline form: | White powder |
|---|---|
| Recrystallization solvent: | Methanol/diethyl ether |
| Melting Point: | 195–196° C. |
| Form: | Free |
Example 669
Structure
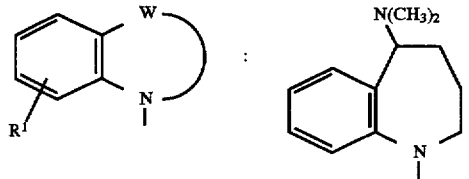
R²: 3-F
R³:
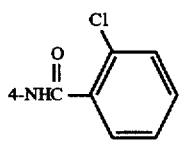
| Crystalline form: | White powder |
|---|---|
| Recrystallization solvent: | Methanol/diethyl ether |
| Melting Point: | 202–204.5° C. |
| Form: | Free |

TABLE 4-continued
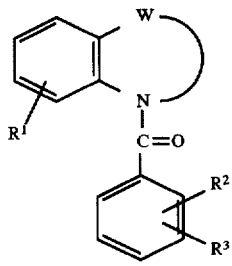
Example 670
Structure
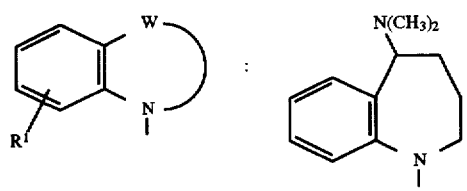
R²: H
R³: 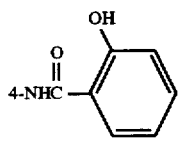
Crystalline form: White powder
Recrystallization solvent: Methanol/diethyl ether
Melting Point: 183–187° C.
Form: Free
Example 671
Structure
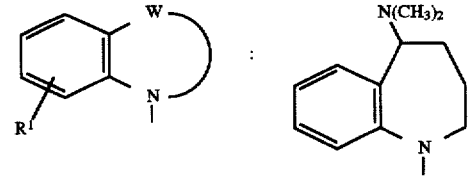
R²: H
R³: 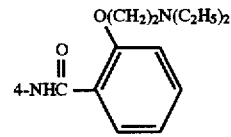
Crystalline form: White powder
Recrystallization solvent: Methanol/diethyl ether
Melting Point: 120–122° C.
Form: Free TABLE 4-continued
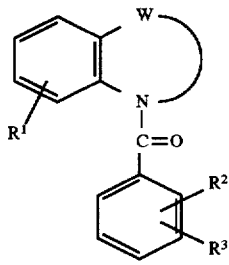
Example 672
Structure
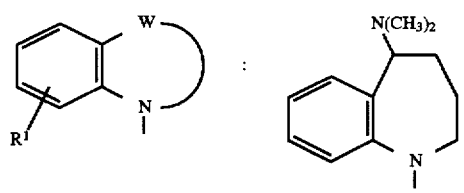
R²: H
R³:
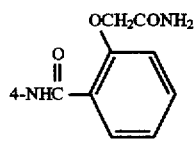
Crystalline form: White powder
Recrystallization solvent: Chloroform/diethyl ether
Melting Point: 208–210° C.
Form: Free
Example 673
Structure
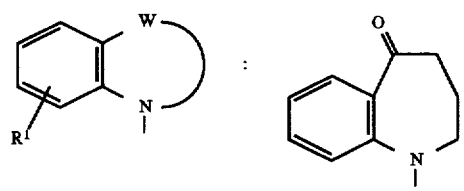
R²: 2-OCH₃
R³:
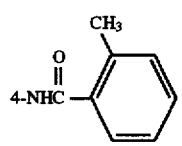
Crystalline form: White powder
Recrystallization solvent: Methanol/diethyl ether
Melting Point: 182–183° C.
Form: Free TABLE 4-continued
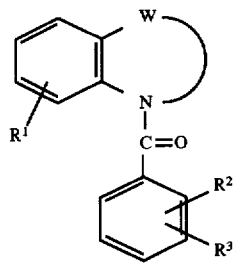
Example 674
Structure
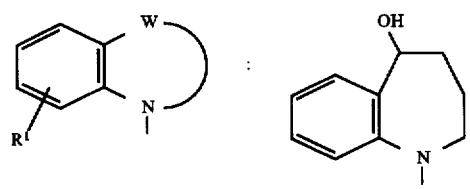
R²: 2-OCH₃
R³:
4-NHC(=O)— (2-methylphenyl)
| Crystalline form: | White powder |
| Recrystallization solvent: | Methanol/diethyl ether |
| Melting Point: | 257–259° C. |
| Form: | Free |
Example 675
Structure
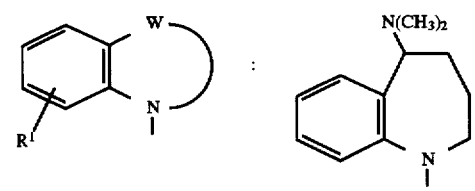
R²: 2-OC₂H₅
R³:
4-NHCOCH₂—phenyl
| Crystalline form: | White powder |
| Recrystallization solvent: | Dichloromethane/diethyl ether |
| Melting Point: | 134–135° C. |
| Form: | Free |

TABLE 4-continued
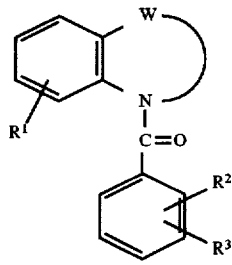
Example 676
Structure
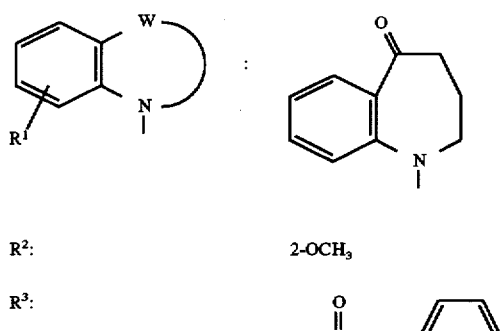
| | |
|---|---|
| R²: | 2-OCH₃ |
| R³: | 4-NHCOCH₂—(phenyl) |
| Crystalline form: | White powder |
| Recrystallization solvent: | Methanol/diethyl ether |
| Melting Point: | 167–169° C. |
| Form: | Free |
Example 677
Structure
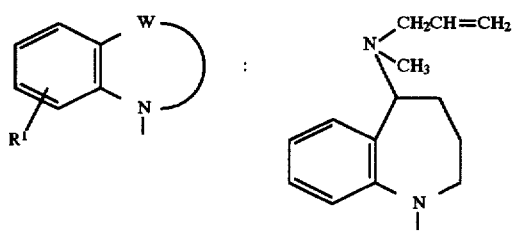
| | |
|---|---|
| R²: | 2-Cl |
| R³: | 4-NHC(=O)—(2-CH₃-phenyl) |
| Crystalline form: | Light brown prisms |
| Recrystallization solvent: | Ethyl acetate/n-hexane |
| Melting Point: | 170–172° C. |
| Form: | Free |

TABLE 4-continued
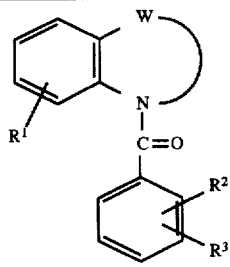
Example 678
Structure
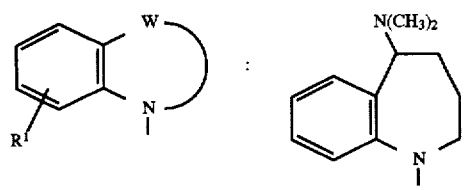
$R^2$: 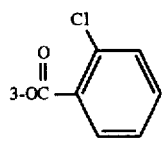
$R^3$: 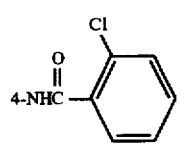
| | |
|---|---|
| Crystalline form: | White powder |
| Recrystallization solvent: | Ethyl acetate/n-hexane |
| Melting Point: | 181.5–182.5° C. |
| Form: | Free |
Example 679
Structure
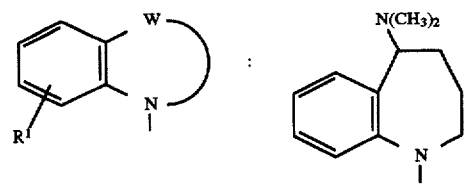
$R^2$: 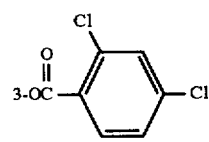
$R^3$: 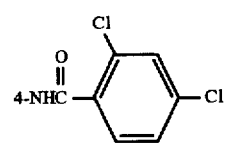
| | |
|---|---|
| Crystalline form: | White powder |
| Recrystallization solvent: | Ethyl acetate/n-hexane |
| Melting Point: | 176.5–177° C. |

TABLE 4-continued
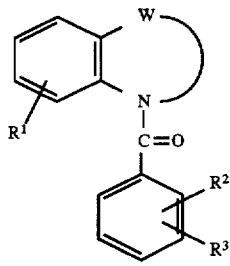
| Form: | Free |
|---|---|
| | Example 680 |
Structure
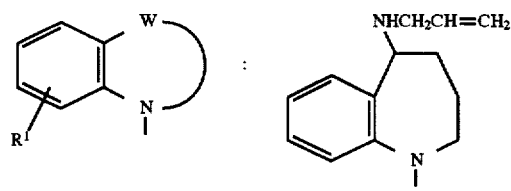 :
| $R^2$: | 2-Cl |
|---|---|
$R^3$:
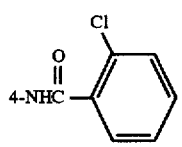
| Crystalline form: | Yellow amorphous |
|---|---|
| NMR analysis: | 117) |
| Form: | Free |
| | Example 681 |
Structure
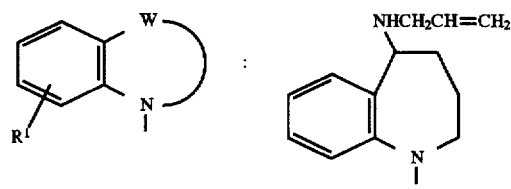 :
| $R^2$: | 2-Cl |
|---|---|
$R^3$:
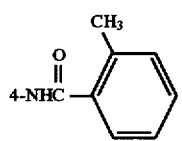
| Crystalline form: | Yellow amorphous |
|---|---|
| NMR analysis: | 118) |
| Form: | Free |

TABLE 4-continued
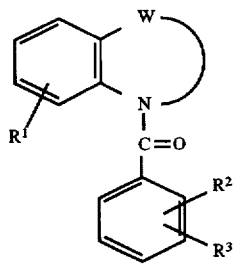
Example 682
Structure
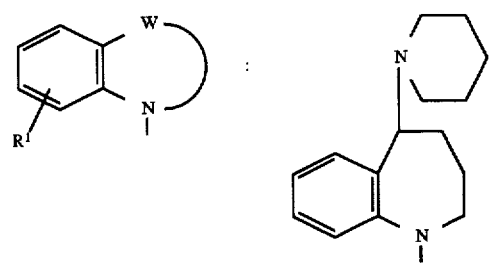
R²: H
R³: 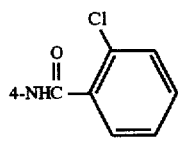
Crystalline form: White powder
Recrystallization solvent: Ethanol
Melting Point: 236–239° C.
Form: Free
Example 683
Structure
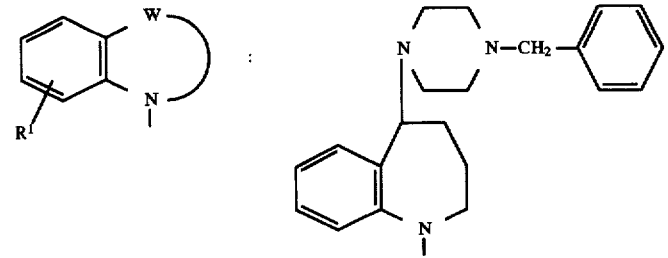
R²: H
R³: 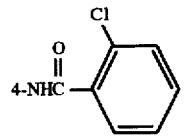
Crystalline form: White powder
Recrystallization solvent: Ethyl acetate/n-hexane
Melting Point: 153–154° C.
Form: Free TABLE 4-continued
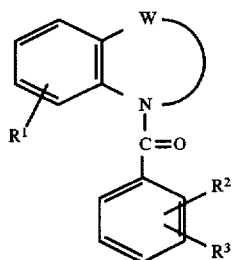
Example 684
Structure
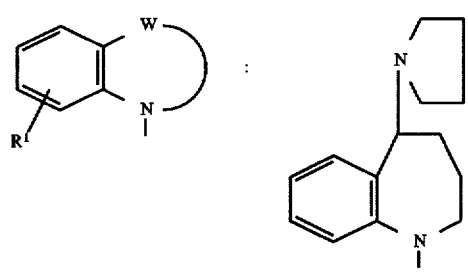
R²: H
R³:
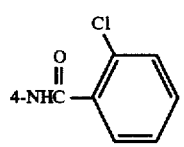
Crystalline form: White powder
Recrystallization solvent: Ethyl acetate
Melting Point: 128–130° C.
Form: Free
Example 685
Structure
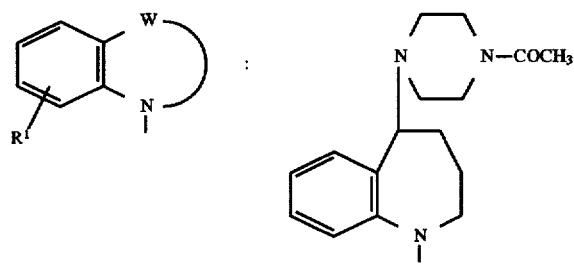
R²: H
R³:
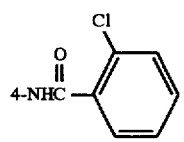
Crystalline form: White powder
Recrystallization solvent: Ethanol/diethyl ether
Melting Point: 231–234° C.
Form: Free TABLE 4-continued
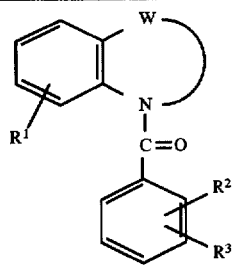
Example 686
Structure
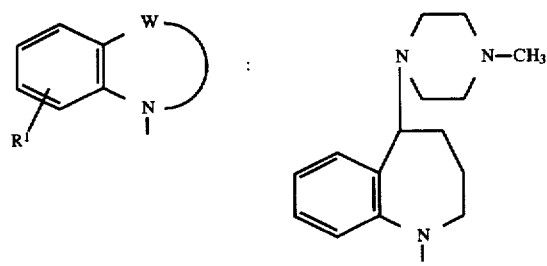
R²: H
R³: 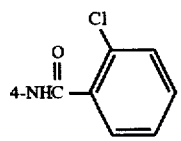
Crystalline form: White powder
Recrystallization solvent: Ethyl acetate
Melting Point: 246–248° C.
Form: Free
Example 687
Structure
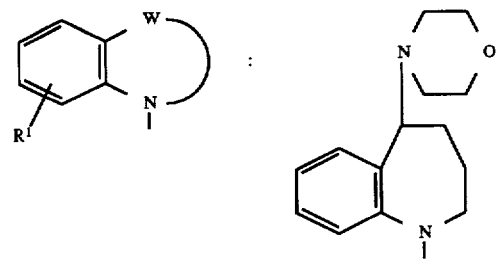
R²: H
R³: 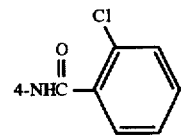
Crystalline form: White powder
Recrystallization solvent: Ethanol/water
Melting Point: 248–248.5° C.
Form: Free TABLE 4-continued
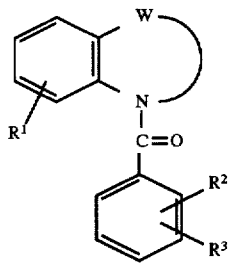
Example 688
Structure
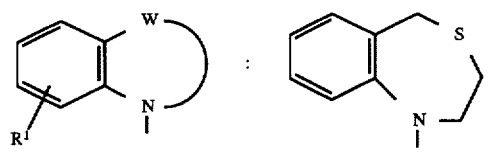
R²: H
R³: 
| Crystalline form: | White powder |
|---|---|
| Recrystallization solvent: | Dichloromethane/diethyl ether |
| Melting Point: | 204–205° C. |
| Form: | Free |
Example 689
Structure
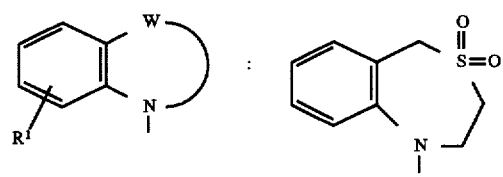
R²: H
R³:
| Crystalline form: | White powder |
|---|---|
| Recrystallization solvent: | Dichloromethane/diethyl ether |
| Melting Point: | >300° C. |
| NMR analysis: | 119) |
| Form: | Free |

TABLE 4-continued
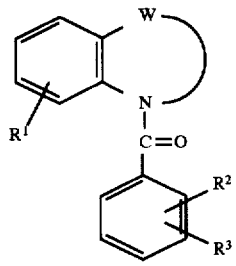
Example 690
Structure
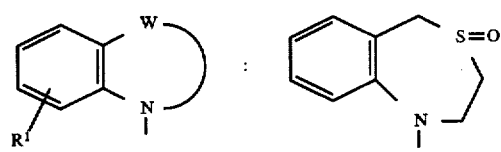
R²: H
R³: 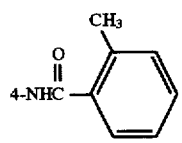
| | |
|---|---|
| Crystalline form: | White powder |
| Recrystallization solvent: | Dichloromethane/diethyl ether |
| Melting Point: | 292–294° C. |
| Form: | Free |
Example 691
Structure
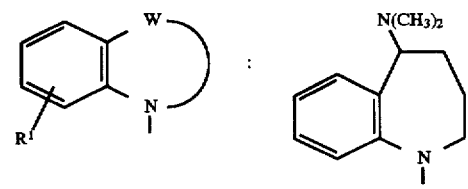
R²: 2-N(CH₃)₂
R³: 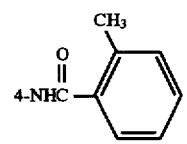
| | |
|---|---|
| Crystalline form: | Colorless amorphous |
| NMR analysis: | 120) |
| Form: | Free |

TABLE 4-continued
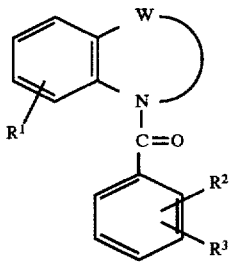
Example 692
Structure
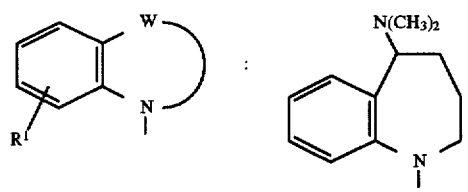
R²: 2-N(CH₃)₂
R³:
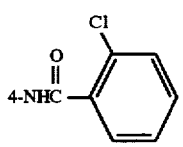
| Crystalline form: | Colorless amorphous |
| --- | --- |
| NMR analysis: | 121) |
| Form: | Free |
Example 693
Structure
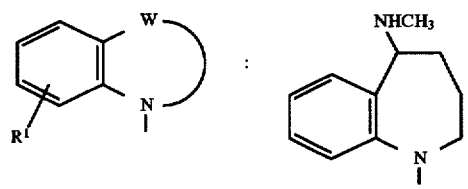
R²: 2-Cl
R³:
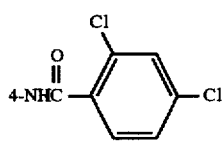
| Crystalline form: | Colorless amorphous |
| --- | --- |
| NMR analysis: | 122) |
| Form: | Free |

TABLE 4-continued
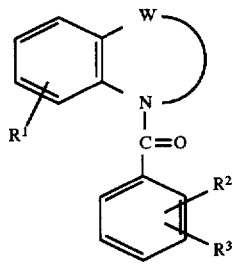
Example 694
Structure
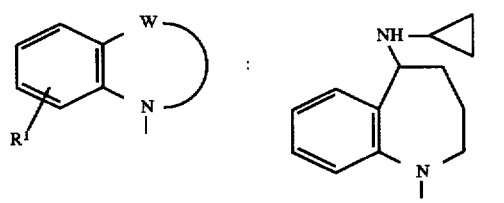
R²: 2-Cl
R³: 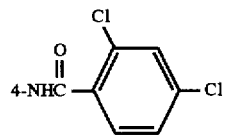
Crystalline form: Colorless amorphous
NMR analysis: 123)
Form: Free
Example 695
Structure
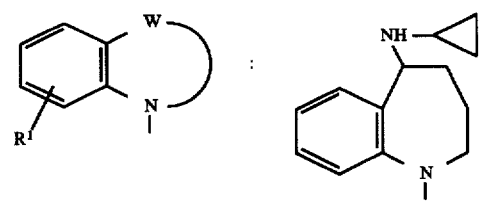
R²: 2-Cl
R³: 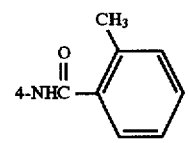
Crystalline form: White powder
Recrystallization solvent: Ethanol
Melting Point: 198.5–199° C.
Form: Free TABLE 4-continued
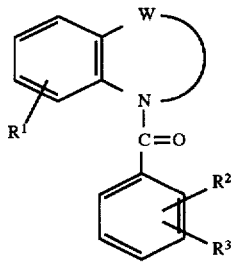
Example 696
Structure
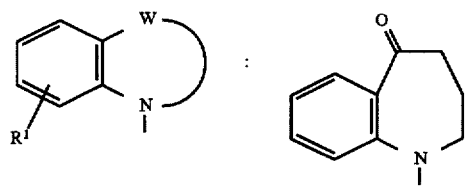
R²: 2-Cl
R³:
| Crystalline form: | White powder |
|---|---|
| Recrystallization solvent: | Diethyl ether/dichloromethane |
| Melting Point: | 168–170° C. |
| Form: | Free |
Example 697
Structure
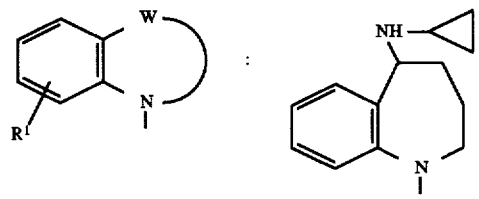
R²: 2-Cl
R³:
| Crystalline form: | White powder |
|---|---|
| Recrystallization solvent: | Diethyl ether/dichloromethane |
| Melting Point: | 175–176° C. |
| Form: | Free |

TABLE 4-continued
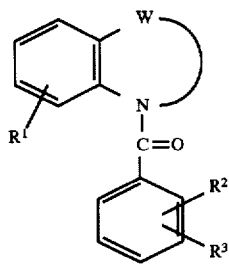
Example 698
Structure
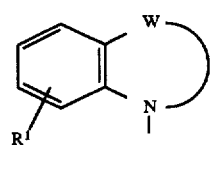 : 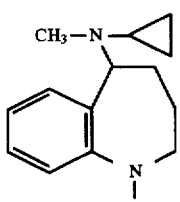
R²: 2-Cl
R³: 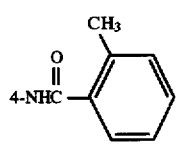
Crystalline form: White powder
Recrystallization solvent: Diethyl ether/dichloromethane
Melting Point: 177–178° C.
Form: Free
Example 699
Structure
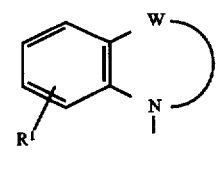 : 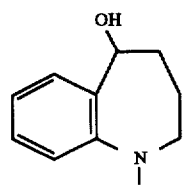
R²: 2-Cl
R³: 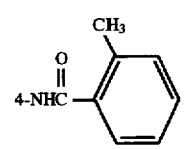
Crystalline form: White powder
Recrystallization solvent: Diethyl ether/dichloromethane
Melting Point: 222–223.5° C.
Form: Free TABLE 4-continued
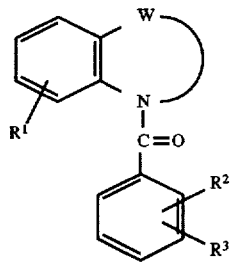
Example 700
Structure
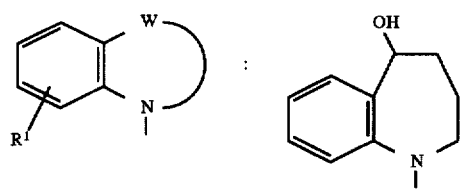
R²: 2-Cl
R³: 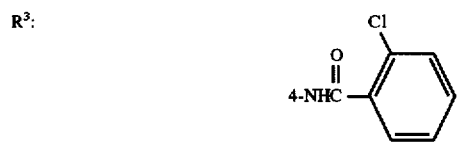
4-NHC(=O)- (2-Cl phenyl)
| Crystalline form: | White powder |
| Recrystallization solvent: | Diethyl ether/dichloromethane |
| Melting Point: | 243–244° C. |
| Form: | Free |
Example 701
Structure
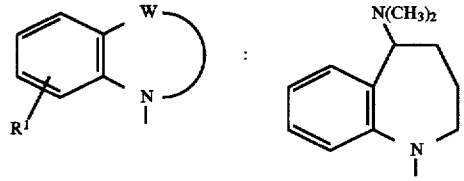
R²: H
R³: 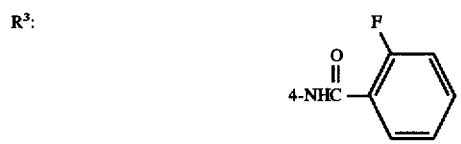
4-NHC(=O)- (2-F phenyl)
| Crystalline form: | White powder |
| Recrystallization solvent: | Diethyl ether/dichloromethane |
| Melting Point: | 180–181° C. |
| Form: | Free |

TABLE 4-continued
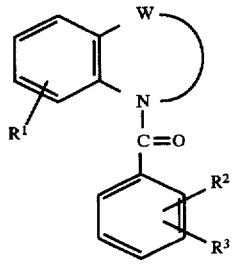
Example 702
Structure
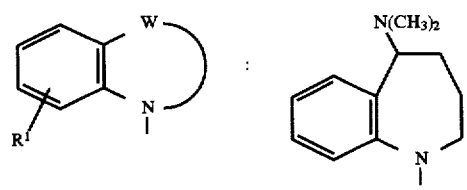
R²: H
R³:
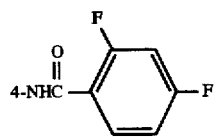
| Crystalline form: | Colorless amorphous |
| NMR analysis: | 124) |
| Form: | Free |
Example 703
Structure
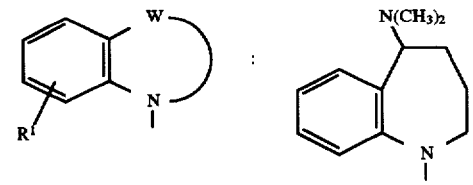
R²: H
R³:
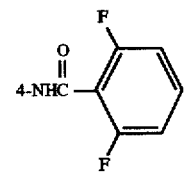
| Crystalline form: | White powder |
| Recrystallization solvent: | Diethyl ether/dichloromethane |
| Melting Point: | 231–233° C. |
| Form: | Free |

TABLE 4-continued
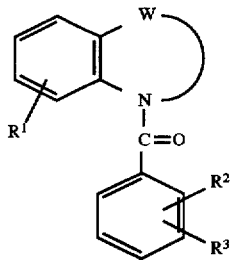
Example 704
Structure
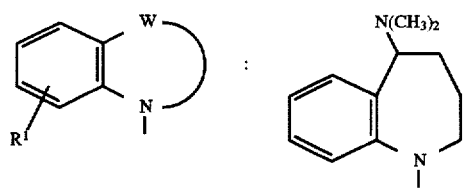
R²: H
R³: 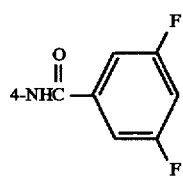
| Crystalline form: | White powder |
| --- | --- |
| Recrystallization solvent: | Diethyl ether/dichloromethane |
| Melting Point: | 196–198° C. |
| Form: | Free |
Example 705
Structure
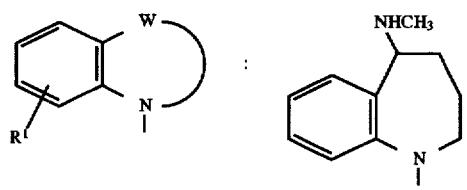
R²: 2-Cl
R³: 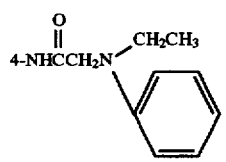
| Crystalline form: | Colorless amorphous |
| --- | --- |
| NMR analysis: | 125) |
| Form: | Free |

TABLE 4-continued
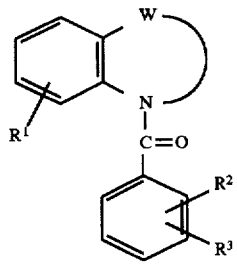
Example 706
Structure
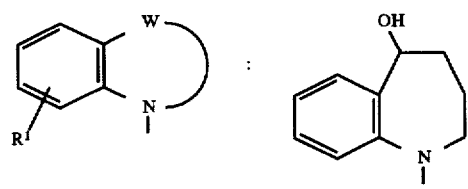
R²:     2-Cl
R³:
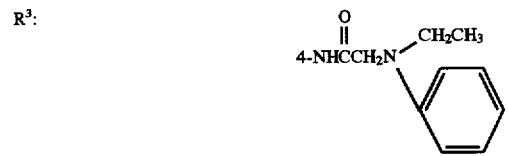
Crystalline form:     Yellow amorphous
NMR analysis:     126)
Form:     Free
Example 707
Structure
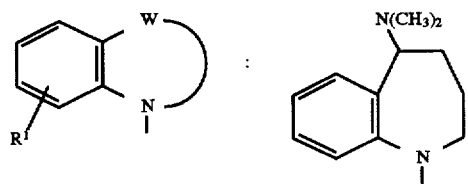
R²:     H
R³:
Crystalline form:     Yellow powder
Recrystallization solvent:     Diethyl ether/dichloromethane
Melting Point:     146–147° C.
Form:     Free TABLE 4-continued
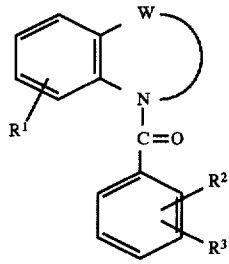
Example 708
Structure
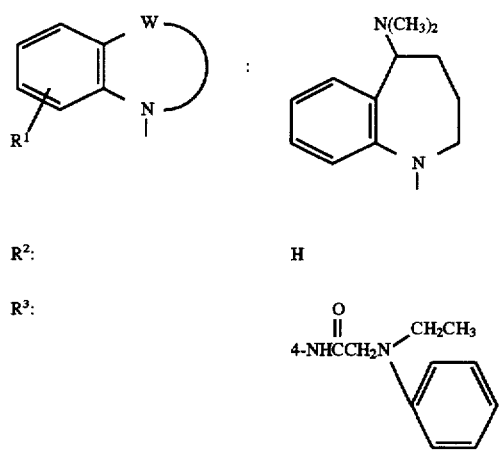
R²: H
R³:
4-NHCCH₂N with O=C, CH₂CH₃, and phenyl group
Crystalline form: Colorless amorphous
NMR analysis: 127)
Form: Free
Example 709
Structure
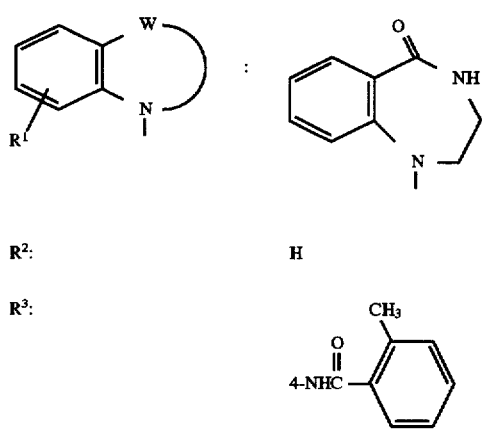
R²: H
R³: 4-NHC(=O)- with 2-methylphenyl
Crystalline form: White powder
Recrystallization solvent: Diethyl ether/dichloromethane
Melting Point: 220–221° C.
Form: Free TABLE 4-continued
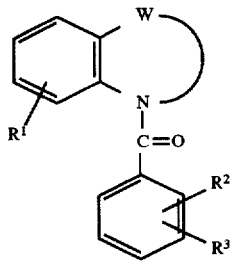
Example 710
Structure
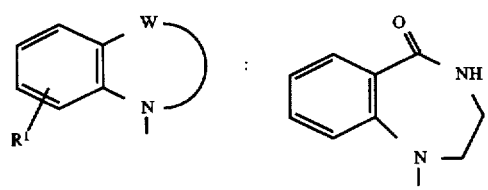
R²: H
R³: 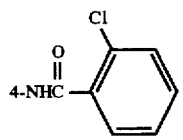
Crystalline form: White powder
Recrystallization solvent: Diethyl ether/dichloromethane
Melting Point: 170–172° C.
Form: Free
Example 711
Structure
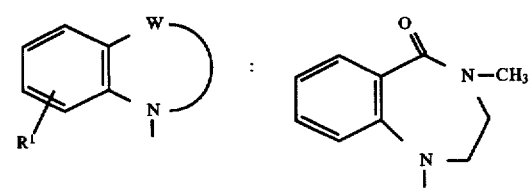
R²: H
R³: 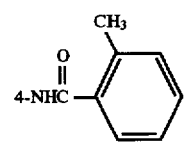
Crystalline form: Colorless amorphous
NMR analysis: 128)
Form: Free TABLE 4-continued
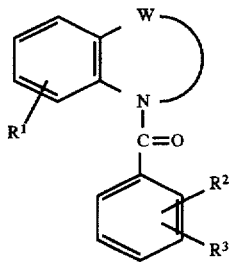
Example 712
Structure
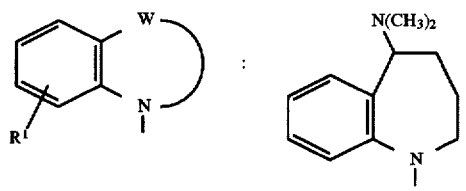
R²: H
R³:
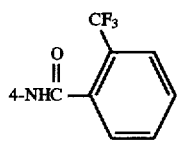
Crystalline form: White powder
Recrystallization solvent: Ethanol
Melting Point: 224–225° C.
Form: Free
Example 713
Structure
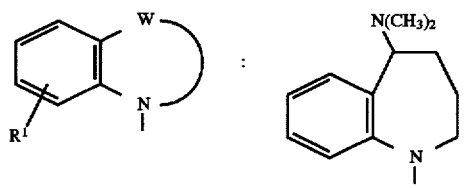
R²: 3-OCH₃
R³:
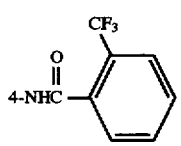
Crystalline form: White powder
Recrystallization solvent: Ethanol
Melting Point: 193–196° C.
Form: Free TABLE 4-continued
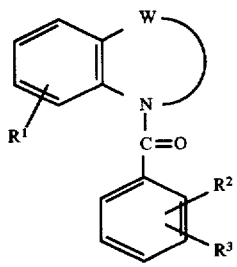
Example 714
Structure
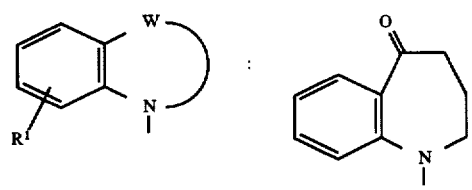
R²: 2-Cl
R³:
| Crystalline form: | White powder |
|---|---|
| Recrystallization solvent: | Ethanol |
| Melting Point: | 212–214° C. |
| Form: | Free |
Example 715
Structure
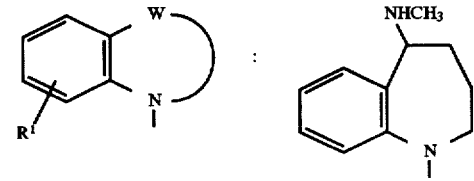
R²: 2-Cl
R³:
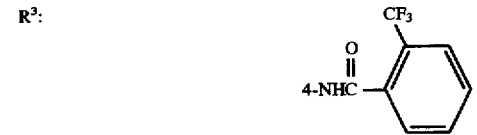
| Crystalline form: | White powder |
|---|---|
| Recrystallization solvent: | Ethanol |
| Melting Point: | 211–213° C. |
| Form: | Free |

TABLE 4-continued
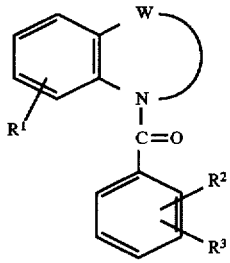
Example 716
Structure
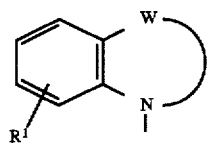 : 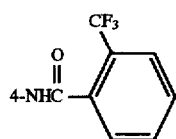
R²:           2-Cl
R³:           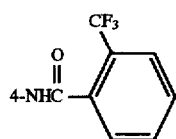

Crystalline form:        White powder
Recrystallization solvent:   Ethanol
Melting Point:           213–215° C.
Form:                    Free
Example 717
Structure
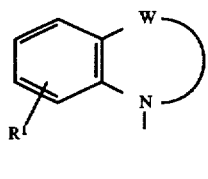 : 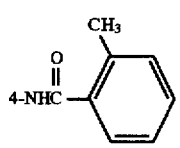
R²:           2-Cl
R³:           
Crystalline form:        White powder
Recrystallization solvent:   Ethanol
Melting Point:           199–201° C.
Form:                    Free TABLE 4-continued
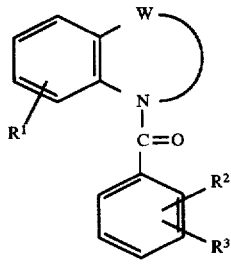
Example 718
Structure
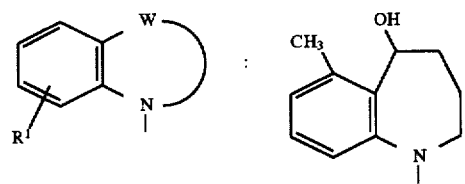
R²: 2-Cl
R³:
| | |
|---|---|
| Crystalline form: | White powder |
| Recrystallization solvent: | Ethanol |
| Melting Point: | 238–240° C. |
| Form: | Free |
Example 719
Structure
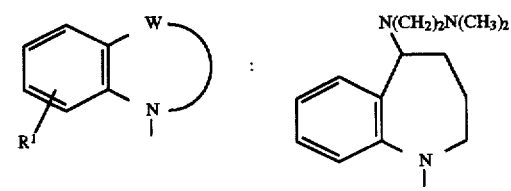
R²: 2-Cl
R³:
| | |
|---|---|
| Crystalline form: | White powder |
| Recrystallization solvent: | Ethanol |
| Melting Point: | 188–189° C. |
| Form: | Free |

TABLE 4-continued
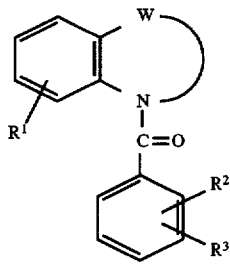
Example 720
Structure
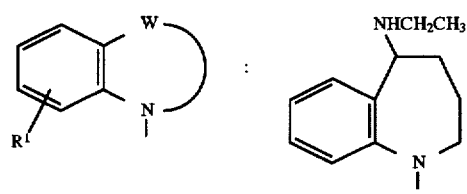
R²: H
R³:
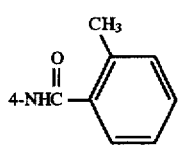
Crystalline form: Colorless prisms
Recrystallization solvent: Dioxane/water
Melting Point: 135.5–137° C.
Form: Free
Example 721
Structure
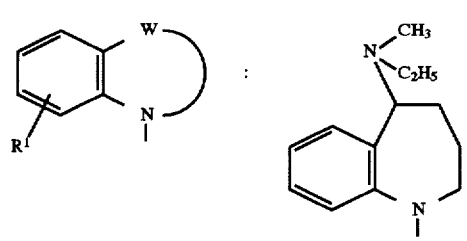
R²: H
R³:
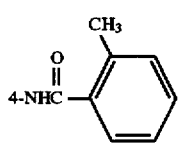
Crystalline form: White powder
Recrystallization solvent: Isopropyl alcohol/petroleum ether
Melting Point: 192–193° C.
Form: Free TABLE 4-continued
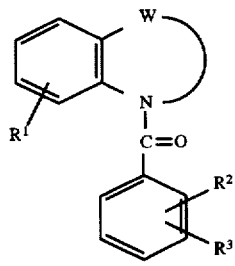
Example 722
Structure
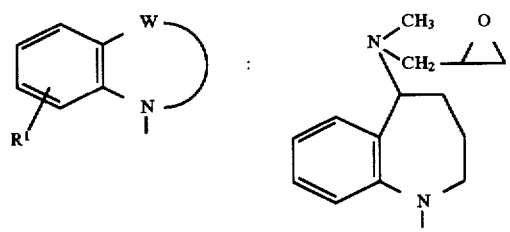
R²: H
R³:
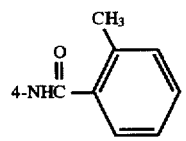
Crystalline form: Colorless needles
Recrystallization solvent: Ethyl acetate
Melting Point: 239–240° C.
Form: Free
Example 723
Structure
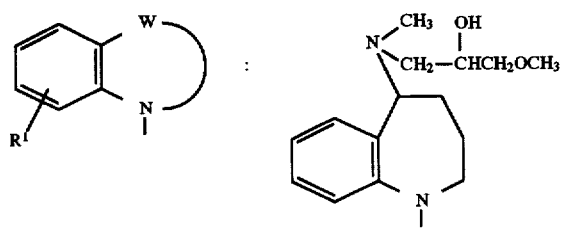
R²: H
R³:
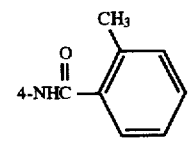
Crystalline form: Colorless amorphous
NMR analysis: 129)
Form: Free TABLE 4-continued
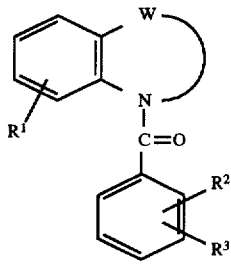
Example 724
Structure
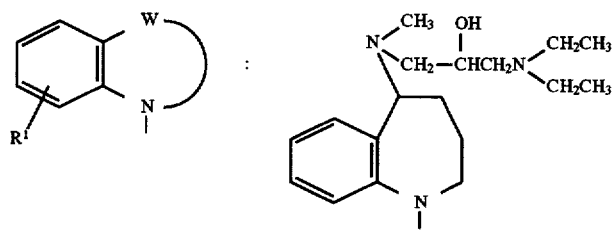
R²: H
R³:
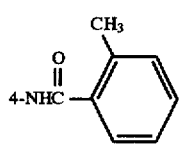
Crystalline form: Colorless amorphous
NMR analysis: 130)
Form: Free
Example 725
Structure
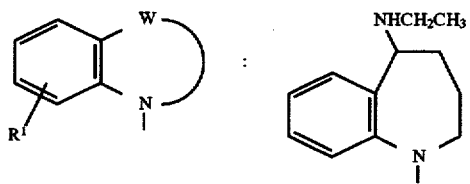
R²: H
R³:
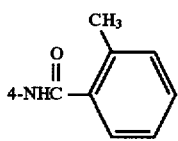
Crystalline form: Colorless needles
Recrystallization solvent: Ethanol/petroleum ether
Melting Point: 193–194° C.
Form: Free TABLE 4-continued
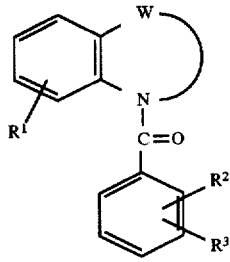
Example 726
Structure
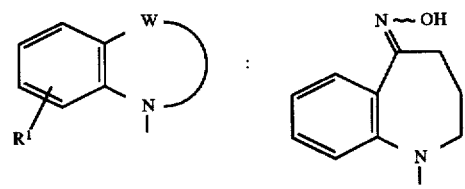
R²: H
R³: 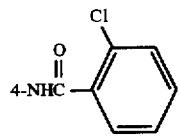
Crystalline form: Light yellow prisms
Recrystallization solvent: Ethanol
Melting Point: 245.5–247° C.
Form: Free
Example 727
Structure
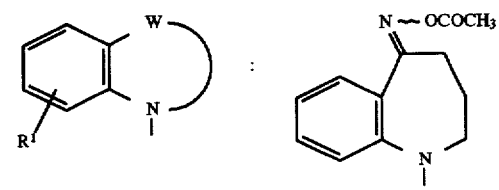
R²: H
R³: 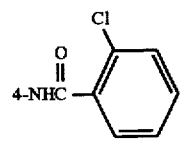
Crystalline form: Colorless prisms
Recrystallization solvent: Ethanol/petroleum ether
Melting Point: 142–144° C.
Form: Free TABLE 4-continued
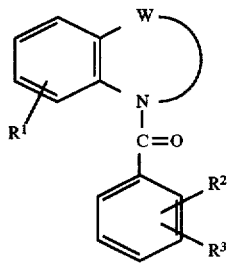
Example 728
Structure
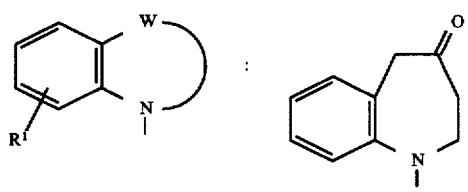
R²: H
R³: 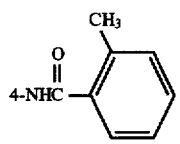
| Crystalline form: | Light yellow prisms |
|---|---|
| Recrystallization solvent: | Ethanol |
| Melting Point: | 214–217° C. |
| Form: | Free |
Example 729
Structure
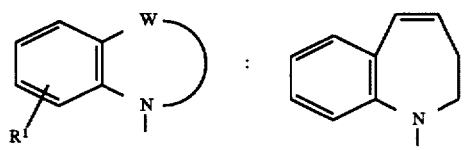
R²: H
R³: 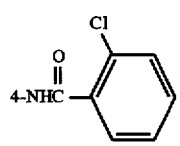
| Crystalline form: | Colorless needles |
|---|---|
| Recrystallization solvent: | Ethanol |
| Melting Point: | 205–207° C. |
| Form: | Free |

TABLE 4-continued
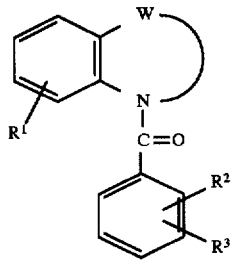
Example 730
Structure
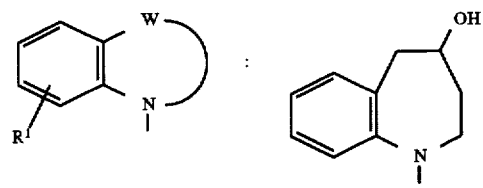
R²: H
R³: 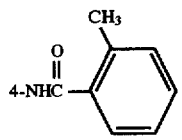
Crystalline form: Colorless needles
Recrystallization solvent: Ethanol/diethyl ether
Melting Point: 201–203° C.
Form: Free
Example 731
Structure
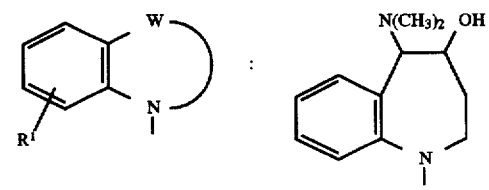
R²: H
R³: 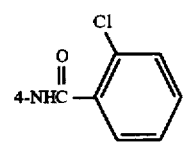
Crystalline form: Colorless needles
Recrystallization solvent: Ethanol/diethyl ether
Melting Point: 180–182° C.
Form: Free TABLE 4-continued
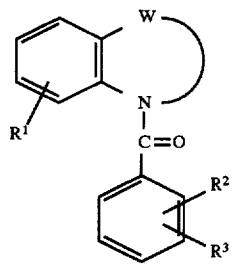
Example 732
Structure
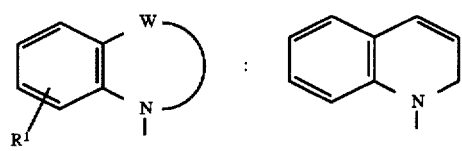
R²: H
R³: 
Crystalline form: Light yellow scales
Recrystallization solvent: Ethanol/diethyl ether
Melting Point: 178–180° C.
Form: Free
Example 733
Structure
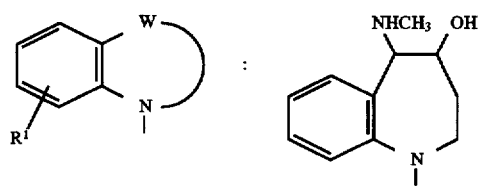
R²: H
R³: 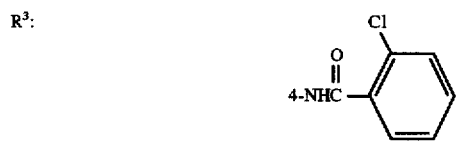
Crystalline form: Colorless needles
Recrystallization solvent: Methanol/diethyl ether
Melting Point: 208–213° C.
Form: Free TABLE 4-continued
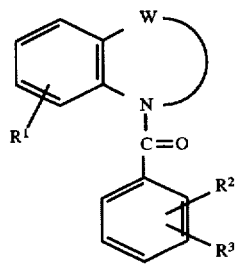
Example 734
Structure
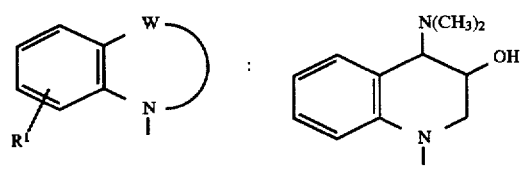
R²: H
R³:
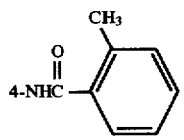
| Crystalline form: | White powder |
| --- | --- |
| Recrystallization solvent: | Ethanol/diethyl ether |
| Melting Point: | 175–177° C. |
| Form: | Free |
Example 735
Structure
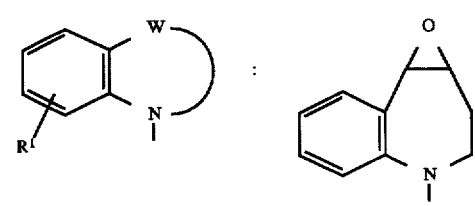
R²: H
R³:
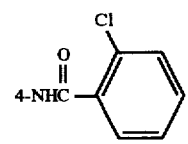
| Crystalline form: | White powder |
| --- | --- |
| NMR analysis: | 131) |
| Form: | Free |

TABLE 4-continued
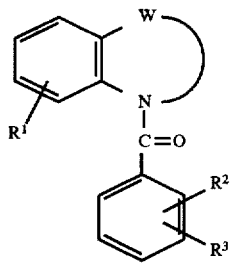
Example 736
Structure
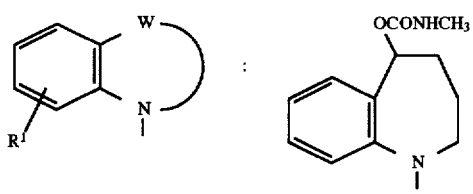
R²: H
R³: 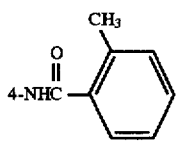
| | |
|---|---|
| Crystalline form: | White powder |
| Recrystallization solvent: | Ethyl acetate/n-hexane |
| Melting Point: | 277–279° C. |
| Form: | Free |
Example 737
Structure
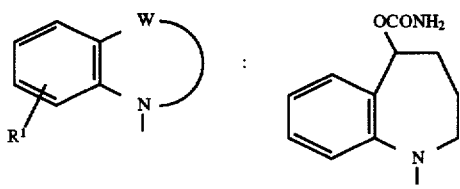
R²: H
R³: 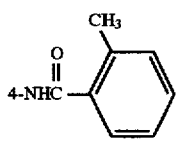
| | |
|---|---|
| Crystalline form: | Colorless amorphous |
| NMR analysis: | 132) |
| Form: | Free |

TABLE 4-continued
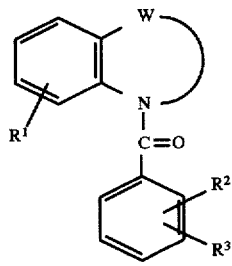
Example 738
Structure
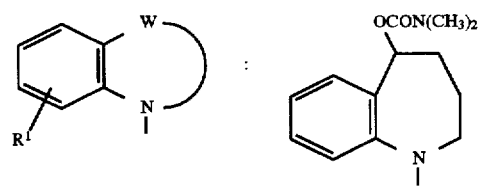
R²: H
R³: 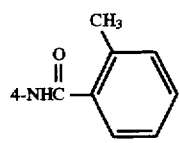
Crystalline form: Colorless amorphous
NMR analysis: 133)
Form: Free
Example 739
Structure
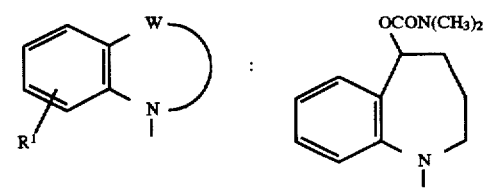
R²: H
R³: 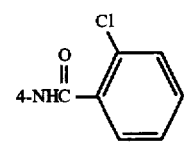
Crystalline form: Colorless amorphous
NMR analysis: 134)
Form: Free

TABLE 4-continued
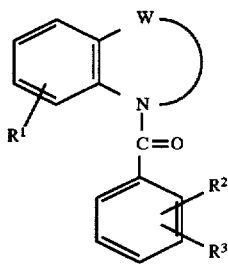
Example 740
Structure
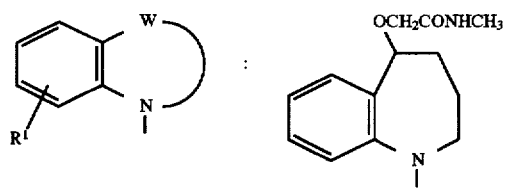
R²: H
R³: 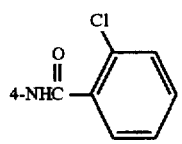
Crystalline form: Colorless amorphous
NMR analysis: 135)
Form: Free
Example 741
Structure
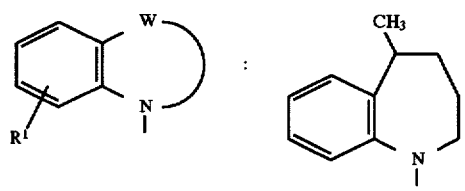
R²: H
R³: 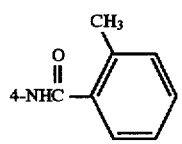
Crystalline form: White powder
Recrystallization solvent: Ethyl acetate/n-hexane
Melting Point: 213–214° C.
Form: Free TABLE 4-continued
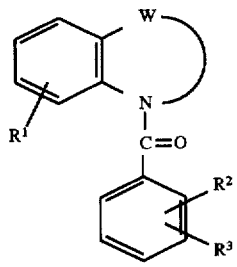
Example 742
Structure
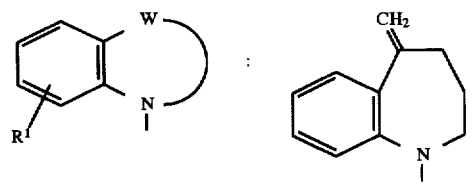
R²: H
R³:
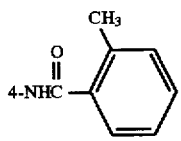
Crystalline form: White powder
Recrystallization solvent: Ethyl acetate/n-hexane
Melting Point: 216–217° C.
Form: Free
Example 743
Structure
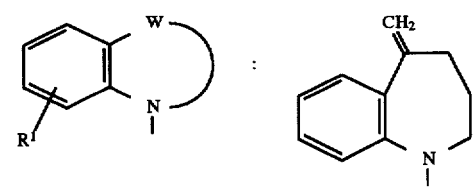
R²: 2-Cl
R³:
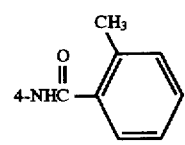
Crystalline form: White powder
Recrystallization solvent: Ethyl acetate/n-hexane
Melting Point: 165–167° C.
Form: Free TABLE 4-continued
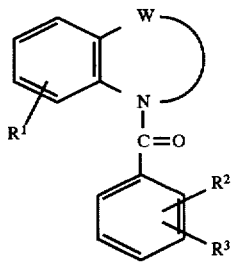
Example 744
Structure
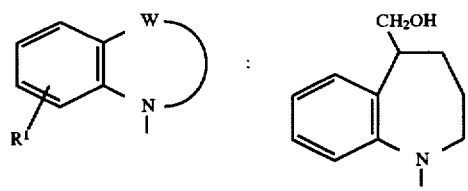
R²: H
R³:
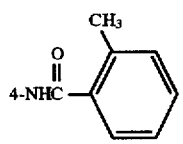
| Crystalline form: | White powder |
| --- | --- |
| Recrystallization solvent: | Ethyl acetate/n-hexane |
| Melting Point: | 202–206° C. |
| Form: | Free |
Example 745
Structure
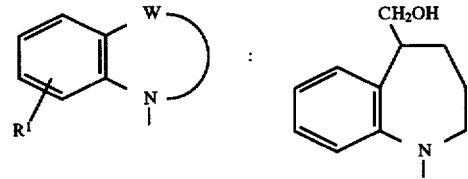
R²: 2-Cl
R³:
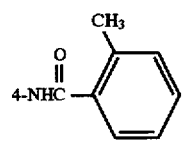
| Crystalline form: | White powder |
| --- | --- |
| Recrystallization solvent: | Ethyl acetate/n-hexane |
| Melting Point: | 220–221.5° C. |
| Form: | Free |

TABLE 4-continued
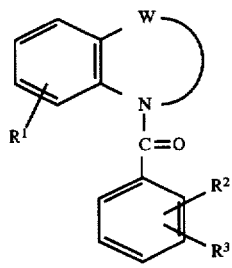
Example 746
Structure
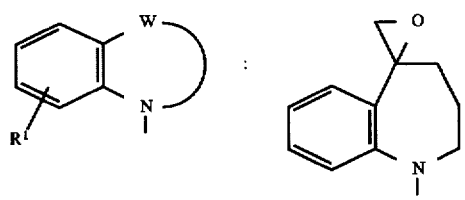
R²: H
R³: 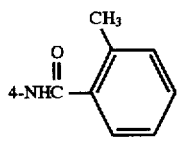
Crystalline form: Colorless needles
Recrystallization solvent: Ethyl acetate/n-hexane
Melting Point: 186–186.5° C.
Form: Free
Example 747
Structure
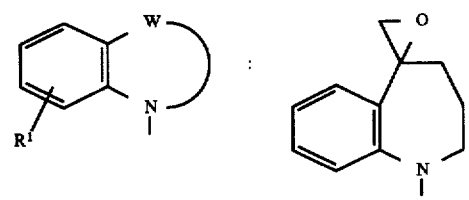
R²: 2-Cl
R³: 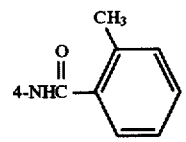
Crystalline form: Colorless amorphous
NMR analysis: 136)
Form: Free TABLE 4-continued
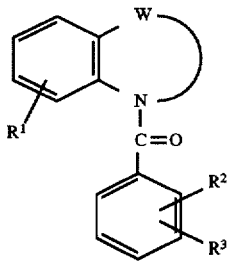
Example 748
Structure
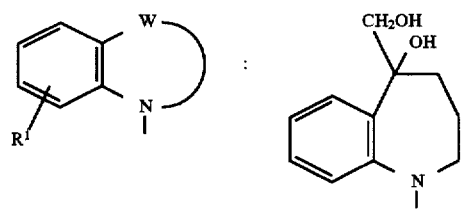
R²: H
R³:
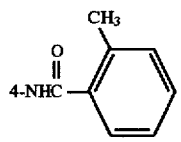
| Crystalline form: | White powder |
| Recrystallization solvent: | Ethyl acetate/n-hexane |
| Melting Point: | 136–140° C. |
| Form: | Free |
Example 749
Structure
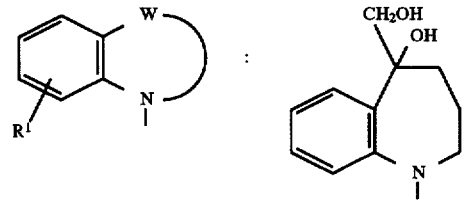
R²: 2-Cl
R³:
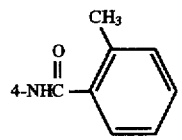
| Crystalline form: | White powder |
| Recrystallization solvent: | Ethyl acetate/n-hexane |
| Melting Point: | 151–153° C. |
| Form: | Free |

TABLE 4-continued
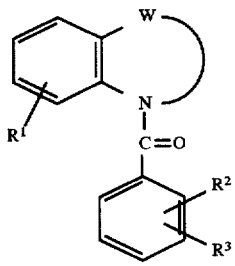
Example 750
Structure
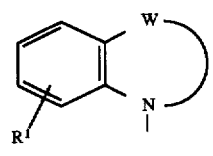 : 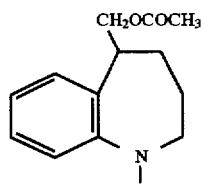
R²: H
R³: 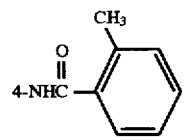
| | |
|---|---|
| Crystalline form: | Colorless needles |
| Recrystallization solvent: | Ethyl acetate/n-hexane |
| Melting Point: | 155–156° C. |
| Form: | Free |
Example 751
Structure
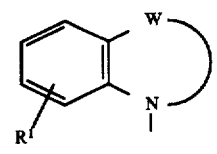 : 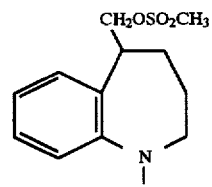
R²: H
R³: 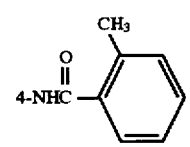
| | |
|---|---|
| Crystalline form: | White powder |
| Recrystallization solvent: | Ethyl acetate/n-hexane |
| Melting Point: | 189–190° C. |
| Form: | Free |

TABLE 4-continued
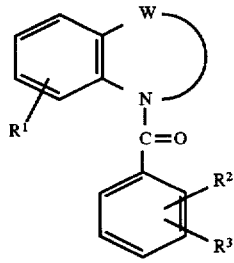
Example 752
Structure
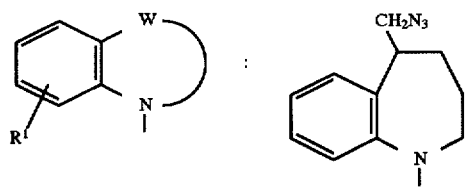
R²: H
R³: 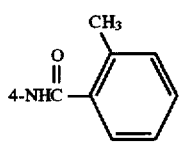
| | |
|---|---|
| Crystalline form: | White powder |
| Recrystallization solvent: | Ethyl acetate/n-hexane |
| Melting Point: | 188–190° C. |
| Form: | Free |
Example 753
Structure
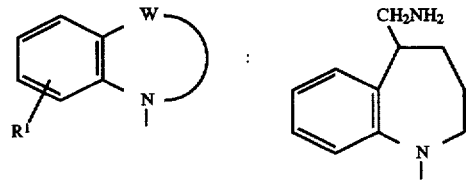
R²: H
R³: 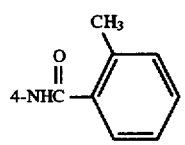
| | |
|---|---|
| Crystalline form: | Colorless needles |
| Recrystallization solvent: | Ethanol |
| Melting Point: | 233–235° C. |
| Form: | Free |

TABLE 4-continued
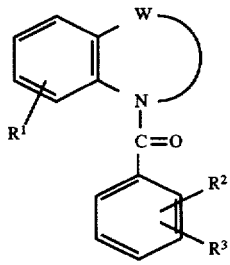
Example 754
Structure
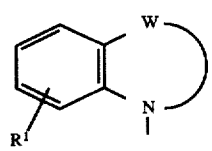 : 
R²: H
R³: 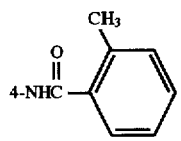
Crystalline form: Colorless amorphous
NMR analysis: 137)
Form: Free
Example 755
Structure
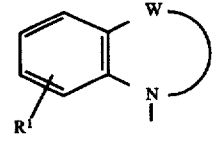 : 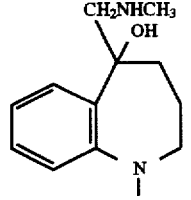
R²: H
R³: 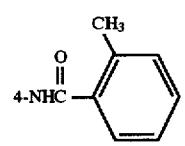
Crystalline form: White powder
Recrystallization solvent: Ethyl acetate/n-hexane
Melting Point: 176–179° C.
Form: Free

TABLE 4-continued

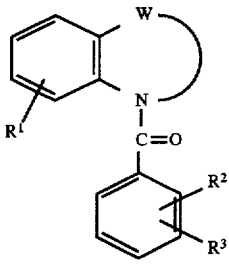

Example 756

Structure

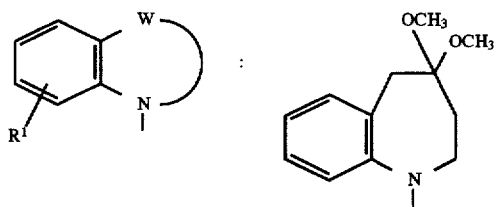

R²: H

R³:

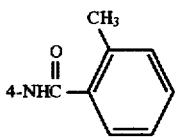

| | |
|---|---|
| Crystalline form: | Colorless needles |
| Recrystallization solvent: | Methanol/diethyl ether |
| Melting Point: | 183–185° C. |
| Form: | Free |

117) $^1$H-NMR(CDCl$_3$) δ; 1.3–2.3 (4H, m), 3.1–3.4 (3H, m), 3.8–4.6 (2H, m), 5.0–5.3 (2H, m), 5.8–6.1 (1H, m), 6.8–8.5 (11H, m)

118) $^1$H-NMR(CDCl$_3$) δ; 1.6–2.2 (4H, m), 2.46, 2.53 (3H, each s), 3.1–3.5 (3H, m), 3.8–4.6 (2H, m), 5.0–5.3 (2H, m), 5.8–6.1 (1H, m), 6.8–8.0 (11H, m)

119) $^1$H-NMR(DMSO-d$_6$) δ; 2.33 (3H, s), 3.36 (2H, m), 3.89 (1H, m), 4.41 (1H, m), 5.07 (1H, m), 5.40 (1H, d, J=14.8 Hz), 6.85 (1H, d, J=7.2 Hz), 7.15–7.65 (11H, m), 10.35 (1H, s)

120) $^1$H-NMR(CDCl$_3$) δ; 1.25–5.05 (22H, m), 6.65–7.65 (11H, m), 7.75–8.25 (1H, m)

121) $^1$H-NMR(CDCl$_3$) δ; 1.15–5.05 (19H, m), 6.75–7.85 (11H, m), 7.85–8.25 (1H, m)

122) $^1$H-NMR(CDCl$_3$) δ; 1.25–2.85 (8H, m), 2.95–4.95 (2H, m), 6.75–7.85 (10H, m), 9.25–9.75 (1H, m)

123) $^1$H-NMR(CDCl$_3$) δ; 0.20–0.70 (4H, m), 0.95–2.35 (6H, m), 2.65–5.00 (2H, m), 6.75–7.90 (10H, m), 8.65–9.25 (1H, m)

124) $^1$H-NMR(CDCl$_3$) δ; 1.20–3.15 (11H, m), 3.45–3.70 (1H, m), 4.05–5.20 (1H, m), 6.60–7.65 (10H, m), 8.15–8.45 (2H, m)

125) $^1$H-NMR(CDCl$_3$) δ; 1.19 (3H, t, J=7 Hz), 1.25–3.25 (8H, m), 3.46 (2H, q, J=7 Hz), 3.40–4.10 (3H, m), 4.45–5.10 (1H, m), 6.65–7.75 (12H, m), 8.30–8.60 (1H, m)

126) $^1$H-NMR(CDCl$_3$) δ; 1.10–1.30 (3H, m), 1.50–2.35 (4H, m), 2.65–3.05 (2H, m), 3.35–3.60 (2H, m), 3.80–4.05 (2H, m), 4.65–5.15 (2H, m), 6.55–7.85 (12H, m), 8.35–8.65 (1H, m)

127) $^1$H-NMR(CDCl$_3$) δ; 1.20 (3H, t, J=7 Hz), 1.10–3.15 (11H, m), 3.45–3.65 (3H, m), 3.88 (2H, s), 3.95–5.15 (1H, m), 6.55–7.65 (13H, m), 8.37 (1H, s)

128) $^1$H-NMR(CDCl$_3$) δ; 2.45 (3H, s), 3.40 (3H, s), 4.01 (2H, m), 4.38 (2H, m), 7.20–7.77 (13H, m)

129) $^1$H-NMR(CDCl$_3$) δ; 1.35–4.55 (22H, m), 6.3–7.8 (13H, m)

130) $^1$H-NMR(CDCl$_3$) δ; 1.10 (6H, t, J=7 Hz), 1.35–5.1 (23H, m), 6.55–7.8 (13H, m)

131) $^1$H-NMR(CDCl$_3$) δ; 1.94–3.21 (3H, m), 3.30–4.82 (3H, m), 6.57 (1H, d, J=7.5 Hz), 6.86–8.10 (11H, m), 8.72 (1H, brs)

132) $^1$H-NMR(DMSO-d$_6$) δ; 1.57–1.85 (2H, m), 1.85–2.28 (2H, m), 2.33 (3H, s), 2.64–2.86 (1H, m), 4.53–5.07 (1H, m), 5.79–5.94 (1H, m), 6.47–7.68 (2H, br), 6.64–6.77 (1H, m), 6.96–7.62 (12H, m)

133) $^1$H-NMR(CDCl$_3$) δ; 1.61–1.97 (2H, m), 2.00–2.54 (2H, m), 2.47 (3H, s), 2.60–3.23 (7H, m), 4.76–5.22 (1H, m), 5.94–6.19 (1H, m), 6.61–6.74 (1H, m), 6.91–7.62 (12H, m)

134) $^1$H-NMR(CDCl$_3$) δ; 1.68–1.97 (2H, m), 2.03–2.53 (2H, n), 2.61–3.24 (7H, m), 4.76–5.22 (1H, m), 5.97–6.17 (1H, m), 6.59–6.74 (1H, m), 6.92–7.13 (1H, m), 7.13–7.58 (9H, m), 7.66–7.85 (1H, m), 7.85–8.00 (1H, m)

135) $^1$H-NMR(CDCl$_3$) δ; 1.57–1.93 (2H, m), 1.93–2.54 (2H, m), 2.54–2.72 (1H, m), 2.79–3.09 (3H, m), 3.90–4.32 (2H, m), 4.49–5.18 (2H, m), 6.31–6.93 (2H, m), 6.96–7.63 (10H, m), 7.63–7.89 (1H, m), 7.89–8.16 (1H, m)

136) $^1$H-NMR(CDCl$_3$) δ; 1.44–1.95 (2H, m), 1.95–2.28 (2H, m), 2.40–2.67 (3H, m), 2.73–3.38 (3H, m), 3.40–3.97 (1H, m), 4.50–5.20 (1H, m), 6.67–8.11 (11H, m)

137) $^1$H-NMR(CDCl$_3$) δ; 1.50–2.10 (3H, m), 2.10–2.28 (1H, m), 2.36 (3H, s), 2.48 (3H, s), 2.68–2.97 (1H, m), 3.26–3.47 (1H, m), 4.16 (1H, d, J=13.8 Hz), 4.25 (1H, d, J=13.8 Hz), 5.95 (1H, brs), 6.60–6.76 (1H, m), 6.97–7.52 (8H, m), 7.52–7.73 (2H, m), 7.73–7.97 (2H, m)

Example 757

A mixture of 5-dimethylamino-1-[4-(2-chlorobenzoylamino)benzoyl]-2,3,4,5-tetrahydro-1H-benzazepine (10 g), methyl iodide (1.7 ml) and chloroform (10 ml) is heated with stirring at 100° C. for 3 hours in an autoclave. After completion of the reaction, the solvent is distilled off under reduced pressure and the resulting residue is dissolved in methanol. The mixture is treated with IRA-400 (trade mark; Organo Co., Ltd., OH$^-$ type). Methanol is distilled off and the resulting residue is suspended in t-butyl alcohol (90 ml), and thereto is added potassium t-butoxide (2.3 g). The mixture is refluxed for 5 hours. The solvent is distilled off under reduced pressure, and the resulting residue is dissolved in dichloromethane. The mixture is washed successively with water and saturated saline solution and dried over magnesium sulfate. The solvent is distilled off and to the resulting residue is added dichloromethane/diethyl ether. The precipitated crude crystal is recrystallized from ethanol to give 1-[4-(2-chlorobenzoylamino)benzoyl]-2,3-dihydro-1H-benzazepine (5.15 g) as colorless needles, m.p. 205°–207° C.

Example 758

1-[4-(2-Chlorobenzoylamino)benzoyl]-2,3-dihydro-1H-benzazepine (4.7 g) is dissolved in dichloromethane (50 ml) and thereto is added 80% m-chloroperbenzoic acid (3 g). The mixture is stirred at room temperature overnight. The dichloromethane layer is washed successively with saturated aqueous sodium hydrogen carbonate solution and saturated saline solution, and the solvent is distilled off under reduced pressure. The resulting residue is purified by silica gel column chromatography (eluent; dichloromethane:methanol=50:1) to give 4,5-epoxy-1-[4-(2-chlorobenzoylamino)benzoyl]-2,3,4,5-tetrahydro-1H-benzazepine (4.26 g) as white powder.

$^1$H-NMR(CDCl$_3$) δ; 1.94–3.21 (3H, m), 3.30–4.82 (3H, m), 6.57 (1H, d, J=7.5 Hz), 6.86–8.10 (11H, m), 8.72 (1H, brs)

Example 759

A mixture of 4,5-epoxy-1-[4-(2-chlorobenzoylamino)benzoyl]-2,3,4,5-tetrahydro-1H-benzazepine (0.5 g), dimethylamine hydrochloride (2.6 g), triethylamine (4.5 g) and methanol (15 ml) is refluxed for 19 hours. After completion of the reaction, the solvent is distilled off and the resulting residue is dissolved in dichloromethane. The mixture is washed successively with water and saturated saline solution. The solvent is distilled off and the resulting residue is purified by silica gel column chromatography (eluent; dichloromethane:methanol=50:1), and recrystallized from ethanol/diethyl ether to give trans-5-dimethylamino-4-hydroxy-1-[4-(2-chlorobenzoylamino)benzoyl]-2,3,4,5-tetrahydro-1H-benzazepine (0.38 g) as colorless needles, m.p. 180°–182° C.

Using the suitable starting materials, the compounds of the above Examples 733 and 734 are obtained in the same manner as in Example 759.

Example 760

Methyltriphenylphosphonium bromide (4.30 g) is suspended in tetrahydrofuran (100 ml) and thereto is added potassium t-butoxide (1.58 g) under ice-cooling. The mixture is stirred at −5° C. for 1 hour and thereto is added 5-oxo-1-[4-(2-methylbenzoylamino)benzoyl]-2,3,4,5-tetrahydro-1H-benzazepine (1.60 g) and the mixture is stirred at room temperature for 1 hour. The reaction solution is poured into ice-water (200 ml) and extracted with ethyl acetate. The extract is washed with saturated saline solution and dried over magnesium sulfate. The solvent is distilled off and the resulting residue is purified by silica gel column chromatography (eluent; ethyl acetate:n-hexane=1:2), and recrystallized from ethyl acetate/n-hexane to give 5-methylidene-1-[4-(2-methylbenzoylamino)benzoyl]-2,3,4,5-tetrahydro-1H-benzazepine (1.34 g) as white powder, m.p. 216°–217° C.

Using the suitable starting materials, the compound of the above Example 743 is obtained in the same manner as in Example 760.

Example 761

5-Methylidene-1-[4-(2-methylbenzoylamino)benzoyl]-2,3,4,5-tetrahydro-1H-benzazepine (2.84 g) is suspended in tetrahydrofuran (50 ml) and thereto is added 1M solution of boran-tetrahydrofuran complex in tetrahydrofuran (43 ml). The mixture is stirred at room temperature for 6 hours. After completion of the reaction, the reaction solution is cooled with ice, and thereto is added water (70 ml). After termination of the evolution of hydrogen gas, to the reaction solution are added 25% aqueous sodium hydroxide solution (7.0 ml), and subsequently 31% aqueous hydrogen peroxide solution (4.7 ml), and the mixture is heated with stirring at 50° C. for 1 hour. After cooling, to the reaction solution is added saturated saline solution and the tetrahydrofuran layer is collected, washed with saturated saline solution and dried over magnesium sulfate. The solvent is distilled off and the resulting residue is recrystallized from ethyl acetate/n-hexane to give 5-hydroxymethyl-1-[4-(2-methylbenzoylamino)benzoyl]-2,3,4,5-tetrahydro-1H-benzazepine (1.96 g) as white powder, m.p. 202°–206° C.

Using the suitable starting materials, the compound of the above Example 745 is obtained in the same manner as in Example 761.

Example 762

5-Methylidene-1-[2-chloro-4-(2-methylbenzoylamino)benzoyl]-2,3,4,5-tetrahydro-1H-benzazepine (0.81 g) is dissolved in dichloromethane (30 ml) and thereto is added m-chloroperbenzoic acid (0.57 g). The mixture is stirred at room temperature for 15 hours. After completion of the reaction, the reaction solution is washed successively with aqueous sodium hydrogensulfite solution, aqueous sodium hydrogen carbonate solution and saturated saline solution, and dried over magnesium sulfate. The solvent is distilled off and the resulting residue is purified with silica gel column chromatography (eluent; ethyl acetate:n-hexane=2:3) to give 5,5-epoxy-1-[2-chloro-4-(2-methylbenzoylamino)benzoyl]-2,3,4,5-tetrahydro-1H-benzazepine (0.70 g) as colorless amorphous.

$^1$H-NMR(CDCl$_3$) δ; 1.44–1.95 (2H, m), 1.95–2.28 (2H, m), 2.40–2.67 (3H, m), 2.73–3.38 (3H, m), 3.40–3.97 (1H, m), 4.50–5.20 (1H, m), 6.67–8.11 (11H, m)

Using the suitable starting materials, the compound of the above Example 746 is obtained in the same manner as in Example 762.

Example 763

To 5-methylidene-1-[4-(2-methylbenzoylamino)benzoyl]-2,3,4,5-tetrahydro-1H-benzazepine (0.60 g) are added successively t-butyl alcohol (6.0 ml), water (1.2 ml), pyridine (0.3 ml), osmium tetroxide (1.2 mg) and trimethylamine N-oxide dihydrate (0.22 g), and the mixture is refluxed with stirring for 2.5 hours. After cooling, to the reaction solution is added 20% aqueous sodium hydrogen-sulfite solution (10 ml), and the mixture is stirred at room temperature for 1.5 hour. The reaction solution is extracted with a mixture of ethyl acetate/tetrahydrofuran (1:1). The extract is washed successively with diluted hydrochloric acid and saturated saline solution, and dried over magnesium sulfate. The solvent is distilled off and the resulting residue is recrystallized from ethyl acetate/n-hexane to give 5-hydroxymethyl-5-hydroxy-1-(4-(2-methylbenzoylamino)benzoyl]-2,3,4,5-tetrahydro-1H-benzazepine (0.55 g) as white powder, m.p. 136°–140° C.

Using the suitable starting materials, the compound of the above Example 749 is obtained in the same manner as in Example 763.

Example 764

To 5-hydroxymethyl-1-[4-(2-methylbenzoylamino)benzoyl]-2,3,4,5-tetrahydro-1H-benzazepine (0.40 g) are added acetic anhydride (4.0 ml) and pyridine (0.5 ml), and the mixture is stirred at room temperature for 5 hours. After completion of the reaction, the reaction solution is poured into ice-water and extracted with ethyl acetate. The extract is washed successively with diluted hydrochloric acid and saturated saline solution, and dried over magnesium sulfate. The solvent is distilled off and the resulting residue is recrystallized from ethyl acetate/n-hexane to give 5-acetyloxymethyl-1-[4-(2-methylbenzoylamino)benzoyl]-2,3,4,5-tetrahydro-1H-benzazepine (0.43 g) as colorless needles, m.p. 155°–156° C.

Example 765

5-Hydroxymethyl-1-[4-(2-methylbenzoylamino)benzoyl]-2,3,4,5-tetrahydro-1H-benzazepine (0.70 g) is dissolved in a mixture (30 ml) of dichloromethane/acetonitrile (1:1) and thereto are added methanesulfonyl chloride (0.8 ml) and pyridine (1.0 ml), and the mixture is refluxed with stirring for 2 hours. After cooling, the reaction solution is evaporated under reduced pressure and to the resulting residue is added water and then extracted with ethyl acetate. The extract is washed successively with diluted hydrochloric acid and saturated saline solution, and dried over magnesium sulfate. The solvent is distilled off and the resulting residue is recrystallized from ethyl acetate/n-hexane to give 5-methanesulfonyloxymethyl-1-[4-(2-methylbenzoylamino)benzoyl]-2,3,4,5-tetrahydro-1H-benzazepine (0.72 g) as white powder, m.p. 189°–190° C.

Example 766

5-Methanesulfonyloxymethyl-1-[4-(2-methylbenzoylamino)benzoyl]-2,3,4,5-tetrahydro-1H-benzazepine (0.49 g) is dissolved in a mixture (25 ml) of acetonitrile/dimethylformamide (4:1) and thereto is added sodium azide (0.11 g). The mixture is refluxed with stirring for 3.5 hours. After cooling, the reaction solution is poured into ice-water (40 ml), extracted with ethyl acetate, washed with saturated saline solution, and dried over magnesium sulfate. The solvent is distilled off and the resulting residue is purified by silica gel column chromatography (eluent; ethyl acetate:n-hexane=1:2), and recrystallized from ethyl acetate/n-hexane to give 5-azidomethyl-1-[4-(2-methylbenzoylamino)benzoly]-2,3,4,5-tetrahydro-1H-benzazepine (0.29 g) as white powder, m.p. 188°–189° C.

Example 767

5-Azidomethyl-1-[4-(2-methylbenzoylamino)benzoyl]-2,3,4,5-tetrahydro-1H-benzazepine (0.27 g) is suspended in ethanol (50 ml) and the mixture is subjected to catalytic hydrogenation at room temperature under 3 kg/cm$^2$ for 6 hours by using 10% Pd—C (27 mg). The catalyst is removed by filtration with celite and the filtrate is distilled off and the resulting residue is recrystallized from ethanol to give 5-aminomethyl-1-[4-(2-methylbenzoylamino)benzoyl]-2,3,4,5-tetrahydro-1H-benzazepine (0.12 g) as colorless needles, m.p. 233°–235° C.

Example 768

To 5,5-epoxy-1-[4-(2-methylbenzoylamino)benzoyl]-2,3,4,5-tetrahydro-1H-benzazepine (0.30 g) is added 30% solution of methylamine in methanol (30 ml), and the mixture is refluxed for 14 hours. After completion of the reaction, the reaction solution is evaporated under reduced pressure and the resulting residue is purified by silica gel column chromatography (eluent; ethyl acetate:n-hexane 1:1→dichloromethane:methanol:aqueous ammonia=60:10:1) to give 5-hydroxymethyl-5-methylamino-1-[4-(2-methylbenzoylamino]benzoyl]-2,3,4,5-tetrahydro-1H-benzazepine (A; 35.3 mg) and 5-methylaminomethyl-5-hydroxy-1-[4-(2-methylbenzoylamino)benzoyl]-2,3,4,5-tetrahydro-1H-benzazepine (B; 109 mg).

(A); Colorless amorphous $^1$H-NMR(CDCl$_3$) δ; 1.50–2.10 (3H, m), 2.10–2.28 (1H, m), 2.36 (3H, s), 2.48 (3H, s), 2.68–2.97 (1H, m), 3.26–3.47 (1H, m), 4.16 (1H, d, J=13.8 Hz), 4.25 (1H, d, J=13.8 Hz), 5.95 (1H, brs), 6.60–6.76 (1H, m), 6.97–7.52 (8H, m), 7.52–7.73 (2H, m), 7.73–7.97 (2H, m)

(B); White powder (recrystallized from ethyl acetate/n-hexane)

m.p. 176°–179° C.

Example 769

5-Methylamino-1-[4-(2-methylbenzoylamino)benzoyl]-2,3,4,5-tetrahydro-1H-benzazepine (1 g) is dissolved in dimethylformamide (10 ml) and thereto are added potassium carbonate (0.5 g) and ethyl iodide (0.45 g). The mixture is stirred at room temperature overnight. After completion of the reaction, the reaction solution is poured into ice-water and the precipitated crystal is collected by filtration, and purified by silica gel column chromatography (eluent; dichloromethane:methanol=90:1), and recrystallized from diisopropyl alcohol/petroleum ether to give 5-(N-methyl-N-ethylamino)-1-[4-(2-methylbenzoylamino)benzoyl]-2,3,4,5-tetrahydro-1H-benzazepine (50 mg) as white powder, m. p. 192°–193° C.

Using the suitable starting materials, the compounds of the above Examples 244, 246–248, 330, 339, 342, 346, 350, 366, 375, 376, 406–418, 453, 455, 457, 460, 464, 467, 506, 507, 537–545, 547, 549–556, 561–566, 568–571, 577, 601–603, 607–625, 654–672, 675, 677–681, 691–695, 697, 698, 701–705, 707, 708, 712, 713, 715, 716, 719, 720 and 722–725 are obtained in the same manner as in Example 769.

Example 770

To a suspension of 5-methylamino-1-[4-(2-methylbenzoylamino)benzoyl]-2,3,4,5-tetrahydro-1H- benzazepine (3 g) in methanol (30 ml) are added potassium carbonate (1.5 g) and epichlorohydrine (5.7 ml), and the mixture is refluxed for 3 hours. The solvent is distilled off and to the resulting residue is added water and extracted three times with dichloromethane. The extract is washed with saturated saline solution and dried over magnesium sulfate. The resulting residue is purified by silica gel column chromatography (eluent; dichloromethane:methanol=80:1) to give 5-(N-methyl-N-oxiranylmethylamino)-1-[4-(2-methylbenzoylamino)benzoyl]-2,3,4,5-tetrahydro-1H-benzazepine (C; 1.92 g) and 5-[N-methyl-N-(2-hydroxy-3-methoxypropyl)amino]-1-[4-(2-methylbenzoylamino)benzoyl]-2,3,4,5-tetrahydro-1H-benzazepine (D; 0.38 g).

(C); Colorless needles (recrystallization from ethyl acetate) m.p. 239°–240° C.

(D); Colorless amorphous $^1$H-NMR(CDCl$_3$) δ; 1.35–4.55 (22H, m), 6.3–7.8 (13H, m)

Example 771

5-[N-Methyl-N-oxiranylmethylamino)-1-[4-(2-methylbenzoylamino)benzoyl]-2,3,4,5-tetrahydro-1H-benzazepine (0.5 g) is dissolved in methanol (10 ml) and thereto is added diethylamine (0.13 ml). The mixture is refluxed for 3 hours. After completion of the reaction, the solvent is distilled off and the resulting residue is purified by silica gel column chromatography (eluent; dichloromethane:methanol=30:1→dichloromethane:methanol:aqueous ammonia=9:1:0.1) to give 5-[N-methyl-N-(2-hydroxy-3-diethylaminopropyl)amino]-1-(4-(2-methylbenzoylamino)benzoyl]-2,3,4,5-tetrahydro-1H-benzazepine (0.38 g) as colorless amorphous.

$^1$H-NMR(CDCl$_3$) δ; 1.10 (6H, t, J=7 Hz), 1.35–5.1 (23H, m), 6.55–7.8 (13H, m)

Example 772

A solution of 5-hydroxyimino-1-[4-(2-chlorobenzoylamino)benzoyl]-2,3,4,5-tetrahydro-1H-benzazepine (1.06 g) in acetic anhydride (10 ml) and pyridine (10 ml) is stirred at room temperature overnight. After completion of the reaction, the reaction solution is concentrated. To the resulting residue is added water and the mixture is extracted with dichloromethane. The extract is washed with saturated saline solution and dried over magnesium sulfate. The solvent is distilled off and the resulting residue is purified by silica gel column chromatography (eluent; dichloromethane:methanol=80:1), and recrystallized from ethanol/petroleum ether to give 5-acetyloxyimino-1-[4-(2-chlorobenzoylamino)benzoyl]-2,3,4,5-tetrahydro-1H-benzazepine (0.75 g) as colorless prisms, m.p. 142°–144° C.

Example 773

Using the suitable starting materials, the compounds of the above Examples 671 and 672 are obtained in the same manner as in Example 380.

Example 774

Using the suitable starting materials, the compounds of the above Examples 674, 699, 700, 706, 718 and 730 are obtained in the same manner as in Example 384.

Example 775

Using the suitable starting materials, the compounds of the above Examples 654–672, 675, 677–687, 691–695, 697, 698, 701–705, 707, 708, 712, 713, 715, 716 and 719–725 are obtained in the same manner as in Example 390.

Example 776

Using the suitable starting materials, the compounds of the above Examples 654–672, 675, 677–679, 691–693, 698, 701–705, 707, 708, 712, 713, 715, 716 and 719–725 are obtained in the same manner as in Example 388.

Example 777

Using the suitable starting materials, the compounds of the above Examples 705, 706 and 708 are obtained in the same manner as in Example 394.

Example 778

Using the suitable starting materials, the compound of the above Example 671 is obtained in the same manner as in Example 397.

Example 779

Using the suitable starting materials, the compound of the above Example 672 is obtained in the same manner as in Example 402.

Example 780

Using the suitable starting materials, the compound of the above Example 726 is obtained in the same manner as in Example 634.

Example 781

Using the suitable starting materials, the compound of the above Example 740 is obtained in the same manner as in Examples 638 and 640.

Example 782

Using the suitable starting materials, the compound of the above Example 689 is obtained in the same manner as in Example 643.

Example 783

Using the suitable starting materials, the compound of the above Example 690 is obtained in the same manner as in Example 644.

Example 784

Using the suitable starting materials, the following compound is obtained in the same manner as in Examples 1, 382, 388 and 390.

5-Dimethylamino-1-[4-(2-methylbenzoylamino)benzoyl]-2,3,4,5-tetrahydro-1H-benzazepine hydrochloride, colorless needles (recrystallized from ethanol/water), m.p. 233°–237° C.

REFERENCE EXAMPLE 13

Using the suitable starting materials, the following compounds are obtained in the same manner as in Reference Example 1.

5-(2-Chloroacetyloxy)-1-(4-nitrobenzoyl)-2,3,4,5-tetrahydro-1H-benzazepine, white powder, m.p. 156°–159° C. (recrystallized from ethyl acetate/n-hexane)

5-(2-Dimethylaminoacetyloxy)-1-(4-nitrobenzoyl)-2,3,4,5-tetrahydro-1H-benzazepine, white powder, m.p. 108°–109° C. (recrystallized from ethyl acetate/n-hexane)

5-Oxo-7-chloro-1-(4-nitrobenzoyl)-2,3,4,5-tetrahydro-1H-benzazepine, white powder, m.p. 157.5°–159.5° C. (recrystallized from diethyl ether/dichloromethane)

5-Oxo-8-chloro-1-(4-nitrobenzoyl)-2,3,4,5-tetrahydro-1H-benzazepine, white powder, m.p. 151.5°–153.5° C. (recrystallized from diethyl ether/dichloromethane)

REFERENCE EXAMPLE 14

Using the suitable starting materials, the following compounds are obtained in the same manner as in Reference Example 2.

5-(2-Dimethylaminoacetyloxy)-1-(4-aminobenzoyl)-2,3,4,5-tetrahydro-1H-benzazepine, colorless amorphous $^1$H-NMR (CDCl$_3$) δ; 1.63–1.98 (2H, m), 1.98–2.25 (1H, m), 2.27 (3H, s), 2.43 (3H, s), 2.65–3.23 (2H, m), 3.38 (2H, s), 3.67 (2H, brs), 4.77–5.28 (1H, m), 6.04–6.31 (1H, m), 6.31–6.56 (2H, m), 6.58–6.86 (1H, m), 6.86–7.46 (5H, m)

5-Oxo-7-chloro-1-(4-aminobenzoyl)-2,3,4,5-tetrahydro-1H-benzazepine, white powder, m.p. 193°–193.5° C. (recrystallized from diethyl ether/dichloromethane)

5-Oxo-8-chloro-1-(4-aminobenzoyl)-2,3,4,5-tetrahydro-1H-benzazepine, white powder, m.p. 171°–174° C. (recrystallized from diethyl ether/dichloromethane)

REFERENCE EXAMPLE 15

Using the suitable starting materials, the following compounds are obtained in the same manner as in Reference Example 1.

5-Dimethylaminocarbonylmethoxy-1-(4-nitrobenzoyl)-2,3,4,5-tetrahydro-1H-benzazepine, white powder, m.p. 129°–131° C. (recrystallized from ethyl acetate/n-hexane)

6-Oxo-1-(4-nitrobenzoyl)-1,2,3,4,5,6-hexahydrobenzazocine, yellow needles $^1$H-NMR (CDCl$_3$) δ; 1.65–2.3 (4H, m), 2.5–5.2 (4H, m), 6.7–6.9 (1H, m), 7.27–7.5 (4H, m), 7.90–8.15 (3H, m)

6-Chloro-5-oxo-1-(4-nitrobenzoyl)-2,3,4,5-tetrahydro-1H-benzazepine, white powder, m.p. 198°–202° C. (recrystallized from dichloromethane/diethyl ether)

REFERENCE EXAMPLE 16

Using the suitable starting materials, the following compounds are obtained in the same manner as in Reference Example 2.

5-Dimethylaminocarbonylmethoxy-1-(4-aminobenzoyl)-2,3,4,5-tetrahydro-1H-benzazepine, colorless amorphous $^1$H-NMR (CDCl$_3$) δ; 1.52–2.10 (3H, m), 2.10–3.20 (2H, m), 2.97 (3H, s), 3.05 (3H, s), 4.03–4.48 (2H, m), 4.50–5.35 (2H, m), 6.26–6.57 (2H, m), 6.57–6.88 (1H, m), 6.88–7.76 (5H, m)

6-Oxo-1-(4-aminobenzoyl)-1,2,3,4,5,6-hexahydrobenzazocine, light yellow amorphous $^1$H-NMR (CDCl$_3$) δ; 1.7–2.2 (4H, m), 2.5–5.2 (6H, m), 6.42 (2H, d, J=8.7 Hz), 6.75–6.9 (1H, m), 7.05–7.4 (4H, m), 7.95–8.1 (1H, m)

6-Chloro-5-oxo-1-(4-aminobenzoyl)-2,3,4,5-tetrahydro-1H-benzazepine, white powder, m.p. 166°–169° C. (recrystallized from dichloromethane/diethyl ether)

9-Chloro-5-oxo-1-(4-aminobenzoyl)-2,3,4,5-tetrahydro-1H-benzazepine, yellow powder, m.p. 192.5°–195° C. (recrystallized from dichloromethane/diethyl ether)

REFERENCE EXAMPLE 17

5-Dimethylamino-1-(2-methyl-4-nitrobenzoyl)-2,3,4,5-tetrahydro-1H-benzazepine (86.0 g) is dissolved in ethanol (800 ml), and thereto is added platinum oxide (10 g). The mixture is subjected to hydrogenation at ordinary temperature under atmospheric pressure of hydrogen for 4 hours. The catalyst is removed by filtration, and the solvent is distilled off. The resulting residue is purified by silica gel column chromatography (eluent; dichloromethane:methanol=200:1→100:1), and further purified by silica gel thin layer chromatography (developer; chloroform:methanol=10:1), and recrystallized from methanol/diethyl ether to give 5-dimethylamino-1-(2-methyl-4-aminobenzoyl)-2,3,4,5-tetrahydro-1H-benzazepine (G) (Rf: 0.52, 27.4 g) and 5-dimethylamino-1-(2-methyl-4-amino-benzoyl)-2,3,4,5-tetrahydro-1H-benzazepine (H) (Rf: 0.48, 12.3 g).

(G): White powder

M.p. 154°–156° C. $[\alpha]_D^{22}$=0° C. (c=1.0, chloroform)

$^1$H-NMR (CDCl$_3$) δ; 1.10–1.50 (1H, m), 1.50–2.00 (1H, m), 2.00–2.35 (11H, m), 2.90–5.18 (5H, m), 6.00–6.76 (3H, m), 6.81–7.64 (4H, m)

(H): White powder

M.p. 169.5°–170° C.

$[\alpha]_D^{22}$=0° (c=1.5, chloroform)

$^1$H-NMR (CDCl$_3$) δ; 1.11–2.90 (13H, m), 2.91–5.23 (5H, m), 6.15–6.53 (1H, m), 6.57–7.62 (6H, m)

Using the suitable starting materials, the compounds of the following Table 5 are obtained in the same manner as in above Examples 1 and 382.

TABLE 5

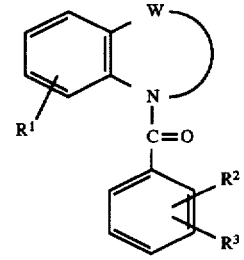

| | Example 785 |
|---|---|
| Structure | 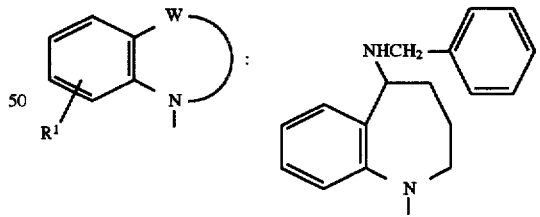 |
| R$^2$: | H |
| R$^3$: | 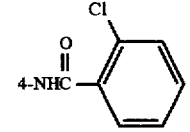 |

Crystalline form: Colorless needles
Recrystallization solvent: Ethanol
Melting Point: 174–175° C.
Form: Free

TABLE 5-continued

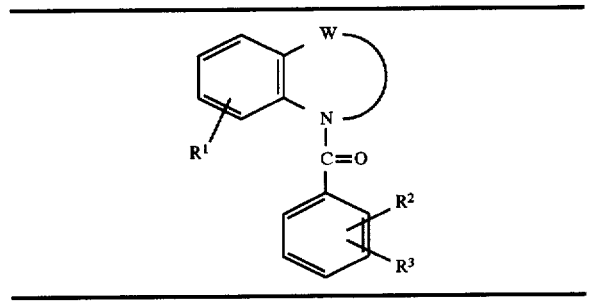

Example 786

Structure

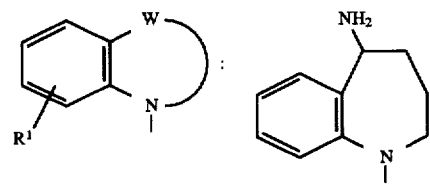

R²: H

R³:
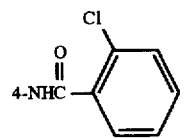
4-NHC(=O)-(2-Cl-phenyl)

Crystalline form: Colorless prisms
Recrystallization solvent: Ethanol/diethyl ether
Melting Point: 176–178° C.
Form: Free

Example 787

Structure

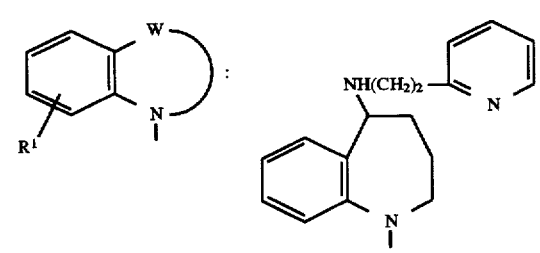

R²: H

R³:
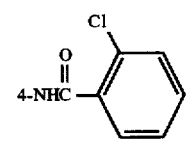
4-NHC(=O)-(2-Cl-phenyl)

Crystalline form: Colorless prisms
Recrystallization solvent: Ethyl acetate/petroleum ether
Melting Point: 154.5–155° C.
Form: Free

TABLE 5-continued

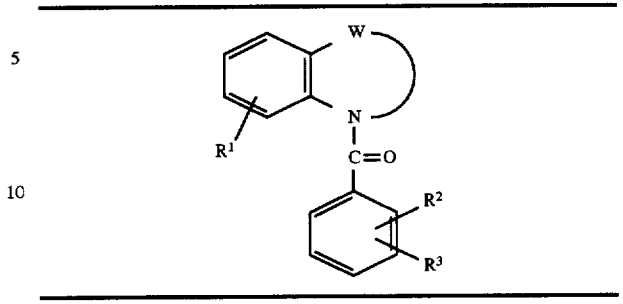

Example 788

Structure

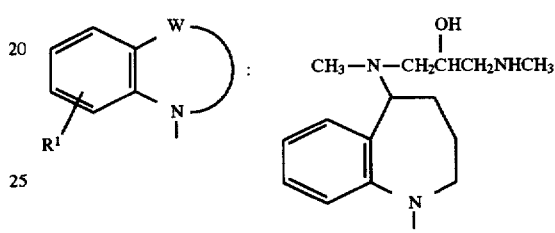

R²: H

R³:
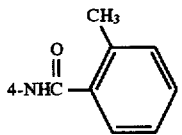
4-NHC(=O)-(2-CH₃-phenyl)

Crystalline form: Colorless amorphous
NMR analysis: 138)
Form: Free

Example 789

Structure

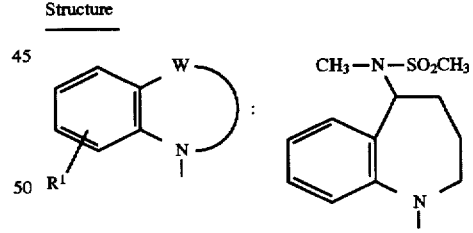

R²: H

R³:
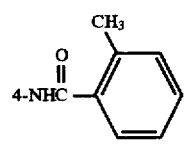
4-NHC(=O)-(2-CH₃-phenyl)

Crystalline form: Colorless scales
Recrystallization solvent: Ethanol
Melting Point: 197–198° C.
Form: Free

TABLE 5-continued

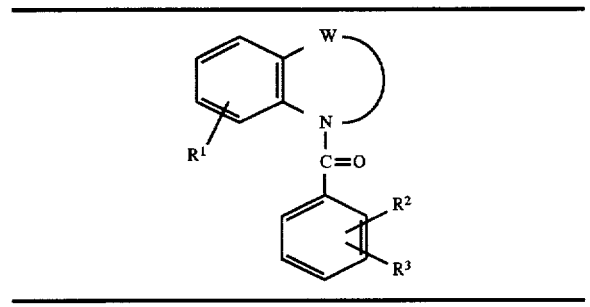

Example 790

Structure

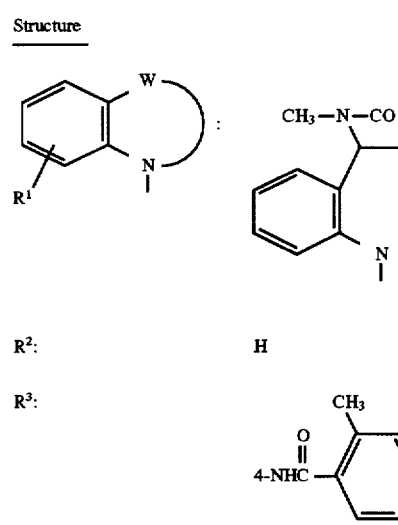

R²: H

R³:

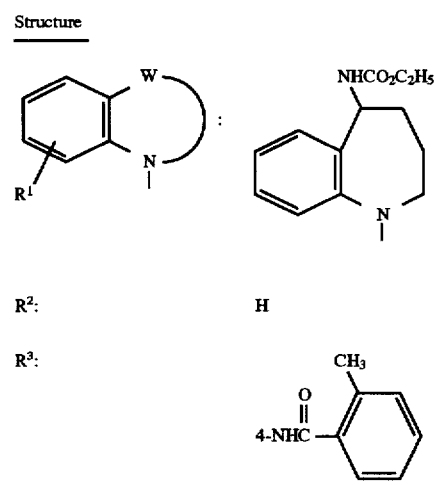

Crystalline form: Colorless needles
Recrystallization solvent: Ethanol
Melting Point: 248–249° C.
Form: Free

Example 791

Structure

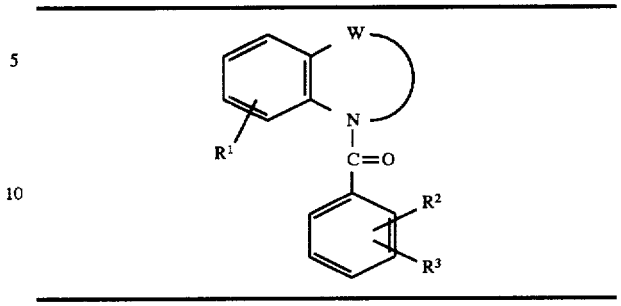

R²: H

R³:

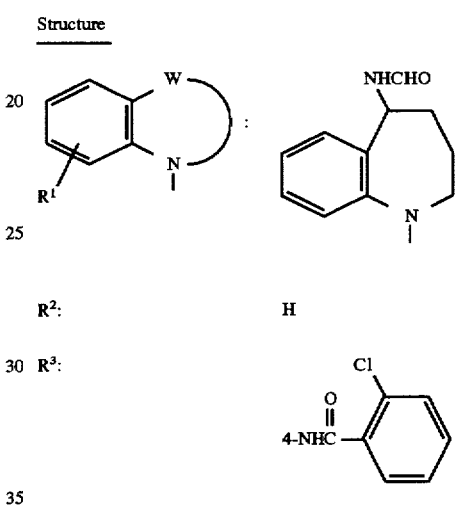

Crystalline form: Colorless needles
Recrystallization solvent: Ethanol/n-hexane
Melting Point: 162–163° C.
Form: Free

TABLE 5-continued

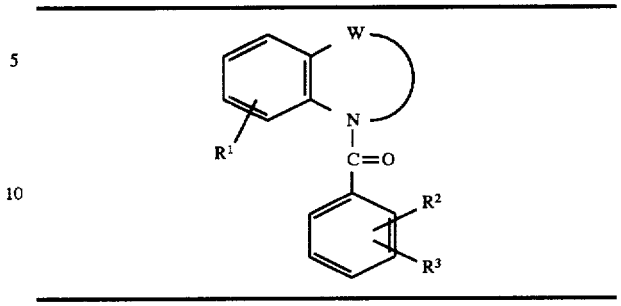

Example 792

Structure

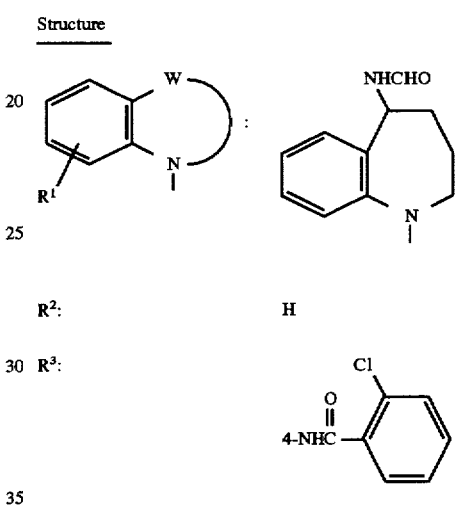

R²: H

R³:

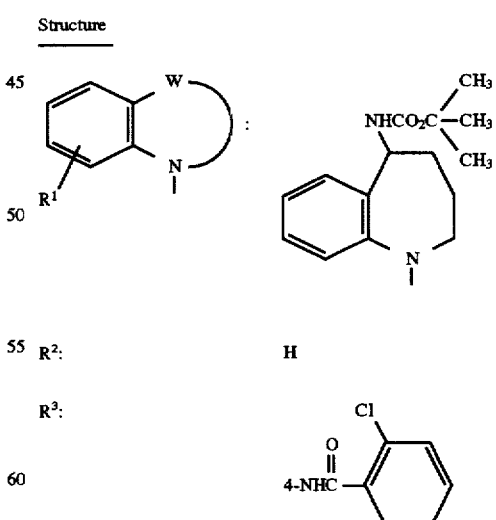

Crystalline form: Colorless prisms
Recrystallization solvent: Ethanol/petroleum ether
Melting Point: 235–236.5° C.
Form: Free

Example 793

Structure

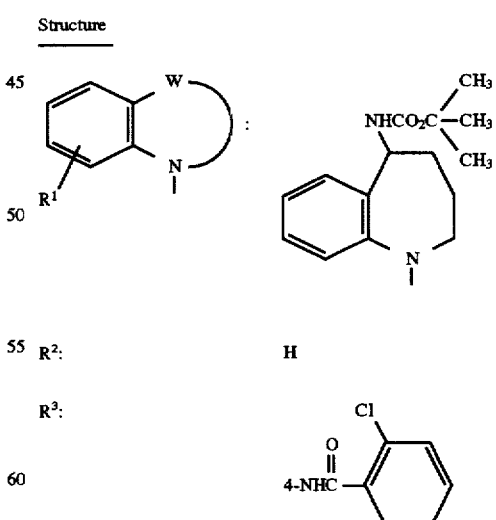

R²: H

R³:

Crystalline form: Colorless amorphous
NMR analysis: 139)
Form: Free

TABLE 5-continued

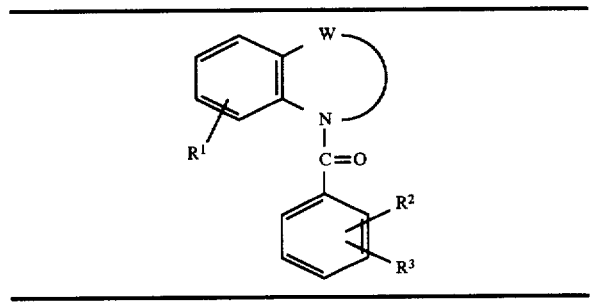

Example 794

Structure

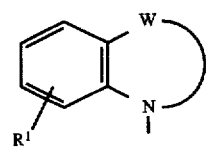 : 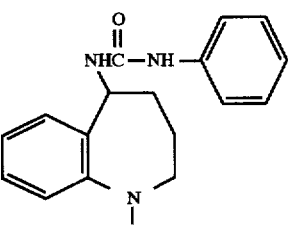

R²: H

R³:
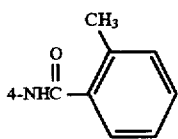

Crystalline form: Colorless prisms
Recrystallization solvent: Dioxane
Melting Point: 269–271° C.
Form: Free Example 795

Structure

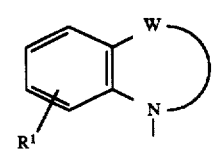 : 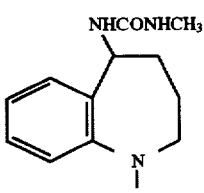

R²: H

R³:
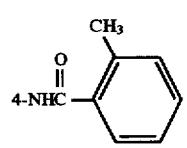

Crystalline form: Colorless prisms
Recrystallization solvent: Dimethylformamide
Melting Point: 286–287° C.
Form: Free TABLE 5-continued

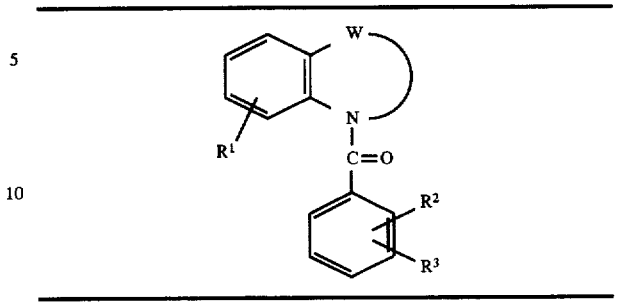

Example 796

Structure

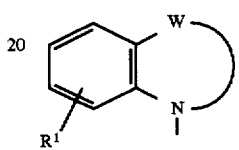 : 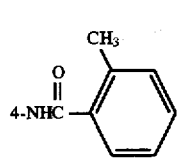

R²: H

R³:
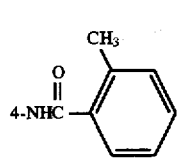

Crystalline form: Colorless needles
Recrystallization solvent: Acetonitrile
Melting Point: 227–228° C.
Form: Free Example 797

Structure

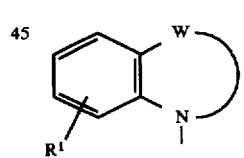 : 

R²: H

R³:
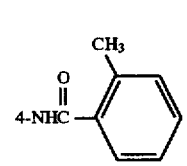

Crystalline form: Colorless amorphous
NMR analysis: 140)
Form: Free

TABLE 5-continued

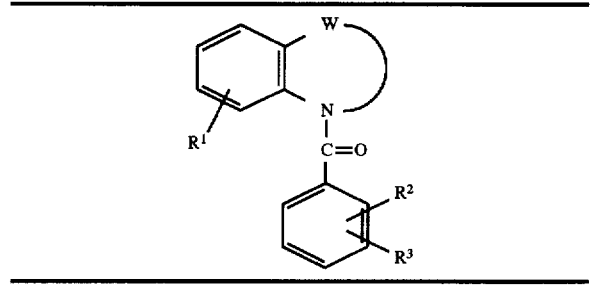

Example 798

Structure

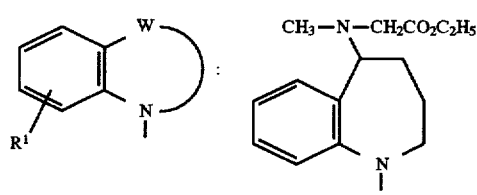

R²: H

R³:

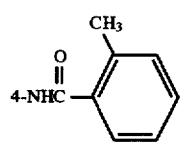

Crystalline form: Colorless prisms
Recrystallization solvent: Ethyl acetate/petroleum ether
Melting Point: 167–168° C.
Form: Free

Example 799

Structure

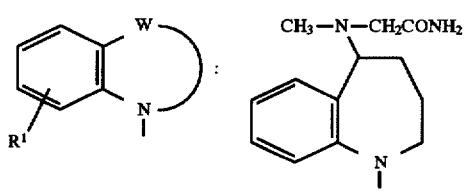

R²: H

R³:

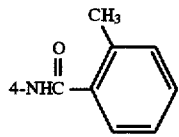

Crystalline form: Colorless amorphous
NMR analysis: 141)

Example 800

Structure

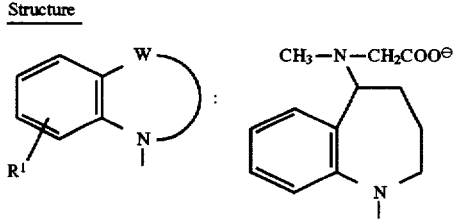

TABLE 5-continued

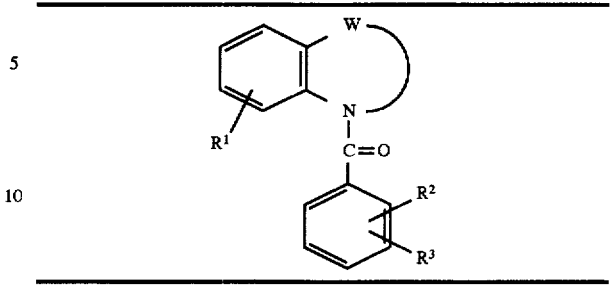

R²: H

R³:

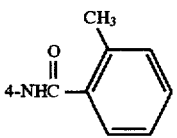

Crystalline form: Colorless needles
Recrystallization solvent: Diethyl ether
Melting Point: 164–171° C.
Form: K⊕

Example 801

Structure

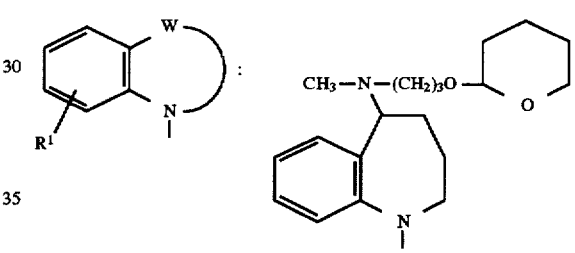

R²: H

R³:

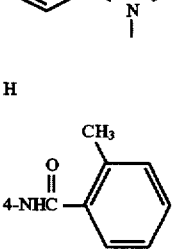

Crystalline form: Colorless amorphous
NMR analysis: 142)
Form: Free

Example 802

Structure

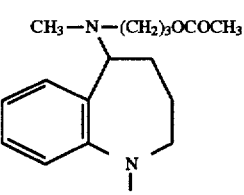

R²: H

R³:

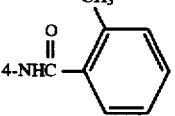

TABLE 5-continued

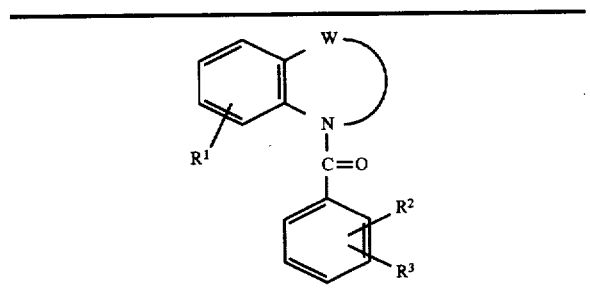

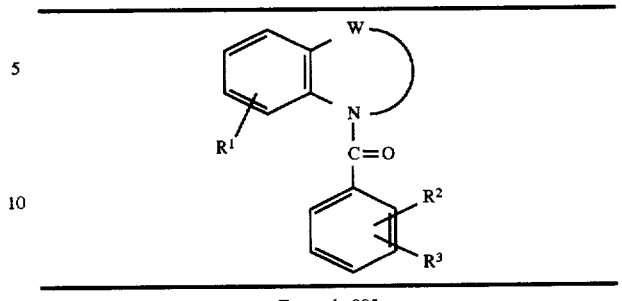

Crystalline form: Colorless amorphous
NMR analysis: 143)
Form: Free

Example 803

Structure

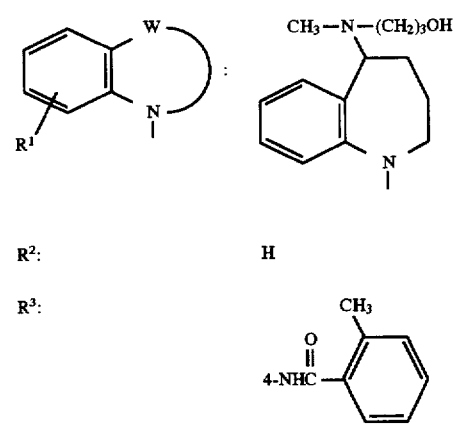

R²: H

R³:

Crystalline form: Colorless amorphous
NMR analysis: 144)
Form: Free

Example 804

Structure

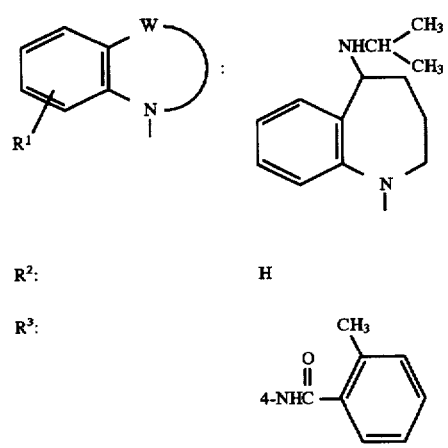

R²: H

R³:

Crystalline form: Colorless amorphous
NMR analysis: 145)
Form: Free

Example 805

Structure

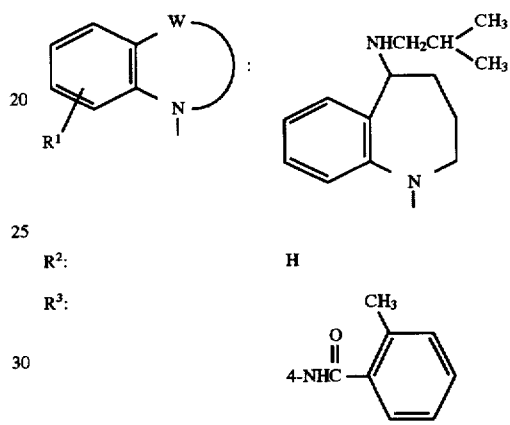

R²: H

R³:

Crystalline form: Colorless needles
Recrystallization solvent: Ethanol
Melting Point: 207–208° C.
Form: Free Example 806

Structure

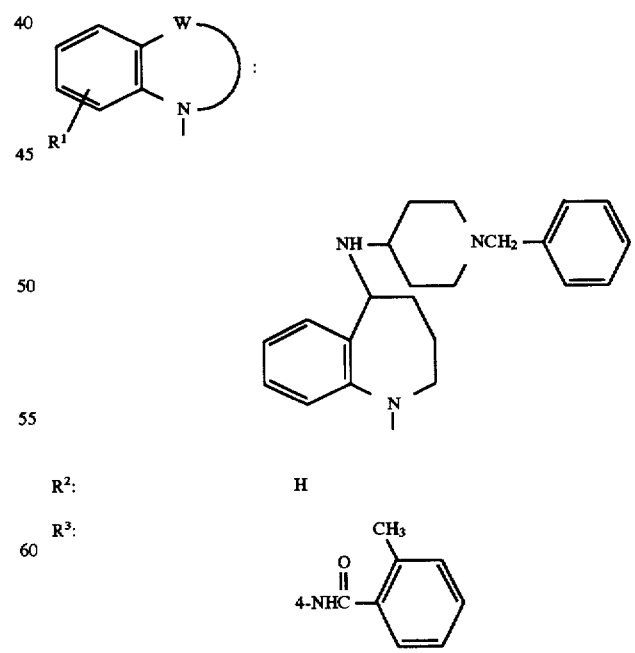

R²: H

R³:

Crystalline form: White powder
Recrystallization solvent: Dichloromethane/diethyl ether

TABLE 5-continued

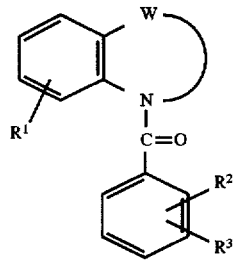

Melting Point: 187–189° C.
Form: Free

Example 807

Structure

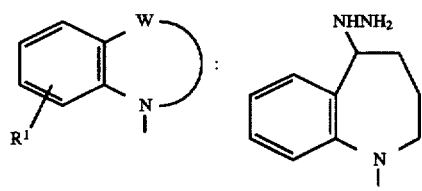

R²: H

R³: 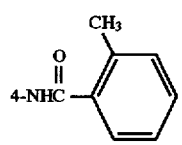

Crystalline form: Colorless prisms
Recrystallization solvent: Ethanol/petroleum ether
Melting Point: 217–218° C.
Form: Free

Example 808

Structure

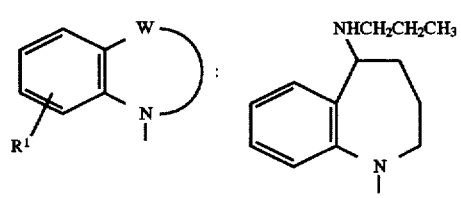

R²: H

R³: 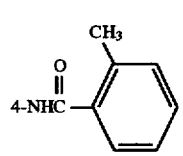

Crystalline form: Colorless needles
Recrystallization solvent: Ethyl acetate
Melting Point: 170–171° C.
Form: Free

TABLE 5-continued

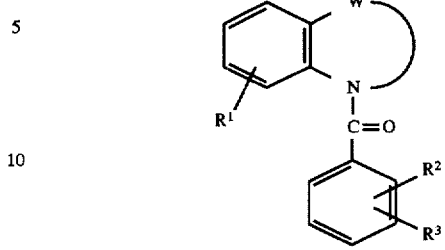

Example 809

Structure

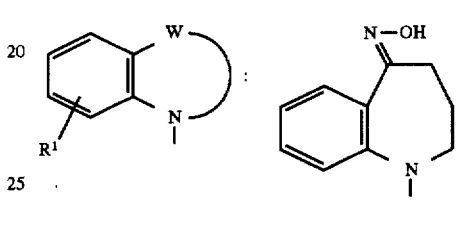

R²: H

R³: 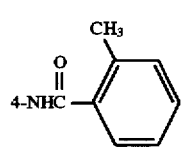

Crystalline form: Colorless prisms
Recrystallization solvent: Ethanol
Melting Point: 239.5–241° C.
Form: Free

Example 810

Structure

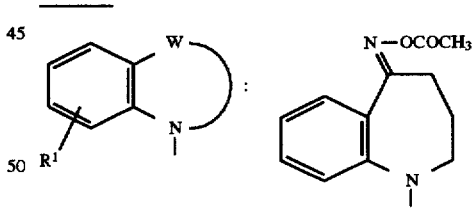

R²: H

R³: 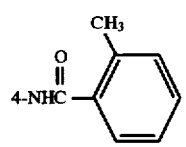

Crystalline form: Colorless needles
Recrystallization solvent: Ethanol
Melting Point: 190–191° C.
Form: Free TABLE 5-continued

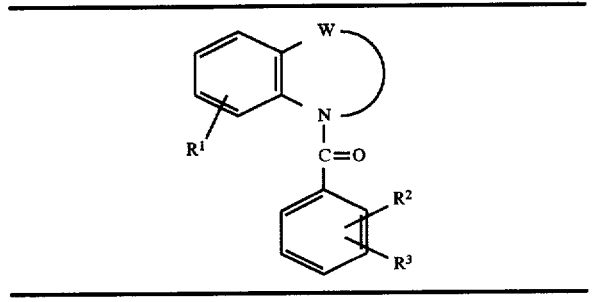

Example 811

Structure

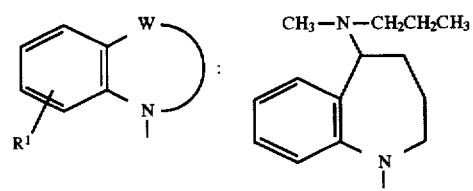

R²: H

R³:

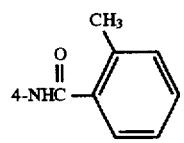

Crystalline form: Colorless prisms
Recrystallization solvent: Diethyl ether
Melting Point: 163–163.5° C.
Form: Free Example 812

Structure

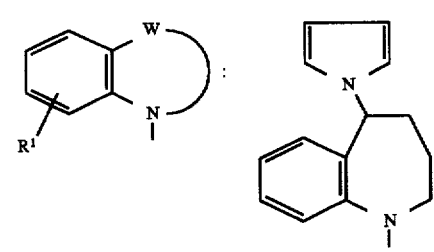

R²: H

R³:

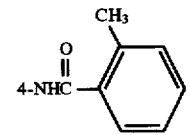

Crystalline form: Colorless prisms
Recrystallization solvent: Ethyl acetate/n-hexane
Melting Point: 208–210° C.
Form: Free TABLE 5-continued

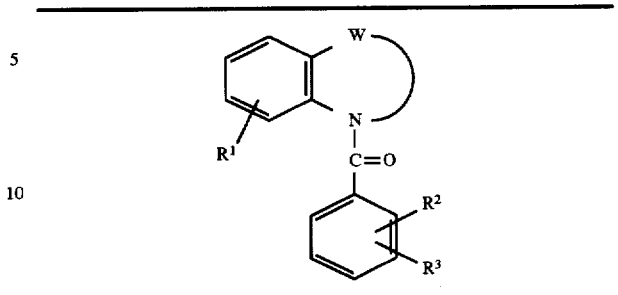

Example 813

Structure

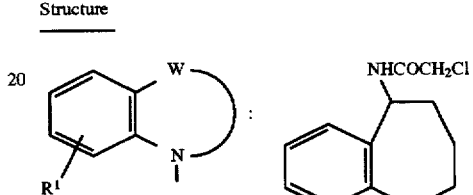

R²: H

R³:

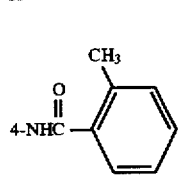

Crystalline form: White powder
NMR analysis: 146)
Form: Free

Example 814

Structure

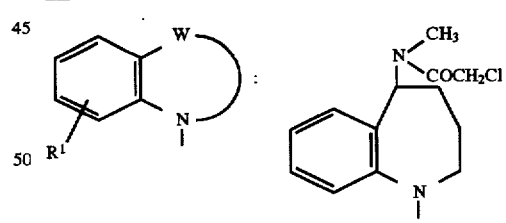

R²: H

R³:

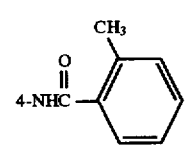

Crystalline form: Colorless amorphous
NMR analysis: 147)
Form: Free

TABLE 5-continued

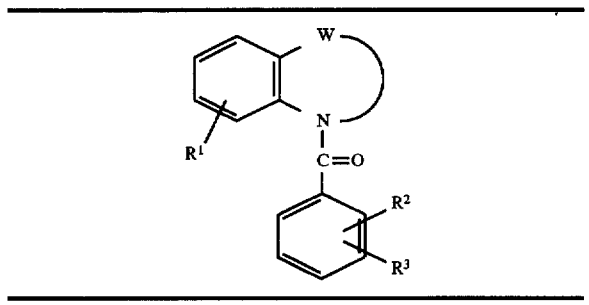

Example 815

Structure

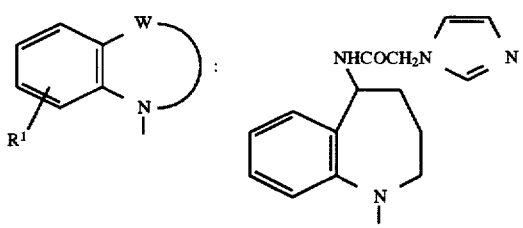

R²: H

R³:

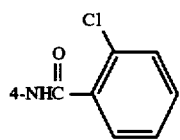

Crystalline form: Colorless needles
Recrystallization solvent: Ethanol/n-hexane
Melting Point: 250–252° C.
Form: Free Example 816

Structure

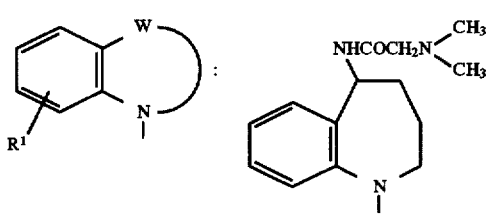

R²: H

R³:

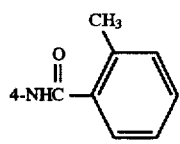

Crystalline form: Colorless prisms
Recrystallization solvent: Ethyl acetate
Melting Point: 214–216° C.
Form: Free TABLE 5-continued

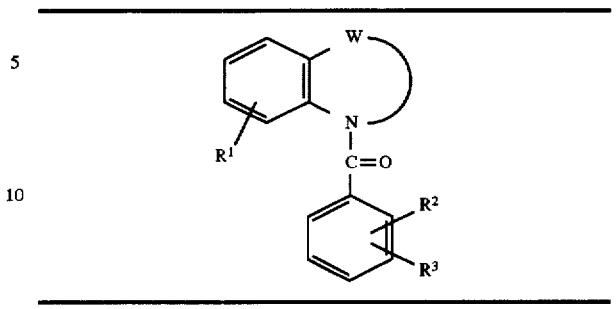

Example 817

Structure

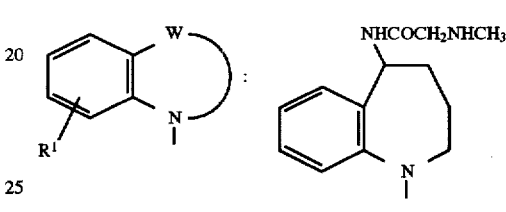

R²: H

R³:

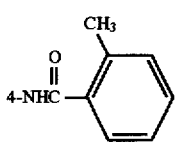

Crystalline form: Colorless prisms
Recrystallization solvent: Ethanol/n-hexane
Melting Point: 243–245° C.
Form: Free Example 818

Structure

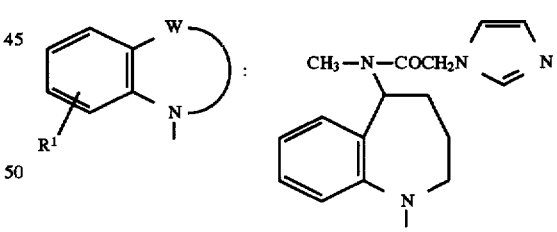

R²: H

R³:

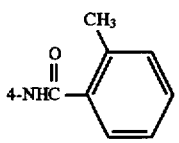

Crystalline form: Colorless prisms
Recrystallization solvent: Diethyl ether
Melting Point: 159–162° C.
Form: Free TABLE 5-continued

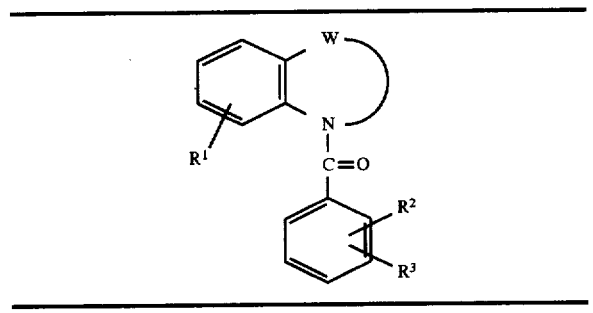

Example 819

Structure

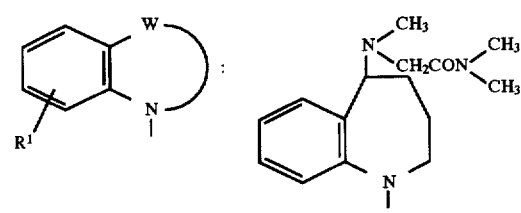

R²:   H

R³:

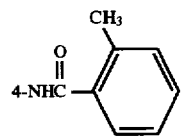

Crystalline form: Colorless amorphous
NMR analysis: 148)
Form: Free

Example 820

Structure

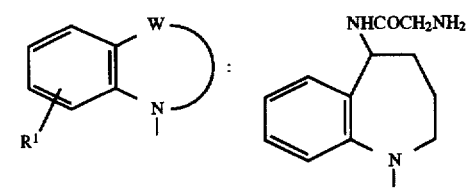

R²:   H

R³:

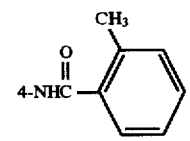

Crystalline form: Colorless prisms
Recrystallization solvent: Ethyl acetate
Melting Point: 287–289° C.
Form: Free TABLE 5-continued

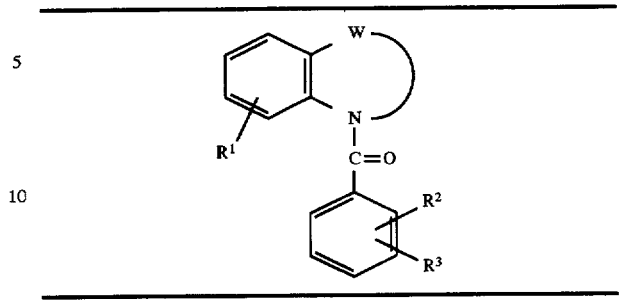

Example 821

Structure

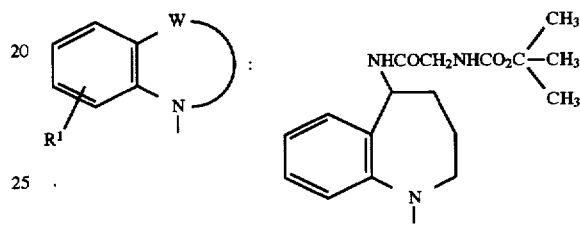

R²:   H

R³:

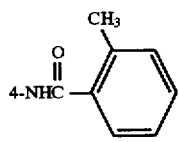

Crystalline form: Colorless prisms
Recrystallization solvent: Diethyl ether
Melting Point: 170–171° C.
Form: Free Example 822

Structure

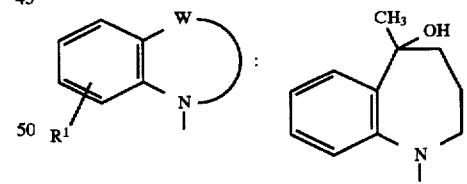

R²:   H

R³:

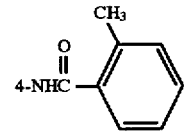

Crystalline form: White powder
Recrystallization solvent: Ethyl acetate/n-hexane
Melting Point: 204–205° C.
Form: Free

TABLE 5-continued

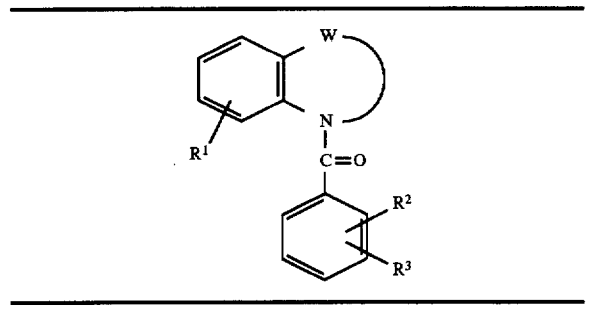

Example 823

Structure

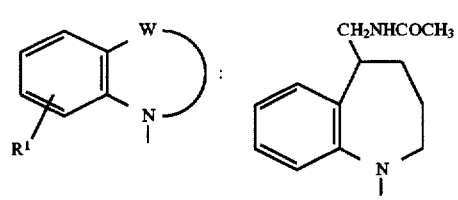

R²: H

R³:

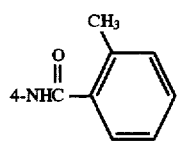

Crystalline form: White powder
Recrystallization solvent: Ethyl acetate/n-hexane
Melting Point: 273–273.5° C.
Form: Free

Example 824

Structure

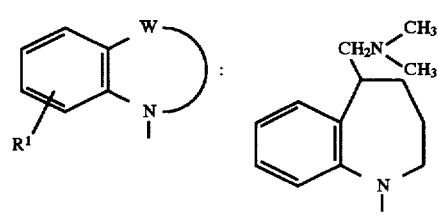

R²: H

R³:

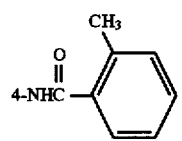

Crystalline form: Colorless amorphous
NMR analysis: 149)
Form: Free

TABLE 5-continued

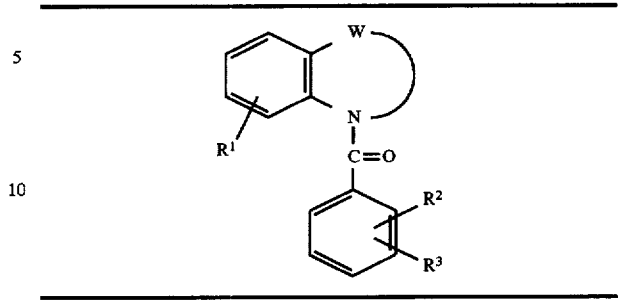

Example 825

Structure

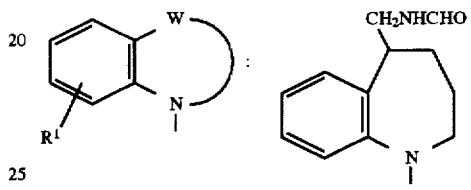

R²: H

R³:

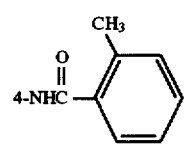

Crystalline form: White powder
Recrystallization solvent: Ethyl acetate/n-hexane
Melting Point: 240–241° C.
Form: Free

Example 826

Structure

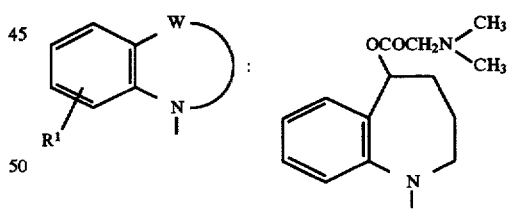

R²: H

R³:

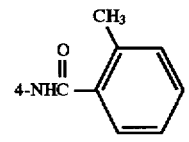

Crystalline form: White powder
Recrystallization solvent: Acetonitrile/ethanol
Melting Point: 231–232° C.
Form: Free TABLE 5-continued

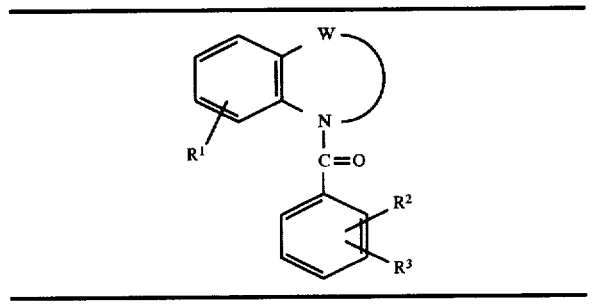

Example 827

Structure

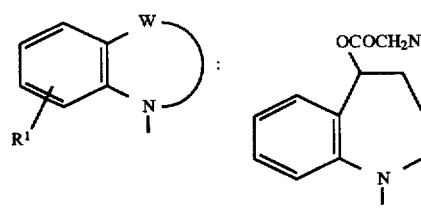

R²: H

R³:
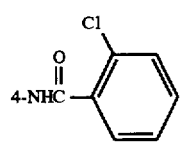

Crystalline form: White powder
Recrystallization solvent: Acetonitrile/ethanol
Melting Point: 222–224° C.
Form: Free Example 828

Structure

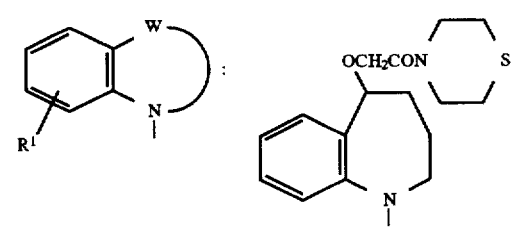

R²: H

R³:
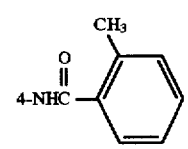

Crystalline form: White powder
Recrystallization solvent: Ethyl acetate/n-hexane
Melting Point: 235–237° C.
Form: Free TABLE 5-continued

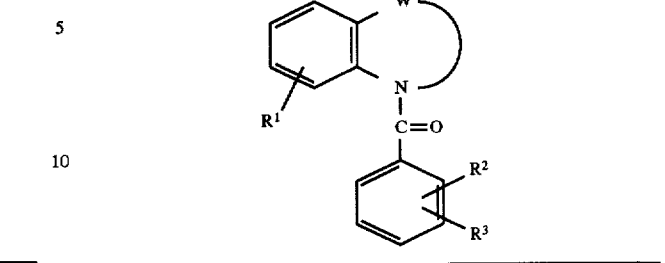

Example 829

Structure

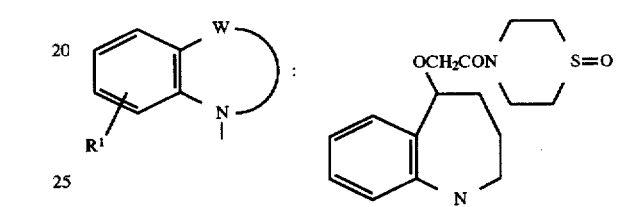

R²: H

R³:
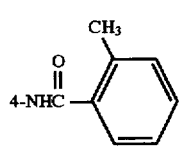

Crystalline form: Colorless amorphous
NMR analysis: 150)
Form: Free

Example 830

Structure

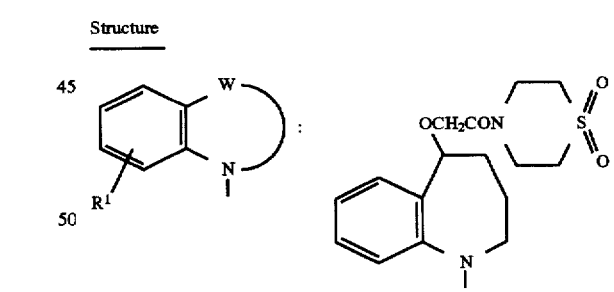

R²: H

R³:
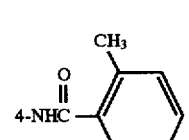

Crystalline form: Colorless amorphous
NMR analysis: 151)
Form: Free

TABLE 5-continued

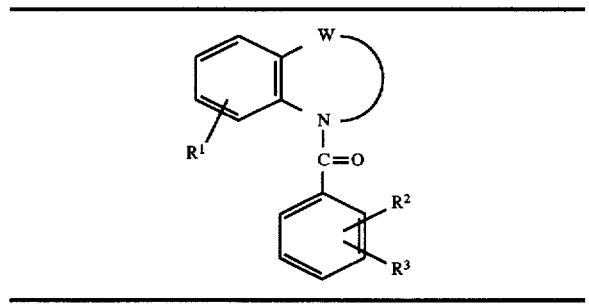

Example 831

Structure

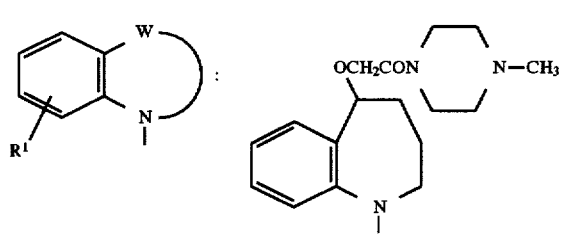

R²: H

R³: 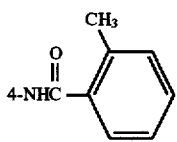

Crystalline form: Colorless amorphous
NMR analysis: 152)
Form: Free

Example 832

Structure

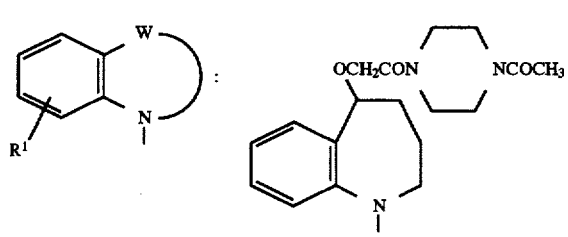

R²: H

R³: 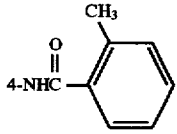

Crystalline form: Colorless amorphous
NMR analysis: 153)
Form: Free

TABLE 5-continued

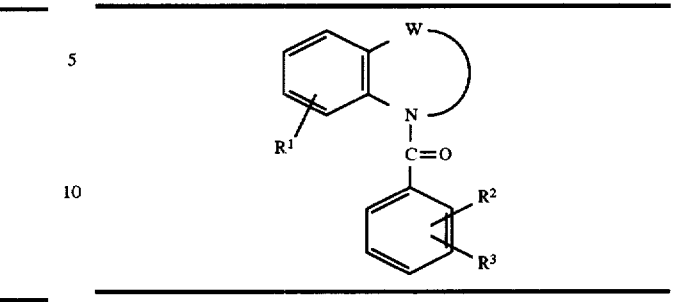

Example 834

Structure

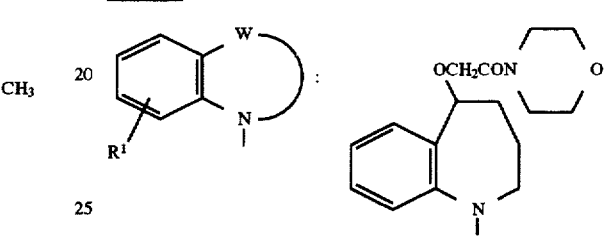

R²: H

R³: 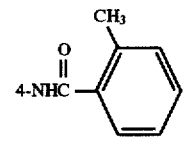

Crystalline form: White powder
Recrystallization solvent: Ethyl acetate/n-hexane
Melting Point: 247–248° C.
Form: Free

Example 835

Structure

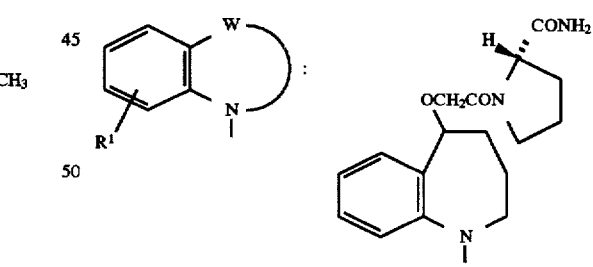

R²: H

R³: 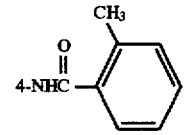

Crystalline form: Colorless amorphous
NMR analysis: 154)
Form: Free

TABLE 5-continued

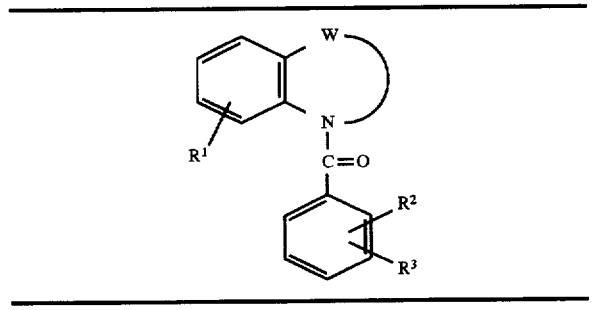

Example 836

Structure

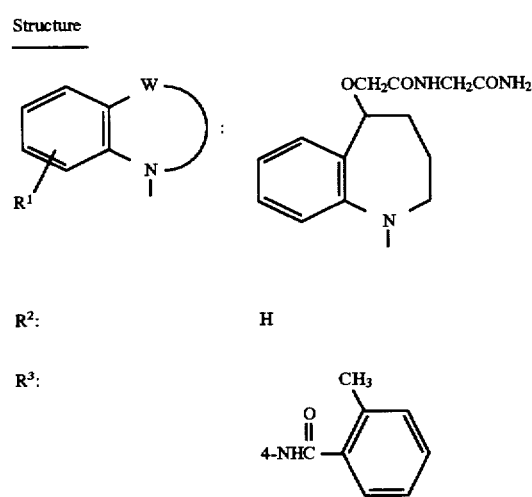

R²: H

R³: 4-NHC(=O)-(2-CH₃-phenyl)

Crystalline form: Colorless amorphous
NMR analysis: 155)
Form: Free

Example 837

Structure

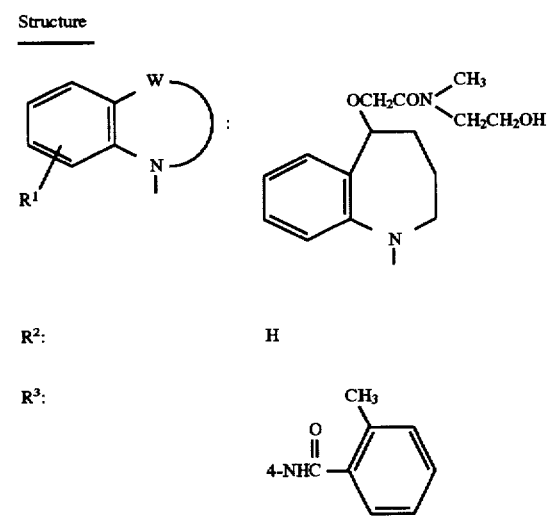

R²: H

R³: 4-NHC(=O)-(2-CH₃-phenyl)

Crystalline form: Colorless amorphous
NMR analysis: 156)
Form: Free

TABLE 5-continued

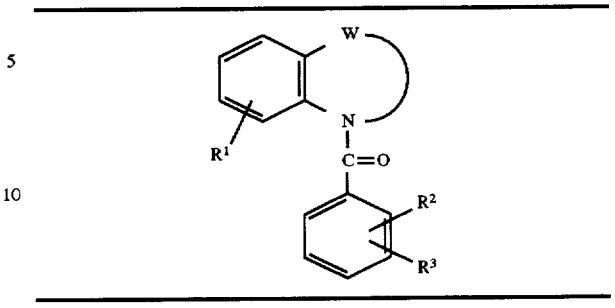

Example 838

Structure

R²: H

R³: 4-NHC(=O)-(2-CH₃-phenyl)

Crystalline form: Colorless amorphous
NMR analysis: 157)
Form: Free

Example 839

Structure

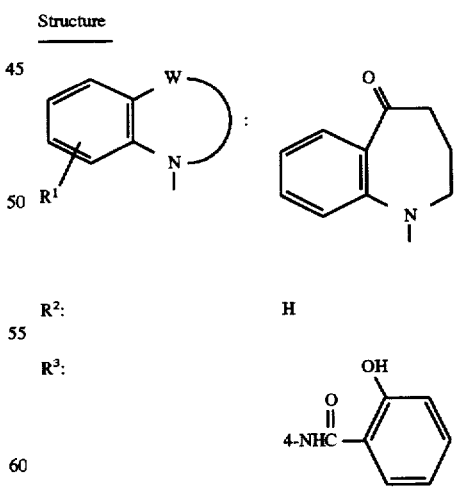

R²: H

R³: 4-NHC(=O)-(2-OH-phenyl)

Crystalline form: White powder
Recrystallization solvent: Ethyl acetate/n-hexane
Melting Point: 234–235° C.
Form: Free TABLE 5-continued

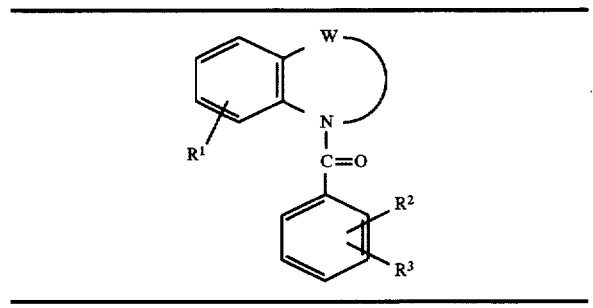

Example 840

Structure

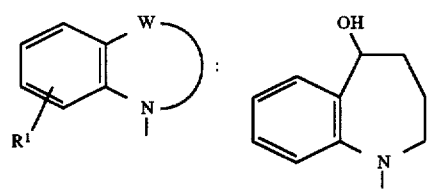

R²: H

R³: 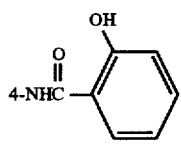

Crystalline form: White powder
Recrystallization solvent: Ethyl acetate/n-hexane
Melting Point: 234–235° C.
Form: Free Example 841

Structure

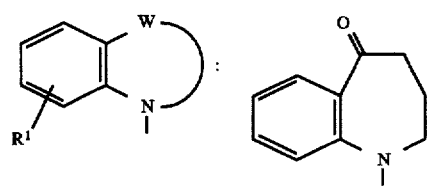

R²: H

R³: 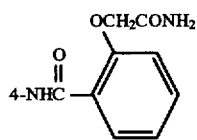

Crystalline form: White powder
Recrystallization solvent: Ethyl acetate/n-hexane
Melting Point: 226–228° C.
Form: Free TABLE 5-continued

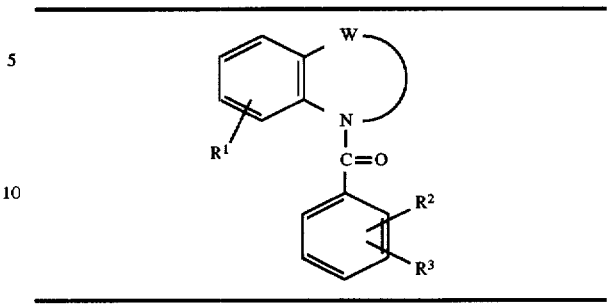

Example 842

Structure

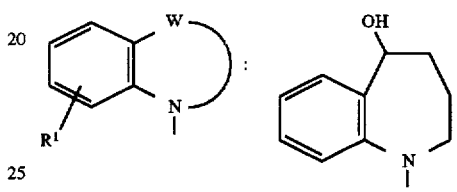

R²: H

R³: 

Crystalline form: White powder
Recrystallization solvent: Ethyl acetate/n-hexane
Melting Point: 230–231° C.
Form: Free Example 843

Structure

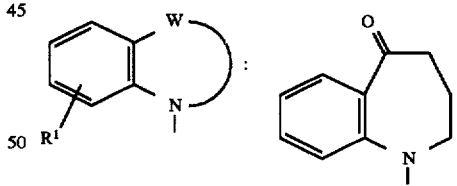

R²: H

R³: 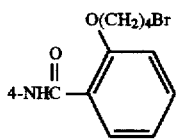

Crystalline form: White powder
Recrystallization solvent: Ethyl acetate/n-hexane
Melting Point: 186–188° C.
Form: Free TABLE 5-continued

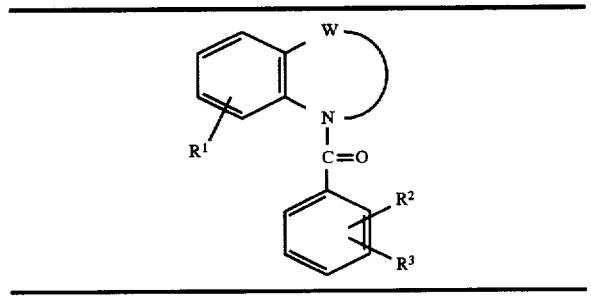

Example 844

Structure

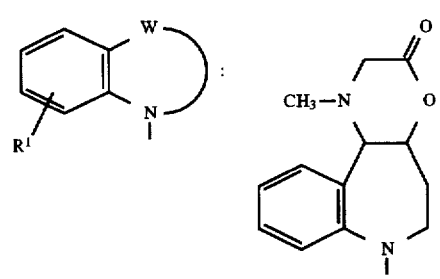

R²: H

R³:

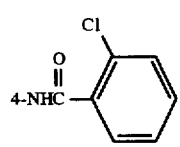

Crystalline form: Colorless prisms
Recrystallization solvent: Chloroform/methanol
Melting Point: 286–290° C.
Form: Free Example 845

Structure

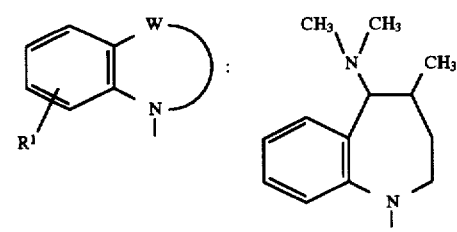

R²: H

R³:

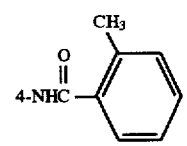

Crystalline form: Colorless needles
Recrystallization solvent: Ethanol
Melting Point: 186–188.5° C.
Form: Free TABLE 5-continued

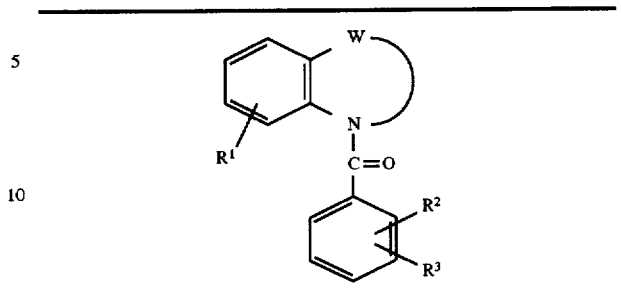

Example 846

Structure

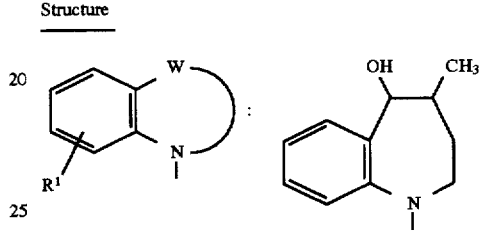

R²: H

R³:

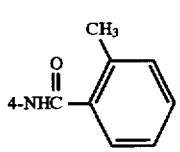

Crystalline form: Colorless prisms
Recrystallization solvent: Ethanol
Melting Point: 220–222° C.
Form: Free Example 847

Structure

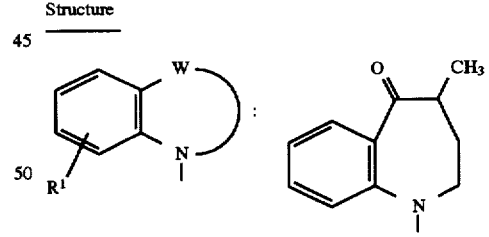

R²: H

R³:

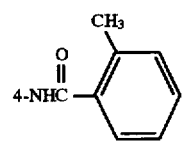

Crystalline form: White powder
NMR analysis: 158)
Form: Free

TABLE 5-continued

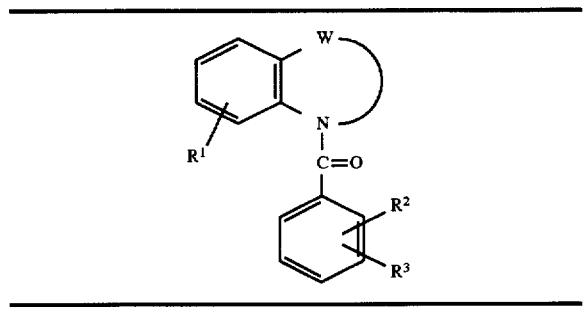

Example 848

Structure

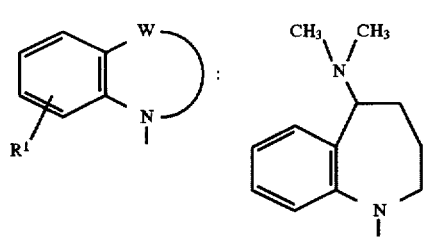

| | |
|---|---|
| R²: | H |
| R³: | 4-NHCOCH₂CONH₂ |

Crystalline form: Colorless prisms
Recrystallization solvent: Dichloromethane/diethyl ether
Melting Point: 189–192° C.
Form: Free Example 849

Structure

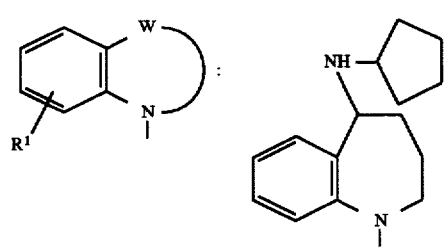

| | |
|---|---|
| R²: | 2-Cl |
| R³: | 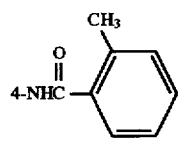 |

Crystalline form: Colorless amorphous
NMR analysis: 159)
Form: Free

TABLE 5-continued

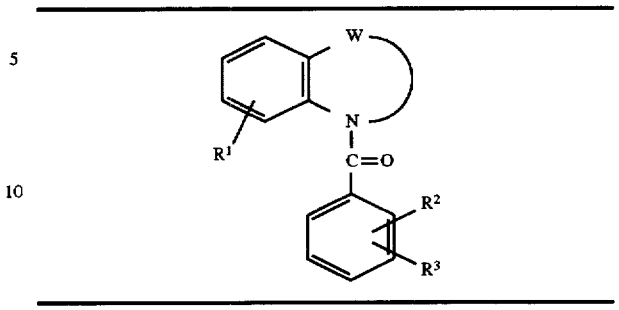

Example 850

Structure

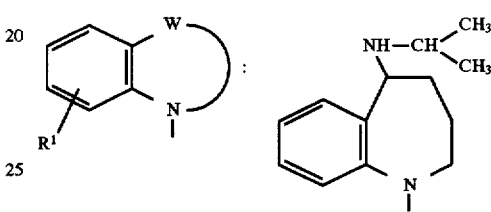

| | |
|---|---|
| R²: | 2-Cl |
| R³: | 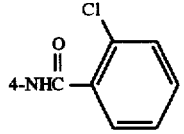 |

Crystalline form: White powder
Recrystallization solvent: Dichloromethane/diethyl ether
Melting Point: 207–209° C. (decomposed)
Form: Free Example 851

Structure

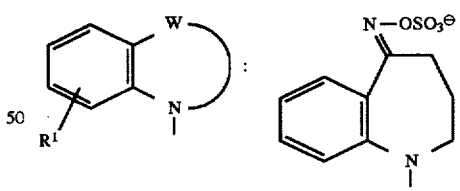

| | |
|---|---|
| R²: | 2-Cl |
| R³: | 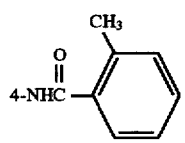 |

Crystalline form: White powder
NMR analysis: 160)
Form: K⊕

TABLE 5-continued

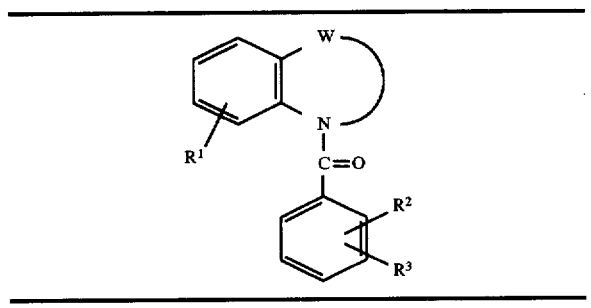

Example 852

Structure

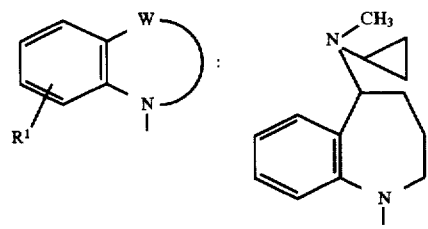

R²: 2-Cl

R³:

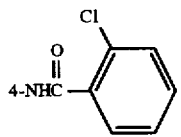

Crystalline form: White powder
Recrystallization solvent: Dichloromethane/diethyl ether
Melting Point: 193–194° C.
Form: Free Example 853

Structure

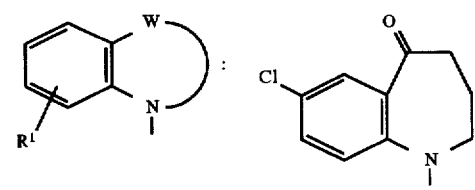

R²: H

R³:

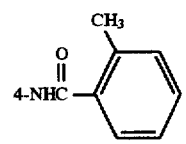

Crystalline form: White powder
Recrystallization solvent: Diethyl ether/dichloromethane
Melting Point: 185.5–186° C.
Form: Free TABLE 5-continued

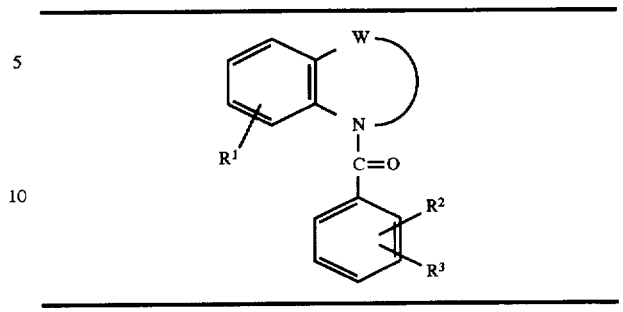

Example 854

Structure

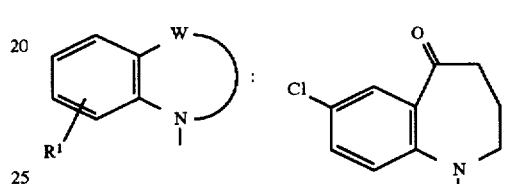

R²: H

R³:

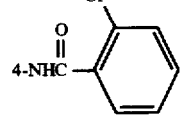

Crystalline form: White powder
Recrystallization solvent: Diethyl ether/dichloromethane
Melting Point: 223.5–226° C. (decomposed)
Form: Free Example 855

Structure

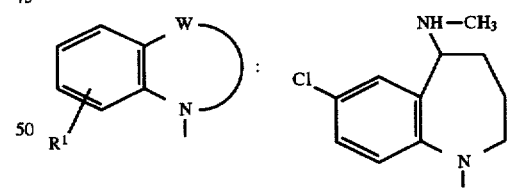

R²: H

R³:

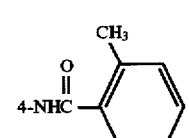

Crystalline form: Colorless amorphous
NMR analysis: 161)
Form: Free

TABLE 5-continued

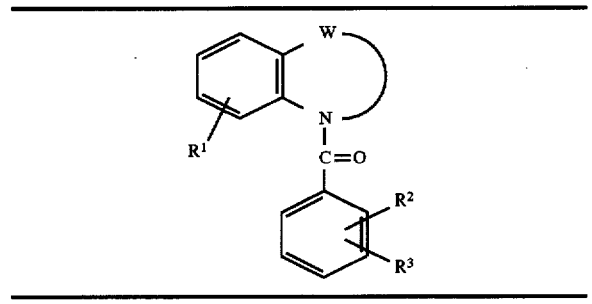

Example 856

Structure

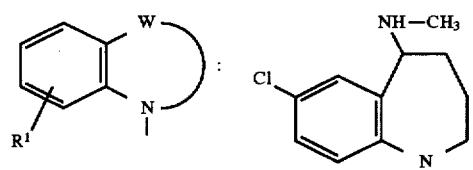

R²: H

R³:

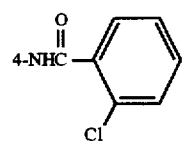

Crystalline form: White powder
Recrystallization solvent: Diethyl ether/dichloromethane
Melting Point: 225.5–227° C.
Form: Free Example 857

Structure

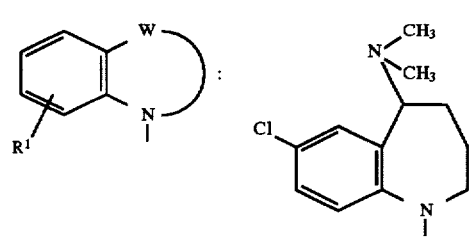

R²: H

R³:

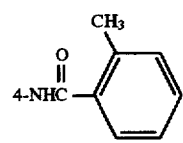

Crystalline form: White powder
Recrystallization solvent: Diethyl ether/dichloromethane
Melting Point: 212–214° C.
Form: Free TABLE 5-continued

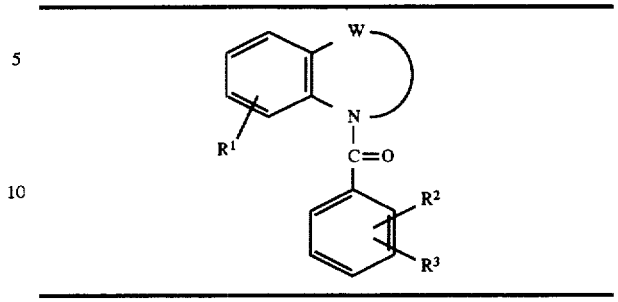

Example 858

Structure

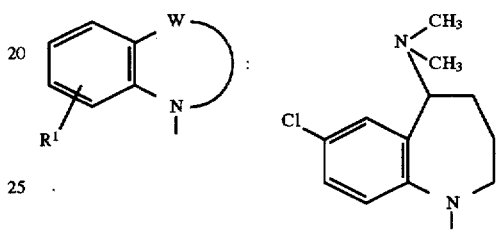

R²: H

R³:

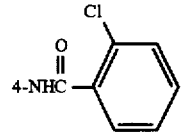

Crystalline form: White powder
Recrystallization solvent: Diethyl ether/dichloromethane
Melting Point: 230.5–233° C.
Form: Free Example 859

Structure

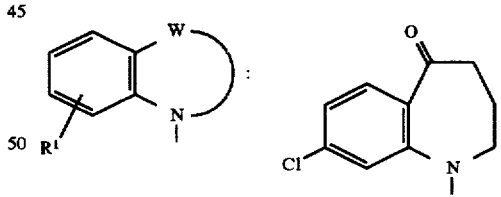

R²: H

R³:

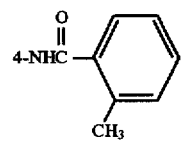

Crystalline form: White powder
Recrystallization solvent: Diethyl ether/dichloromethane
Melting Point: 212.5–215° C. (decomposed)
Form: Free TABLE 5-continued

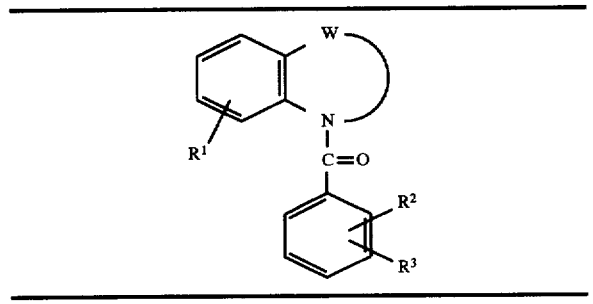

Example 860

Structure

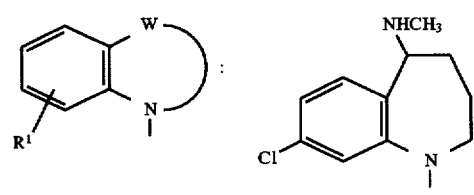

R²: H

R³:
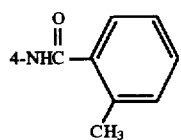

Crystalline form: White powder
Recrystallization solvent: Diethyl ether/dichloromethane
Melting Point: 192–194.5° C.
Form: Free Example 861

Structure

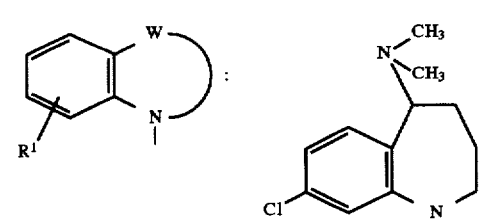

R²: H

R³:
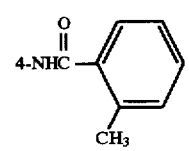

Crystalline form: White powder
Recrystallization solvent: Diethyl ether/dichloromethane
Melting Point: 175–177° C.
Form: Free TABLE 5-continued

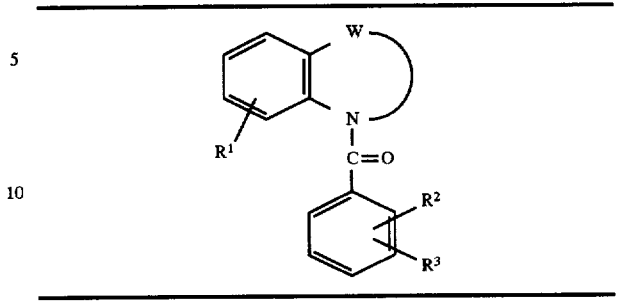

Example 862

Structure

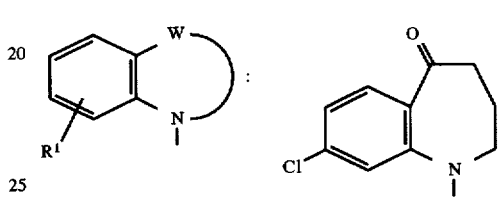

R²: H

R³:
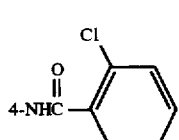

Crystalline form: White powder
Recrystallization solvent: Diethyl ether/dichloromethane
Melting Point: 205.5–209.5° C.
Form: Free Example 863

Structure

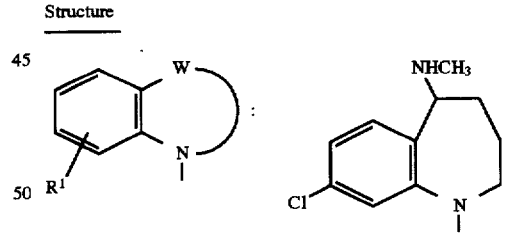

R²: H

R³:
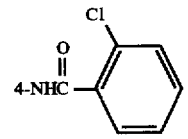

Crystalline form: White powder
Recrystallization solvent: Diethyl ether/dichloromethane
Melting Point: 191–193.5° C.
Form: Free TABLE 5-continued

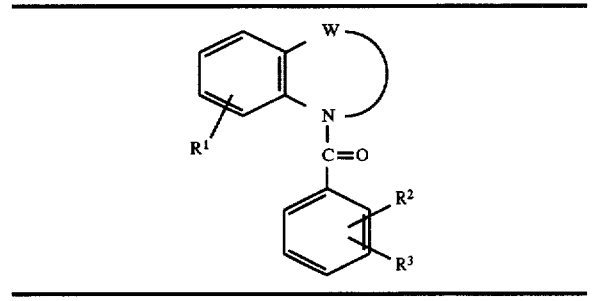

Example 864

Structure

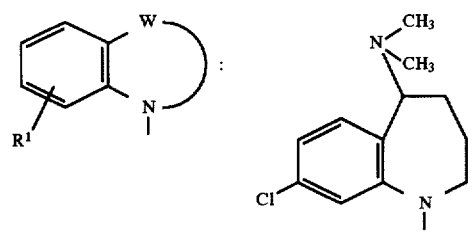

R²:  H

R³:  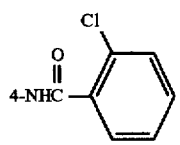

Crystalline form: White powder
Recrystallization solvent: Diethyl ether/dichloromethane
Melting Point: 204–205.5° C.
Form: Free

Example 865

Structure

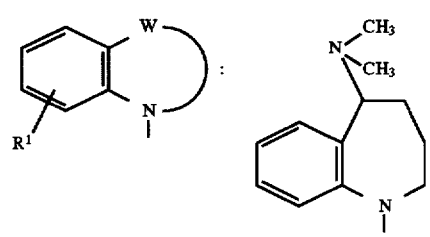

R²:  H

R³:  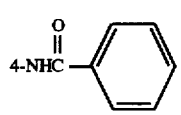

Crystalline form: Light yellow prisms
Recrystallization solvent: Ethanol
Melting Point: 221–223° C.
Form: Free TABLE 5-continued

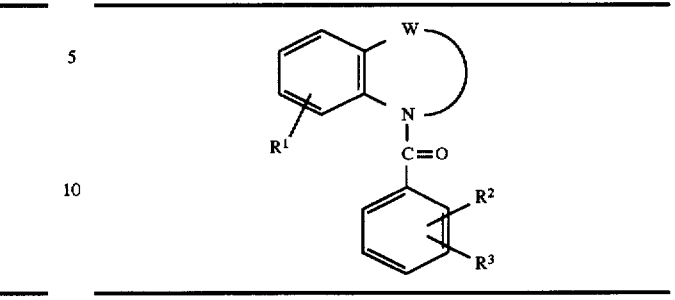

Example 866

Structure

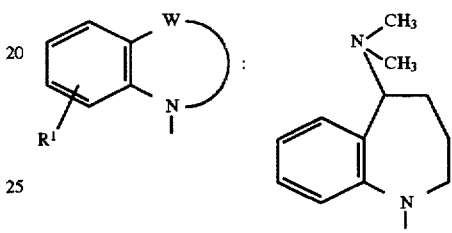

R²:  H

R³:  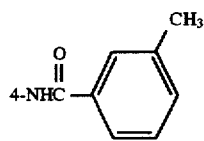

Crystalline form: Colorless prisms
Recrystallization solvent: Ethyl acetate
Melting Point: 171–173° C.
Form: Free

Example 867

Structure

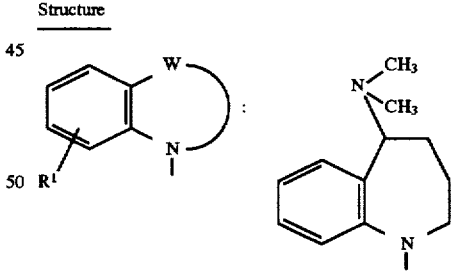

R²:  H

R³:  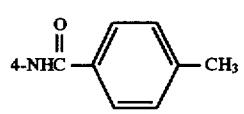

Crystalline form: Colorless prisms
Recrystallization solvent: Ethyl acetate
Melting Point: 185–187° C.
Form: Free TABLE 5-continued

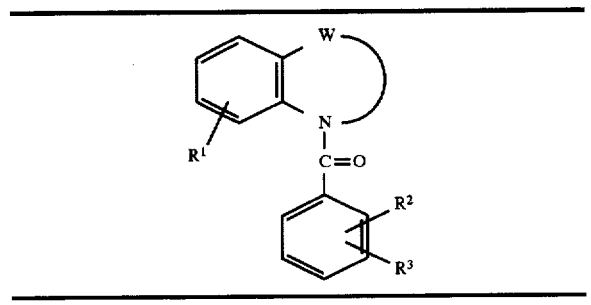

Example 868

Structure

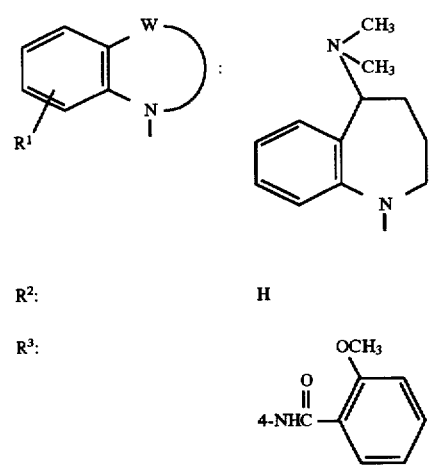

R²: H

R³:

-phenyl-OCH3 (ortho))

Crystalline form: Colorless prisms
Recrystallization solvent: Ethanol
Melting Point: 190–192° C.
Form: Free

Example 869

Structure

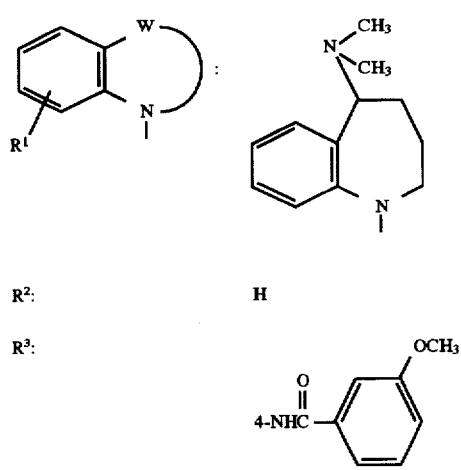

R²: H

R³:

-phenyl-OCH3 (meta))

Crystalline form: Colorless prisms
Recrystallization solvent: Ethanol
Melting Point: 175–177° C.
Form: Free TABLE 5-continued

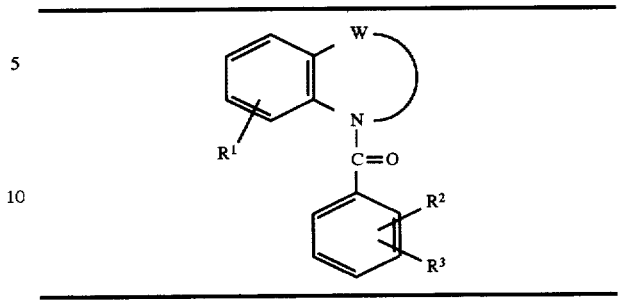

Example 870

Structure

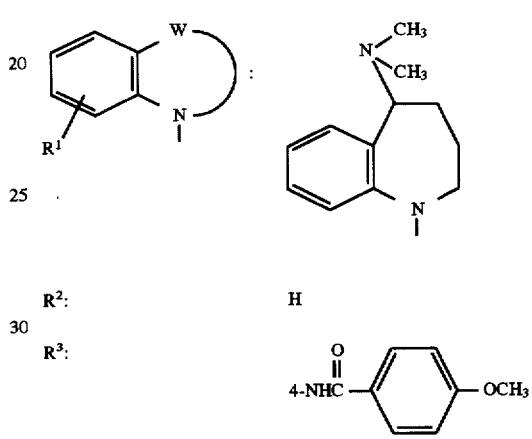

R²: H

R³:

-phenyl-OCH3 (para))

Crystalline form: Colorless powder
Recrystallization solvent: Ethyl acetate/n-hexane
Melting Point: 148–151° C.
Form: Free

Example 871

Structure

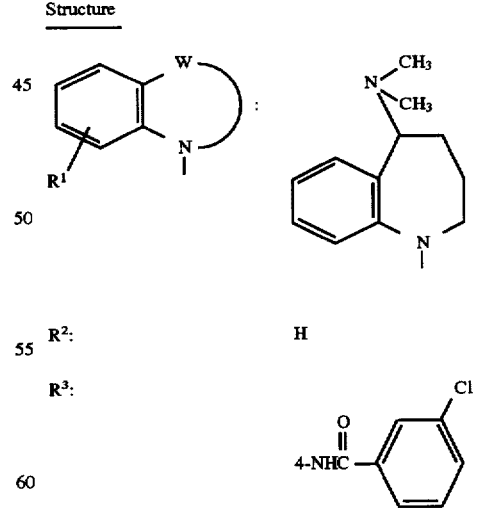

R²: H

R³:

-phenyl-Cl)

Crystalline form: Colorless prisms
Recrystallization solvent: Ethanol
Melting Point: 200–202° C.
Form: Free

TABLE 5-continued

Example 872

Structure

R²: H

R³: 4-NHC(=O)—C₆H₄—Cl (4-Cl)

Crystalline form: Colorless prisms
Recrystallization solvent: Ethanol
Melting Point: 200–202° C.
Form: Free

Example 873

Structure

R²: H

R³: 4-NHC(=O)—C₆H₄—NO₂ (2-NO₂)

Crystalline form: Light yellow powder
Recrystallization solvent: Acetone
Melting Point: 235–238° C.
Form: Free

TABLE 5-continued

Example 874

Structure

R²: H

R³: 4-NHC(=O)—C₆H₄—NO₂ (3-NO₂)

Crystalline form: Light yellow powder
Recrystallization solvent: Acetone
Melting Point: 198–201° C.
Form: Free

Example 875

Structure

R²: H

R³: 4-NHC(=O)—C₆H₄—NO₂ (4-NO₂)

Crystalline form: Light yellow needles
Recrystallization solvent: Chloroform/ethyl acetate
Melting Point: 232–237° C.
Form: Free TABLE 5-continued

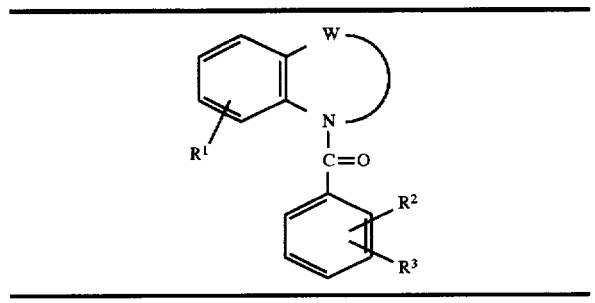

Example 876

Structure

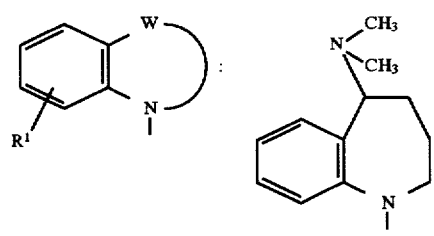

R²: H

R³:

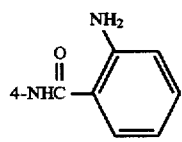

Crystalline form: Colorless prisms
Recrystallization solvent: Chloroform/ethyl acetate
Melting Point: 224–227° C.
Form: Free Example 877

Structure

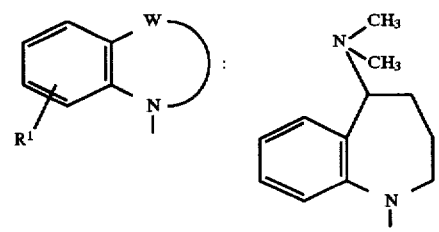

R²: H

R³:

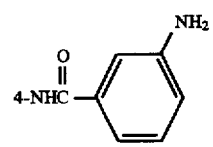

Crystalline form: Colorless prisms
Recrystallization solvent: Ethanol
Melting Point: 211–214° C.
Form: Free TABLE 5-continued

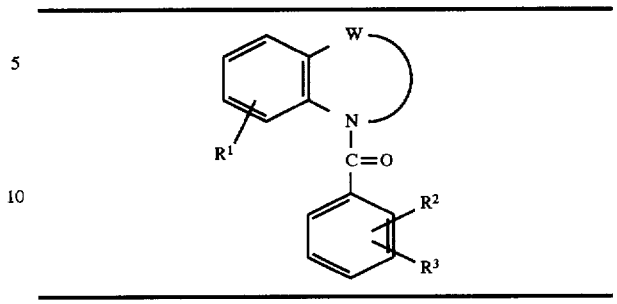

Example 878

Structure

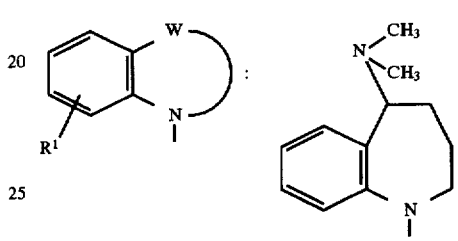

R²: H

R³:

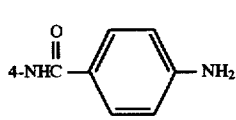

Crystalline form: Colorless powder
Recrystallization solvent: Dichloromethane/n-hexane
Melting Point: 238–243° C.
Form: Free Example 879

Structure

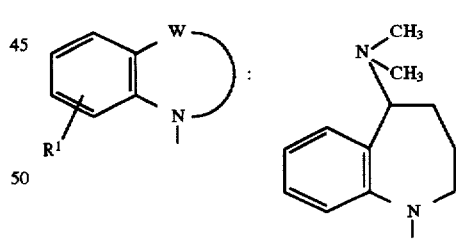

R²: H

R³:

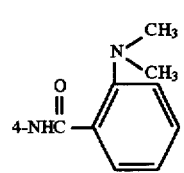

Crystalline form: Colorless amorphous
NMR analysis: 162)
Form: Free

TABLE 5-continued

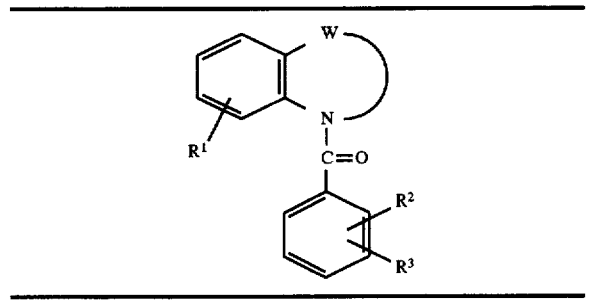

Example 880

Structure

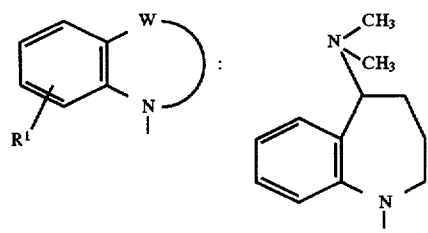

R²: H

R³:

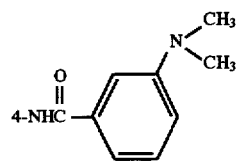

Crystalline form: Colorless amorphous
NMR analysis: 163)
Form: Free

Example 881

Structure

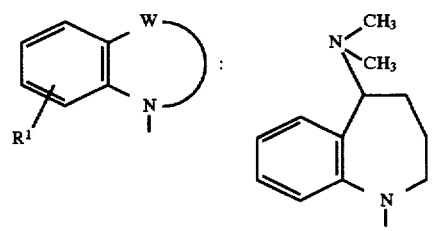

R²: H

R³:

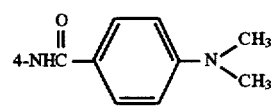

Crystalline form: Colorless prisms
Recrystallization solvent: Dichloromethane/diethyl ether
Melting Point: 198–202° C.
Form: Free

TABLE 5-continued

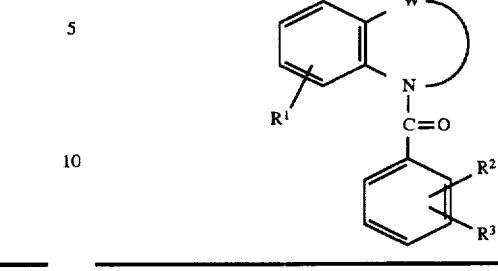

Example 882

Structure

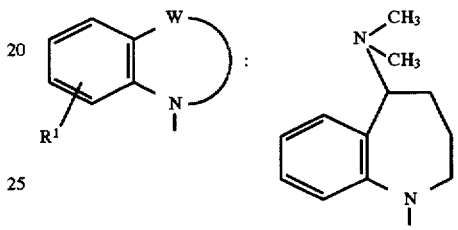

R²: H

R³:

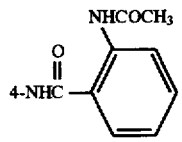

Crystalline form: Colorless prisms
Recrystallization solvent: Chloroform/ethyl acetate
Melting Point: 226–229° C.
Form: Free

Example 883

Structure

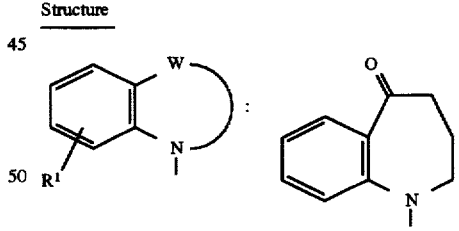

R²: 2-CH₃

R³:

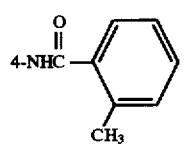

Crystalline form: White powder
Recrystallization solvent: Methanol/diethyl ether
Melting Point: 139–140° C.
Form: Free

TABLE 5-continued

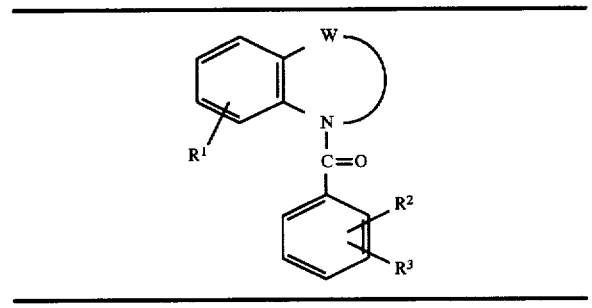

Example 884

Structure

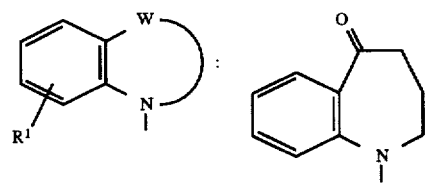

R²:  2-CH₃

R³:

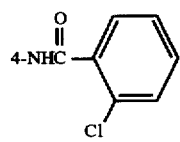

Crystalline form: White powder
Recrystallization solvent: Methanol/diethyl ether
Melting Point: 149–152° C.
Form: Free

Example 885

Structure

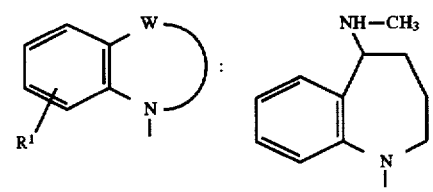

R²:  2-CH₃

R³:

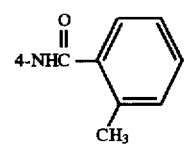

Crystalline form: White powder
Recrystallization solvent: Methanol/diethyl ether
Melting Point: 180.5–182° C.
Form: Free

TABLE 5-continued

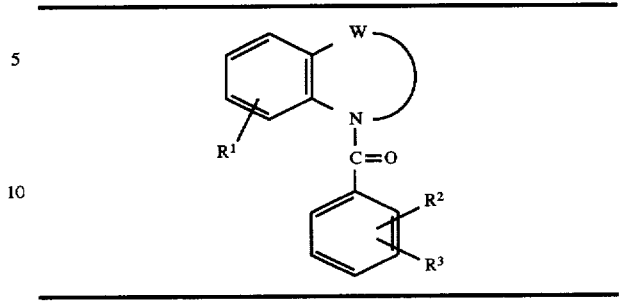

Example 886

Structure

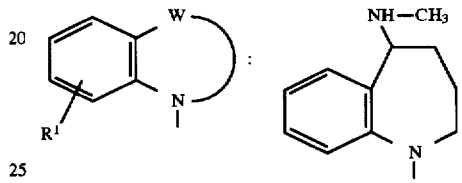

R²:  2-CH₃

R³:

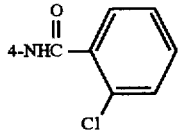

Crystalline form: White powder
Recrystallization solvent: Chloroform/diethyl ether
Melting Point: 211–214° C.
Form: Free

Example 887

Structure

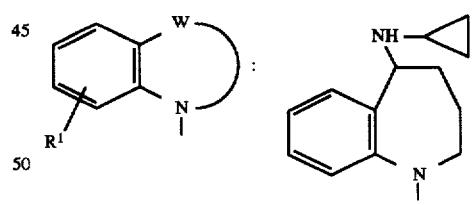

R²:  2-CH₃

R³:

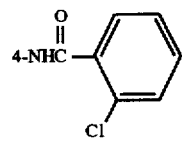

Crystalline form: White powder
Recrystallization solvent: Chloroform/diethyl ether
Melting Point: 171–174.5° C.
Form: Free TABLE 5-continued

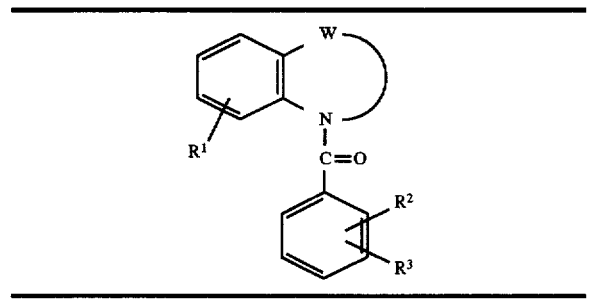

Example 888

Structure

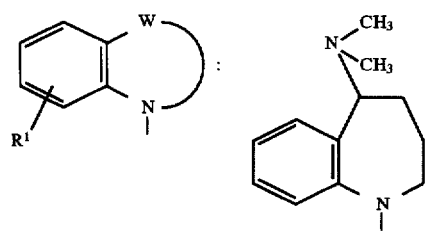

R²: H

R³:
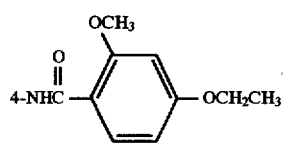

Crystalline form: White powder
Recrystallization solvent: Methanol/diethyl ether
Melting Point: 203–205° C.
Form: Free

Example 889

Structure

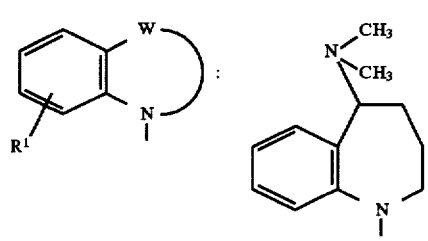

R²: 3-OCH₃

R³:
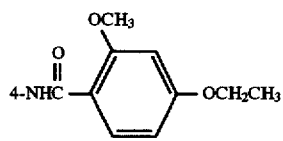

Crystalline form: White powder
Recrystallization solvent: Ethanol
Melting Point: 202–202.5° C.
Form: Free TABLE 5-continued

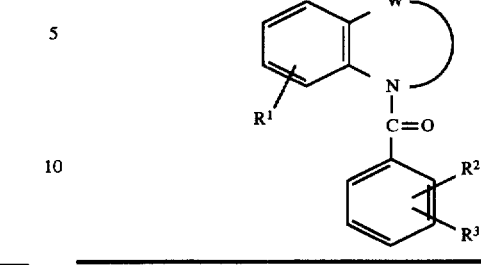

Example 890

Structure

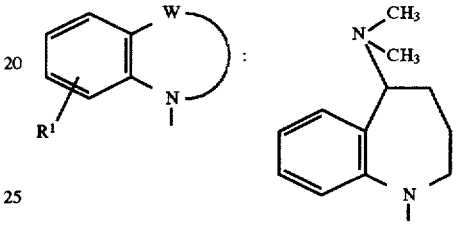

R²: 3-OCH₂CONH₂

R³:
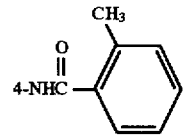

Crystalline form: White powder
Recrystallization solvent: Methanol/diethyl ether
Melting Point: 130–133° C.
Form: Free

Example 891

Structure

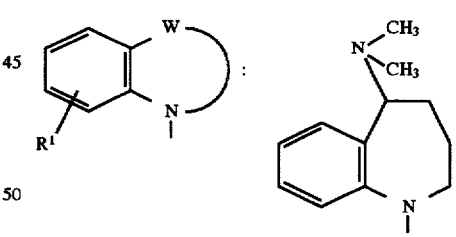

R²: 3-O(CH₂)₂N(CH₂CH₃)(CH₂CH₃)

R³:
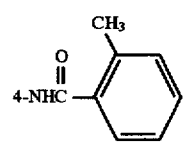

Crystalline form: White powder
Recrystallization solvent: Methanol/n-hexane
Melting Point: 104.5–106° C.
Form: Free TABLE 5-continued

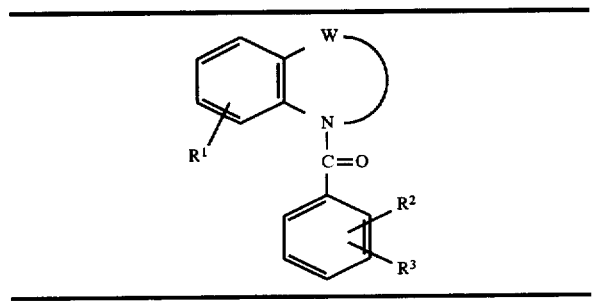

Example 892

Structure

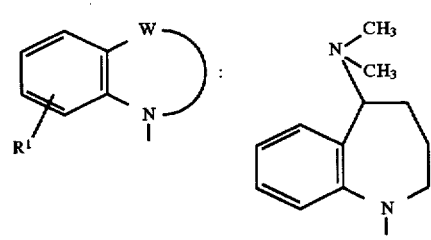

R²: H

R³:
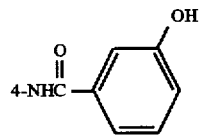

Crystalline form: White powder
Recrystallization solvent: Methanol/diethyl ether
Melting Point: 197-198° C.
Form: Free Example 893

Structure

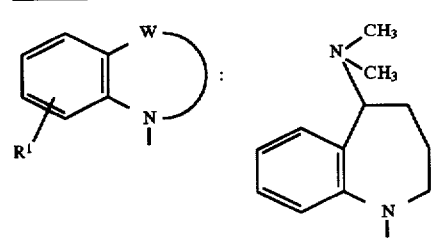

R²: 2-CH₃

R³:
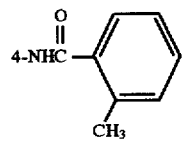

Crystalline form: White powder
Recrystallization solvent: Dichloromethane/ethyl acetate
Melting Point: 191-192° C.
Form: Free TABLE 5-continued

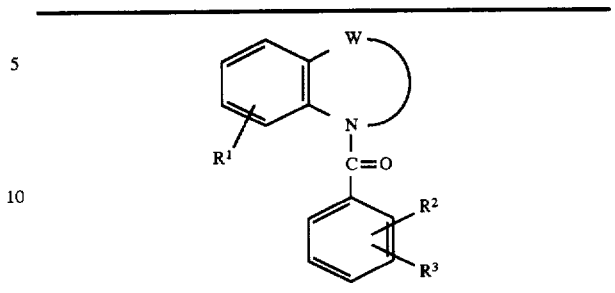

Example 894

Structure

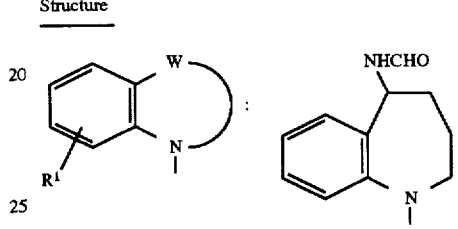

R²: H

R³:
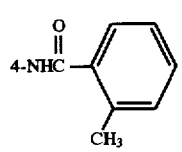

Crystalline form: Colorless columnar
Recrystallization solvent: Ethanol/petroleum ether
Melting Point: 211-213° C.
Form: Free Example 895

Structure

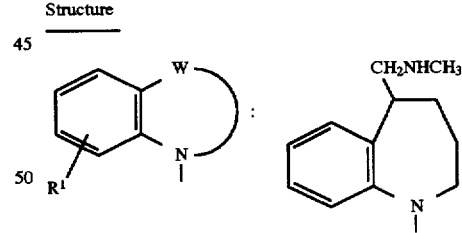

R²: H

R³:
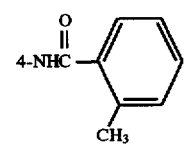

Crystalline form: Colorless amorphous
NMR analysis: 164)
Form: Free

TABLE 5-continued

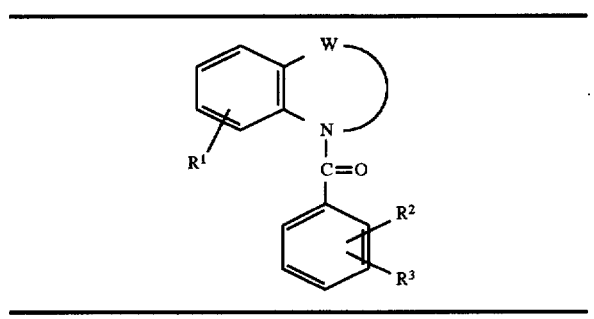

Example 896

Structure

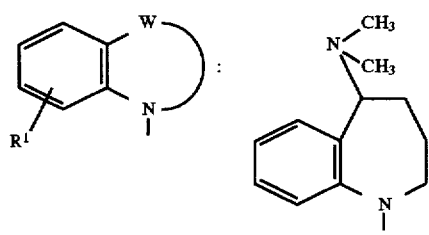

R²: H

R³:
4-NHCCH₂CO₂C₂H₅

Crystalline form: Colorless amorphous
NMR analysis: 165)
Form: Free

Example 897

Structure

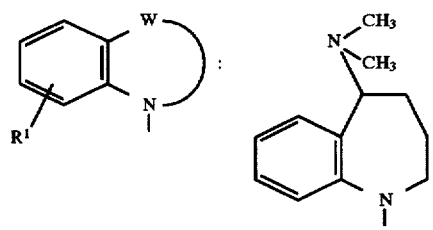

R²: H

R³:
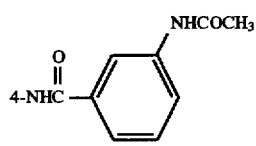
4-NHC—⟨⟩—NHCOCH₃

Crystalline form: Colorless amorphous
NMR analysis: 166)
Form: Free

TABLE 5-continued

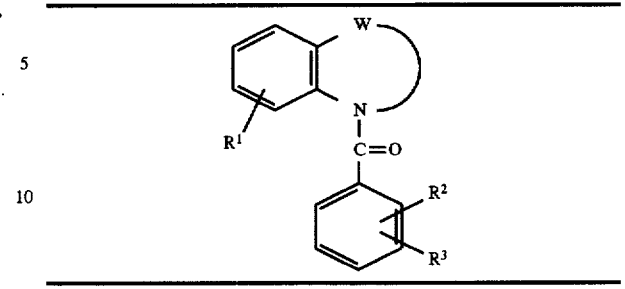

Example 898

Structure

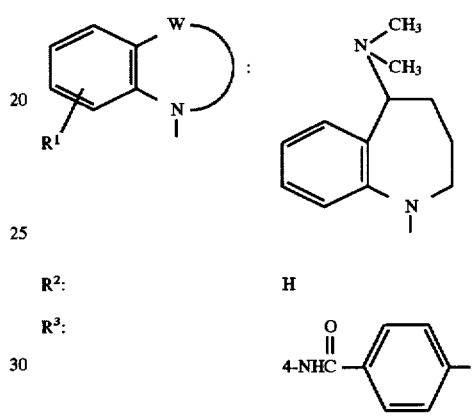

R²: H

R³:
4-NHC—⟨⟩—CO₂CH₃

Crystalline form: Colorless prisms
Recrystallization solvent: Ethanol
Melting Point: 224–228° C.
Form: Free 138) $^1$H-NMR (CDCl$_3$) δ; 1.3–2.95 (19H, m), 3.05–3.3 (1H, m), 3.85–4.1 (2H, m), 4.3–4.6 (1H, m), 6.64 (1H, d, J=7.8 Hz), 6.9–7.8 (12H, m)

139) $^1$H-NMR (CDCl$_3$) δ; 1.1–2.3 (13H, m), 2.65–3.2 (1H, m), 4.55–5.6 (3H, m), 6.55–6.7 (1H, m), 6.9–7.6 (12H, m)

140) $^1$H-NMR (CDCl$_3$) δ; 1.3–4.15 (19H, m), 4.3–5.0 (1H, m), 6.65 (1H, d, J=7.7 Hz), 6.9–8.05 (12H, m)

141) $^1$H-NMR (CDCl$_3$) δ; 1.4–3.0 (9H, m), 3.05–3.6 (3H, m), 3.9–4.1 (1H, m), 4.35–4.55 (1H, m), 4.9–5.65 (1H, m), 6.67 (1H, d, J=7.4 Hz), 6.85–7.6 (12H, m), 7.6–7.85 (2H, m)

142) $^1$H-NMR (CDCl$_3$) δ; 1.3–2.85 (21H, m), 3.2–4.0 (4H, m), 4.3–4.4 (1H, m), 4.45–5.2 (2H, m), 6.61 (1H, d, J=7.6 Hz), 6.9–7.65 (12H, m)

143) $^1$H-NMR (CDCl$_3$) δ; 1.3–3.45 (17H, m), 3.8–5.7 (5H, m), 6.5–7.65 (13H, m)

144) $^1$H-NMR (CDCl$_3$) δ; 1.25–3.1 (14H, m), 3.3–4.0 (4H, m), 4.15–4.4 (1H, m), 4.45–5.2 (1H, m), 6.64 (1H, d, J=7.4 Hz), 6.9–7.7 (12H, m)

145) $^1$H-NMR (CDCl$_3$) δ; 0.9–3.25 (16H, m), 3.9–5.9 (2H, m), 6.65 (1H, d, J=7.4 Hz), 6.85–7.5 (11H, m), 7.9–8.3 (1H, m)

146) $^1$H-NMR (DMSO-d$_6$) δ; 1.3–2.15 (4H, m), 2.32 (3H, s), 2.8–3.05 (1H, m), 4.24 (2H, AB-q, J=12.8, 15.4 Hz), 4.35–4.55 (1H, m), 4.9–5.25 (1H, m), 6.68 (1H, d, J=7.6 Hz), 6.9–7.45 (9H, m), 7.52 (2H, d, J=8.6 Hz), 8.9–9.05 (1H, m), 10.31 (1H, s)

147) $^1$H-NMR (CDCl$_3$) δ; 1.5–2.35 (4H, m), 2.45 (3H, s), 2.6–2.85 (1H, m), 3.32 (3H, s), 4.19 (2H, AB-q, J=12.2 Hz, 15.6 Hz), 5.0–5.2 (1H, m), 5.82 (1H, d, J=10.3 Hz), 6.69 (1H, d, J=7.8 Hz), 6.75–7.95 (12H, m)

148) ¹H-NMR (CDCl₃) δ; 1.2–3.3 (17H, m), 3.45 (2H, AB-q, J=14.7, 22.9 Hz), 3.9–4.35 (2H, m), 6.60 (2H, d, J=7.7 Hz), 6.8–8.0 (11H, m), 8.39 (1H, s)

149) ¹H-NMR (CDCl₃) δ; 1.45–3.40 (8H, m), 2.23 (3H, s), 2.33 (3H, s), 2.46 (3H, s), 4.44–5.23 (1H, m), 6.54–6.78 (1H, m), 6.84–7.94 (12H, m)

150) ¹H-NMR (CDCl₃) δ; 1.50–1.92 (3H, m), 1.92–2.05 (1H, m), 2.47 (3H, s), 2.55–3.06 (5H, m), 3.43–5.76 (8H, m), 6.63–6.82 (1H, m), 6.97–8.08 (12H, m)

151) ¹H-NMR (CDCl₃) δ; 1.43–2.65 (4H, m), 2.48 (3H, s), 2.69–3.25 (5H, m), 3.90–5.40 (8H, m), 6.64–6.94 (1H, m), 6.94–7.77 (12H, m)

152) ¹H-NMR (CDCl₃) δ; 1.50–1.90 (3H, m), 1.90–2.20 (1H, m), 2.20–2.64 (4H, m), 2.32 (3H, s), 2.47 (3H, s), 2.64–3.27 (1H, m), 3.36–3.83 (4H, m), 3.93–4.52 (2H, m), 4.52–5.27 (2H, m), 6.57–6.82 (1H, m), 6.93–7.87 (12H, m)

153) ¹H-NMR (CDCl₃) δ; 1.52–1.93 (2H, m), 1.93–2.23 (4H, m), 2.23–2.57 (1H, m), 2.45 (3H, s), 2.72–3.02 (1H, m), 3.02–3.77 (8H, m), 3.93–4.50 (2H, m), 4.50–5.20 (2H, m), 6.60–6.80 (1H, m), 6.94–7.64 (11H, m), 8.16 (1H, brs)

154) ¹H-NMR (CDCl₃) δ; 1.48–2.60 (8H, m), 2.46 (3H, s), 2.65–3.01 (1H, m), 3.20–3.74 (2H, m), 3.80–5.14 (4H, m), 5.30–5.84 (1H, m), 6.51–8.14 (13H, m)

155) ¹H-NMR (CDCl₃) δ; 1.54–1.91 (2H, m), 1.91–2.20 (1H, m), 2.22–2.64 (1H, m), 2.44 (3H, s), 2.70–3.13 (1H, m), 3.60–4.40 (4H, m), 4.50–5.20 (2H, m), 6.07–8.00 (13H, m), 9.93 (1H, s)

156) ¹H-NMR (CDCl₃) δ; 1.56–1.92 (2H, m), 1.92–2.19 (1H, m), 2.19–2.60 (1H, m), 2.46 (3H, s), 2.66–3.26 (4H, m), 3.33–3.95 (4H, m), 4.00–5.20 (4H, m), 6.58–6.82 (1H, m), 6.93–8.21 (12H, m)

157) ¹H-NMR (CDCl₃) δ; 1.57–2.17 (3H, m), 2.21–2.68 (1H, m), 2.47 (3H, s), 2.73–3.04 (1H, m), 3.91–4.42 (4H, m), 4.50–5.17 (2H, m), 6.61–6.99 (2H, m), 6.99–8.10 (14H, m), 8.21–8.71 (2H, m)

158) ¹H-NMR (CDCl₃) δ; 1.31 (3H, d, J=6.7 Hz), 1.53–1.90 (1H, m), 2.29–2.58 (1H, m), 2.47 (3H, s), 2.94–3.63 (2H, m), 4.57–5.05 (1H, m), 6.68–6.82 (1H, m), 7.10–7.59 (10H, m), 7.72 (1H, s), 7.78–7.96 (1H, m)

159) ¹H-NMR (CDCl₃) δ; 1.20–2.60 (17H, m), 2.65–5.10 (3H, m), 6.85–3.85 (12H, m)

160) ¹H-NMR (DMSO-d₆) δ; 1.40–1.75 (1H, m), 1.90–2.15 (1H, m), 2.33 (3H, s), 2.50–2.80 (2H, m), 3.10–3.50 (1H, m), 4.40–4.65 (1H, m), 6.85–7.60 (10H, m), 7.85 (1H, s), 10.44 (1H, s)

161) ¹H-NMR (CDCl₃) δ; 1.30–2.70 (11H, m), 3.00–5.20 (3H, m), 6.58 (1H, d, J=8 Hz), 6.90–7.05 (1H, m), 7.10–7.70 (10H, m)

162) ¹H-NMR (CDCl₃) δ; 1.25–2.90 (4H, m), 2.44 (6H, s), 2.79–3.57 (2H, m), 2.79 (6H, s), 4.10–5.25 (1H, m), 6.60–6.80 (1H, m), 6.94–7.60 (10H, m), 8.23 (1H, d, J=6.2 Hz), 12.41 (1H, m)

163) ¹H-NMR (CDCl₃) δ; 1.25–3.00 (4H, m), 2.42 (6H, s), 2.99 (6H, s), 3.40–3.65 (2H, m), 4.01–5.15 (1H, m), 6.58–7.59 (12H, m), 7.94 (1H, brs)

164) ¹H-NMR (DMSO-d₆) δ; 1.40–2.18 (4H, m), 2.34 (3H, s), 2.47 (3H, s), 2.54–3.50 (4H, m), 4.30–5.08 (1H, m), 6.56–6.82 (1H, m), 6.87–7.48 (10H, m), 7.48–7.75 (2H, m), 10.35 (1H, s)

165) ¹H-NMR (CDCl₃) δ; 1.08–5.20 [20H, m, 1.30 (3H, t, J=7.2 Hz), 3.41 (2H, s), 4.22 (2H, q, J=7.2 Hz)], 6.49–7.73 (8H, m), 9.25–9.58 (1H, m)

166) ¹H-NMR (CDCl₃) δ; 1.17–2.80 (4H, m), 2.05 (3H, s), 2.42 (6H, s), 3.02–3.53 (2H, m), 4.06–5.15 (1H, m), 6.55–7.80 (12H, m), 8.53–8.74 (2H, m)

Example 899

To a solution of 5-acetyloxyimino-1-[4-(2-chlorobenzoylamino)benzoyl]-2,3,4,5-tetrahydro-1H-benzazepine (0.48 g) in acetic acid (20 ml) is added platinum oxide (0.05 g) and the mixture is subjected to catalytic reduction under hydrogen atmosphere. After completion of the reaction, the catalyst is removed by filtration, and the filtrate is concentrated. The resulting residue is purified by silica gel column chromatography (eluent; dichloromethane:methanol=20:1→10:1), and recrystallized from ethanol/diethyl ether to give 5-amino-1-[4-(2-chlorobenzoylamino)benzoyl]-2,3,4,5-tetrahydro-1H-benzazepine (0.19 g) as colorless prisms, m.p. 176°–178° C.

Example 900

To a solution of 5-methylamino-1-[4-(2-methylbenzoylamino)benzoyl]-2,3,4,5-tetrahydro-1H-benzazepine (0.6 g) in dichloromethane (10 ml) is added triethylamine (0.24 ml). Subsequently, thereto is added methanesulfonyl chloride (0.14 ml) under ice-cooling, and then, the mixture is warmed to room temperature and stirred overnight. Water is added to the reaction solution, extracted three times with dichloromethane. The extract is washed with saturated saline solution, and dried over magnesium sulfate. The solvent is distilled off and the resulting residue is purified by silica gel column chromatography (eluent; dichloromethane:methanol=20:1), and recrystallized from ethanol to give 5-(N-methyl-N-methanesulfonylamino)-1-[4-(2-methylbenzoylamino)benzoyl]-2,3,4,5-tetrahydro-1H-benzazepine (0.48 g) as colorless scales, m.p. 197°–198° C.

Example 901

To a solution of 5-methylamino-1-[4-(2-methylbenzoylamino)benzoyl]-2,3,4,5-tetrahydro-1H-benzazepine (0.6 g) in dichloromethane is added triethylamine (0.24 ml). Subsequently, thereto is added benzoyl chloride (0.2 ml) under ice-cooling, and the temperature thereof is raised to room temperature, and the mixture is stirred overnight. Water is added to the reaction solution and extracted three times with dichloromethane. The extract is washed with saturated saline solution and dried over magnesium sulfate. The solvent is distilled off and the resulting residue is purified by silica gel column chromatography (eluent; dichloromethane:methanol=20:1), and recrystallized from ethanol to give 5-(N-methyl-N-benzoylamino)-1-[4-(2-methylbenzoylamino)benzoyl]-2,3,4,5-tetrahydro-1H-benzazepine (0.64 g) as colorless needles, m.p. 248°–249° C.

Example 902

A mixture of 5-amino-1-[4-(2-methylbenzoylamino)benzoyl]-2,3,4,5-tetrahydro-1H-benzazepine (0.6 g) and ethyl formate (10 ml) is refluxed for 4 hours. The reaction solution is concentrated and the resulting residue is recrystallized from ethanol/petroleum ether to give 5-formylamino-1-[4-(2-methylbenzoylamino)benzoyl]-2,3,4,5-tetrahydro-1H-benzazepine (0.38 g) as colorless columnar crystal, m.p. 211°–213° C.

Using the suitable starting materials, the compounds of above Examples 825 and 894 are obtained in the same manner as in above Example 902.

Example 903

To a solution of 5-amino-1-[4-(2-chlorobenzoylamino)benzoyl]-2,3,4,5-tetrahydro-1H-benzazepine (0.6 g) in dichloromethane (10 ml) is added triethylamine (0.22 ml). Subsequently, thereto is added di-tert-butyl dicarbonate (0.34 g) at room temperature and the mixture is stirred for 2 hours. Then, thereto is added additional di-tert-butyl dicarbonate (0.1 g) and the mixture is stirred for 1 hour. The reaction mixture is concentrated and the resulting residue is purified by silica gel column chromatography (eluent; n-hexane:ethyl acetate=1:1) to give 5-t-butoxycarbonylamino-1-[4-(2-chlorobenzoylamino) benzoyl]-2,3,4,5-tetrahydro-1H-benzazepine (0.66 g) as colorless amorphous.

$^1$H-NMR (CDCl$_3$) δ; 1.1–2.3 (13H, m), 2.65–3.2 (1H, m), 4.55–5.6 (3H, m), 6.55–6.7 (1H, m), 6.9–7.6 (12H, m)

Using the suitable starting materials, the compound of above Example 791 is obtained in the same manner as in above Example 903.

Example 904

To a solution of 5-amino-1-[4-(2-methylbenzoylamino) benzoyl]-2,3,4,5-tetrahydro-1H-benzazepine (0.6 g) in dichloromethane (10 ml) is added phenyl isocyanate (0.2 g) under ice-cooling. The mixture is stirred at the same temperature for 30 minutes, and the temperature thereof is raised to room temperature and then the mixture is stirred overnight. The reaction solution is distilled off and the resulting residue is recrystallized from dioxane to give 5-anilinocarbonylamino-1-[4-(2-methylbenzoylamino) benzoyl]-2,3,4,5-tetrahydro-1H-benzazepine (0.65 g) as colorless prisms, m.p. 269°–271° C.

Using the suitable starting materials, the compound of above Example 795 is obtained in the same manner as in above Example 904.

Example 905

To a solution of 5-methylamino-1-[4-(2-methylbenzoylamino)benzoyl]-2,3,4,5-tetrahydro-1H-benzazepine (0.6 g) in methanol (10 ml) is added glycolonitrile (50%, 0.19 ml) and the mixture is stirred at room temperature for 20 minutes, and then refluxed for 30 minutes. Thereto is added additional glycolonitrile (0.5 ml) and the mixture is refluxed for 5.5 hours. The reaction solution is concentrated and to the resulting residue is added ethyl acetate. The precipitated crystal is collected by filtration, and recrystallized from acetonitrile to give 5-(N-methyl-N-cyanomethylamino)-1-[4-(2-methylbenzoylamino)benzoyl]-2,3,4,5-tetrahydro-1H-benzazepine (0.32 g) as colorless needles, m.p. 227°–228° C.

Example 906

To 5-(N-methyl-N-oxiranylmethylamino)-1-[4-(2-methylbenzoylamino)benzoyl]-2,3,4,5-tetrahydro-1H-benzazepine (0.62 g) is added trifluoroacetic acid (1.22 ml) under ice-cooling and the mixture is stirred for 4 hours. The reaction solution is neutralized with aqueous sodium carbonate solution, and extracted three times with dichloromethane. The extract is washed with saturated saline solution and dried over magnesium sulfate. The solvent is distilled off and the resulting residue is dissolved in methanol (10 ml). Thereto is added 40% aqueous sodium hydroxide solution (10 ml) and water (10 ml), and the mixture is stirred at room temperature overnight. Methanol is distilled off and the resulting residue is purified by silica gel column chromatography (eluent; dichloromethane:methanol=30:1) to give 5-[N-methyl-N-(2,3-dihydroxypropyl)amino)-1-[4-(2-methylbenzoylamino)benzoyl]-2,3,4,5-tetrahydro-1H-benzazepine (0.23 g) as colorless amorphous.

$^1$H-NMR (CDCl$_3$) δ; 1.3–4.15 (19H, m), 4.3–5.0 (1H, m), 6.65 (1H, d, J=7.7 Hz), 6.9–8.05 (12H, m)

Example 907

A mixture of 5-methylamino-1-[4-(2-methylbenzoylamino)benzoyl]-2,3,4,5-tetrahydro-1H-benzazepine (1.64 g), acetonitrile (20 ml), potassium carbonate (0.6 g) and ethyl bromoacetate (0.44 ml) is refluxed for 3 hours. The reaction solution is concentrated and water is added to the resulting residue, and the mixture is extracted three times with dichloromethane. The extract is washed with saturated saline solution, and dried over magnesium sulfate. The solvent is distilled off and the resulting residue is purified by silica gel column chromatography (eluent; dichloromethane:methanol=30:1), and recrystallized from ethyl acetate/petroleum ether to give 5-(N-methyl-N-ethoxycarbonylmethylamino)-1-[4-(2-methylbenzoylamino)benzoyl]-2,3,4,5-tetrahydro-1H-benzazepine (0.82 g) as colorless prisms, m.p. 167°–168° C.

Using the suitable starting materials, the compounds of above Examples 785, 787, 799, 800, 802–806, 808, 811, 819, 824, 826, 827, 845, 848, 849, 850, 852, 855–858, 860, 861, 863–882, 885–893 and 895–898 are obtained in the same manner as in above Example 907.

Example 908

5-(N-Methyl-N-ethoxycarbonylmethylamino)-1-[4-(2-methylbenzoylamino)benzoyl]-2,3,4,5-tetrahydro-1H-benzazepine (0.6 g) is dissolved in saturated solution of ammonia in methanol (20 ml), and the mixture is heated at 100° C. for 8 hours in a sealed tube. The reaction solution is concentrated and the resulting residue is purified by silica gel column chromatography (eluent; dichloromethane:methanol=30:1) to give 5-(N-methyl-N-carbamoylmethylamino)-1-[4-(2-methylbenzoylamino) benzoyl]-2,3,4,5-tetrahydro-1H-benzazepine (0.4 g) as colorless amorphous.

$^1$H-NMR (CDCl$_3$) δ; 1.4–3.0 (9H, m), 3.05–3.6 (3H, m), 3.9–4.1 (1H, m), 4.35–4.55 (1H, m), 4.9–5.65 (1H, m), 6.67 (1H, d, J=7.4 Hz), 6.85–7.6 (12H, m), 7.6–7.85 (2H, m)

Example 909

To a solution of 5-(N-methyl-N-ethoxycarbonylmethylamino)-1-[4-(2-methylbenzoylamino)benzoyl]-2,3,4,5-tetrahydro-1H-benzazepine (0.6 g) in dioxane (10 ml) is added aqueous solution (1 ml) of sodium hydroxide (0.07 g) and the mixture is stirred at room temperature for 2 days. The reaction solution is concentrated and to the resulting residue is added water. The insoluble materials are removed by filtration. The filtrate is neutralized with 10% hydrochloric acid and extracted three times with dichloromethane. The extract is washed with saturated saline solution and dried over magnesium sulfate. The solvent is distilled off and to the resulting residue is added a solution of potassium ethylhexanoate (0.2 g) in dichloromethane (20 ml). The solvent is distilled off, and diethyl ether is added to the resulting residue. The precipitated crystal is collected by filtration, and recrystallized from diethyl ether to give potassium 2-[N-methyl-N-{1-[4-(2-methylbenzoylamino) benzoyl]-2,3,4,5-tetrahydro-1H-benzazepin-5-yl}amino] acetate (0.6 g) as colorless needles, m.p. 164°–171° C.

Example 910

To a solution of 5-methylamino-1-[4-(2-methylbenzoylamino)benzoyl]-2,3,4,5-tetrahydro-1H-benzazepine (1.5 g) in dimethylformamide (20 ml) are added potassium carbonate (0.6 g), potassium iodide (0.72 g) and 2-(3-bromopropyloxy)-3,4,5,6-tetrahydro-2H-pyrane (0.97 g) and the mixture is stirred at room temperature overnight. The reaction solution is concentrated and to the resulting residue is added water. The mixture is extracted three times with dichloromethane. The extract is washed with saturated saline solution, and dried over magnesium sulfate. The solvent is distilled off and the resulting residue is purified by silica gel column chromatography (eluent; dichloromethane→dichloromethane:methanol=50:1) to give 5-{N-methyl-N-[3-(3,4,5,6-tetrahydro-2H-pyran-2-yloxy)propyl]amino}-1-[4-(2-methylbenzoylamino)benzoyl]-2,3,4,5-tetrahydro-1H-benzazepine (1.3 g) as colorless amorphous.

$^1$H-NMR (CDCl$_3$); 1.3–2.85 (21H, m), 3.2–4.0 (4H, m), 4.3–4.4 (1H, m), 4.45–5.2 (2H, m), 6.61 (1H, d, J=7.6 Hz), 6.9–7.65 (12H, m)

Example 911

To 5-{N-methyl-N-[3-(3,4,5,6-tetrahydro-2H-pyran-2-yloxy)propyl]amino}-1-[4-(2-methylbenzoylamino)benzoyl]-2,3,4,5-tetrahydro-1H-benzazepine (0.4 g) is added a mixture of acetyl chloride (0.5 ml) and acetic acid (5 ml) at room temperature, and the mixture is stirred overnight. The reaction solution is concentrated and the resulting residue is purified by silica gel column chromatography (eluent; dichloromethane:methanol=30:1), and further purified again by silica gel column chromatography (eluent; n-hexane:ethyl acetate=1:2) to give 5-[N-methyl-N-(3-acetyloxypropyl)amino]-1-[4-(2-methylbenzoylamino)benzoyl]-2,3,4,5-tetrahydro-1H-benzazepine (0.06 g) as colorless amorphous.

$^1$H-NMR (CDCl$_3$) δ; 1.3–3.45 (17H, m), 3.8–5.7 (5H, m), 6.5–7.65 (13H, m)

Example 912

To a solution of 5-{N-methyl-N-[3-(3,4,5,6-tetrahydro-2H-pyran-2-yloxy)propyl]amino}-1-[4-(2-methylbenzoylamino)benzoyl]-2,3,4,5-tetrahydro-1H-benzazepine (0.55 g) in ethanol (10 ml) is added pyridinium p-toluenesulfonate (0.03 g) and the mixture is heated at 60° C. overnight. After the mixture is refluxed for more 2 hours, water and pyridinium p-toluenesulfonate (0.03 g) are added thereto. The mixture is refluxed for 4 hours. The reaction solution is concentrated and to the resulting residue is added dichloromethane. The mixture is basified with aqueous sodium hydrogen carbonate solution and extracted three times with dichloromethane. The extract is washed with saturated saline solution and dried over magnesium sulfate. The solvent is distilled off and the resulting residue is purified by silica gel column chromatography (eluent; dichloromethane:methanol=30:1) to give 5-[N-methyl-N-(3-hydroxypropyl)amino]-1-[4-(2-methylbenzoylamino)benzoyl]-2,3,4,5-tetrahydro-1H-benzazepine (0.26 g) as colorless amorphous.

$^1$H-NMR (CDCl$_3$) δ; 1.25–3.1 (14H, m), 3.3–4.0 (4H, m), 4.15–4.4 (1H, m), 4.45–5.2 (1H, m), 6.64 (1H, d, J=7.4 Hz), 6.9–7.7 (12H, m)

Example 913

To a solution of 5-amino-1-[4-(2-methylbenzoylamino)benzoyl]-2,3,4,5-tetrahydro-1H-benzazepine (0.6 g) in acetic acid (10 ml) is added dropwise 2,5-dimethoxytetrahydrofuran (0.19 ml), and the mixture is refluxed for 1 hour. The reaction solution is concentrated and the resulting residue is purified by silica gel column chromatography (eluent; dichloromethane:methanol=50:1), and recrystallized from ethyl acetate/n-hexane to give 5-(1-pyrrolyl)-1-[4-(2-methylbenzoylamino)benzoyl]-2,3,4,5-tetrahydro-1H-benzazepine (0.31 g) as colorless prisms, m.p. 208°–210° C.

Example 914

To a solution of 5-amino-1-[4-(2-methylbenzoylamino)benzoyl]-2,3,4,5-tetrahydro-1H-benzazepine (2.5 g) in dichloromethane (30 ml) is added triethylamine (0.96 ml) and further thereto is added dropwise chloroacetyl chloride (0.55 ml) under ice-cooling. The mixture is stirred for 5 minutes. The reaction solution is concentrated and to the resulting residue is added water. The precipitated crystal is collected by filtration, washed with water, and dried to give 5-(2-chloroacetylamino)-1-[4-(2-methylbenzoylamino)benzoyl]-2,3,4,5-tetrahydro-1H-benzazepine (1.4 g) as white powder.

$^1$H-NMR (DMSO-d$_6$) δ; 1.3–2.15 (4H, m), 2.32 (3H, s), 2.8–3.05 (1H, m), 4.24 (2H, AB-q, J=12.8, 15.4 Hz), 4.35–4.55 (1H, m), 4.9–5.25 (1H, m), 6.68 (1H, d, J=7.6 Hz), 6.9–7.45 (9H, m), 7.52 (2H, d, J=8.6 Hz), 8.9–9.05 (1H, m), 10.31 (1H, s)

Using the suitable starting materials, the compound of above Example 814 is obtained in the same manner as in above Example 914.

Example 915

A mixed solution of 5-(2-chloroacetylamino)-1-[4-(2-methylbenzoylamino)benzoyl]-2,3,4,5-tetrahydro-1H-benzazepine (0.6 g), imidazole (0.1 g) and potassium carbonate (0.19 g) in acetonitrile (30 ml) is refluxed for 8 hours. The reaction solution is concentrated and the resulting residue is washed with water and separated by decantation. The remainder is purified by silica gel column chromatography (eluent; dichloromethane:methanol=20:1→15:1), and recrystallized from ethanol/n-hexane to give 5-[2-(1-imidazolyl)acetylamino]-1-[4-(2-methylbenzoylamino)benzoyl]-2,3,4,5-tetrahydro-1H-benzazepine (0.15 g) as colorless needles, m.p. 250°–252° C.

Using the suitable starting materials, the compound of above Example 818 is obtained in the same manner as in above Example 915.

Example 916

To a solution of 5-(2-chloroacetylamino)-1-[4-(2-methylbenzoylamino)benzoyl]-2,3,4,5-tetrahydro-1H-benzazepine (0.6 g) in dimethylformamide (20 ml) are added dimethylamine hydrochloride (0.21 g) and potassium carbonate (0.54 g), and the mixture is stirred at room temperature for 2 days. The reaction solution is concentrated and water is added to the resulting residue. The precipitated crystal is collected by filtration, and recrystallized from ethyl acetate to give 5-(2-dimethylaminoacetylamino)-1-[4-(2-methylbenzoylamino)benzoyl]-2,3,4,5-tetrahydro-1H-benzazepine (0.24 g) as colorless prisms, m.p. 214°–216° C.

Using the suitable starting materials, the compounds of above Examples 816, 817, 820, 821, 826 and 827 are obtained in the same manner as above Example 916.

Example 917

A mixture of 5-methylamino-1-[4-(2-methylbenzoylamino)benzoyl]-2,3,4,5-tetrahydro-1H-benzazepine (0.6 g), N,N-dimethyl-2-chloroacetamide (0.19 g) and potassium carbonate (0.22 g) is refluxed for 24 hours. The reaction solution is concentrated and water is added to the resulting residue. The mixture is extracted three times with dichloromethane. The extract is washed with saturated saline solution, and dried over magnesium sulfate. The solvent is distilled off and the resulting residue is purified by silica gel column chromatography (eluent; dichloromethane:methanol=30:1) to give 5-[N-methyl-N-(dimethylaminocarbonylmethyl)amino]-1-[4-(2-methylbenzoyl amino)benzoyl]-2,3,4,5-tetrahydro-1H-benzazepine (0.05 g) as colorless amorphous.

¹H-NMR (CDCl₃) δ; 1.2–3.3 (17H, m), 3.45 (2H, AB-q, J=14.7, 22.9 Hz), 3.9–4.35 (2H, m), 6.60 (1H, d, J=7.7 Hz), 6.8–8.0 (11H, m), 8.39 (1H, s)

Example 918

To a solution of t-butoxycarbonylglycine (0.84 g) in dimethylformamide (20 ml) are added diethyl cyanophosphate (0.73 ml) and 5-amino-1-[4-(2-methylbenzoylamino)benzoyl]-2,3,4,5-tetrahydro-1H-benzazepine (1.74 g), and further thereto is added triethylamine (1.8 ml) under ice-cooling. The mixture is stirred for 30 minutes, and then stirred at room temperature overnight. The reaction solution is concentrated and water is added to the resulting residue. The precipitated crystal is collected by filtration, washed with water, and recrystallized from ethyl acetate to give 5-(2-aminoacetylamino)-1-[4-(2-methylbenzoylamino)benzoyl]-2,3,4,5-tetrahydro-1H-benzazepine (E) (0.16 g). Separately, the filtrate is concentrated and purified by silica gel column chromatography (eluent; dichloromethane:methanol=50:1), and recrystallized from diethyl ether to give 5-[2-(t-butoxycarbonylamino)acetylamino]-1-[4-(2-methylbenzoylamino)benzoyl]-2,3,4,5-tetrahydro-1H-benzazepine (F) (0.19 g).
(E): Colorless prisms, m.p. 287°–289° C.
(F): Colorless prisms, m.p. 170°–171° C.

Example 919

5-Oxo-1-[4-(2-methylbenzoylamino)benzoyl]-2,3,4,5-tetrahydro-1H-benzazepine (0.50 g) is suspended in tetrahydrofuran (20 ml), and thereto is added dropwise a 3.0M solution of methyl magnesium bromide in diethyl ether (1.5 ml) at room temperature. The mixture is stirred at room temperature for 1 hour. The reaction solution is poured into ice-water (20 ml), and extracted with ethyl acetate. The extract is dried over magnesium sulfate, and the solvent is distilled off. The resulting residue is purified by silica gel column chromatography (eluent; ethyl acetate:n-hexane= 2:3→1:1), and recrystallized from ethyl acetate/n-hexane to give 5-methyl-5-hydroxy-1-[4-(2-methylbenzoylamino)benzoyl]-2,3,4,5-tetrahydro-1H-benzazepine (0.23 g) as white powder, m.p. 204°–205° C.

Example 920

To a solution of 5-carboxymethoxy-1-[4-(2-methylbenzoylamino)benzoyl]-2,3,4,5-tetrahydro-1H-benzazepine (1.50 g) in dimethylformamide (60 ml) are added successively thiomorpholine (0.66 ml), diethyl cyanophosphate (0.89 g) and triethylamine (1.37 ml) with stirring under ice-cooling. The mixture is stirred for 30 minutes under ice-cooling, and at room temperature for 20 minutes. Water (60 ml) is added to the reaction solution, and extracted with dichloromethane. The extract is dried over magnesium sulfate, and the solvent is distilled off. The resulting residue is purified by silica gel column chromatography (eluent; ethyl acetate:n-hexane=5:2→3:1), and recrystallized from ethyl acetate/n-hexane to give 5-(thiomorpholinocarbonylmethoxy)-1-[4-(2-methylbenzoylamino)benzoyl]-2,3,4,5-tetrahydro-1H-benzazepine (1.60 g) as white powder, m.p. 235°–237° C.

Using the suitable starting materials, the compounds of above Examples 829–838 are obtained in the same manner as in above Example 920.

Example 921

To a solution of 5-(thiomorpholinocarbonylmethoxy)-1-[4-(2-methylbenzoylamino)benzoyl]-2,3,4,5-tetrahydro-1H-benzazepine (0.40 g) in dichloromethane (40 ml) is added 80% m-chloroperbenzoic acid (175 mg) with stirring at –8° C., and the mixture is stirred at –8° C, for 1 hour. To the reaction solution is added 20% aqueous sodium hydrogensulfite solution (40 ml) and the mixture is stirred at room temperature for 30 minutes. The dichloromethane layer is collected, washed with saturated saline solution and dried over magnesium sulfate. The solvent is distilled off and the resulting residue is purified by silica gel column chromatography (eluent; dichloromethane:methanol=20:1) to give 5-[(1-oxothiomorpholino)carbonylmethoxy]-1-[4-(2-methylbenzoylamino)benzoyl]-2,3,4,5-tetrahydro-1H-benzazepine (0.32 g) as colorless amorphous.

¹H-NMR (CDCl₃) δ; 1.50–1.92 (3H, m), 1.92–2.05 (1H, m), 2.47 (3H, s), 2.55–3.06 (5H, m), 3.43–5.76 (8H, m), 6.63–6.82 (1H, m), 6.97–8.08 (12H, m)

Example 922

To a solution of 5-(thiomorpholinocarbonylmethoxy)-1-[4-(2-methylbenzoylamino)benzoyl]-2,3,4,5-tetrahydro-1H-benzazepine (0.40 g) in dichloromethane (40 ml) is added 80% m-chloroperbenzoic acid (0.35 g), and the mixture is stirred at room temperature for 1 hour. The reaction solution is washed successively with an aqueous sodium hydrogensulfite solution and saturated saline solution, and dried over magnesium sulfate. The solvent is distilled off to give 5-[(1,1-dioxothiomorpholino)carbonylmethoxy]-1-[4-(2-methylbenzoylamino)benzoyl]-2,3,4,5-tetrahydro-1H-benzazepine (0.41 g) as colorless amorphous.

¹H-NMR (CDCl₃) δ; 1.43–2.65 (4H, m), 2.48 (3H, s), 2.69–3.25 (5H, m), 3.90–5.40 (8H, m), 6.64–6.94 (1H, m), 6.94–7.77 (12H, m)

Example 923

To a solution of 5-oxo-1-[4-(2-hydroxybenzoylamino) benzoyl]-2,3,4,5-tetrahydro-1H-benzazepine (400 mg) in acetone (20 ml) are added potassium carbonate (210 mg), potassium iodide (250 mg) and 2-chloroacetamide (120 mg), and the mixture is refluxed for 2 hours. The insoluble materials are removed by filtration, and the filtrate is distilled off. Dichloromethane is added to the resulting residue, and the mixture is washed with saturated saline solution, and dried over magnesium sulfate. The solvent is distilled off and the resulting residue is recrystallized from ethyl acetate/n-hexane to give 5-oxo-1-[4-(2-carbamoylmethoxybenzoylamino)benzoyl]-2,3,4,5-tetrahydro-1H-benzazepine (436 mg) as white powder, m.p. 226°–228° C.

Using the suitable starting materials, the compound of above Example 842 is obtained in the same manner as above Example 923.

Example 924

A mixture of 5-methylamino-4-hydroxy-1-[4-(2-chlorobenzoylamino)benzoyl]-2,3,4,5-tetrahydro-1H-benzazepine (0.13 g), ethyl α-bromoacetate (58 mg), diisopropylethylamine (49 mg) and acetonitrile (5 ml) is refluxed for 10 hours. Acetonitrile is distilled off under reduced pressure, and the resulting residue is dissolved in dichloromethane, washed with water, dried over magnesium sulfate, and distilled off under reduced pressure. The resulting residue is purified by silica gel column chromatography (eluent; dichloromethane:methanol=50:1), and recrystallized from chloroform/methanol to give 7-[4-(2-chlorobenzoylamino)benzoyl]-1-methyl-1,2,3,4a,5,6,7,11b-octahydro- 3-oxo[1]benzazepino[4,5-b][1,4]oxazine (80 mg) as colorless prisms, m.p. 286°–290° C.

Example 925

To a solution of 5-oxo-1-[2-chloro-4-(2-methylbenzoylamino)benzoyl]-2,3,4,5-tetrahydro-1H-benzazepine (1 g) in methanol (20 ml) and dichloromethane (20 ml) is added hydroxylamine-O-sulfonic acid (0.28 g) with stirring at room temperature, and the mixture is stirred at the same temperature for 1 hour. Subsequently, to the reaction solution is added with stirring an aqueous solution of potassium carbonate (0.34 g) in water (1 ml) at room temperature, and the mixture is stirred at the same temperature for 2 hours. The precipitated crystal is removed by filtration, and the filtrate is concentrated under reduced pressure. The resulting residue is purified by silica gel column chromatography to give potassium {1-[2-chloro-4-(2-methylbenzoylamino)benzoyl]-2,3,4,5-tetrahydro-1H-benzazepin-5-yl}imino-O-sulfonate (0.4 g) as white powder.

$^1$H-NMR (DMSO-d$_6$) δ; 1.40–1.75 (1H, m), 1.90–2.15 (1H, m), 2.33 (3H, s), 2.50–2.80 (2H, m), 3.10–3.50 (1H, m), 4.40–4.65 (1H, m), 6.85–7.60 (10H, m), 7.85 (1H, s), 10.44 (1H, s)

Example 926

Using the suitable starting materials, the compounds of above Examples 841–843, 868–870, 888 and 889 are obtained in the same manner as in above Example 380.

Example 927

Using the suitable starting materials, the compounds of above Examples 876–878 are obtained in the same manner as in above Example 381.

Example 928

Using the suitable starting materials, the compounds of above Examples 840, 842 and 846 are obtained in the same manner as in above Example 384.

Example 929

Using the suitable starting materials, the compounds of above Examples 788–790, 796–804, 805, 808, 811, 814, 818, 819, 824, 826, 827, 837, 845, 848, 850, 852, 855, 856–858, 860, 861, 863–882, 885, 886, 888–893 and 895–898 are obtained in the same manner as in above Example 388.

Example 930

Using the suitable starting materials, the compound of above Example 848 is obtained in the same manner as in above Example 393.

Example 931

Using the suitable starting materials, the compounds of above Examples 841 and 842 are obtained in the same manner as in above Example 402.

Example 932

Using the suitable starting materials, the compounds of above Examples 882 and 897 are obtained in the same manner as in above Example 403.

Example 933

Using the suitable starting materials, the compound of above Example 809 is obtained in the same manner as in above Example 634.

Example 934

Using the suitable starting materials, the compounds of above Examples 828–838 are obtained in the same manner as in above Example 640.

Example 935

Using the suitable starting materials, the compound of above Example 810 is obtained in the same manner as in above Example 772.

Example 936

Using the suitable starting materials, the compound of above Example 788 is obtained in the same manner as in above Example 771.

Example 937

Using the suitable starting materials, the compounds of above Examples 785, 787, 788–790, 796–805, 806, 807, 808, 811, 814, 818, 819, 845, 848, 849, 850, 852, 855, 856–858, 860, 861, 863–882, 885, 886, 888–893 and 896–898 are obtained in the same manner as in above Example 390.

Example 938

To 5-methanesulfonyloxymethyl-1-[4-(2-methylbenzoylamino)benzoyl]-2,3,4,5-tetrahydro-1H-benzazepine (0.50 g) is added a 30% solution of methylamine in methanol (50 ml), and the mixture is heated at 100° C. for 3 hours in a sealed tube. After cooling, the reaction solution is evaporated under reduced pressure, and the resulting residue is purified by silica gel column chromatography (eluent; dichloromethane:methanol:aqueous ammonia=100:10:1) to give 5-methylaminomethyl-1-[4-(2-methylbenzoylamino)benzoyl]-2,3,4,5-tetrahydro-1H-benzazepine (0.07 g).

$^1$H-NMR (DMSO-d$_6$) δ; 1.40–2.18 (4H, m), 2.34 (3H, s), 2.47 (3H, s), 2.54–3.50 (4H, m), 4.30–5.08 (1H, m), 6.56–6.82 (1H, m), 6.87–7.48 (10H, m), 7.48–7.75 (2H, m), 10.35 (1H, s)

Using the suitable starting materials, the compounds of above Examples 823–825 are obtained in the same manner as in above Example 938.

Using the above suitable starting materials, the compounds of the following Table 6 are obtained in the same manner as in Examples 1 and 382.

TABLE 6

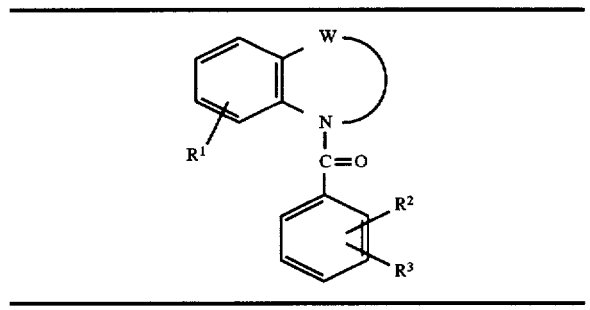

Example 939

Structure

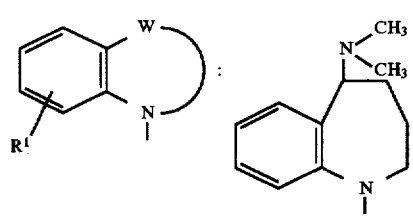

R²: H

R³:
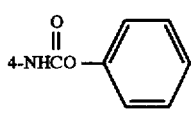
4-NHCO—⟨phenyl⟩

Crystalline form: White powder
Recrystallization solvent: Ethanol
Melting Point: 208–211° C.
Form: Free

Example 940

Structure

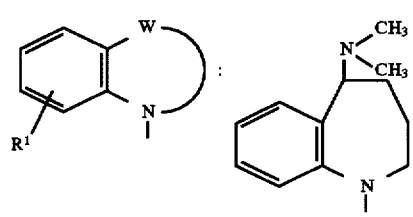

R²: H

R³:
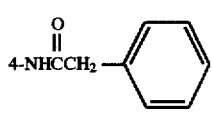
4-NHCCH₂—⟨phenyl⟩

Crystalline form: White powder
Recrystallization solvent: Methanol/diethyl ether
Melting Point: 171.5–172.5° C.
Form: Free

TABLE 6-continued

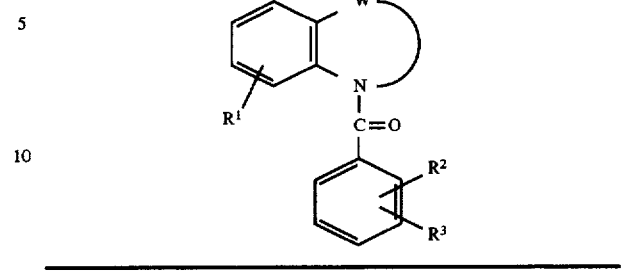

Example 941

Structure

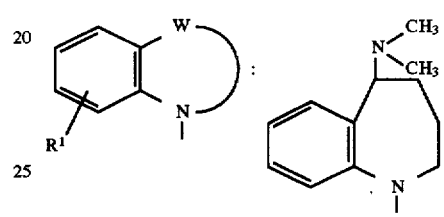

R²: H

R³:
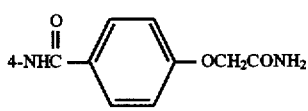
4-NHC—⟨phenyl⟩—OCH₂CONH₂

Crystalline form: White powder
Recrystallization solvent: Methanol/diethyl ether
Melting Point: 151–154° C.
Form: Free

Example 942

Structure

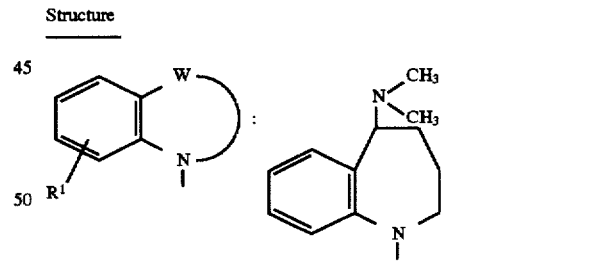

R²: H

R³:
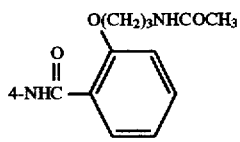
4-NHC—⟨phenyl⟩—O(CH₂)₃NHCOCH₃

Crystalline form: Colorless amorphous
NMR analysis: 167)
Form: Free

TABLE 6-continued

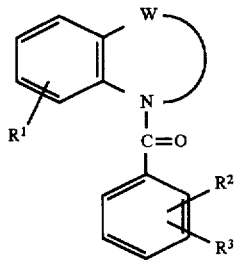

Example 943

Structure

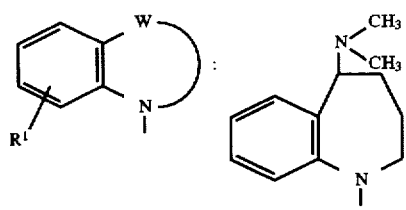

R²: H

R³:

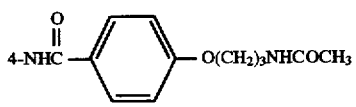
4-NHC(=O)—⟨phenyl⟩—O(CH₂)₃NHCOCH₃

Crystalline form: White powder
Recrystallization solvent: Methanol/diethyl ether
Melting Point: 180–183° C.
Form: Free Example 944

Structure

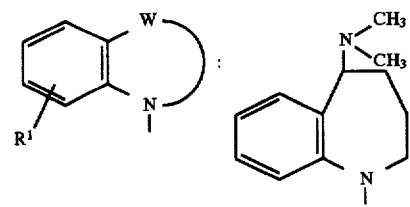

R²: H

R³:

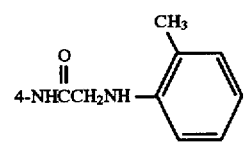
4-NHCCH₂NH—⟨2-CH₃-phenyl⟩

Crystalline form: White powder
Recrystallization solvent: Methanol/diethyl ether
Melting Point: 109–110° C.
Form: Free TABLE 6-continued

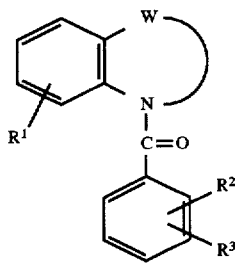

Example 945

Structure

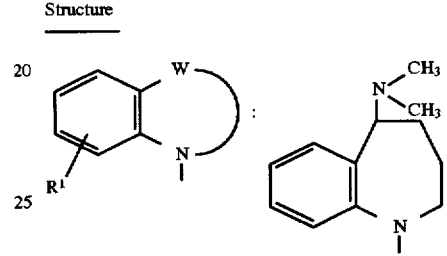

R²: H

R³:

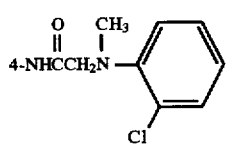
4-NHCCH₂N(CH₃)—⟨2-Cl-phenyl⟩

Crystalline form: Colorless oil
NMR analysis: 168)
Form: Free

Example 946

Structure

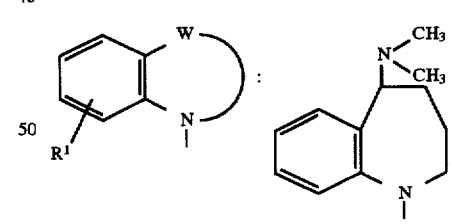

R²: H

R³:

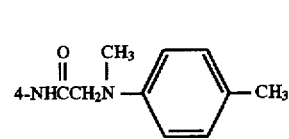
4-NHCCH₂N(CH₃)—⟨4-CH₃-phenyl⟩

Crystalline form: Colorless oil
NMR analysis: 169)
Form: Free

TABLE 6-continued

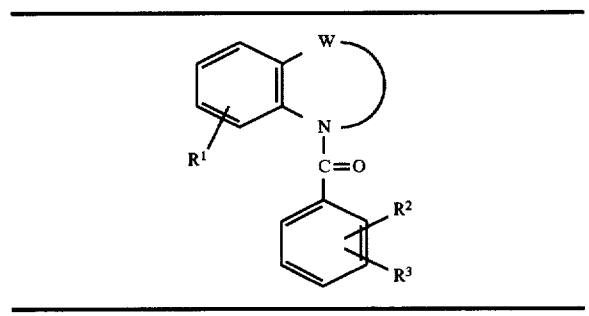

Example 947

Structure

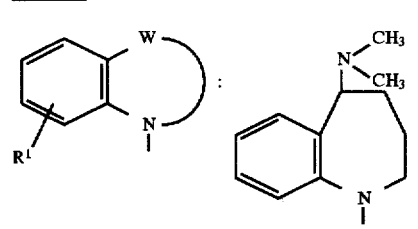

R²: H

R³:

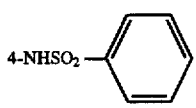

4-NHSO₂—

Crystalline form: White powder
Recrystallization solvent: Methanol/diethyl ether
Melting Point: 177–178.5° C.
Form: Free

Example 948

Structure

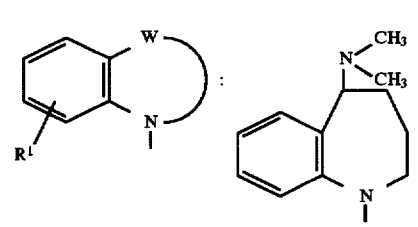

R²: H

R³:

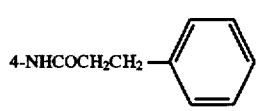

4-NHCOCH₂CH₂—

Crystalline form: Colorless amorphous
NMR analysis: 170)
Form: Free

TABLE 6-continued

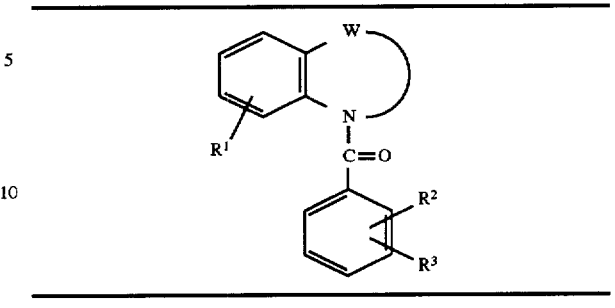

Example 949

Structure

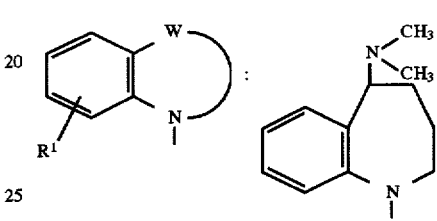

R²: H

R³:

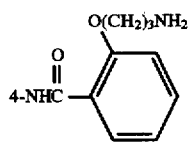

Crystalline form: White powder
Recrystallization solvent: Methanol/diethyl ether
Melting Point: 162–165° C.
Form: Free

Example 950

Structure

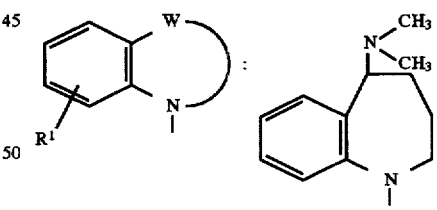

R²: H

R³:

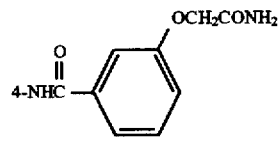

Crystalline form: White powder
Recrystallization solvent: Methanol/diethyl ether
Melting Point: 212–215° C.
Form: Free TABLE 6-continued

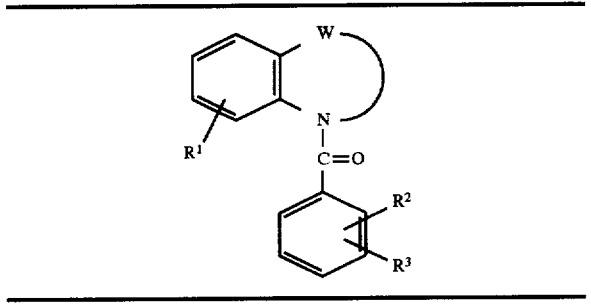

Example 951

Structure

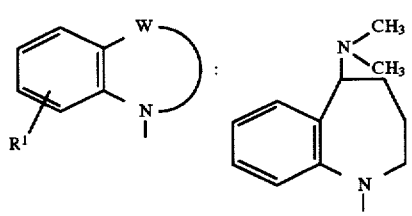

R²: H

R³: 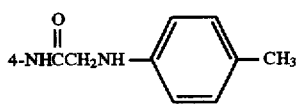

Crystalline form: Colorless oil
NMR analysis: 171)
Form: Free

Example 952

Structure

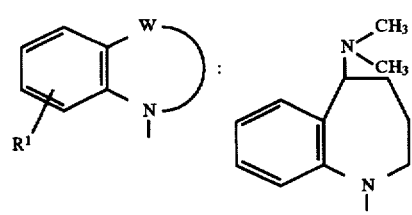

R²: H

R³: 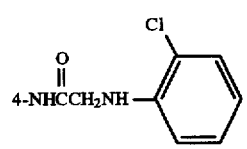

Crystalline form: White powder
Recrystallization solvent: Methanol/diethyl ether
Melting Point: 112–114° C.
Form: Free TABLE 6-continued

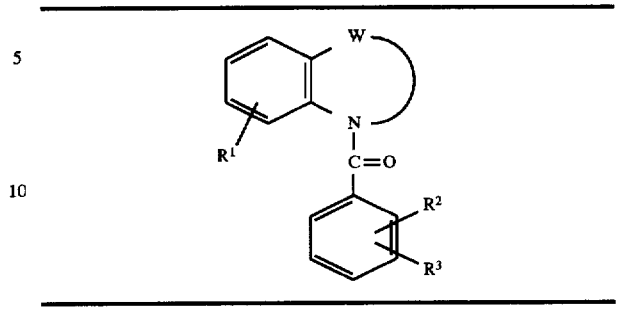

Example 953

Structure

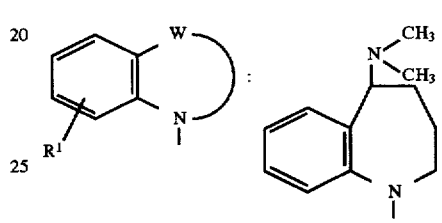

R²: H

R³: 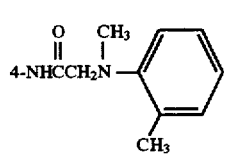

Crystalline form: Colorless oil
NMR analysis: 172)
Form: Free

Example 954

Structure

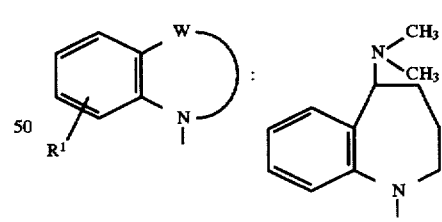

R²: H

R³: 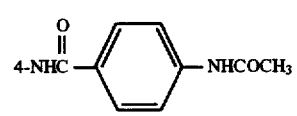

Crystalline form: Colorless amorphous
NMR analysis: 173)
Form: Free

TABLE 6-continued

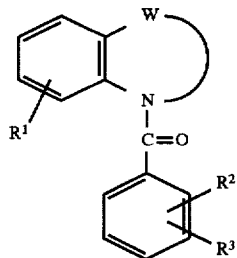

Example 955

Structure

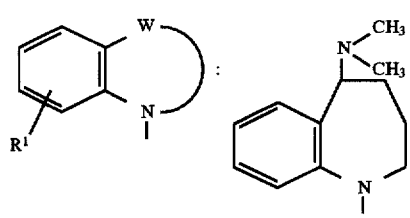

R²: H

R³:

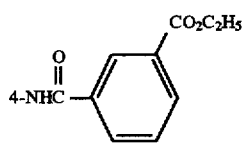

Crystalline form: Light yellow amorphous
NMR analysis: 174)
Form: Free

Example 956

Structure

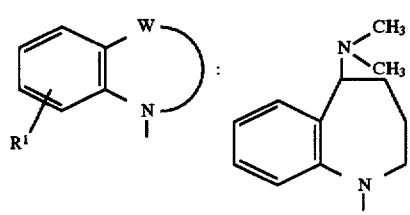

R²: H

R³:

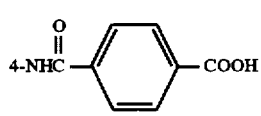

Crystalline form: White powder
Recrystallization solvent: Diethyl ether
Melting Point: 189–193° C.
Form: Free

TABLE 6-continued

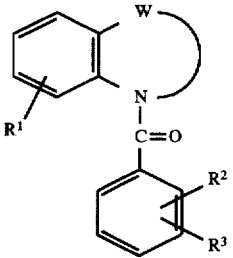

Example 957

Structure

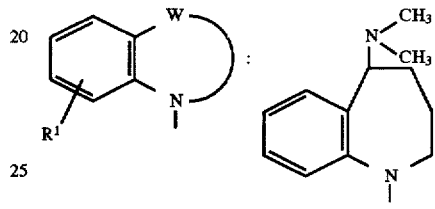

R²: H

R³:

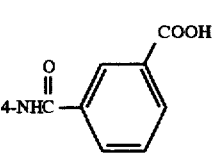

Crystalline form: Colorless amorphous
NMR analysis: 175)
Form: Free

Example 958

Structure

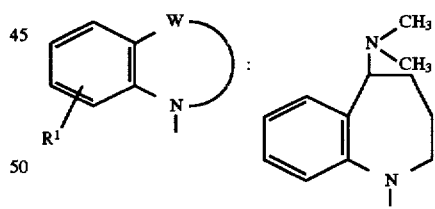

R²: H

R³:

Crystalline form: Colorless prisms
Recrystallization solvent: Ethanol
Melting Point: 234–238° C.
Form: Free TABLE 6-continued

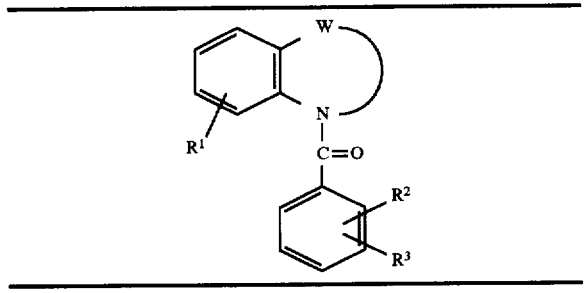

Example 959

Structure

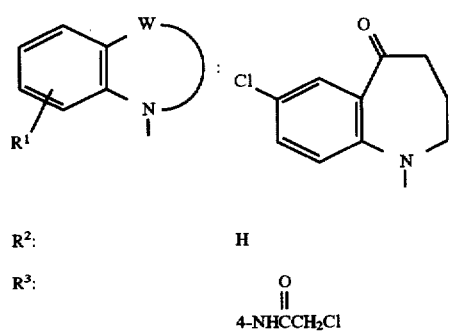

R²: H

R³:
4-NHCCH₂Cl
(with C=O)

Crystalline form: White powder
Recrystallization solvent: Diethyl ether/dichloromethane
Melting Point: 183–184.5° C.
Form: Free

Example 960

Structure

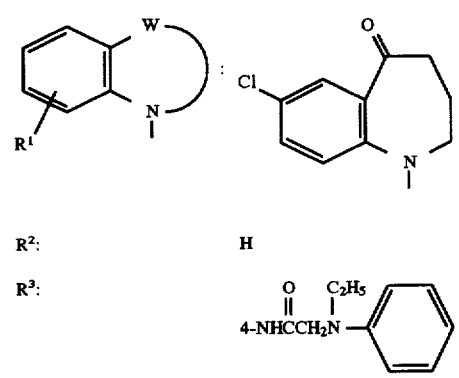

R²: H

R³:
4-NHCCH₂N with C₂H₅ and phenyl
(with C=O)

Crystalline form: Brown oil
NMR analysis: 176)
Form: Free

Example 961

Structure

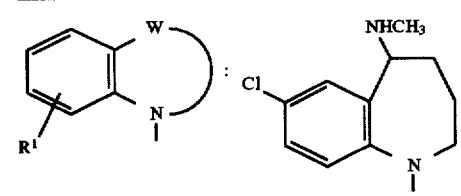

R²: H

---

TABLE 6-continued

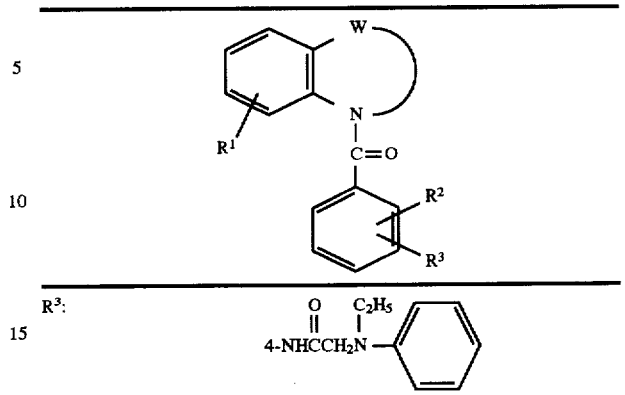

R³:
4-NHCCH₂N with C₂H₅ and phenyl
(with C=O)

Crystalline form: Colorless amorphous
NMR analysis: 177)
Form: Free

Example 962

Structure

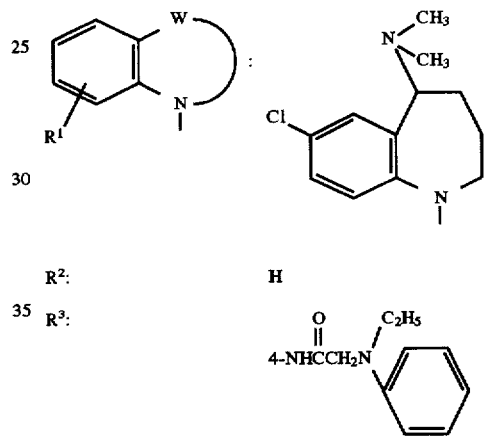

R²: H

R³:
4-NHCCH₂N with C₂H₅ and phenyl
(with C=O)

Crystalline form: Colorless amorphous
NMR analysis: 178)
Form: Free

Example 963

Structure

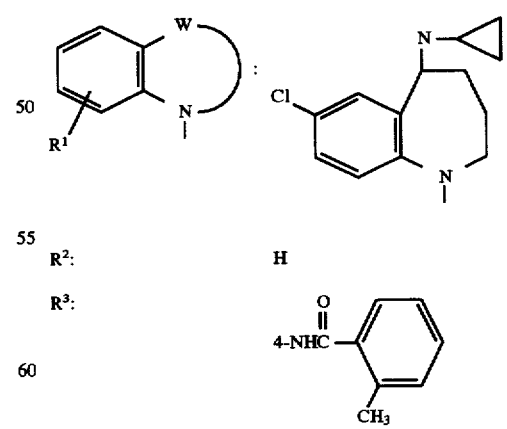

R²: H

R³:
4-NHC— (with C=O) phenyl with 2-CH₃

Crystalline form: White powder
Recrystallization solvent: Dichloromethane/diethyl ether
Melting Point: 202.5–204.5° C.
Form: Free

TABLE 6-continued

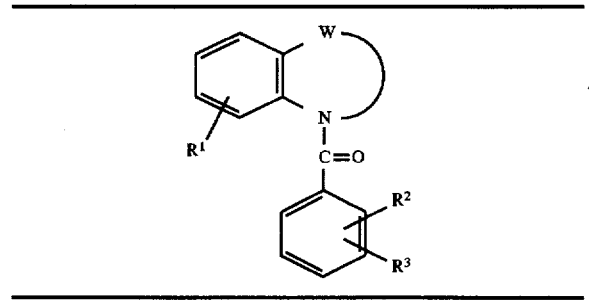

Example 964

Structure

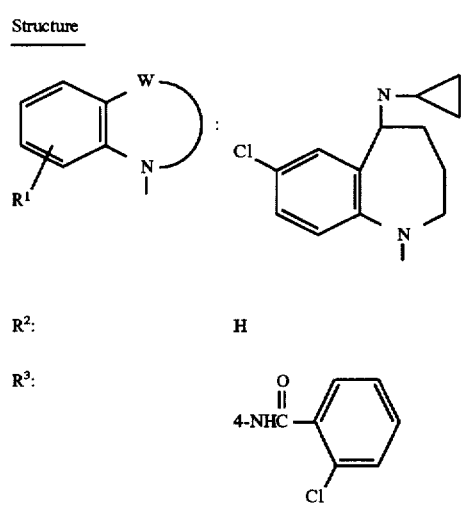

R²: H

R³: 
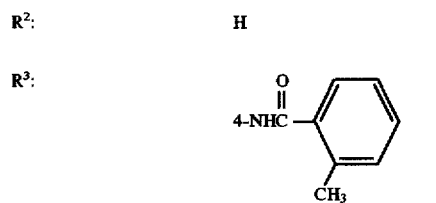

Crystalline form: White powder
Recrystallization solvent: Dichloromethane/diethyl ether
Melting Point: 199.5–201° C.
Form: Free

Example 965

Structure

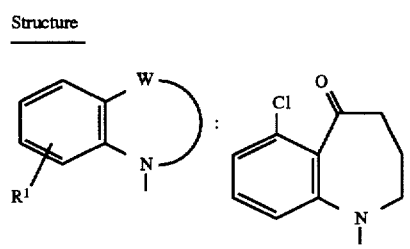

R²: H

R³: 
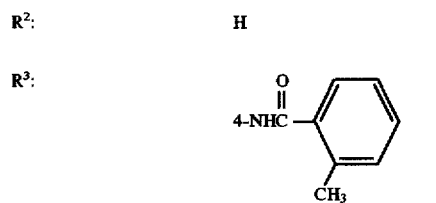

Crystalline form: White powder
Recrystallization solvent: Dichloromethane/diethyl ether
Melting Point: 196.5–197° C.
Form: Free

TABLE 6-continued

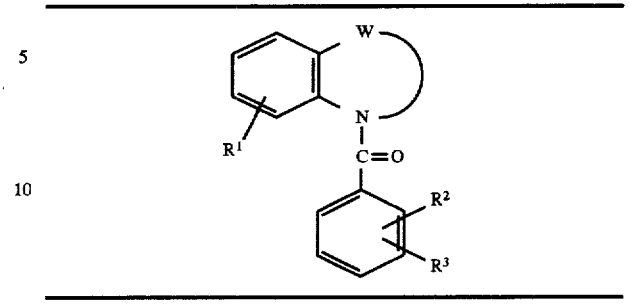

Example 966

Structure

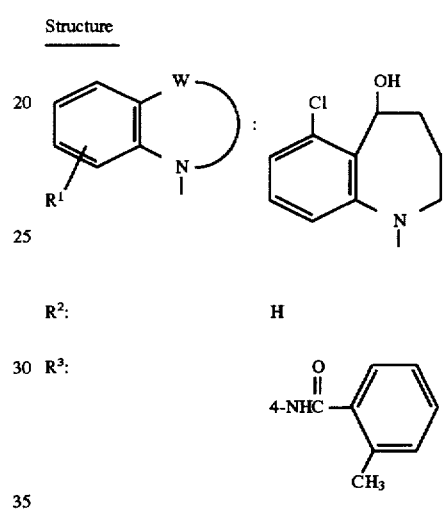

R²: H

R³:
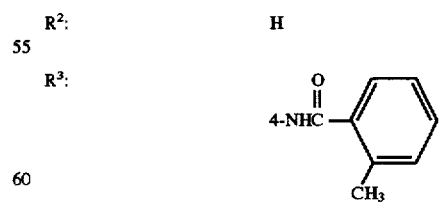

Crystalline form: White powder
Recrystallization solvent: Dichloromethane/diethyl ether
Melting Point: 204–205° C.
Form: Free

Example 967

Structure

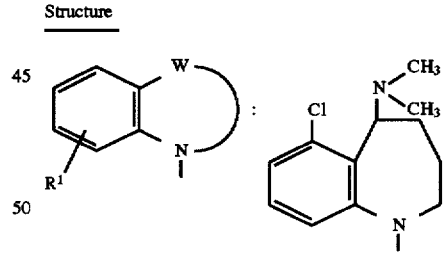

R²: H

R³:
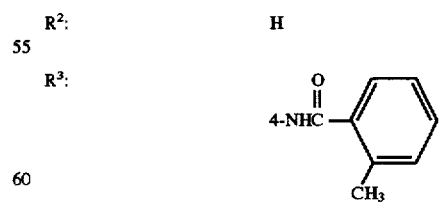

Crystalline form: White powder
Recrystallization solvent: Dichloromethane/diethyl ether
Melting Point: 175–177° C.
Form: Free TABLE 6-continued

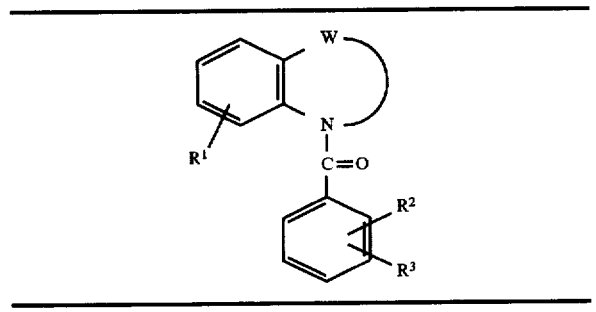

Example 968

Structure

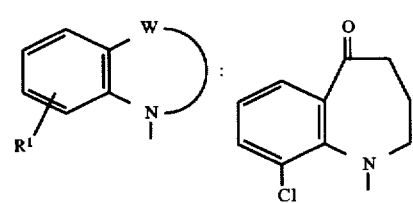

R²: H

R³:

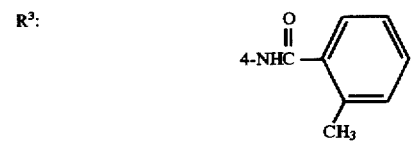

Crystalline form: Pink amorphous
NMR analysis: 179)
Form: Free

Example 969

Structure

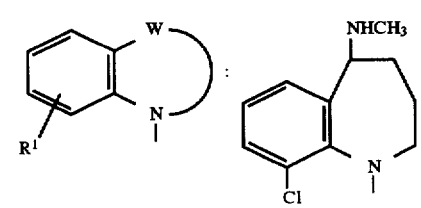

R²: H

R³:

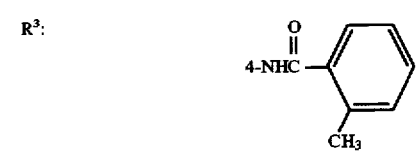

Crystalline form: White powder
Recrystallization solvent: Dichloromethane/diethyl ether
Melting Point: 186–189° C.
Form: Free TABLE 6-continued

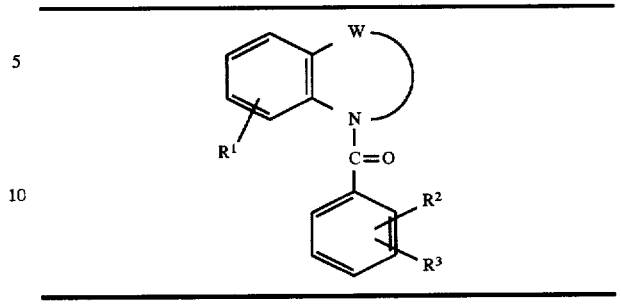

Example 970

Structure

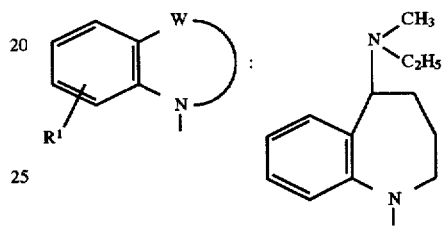

R²: 2-Cl

R³:

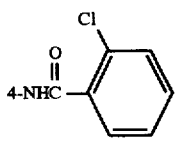

Crystalline form: Colorless prisms
Recrystallization solvent: Ethyl acetate/n-hexane
Melting Point: 211–212° C.
Form: Free Example 971

Structure

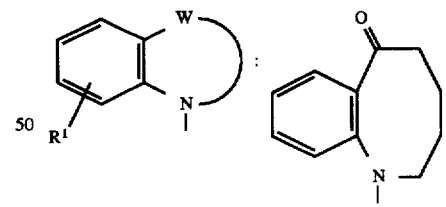

R²: H

R³:

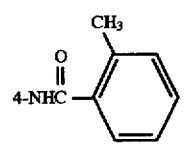

Crystalline form: Colorless amorphous
NMR analysis: 180)
Form: Free

TABLE 6-continued

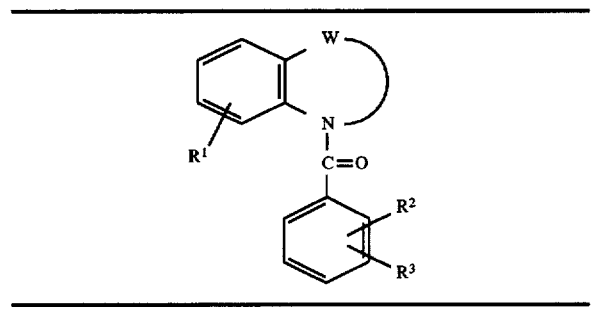

Example 972

Structure

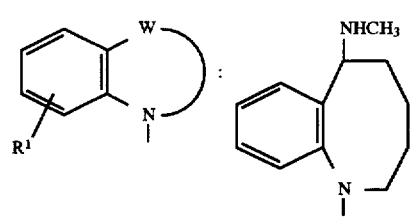

R²: H

R³:

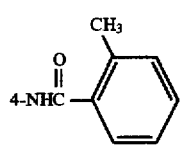

Crystalline form: Colorless needles
Recrystallization solvent: Ethanol
Melting Point: 206–207° C.
Form: Free

Example 973

Structure

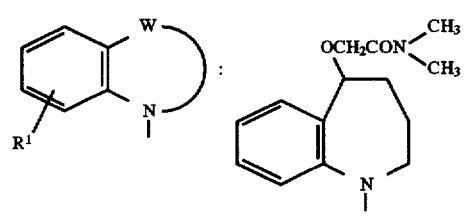

R²: H

R³:

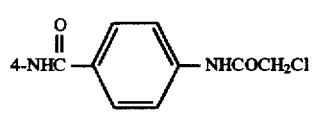

Crystalline form: Colorless amorphous
NMR analysis: 181)
Form: Free

TABLE 6-continued

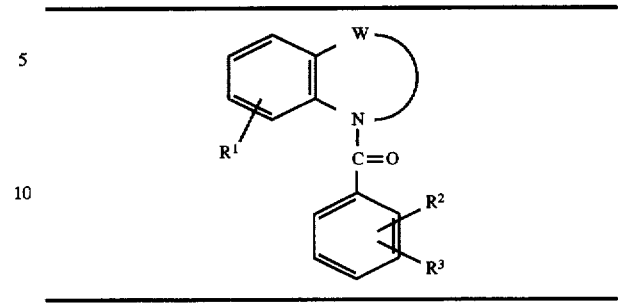

Example 974

Structure

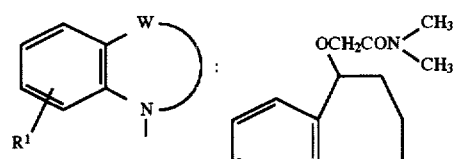

R²: H

R³:

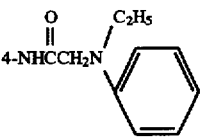

Crystalline form: White powder
Recrystallization solvent: Ethyl acetate/n-hexane
Melting Point: 152–154° C.
Form: Free

Example 975

Structure

R²: H

R³:

Crystalline form: Colorless amorphous
NMR analysis: 182)
Form: Free

TABLE 6-continued

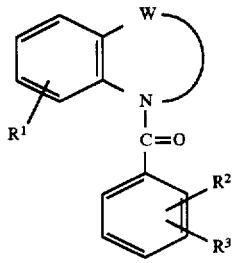

Example 976

Structure

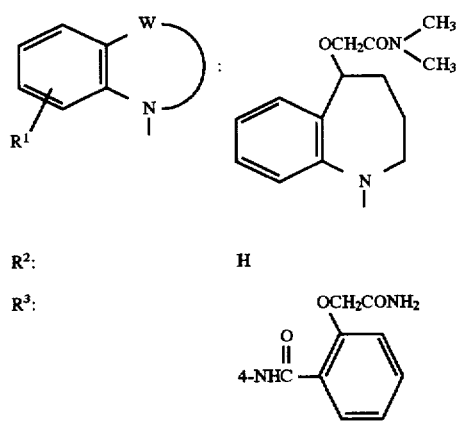

R²: H

R³: 
(structure: 4-NHC(=O)-phenyl-OCH₂CONH₂)

Crystalline form: White powder
Recrystallization solvent: Ethyl acetate/n-hexane
Melting Point: 204–206° C.
Form: Free

Example 977

Structure

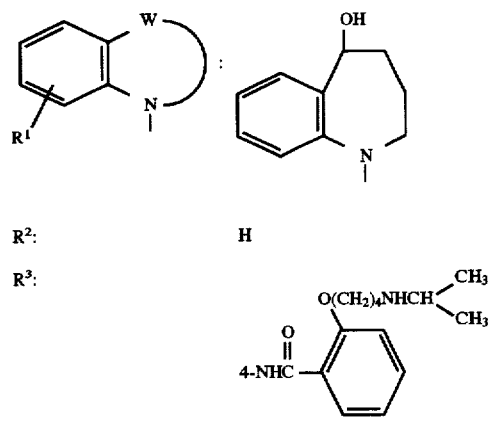

R²: H

R³:
(structure: 4-NHC(=O)-phenyl-O(CH₂)₄NHCH(CH₃)₂)

Crystalline form: Colorless needles
Recrystallization solvent: Ethyl acetate/n-hexane
Melting Point: 162–163° C.
Form: Free 167) $^1$H-NMR (CDCl$_3$) δ; 1.14–2.83 (13H, m), 2.43 (3H, s), 2.95–5.19 (4H, m), 4.12 (2H, t, J=6.2 Hz), 6.27–6.83 (2H, m), 6.83–7.36 (6H, m), 7.36–7.67 (4H, m), 7.93–8.11 (1H, m), 9.77 (1H, brs)

168) $^1$H-NMR (CDCl$_3$) δ; 1.11–2.98 (11H, m), 2.80 (3H, s), 3.69 (2H, s), 2.98–5.24 (2H, m), 6.50–7.71 (12H, m), 9.37 (1H, brs)

169) $^1$H-NMR (CDCl$_3$) δ; 1.10–2.80 (14H, m), 2.99 (3H, s), 3.39–5.20 (2H, m), 4.00 (2H, s), 6.49–7.67 (12H, m), 8.51 (1H, brs)

170) $^1$H-NMR (CDCl$_3$) δ; 1.10–1.98 (3H, m), 1.98–2.82 (10H, m), 2.82–3.20 (2H, m), 3.34–5.15 (2H, m), 6.48–7.68 (15H, m), 7.86 (1H, brs)

171) $^1$H-NMR (CDCl$_3$) δ; 1.10–2.84 (10H, m), 2.40 (3H, s), 2.90–5.20 (2H, m), 3.79 (2H, d, J=2.7 Hz), 4.33 (1H, br), 6.30–7.68 (12H, m), 8.67 (1H, brs)

172) $^1$H-NMR (CDCl$_3$) δ; 1.10–2.85 (14H, m), 2.72 (3H, s), 2.98–5.20 (2H, m), 3.62 (2H, s), 6.50–7.75 (12H, m), 9.18 (1H, brs)

173) $^1$H-NMR (DMSO-d$_6$) δ; 1.28–2.62 (4H, m), 2.07 (3H, s), 2.34 (6H, s), 3.04–3.57 (2H, m), 3.99–4.86 (1H, m), 6.62–7.88 (12H, m), 10.12–10.20 (2H, m)

174) $^1$H-NMR (CDCl$_3$) δ; 1.39 (3H, t, J=7.1 Hz), 1.64–2.68 (4H, m), 2.42 (6H, s), 3.04–3.58 (2H, m), 3.98–5.01 (1H, m), 4.38 (2H, q, J=7.1 Hz), 6.57–8.57 (13H, m)

175) $^1$H-NMR (DMSO-d$_6$) δ; 1.67–5.02 (7H, m), 3.35 (6H, s), 6.75–8.17 (12H, m), 8.46 (1H, s), 10.54 (1H, s)

176) $^1$H-NMR (CDCl$_3$) δ; 1.21 (3H, t, J=7.1 Hz), 1.95–2.30 (2H, m), 2.88 (2H, t, J=6.2 Hz), 3.40–3.65 (2H, m), 3.70–4.50 (2H, m), 3.91 (2H, s), 6.66 (1H, d, J=8.5 Hz), 6.70–7.00 (3H, m), 7.10–7.50 (7H, m), 7.81 (1H, d, J=2.5 Hz), 8.44 (1H, s)

177) $^1$H-NMR (CDCl$_3$) δ; 1.21 (3H, t, J=7 Hz), 1.30–5.20 (11H, m), 3.48 (2H, q, J=7 Hz), 3.90 (2H, s), 6.53 (1H, d, J=8.3 Hz), 6.65–7.00 (4H, m), 7.00–7.40 (6H, m), 7.51 (1H, d, J=2.5 Hz), 8.40 (1H, s)

178) $^1$H-NMR (CDCl$_3$) δ; 1.21 (3H, t, J=7 Hz), 1.20–5.20 (15H, m), 3.90 (2H, s), 6.48 (1H, d, J=8.3 Hz), 6.50–7.70 (11H, m), 8.39 (1H, s)

179) $^1$H-NMR (CDCl$_3$) δ; 1.60–2.20 (1H, m), 2.10–2.35 (1H, m), 2.45 (3H, s), 2.70–2.95 (2H, m), 3.25–3.45 (1H, m), 4.60–4.85 (1H, m), 7.10–7.80 (12H, m)

180) $^1$H-NMR (CDCl$_3$) δ; 1.65–2.15 (4H, m), 2.46 (3H, s), 2.6–5.15 (4H, m), 6.75–6.95 (1H, m), 7.15–7.55 (10H, m), 7.61 (1H, s), 7.95–8.1 (1H, m)

181) $^1$H-NMR (CDCl$_3$) δ; 1.60–2.15 (3H, m), 2.15–2.90 (2H, m), 2.90–3.22 (6H, m), 4.00–4.50 (2H, m), 4.13 (2H, s), 4.58–5.22 (2H, m), 6.53–6.80 (1H, m), 6.90–7.90 (7H, m), 8.48 (1H, s)

182) $^1$H-NMR (CDCl$_3$) δ; 1.48–2.20 (3H, m), 2.20–2.85 (2H, m), 2.85–3.27 (6H, m), 4.05–4.47 (2H, m), 4.47–5.22 (2H, m), 6.50–6.76 (1H, m), 6.76–6.91 (1H, m), 6.91–7.69 (9H, m), 7.69–8.13 (1H, m), 9.28 (1H, s), 11.87 (1H, brs)

Example 978

5-Dimethylamino-1-(2-methyl-4-aminobenzoyl)-2,3,4,5-tetrahydro-1H-benzazepine (H) (1.00 g) is dissolved in dichloromethane (30 ml), and thereto is added triethylamine (0.48 ml) under ice-cooling, and further added dropwise 2-methylbenzoyl chloride (0.44 ml). The mixture is stirred at room temperature for 1 hour. The reaction solution is washed with water, and dried over magnesium sulfate. The solvent is distilled off, and the resulting residue is crystallized by adding thereto ethyl acetate. The precipitated crystal is recrystallized from dichloromethane/ethyl acetate to give 5-dimethylamino-1-[2-methyl-4-(2-methylbenzoylamino)benzoyl]-2,3,4,5-tetrahydro-1H-benzazepine (0.92 g) as white powder, m.p. 191°–192° C. HPLC retention time: 7.5 minutes Column; Wakosil II 5C$_{18}$ (trade mark; Wako Pure Chemical Co., Ltd.)

Solvent; acetonitrile: 50 mN aqueous Na$_2$SO$_4$ solution-:acetic acid=27:73:1

Rate; 1.0 ml/min.

$[\alpha]_D{}^{22}$=0° (c=1.0, chloroform)

$^1$H-NMR (CDCl$_3$) δ; 1.15-3.25 (17H, m), 3.35-5.14 (2H, m), 6.62-8.05 (12H, m)

Figure 2:
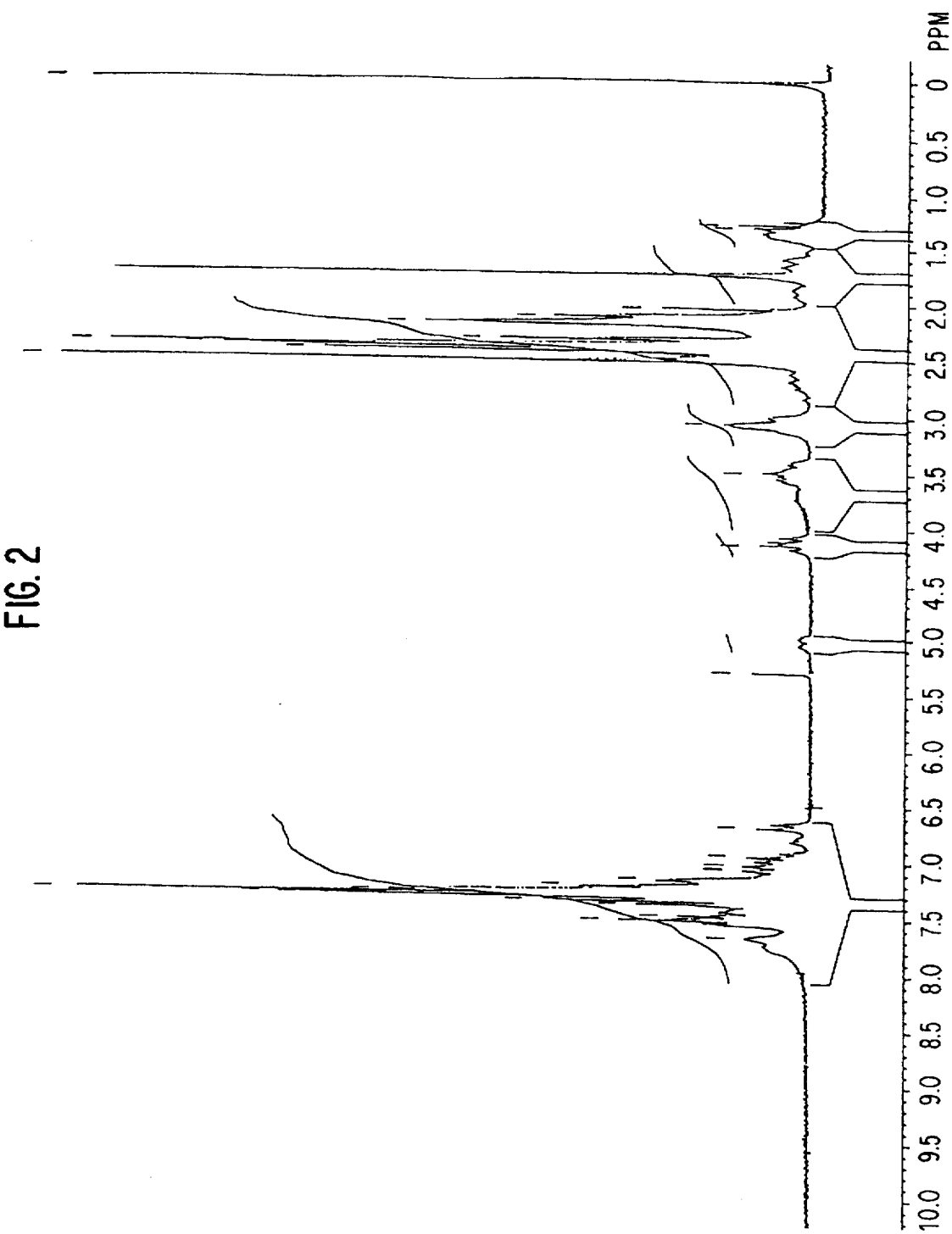

Charts of $^1$H-NMR (CDCl$_3$) of the starting compound (H) and the compound obtained in Example 978 are shown in FIG. 1 and FIG. 2, respectively.

Example 979

Using 5-dimethylamino-1-(2-methyl-4-aminobenzoyl)-2,3,4,5-tetrahydro-1H-benzazepine (G) (1.00 g), 5-dimethylamino-1-[2-methyl-4-(2-methylbenzoylamino)benzoyl]-2,3,4,5-tetrahydro-1H-benzazepine (0.48 g) is obtained in the same manner as in Example 978 except that methanol/diethyl ether is used instead of ethyl acetate as recrystallization solvent, as white powder, m.p. 183°-185° C.

HPLC retention time: 8.1 minutes (the conditions of HPLC are same as those in Example 978)

$[\alpha]_D{}^{22}$=0° (c=1.3, chloroform)

$^1$H-NMR (CDCl$_3$) δ; 1.10-3.20 (17H, m), 3.35-5.15 (2H, m), 6.50-6.80 (1H, m), 6.86-7.62 (10H, m), 7.65-8.09 (1H, m)

Figure 3:
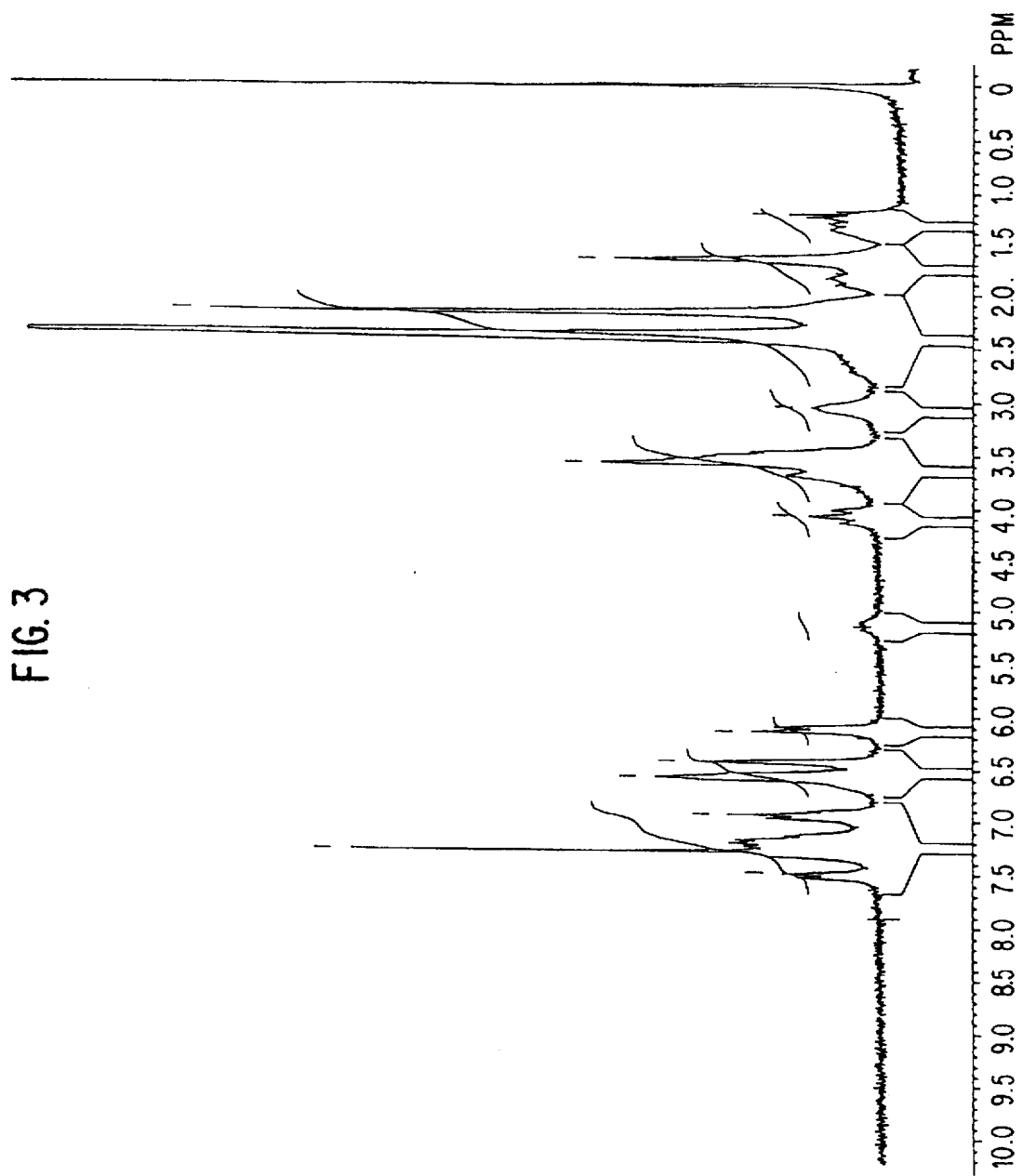
Figure 4:
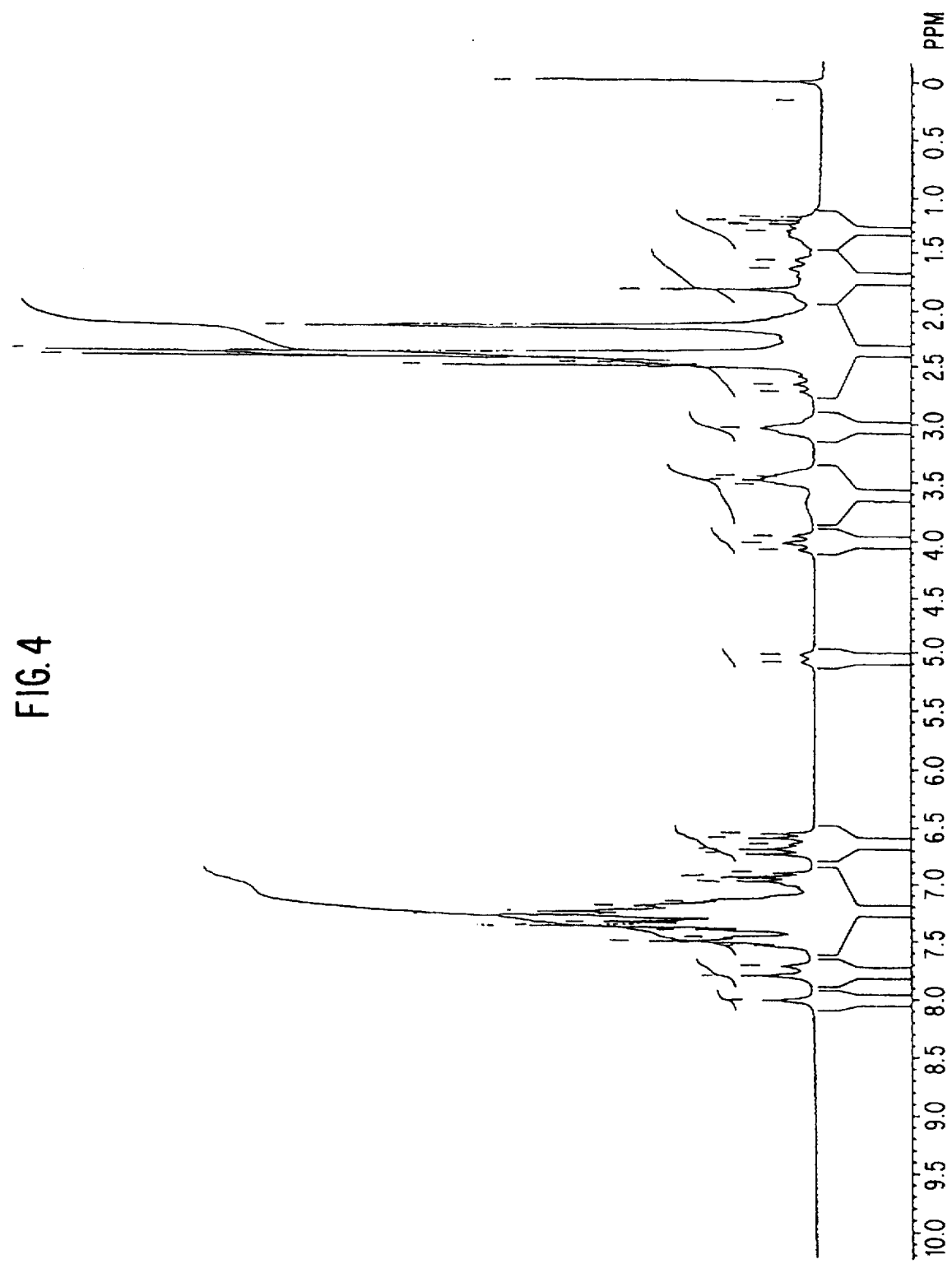

Charts of $^1$H-NMR (CDCl$_3$) of the starting compound (G) and the compound obtained in Example 979 are shown in FIG. 3 and FIG. 4, respectively.

REFERENCE EXAMPLE 18

Using the suitable starting materials, the following compounds are obtained in the same manner as in Reference Example 1.

7-Methoxy-5-oxo-1-(4-nitrobenzoyl)-2,3,4,5-tetrahydro-1H-benzazepine, colorless needles, m.p. 178°-178.5° C. (recrystallized from ethyl acetate/n-hexane)

7-Methoxy-5-oxo-1-(2-chloro-4-nitrobenzoyl)-2,3,4,5-tetrahydro-1H-benzazepine, white powder, m.p. 150°-151° C. (recrystallized from ethyl acetate/n-hexane)

7-Methoxy-5-oxo-1-(3-methoxy-4-nitrobenzoyl)-2,3,4,5-tetrahydro-1H-benzazepine, white powder, m.p. 116°-118° C. (recrystallized from ethyl acetate/n-hexane)

7-Chloro-5-oxo-1-(3-methoxy-4-nitrobenzoyl)-2,3,4,5-tetrahydro-1H-benzazepine, yellow powder, m.p. 156°-158° C. (recrystallized from diethyl ether/dichloromethane)

REFERENCE EXAMPLE 19

Using the suitable starting materials, the following compounds are obtained in the same manner as in Reference Example 2.

7-Methoxy-5-oxo-1-(4-aminobenzoyl)-2,3,4,5-tetrahydro-1H-benzazepine, white powder, m.p. 172.5°-173.5° C. (recrystallized from ethyl acetate/n-hexane)

7-Methoxy-5-oxo-1-(2-chloro-4-aminobenzoyl)-2,3,4,5-tetrahydro-1H-benzazepine, white powder, m.p. 153°-155° C. (recrystallized from ethyl acetate/n-hexane)

7-Methoxy-5-oxo-1-(3-methoxy-4-aminobenzoyl)-2,3,4,5-tetrahydro-1H-benzazepine, colorless needles, m.p. 170°-171° C. (recrystallized from ethyl acetate/n-hexane)

7-Chloro-5-oxo-1-(3-methoxy-4-aminobenzoyl)-2,3,4,5-tetrahydro-1H-benzazepine, yellow oil $^1$H-NMR (CDCl$_3$) δ; 2.05-2.30 (2H, m), 2.85-3.00 (2H, m), 3.70 (3H, s), 3.85-4.30 (4H, m), 6.42 (1H, d, J=8.1 Hz), 6.64 (1H, dd, J=1.7 Hz, 8.1 Hz), 6.72 (1H, d, J=8.5 Hz), 6.80 (1H, d, J=1.8 Hz), 7.19 (1H, dd, J=2.6 Hz, 8.5 Hz), 7.81 (1H, d, J=2.5 Hz)

Using the suitable starting materials, the compounds of the following Table 7 are obtained in the same manner as in above Examples 1 and 382.

TABLE 7

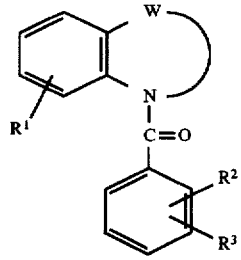

| Example 980 |
|---|
| Structure |

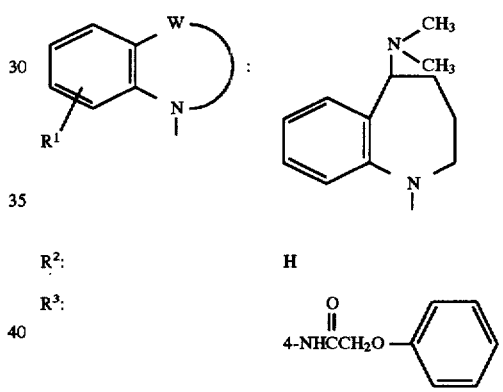

R$^2$: H

R$^3$: 4-NHCCH$_2$O—(phenyl) (with C=O)

Crystalline form: Colorless amorphous
NMR analysis: 183)
Form: Free

| Example 981 |
|---|
| Structure |

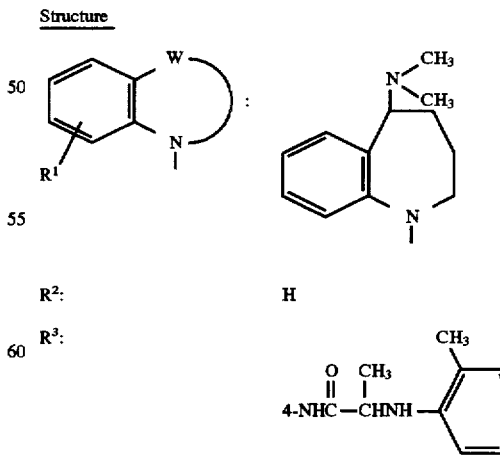

R$^2$: H

R$^3$: 4-NHC—CHNH—(o-tolyl) (with C=O and CH$_3$)

Crystalline form: Colorless amorphous
NMR analysis: 184)

TABLE 7-continued

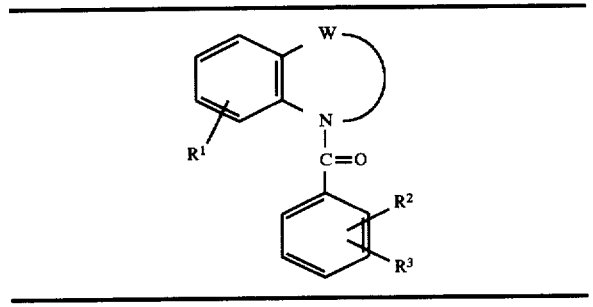

Example 982

Structure

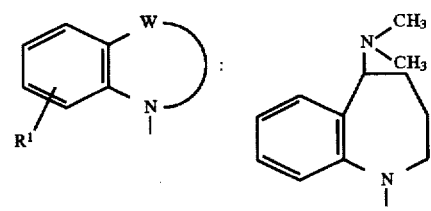

R²: H

R³:
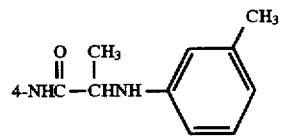

Crystalline form: Colorless amorphous
NMR analysis: 185)
Form: Free

Example 983

Structure

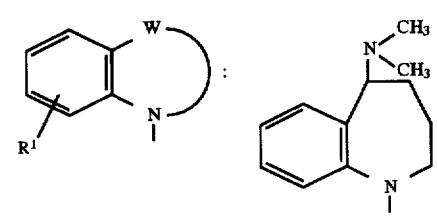

R²: H

R³:
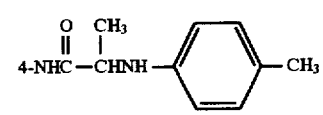

Crystalline form: Colorless amorphous
NMR analysis: 186)
Form: Free

TABLE 7-continued

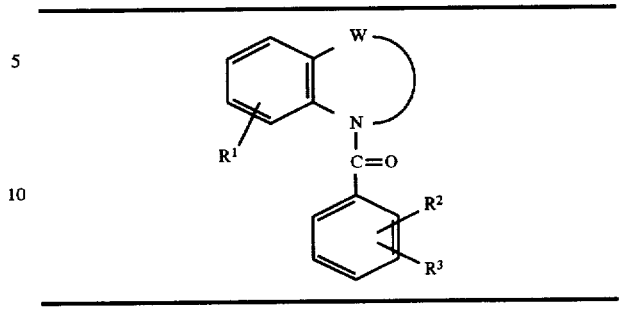

Example 984

Structure

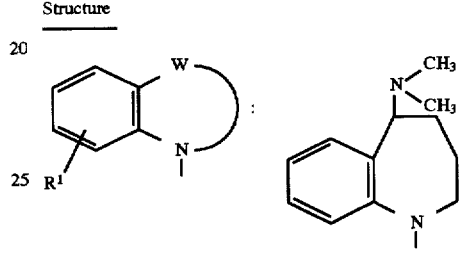

R²: H

R³:
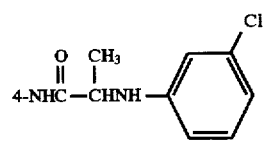

Crystalline form: Colorless amorphous
NMR analysis: 187)
Form: Free

Example 985

Structure

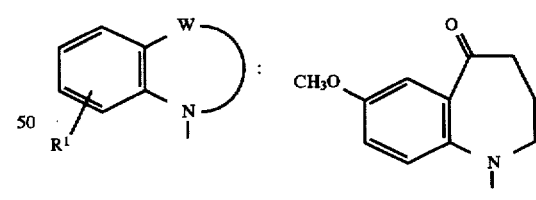

R²: 2-Cl

R³:
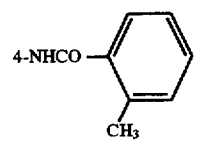

Crystalline form: Colorless amorphous
NMR analysis: 188)
Form: Free

TABLE 7-continued

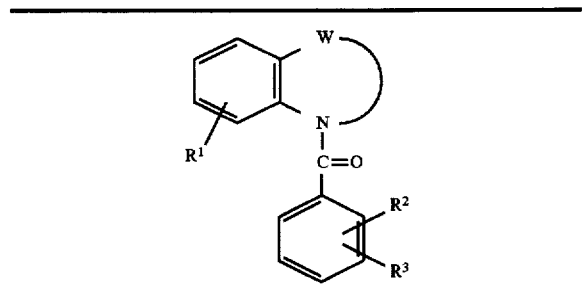

Example 986

Structure

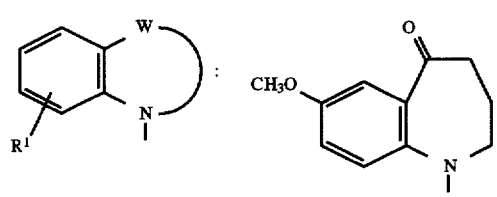

R²: 2-Cl

R³:

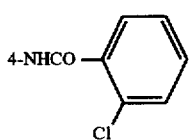

4-NHCO—⟨phenyl⟩—Cl

Crystalline form: Colorless amorphous
NMR analysis: 189)
Form: Free

Example 987

Structure

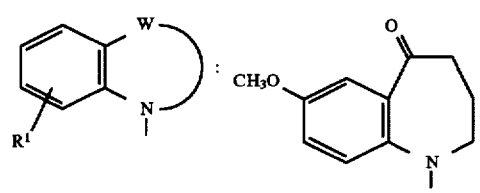

R²: H

R³:

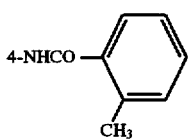

4-NHCO—⟨phenyl⟩—CH₃

Crystalline form: White powder
Recrystallization solvent: Ethanol/water
Melting Point: 267–268° C.
Form: Free TABLE 7-continued

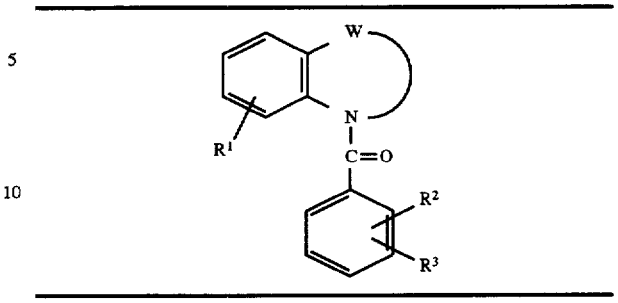

Example 988

Structure

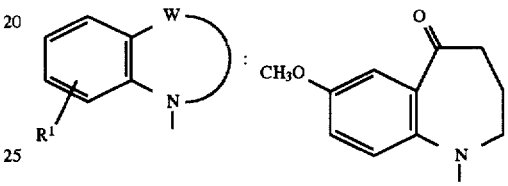

R²: H

R³:

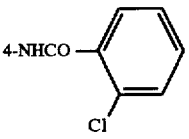

4-NHCO—⟨phenyl⟩—Cl

Crystalline form: White powder
Recrystallization solvent: Ethanol/water
Melting Point: 264–266° C.
Form: Free Example 989

Structure

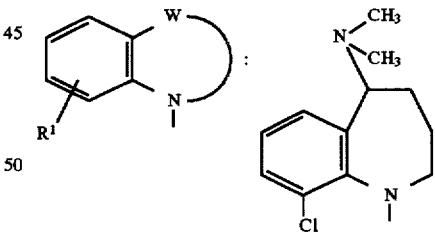

R²: H

R³:

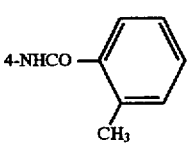

4-NHCO—⟨phenyl⟩—CH₃

Crystalline form: White powder
Recrystallization solvent: Dichloromethane/diethyl ether
Melting Point: 218–220° C.
Form: Free

TABLE 7-continued

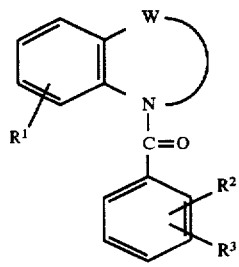

Example 990

Structure

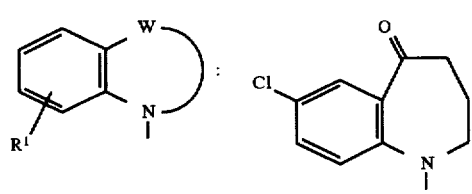

R²:  3-OCH₃

R³:

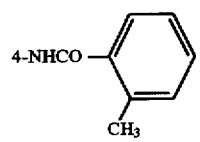

Crystalline form: Yellow oil
NMR analysis: 190)
Form: Free

Example 991

Structure

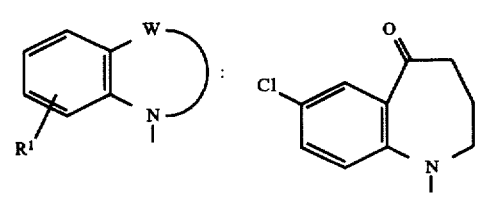

R²:  3-OCH₃

R³:

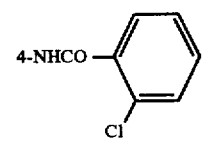

Crystalline form: Yellow oil
NMR analysis: 191)
Form: Free

TABLE 7-continued

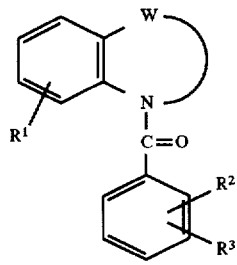

Example 992

Structure

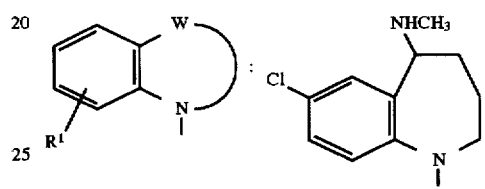

R²:  3-OCH₃

R³:

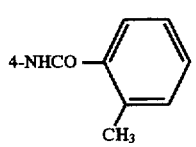

Crystalline form: Yellow powder
Recrystallization solvent: Dichloromethane/diethyl ether
Melting Point: 174–177° C.
Form: Free

Example 993

Structure

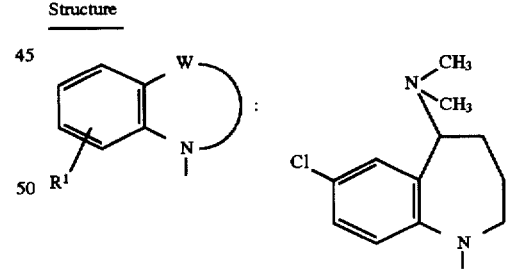

R²:  3-OCH₃

R³:

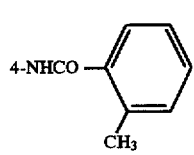

Crystalline form: Yellow amorphous
NMR analysis: 192)
Form: Free

TABLE 7-continued

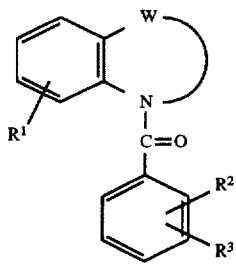

Example 994

Structure

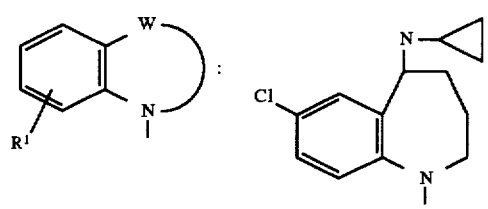

R²:     3-OCH₃

R³:

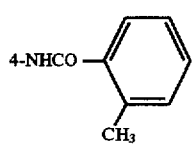

Crystalline form: Colorless amorphous
NMR analysis: 193)
Form: Free

Example 995

Structure

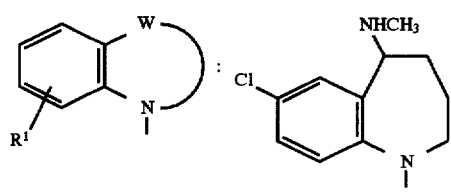

R²:     3-OCH₃

R³:

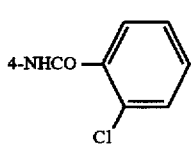

Crystalline form: White powder
Recrystallization solvent: Diethyl ether/dichloromethane
Melting Point: 163–165° C.
Form: Free

TABLE 7-continued

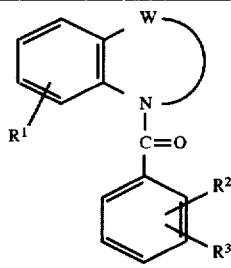

Example 996

Structure

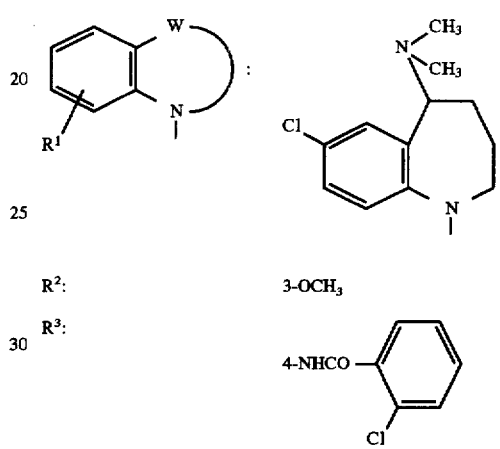

R²:     3-OCH₃

R³:

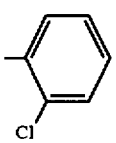

Crystalline form: Colorless amorphous
NMR analysis: 194)
Form: Free

Example 997

Structure

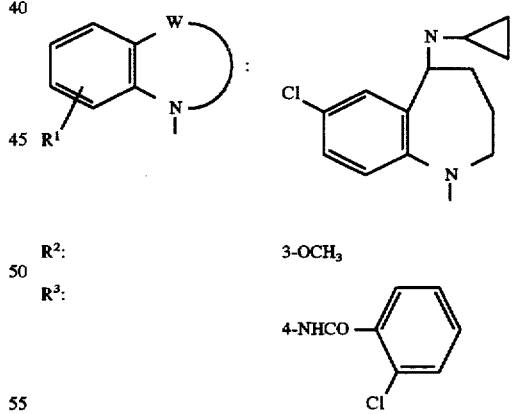

R²:     3-OCH₃

R³:

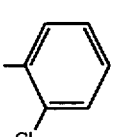

Crystalline form: Colorless amorphous
NMR analysis: 195)
Form: Free

183) ¹H-NMR (CDCl₃) δ; 1.10–2.83 (11H, m), 2.96–5.21 (2H, m), 4.55 (2H, s), 6.48–7.72 (13H, m), 8.30 (1H, brs)

184) ¹H-NMR (CDCl₃) δ; 1.10–2.85 (11H, m), 1.58 (3H, d, J=6.8 Hz), 2.23 (3H, s), 2.95–5.19 (4H, m), 6.38–7.70 (12H, m), 8.69 (1H, brs)

185) ¹H-NMR (CDCl₃) δ; 1.10–2.85 (14H, m), 2.26 (3H, s), 2.96–5.19 (4H, m), 6.36–7.68 (12H, m), 8.72 (1H, brs)

186) ¹H-NMR (CDCl₃) δ; 1.09–2.72 (11H, m), 1.53 (3H, d, J=6.9 Hz), 2.24 (3H, s), 2.93–5.21 (4H, m), 6.30–7.78 (12H, m), 8.76 (1H, brs)

187) ¹H-NMR (CDCl₃) δ; 1.10–2.82 (14H, m), 2.96–5.20 (4H, m), 6.38–7.70 (12H, m), 8.54 (1H, brs)

188) ¹H-NMR (CDCl₃) δ; 1.64–2.28 (2H, m), 2.41 (3H, s), 2.60–2.90 (2H, m), 2.90–3.70 (1H, m), 3.76 (3H, s), 4.10–5.10 (1H, m), 6.60–7.70 (10H, m), 8.51 (1H, s)

189) ¹H-NMR (CDCl₃) δ; 1.64–2.43 (2H, m), 2.67–2.97 (2H, m), 3.00–3.70 (1H, m), 3.77 (3H, s), 4.20–5.10 (1H, m), 6.60–7.75 (10H, m), 8.51 (1H, s)

190) ¹H-NMR (CDCl₃) δ; 2.00–2.35 (2H, m), 2.49 (3H, s), 2.89 (2H, t, J=6.2 Hz), 3.72 (3H, s), 3.40–4.80 (2H, m), 6.74 (2H, d, J=8.5 Hz), 6.80–7.00 (2H, m), 7.25–7.60 (5H, m), 7.80 (1H, d, J=2.6 Hz), 8.16 (1H, s), 8.37 (1H, d, J=8.6 Hz)

191) ¹H-NMR (CDCl₃) δ; 1.90–2.40 (2H, m), 2.90 (2H, t, J=6.2 Hz), 3.75 (3H, s), 3.40–4.80 (2H, m), 6.74 (1H, d, J=8.5 Hz), 6.80–7.00 (2H, m), 7.10–7.50 (4H, m), 7.73 (1H, dd, J=2.3 Hz, 6 Hz), 7.80 (1H, d, J=2.5 Hz), 8.38 (1H, d, J=8.8 Hz), 8.65 (1H, s)

192) ¹H-NMR (CDCl₃) δ; 1.10–2.10 (13H, m), 2.90–5.20 (6H, m), 6.56 (1H, d, J=8.4 Hz), 6.69 (1H, d, J=7 Hz), 6.85–7.70 (7H, m), 8.15 (1H, s), 8.31 (1H, d, J=8.4 Hz)

193) ¹H-NMR (CDCl₃) δ; 0.30–0.65 (4H, m), 1.20–2.50 (7H, m), 2.50 (3H, s), 3.10–5.20 (2H, m), 3.75 (3H, s), 6.60 (1H, d, J=8.3 Hz), 6.70–7.60 (8H, m), 8.14 (1H, s), 8.20–8.40 (1H, m)

194) ¹H-NMR (CDCl₃) δ; 0.80–2.50 (10H, m), 2.90–4.10 (6H, m), 6.50–7.80 (9H, m), 8.32 (1H, d, J=8 Hz), 8.62 (1H, s)

195) ¹H-NMR (CDCl₃) δ; 0.30–0.65 (4H, m), 0.70–2.40 (6H, m), 2.60–5.20 (6H, m), 6.50–7.80 (9H, m), 8.30 (1H, d, J=8 Hz), 8.62 (1H, s)

REFERENCE EXAMPLE 20

Using the suitable starting materials, the following compounds are obtained in the same manner as in Reference Example 1.

7-Methyl-5-oxo-1-(4-nitrobenzoyl)-2,3,4,5-tetrahydro-1H-benzazepine, white needles ¹H-NMR (CDCl₃) δ; 2.20 (2H, brs), 2.32 (3H, s), 2.88 (2H, t, J=6.3 Hz), 3.40–4.79 (2H, m), 6.57 (1H, d, J=8.0 Hz), 7.04 (1H, d, J=7.7 Hz), 7.36 (2H, d, J=8.6 Hz), 7.62 (1H, d, J=1.7 Hz), 8.04 (2H, d, J=8.7 Hz)

7-Dimethylamino-5-oxo-1-(4-nitrobenzoyl)-2,3,4,5-tetrahydro-1H-benzazepine, red brown prisms (recrystallized from dichloromethane/diethyl ether)

¹H-NMR (CDCl₃) δ; 1.75–2.47 (2H, m), 2.60–3.62, 4.51–4.92 (total 4H, m), 2.93 (6H, s), 6.46 (1H, dd, J=2.2 Hz, 7.0 Hz), 6.52 (1H, d, J=7.0 Hz), 7.33 (2H, d, J=7.0 Hz), 8.00 (2H, d, J=7.0 Hz)

7-Bromo-5-oxo-1-(4-nitrobenzoyl)-2,3,4,5-tetrahydro-1H-benzazepine, white powder (recrystallized from dichloromethane/diethyl ether), m.p. 177°–182° C.

7-Chloro-5-oxo-1-(2-methyl-4-nitrobenzoyl)-2,3,4,5-tetrahydro-1H-benzazepine, white powder (recrystallized from dichloromethane/diethyl ether)

¹H-NMR (CDCl₃) δ; 1.78–2.37 (2H, m), 2.48 (3H, s), 2.88 (2H, t, J=6.1 Hz), 3.30–5.12 (2H, m), 6.47–6.82 (1H, m), 6.82–7.09 (1H, m), 7.09–7.27 (1H, m), 7.48–8.35 (3H, m)

6-Oxo-1-(2-chloro-4-nitrobenzoyl)-1,2,3,4,5,6-hexahydrobenzazocine, yellow amorphous ¹H-NMR (CDCl₃) δ; 1.7–2.1 (4H, m), 2.85–4.7 (4H, m), 7.12 (1H, d, J=8.4 Hz), 7.17–7.51 (4H, m), 7.89 (1H, dd, J=7.8 Hz, 2.1 Hz), 8.11 (1H, d, J=2.2 Hz)

8-Chloro-6-oxo-1-(2-chloro-4-nitrobenzoyl)-1,2,3,4,5,6-hexahydrobenzazocine, yellow amorphous ¹H-NMR (CDCl₃) δ; 1.7–2.15 (4H, m), 2.85–4.8 (4H, m), 7.14 (1H, d, J=8.5 Hz), 7.16 (1H, d, J=8.4 Hz), 7.34 (1H, dd, J=8.3 Hz, 2.5 Hz), 7.85 (1H, d, J=2.5 Hz), 7.94 (1H, dd, J=8.4 Hz, 2.2 Hz), 8.13 (1H, d, J=2.1 Hz)

8-Methyl-6-oxo-1-(2-chloro-4-nitrobenzoyl)-1,2,3,4,5,6-hexahydrobenzazocine, yellow amorphous ¹H-NMR (CDCl₃) δ; 1.65–2.2 (4H, m), 2.33 (3H, s), 2.7–5.0 (4H, m), 7.0–7.25 (3H, m), 7.67 (1H, d, J=2.0 Hz), 7.89 (1H, dd, J=8.4 Hz, 2.2 Hz), 8.10 (1H, d, J=2.1 Hz)

8-Methoxy-6-oxo-1-(2-chloro-4-nitrobenzoyl)-1,2,3,4,5,6-hexahydrobenzazocine, light yellow amorphous ¹H-NMR (CDCl₃) δ; 1.6–2.05 (4H, m), 2.8–5.2 (4H, m), 3.78 (3H, s), 6.88 (1H, dd, J=8.6 Hz, 3.1 Hz), 7.11 (1H, d, J=8.4 Hz), 7.12 (1H, d, J=8.6 Hz), 7.38 (1H, d, J=3.0 Hz), 7.90 (1H, dd, J=8.4 Hz, 2.2 Hz), 8.11 (1H, d, J=2.2 Hz)

7-Chloro-5-oxo-1-(2-chloro-4-nitrobenzoyl)-2,3,4,5-tetrahydro-1H-benzazepine, yellow powder (recrystallized from diethyl ether/dichloromethane), m.p. 125°–126.5° C.

REFERENCE EXAMPLE 21

Using the suitable starting materials, the following compounds are obtained in the same manner as in Reference Example 2.

7-Methyl-5-oxo-1-(4-aminobenzoyl)-2,3,4,5-tetrahydro-1H-benzazepine, yellow powder ¹H-NMR (CDCl₃) δ; 2.13 (2H, brs), 2.32 (3H, s), 2.86 (2H, t, J=6.2 Hz), 2.89–5.29 (2H, m), 3.86 (2H, brs), 6.41 (2H, m), 6.65 (1H, d, J=8.1 Hz), 7.06 (3H, m), 7.65 (1H, d, J=1.7 Hz)

7-Dimethylamino-5-oxo-1-(4-aminobenzoyl)-2,3,4,5-tetrahydro-1H-benzazepine, yellow needles (recrystallized from dichloromethane/diethyl ether)

¹H-NMR (CDCl₃) δ; 1.78–2.49 (2H, m), 2.64–3.78, 4.07–5.02 (total 4H, m), 2.93 (6H, m), 3.96 (2H, m), 6.38 (2H, d, J=8.7 Hz), 6.55 (1H, dd, J=2.7, 8.7 Hz), 6.62 (1H, d, J=8.7 Hz), 6.96–7.18 (3H, m)

7-Bromo-5-oxo-1-(4-aminobenzoyl)-2,3,4,5-tetrahydro-1H-benzazepine, white powder (recrystallized from methanol/diethyl ether)

¹H-NMR (CDCl₃) δ; 1.98–2.37 (2H, m), 2.88 (2H, t, J=6.3 Hz), 3.52–4.55 (4H, m), 6.28–6.57 (2H, m), 6.57–6.76 (1H, m), 6.92–7.20 (2H, m), 7.28–7.42 (1H, m), 7.90–8.09 (1H, m)

7-Chloro-5-oxo-1-(2-methyl-4-aminobenzoyl)-2,3,4,5-tetrahydro-1H-benzazepine, white powder (recrystallized from dichloromethane/diethyl ether), m.p. 190°–191° C.

6-Oxo-1-(2-chloro-4-aminobenzoyl)-1,2,3,4,5,6-hexahydrobenzazocine, light yellow amorphous ¹H-NMR (CDCl₃) δ; 1.3–2.25 (4H, m), 2.8–4.4 (6H, m), 6.1–6.9 (3H, m), 6.95–7.75 (3H, m), 7.8–8.3 (1H, m)

8-Chloro-6-oxo-1-(2-chloro-4-aminobenzoyl)-1,2,3,4,5,6-hexahydrobenzazocine, light yellow amorphous ¹H-NMR (CDCl₃) δ; 1.59–2.2 (4H, m), 2.6–4.4 (6H, m), 6.1–6.9 (3H, m), 6.95–7.5 (2H, m), 7.8–8.05 (1H, m)

7-Chloro-5-oxo-1-(2-chloro-4-aminobenzoyl)-2,3,4,5-tetrahydro-1H-benzazepine, yellow powder (recrystallized from diethyl ether/dichloromethane), m.p. 188°–191.5° C.

Using the suitable starting materials, the compounds of the following Table 8 are obtained in the same manner as in above Examples 1 and 382.

TABLE 8

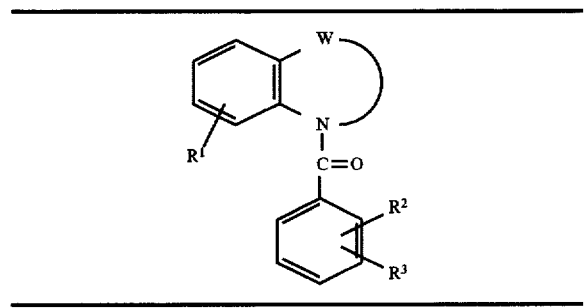

Example 998

Structure

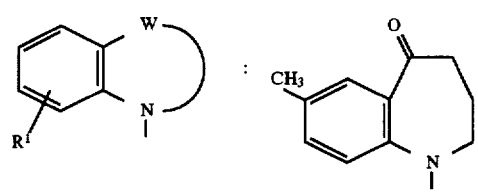

R²: H

R³:
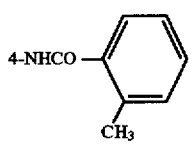
4-NHCO— (2-CH₃-phenyl)

| | |
|---|---|
| Crystalline form: | White powder |
| NMR analysis: | 196) |
| Form: | Free |

Example 999

Structure

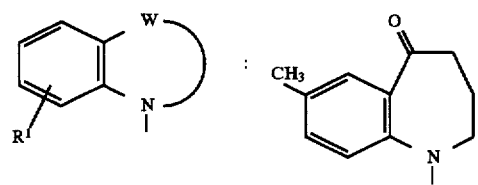

R²: H

R³:
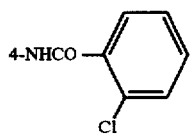
4-NHCO— (2-Cl-phenyl)

| | |
|---|---|
| Crystalline form: | White powder |
| NMR analysis: | 197) |
| Form: | Free |

TABLE 8-continued

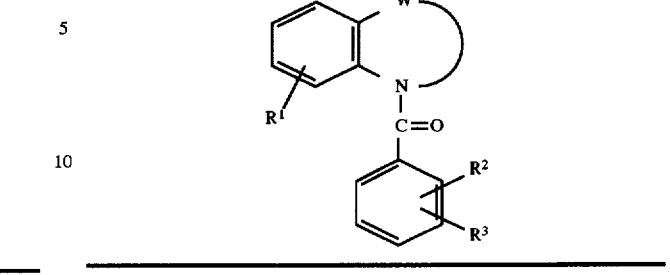

Example 1000

Structure

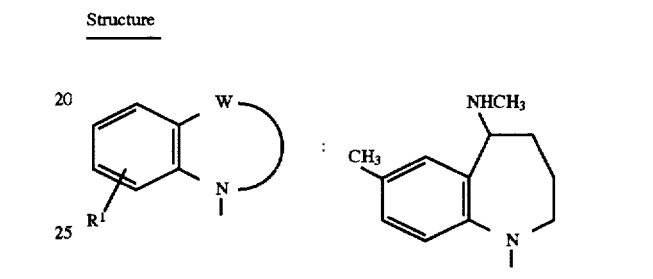

R²: H

R³:
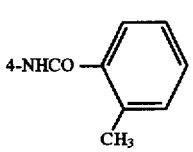
4-NHCO— (2-CH₃-phenyl)

| | |
|---|---|
| Crystalline form: | White powder |
| Recrystallization solvent: | Dichloromethane/diethyl ether |
| Melting Point: | 200–205° C. |
| Form: | Free |

Example 1001

Structure

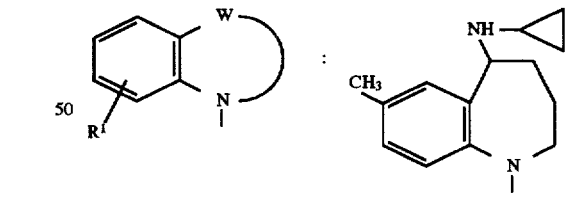

R²: H

R³:
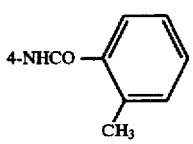
4-NHCO— (2-CH₃-phenyl)

| | |
|---|---|
| Crystalline form: | Colorless amorphous |
| NMR analysis: | 198) |
| Form: | Free |

TABLE 8-continued

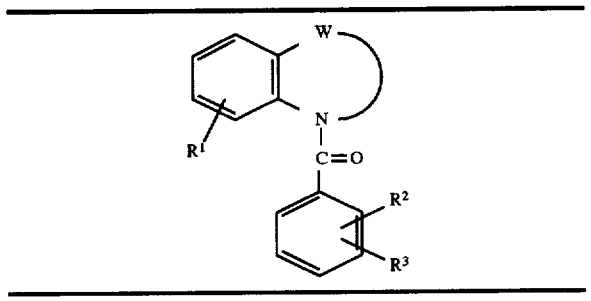

Example 1002

Structure

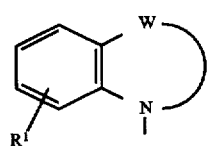 : 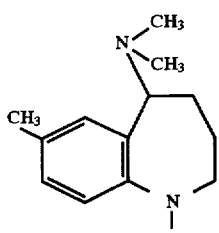

R²: H

R³: 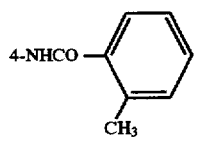 4-NHCO—⟨⟩—CH₃

Crystalline form: White powder
Recrystallization solvent: Dichloromethane/diethyl ether
Melting Point: 234–238° C.
Form: Free

Example 1003

Structure

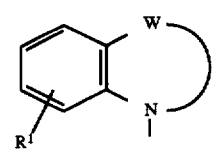 : 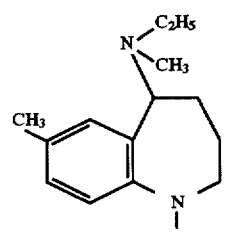

R²: H

R³: 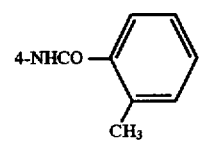 4-NHCO—⟨⟩—CH₃

Crystalline form: White powder
Recrystallization solvent: Ethyl acetate/n-hexane
Melting Point: 174–178° C.
Form: Free

TABLE 8-continued

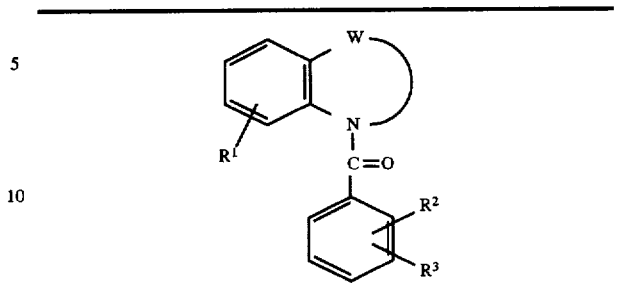

Example 1004

Structure

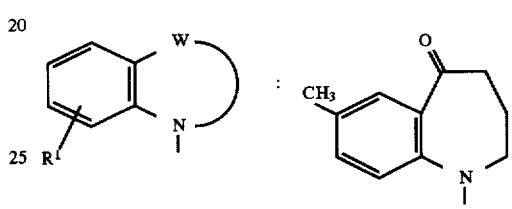

R²: 2-Cl

R³: 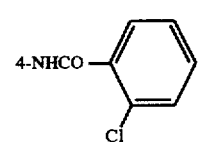 4-NHCO—⟨⟩—Cl

Crystalline form: Light yellow amorphous
NMR analysis: 199)
Form: Free

Example 1005

Structure

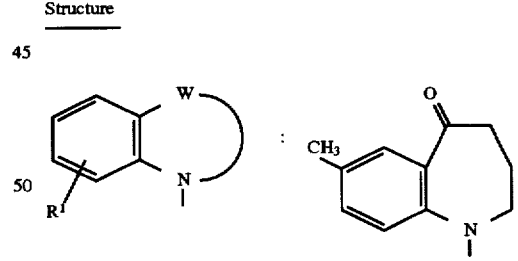

R²: 2-Cl

R³: 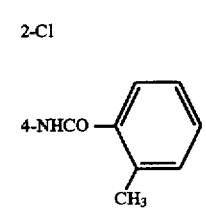 4-NHCO—⟨⟩—CH₃

Crystalline form: Light yellow amorphous
NMR analysis: 200)
Form: Free

TABLE 8-continued

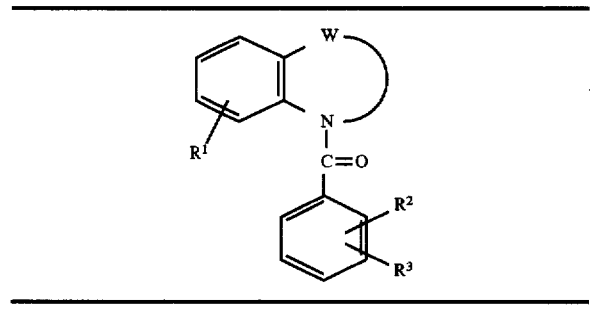

Example 1006

Structure

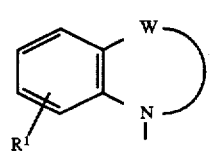 : 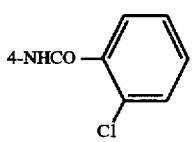

R²: 2-Cl

R³:

4-NHCO—⟨benzene⟩—Cl

Crystalline form: Light yellow amorphous
NMR analysis: 201)
Form: Free

Example 1007

Structure

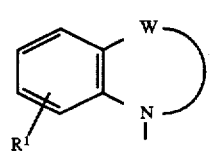 : 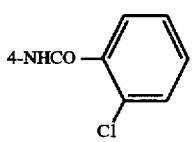

R²: 2-Cl

R³:

4-NHCO—⟨benzene⟩—CH₃

Crystalline form: Light yellow amorphous
NMR analysis: 202)
Form: Free

TABLE 8-continued

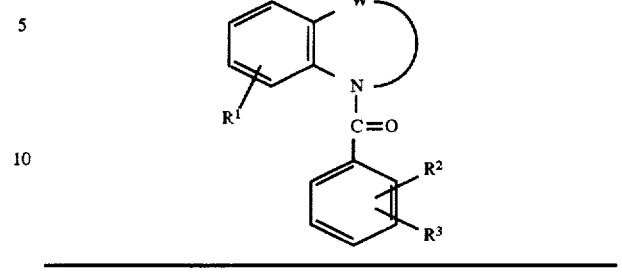

Example 1008

Structure

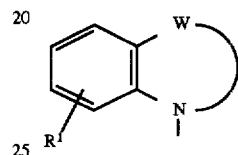 : 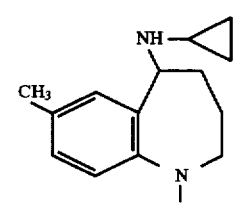

R²: 2-Cl

R³:

4-NHCO—⟨benzene⟩—Cl

Crystalline form: Light yellow amorphous
NMR analysis: 203)
Form: Free

Example 1009

Structure

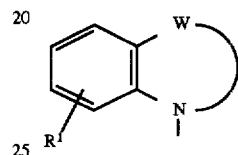 : 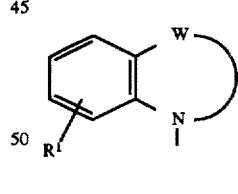

R²: 2-Cl

R³:

4-NHCO—⟨benzene⟩—CH₃

Crystalline form: Light yellow amorphous
NMR analysis: 204)
Form: Free

TABLE 8-continued

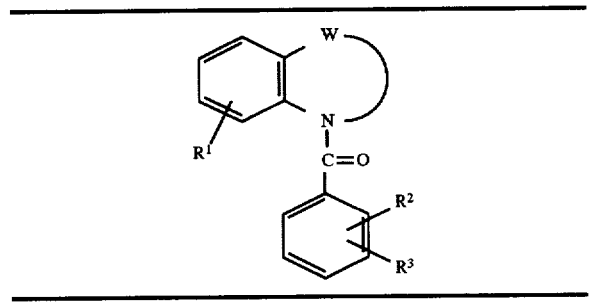

Example 1010

Structure

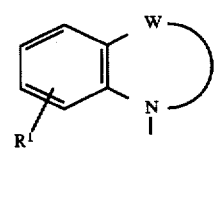 : 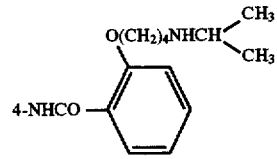

R²: H

R³:
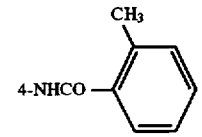

Crystalline form: Colorless amorphous
NMR analysis: 205)
Form: Free

Example 1011

Structure

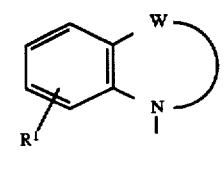 :

Actually for 1011:

R²: 3-OCH₃

R³:

Crystalline form: White powder
Recrystallization solvent: Ethyl acetate/n-hexane
Melting Point: 153–155° C.
Form: Free TABLE 8-continued

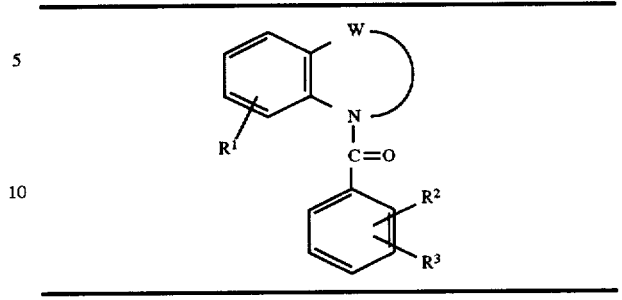

Example 1012

Structure

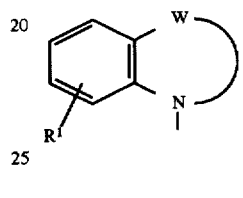 : 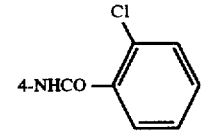

R²: 3-OCH₃

R³:

Crystalline form: White powder
Recrystallization solvent: Ethyl acetate/n-hexane
Melting Point: 142–143° C.
Form: Free Example 1013

Structure

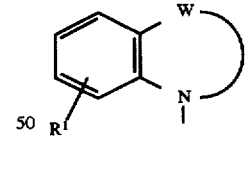 : 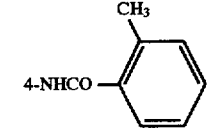

R²: H

R³:

Crystalline form: White powder
Recrystallization solvent: Ethyl acetate/n-hexane
Melting Point: 176–178° C.
Form: Free TABLE 8-continued

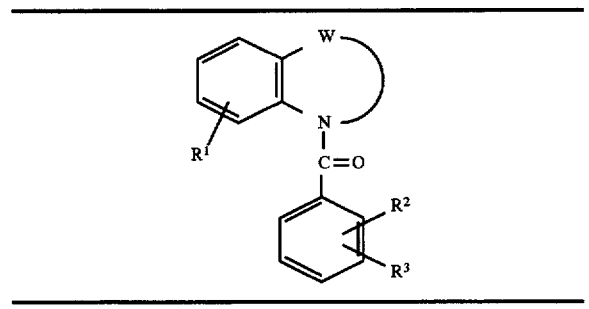

Example 1014

Structure

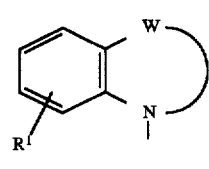 : 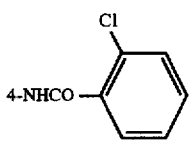

R²: H

R³: 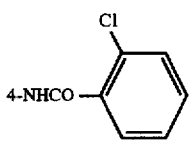
(4-NHCO—phenyl-Cl)

Crystalline form: White powder
Recrystallization solvent: Ethyl acetate/n-hexane
Melting Point: 186–188° C.
Form: Free

Example 1015

Structure

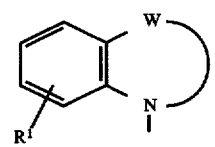 : 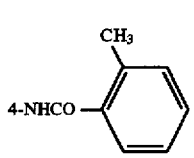

R²: 2-Cl

R³: (4-NHCO—phenyl-CH₃)

Crystalline form: Colorless amorphous
NMR analysis: 206)
Form: Free

TABLE 8-continued

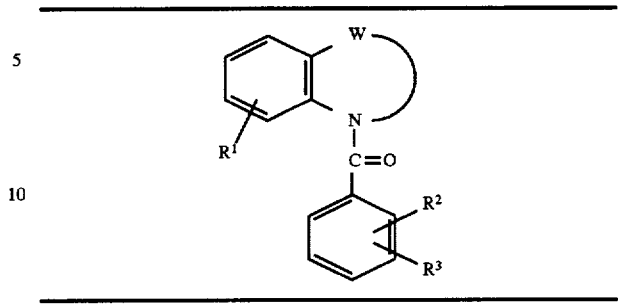

Example 1016

Structure

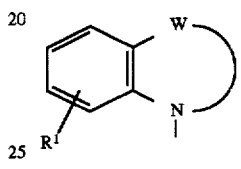 : 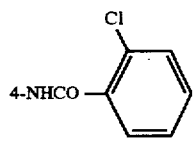

R²: 2-Cl

R³: (4-NHCO—phenyl-Cl)

Crystalline form: Colorless amorphous
NMR analysis: 207)
Form: Free

Example 1017

Structure

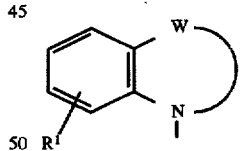 : 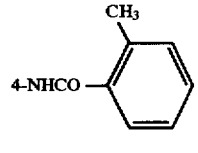

R²: 3-OCH₃

R³: (4-NHCO—phenyl-CH₃)

Crystalline form: White powder
Recrystallization solvent: Ethyl acetate/n-hexane
Melting Point: 191–191.5° C.
Form: Free

TABLE 8-continued

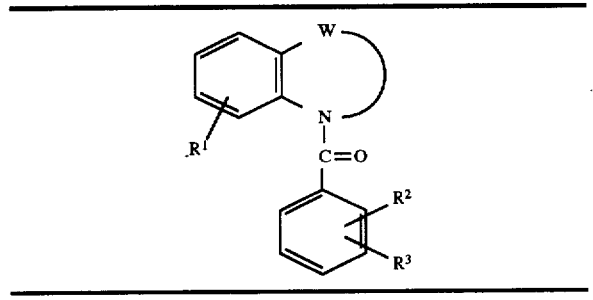

Example 1018

Structure

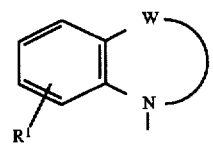 : 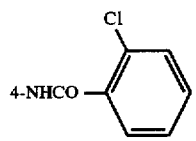

R²: 3-OCH₃

R³:

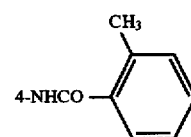
4-NHCO—

Crystalline form: White powder
Recrystallization solvent: Ethyl acetate/n-hexane
Melting Point: 210–212° C.
Form: Free

Example 1019

Structure

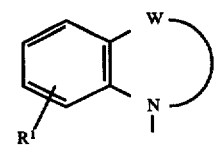 : 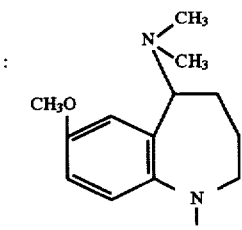

R²: H

R³:

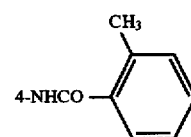
4-NHCO—

Crystalline form: White powder
Recrystallization solvent: Ethyl acetate/n-hexane
Melting Point: 196–198° C.
Form: Free

TABLE 8-continued

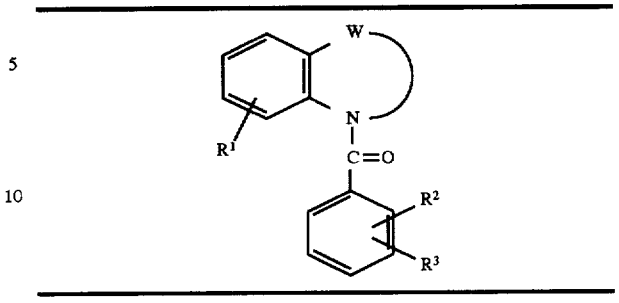

Example 1020

Structure

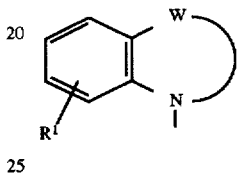 : 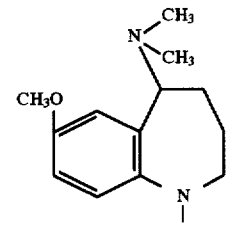

R²: H

R³:

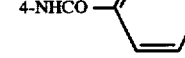
4-NHCO—

Crystalline form: Colorless amorphous
NMR analysis: 208)
Form: Free

Example 1021

Structure

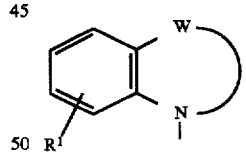 : 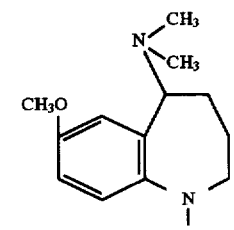

R²: 2-Cl

R³:

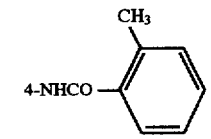
4-NHCO—

Crystalline form: Colorless amorphous
NMR analysis: 209)
Form: Free

TABLE 8-continued

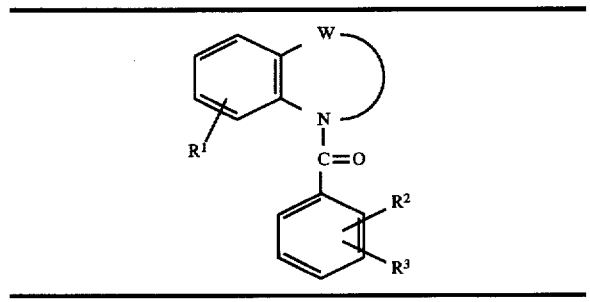

Example 1022

Structure

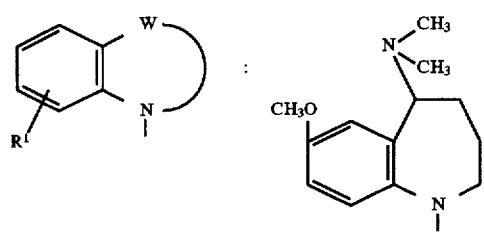

R²: 2-Cl

R³:

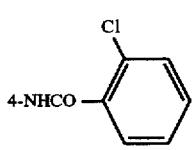
4-NHCO— (2-Cl phenyl)

Crystalline form: Colorless amorphous
NMR analysis: 210)
Form: Free

Example 1023

Structure

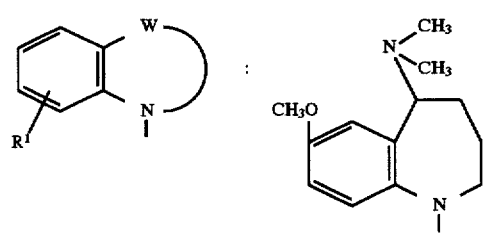

R²: 3-OCH₃

R³:

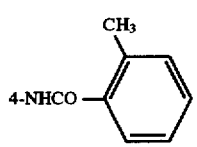
4-NHCO— (2-CH₃ phenyl)

Crystalline form: Colorless amorphous
NMR analysis: 211)
Form: Free

TABLE 8-continued

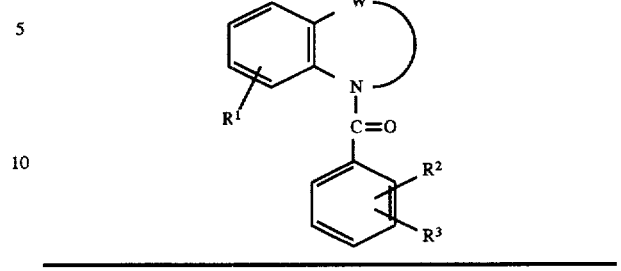

Example 1024

Structure

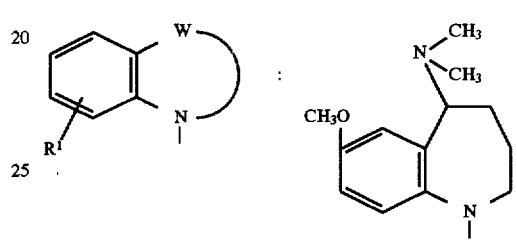

R²: 3-OCH₃

R³:

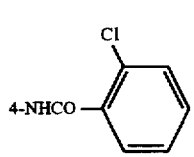
4-NHCO— (2-Cl phenyl)

Crystalline form: Colorless amorphous
NMR analysis: 212)
Form: Free

Example 1025

Structure

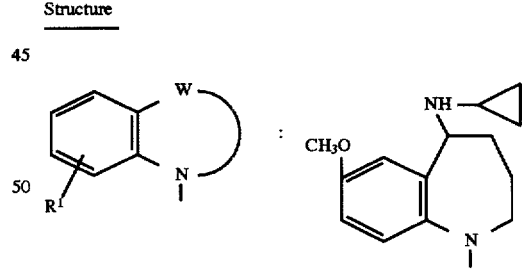

R²: 2-Cl

R³:

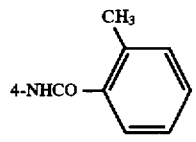
4-NHCO— (2-CH₃ phenyl)

Crystalline form: Colorless amorphous
NMR analysis: 213)
Form: Free

TABLE 8-continued

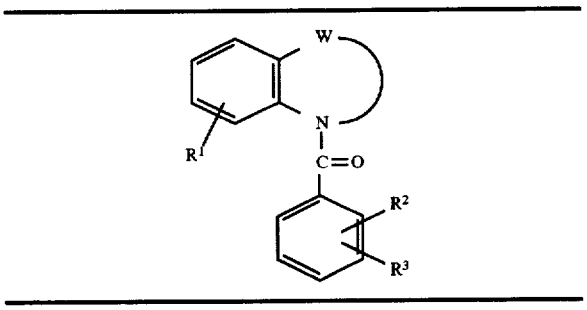

Example 1026

Structure

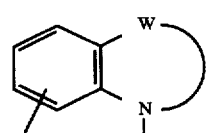 : 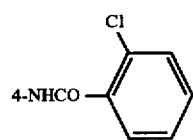

R²: 2-Cl

R³:

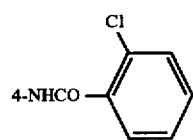
4-NHCO— (2-Cl phenyl)

Crystalline form: Colorless amorphous
NMR analysis: 214)
Form: Free

Example 1027

Structure

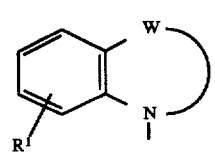 : 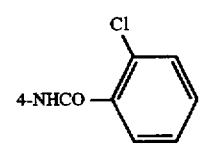

R²: 2-Cl

R³:

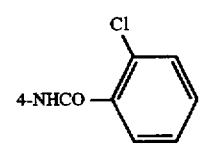
4-NHCO— (2-Cl phenyl)

Crystalline form: Colorless prisms
Recrystallization solvent: Ethanol
Melting Point: 207–208° C.
Form: Free

TABLE 8-continued

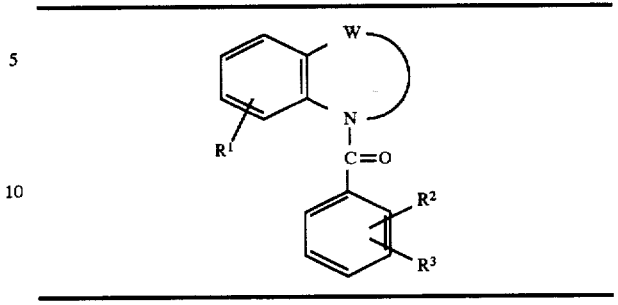

Example 1028

Structure

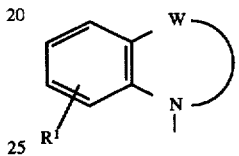 : 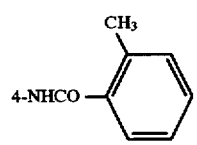

R²: 2-Cl

R³:

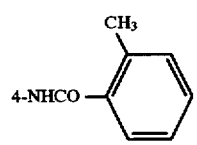
4-NHCO— (2-CH₃ phenyl)

Crystalline form: White powder
Recrystallization solvent: Ethanol
Melting Point: 201–202° C.
Form: Free Example 1029

Structure

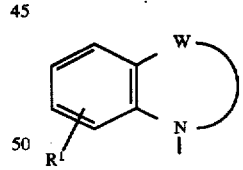 : 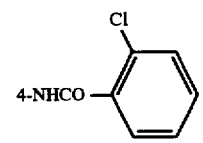

R²: 2-Cl

R³:

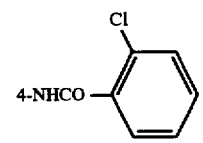
4-NHCO— (2-Cl phenyl)

Crystalline form: White powder
Recrystallization solvent: Ethanol
Melting Point: 193–194° C.
Form: Free TABLE 8-continued

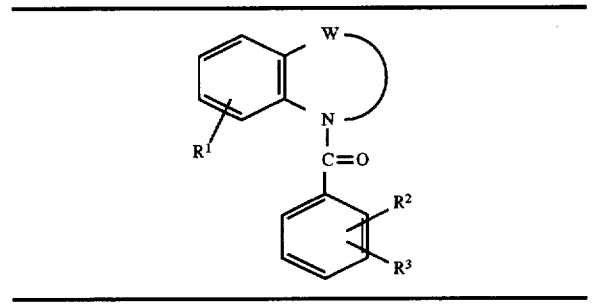

Example 1030

Structure

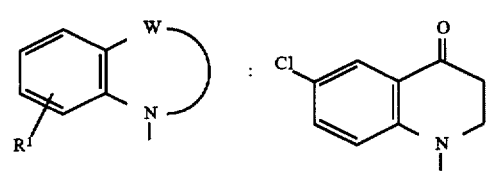

R²: H

R³: 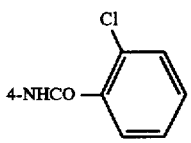
4-NHCO— (2-Cl phenyl)

| | |
|---|---|
| Crystalline form: | White powder |
| Recrystallization solvent: | Ethanol |
| Melting Point: | 205–208° C. |
| Form: | Free |

Example 1031

Structure

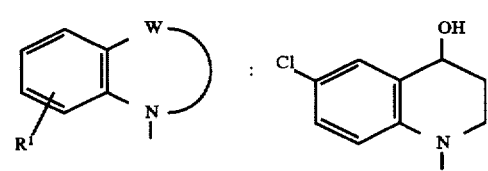

R²: H

R³: 
4-NHCO— (2-Cl phenyl)

| | |
|---|---|
| Crystalline form: | White powder |
| Recrystallization solvent: | Ethanol |
| Melting Point: | 214–216° C. |
| Form: | Free |

TABLE 8-continued

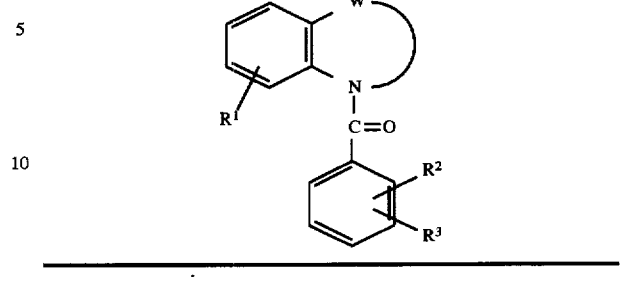

Example 1032

Structure

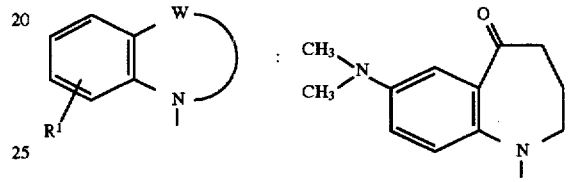

R²: H

R³: 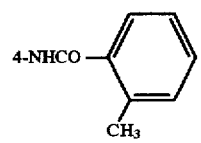
4-NHCO— (2-CH₃ phenyl)

| | |
|---|---|
| Crystalline form: | Yellow needles |
| Recrystallization solvent: | Ethanol |
| Melting Point: | 223–226° C. |
| Form: | Free |

Example 1033

Structure

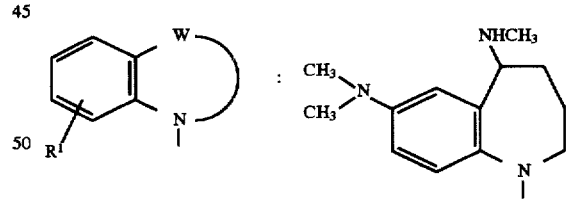

R²: H

R³: 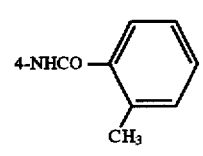
4-NHCO— (2-CH₃ phenyl)

| | |
|---|---|
| Crystalline form: | Colorless needles |
| Recrystallization solvent: | Ethanol/diethyl ether |
| Melting Point: | 203–206° C. |
| Form: | Free |

TABLE 8-continued

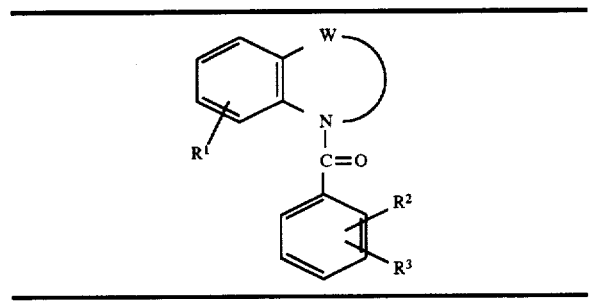

Example 1034

Structure

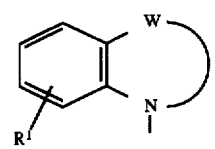 : 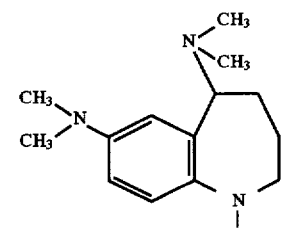

R²: H

R³: 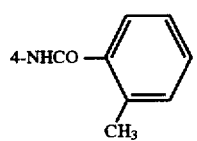
4-NHCO—⟨ ⟩—CH₃

| | |
|---|---|
| Crystalline form: | Colorless needles |
| Recrystallization solvent: | Ethanol/diethyl ether/n-hexane |
| Melting Point: | 168–171° C. |
| Form: | Free |

Example 1035

Structure

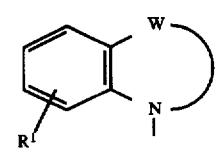 : 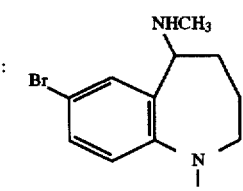

R²: H

R³: 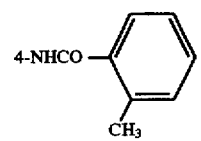
4-NHCO—⟨ ⟩—CH₃

| | |
|---|---|
| Crystalline form: | White powder |
| Recrystallization solvent: | Methanol/diethyl ether |
| Melting Point: | 206–208° C. |
| Form: | Free |

TABLE 8-continued

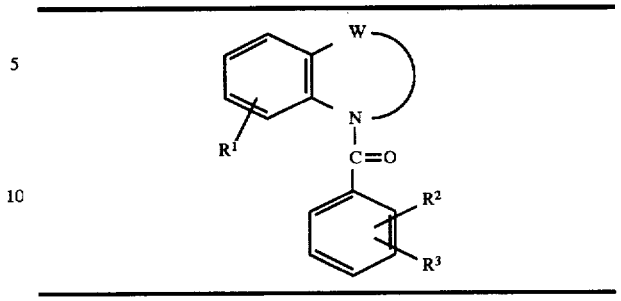

Example 1036

Structure

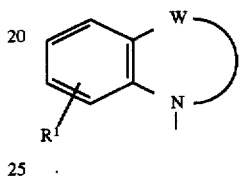 : 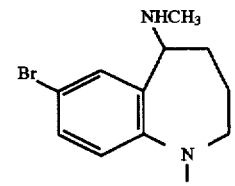

R²: H

R³: 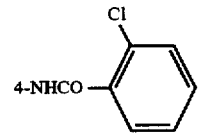
4-NHCO—⟨ ⟩—Cl

| | |
|---|---|
| Crystalline form: | White powder |
| Recrystallization solvent: | Methanol/diethyl ether |
| Melting Point: | 229–232° C. |
| Form: | Free |

Example 1037

Structure

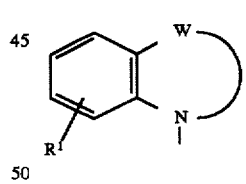 : 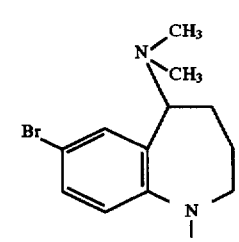

R²: H

R³: 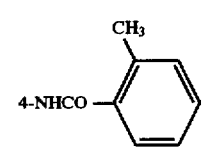
4-NHCO—⟨ ⟩—CH₃

| | |
|---|---|
| Crystalline form: | White powder |
| Recrystallization solvent: | Methanol/diethyl ether |
| Melting Point: | 220–222° C. |
| Form: | Free |

TABLE 8-continued

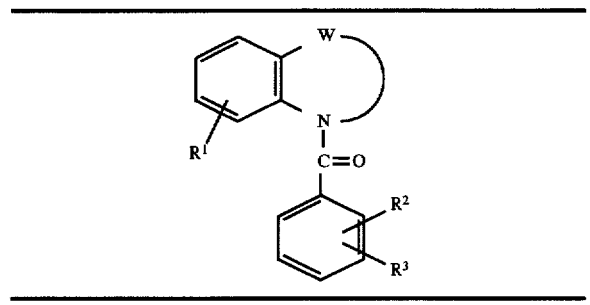

Example 1038

Structure

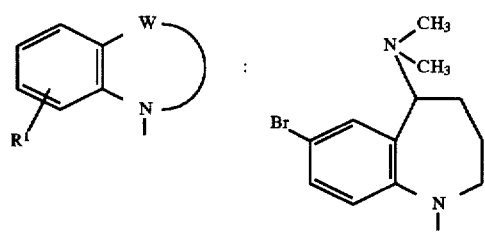

R²: H

R³: 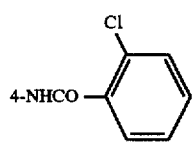
4-NHCO—⟨ ⟩—Cl (2-position)

Crystalline form: White powder
Recrystallization solvent: Methanol/diethyl ether
Melting Point: 232–233.5° C.
Form: Free

Example 1039

Structure

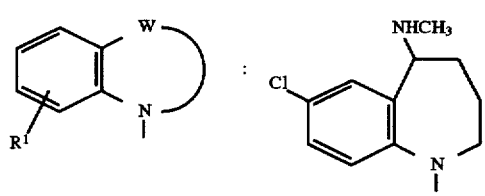

R²: 2-CH₃

R³: 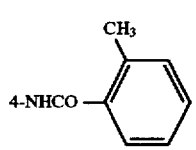
4-NHCO—⟨ ⟩—CH₃

Crystalline form: Colorless amorphous
NMR analysis: 215)
Form: Free

TABLE 8-continued

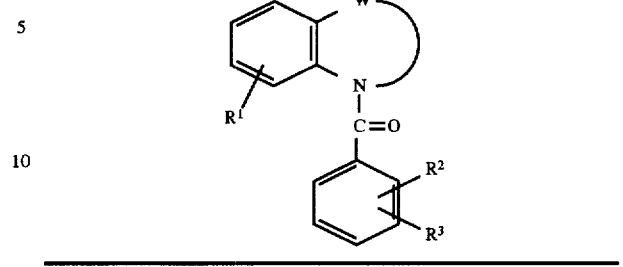

Example 1040

Structure

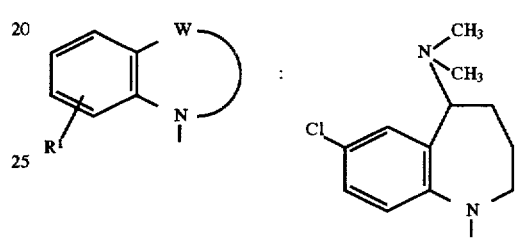

R²: 2-CH₃

R³: 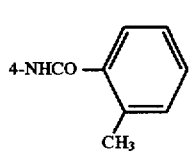
4-NHCO—⟨ ⟩—CH₃ (2-position)

Crystalline form: Colorless amorphous
NMR analysis: 216)
Form: Free

Example 1041

Structure

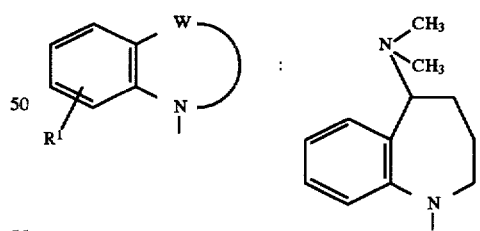

R²: H

R³: 
$$4\text{-NHCOCHBr} \atop |\ \ \ CH_3$$

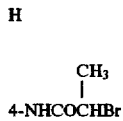

Crystalline form: White powder
Recrystallization solvent: Methanol/diethyl ether
Melting Point: 147–151° C.
Form: Free TABLE 8-continued

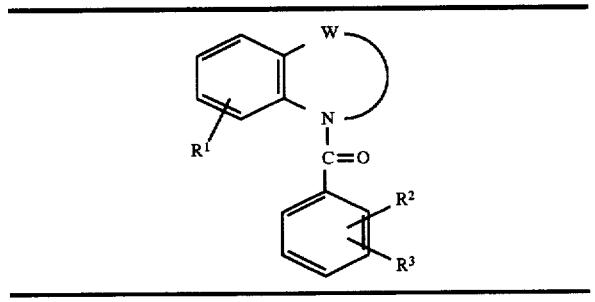

Example 1042

Structure

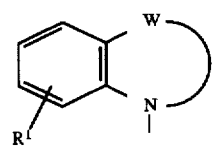 : 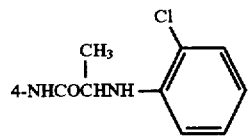

R²: H

R³:
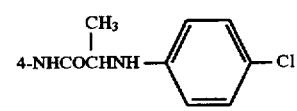

| Crystalline form: | White powder |
|---|---|
| Recrystallization solvent: | Methanol/n-hexane |
| Melting Point: | 127–129° C. |
| Form: | Free |

Example 1043

Structure

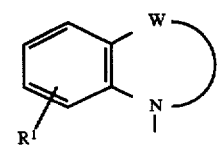 :

(structure with N(CH₃)₂ benzazepine)

R²: H

R³:

CH₃
|
4-NHCOCHNH—⟨C₆H₄⟩—Cl

| Crystalline form: | White powder |
|---|---|
| Recrystallization solvent: | Methanol/n-hexane |
| Melting Point: | 109–112° C. |
| Form: | Free |

TABLE 8-continued

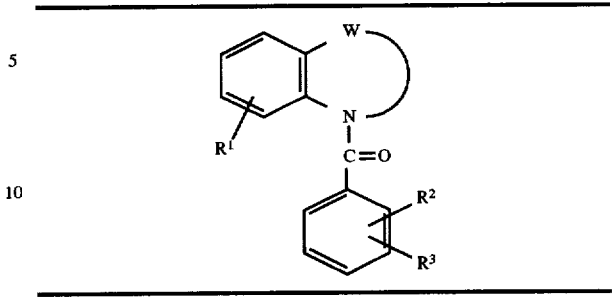

Example 1044

Structure

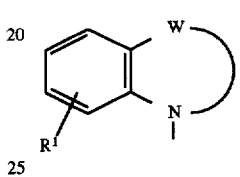 : 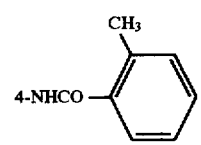

R²: H

R³:
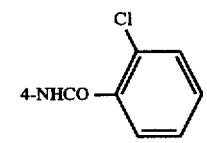
4-NHCO—⟨C₆H₄⟩—CH₃

| Crystalline form: | White powder |
|---|---|
| Recrystallization solvent: | Methanol/diethyl ether |
| Melting Point: | 198–200° C. |
| Form: | Free |

Example 1045

Structure

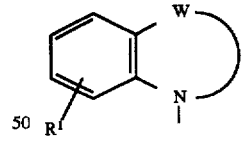 :

(structure with Br-benzazepinone)

R²: H

R³:

4-NHCO—⟨C₆H₄⟩—Cl

| Crystalline form: | White powder |
|---|---|
| Recrystallization solvent: | Methanol/diethyl ether |
| Melting Point: | 210–211° C. |
| Form: | Free |

TABLE 8-continued

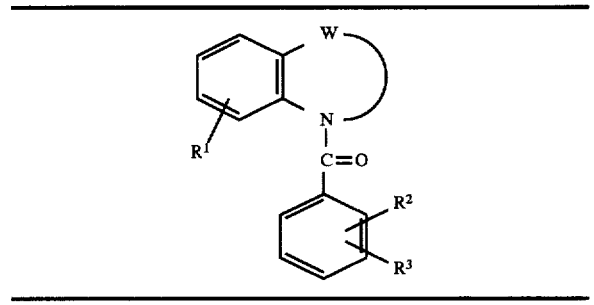

Example 1046

Structure

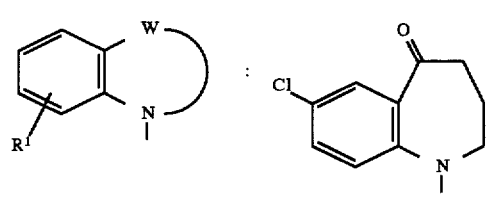

| | |
|---|---|
| R²: | 2-CH₃ |
| R³: | 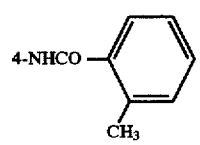 4-NHCO—⟨ ⟩—CH₃ |
| Crystalline form: | Colorless amorphous |
| NMR analysis: | 217) |
| Form: | Free |

Example 1047

Structure

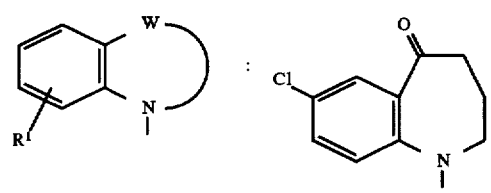

| | |
|---|---|
| R²: | 2-CH₃ |
| R³: | 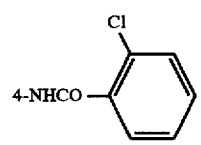 4-NHCO—⟨ ⟩—Cl |
| Crystalline form: | Colorless amorphous |
| NMR analysis: | 218) |
| Form: | Free |

TABLE 8-continued

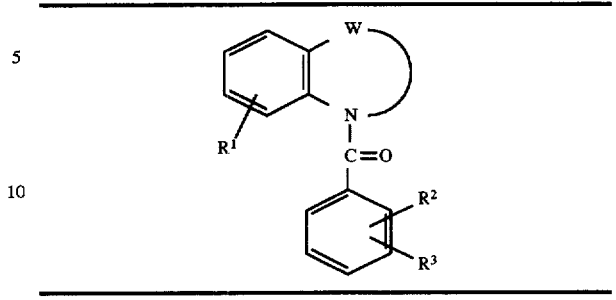

Example 1048

Structure

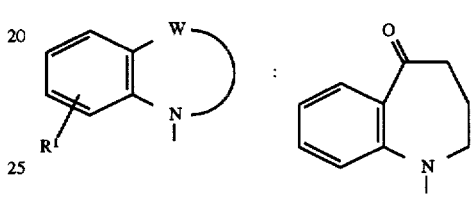

| | |
|---|---|
| R²: | H |
| R³: | 4-NHCO—⟨ ⟩—Cl |
| Crystalline form: | Colorless amorphous |
| NMR analysis: | 219) |
| Form: | Free |

Example 1049

Structure

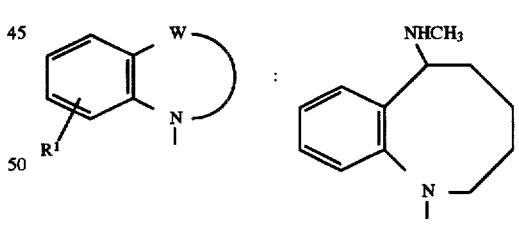

| | |
|---|---|
| R²: | H |
| R³: | 4-NHCO—⟨ ⟩—Cl |
| Crystalline form: | Colorless needles |
| Recrystallization solvent: | Ethanol |
| Melting Point: | 243–243.5° C. |
| Form: | Free |

TABLE 8-continued

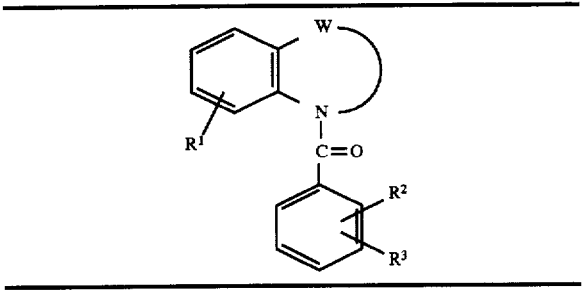

Example 1050

Structure

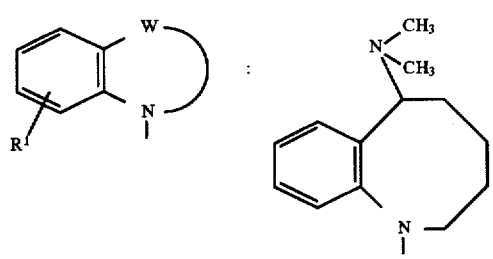 :

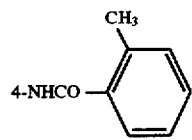

R²: H

R³:

4-NHCO— (2-CH₃ phenyl)

Crystalline form: Colorless prisms
Recrystallization solvent: Ethanol/petroleum ether
Melting Point: 207–209° C.
Form: Free

Example 1051

Structure

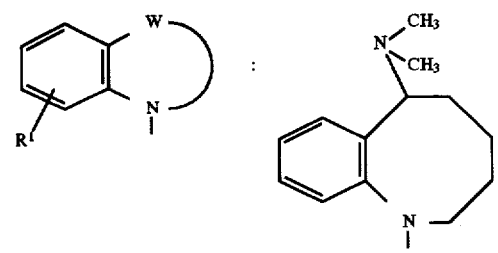 :

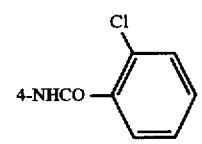

R²: H

R³: 4-NHCO— (2-Cl phenyl)

Crystalline form: Colorless needles
Recrystallization solvent: Ethanol/petroleum ether
Melting Point: 239–241° C.
Form: Free

TABLE 8-continued

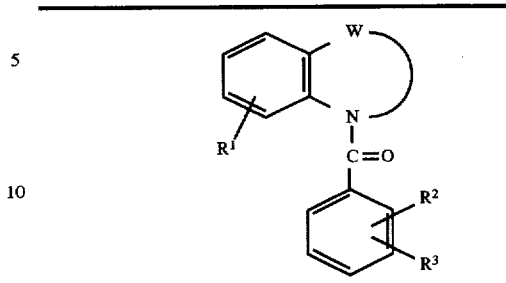

Example 1052

Structure

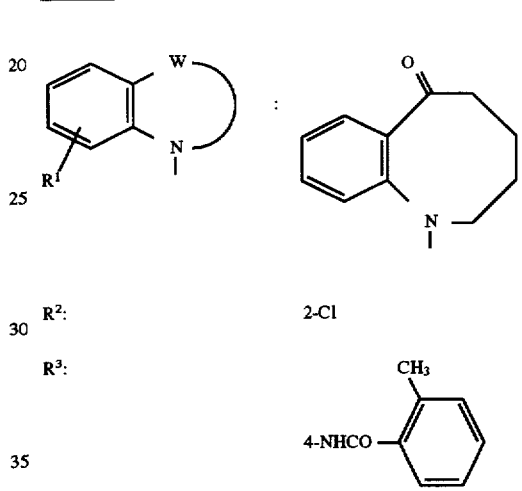 :

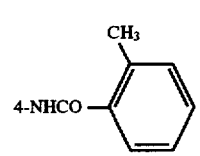

R²: 2-Cl

R³: 4-NHCO— (2-CH₃ phenyl)

Crystalline form: Colorless amorphous
NMR analysis: 220)
Form: Free

Example 1053

Structure

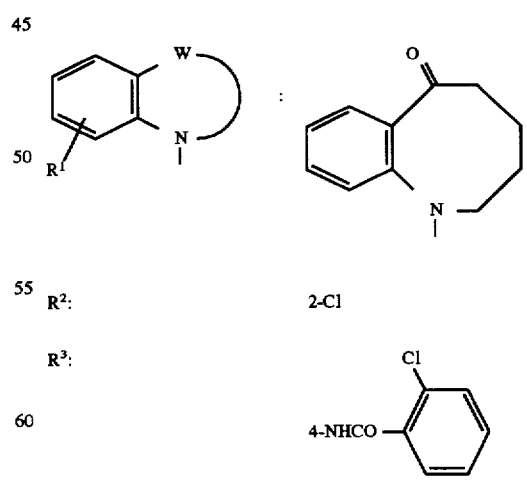 :

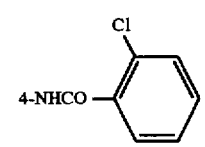

R²: 2-Cl

R³: 4-NHCO— (2-Cl phenyl)

Crystalline form: Colorless amorphous
NMR analysis: 221)
Form: Free

TABLE 8-continued

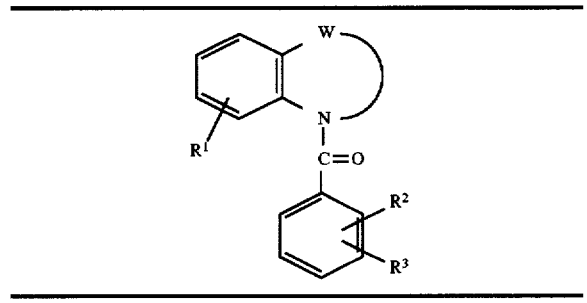

Example 1054

Structure

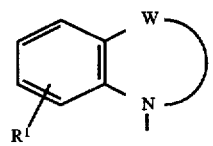 : 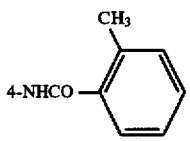

R²: 2-Cl

R³: 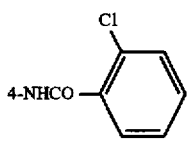

| | |
|---|---|
| Crystalline form: | Light yellow amorphous |
| NMR analysis: | 222) |
| Form: | Free |

Example 1055

Structure

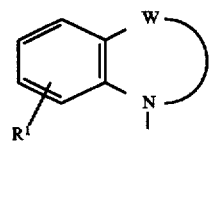 : 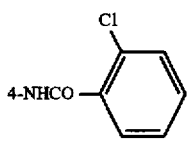

R²: 2-Cl

R³:

| | |
|---|---|
| Crystalline form: | Light yellow amorphous |
| NMR analysis: | 223) |
| Form: | Free |

TABLE 8-continued

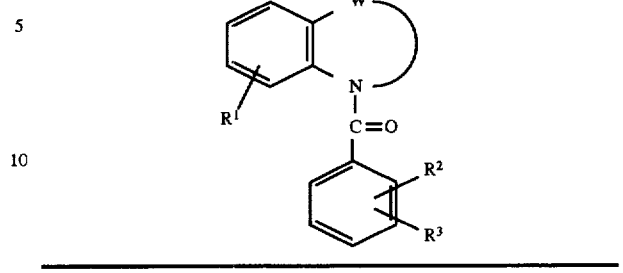

Example 1056

Structure

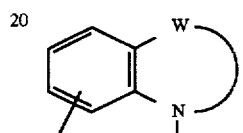 : 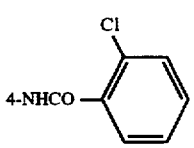

R²: 2-Cl

R³:

| | |
|---|---|
| Crystalline form: | White powder |
| Recrystallization solvent: | Diethyl ether/dichloromethane |
| Melting Point: | 169.5–173° C. |
| Form: | Free |

Example 1057

Structure

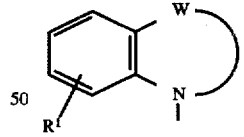 : 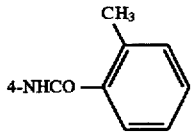

R²: 2-Cl

R³:

| | |
|---|---|
| Crystalline form: | Colorless amorphous |
| NMR analysis: | 224) |
| Form: | Free |

TABLE 8-continued

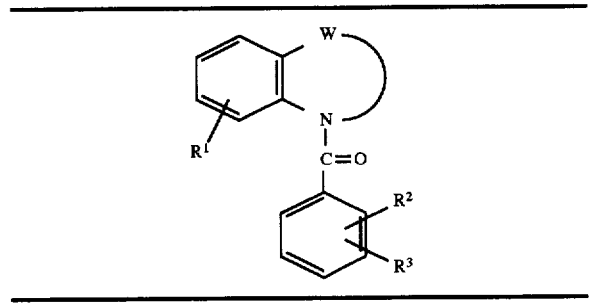

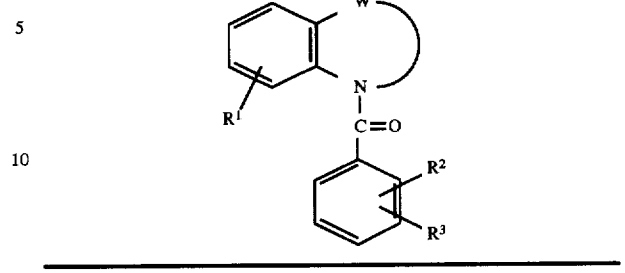

Example 1058

Structure

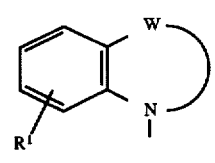 : 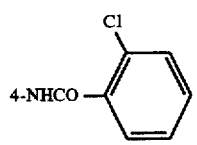

R²: 2-Cl

R³:

4-NHCO— 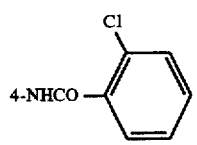

Example 1060

Structure

R²: 2-Cl

R³: 4-NHCO—(2-Cl phenyl)

Crystalline form: Colorless amorphous
NMR analysis: 225)

Example 1059

Structure

R²: 2-Cl

R³: 4-NHCO—(2-Cl phenyl)

Crystalline form: Colorless amorphous
NMR analysis: 226)
Form: Free

Crystalline form: Colorless amorphous
NMR analysis: 227)
Form: Free

Example 1061

Structure

R²: 2-Cl

R³: 4-NHCO—(2-Cl phenyl)

Crystalline form: Colorless amorphous
NMR analysis: 228)
Form: Free

TABLE 8-continued

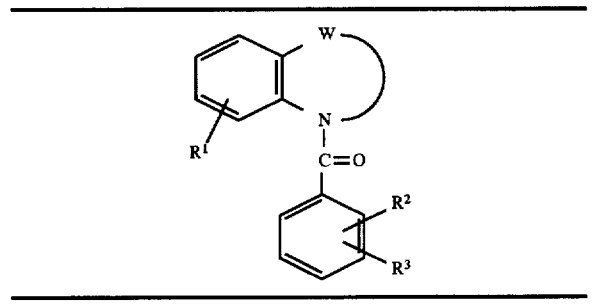

| | Example 1062 |
|---|---|
| Structure | 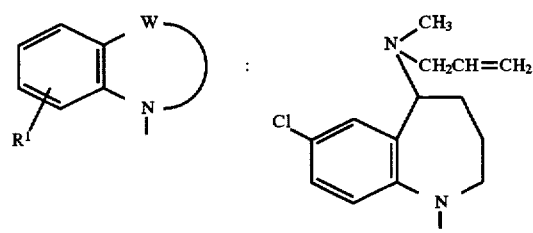 |
| $R^2$: | 2-Cl |
| $R^3$: | 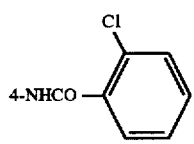 |
| Crystalline form: | Colorless amorphous |
| NMR analysis: | 229) |
| Form: | Free |

| | Example 1063 |
|---|---|
| Structure | 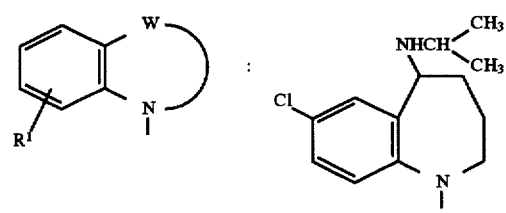 |
| $R^2$: | 2-Cl |
| $R^3$: | 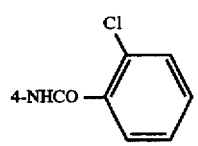 |
| Crystalline form: | Colorless amorphous |
| NMR analysis: | 230) |
| Form: | Free |

TABLE 8-continued

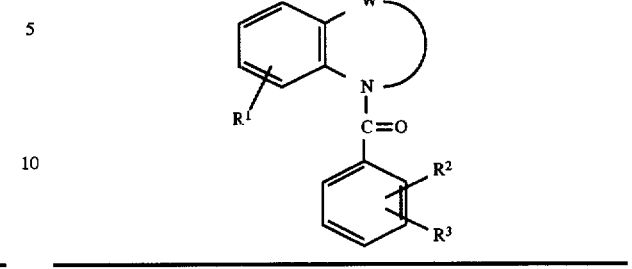

| | Example 1064 |
|---|---|
| Structure | 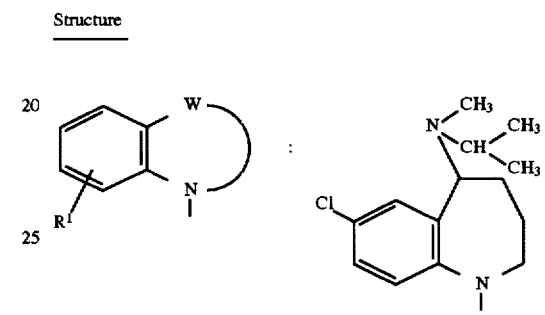 |
| $R^2$: | 2-Cl |
| $R^3$: | 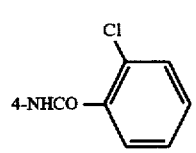 |
| Crystalline form: | Colorless amorphous |
| NMR analysis: | 231) |
| Form: | Free |

| | Example 1065 |
|---|---|
| Structure | 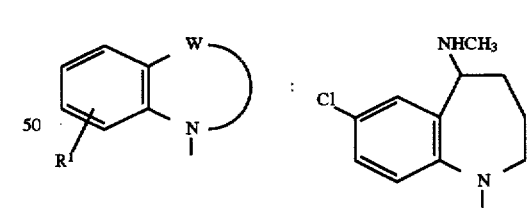 |
| $R^2$: | 2-Cl |
| $R^3$: | 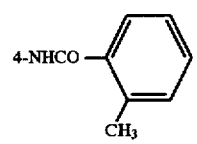 |
| Crystalline form: | Colorless amorphous |
| NMR analysis: | 232) |
| Form: | Free |

TABLE 8-continued

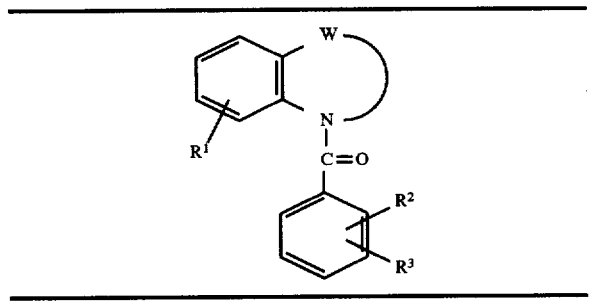

Example 1066

Structure

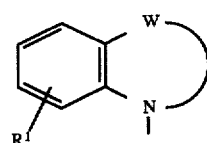 : 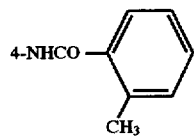

R²: 2-Cl

R³:

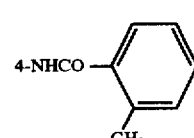

TABLE 8-continued

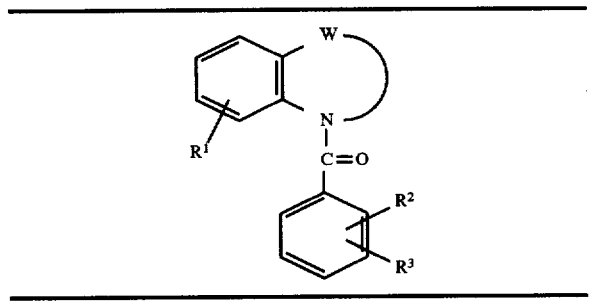

Example 1066

Structure

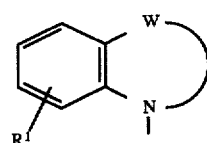 : 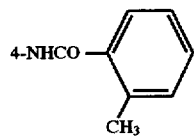

R²: 2-Cl

R³: 4-NHCO— (2-methylphenyl)

Crystalline form: Colorless amorphous
NMR analysis: 233)
Form: Free

Example 1067

Structure

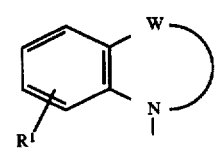 : 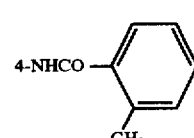

R²: 2-Cl

R³: 4-NHCO— (2-methylphenyl)

Crystalline form: Colorless amorphous
NMR analysis: 234)
Form: Free

TABLE 8-continued

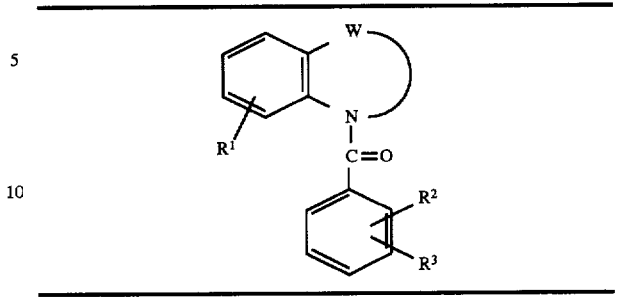

Example 1068

Structure

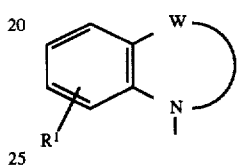 : 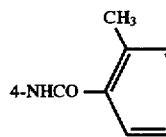

R²: 2-Cl

R³: 4-NHCO— (2-methylphenyl)

Crystalline form: Colorless amorphous
NMR analysis: 235)
Form: Free

Example 1069

Structure

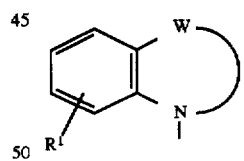 : 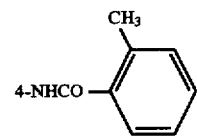

R²: 2-Cl

R³: 4-NHCO— (2-methylphenyl)

Crystalline form: Colorless amorphous
NMR analysis: 236)
Form: Free

TABLE 8-continued

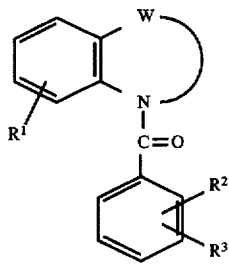

Example 1070

Structure

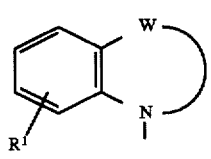  :  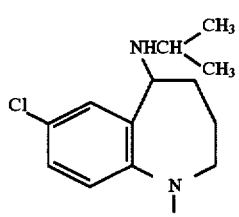

R²: 2-Cl

R³: 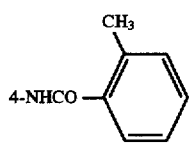
4-NHCO—⟨phenyl⟩—CH₃ (2-)

Crystalline form: Colorless amorphous
NMR analysis: 237)
Form: Free

196) ¹H-NMR (CDCl₃) δ; 2.14 (2H, brs), 2.33 (3H, s), 2.46 (3H, s), 2.85 (2H, t, J=6.1 Hz), 4.83 (2H, brs), 6.64 (1H, d, J=8.1 Hz), 7.07 (1H, d, J=8.0 Hz), 7.21–7.48 (8H, m), 7.65 (1H, m), 7.74 (1H, brs)

197) ¹H-NMR (CDCl₃) δ; 2.12 (2H, brs), 2.33 (3H, s), 2.85 (2H, t, J=6.2 Hz), 2.88–5.28 (2H, m), 6.63 (1H, d, J=8.1 Hz), 7.06 (1H, dd, J=1.7 Hz, 8.1 Hz), 7.19–7.69 (9H, m), 8.26 (1H, brs)

198) ¹H-NMR (CDCl₃) δ; 0.49 (4H, m), 1.25–5.13 (9H, m), 2.33 (3H, s), 2.45 (3H, s), 6.53 (1H, m), 6.79 (1H, m), 7.07–7.42 (9H, m), 7.73 (1H, m)

199) ¹H-NMR (CDCl₃) δ; 2.04 (2H, brs), 2.29 (3H, s), 2.82 (2H, t, J=5.9 Hz), 2.85–5.29 (2H, m), 6.82–7.69 (10H, m), 8.31 (1H, brs)

200) ¹H-NMR (CDCl₃) δ; 2.05 (2H, brs), 2.29 (3H, s), 2.44 (3H, s), 2.79 (2H, t, J=5.5 Hz), 2.82–5.28 (2H, m), 6.82–8.12 (11H, m)

201) ¹H-NMR (CDCl₃) δ; 1.40–4.85 (11H, m), 2.51 (3H, s), 6.78–7.63 (10H, m), 8.64 (1H, brs)

202) ¹H-NMR (CDCl₃) δ; 1.40–4.85 (11H, m), 2.45 (3H, s), 2.50 (3H, s), 6.78–7.55 (10H, m), 8.10 (1H, brs)

203) ¹H-NMR (CDCl₃) δ; 0.49 (4H, m), 1.25–4.85 (9H, m), 2.28 (3H, s), 6.77–7.62 (10H, m), 8.64 (1H, brs)

204) ¹H-NMR (CDCl₃) δ; 0.48 (4H, m), 1.26–4.85 (9H, m), 2.29 (3H, s), 2.44 (3H, s), 6.78–7.58 (10H, m), 8.18 (1H, brs)

205) ¹H-NMR (CDCl₃) δ; 1.14 (6H, d, J=6.3 Hz), 1.52–2.20 (7H, m), 2.20–2.60 (1H, m), 2.64–3.66 (10H, m), 4.00–4.50 (4H, m), 4.50–5.23 (2H, m), 6.57–7.90 (11H, m), 8.10–8.30 (1H, m), 9.97 (1H, s)

206) ¹H-NMR (CDCl₃) δ; 1.24–2.08 (4H, m), 2.08–2.26 (3H, m), 2.26–3.16 (4H, m), 3.47–4.03 (4H, m), 4.18–4.92 (1H, m), 6.40–7.94 (10H, m), 8.45–9.03 (1H, m)

207) ¹H-NMR (CDCl₃) δ; 1.26–2.10 (4H, m), 2.10–2.28 (3H, m), 2.28–3.20 (1H, m), 3.43–4.06 (4H, m), 4.20–4.93 (1H, m), 6.40–8.00 (10H, m), 8.78–9.30 (1H, m)

208) ¹H-NMR (CDCl₃) δ; 1.10–1.98 (4H, m), 1.98–3.10 (7H, m), 3.30–3.90 (4H, m), 3.90–5.10 (1H, m), 6.45–8.25 (12H, m)

209) ¹H-NMR (CDCl₃) δ; 1.06–1.94 (4H, m), 1.94–3.19 (10H, m), 3.19–3.90 (4H, m), 3.90–5.10 (1H, m), 6.44–8.60 (11H, m)

210) ¹H-NMR (CDCl₃) δ; 1.06–1.97 (4H, m), 1.97–3.20 (7H, m), 3.20–3.92 (4H, m), 3.92–5.10 (1H, m), 6.44–8.55 (11H, m)

211) ¹H-NMR (CDCl₃) δ; 1.07–1.98 (4H, m), 1.98–3.10 (10H, m), 3.37–5.20 (8H, m), 6.44–6.86 (3H, m), 6.97–7.60 (6H, m), 8.13 (1H, s), 8.19–8.38 (1H, m)

212) ¹H-NMR (CDCl₃) δ; 1.08–1.99 (4H, m), 1.99–3.13 (7H, m), 3.33–5.14 (8H, m), 6.40–6.90 (3H, m), 6.95–7.56 (5H, m), 7.63–7.87 (1H, m), 8.17–8.37 (1H, m), 8.60 (1H, s)

213) ¹H-NMR (CDCl₃) δ; 0.30–0.64 (4H, m), 0.70–3.42 (9H, m), 3.42–5.10 (5H, m), 6.40–8.70 (11H, m)

214) ¹H-NMR (CDCl₃) δ; 0.30–0.76 (4H, m), 0.80–3.43 (6H, m), 3.50–5.00 (5H, m), 6.40–9.04 (11H, m)

215) ¹H-NMR (CDCl₃) δ; 1.25–3.25 (14H, m), 3.55–5.06 (2H, m), 6.43–7.00 (2H, m), 7.00–7.71 (8H, m), 7.91–8.45 (1H, m)

216) ¹H-NMR (CDCl₃) δ; 1.11–3.20 (17H, m), 3.28–5.12 (2H, m), 6.41–7.01 (2H, m), 7.02–7.63 (8H, m), 7.76–8.21 (1H, m)

217) ¹H-NMR (CDCl₃) δ; 1.92–2.29 (2H, m), 2.36 (3H, s), 2.45 (3H, s), 2.84 (2H, t, J=6.3 Hz), 3.32–4.64 (2H, m), 6.40–8.10 (11H, m)

218) ¹H-NMR (CDCl₃) δ; 1.92–2.25 (2H, m), 2.34 (3H, s), 2.83 (2H, t, J=6.3 Hz), 3.21–4.52 (2H, m), 6.39–7.97 (10H, m), 8.43 (1H, brs)

219) ¹H-NMR (CDCl₃) δ; 1.7–2.15 (4H, m), 2.5–5.2 (4H, m), 6.75–6.9 (1H, m), 7.27–7.6 (9H, m), 7.65–7.85 (1H, m), 7.9–8.15 (2H, m)

220) ¹H-NMR (CDCl₃) δ; 1.65–2.1 (4H, m), 2.44 (3H, s), 2.8–4.5 (4H, m), 6.75–8.0 (12H, m)

221) ¹H-NMR (CDCl₃) δ; 1.65–2.3 (4H, m), 2.7–4.8 (4H, m), 6.75–8.4 (12H, m)

222) ¹H-NMR (CDCl₃) δ; 1.45–2.15 (4H, m), 2.45–2.55 (3H, m), 2.85–4.6 (4H, m), 6.8–8.25 (11H, m)

223) ¹H-NMR (CDCl₃) δ; 1.5–2.2 (4H, m), 2.8–4.7 (4H, m), 6.8–8.4 (11H, m)

224) ¹H-NMR (CDCl₃) δ; 1.75–2.25 (2H, m), 2.30–2.70 (3H, m), 2.70–2.95 (2H, m), 3.20–5.10 (2H, m), 6.70–8.40 (11H, m)

225) ¹H-NMR (CDCl₃) δ; 1.20–2.60 (8H, m), 2.60–5.10 (3H, m), 6.80–7.90 (10H, m), 8.20–8.60 (1H, m)

226) ¹H-NMR (CDCl₃) δ; 1.20–2.60 (10H, m), 2.60–5.10 (3H, m), 6.80–8.15 (11H, m)

227) ¹H-NMR (CDCl₃) δ; 0.30–0.70 (4H, m), 1.20–2.45 (6H, m), 2.60–5.10 (3H, m), 6.80–7.95 (10H, m), 8.15–8.50 (1H, m)

228) ¹H-NMR (CDCl₃) δ; 1.20–2.40 (5H, m), 2.60–5.35 (7H, m), 5.80–6.15 (1H, m), 6.75–7.95 (10H, m), 8.20–8.70 (1H, m)

229) ¹H-NMR (CDCl₃) δ; 1.20–2.55 (7H, m), 2.60–5.35 (7H, m), 5.85–6.05 (1H, m), 6.70–7.10 (2H, m), 7.10–7.90 (8H, m), 8.15–8.60 (1H, m)

230) ¹H-NMR (CDCl₃) δ; 1.00–1.20 (6H, m), 1.00–2.40 (5H, m), 2.60–5.10 (4H, m), 6.80–8.00 (10H, m), 8.15–8.65 (1H, m)

231) ¹H-NMR (CDCl₃) δ; 0.80–2.50 (13H, m), 2.60–5.10 (4H, m), 6.70–8.85 (10H, m), 8.25–8.60 (1H, m)

232) ¹H-NMR (CDCl₃) δ; 1.30–2.60 (11H, m), 2.60–5.10 (3H, m), 6.80–8.15 (11H, m)

233) ¹H-NMR (CDCl₃) δ; 1.10–2.50 (13H, m), 2.50–5.10 (3H, m), 6.75–8.40 (11H, m)

234) ¹H-NMR (CDCl₃) δ; 0.30–0.65 (4H, m), 1.20–2.30 (6H, m), 2.35–2.55 (3H, m), 2.60–5.10 (3H, m), 6.75–8.35 (11H, m)

235) ¹H-NMR (CDCl₃) δ; 1.20–2.60 (8H, m), 2.60–5.40 (7H, m), 5.80–6.15 (1H, m), 6.80–8.20 (11H, m)

236) ¹H-NMR (CDCl₃) δ; 1.25–2.60 (10H, m), 2.60–5.40 (7H, m), 5.75–6.10 (1H, m), 6.75–7.10 (2H, m), 7.10–8.40 (9H, m)

237) ¹H-NMR (CDCl₃) δ; 0.95–1.20 (6H, m), 0.95–2.25 (5H, m), 2.40–2.60 (3H, m), 2.60–5.10 (4H, m), 6.75–7.05 (2H, m), 7.10–8.30 (9H, m)

REFERENCE EXAMPLE 22

Using the suitable starting materials, the following compounds are obtained in the same manner as in Reference Example 1.

8-Chloro-6-oxo-1-(4-nitrobenzoyl)-1,2,3,4,5,6-hexahydrobenzazocine, yellow prisms ¹H-NMR (DMSO-d₆) δ; 1.3–2.2 (4H, m), 2.6–5.0 (4H, m), 7.05–8.5 (7H, m)

5-Oxo-7-methyl-1-(2-chloro-4-nitrobenzoyl)-2,3,4,5-tetrahydro-1H-benzazepine, light yellow amorphous ¹H-NMR (CDCl₃) δ; 1.71–2.32 (2H, m), 2.29 (3H, s), 2.86 (2H, t, J=6.3 Hz), 3.10–5.30 (2H, m), 6.84–8.38 (6H, m)

5-Oxo-7-methyl-1-(3-methoxy-4-nitrobenzoyl)- 2,3,4,5-tetrahydro-1H-benzazepine, light yellow amorphous ¹H-NMR (CDCl₃) δ; 2.17 (2H, brs), 2.34 (3H, s), 2.84 (2H, t, J=6.0 Hz), 3.10–5.29 (2H, m), 3.77 (3H, s), 6.67 (1H, d, J=7.9 Hz), 6.85 (2H, m), 7.10 (1H, d, J=8.0 Hz), 7.57–7.65 (2H, m)

5-Oxo-7-dimethylamino-1-(2-chloro-4-nitrobenzoyl)-2,3,4,5-tetrahydro-1H-benzazepine, yellow powder ¹H-NMR (CDCl₃) δ; 1.66–2.38 (2H, m), 2.65–2.88 (2H, m), 2.92 (6H, s), 3.08–3.64, 4.58–5.01 (total 2H, m), 6.49 (1H, dd, J=3.1, 8.7 Hz), 6.82 (1H, d, J=8.7 Hz), 6.90 (1H, d, J=3.1 Hz), 7.02–7.37 (1H, m), 7.94 (1H, dd, J=1.9, 8.4 Hz), 8.08 (1H, d, J=1.9 Hz)

REFERENCE EXAMPLE 23

Using the suitable starting materials, the following compounds are obtained in the same manner as in Reference Example 2.

8-Chloro-6-oxo-1-(4-aminobenzoyl)-1,2,3,4,5,6-hexahydrobenzazocine, light yellow amorphous ¹H-NMR (CDCl₃) δ; 1.7–2.2 (4H, m), 2.3–4.8 (6H, m), 6.4–6.6 (2H, m), 6.74 (1H, d, J=8.5 Hz), 7.1–7.4 (3H, m), 7.99 (1H, d, J=2.6 Hz)

8-Methyl-6-oxo-(2-chloro-4-aminobenzoyl)-1,2,3,4,5,6-hexahydrobenzazocine, colorless amorphous ¹H-NMR (CDCl₃) δ; 1.4–2.1 (4H, m), 2.15–2.6 (3H, m), 2.7–4.4 (6H, m), 6.15–6.35 (1H, m), 6.51 (1H, s), 6.6–6.85 (1H, m), 6.9–7.25 (2H, m), 7.72 (1H, s)

8-Methoxy-6-oxo-(2-chloro-4-aminobenzoyl)-1,2,3,4,5,6-hexahydrobenzazocine, light yellow amorphous ¹H-NMR (CDCl₃) δ; 1.4–2.2 (4H, m), 2.7–5.0 (9H, m), 6.25 (1H, dd, J=8.3 Hz, 2.2 Hz), 6.51 (1H, d, J=2.2 Hz), 6.66 (1H, d, J=8.3 Hz), 6.88 (1H, dd, J=8.6 Hz, 3.0 Hz), 7.23 (1H, d, J=8.6 Hz), 7.43 (1H, d, J=3.0 Hz)

5-Oxo-7-chloro-1-(2-methoxy-4-aminobenzoyl)-2,3,4,5-tetrahydro-1H-benzazepine, colorless particles (recrystallized from methanol/diethyl ether), m.p. 206°–208° C.

5-Oxo-7-methyl-1-(2-chloro-4-aminobenzoyl)-2,3,4,5-tetrahydro-1H-benzazepine, light yellow amorphous ¹H-NMR (CDCl₃) δ; 2.09 (2H, brs), 2.29 (3H, s), 3.10–5.00 (2H, m), 3.78 (2H, brs), 6.34–7.54 (6H, m)

5-Oxo-7-methyl-1-(3-methoxy-4-aminobenzoyl)-2,3,4,5-tetrahydro-1H-benzazepine, light yellow amorphous ¹H-NMR (CDCl₃) δ; 2.12 (2H, brs), 2.32 (3H, s), 2.85 (2H, t, J=5.9 Hz), 3.30–5.00 (2H, m), 3.65 (3H, s), 3.98 (2H, brs), 6.40 (1H, d, J=8.1 Hz), 6.64–6.76 (3H, m), 7.06 (1H, dd, J=1.6, 8.1 Hz), 7.63 (1H, d, J=2.0 Hz)

5-Oxo-7-dimethylamino-1-(2-chloro-4-aminobenzoyl)-2,3,4,5-tetrahydro-1H-benzazepine, yellow amorphous ¹H-NMR (CDCl₃) δ; 1.60–2.32 (2H, m), 2.67–5.13 (4H, m), 2.92 (6H, s), 3.75 (2H, s), 6.31 (1H, dd, J=2.1, 8.3 Hz), 6.46 (1H, d, J=2.1 Hz), 6.48 (1H, dd, J=3.1, 8.7 Hz), 6.66–6.89 (2H, m), 6.95 (1H, d, J=3.1 Hz)

Using the suitable starting materials, the compounds of the following Table 9 are obtained in the same manner as in above Examples 1 and 382.

TABLE 9

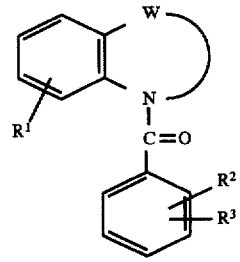

| | Example 1071 |
|---|---|
| Structure | 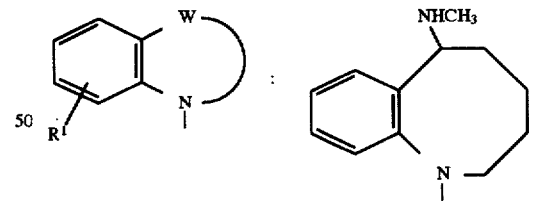 |
| R²: | 2-Cl |
| R³: | 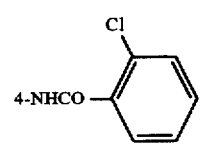 |
| Crystalline form: | Colorless prisms |
| Recrystallization solvent: | Ethanol |
| Melting Point: | 227–230° C. |
| Form: | Free |

TABLE 9-continued

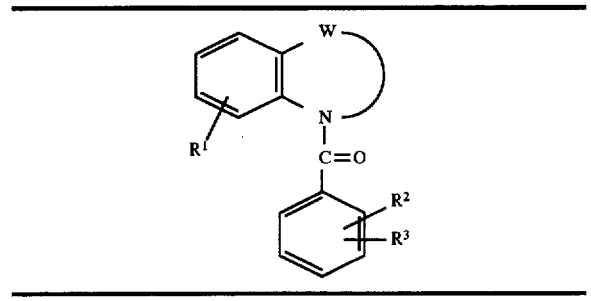

Example 1072

Structure

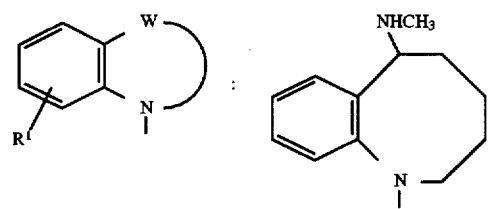

| | |
|---|---|
| R²: | 2-Cl |
| R³: | 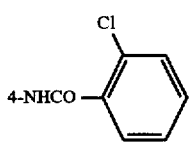 |
| | 4-NHCO— |
| Crystalline form: | Colorless needles |
| Recrystallization solvent: | Ethanol/petroleum ether |
| Melting Point: | 216–218° C. |
| Form: | Free |

Example 1073

Structure

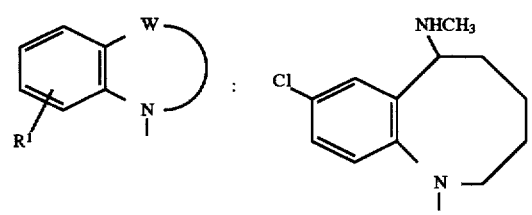

| | |
|---|---|
| R²: | 2-Cl |
| R³: | 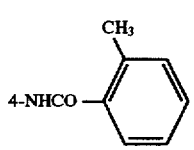 |
| | 4-NHCO— |
| Crystalline form: | Colorless prisms |
| Recrystallization solvent: | Ethyl acetate/n-hexane |
| Melting Point: | 227–228° C. |
| Form: | Free |

TABLE 9-continued

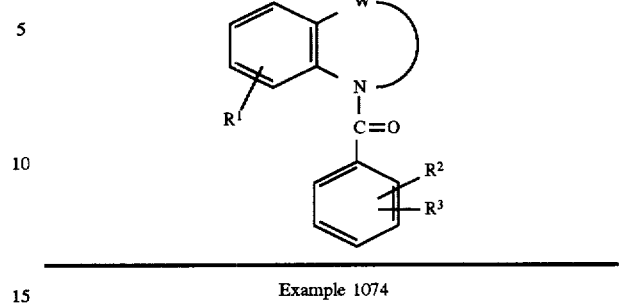

Example 1074

Structure

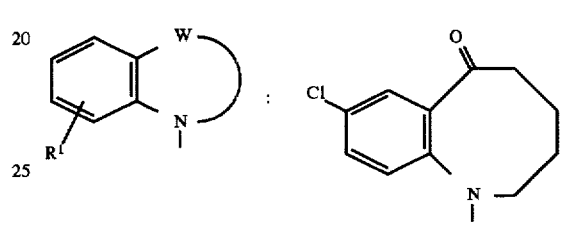

| | |
|---|---|
| R²: | H |
| R³: | 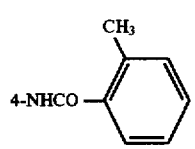 |
| | 4-NHCO— |
| Crystalline form: | White powder |
| NMR analysis: | 238) |
| Form: | Free |

Example 1075

Structure

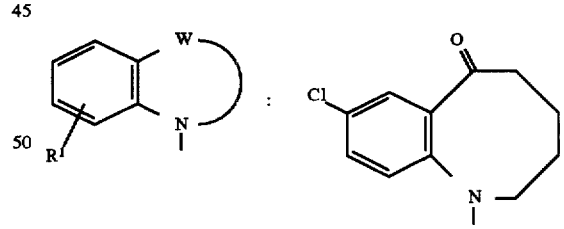

| | |
|---|---|
| R²: | H |
| R³: | 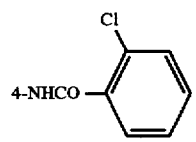 |
| | 4-NHCO— |
| Crystalline form: | White powder |
| NMR analysis: | 239) |
| Form: | Free |

TABLE 9-continued

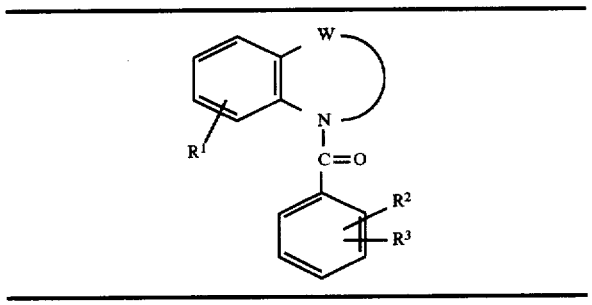

Example 1076

Structure

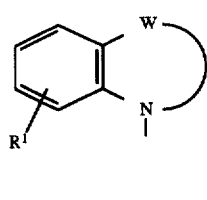  :  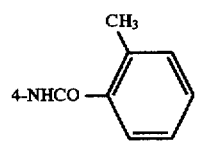

R²:  2-Cl

R³:
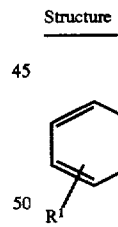

Crystalline form:  Light yellow amorphous
NMR analysis:  240)
Form:  Free

Example 1077

Structure

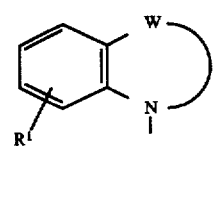  :  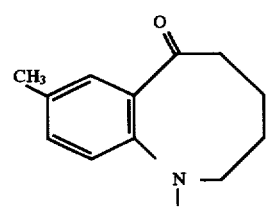

R²:  2-Cl

R³:
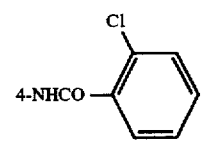

Crystalline form:  Light yellow amorphous
NMR analysis:  241)
Form:  Free

TABLE 9-continued

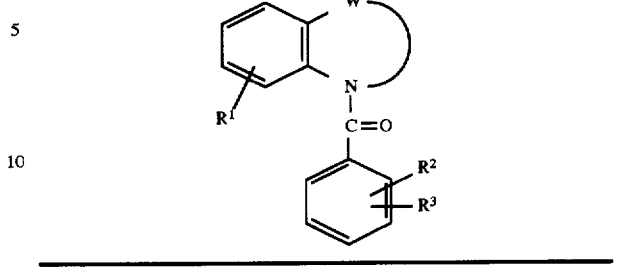

Example 1078

Structure

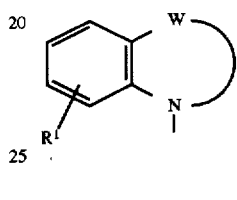  :  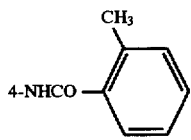

R²:  2-Cl

R³:
4-NHCO—⟨phenyl with CH₃⟩

Crystalline form:  Colorless amorphous
NMR analysis:  242)
Form:  Free

Example 1079

Structure

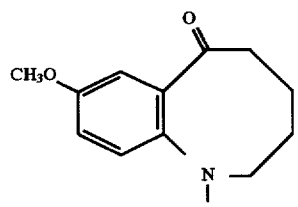  :  (ketone-methoxy benzazocine)

R²:  2-Cl

R³:
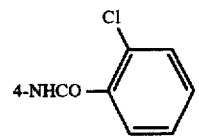

Crystalline form:  Colorless amorphous
NMR analysis:  243)
Form:  Free

TABLE 9-continued

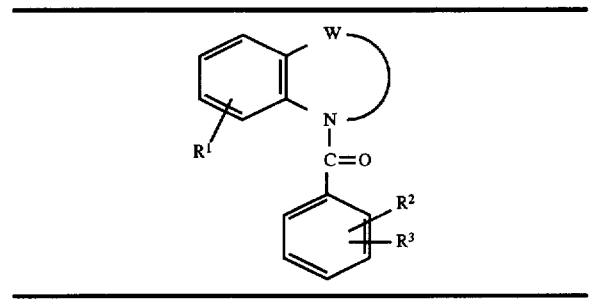

Example 1080

Structure

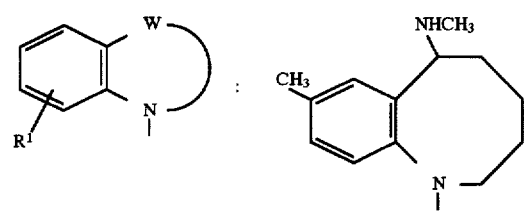

| | |
|---|---|
| R²: | 2-Cl |
| R³: | 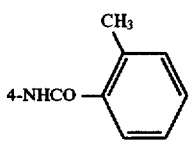 |
| Crystalline form: | Light yellow powder |
| Recrystallization solvent: | Ethyl acetate/diethyl ether |
| Melting Point: | 179–181° C. |
| Form: | Free |

Example 1081

Structure

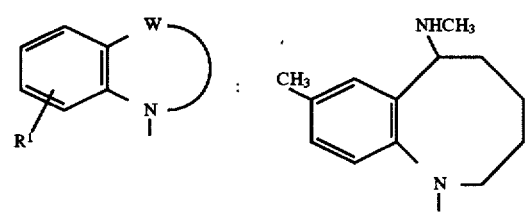

| | |
|---|---|
| R²: | 2-Cl |
| R³: | 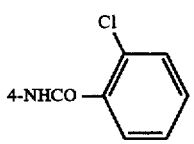 |
| Crystalline form: | White powder |
| Recrystallization solvent: | Ethyl acetate/diethyl ether |
| Melting Point: | 213–216° C. |
| Form: | Free |

TABLE 9-continued

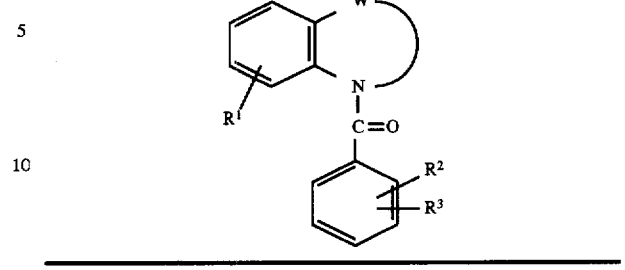

Example 1082

Structure

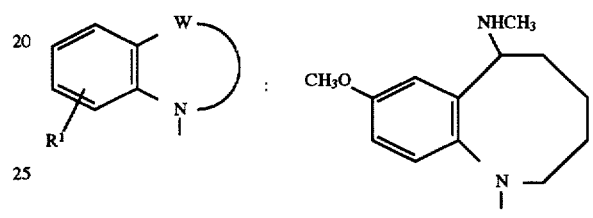

| | |
|---|---|
| R²: | 2-Cl |
| R³: | 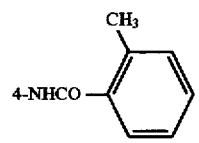 |
| Crystalline form: | Light yellow powder |
| Recrystallization solvent: | Ethyl acetate/diethyl ether |
| Melting Point: | 185–187° C. |
| Form: | Free |

Example 1083

Structure

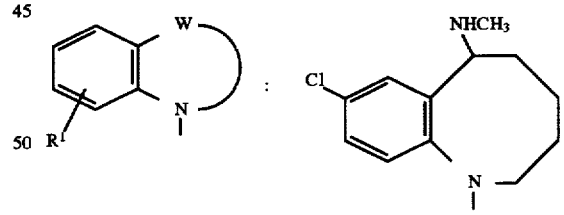

| | |
|---|---|
| R²: | H |
| R³: | 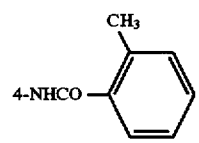 |
| Crystalline form: | Colorless prisms |
| Recrystallization solvent: | Ethanol |
| Melting Point: | 249–251° C. |
| Form: | Free |

TABLE 9-continued

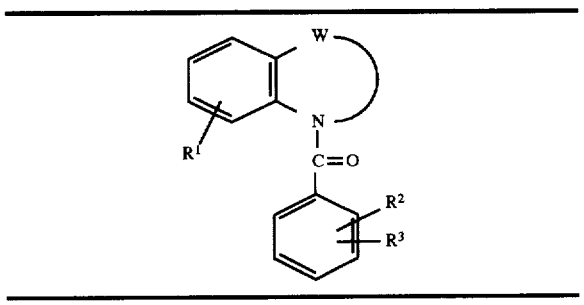

| | Example 1084 |
|---|---|
| Structure | 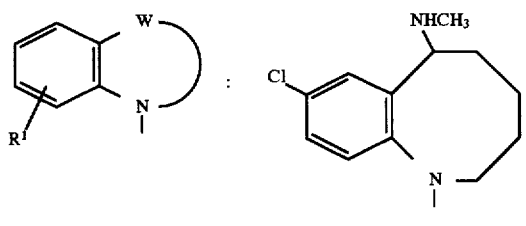 |
| R²: | H |
| R³: | 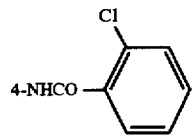 4-NHCO—⟨Cl⟩ |
| Crystalline form: | Colorless needles |
| Recrystallization solvent: | Ethanol |
| Melting Point: | 239–241° C. |
| Form: | Free |

| | Example 1085 |
|---|---|
| Structure | 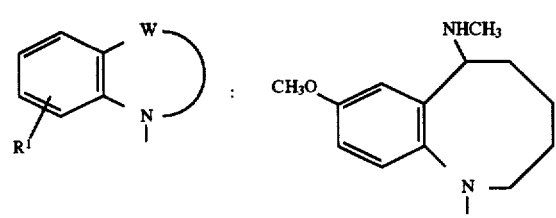 |
| R²: | 2-Cl |
| R³: | 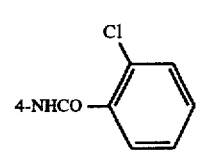 4-NHCO—⟨Cl⟩ |
| Crystalline form: | White powder |
| Recrystallization solvent: | Ethyl acetate/diethyl ether |
| Melting Point: | 208–210° C. |
| Form: | Free |

TABLE 9-continued

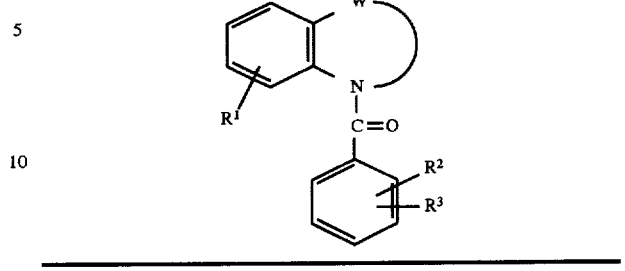

| | Example 1086 |
|---|---|
| Structure | 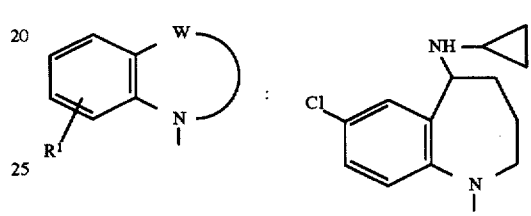 |
| R²: | 2-CH₃ |
| R³: | 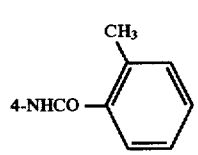 4-NHCO—⟨CH₃⟩ |
| Crystalline form: | White powder |
| Recrystallization solvent: | Methanol/n-hexane |
| Melting Point: | 178–180.5° C. |
| Form: | Free |

| | Example 1087 |
|---|---|
| Structure | 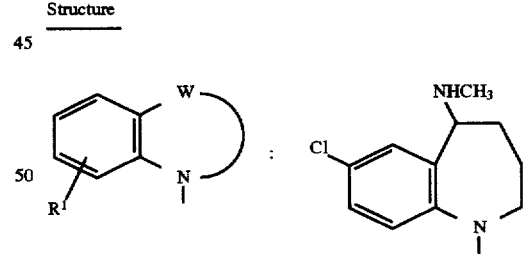 |
| R²: | 2-CH₃ |
| R³: | 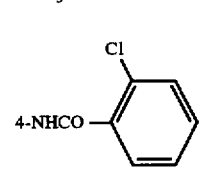 4-NHCO—⟨Cl⟩ |
| Crystalline form: | Colorless amorphous |
| NMR analysis: | 244) |
| Form: | Free |

TABLE 9-continued

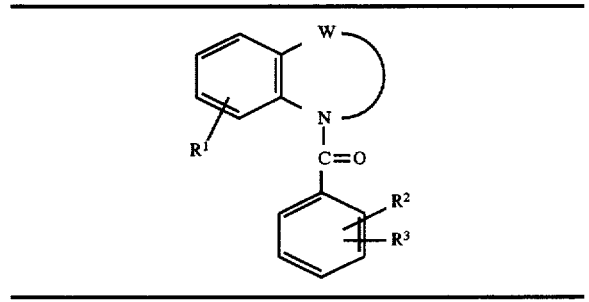

Example 1088

Structure

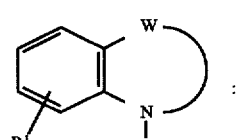 : 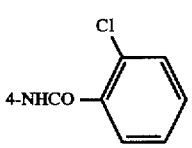

R²: 2-CH₃

R³:

4-NHCO— (2-Cl-phenyl)

Crystalline form: Colorless amorphous
NMR analysis: 245)
Form: Free

Example 1089

Structure

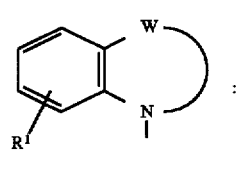 : (chlorobenzazepinone structure)

R²: 2-OCH₃

R³:

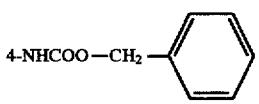
4-NHCOO—CH₂—phenyl

Crystalline form: White powder
Recrystallization solvent: Methanol/diethyl ether
NMR analysis: 246)
Form: Free TABLE 9-continued

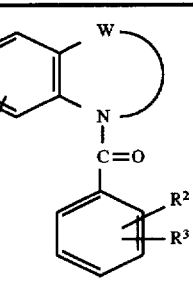

Example 1090

Structure

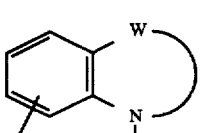 : 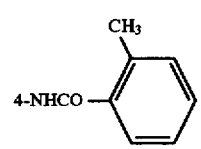

R²: 2-OCH₃

R³:

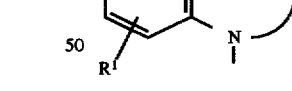
4-NHCO— (2-methylphenyl)

Crystalline form:
NMR analysis: 247)
Form: Free

Example 1091

Structure (benzazepine W structure) : (chlorobenzazepinone structure)

R²: 2-OCH₃

R³:

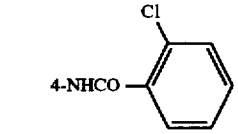
4-NHCO— (2-Cl-phenyl)

Crystalline form: Colorless amorphous
NMR analysis: 248)
Form: Free

TABLE 9-continued

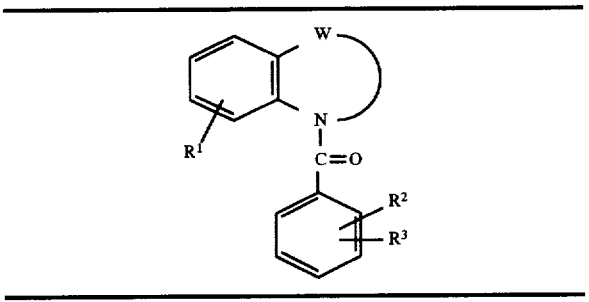

Example 1092

Structure

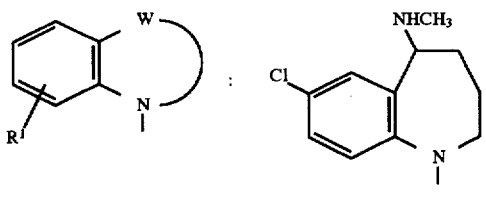

R²: 2-OCH₃

R³: 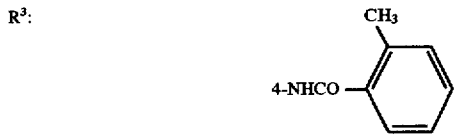
4-NHCO—⟨phenyl⟩—CH₃

Crystalline form: Colorless amorphous
NMR analysis: 249)
Form: Free

Example 1093

Structure

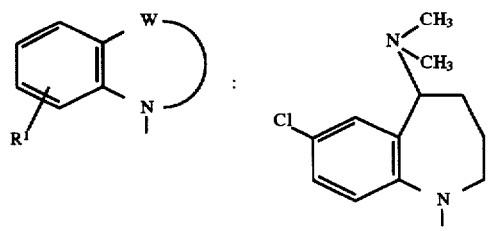

R²: 2-OCH₃

R³: 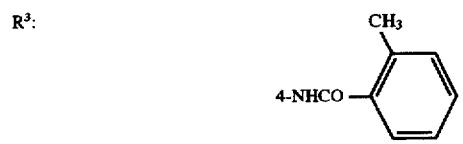
4-NHCO—⟨phenyl⟩—CH₃

Crystalline form: White powder
Recrystallization solvent: Methanol/diethyl ether
Melting Point: 205–206° C.
Form: Free TABLE 9-continued

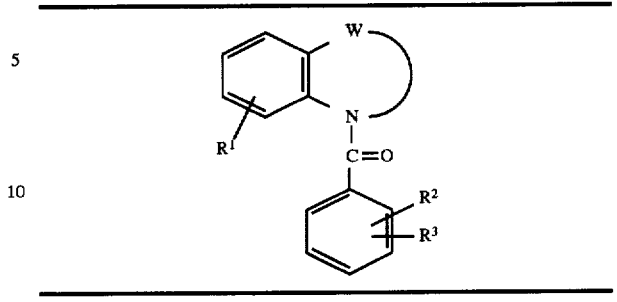

Example 1094

Structure

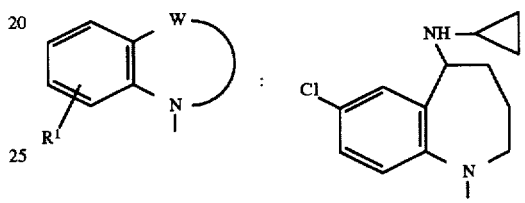

R²: 2-OCH₃

R³: 
4-NHCO—⟨phenyl⟩—CH₃

Crystalline form: Colorless amorphous
NMR analysis: 250)
Form: Free

Example 1095

Structure

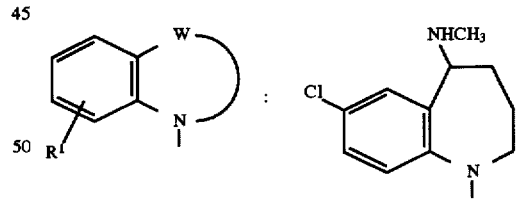

R²: 2-OCH₃

R³: 
4-NHCO—⟨phenyl⟩—Cl

Crystalline form: White powder
Recrystallization solvent: Methanol/n-hexane
Melting Point: 172.5–174° C.
Form: Free TABLE 9-continued

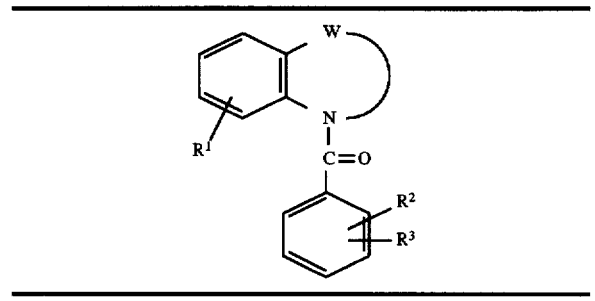

Example 1096

Structure

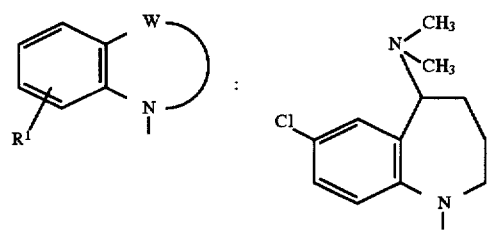

| R²: | 2-OCH₃ |
| R³: | 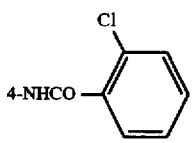 4-NHCO- (2-Cl phenyl) |

| Crystalline form: | White powder |
| Recrystallization solvent: | Methanol/diethyl ether |
| Melting Point: | 215–216.5° C. |
| Form: | Free |

Example 1097

Structure

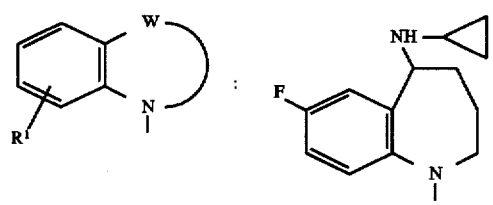

| R²: | H |
| R³: | 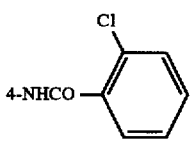 4-NHCO- (2-Cl phenyl) |

| Crystalline form: | White powder |
| Recrystallization solvent: | Methanol/diethyl ether |
| Melting Point: | 133–136° C. |
| Form: | Free |

TABLE 9-continued

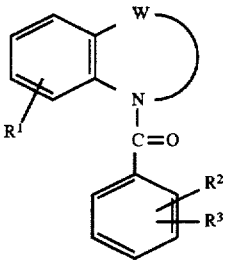

Example 1098

Structure

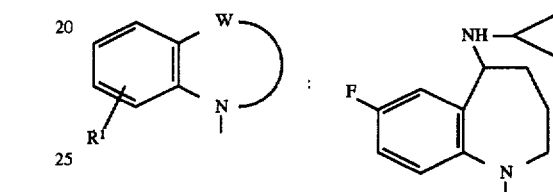

| R²: | 2-Cl |
| R³: | 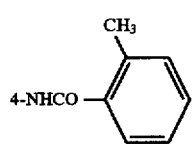 4-NHCO- (2-CH₃ phenyl) |

| Crystalline form: | Colorless amorphous |
| NMR analysis: | 251) |
| Form: | Free |

Example 1099

Structure

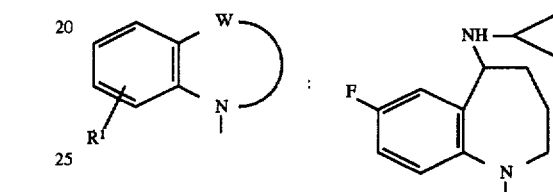

| R²: | 2-Cl |
| R³: | 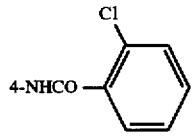 4-NHCO- (2-Cl phenyl) |

| Crystalline form: | White powder |
| Recrystallization solvent: | Methanol/n-hexane |
| Melting Point: | 179–180° C. |
| Form: | Free |

TABLE 9-continued

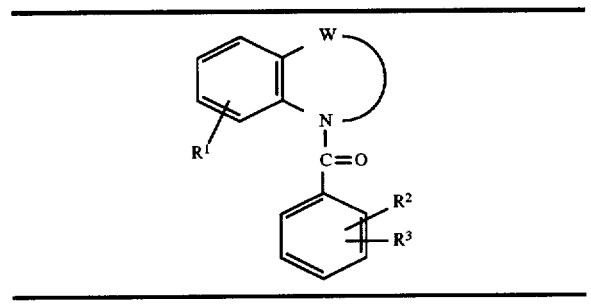

Example 1100

Structure

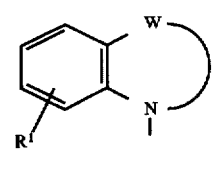 : 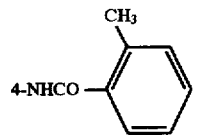

R²: 3-OCH₃

R³: 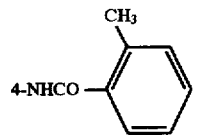
4-NHCO— (2-methylphenyl)

| | |
|---|---|
| Crystalline form: | White powder |
| Recrystallization solvent: | Methanol/n-hexane |
| Melting Point: | 167.5–169.5° C. |
| Form: | Free |

Example 1101

Structure

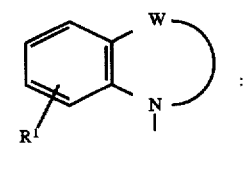 : 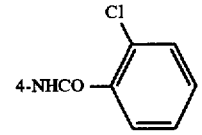

R²: 3-OCH₃

R³: 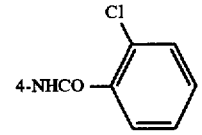
4-NHCO— (2-chlorophenyl)

| | |
|---|---|
| Crystalline form: | White powder |
| Recrystallization solvent: | Methanol/diethyl ether |
| Melting Point: | 176–178° C. |
| Form: | Free |

TABLE 9-continued

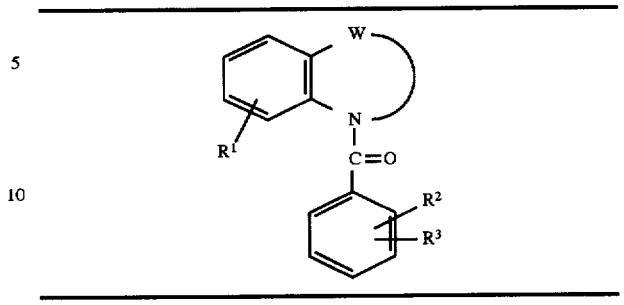

Example 1102

Structure

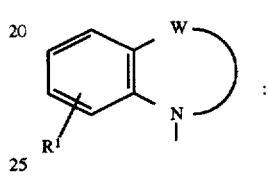 : 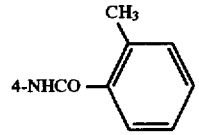

R²: 2-OCH₃

R³: 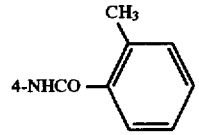
4-NHCO— (2-methylphenyl)

| | |
|---|---|
| Crystalline form: | Colorless amorphous |
| NMR analysis: | 252) |
| Form: | Free |

Example 1103

Structure

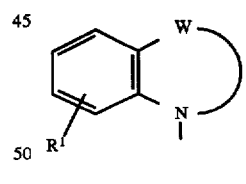 : 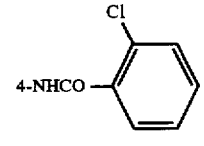

R²: 2-OCH₃

R³: 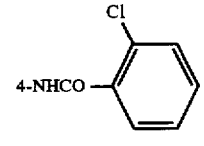
4-NHCO— (2-chlorophenyl)

| | |
|---|---|
| Crystalline form: | White powder |
| Recrystallization solvent: | Methanol/diethyl ether |
| Melting Point: | 185–188° C. |
| Form: | Free |

TABLE 9-continued

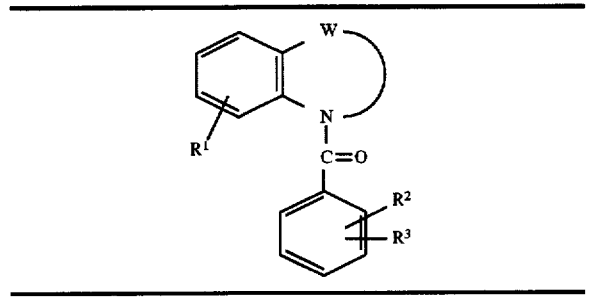

Example 1104

Structure

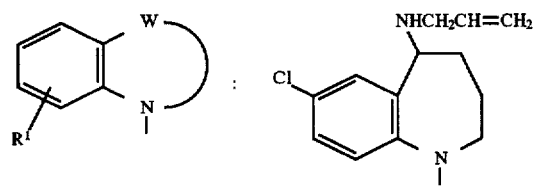

R²: H

R³:

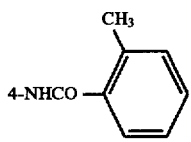

Crystalline form: White powder
Recrystallization solvent: Methanol/diethyl ether
Melting Point: 180–181.5° C.
Form: Free Example 1105

Structure

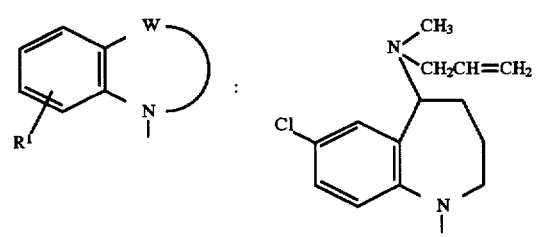

R²: H

R³:

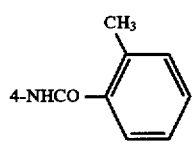

Crystalline form: White powder
Recrystallization solvent: Methanol/diethyl ether
Melting Point: 181–184° C.
Form: Free TABLE 9-continued

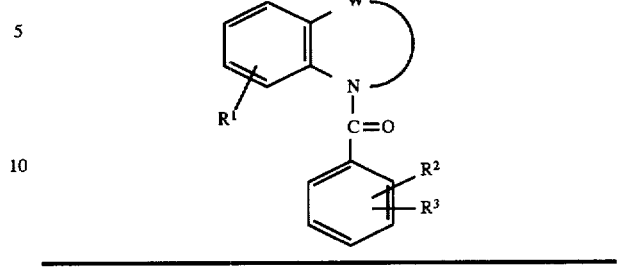

Example 1106

Structure

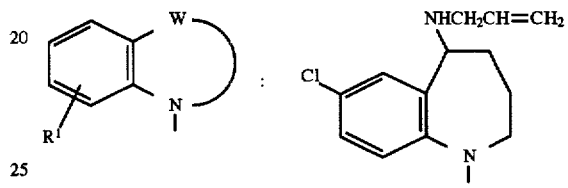

R²: H

R³:

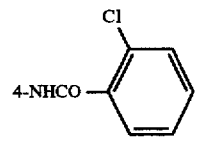

Crystalline form: White powder
Recrystallization solvent: Methanol/diethyl ether
Melting Point: 186.5–187° C.
Form: Free Example 1107

Structure

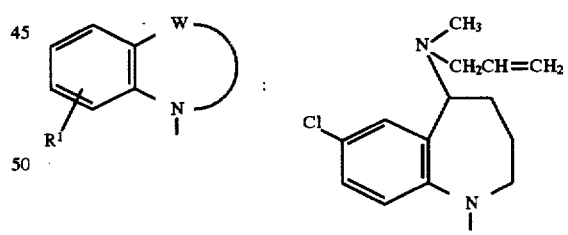

R²: H

R³:

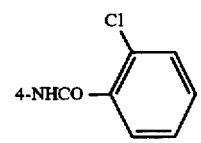

Crystalline form: White powder
Recrystallization solvent: Methanol/diethyl ether
Melting Point: 183–184° C.
Form: Free

TABLE 9-continued

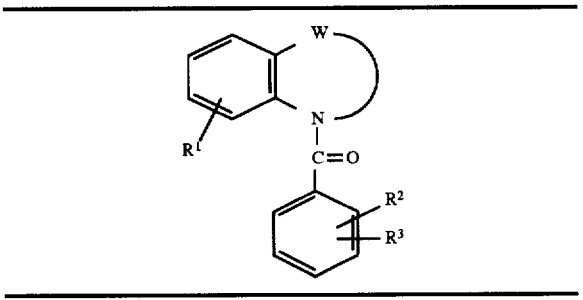

Example 1108

Structure

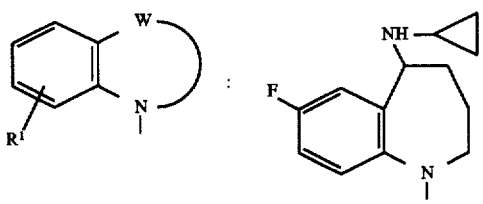

R²: H

R³: 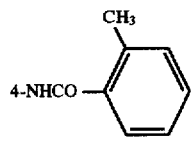
4-NHCO— (2-CH₃-phenyl)

| | |
|---|---|
| Crystalline form: | White powder |
| Recrystallization solvent: | Methanol/diethyl ether |
| Melting Point: | 151–153° C. |
| Form: | Free |

Example 1109

Structure

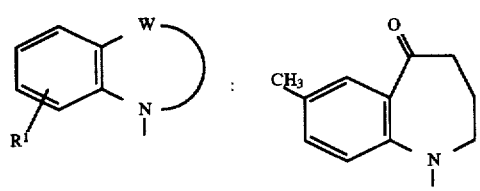

R²: 3-OCH₃

R³: 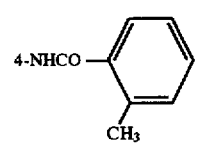
4-NHCO— (2-CH₃-phenyl)

| | |
|---|---|
| Crystalline form: | Colorless amorphous |
| NMR analysis: | 253) |
| Form: | Free |

TABLE 9-continued

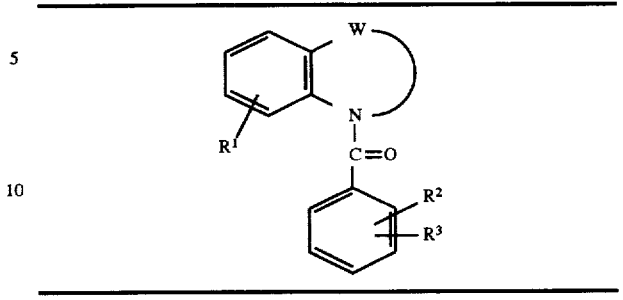

Example 1110

Structure

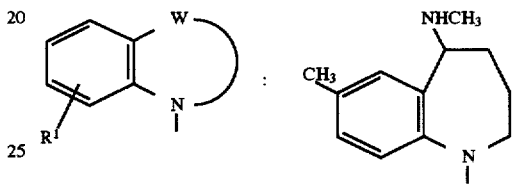

R²: H

R³: 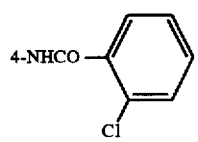
4-NHCO— (2-Cl-phenyl)

| | |
|---|---|
| Crystalline form: | Colorless amorphous |
| NMR analysis: | 254) |
| Form: | Free |

Example 1111

Structure

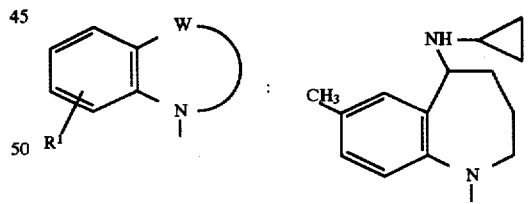

R²: H

R³: 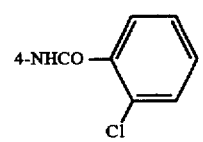
4-NHCO— (2-Cl-phenyl)

| | |
|---|---|
| Crystalline form: | White needles |
| Recrystallization solvent: | Ethanol/n-hexane |
| Melting Point: | 191–195° C. |
| Form: | Free |

TABLE 9-continued

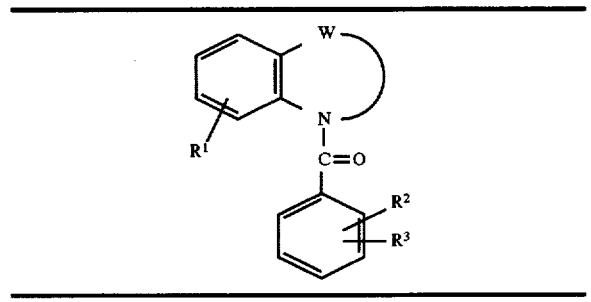

Example 1112

Structure

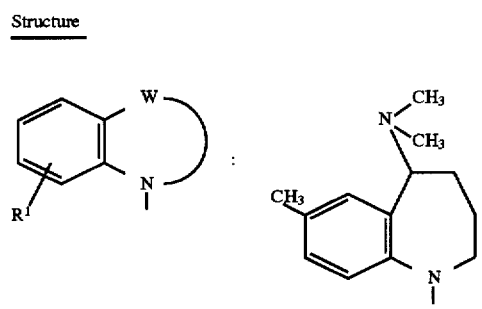

| | |
|---|---|
| R²: | H |
| R³: | 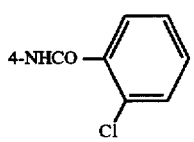 4-NHCO-Cl |
| Crystalline form: | White powder |
| Recrystallization solvent: | Diethyl ether/n-hexane |
| Melting Point: | 227–230° C. |
| Form: | Free |

Example 1113

Structure

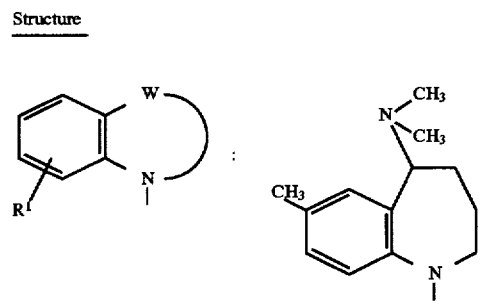

| | |
|---|---|
| R²: | 2-Cl |
| R³: | 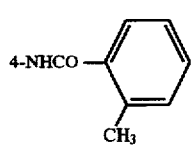 4-NHCO-CH₃ |
| Crystalline form: | Colorless amorphous |
| NMR analysis: | 289) |
| Form: | Free |

TABLE 9-continued

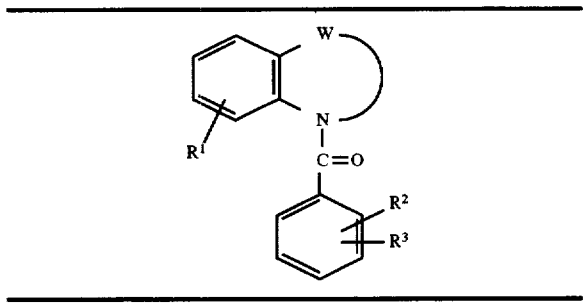

Example 1114

Structure

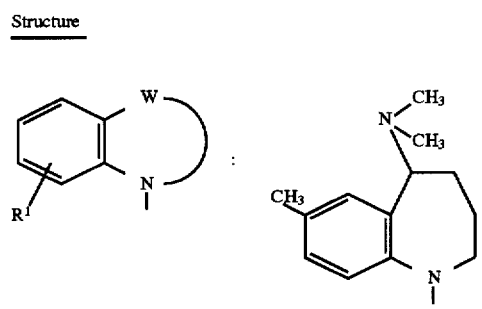

| | |
|---|---|
| R²: | 2-Cl |
| R³: | 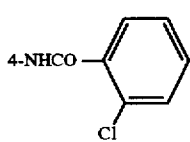 4-NHCO-Cl |
| Crystalline form: | Light yellow amorphous |
| NMR analysis: | 255) |

Example 1115

Structure

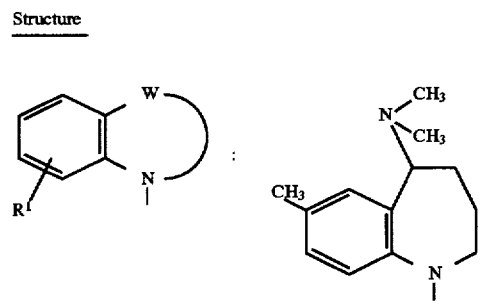

| | |
|---|---|
| R²: | 3-OCH₃ |
| R³: | 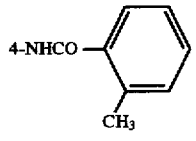 4-NHCO-CH₃ |
| Crystalline form: | White powder |
| Recrystallization solvent: | Diethyl ether/n-hexane |
| Melting Point: | 172–174° C. |
| Form: | Free |

TABLE 9-continued

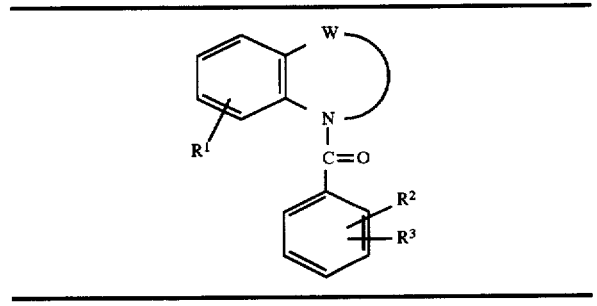

Example 1116

Structure

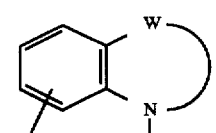 : 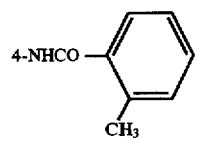

R²:  3-OCH₃

R³:

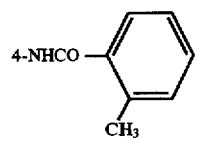
4-NHCO— (phenyl with 2-CH₃)

Crystalline form:  Colorless amorphous
NMR analysis:  305)
Form:  Free

Example 1117

Structure

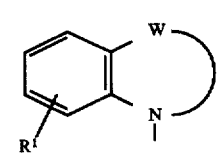 : 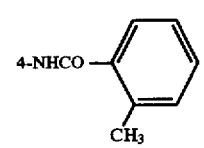

R²:  2-CH₃

R³:  4-NHCO—(phenyl with 2-CH₃)

Crystalline form:  Colorless amorphous
NMR analysis:  290)
Form:  Free

TABLE 9-continued

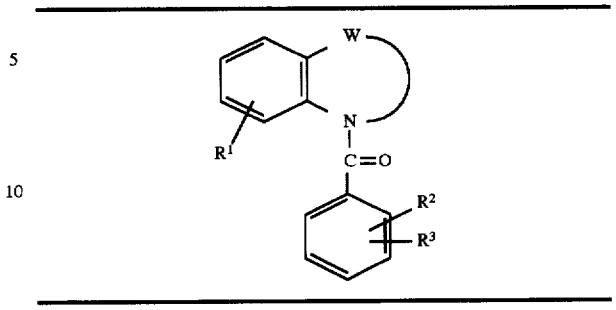

Example 1118

Structure

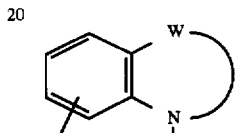 : 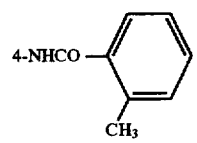

R²:  2-CH₃

R³:  4-NHCO—(phenyl with 2-CH₃)

Crystalline form:  Colorless amorphous
NMR analysis:  291)
Form:  Free

Example 1119

Structure

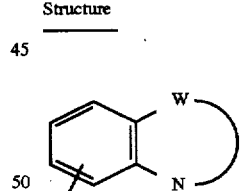 : 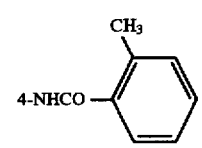

R²:  H

R³:  4-NHCO—(phenyl with 2-CH₃)

Crystalline form:  Colorless amorphous
NMR analysis:  264)
Form:  Free

TABLE 9-continued

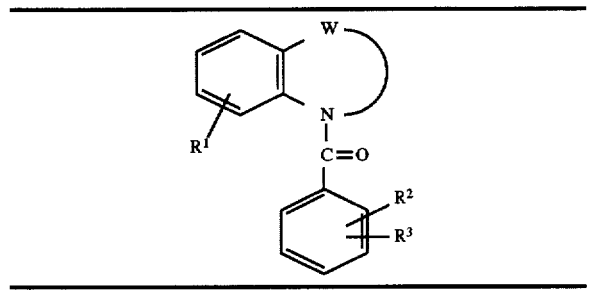

Example 1120
Structure

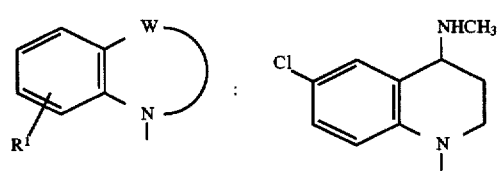

R²: H

R³:

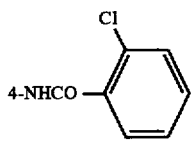
4-NHCO

Crystalline form: Colorless amorphous
NMR analysis: 265)
Form: Free

Example 1121
Structure

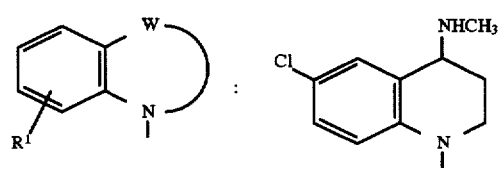

R²: 2-Cl

R³:

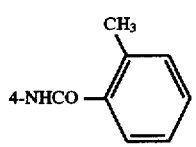
4-NHCO

Crystalline form: Colorless amorphous
NMR analysis: 266)
Form: Free

Example 1122
Structure

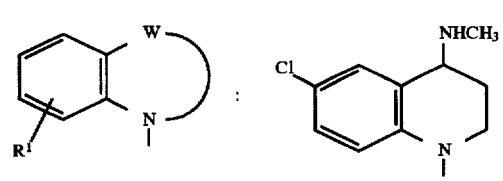

TABLE 9-continued

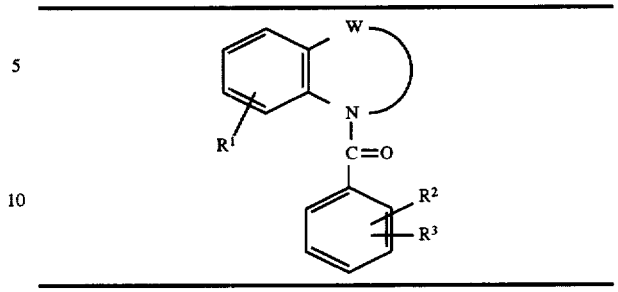

R²: 2-Cl

R³:

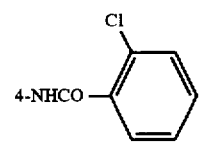
4-NHCO

Crystalline form: Colorless amorphous
NMR analysis: 267)
Form: Free

Example 1123
Structure

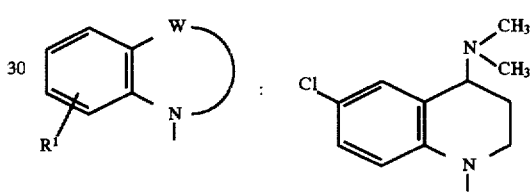

R²: H

R³:

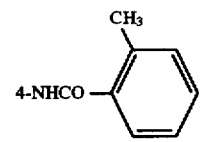
4-NHCO

Crystalline form: Colorless amorphous
NMR analysis: 268)
Form: Free

Example 1124
Structure

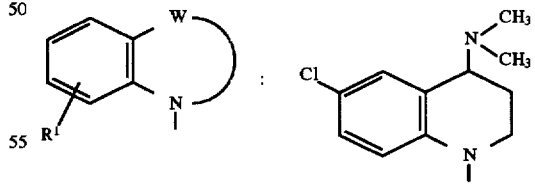

R²: H

R³:

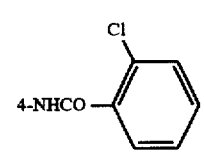
4-NHCO

Crystalline form: Colorless amorphous

TABLE 9-continued

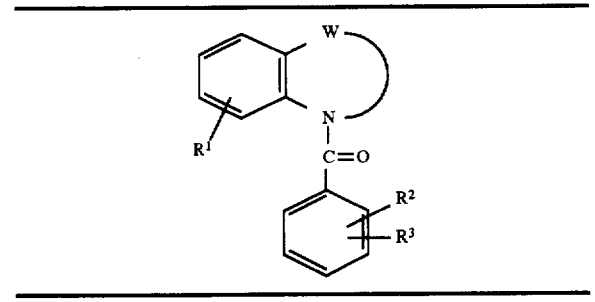

NMR analysis: 269)
Form: Free

Example 1125

Structure

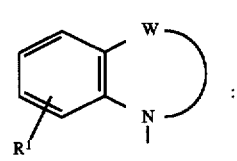 : 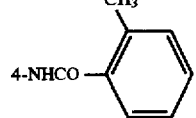

R²: 2-Cl

R³:

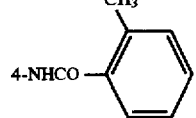
4-NHCO— (with CH₃)

Crystalline form: Colorless amorphous
NMR analysis: 270)
Form: Free

Example 1126

Structure

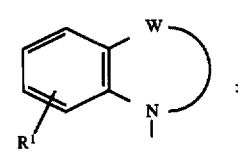 : 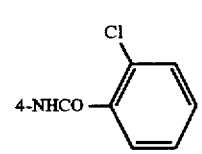

R²: 2-Cl

R³:

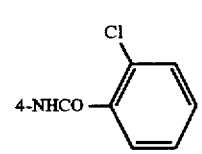
4-NHCO— (with Cl)

Crystalline form: Colorless amorphous
NMR analysis: 271)
Form: Free

TABLE 9-continued

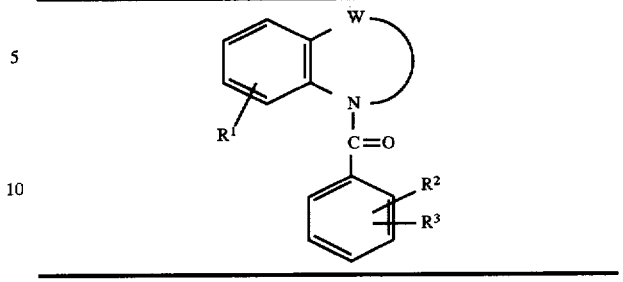

Example 1127

Structure

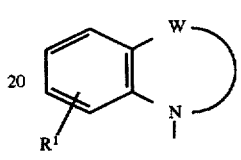 : 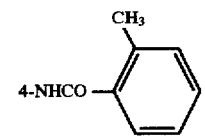

R²: H

R³:

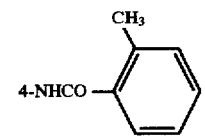
4-NHCO— (with CH₃)

Crystalline form: Colorless amorphous
NMR analysis: 272)
Form: Free

Example 1128

Structure

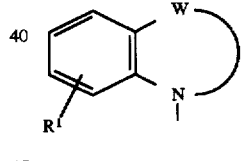 : 

R²: H

R³:

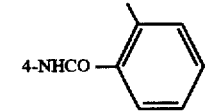
4-NHCO— (with Cl)

Crystalline form: Colorless amorphous
NMR analysis: 273)
Form: Free

Example 1129

Structure

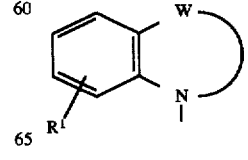 : 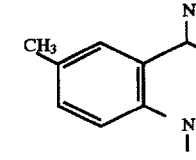

TABLE 9-continued

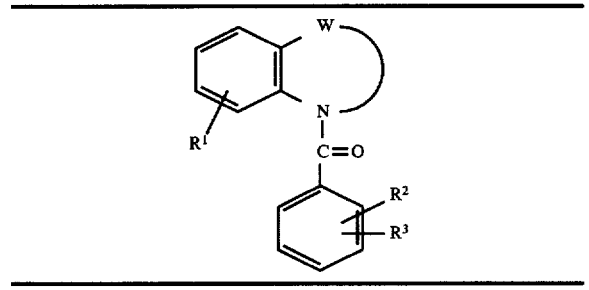

R²:  2-Cl
R³:  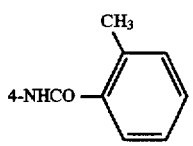 4-NHCO- (2-CH₃ phenyl)

Crystalline form:  Colorless amorphous
NMR analysis:  274)
Form:  Free

Example 1130

Structure

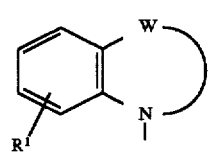 : 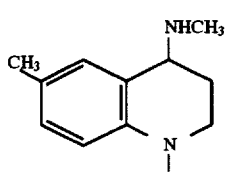

R²:  2-Cl
R³:  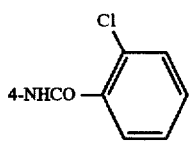 4-NHCO- (2-Cl phenyl)

Crystalline form:  Colorless amorphous
NMR analysis:  275)
Form:  Free

Example 1131

Structure

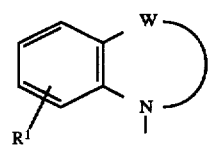 : 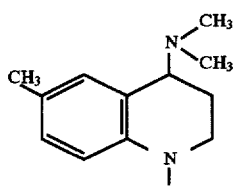

R²:  H
R³:  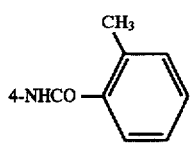 4-NHCO- (2-CH₃ phenyl)

Crystalline form:  Colorless amorphous
NMR analysis:  276)

TABLE 9-continued

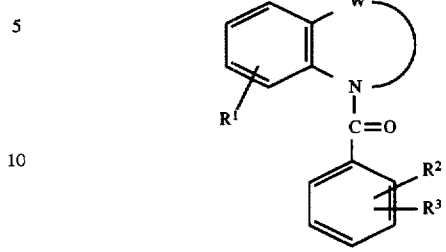

Form:  Free

Example 1132

Structure

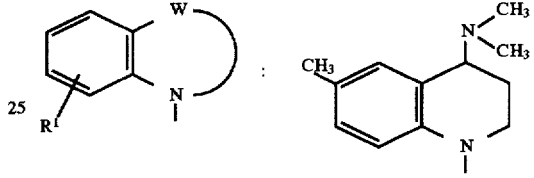

R²:  H
R³:  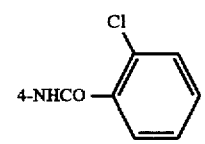 4-NHCO- (2-Cl phenyl)

Crystalline form:  Colorless amorphous
NMR analysis:  277)
Form:  Free

Example 1133

Structure

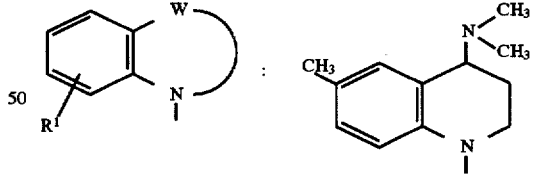

R²:  2-Cl
R³:  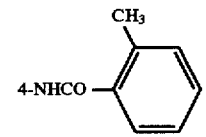 4-NHCO- (2-CH₃ phenyl)

Crystalline form:  Colorless amorphous
NMR analysis:  278)
Form:  Free

TABLE 9-continued
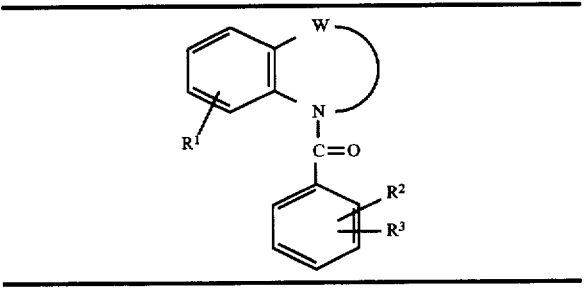
Example 1134
Structure
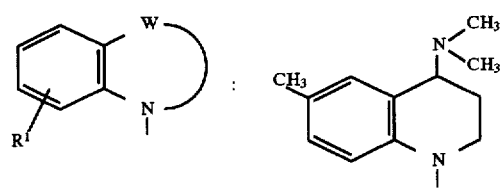
| R²: | 2-Cl |
|---|---|
| R³: | 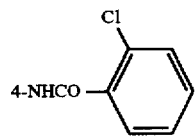 |
| Crystalline form: | Colorless amorphous |
| NMR analysis: | 279) |
| Form: | Free |
Example 1135
Structure
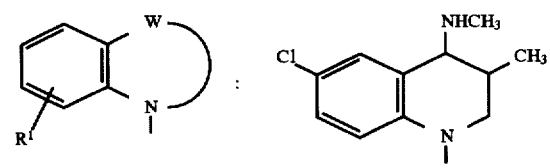
| R²: | H |
|---|---|
| R³: | 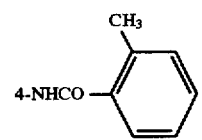 |
| NMR analysis: | 280) |
| Form: | Free |
Example 1136
Structure
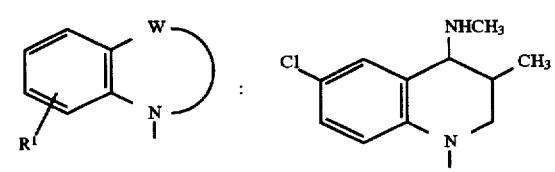
TABLE 9-continued
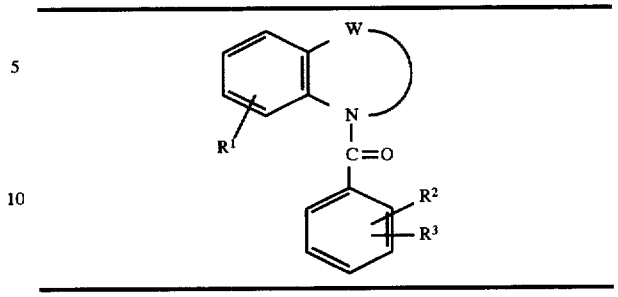
| R²: | H |
|---|---|
| R³: | 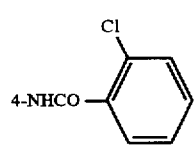 |
| NMR analysis: | 281) |
| Form: | Free |
Example 1137
Structure
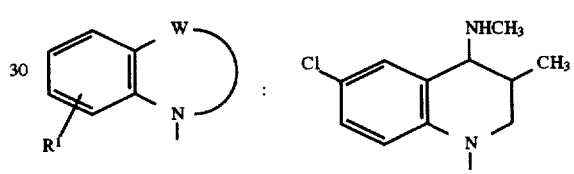
| R²: | 2-Cl |
|---|---|
| R³: | 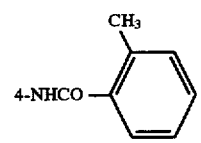 |
| NMR analysis: | 282) |
| Form: | Free |
Example 1138
Structure
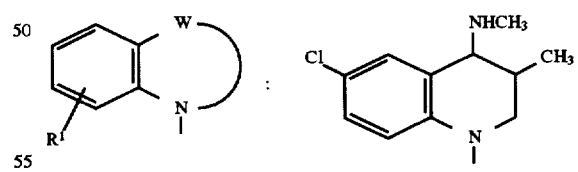
| R²: | 2-Cl |
|---|---|
| R³: | 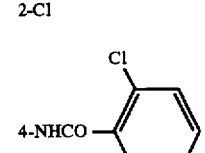 |
| NMR analysis: | 283) |
| Form: | Free |

TABLE 9-continued

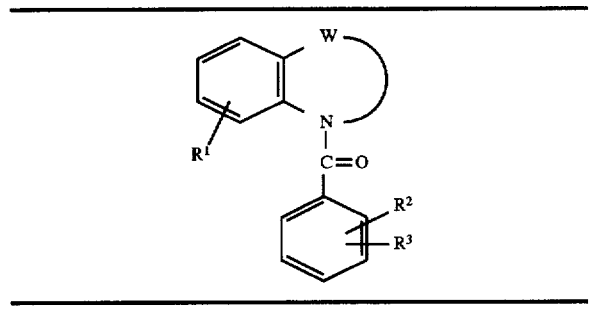

Example 1139

Structure

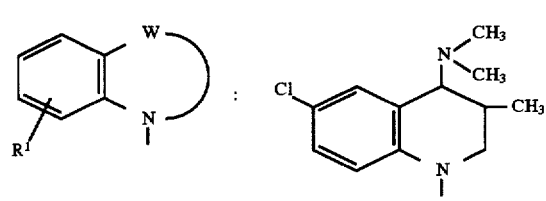

R²: 2-Cl

R³: 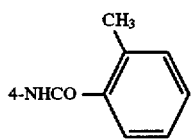
4-NHCO—⟨phenyl⟩-CH₃

NMR analysis: 306)
Form: Free

Example 1140

Structure

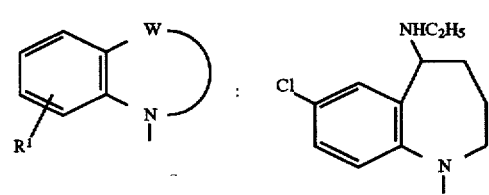

R²: 2-Cl

R³: 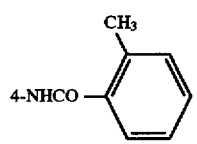
4-NHCO—⟨phenyl⟩-CH₃

Crystalline form: Colorless amorphous
NMR analysis: 284)
Form: Free

TABLE 9-continued

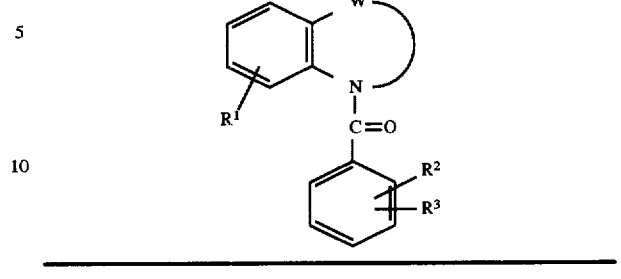

Example 1141

Structure

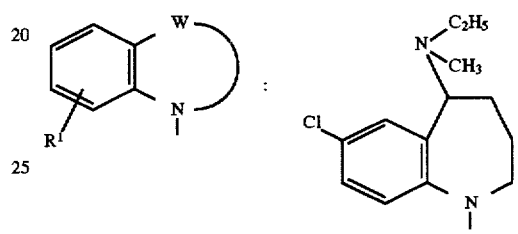

R²: 2-Cl

R³: 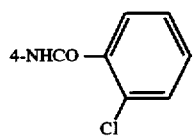
4-NHCO—⟨phenyl⟩-Cl

Crystalline form: Colorless amorphous
NMR analysis: 285)
Form: Free

Example 1142

Structure

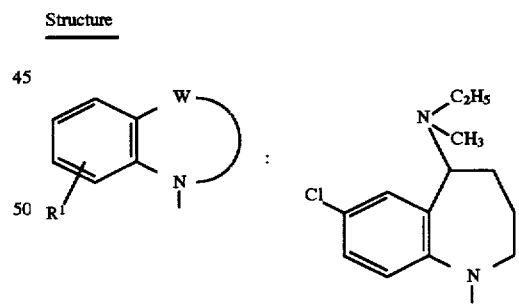

R²: 2-Cl

R³: 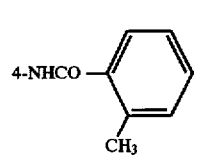
4-NHCO—⟨phenyl⟩-CH₃

Crystalline form: Colorless amorphous
NMR analysis: 286)
Form: Free

TABLE 9-continued

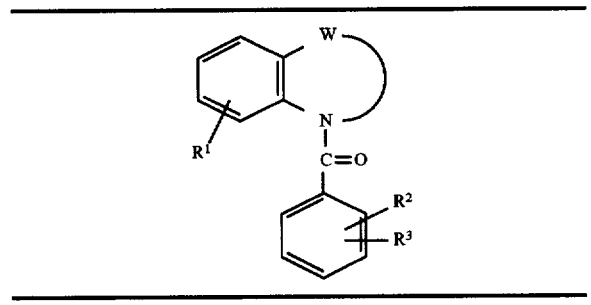

Example 1143

Structure

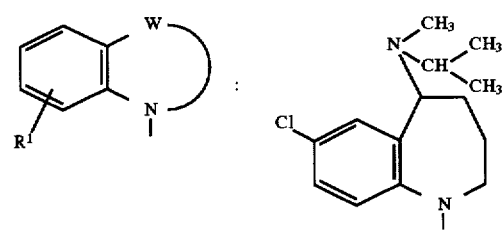

R²: 2-Cl

R³:

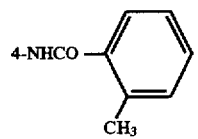
4-NHCO—⟨phenyl⟩—CH₃

| Crystalline form: | Colorless amorphous |
| --- | --- |
| NMR analysis: | 287) |
| Form: | Free |

Example 1144

Structure

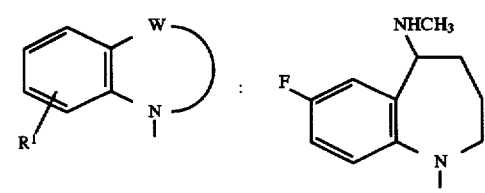

R²: H

R³:

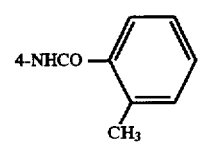
4-NHCO—⟨phenyl⟩—CH₃

| Crystalline form: | White powder |
| --- | --- |
| Recrystallization solvent: | Dichloromethane/diethyl ether |
| Melting Point: | 203–207° C. |
| Form: | Free |

TABLE 9-continued

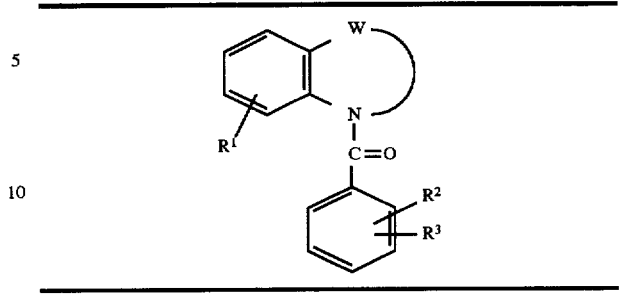

Example 1145

Structure

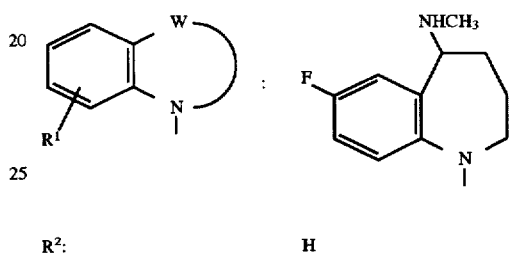

R²: H

R³:

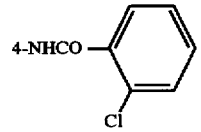
4-NHCO—⟨phenyl⟩—Cl

| Crystalline form: | White powder |
| --- | --- |
| Recrystallization solvent: | Dichloromethane/diethyl ether |
| Melting Point: | 199–203° C. |
| Form: | Free |

Example 1146

Structure

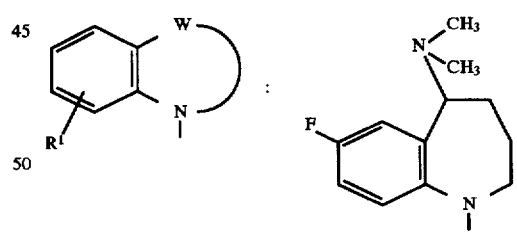

R²: H

R³:

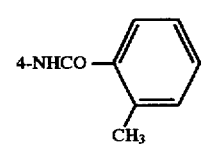
4-NHCO—⟨phenyl⟩—CH₃

| Crystalline form: | White powder |
| --- | --- |
| Recrystallization solvent: | Dichloromethane/diethyl ether |
| Melting Point: | 210–212° C. |
| Form: | Free |

TABLE 9-continued

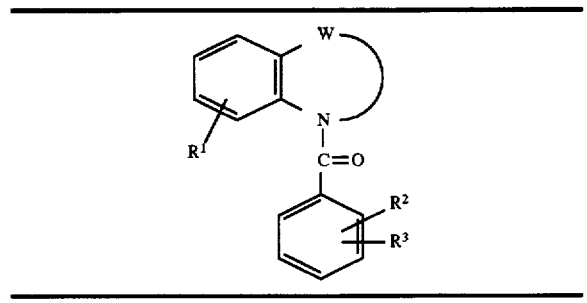

Example 1147

Structure

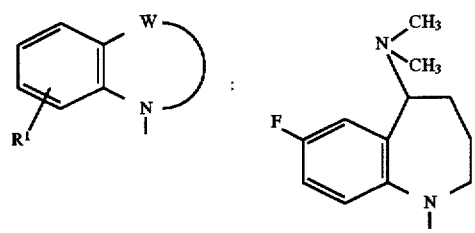

R²: H

R³:

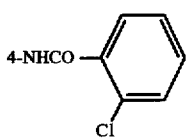
4-NHCO—⟨⟩—Cl

| Crystalline form: | White powder |
| --- | --- |
| Recrystallization solvent: | Dichloromethane/diethyl ether |
| Melting Point: | 211–214° C. |
| Form: | Free |

Example 1148

Structure

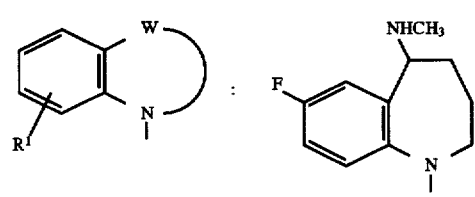

R²: 2-Cl

R³:

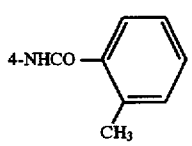
4-NHCO—⟨⟩—CH₃

| Crystalline form: | White powder |
| --- | --- |
| Recrystallization solvent: | Dichloromethane/diethyl ether |
| Melting Point: | 186–189° C. |
| Form: | Free |

TABLE 9-continued

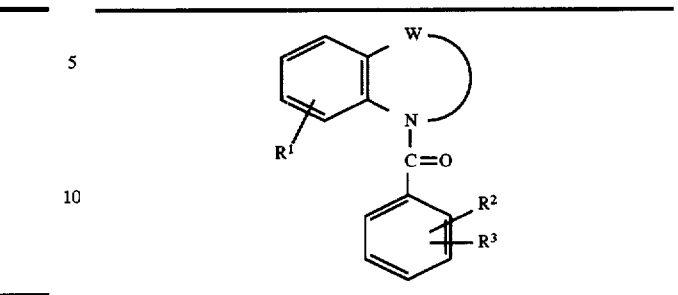

Example 1149

Structure

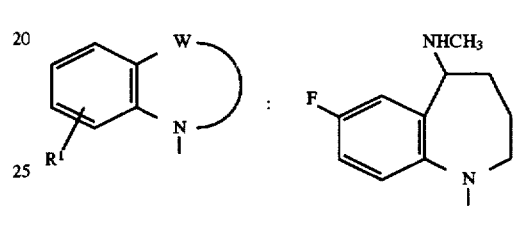

R²: 2-Cl

R³:

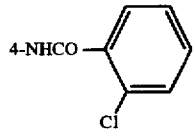
4-NHCO—⟨⟩—Cl

| Crystalline form: | Colorless amorphous |
| --- | --- |
| NMR analysis: | 288) |
| Form: | Free |

Example 1150

Structure

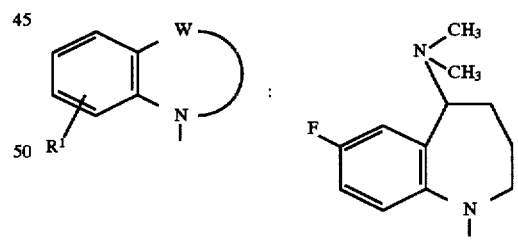

R²: 2-Cl

R³:

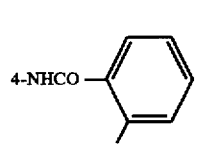
4-NHCO—⟨⟩—CH₃

| Crystalline form: | Colorless amorphous |
| --- | --- |
| NMR analysis: | 292) |
| Form: | Free |

TABLE 9-continued

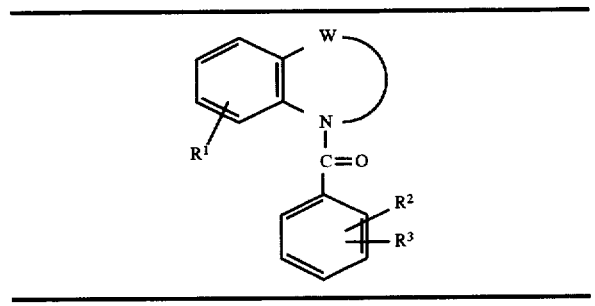

Example 1151

Structure

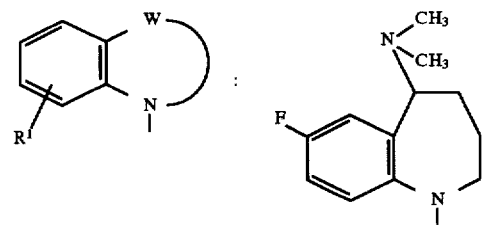

R²: 2-Cl

R³: 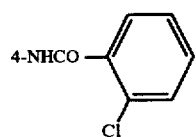

| Crystalline form: | Colorless amorphous |
| --- | --- |
| NMR analysis: | 293) |
| Form: | Free |

Example 1152

Structure

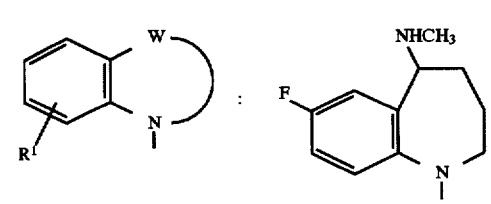

R²: 3-OCH₃

R³: 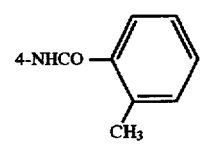

| Crystalline form: | White powder |
| --- | --- |
| Recrystallization solvent: | Dichloromethane/diethyl ether |
| Melting Point: | 144–145° C. |
| Form: | Free |

TABLE 9-continued

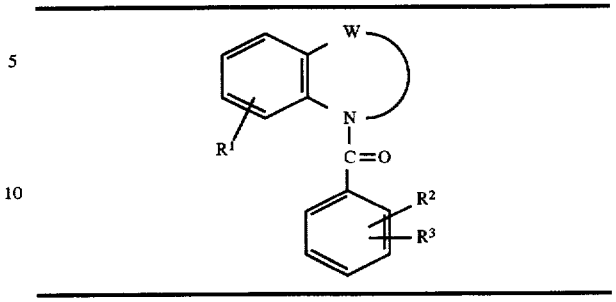

Example 1153

Structure

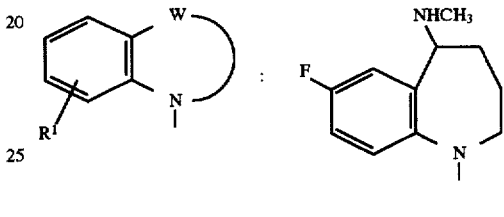

R²: 3-OCH₃

R³: 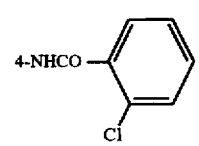

| Crystalline form: | White powder |
| --- | --- |
| Recrystallization solvent: | Dichloromethane/diethyl ether |
| Melting Point: | 149–150° C. |
| Form: | Free |

Example 1154

Structure

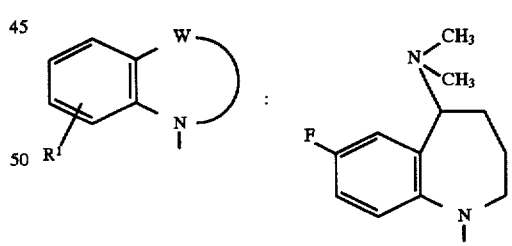

R²: 3-OCH₃

R³: 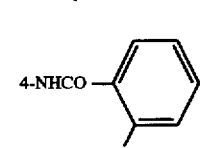

| Crystalline form: | Colorless amorphous |
| --- | --- |
| NMR analysis: | 294) |
| Form: | Free |

TABLE 9-continued

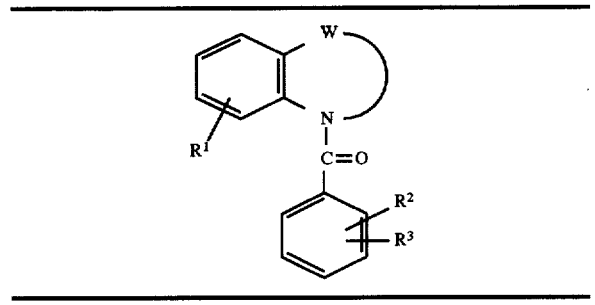

Example 1155

Structure

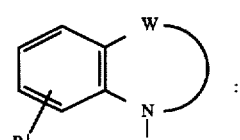 : 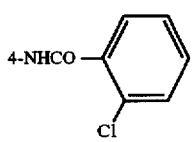

R²:  3-OCH₃

R³:

4-NHCO—⟨benzene ring with Cl⟩

Crystalline form:  Colorless amorphous
NMR analysis:  295)
Form:  Free

Example 1156

Structure

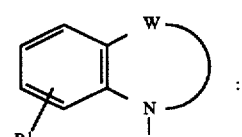 : 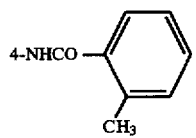

R²:  2-CH₃

R³:

4-NHCO—⟨benzene ring with CH₃⟩

Crystalline form:  Colorless amorphous
NMR analysis:  301)
Form:  Free

TABLE 9-continued

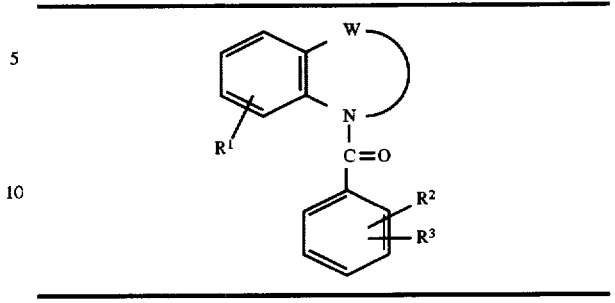

Example 1157

Structure

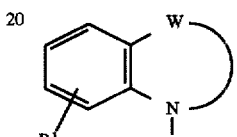 : 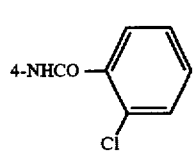

R²:  2-CH₃

R³:

4-NHCO—⟨benzene ring with Cl⟩

Crystalline form:  Colorless amorphous
NMR analysis:  302)
Form:  Free

Example 1158

Structure

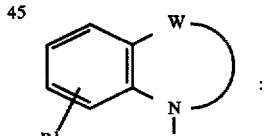 : 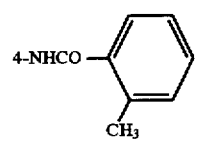

R²:  2-CH₃

R³:

4-NHCO—⟨benzene ring with CH₃⟩

Crystalline form:  Colorless amorphous
NMR analysis:  303)
Form:  Free

TABLE 9-continued

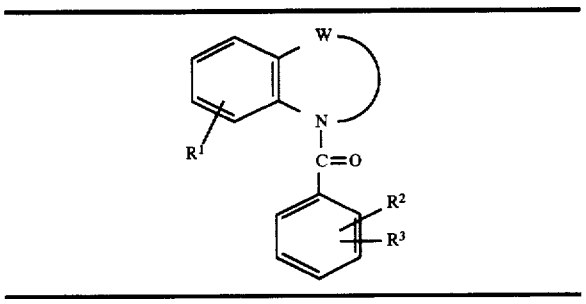

Example 1159

Structure

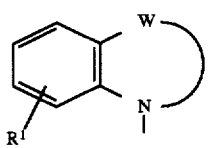 : 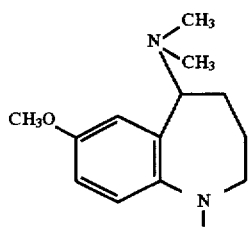

R²: 2-CH₃

R³:
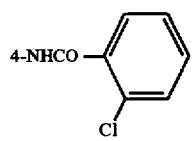

Crystalline form: Colorless amorphous
NMR analysis: 304)
Form: Free

Example 1160

Structure

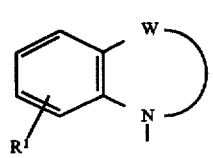 : 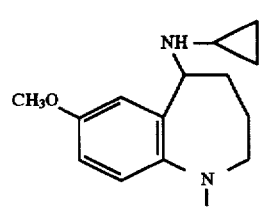

R²: H

R³:
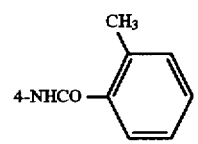

Crystalline form: White powder
Recrystallization solvent: Ethyl acetate/diisopropyl ether
Melting Point: 191–193° C.
Form: Free TABLE 9-continued

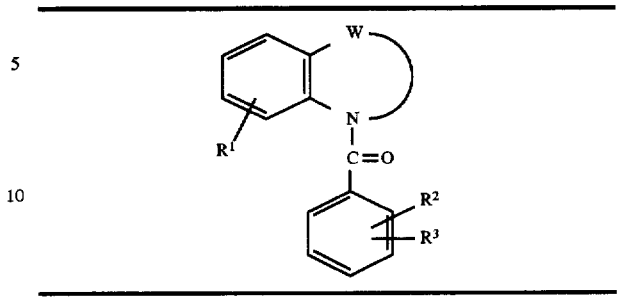

Example 1161

Structure

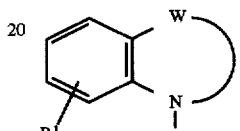 : 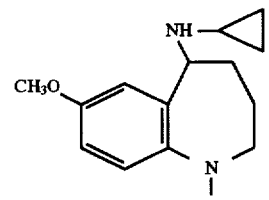

R²: H

R³:
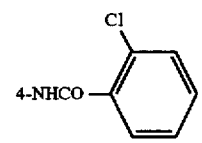

Crystalline form: White powder
Recrystallization solvent: Ethyl acetate/diisopropyl ether
Melting Point: 221–223° C.
Form: Free Example 1162

Structure

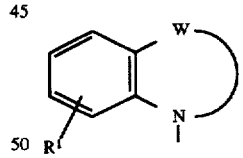 : 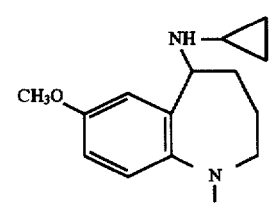

R²: 3-OCH₃

R³:
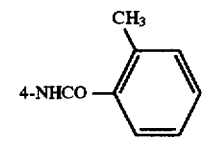

Crystalline form: White powder
Recrystallization solvent: Ethyl acetate/n-hexane
Melting Point: 159–161° C.
Form: Free TABLE 9-continued

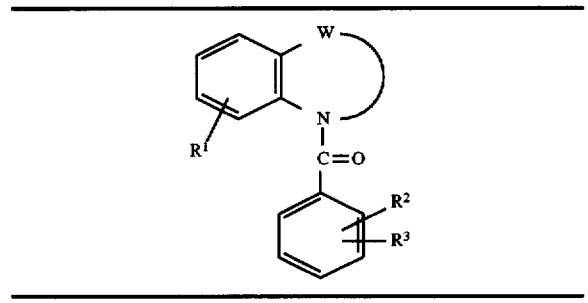

Example 1163

Structure

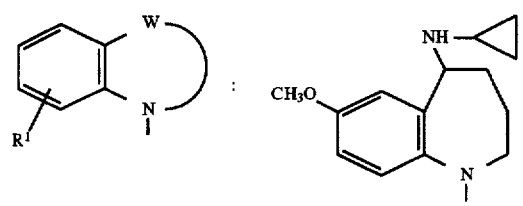

R²: 3-OCH₃

R³: 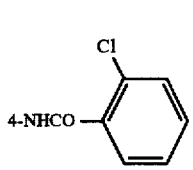
4-NHCO— (2-Cl phenyl)

Crystalline form: White powder
Recrystallization solvent: Ethyl acetate/n-hexane
Melting Point: 174–175° C.
Form: Free Example 1164

Structure

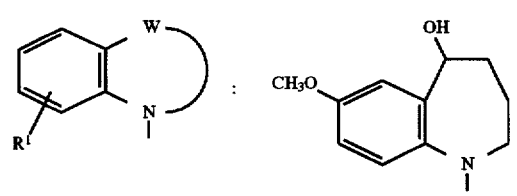

R²: 2-Cl

R³: 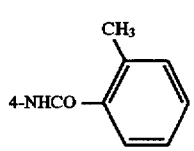
4-NHCO— (2-CH₃ phenyl)

Crystalline form: Colorless amorphous
NMR analysis: 256)
Form: Free

TABLE 9-continued

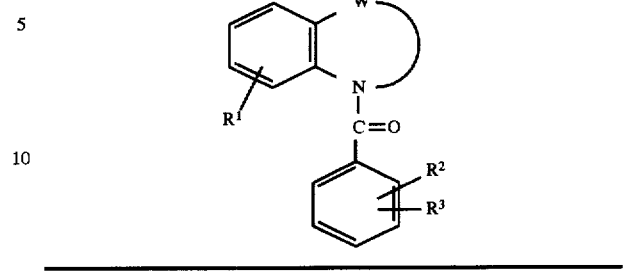

Example 1165

Structure

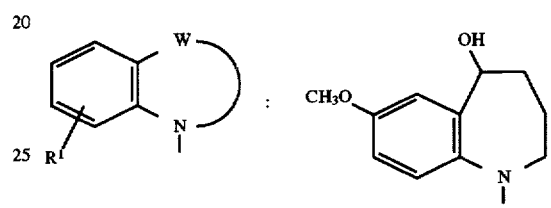

R²: 2-Cl

R³: 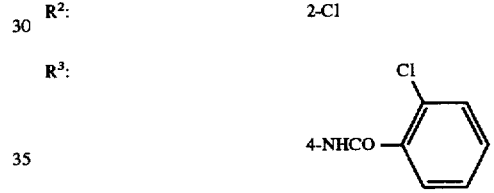
4-NHCO— (2-Cl phenyl)

Crystalline form: Colorless amorphous
NMR analysis: 257)
Form: Free

Example 1166

Structure

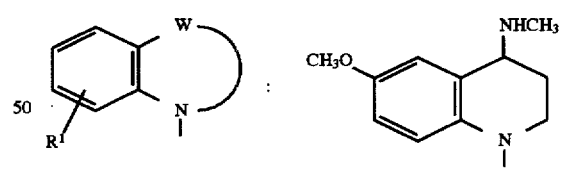

R²: H

R³: 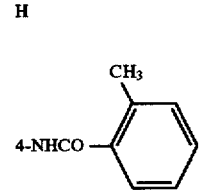
4-NHCO— (2-CH₃ phenyl)

Crystalline form: Colorless amorphous
NMR analysis: 258)
Form: Free

TABLE 9-continued

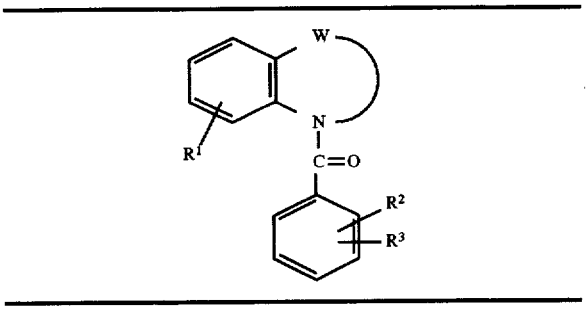

Example 1167

Structure

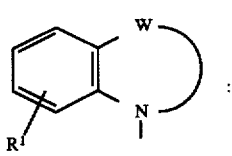 : 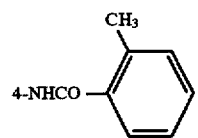

R²: 2-Cl

R³:

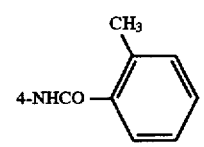

| Crystalline form: | Colorless amorphous |
|---|---|
| NMR analysis: | 259) |
| Form: | Free |

Example 1168

Structure

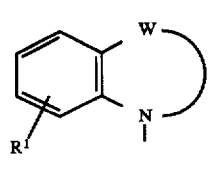 : 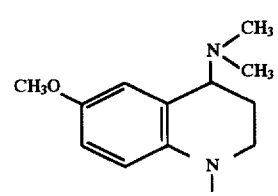

R²: H

R³:

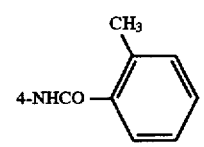

| Crystalline form: | Colorless amorphous |
|---|---|
| NMR analysis: | 260) |
| Form: | Free |

TABLE 9-continued

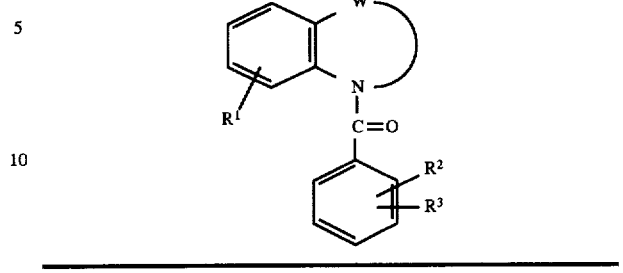

Example 1169

Structure

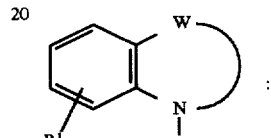 : 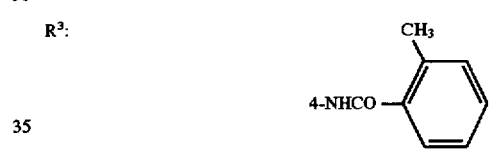

R²: 2-Cl

R³:

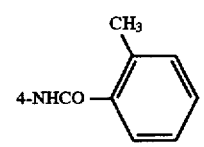

| Crystalline form: | Colorless amorphous |
|---|---|
| NMR analysis: | 261) |
| Form: | Free |

Example 1170

Structure

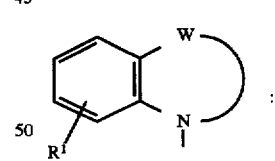 : 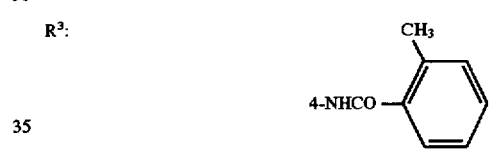

R²: H

R³:

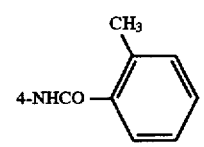

| Crystalline form: | Colorless amorphous |
|---|---|
| NMR analysis: | 296) |
| Form: | Free |

TABLE 9-continued

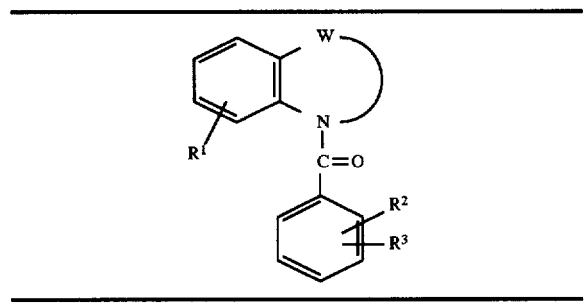

Example 1171

Structure

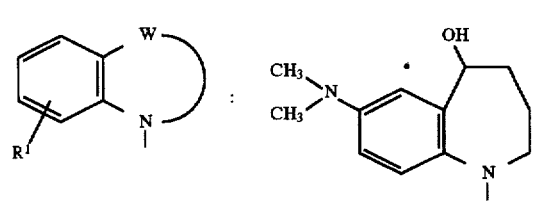

R²:  2-Cl

R³:

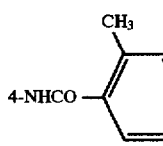

4-NHCO-  (2-CH₃-phenyl)

Crystalline form: White powder
Recrystallization solvent: Ethanol/diethyl ether/n-hexane
Melting Point: 159–162° C.
Form: Free Example 1172

Structure

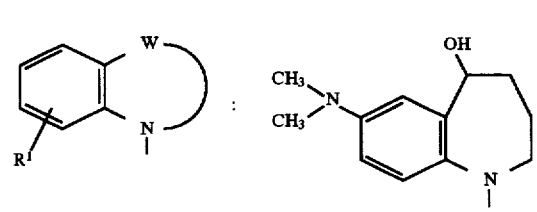

R²:  2-Cl

R³:

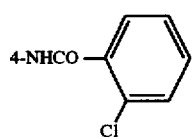

4-NHCO-  (2-Cl-phenyl)

Crystalline form: Colorless needles
Recrystallization solvent: Ethanol/diethyl ether/n-hexane
Melting Point: 221–224° C.
Form: Free TABLE 9-continued

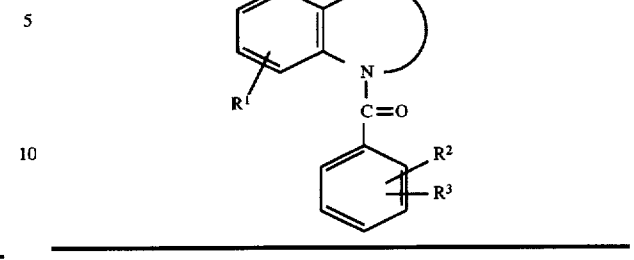

Example 1173

Structure

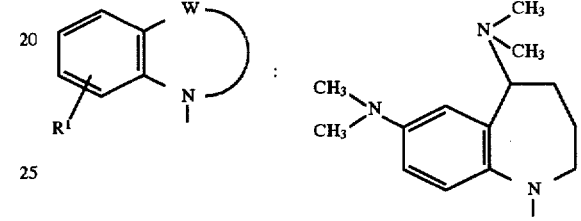

R²:  2-Cl

R³:

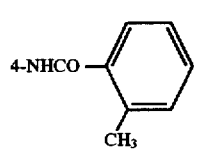

4-NHCO-  (2-CH₃-phenyl)

Crystalline form: Colorless prisms
Recrystallization solvent: Ethanol/diethyl ether
Melting Point: 199–202° C.
Form: Free Example 1174

Structure

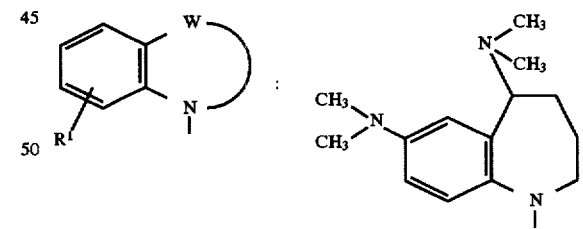

R²:  2-Cl

R³:

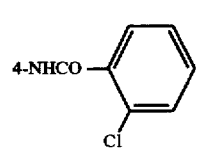

4-NHCO-  (2-Cl-phenyl)

Crystalline form: Colorless prisms
Recrystallization solvent: Ethanol/diethyl ether
Melting Point: 215–218° C.
Form: Free

TABLE 9-continued

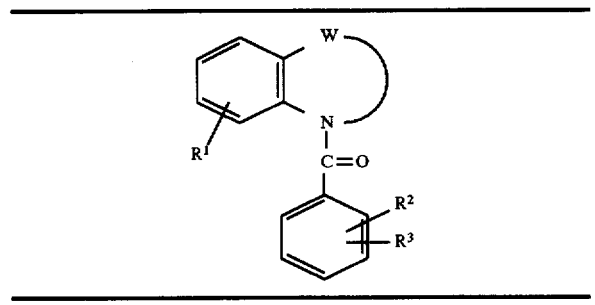

Example 1175

Structure

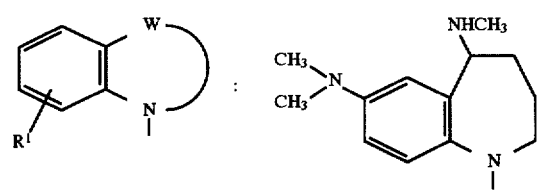

R²: 2-Cl

R³:
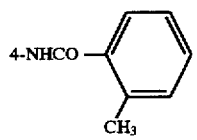
4-NHCO—⟨⟩—CH₃

Crystalline form: Colorless needles
Recrystallization solvent: Ethanol/diethyl ether/n-hexane
Melting Point: 167–170° C.
Form: Free

Example 1176

Structure

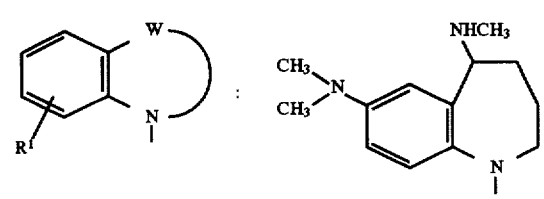

R²: 2-Cl

R³:
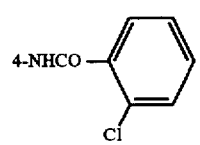
4-NHCO—⟨⟩—Cl

Crystalline form: White powder
Recrystallization solvent: Ethanol/diethyl ether/n-hexane
Melting Point: 191–193° C.
Form: Free

TABLE 9-continued

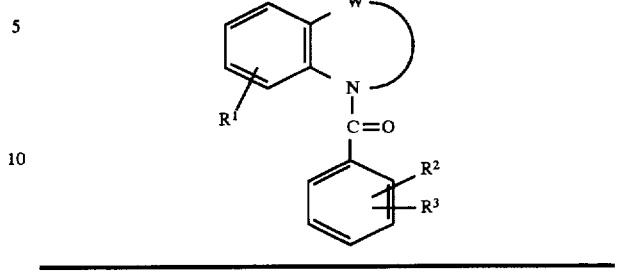

Example 1177

Structure

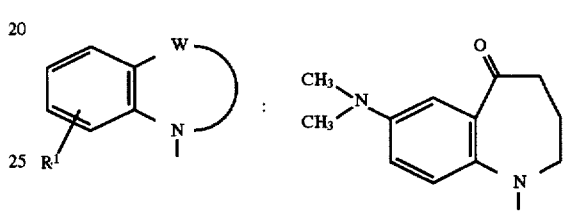

R²: 2-Cl

R³:
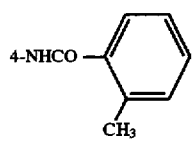
4-NHCO—⟨⟩—CH₃

Crystalline form: Light yellow amorphous
NMR analysis: 262)
Form: Free

Example 1178

Structure

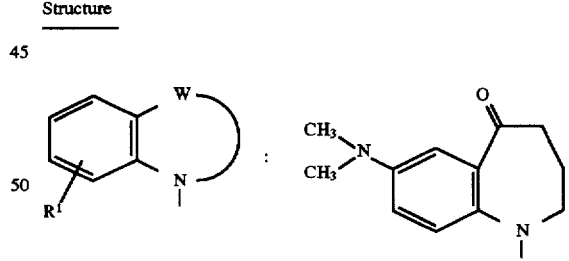

R²: 2-Cl

R³:
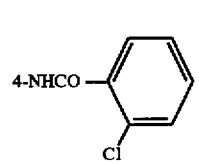
4-NHCO—⟨⟩—Cl

Crystalline form: Light yellow amorphous
NMR analysis: 263)
Form: Free

TABLE 9-continued

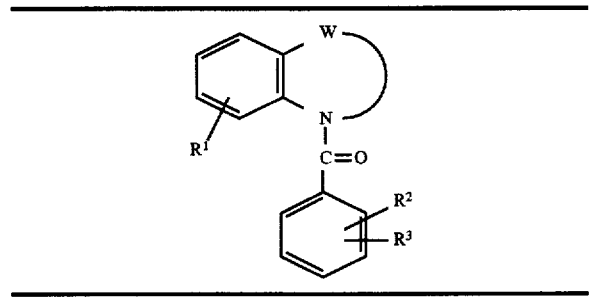

Example 1179

Structure

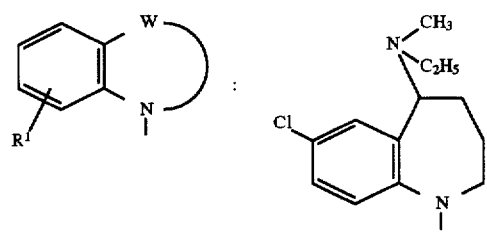

R²: 3-OCH₃

R³:

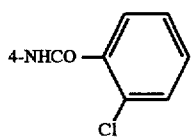
4-NHCO—⟨Ph⟩—Cl

Crystalline form: Colorless amorphous
NMR analysis: 297)
Form: Free

Example 1180

Structure

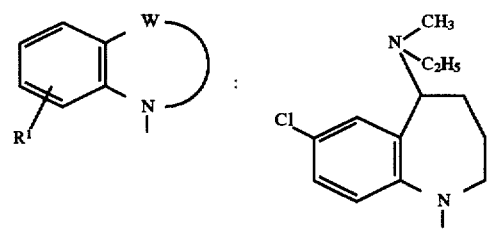

R²: 3-OCH₃

R³:

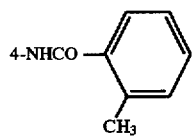
4-NHCO—⟨Ph⟩—CH₃

Crystalline form: Colorless amorphous
NMR analysis: 298)
Form: Free

TABLE 9-continued

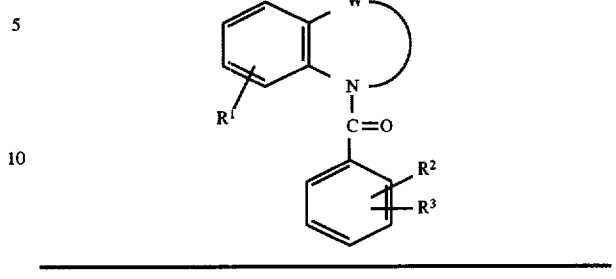

Example 1181

Structure

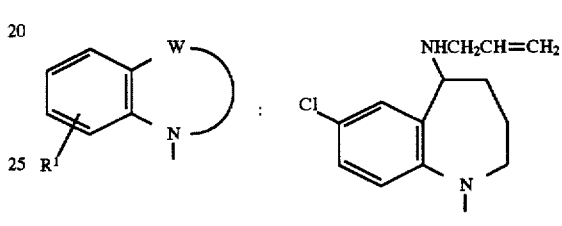

R²: 3-OCH₃

R³:

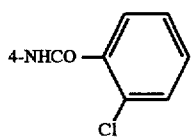
4-NHCO—⟨Ph⟩—Cl

Crystalline form: Colorless amorphous
NMR analysis: 299)
Form: Free

Example 1182

Structure

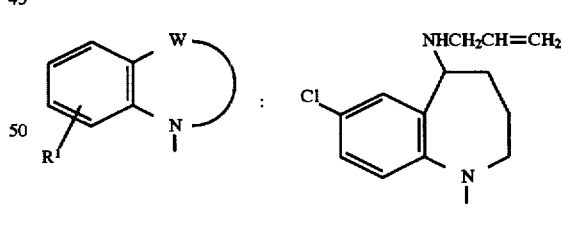

R²: 3-OCH₃

R³:

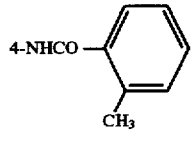
4-NHCO—⟨Ph⟩—CH₃

Crystalline form: Colorless amorphous
NMR analysis: 300)
Form: Free

TABLE 9-continued

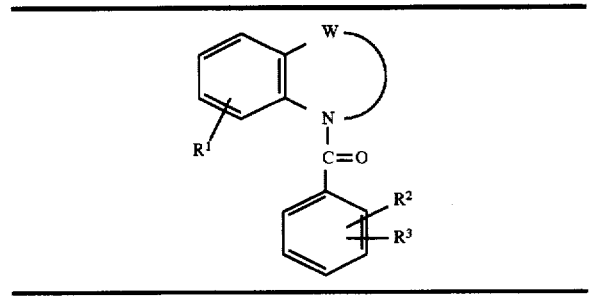

Example 1183

Structure

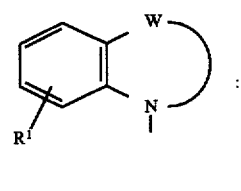 : 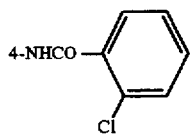

R²: 3-OCH₃

R³:

| | |
|---|---|
| Crystalline form: | Colorless amorphous |
| NMR analysis: | 307) |
| Form: | Free |

Example 1184

Structure

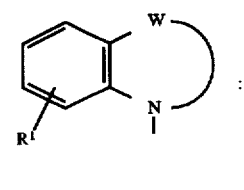 : 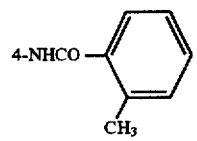

R²: 3-OCH₃

R³:

| | |
|---|---|
| Crystalline form: | Colorless amorphous |
| NMR analysis: | 308) |
| Form: | Free |

TABLE 9-continued

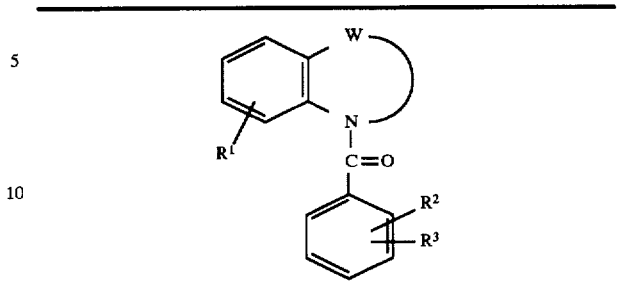

Example 1185

Structure

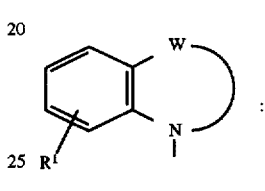 : 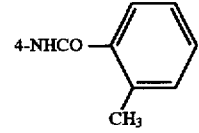

R²: 2-OCH₃

R³:

| | |
|---|---|
| Crystalline form: | Colorless amorphous |
| NMR analysis: | 309) |
| Form: | Free |

Example 1186

Structure

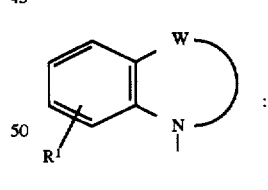 : 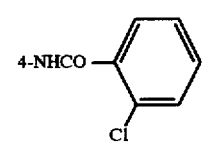

R²: 2-OCH₃

R³:

| | |
|---|---|
| Crystalline form: | Colorless amorphous |
| NMR analysis: | 310) |
| Form: | Free |

TABLE 9-continued

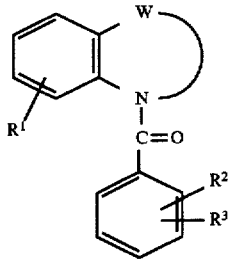

Example 1187

Structure

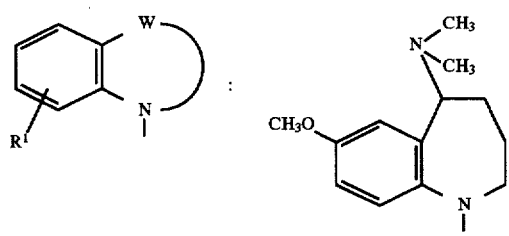

R²: 2-OCH₃

R³: 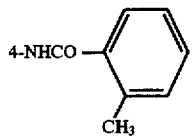
4-NHCO—⟨benzene⟩—CH₃

Crystalline form: Colorless amorphous
NMR analysis: 311)
Form: Free

Example 1188

Structure

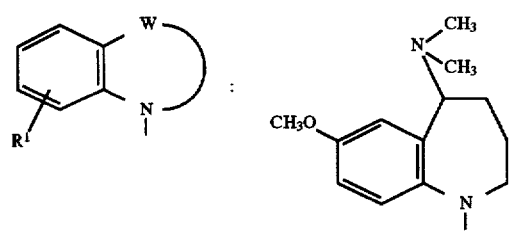

R²: 2-OCH₃

R³: 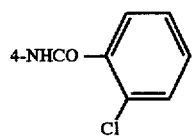
4-NHCO—⟨benzene⟩—Cl

Crystalline form: Colorless amorphous
NMR analysis: 312)
Form: Free

238) ¹H-NMR (DMSO-d₆) δ; 1.4–2.1 (4H, m), 2.34 (3H, s), 2.8–5.4 (4H, m), 7.09 (1H, d, J=8.4 Hz), 7.15–7.7 (9H, m), 7.76 (1H, d, J=2.6 Hz), 10.41 (1H, s)

239) ¹H-NMR (DMSO-d₆) δ; 1.5–2.2 (4H, m), 2.8–5.2 (4H, m), 7.09 (1H, d, J=8.4 Hz), 7.2–7.7 (9H, m), 7.76 (1H, d, J=2.6 Hz), 10.63 (1H, s)

240) ¹H-NMR (CDCl₃) δ; 1.65–2.2 (4H, m), 2.25–2.65 (6H, m), 2.75–4.6 (4H, m), 6.8–8.15 (11H, m)

241) ¹H-NMR (CDCl₃) δ; 1.4–2.25 (4H, m), 2.25–2.55 (3H, m), 2.7–4.8 (4H, m), 6.8–8.3 (11H, m)

242) ¹H-NMR (CDCl₃) δ; 1.4–2.1 (4H, m), 2.35–2.6 (3H, m), 2.8–5.2 (7H, m), 6.8–8.05 (11H, m)

243) ¹H-NMR (CDCl₃) δ; 1.4–2.15 (4H, m), 2.4–5.2 (7H, m), 6.8–7.85 (10H, m), 7.9–8.3 (1H, m)

244) ¹H-NMR (CDCl₃) δ; 1.20–2.38 (11H, m), 2.98–5.10 (3H, m), 6.45–7.04 (2H, m), 7.05–7.86 (8H, m), 8.00–8.50 (1H, m)

245) ¹H-NMR (CDCl₃) δ; 1.05–2.78 (14H, m), 2.78–5.18 (2H, m), 6.36–7.03 (2H, m), 7.06–7.90 (8H, m), 7.98–8.39 (1H, m)

246) ¹H-NMR (CDCl₃) δ; 1.75–2.54 (2H, m), 2.60–4.03 (4H, m), 3.37 (3H, brs), 5.17 (2H, s), 6.60–6.83 (3H, m), 6.90–7.07 (1H, m), 7.07–7.20 (1H, m), 7.22–7.50 (6H, m), 7.73–7.84 (1H, m)

247) ¹H-NMR (CDCl₃) δ; 1.60–2.40 (2H, m), 2.45 (3H, s), 2.65–3.06 (2H, m), 3.06–5.28 (2H, m), 3.35 (3H, brs), 6.59–7.60 (9H, m), 7.67–7.88 (1H, m), 8.12 (1H, brs)

248) ¹H-NMR (CDCl₃) δ; 1.60–2.52 (2H, m), 2.64–5.32 (4H, m), 3.37 (3H, brs), 6.60–7.98 (10H, m), 8.50 (1H, brs)

249) ¹H-NMR (CDCl₃) δ; 1.18–3.15 (12H, m), 3.40–4.38 (5H, m), 6.58–7.75 (10H, m), 8.30–8.71 (1H, m)

250) ¹H-NMR (CDCl₃) δ; 0.26–0.71 (4H, m), 1.15–3.29 (10H, m), 3.40–4.95 (5H, m), 6.60–7.85 (10H, m), 8.18–8.68 (1H, m)

251) ¹H-NMR (CDCl₃) δ; 0.25–0.72 (4H, m), 1.16–2.35 (6H, m), 2.35–3.30 (4H, m), 3.43–4.98 (2H, m), 6.57–7.94 (10H, m), 8.22–8.89 (1H, m)

252) ¹H-NMR (CDCl₃) δ; 0.69–2.90 (9H, m), 2.90–5.10 (5H, m), 6.40–7.85 (10H, m), 8.25–8.54 (1H, m)

253) ¹H-NMR (CDCl₃) δ; 2.17 (2H, brs), 2.34 (3H, s), 2.49 (3H, s), 2.87 (2H, t, J=6.0 Hz), 3.10–5.00 (2H, m), 3.70 (3H, s), 6.67 (1H, d, J=8.0 Hz), 6.85–6.88 (2H, m), 7.09 (1H, dd, J=1.5, 8.0 Hz), 7.21–7.50 (4H, m), 7.64 (1H, d, J=1.9 Hz), 8.11 (1H, m), 8.33 (1H, d, J=8.8 Hz)

254) ¹H-NMR (CDCl₃) δ; 1.42–5.06 (13H, m), 6.51 (1H, d, J=7.8 Hz), 6.76 (1H, m), 7.01–7.63 (10H, m), 8.53 (1H, m)

255) ¹H-NMR (CDCl₃) δ; 1.26–4.93 (16H, m), 6.69–7.73 (10H, m), 8.62–8.84 (1H, m)

256) ¹H-NMR (CDCl₃) δ; 1.45–1.90 (2H, m), 1.90–2.33 (2H, m), 2.33–3.25 (4H, m), 3.60–3.93 (3H, m), 4.45–5.15 (2H, m), 6.40–8.25 (11H, m)

257) ¹H-NMR (CDCl₃) δ; 1.49–1.97 (2H, m), 1.97–3.10 (3H, m), 3.58–3.98 (3H, m), 4.60–5.26 (2H, m), 6.44–8.36 (11H, m)

258) ¹H-NMR (CDCl₃) δ; 1.82–2.13 (1H, m), 2.13–2.43 (1H, m), 2.50 (3H, s), 2.57 (3H, s), 3.69–4.06 (3H, m), 3.78 (3H, s), 6.45–6.80 (2H, m), 6.85–7.00 (1H, m), 7.18–7.80 (9H, m)

259) ¹H-NMR (CDCl₃) δ; 1.72–2.05 (1H, m), 2.11–2.40 (1H, m), 2.51 (3H, s), 2.57 (3H, s), 3.40–4.20 (3H, m), 3.77 (3H, s), 6.35–6.64 (1H, m), 6.79–6.96 (1H, m), 7.15–8.13 (9H, m)

260) ¹H-NMR (CDCl₃) δ; 1.71–2.05 (1H, m), 2.07–2.32 (1H, m), 2.33 (6H, s), 2.47 (3H, s), 3.50–3.80 (2H, m), 3.76 (3H, s), 3.95–4.17 (1H, m), 6.40–6.70 (2H, m), 6.90–7.03 (1H, m), 7.14–7.77 (8H, m), 7.90–8.14 (1H, m)

261) ¹H-NMR (CDCl₃) δ; 1.76–2.70 (2H, m), 2.30 (6H, s), 2.47 (3H, s), 3.23–4.40 (3H, m), 3.73 (3H, s), 6.30–6.65 (2H, m), 6.65–8.76 (9H, m)

262) ¹H-NMR (CDCl₃) δ; 1.68–2.35 (2H, m), 2.36–5.11 [13H, m, 2.45 (3H, s), 2.92 (6H, s)], 6.56 (1H, dd, J=3.1, 8.7 Hz), 6.78–7.06 (2H, m), 6.82 (1H, d, J=8.7 Hz), 7.11–7.68 (6H, m), 7.97 (1H, brs)

263) ¹H-NMR (CDCl₃) δ; 1.69–2.30 (2H, m), 2.59–5.10 [10H, m, 2.92 (6H, s)], 6.56 (1H, dd, J=3.1, 8.8 Hz), 6.72–7.90 (9H, m), 8.42 (1H, brs)

264) ¹H-NMR (CDCl₃) δ; 1.49 (1H, brs), 1.82–2.01 (1H, m), 2.03–2.26 (1H, m), 2.46 (3H, s), 2.54 (3H, s), 3.67–3.76 (1H, m), 3.86 (2H, t, J=6.8 Hz), 6.67 (1H, d, J=8.6 Hz), 6.93 (1H, dd, J=8.6, 2.5 Hz), 7.13–7.43 (9H, m), 8.15 (1H, brs)

265) ¹H-NMR (CDCl₃) δ; 1.58 (1H, brs), 1.86–2.03 (1H, m), 2.08–2.30 (1H, m), 2.56 (3H, s), 3.69–3.78 (1H, m), 3.91 (2H, t, J=6.5 Hz), 6.69 (1H, d, J=8.7 Hz), 6.94 (1H, dd, J=8.6, 2.5 Hz), 7.33–7.47 (6H, m), 7.54–7.63 (2H, m), 7.67–7.77 (1H, m), 8.16 (1H, brs)

266) ¹H-NMR (CDCl₃) δ; 1.50 (1H, brs), 1.76–2.23 (2H, m), 2.42 (3H, s), 2.47 (3H, s), 3.55–3.94 (3H, m), 6.28–7.78 (10H, m), 8.91 (1H, brs)

267) ¹H-NMR (CDCl₃) δ; 1.46 (1H, brs), 1.82–2.28 (2H, m), 2.50 (3H, s), 3.52–4.08 (3H, m), 6.34–7.75 (10H, m), 8.61 (1H, brs)

268) ¹H-NMR (CDCl₃) δ; 1.80–2.31 (2H, m), 2.32 (3H, s), 2.48 (3H, s), 3.51–3.82 (2H, m), 3.95–4.15 (1H, m), 6.59 (1H, d, J=8.6 Hz), 6.90 (1H, dd, J=8.6, 2.5 Hz), 7.16–7.61 (9H, m), 7.88 (1H, brs)

269) ¹H-NMR (CDCl₃) δ; 1.86–2.04 (1H, m), 2.13–2.31 (1H, m), 2.33 (3H, s), 3.53–3.62 (1H, m), 3.76 (1H, dt, J=12.8, 6.4 Hz), 6.60 (1H, d, J=8.7 Hz), 6.91 (1H, dd, J=8.7, 2.5 Hz), 7.33–7.52 (6H, m), 7.54–7.66 (2H, m), 7.73–7.82 (1H, m), 8.07 (1H, brs)

270) ¹H-NMR (CDCl₃) δ; 1.65–2.27 (2H, m), 2.28 (6H, s), 2.48 (3H, s), 3.37–4.07 (3H, m), 6.33–7.91 (10H, m), 8.20 (1H, brs)

271) ¹H-NMR (CDCl₃) δ; 1.71–2.26 (2H, m), 2.28 (6H, s), 3.36–4.10 (3H, m), 6.35–2.95 (10H, m), 8.59 (1H, brs)

272) ¹H-NMR (CDCl₃) δ; 2.02–2.23 (2H, m), 2.28 (3H, s), 2.47 (3H, s), 2.56 (3H, s), 3.73–4.07 (3H, m), 4.68 (1H, brs), 6.61 (1H, d, J=8.1 Hz), 6.72–6.83 (1H, m), 7.17–7.63 (11H, m), 8.03 (1H, brs)

273) ¹H-NMR (CDCl₃) δ; 1.61 (1H, brs), 1.87–2.25 (2H, m), 2.29 (3H, s), 2.56 (3H, s), 3.67–3.78 (1H, m), 3.91 (2H, t, J=6.9 Hz), 6.52–6.79 (2H, m), 7.09–7.15 (1H, m), 7.30–7.90 (8H, m), 8.23 (1H, brs)

274) ¹H-NMR (CDCl₃) δ; 1.58 (1H, brs), 1.82–2.23 (2H, m), 2.27 (3H, s), 2.48 (3H, s), 2.50 (3H, s), 3.47–4.05 (3H, m), 6.23–6.83 (2H, m), 7.00–7.50 (7H, m), 7.53–7.74 (1H, m), 8.28 (1H, brs)

275) ¹H-NMR (CDCl₃) δ; 1.60 (1H, brs), 1.82–2.35 (5H, m), 2.49 (3H, s), 3.41–4.08 (3H, m), 6.30–6.80 (1H, m), 6.98–7.68 (8H, m), 7.31–7.82 (1H, m), 8.77 (1H, brs)

276) ¹H-NMR (CDCl₃) δ; 1.76–2.03 (2H, m), 2.27 (3H, s), 2.32 (6H, s), 2.47 (3H, s), 3.48–3.58 (1H, m), 3.66 (1H, dt, J=12.7, 6.1 Hz), 3.97–4.14 (1H, m), 6.48 (1H, d, J=8.2 Hz), 6.65–6.77 (1H, m), 7.14–7.59 (9H, m), 7.96 (1H, m)

277) ¹H-NMR (CDCl₃) δ; 1.75–2.04 (2H, m), 2.27 (3H, s), 2.33 (6H, s), 3.48–3.58 (1H, m), 3.67 (1H, dt, J=12.7, 6.1 Hz), 3.98–4.16 (1H, m), 6.48 (1H, d, J=8.2 Hz), 6.72 (1H, dd, J=8.2, 1.9 Hz), 7.16 (1H, d, J=1.9 Hz), 7.27–7.91 (8H, m), 8.31 (1H, brs)

278) ¹H-NMR (CDCl₃) δ; 1.72–2.05 (2H, m), 2.28 (9H, s), 2.47 (3H, s), 3.16–4.34 (3H, m), 6.38–7.79 (10H, m), 8.37 (1H, brs)

279) ¹H-NMR (CDCl₃) δ; 1.65–2.07 (2H, m), 2.28 (9H, s), 3.26–4.38 (3H, m), 6.34–8.06 (10H, m), 8.53 (1H, brs)

280) Two stereoisomers: Both colorless amorphous
Isomer A
$[\alpha]_D^{22}=0°$ (chloroform, c=1.0)
¹H-NMR (CDCl₃) δ; 1.04 (3H, d, J=6.9 Hz), 1.59 (1H, brs), 2.25–2.45 (1H, m), 2.49 (3H, s), 2.52 (3H, s), 3.53–3.69 (2H, m), 3.91 (1H, abq, J=7.2, 12.9 Hz), 6.60 (1H, d, J=8.6 Hz), 6.93 (1H, dd, J=8.6, 2.5 Hz), 7.18–7.60 (9H, m), 7.76 (1H, brs)
Isomer B
$[\alpha]_D^{22}=0°$ (chloroform, c=1.0)
¹H-NMR (CDCl₃) δ; 1.06 (3H, d, J=6.9 Hz), 1.60 (1H, brs), 2.21–2.43 (1H, m), 2.47 (3H, s), 2.52 (3H, s), 3.51–3.66 (2H, m), 3.93 (1H, abq, J=7.5, 12.9 Hz), 6.60–6.68 (1H, m), 6.95 (1H, dt, J=7.5, 1.8 Hz), 7.03 (1H, dt, J=7.4, 1.4 Hz), 7.17–7.55 (8H, m), 7.81 (1H, brs)

281) Two stereoisomers: Both colorless amorphous
Isomer A
$[\alpha]_D^{22}=0°$ (chloroform, c=1.0)
¹H-NMR (CDCl₃) δ; 1.04 (3H, d, J=6.9 Hz), 1.55 (1H, brs), 2.23–2.46 (1H, m), 2.53 (3H, s), 3.53–3.67 (2H, m), 3.91 (1H, abq, J=7.1, 12.9 Hz), 6.61 (1H, d, J=8.6 Hz), 6.93 (1H, dd, J=8.6, 2.5 Hz), 7.28–7.52 (6H, m), 7.54–7.65 (2H, m), 7.70–7.79 (1H, m), 8.16 (1H, brs)
Isomer B
$[\alpha]_D^{22}=0°$ (chloroform, c=1.0)
¹H-NMR (CDCl₃) δ; 1.06 (3H, d, J=6.9 Hz), 1.61 (1H, brs), 2.21–2.42 (1H, m), 2.51 (3H, s), 3.48–3.67 (2H, m), 3.90 (1H, abq, J=7.4, 12.9 Hz), 6.59–6.67 (1H, m), 6.94 (1H, dt, J=7.5, 1.9 Hz), 7.03 (1H, dt, J=7.4, 1.4 Hz), 7.23–7.75 (8H, m), 8.41 (1H, brs)

282) Two stereoisomers: Both colorless amorphous
Isomer A
$[\alpha]_D^{22}=0°$ (chloroform, c=1.0)
¹H-NMR (CDCl₃) δ; 0.99 (3H, d, J=6.5 Hz), 1.37 (1H, brs), 2.16–2.40 (1H, m), 2.46 (3H, s), 2.48 (3H, s), 3.38–3.96 (3H, m), 6.30–7.28 (10H, m), 8.26 (1H, brs)
Isomer B
$[\alpha]_D^{22}=0°$ (chloroform, c=1.0)
¹H-NMR (CDCl₃) δ; 1.03 (3H, d, J=6.7 Hz), 1.44 (1H, brs), 2.17–2.40 (1H, m), 2.45 (3H, s), 2.47 (3H, s), 3.40–3.98 (3H, m), 6.47–7.73 (10H, m), 8.23 (1H, brs)

283) Two stereoisomers: Both colorless amorphous
Isomer A
$[\alpha]_D^{22}=0°$ (chloroform, c=1.0)
¹H-NMR (CDCl₃) δ; 1.00 (3H, d, J=6.6 Hz), 1.40 (1H, brs), 2.18–2.42 (1H, m), 2.47 (3H, s), 3.36–4.02 (3H, m), 6.32–7.78 (10H, m), 8.55 (1H, brs)
Isomer B
$[\alpha]_D^{22}=0°$ (chloroform, c=1.0)
¹H-NMR (CDCl₃) δ; 1.03 (3H, d, J=6.5 Hz), 1.39 (1H, brs), 2.14–2.39 (1H, m), 2.45 (3H, s), 3.34–3.98 (3H, m), 6.53–7.98 (10H, m), 8.78 (1H, brs)

284) ¹H-NMR (CDCl₃) δ; 1.05–1.25 (3H, m), 1.25–2.80 (10H, m), 3.00–5.10 (3H, m), 6.75–8.40 (11H, m)

285) ¹H-NMR (CDCl₃) δ; 1.00–2.80 (12H, m), 3.00–5.10 (3H, m), 6.70–7.80 (10H, m), 8.30–8.80 (1H, m)

286) ¹H-NMR (CDCl₃) δ; 0.95–2.80 (15H, m), 2.80–5.15 (3H, m), 6.70–7.05 (2H, m), 7.10–7.80 (10H, m), 7.95–8.45 (1H, m)

287) ¹H-NMR (CDCl₃) δ; 0.80–2.60 (16H, m), 2.60–5.05 (4H, m), 6.70–7.70 (10H, m), 7.85–8.40 (1H, m)

288) ¹H-NMR (CDCl₃) δ; 1.30–2.60 (8H, m), 2.60–5.10 (3H, m), 6.60–7.95 (10H, m), 8.25–8.70 (1H, m)

289) ¹H-NMR (CDCl₃) δ; 1.27–4.91 (19H, m), 6.68–7.73 (10H, m), 8.40–8.71 (1H, m)

290) ¹H-NMR (CDCl₃) δ; 1.81–2.54 (6H, m), 2.15 (3H, s), 2.41 (3H, s), 2.46 (3H, s), 3.61–3.71 (3H, m), 6.91–7.43 (10H, m), 8.60 (1H, s)

291) ¹H-NMR (CDCl₃) δ; 1.86–2.50 (3H, m), 2.28 (9H, s), 2.49 (3H, s), 6.60–7.47 (10H, m), 7.75 (1H, m)

292) ¹H-NMR (CDCl₃) δ; 1.15–2.55 (13H, m), 2.55–5.10 (3H, m), 6.60–8.40 (11H, m)

293) ¹H-NMR (CDCl₃) δ; 1.15–2.45 (10H, m), 2.55–5.10 (3H, m), 6.60–7.80 (10H, m), 8.30–8.70 (1H, m)

294) $^1$H-NMR (CDCl$_3$) δ; 1.10–2.60 (4H, m), 2.41 (6H, s), 2.49 (3H, s), 3.76 (3H, s), 2.60–5.20 (3H, m), 6.50–6.80 (3H, m), 6.90–7.60 (6H, m), 8.13 (1H, s), 8.30 (1H, d, J=8.5 Hz)

295) $^1$H-NMR (CDCl$_3$) δ; 1.15–2.50 (4H, m), 2.41 (6H, s), 2.60–5.20 (3H, m), 3.77 (3H, s), 6.50–7.50 (8H, m), 7.65–7.80 (1H, m), 8.31 (1H, d, J=8.4 Hz), 8.61 (1H, s)

296) $^1$H-NMR (CDCl$_3$) δ; 1.55–3.13 (12H, m), 2.44 (3H, s), 4.60–5.14 (2H, m), 6.28 (1H, dd, J=2.5, 8.5 Hz), 6.48 (1H, d, J=8.5 Hz), 6.99 (1H, d, J=2.5 Hz), 7.07–7.58 (8H, m), 7.80 (1H, brs)

297) $^1$H-NMR (CDCl$_3$) δ; 1.01–2.88, 3.22–4.41, 4.90–5.28 [total 18H, 1.17 (3H, t, J=7.2 Hz), 2.40 (3H, s), 3.77 (3H, s)], 6.55 (1H, d, J=8.1 Hz), 6.60–7.98 (8H, m), 8.23–8.75 (2H, m)

298) $^1$H-NMR (CDCl$_3$) δ; 1.00–3.04, 3.24–4.45, 4.91–5.27 [total 21H, m, 1.17 (3H, t, J=7.0 Hz), 2.39 (3H, s), 2.50 (3H, s), 3.75 (3H, s)], 8.56 (1H, d, J=8.3 Hz), 6.69 (1H, d, J=8.3 Hz), 6.82–7.75 (7H, m), 8.05–8.49 (2H, m)

299) $^1$H-NMR (CDCl$_3$) δ; 1.21–4.62, 4.90–5.43 (total 15H, m), 5.70–6.11 (1H, m), 6.35–7.90 (9H, m), 8.07–8.92 (2H, m)

300) $^1$H-NMR (CDCl$_3$) δ; 1.20–4.68, 5.01–5.3 [total 18H, m, 2.50 (3H, s)], 5.72–6.14 (1H, m), 6.49–7.69 (9H, m), 8.01–8.58 (2H, m)

301) $^1$H-NMR (CDCl$_3$) δ; 1.25–2.80 (14H, m), 3.00–5.10 (6H, m), 6.40–8.00 (11H, m)

302) $^1$H-NMR (CDCl$_3$) δ; 1.30–2.90 (11H, m), 3.00–5.10 (6H, m), 6.40–7.80 (10H, m), 8.00–8.35 (1H, m)

303) $^1$H-NMR (CDCl$_3$) δ; 1.10–2.80 (16H, m), 2.85–5.15 (6H, m), 6.40–7.80 (11H, m)

304) $^1$H-NMR (CDCl$_3$) δ; 1.10–2.80 (13H, m), 2.90–5.10 (6H, m), 6.40–7.85 (10H, m), 7.90–8.20 (1H, m)

305) $^1$H-NMR (CDCl$_3$) δ; 1.27–5.28 (19H, m), 3.75 (3H, s), 6.51 (1H, d, J=7.9 Hz), 6.69–6.81 (2H, m), 7.05–7.49 (6H, m), 8.14 (1H, m), 8.27 (1H, d, J=8.4 Hz)

306) Two stereoisomers: Both colorless amorphous
Isomer A
$[\alpha]_D^{22}$=0° (chloroform, c=1.0)
$^1$H-NMR (CDCl$_3$) δ; 0.78–1.02 (3H, m), 2.23–2.52 (1H, m), 2.39 (6H, s), 2.48 (3H, s), 3.17–4.30 (3H, m), 6.85–7.84 (10H, m), 8.17 (1H, brs)
Isomer B
$[\alpha]_D^{22}$=0° (chloroform, c=1.0)
$^1$H-NMR (CDCl$_3$) δ; 0.73–1.00 (3H, m), 2.17–2.52 (1H, m), 2.39 (6H, s), 2.49 (3H, s), 3.15–4.33 (3H, m), 6.36–7.55 (8H, m), 7.58–7.83 (2H, m), 8.19 (1H, brs)

307) $^1$H-NMR (CDCl$_3$) δ; 1.25–4.44, 4.98–5.41 [total 17H, m, 2.40 (3H, s), 3.76 (3H, s)], 5.72–6.13 (1H, m), 6.56 (1H, d, J=8.4 Hz), 6.69 (1H, d, J=7.9 Hz), 6.77–7.93 (7H, m), 8.32 (1H, d, J=8.3 Hz), 8.49–8.95 (1H, m)

308) $^1$H-NMR (CDCl$_3$) δ; 1.23–5.42 (20H, m), 5.78–6.09 (1H, m), 6.56 (1H, d, J=8.3 Hz), 6.61–7.82 (8H, m), 8.14 (1H, s), 8.30 (1H, d, J=8 Hz)

309) $^1$H-NMR (CDCl$_3$) δ; 1.20–2.70 (11H, m), 2.80–4.90 (9H, m), 6.40–7.70 (10H, m), 8.30–8.70 (1H, m)

310) $^1$H-NMR (CDCl$_3$) δ; 1.20–2.80 (8H, m), 2.85–5.05 (9H, m), 6.40–7.80 (10H, m), 8.10–8.50 (1H, m)

311) $^1$H-NMR (CDCl$_3$) δ; 1.20–2.75 (13H, m), 2.80–5.10 (9H, m), 6.40–8.00 (11H, m)

312) $^1$H-NMR (CDCl$_3$) δ; 1.20–2.80 (10H, m), 2.90–5.10 (9H, m), 6.40–7.80 (10H, m), 8.00–8.40 (1H, m)

Example 1189

By using di-p-toluoyl-L-tartaric acid monohydride or di-p-toluoyl-D-tartaric acid monohydride, the compound obtained in above Example 408 is optically resolved to give the following compounds.

(+)-5-Dimethylamino-1-[4-(2-methylbenzoylamino) benzoyl]-2,3,4,5-tetrahydro-1H-benzazepine hydrochloride
White amorphous $[\alpha]_D^{25}$=+234° (methanol, c=0.2)
Purity; more than 99% ee, determined by HPLC using an optical active column HPLC conditions;
Mobile phase; n-hexane:ethanol:diethylamine=950:50:1
Flow rate; 1.0 ml/min.
Column; CHIRALCEL OD, 25 cm×0.46 cm (manufactured by Daicel Chemical Ind. Ltd.)
Concentration of sample; 0.1% in methanol
Retention time; 34 minutes $^1$H-NMR (DMSO-d$_6$) δ; 0.85–1.20, 1.56–4.06, 4.94–5.21 (total 13H, m), 2.36 (3H, s), 6.79 (1H, d, J=7.6 Hz), 7.12–7.60 (8H, m), 7.62 (2H, d, J=8.4 Hz), 8.00 (1H, d, J=7.6 Hz), 10.43 (1H, s), 11.80 (1H, brs)

(−)-5-Dimethylamino-1-[4-(2-methylbenzoylamino) benzoyl]-2,3,4,5-tetrahydro-1H-benzazepine hydrochloride White amorphous $[\alpha]_D^{25}$=−23.1° (methanol, c=0.2)
Purity; more than 99% ee, determined by HPLC using an optical active column, and the conditions are the same as above except that the retention time is 40 minutes.

$^1$H-NMR (DMSO-d$_6$) δ; 0.83–1.19, 1.55–4.06, 4.94–5.20 (total 13H, m), 2.36 (3H, s), 6.80 (1H, d, J=7.8 Hz), 7.12–7.60 (8H, m), 7.63 (2H, d, J=8.5 Hz), 8.00 (1H, d, J=7.8 Hz), 10.44 (1H, s), 11.74 (1H, brs)

Pharmacological Test

Experiment 1: V$_1$ receptor binding assay

Using rat liver plasma membrane preparations prepared according to Ichihara's method [cf: Akira Ichihara, J. Bio. Chem., 258, 9283 (1983)], the plasma membrane ((50000 dpm, 2×10$^{-10}$M) of [$^3$H]-Arg-vasopressin and a test compound (60 μg, 10$^{-8}$–10$^{-4}$M) are incubated at 37° C. for 10 minutes in 100 mM Tris-HCl buffer (pH: 8.0, 250 μl) containing 5 mM MgCl$_2$, 1 mM EDTA and 0.1% BSA. After incubation, the mixture is filtered three times using the glass filter (GF/F) so as to separate the membrane preparation combined with vasopressin and then washed with the buffer (5 ml). This glass filter is taken out and mixed with liquid scintillation cocktail. The amount of [$^3$H]-vasopressin combined with the membrane is measured by liquid scintillation counter and the rate of the inhibitory effect of the test compound is estimated according to the following equation.

$$\text{Rate of the inhibitory effect (\%)} = 100 - \frac{C_1 - B_1}{C_0 - B_1} \times 100$$

C$^1$: The amount of [$^3$H]-vasopressin combined with the membrane in the presence of the test compound (in prescribed amount).

C$^0$: The amount of [$^3$H]-vasopressin combined with the membrane in the absence of the test compound.

B$^1$: The amount of ($^3$H]-vasopressin combined with the membrane in the presence of the excess amount of vasopressin (10$^{-6}$M).

The results are expressed as IC$_{50}$ values, which is the concentration of the test compound required to achieve the inhibitory effect in the rate of 50%.

The results are shown in the following Table 10.
Test compound
1. 1-(4-Benzoylaminobenzoyl)-1,2,3,4-tetrahydroquinoline
2. 1-[4-(3-Chlorobenzoylamino)benzoyl]-1,2,3,4-tetrahydroquinoline
3. 1-[4-(3-Methoxybenzoylamino)benzoyl]-1,2,3,4-tetrahydroquinoline
4. 1-[4-(3-Cyanobenzoylamino)benzoyl]-1,2,3,4-tetrahydroquinoline 5. 1-[4-(3-Aminobenzoylamino)benzoyl]-1,2,3,4-tetrahydroquinoline
6. 1-[4-(2,3-Dimethylbenzoylamino)benzoyl]-1,2,3,4-tetrahydroquinoline
7. 1-[4-(2-Methylbenzoylamino)benzoyl]-1,2,3,4-tetrahydroquinoline
8. 1-[4-(2-Trifluoromethylbenzoylamino)benzoyl]-1,2,3,4-tetrahydroquinoline
9. 1-[4-(2-Nitrobenzoylamino)benzoyl]-1,2,3,4-tetrahydroquinoline
10. 1-[4-(3,5-Dichlorobenzoylamino)benzoyl]-1,2,3,4-tetrahydroquinoline
11. 1-[4-(3,3-Dimethylbutyrylamino)benzoyl]-1,2,3,4-tetrahydroquinoline
12. 1-[4-(2-Cyclohexylacetylamino)benzoyl]-1,2,3,4-tetrahydroquinoline
13. 1-[4-(2-Phenylacetylamino)benzoyl]-1,2,3,4-tetrahydroquinoline
14. 1-(4-Cyclohexylcarbonylaminobenzoyl)-1,2,3,4-tetrahydroquinoline
15. 1-(4-Cycloheptylcarbonylaminobenzoyl)-1,2,3,4-tetrahydroquinoline
16. 1-(4-Cyclooctylcarbonylaminobenzoyl)-1,2,3,4-tetrahydroquinoline
17. 1-(4-Tricyclo[3.3.1.1]decanylcarbonylaminobenzoyl)-1,2,3,4-tetrahydroquinoline
18. 1-(4-(α-Naphthylcarbonylamino)benzoyl]-1,2,3,4-tetrahydroquinoline
19. 1-[4-(3-Thenoyl)benzoyl]-1,2,3,4-tetrahydroquinoline
20. 1-[2-(β-Naphthylcarbonylamino)benzoyl]-1,2,3,4-tetrahydroquinoline
21. 1-[4-(4-Methoxyanilinocarbonyl)benzoyl]-1,2,3,4-tetrahydroquinoline
22. 1-[4-(2-Methylanilinocarbonyl)benzoyl]-1,2,3,4-tetrahydroquinoline
23. 1-[4-(3-Chloroanilinocarbonyl)benzoyl]-1,2,3,4-tetrahydroquinoline
24. 1-[4-(3,5-Dichloroanilinocarbonyl)benzoyl]-1,2,3,4-tetrahydroquinoline
25. 1-(4-Cyclohexylaminocarbonylbenzoyl)-1,2,3,4-tetrahydroquinoline
26. 1-(4-Cyclohexylcarbonylaminobenzoyl)-2,3,4,5-tetrahydro-1H-benzazepine
27. 1-(4-Benzoylaminobenzoyl)-2,3,4,5-tetrahydro-1H-benzazepine
28. 1-[4-(2-Methylbenzoylamino)benzoyl]-2,3,4,5-tetrahydro-1H-benzazepine
29. 1-[4-(3-Methoxybenzoylamino)benzoyl]-2,3,4,5-tetrahydro-1H-benzazepine
30. 1-[4-(3-Chlorobenzoylamino)benzoyl]-2,3,4,5-tetrahydro-1H-benzazepine
31. 1-[4-(3-Cyanobenzoylamino)benzoyl]-2,3,4,5-tetrahydro-1H-benzazepine
32. 1-[4-(3,5-Dichlorobenzoylamino)benzoyl]-2,3,4,5-tetrahydro-1H-benzazepine
33. 1-[4-(2,3-Dimethylbenzoylamino)benzoyl]-2,3,4,5-tetrahydro-1H-benzazepine
34. 1-(4-Cyclohexylcarbonylaminobenzoyl)-1,2,3,4,5,6-hexahydrobenzazocine
35. 1-(4-Benzoylaminobenzoyl)-1,2,3,4,5,6-hexahydrobenzazocine
36. 1-[4-(2-Methylbenzoylamino)benzoyl]-1,2,3,4,5,6-hexahydrobenzazocine
37. 1-[4-(3-Methoxybenzoylamino)benzoyl]-1,2,3,4,5,6-hexahydrobenzazocine
38. 1-[4-(2,3-Dimethylbenzoylamino)benzoyl]-1,2,3,4,5,6-hexahydrobenzazocine
39. 1-[4-(3,5-Dichlorobenzoylamino)benzoyl]-1,2,3,4,5,6-hexahydrobenzazocine
40. 1-(4-Cyclohexylcarbonylaminobenzoyl)-1,2,3,5-tetrahydro-4,1-benzoxazepine
41. 1-(4-(3-Methylbenzoylamino)benzoyl)-1,2,3,5-tetrahydro-4,1-benzoxazepine
42. 1-[4-(2,3-Dimethylbenzoylamino)benzoyl]-1,2,3,5-tetrahydro-4,1-benzoxazepine
43. 1-[4-(3,5-Dichlorobenzoylamino)benzoyl]-1,2,3,5-tetrahydro-4,1-benzoxazepine
44. 3-Methyl-1-(4-cyclohexylcarbonylaminobenzoyl)-1,2,3,4-tetrahydroquinoline
45. 3-Methyl-1-(4-benzoylaminobenzoyl)-1,2,3,4-tetrahydroquinoline
46. 3-Methyl-1-[4-(2-methylbenzoylamino)benzoyl]-1,2,3,4-tetrahydroquinoline
47. 3-Methyl-1-[4-(3-methoxybenzoylamino)benzoyl]-1,2,3,4-tetrahydroquinoline
48. 3-Methyl-1-[4-(2,3-dimethylbenzoylamino)-benzoyl]-1,2,3,4-tetrahydroquinoline
49. 3-Methyl-1-[4-(3,5-dichlorobenzoylamino)-benzoyl]-1,2,3,4-tetrahydroquinoline
50. 4-Methyl-1-(4-cyclohexylcarbonylaminobenzoyl)-1,2,3,4-tetrahydroquinoxaline
51. 4-Methyl-1-[4-(2-methylbenzoylamino)benzoyl]-1,2,3,4-tetrahydroquinoxaline
52. 4-Methyl-1-[4-(2,3-dimethylbenzoylamino)-benzoyl]-1,2,3,4-tetrahydroquinoxaline
53. 4-Methyl-1-[4-(3,5-dichlorobenzoylamino)-benzoyl]-1,2,3,4-tetrahydroquinoxaline
54. 2-Methyl-1-[4-(3,5-dichlorobenzoylamino)-benzoyl]-1,2,3,4-tetrahydroquinoline
55. 4-Methyl-1-[4-(3,5-dichlorobenzoylamino)-benzoyl]-1,2,3,4-tetrahydroquinoline
56. 1-[4-(2-Bromobenzoylamino)benzoyl]-2,3,4,5-tetrahydro-1H-benzazepine
57. 1-[4-(3-Nitrobenzoylamino)benzoyl]-2,3,4,5-tetrahydro-1H-benzazepine
58. 1-[4-(3-Trifluoromethylbenzoylamino)benzoyl]-2,3,4,5-tetrahydro-1H-benzazepine
59. 1-[4-(3-Ethoxybenzoylamino)benzoyl]-2,3,4,5-tetrahydro-1H-benzazepine
60. 1-[4-(3,5-Dimethoxybenzoylamino)benzoyl]-2,3,4,5-tetrahydro-1H-benzazepine
61. 1-[4-(2-Chloro-4-nitrobenzoylamino)benzoyl]-2,3,4,5-tetrahydro-1H-benzazepine
62. 1-[4-(2,4-Dichlorobenzoylamino)benzoyl]-2,3,4,5-tetrahydro-1H-benzazepine
63. 1-[4-(2-Chloro-6-fluorobenzoylamino)benzoyl]-2,3,4,5-tetrahydro-1H-benzazepine
64. 1-[4-(2,6-Dimethylbenzoylamino)benzoyl]-2,3,4,5-tetrahydro-1H-benzazepine
65. 1-[4-(2-Chloro-4-aminobenzoylamino)benzoyl]-2,3,4,5-tetrahydro-1H-benzazepine
66. 1-[4-(2-Chloro-4-acetylaminobenzoylamino)benzoyl]-2,3,4,5-tetrahydro-1H-benzazepine 67. 1-[4-(3-Aminobenzoylamino)benzoyl]-2,3,4,5-tetrahydro-1H-benzazepine
68. 1-{4-[2-(4-Isopropylaminobutoxy)benzoylamino]benzoyl}-2,3,4,5-tetrahydro-1H-benzazepine hydrochloride
69. 1-[4-(3-Hydroxybenzoylamino)benzoyl]-2,3,4,5-tetrahydro-1H-benzazepine
70. 1-{4-[2-(4-Aminobutoxy)benzoylamino]benzoyl}-2,3,4,5-tetrahydro-1H-benzazepine
71. 1-{4-[2-(2-Diethylaminoethoxy)benzoylamino]benzoyl}-2,3,4,5-tetrahydro-1H-benzazepine hydrochloride
72. 1-{4-[2-(4-Acetylaminobutoxy)benzoylamino]benzoyl}-2,3,4,5-tetrahydro-1H-benzazepine
73. 1-{4-[2-(6-Phthalimidohexyloxy)benzoylamino]benzoyl}-2,3,4,5-tetrahydro-1H-benzazepine
74. 1-{4-[2-(6-Morpholinohexyloxy)benzoylamino]benzoyl}-2,3,4,5-tetrahydro-1H-benzazepine
75. 1-{4-[2-(6-[4-Methyl-1-piperazinyl]hexyloxy)benzoylamino]benzoyl}-2,3,4,5-tetrahydro-1H-benzazepinedihydrochloride
76. 1-(3-Methoxy-4-cyclohexylcarbonylaminobenzoyl)-2,3,4,5-tetrahydro-1H-benzazepine
77. 1-(3-methoxy-4-benzoylamino)benzoyl]-2,3,4,5-tetrahydro-1H-benzazepine
78. 1-[3-Methyl-4-(2-methylbenzoylamino)benzoyl]-2,3,4,5-tetrahydro-1H-benzazepine
79. 4-Methyl-1-(4-cyclohexylcarbonylaminobenzoyl)-2,3,4,5-tetrahydro-1H-1,4-benzodiazepine hydrochloride
80. 4-Methyl-1-[4-(3,5-dichlorobenzoylamino)benzoyl]-2,3,4,5-tetrahydro-1H-1,4-benzodiazepine hydrochloride
81. 4-Methyl-1-[4-(2,3-dimethylbenzoylamino)benzoyl]-2,3,4,5-tetrahydro-1H-1,4-benzodiazepine hydrochloride
82. 4-Methyl-1-[4-(2-methylbenzoylamino)benzoyl]-2,3,4,5-tetrahydro-1H-1,4-benzodiazepine hydrochloride
83. 4-Methyl-1-[4-(3-methoxybenzoylamino)benzoyl]-2,3,4,5-tetrahydro-1H-1,4-benzodiazepine
84. 4-Methyl-1-[4-(3-chlorobenzoylamino)benzoyl]-2,3,4,5-tetrahydro-1H-1,4-benzodiazepine
85. 4-Methyl-1-[4-(2,3,5-trichlorobenzoylamino)benzoyl]-2,3,4,5-tetrahydro-1H-1,4-benzodiazepine
86. 4-Propyl-1-[4-(2,3-dimethylbenzoylamino)benzoyl]-2,3,4,5-tetrahydro-1H-1,4-benzodiazepine hydrochloride
87. 5-Methyl-1-(4-benzoylaminobenzoyl)-2,3,4,5-tetrahydro-1H-1,5-benzodiazepine
88. 5-Methyl-1-(4-cyclohexylcarbonylaminobenzoyl)-2,3,4,5-tetrahydro-1H-1,5-benzodiazepine
89. 5-Methyl-1-[4-(3,5-dichlorobenzoylamino)benzoyl]-2,3,4,5-tetrahydro-1H-1,5-benzodiazepine
90. 5-Methyl-1-[4-(2-methylbenzoylamino)benzoyl]-2,3,4,5-tetrahydro-1H-1,5-benzodiazepine
91. 5-Methyl-1-[4-(2,3-dimethylbenzoylamino)benzoyl]-2,3,4,5-tetrahydro-1H-1,5-benzodiazepine
92. 4-Methyl-1-[3-methoxy-4-(3,5-dichlorobenzoylamino)benzoyl]-2,3,4,5-tetrahydro-1H-1,4-benzodiazepine
93. 3-(1-Pyrrolidinyl)-1-[4-(2,3-dimethylbenzoylamino)benzoyl]-1,2,3,4-tetrahydroquinoline
94. 6-Methyl-1-[4-(3,5-dichlorobenzoylamino)benzoyl]-1,2,3,4-tetrahydroquinoline
95. 6-Methoxy-1-[4-(3,5-dichlorobenzoylamino)benzoyl]-1,2,3,4-tetrahydroquinoline
96. 3-Hydroxymethyl-1-[4-(3,5-dichlorobenzoylamino)benzoyl]-1,2,3,4-tetrahydroquinoline
97. 4-Methylamino-1-[4-(3,5-dichlorobenzoylamino)benzoyl]-1,2,3,4-tetrahydroquinoline
98. 3-Amino-1-[4-(3,5-dichlorobenzoylamino)benzoyl]-1,2,3,4-tetrahydroquinoline
99. 3-Acetylamino-1-[4-(3,5-dichlorobenzoylamino)benzoyl]-1,2,3,4-tetrahydroquinoline
100. 4-Dimethylamino-1-[4-(3,5-dichlorobenzoylamino)benzoyl]-1,2,3,4-tetrahydroquinoline
101. 1-[4-(2-t-Butylaminoacetylamino)benzoyl]-2,3,4,5-tetrahydroquinoline-1H-benzazepine
102. 1-{4-[2-(N-Cyclohexyl-N-ethyl)acetylamino]benzoyl}-2,3,4,5-tetrahydro-1H-benzazepine
103. 1-{4-[2-(1-Piperidinyl)acetylamino]benzoyl}-2,3,4,5-tetrahydro-1H-benzazepine
104. 1-[4-(2-Phenoxyacetylamino)benzoyl]-2,3,4,5-tetrahydro-1H-benzazepine
105. 1-[4-(2-Phthalimidoacetylamino)benzoyl]-2,3,4,5-tetrahydro-1H-benzazepine
106. 1-{4-[2-(1,1-Dimethyl-2-phenoxyethyl)aminoacetylamino]benzoyl)-2,3,4,5-tetrahydro-1H-benzazepine
107. 1-{4-[2-(3-Methylphenoxy)acetylamino]benzoyl}-2,3,4,5-tetrahydro-1H-benzazepine
108. 1-{4-[2-(3-Methoxyanilino)acetylamino]benzoyl}-2,3,4,5-tetrahydro-1H-benzazepine
109. 1-{4-[2-(β-Naphthyloxy)acetyamino]benzoyl}-2,3,4,5-tetrahydro-1H-benzazepine
110. 1-{4-[2-(4-Methylanilino)acetylamino]benzoyl}-2,3,4,5-tetrahydro-1H-benzazepine
111. 1-{4-[2-(3-Methoxyphenoxy)acetylamino]benzoyl}-2,3,4,5-tetrahydro-1H-benzazepine
112. 1-[4-(4-Pyridylcarbonylaminobenzoyl]-2,3,4,5-tetrahydro-1H-benzazepine
113. 1-{4-[2-(2,4-Dimethylanilino)acetylamino]benzoyl}-2,3,4,5-tetrahydro-1H-benzazepine
114. 1-{4-[2-(N-Ethylanilino)acetylamino]benzoyl}-2,3,4,5-tetrahydro-1H-benzazepine
115. 1-{4-[2-(N-Allylanilino)acetylamino]benzoyl}-2,3,4,5-tetrahydro-1H-benzazepine
116. 1-{4-[2-(2-Chloroanilino)acetylamino]benzoyl}-2,3,4,5-tetrahydro-1H-benzazepine
117. 1-{4-[2-(4-Acetyloxybutoxy)benzoylamino]benzoyl}-2,3,4,5-tetrahydro-1H-benzazepine
118. 1-[4-(2-Carboxymethoxybenzoylamino)benzoyl]-2,3,4,5-tetrahydro-1H-benzazepine
119. 1-[4-(2-Carbamoylmethoxybenzoylamino)benzoyl]-2,3,4,5-tetrahydro-1H-benzazepine
120. 1-{4-[2-(4-Hydroxybutoxy)benzoylamino]benzoyl}-2,3,4,5-tetrahydro-1H-benzazepine
121. 1-[4-(2-Ethoxycarbonylmethoxybenzoylamino)benzoyl]-2,3,4,5-tetrahydro-1H-benzazepine
122. 6-Fluoro-1-[4-(3,5-dichlorobenzoylamino)benzoyl]-1,2,3,4-tetrahydroquinoline
123. 6-Fluoro-1-{4-[di-(3,5-dichlorobenzoyl)amino]benzoyl}-1,2,3,4-tetrahydroquinoline
124. 1-[4-(2-Diethylaminocarbonylmethoxybenzoylamino)benzoyl]-2,3,4,5-tetrahydro-1H-benzazepine
125. 1-{4-[2-(2-[(N-(2-hydroxyethyl)-N-methylamino]ethoxy)benzoylamino]benzoyl}-2,3,4,5-tetrahydro-1H-benzoazepine hydrochloride 126. 1-[4-(2-Methylanilinocarbonylamino)benzoyl]-2,3,4,5-tetrahydro-1H-benzazepine
127. 1-[4-(2-Chlorophenylsulfonylamino)benzoyl]-2,3,4,5-tetrahydro-1H-benzazepine
128. 1-{4-[2-(4-Aminomethylanilino)acetylamino]benzoyl}-2,3,4,5-tetrahydro-1H-benzazepine
129. 1-{4-[2-(N-Phenyl-N-(3-acetylaminopropyl)amino)acetylamino]benzoyl}-2,3,4,5-tetrahydro-1H-benzazepine
130. 1-{4-[2-(N-Phenyl-N-propargylamino)acetylamino]benzoyl}-2,3,4,5-tetrahydro-1H-benzazepine
131. 4-(N-Methyl-N-ethylamino)-1-[4-(3,5-dichlorobenzoylamino)benzoyl]-1,2,3,4-tetrahydroquinoline
132. 5-Dimethylamino-1-[4-(2,4-dichlorobenzoylamino)benzoyl]-2,3,4,5-tetrahydro-1H-benzazepine
133. 4-Dimethylamino-1-[3-methoxy-4-(2-methylbenzoylamino)benzoyl]-1,2,3,4-tetrahydroquinoline
134. 5-Dimethylamino-1-[3-methoxy-4-(2-chlorobenzoylamino)benzoyl]-2,3,4,5-tetrahydro-1H-benzazepine
135. 1-[4-(2,3-Dimethylbenzoylamino)benzoyl]-4-ethyl-2,3,4,5-tetrahydro-1H-1,4-benzodiazepine
136. 1-[4-(3,5-Dichlorobenzoylamino)benzoyl]-4-isopropyl-2,3,4,5-tetrahydro-1H-1,4-benzodiazepine
137. 1-[4-(2-Methylbenzoylamino)benzoyl]-5-methyl-1,2,3,4,5,6-hexahydro-1,5-benzodiazocine
138. 1-[4-(2-Methylbenzoylamino)benzoyl]-1,2,3,4-tetrahydro-5,1-benzoxazepine
139. 5-Oxo-1-[4-(3,5-dichlorobenzoylamino)benzoyl]-2,3,4,5-tetrahydro-1H-benzazepine
140. 4-Methyl-1-[2-chloro-4-(3,5-dichlorobenzoylamino)benzoyl]-2,3,4,5-tetrahydro-1H-1,4-benzodiazepine
141. 5-Methylamino-1-[4-(3,5-dichlorobenzoylamino)benzoyl]-2,3,4,5-tetrahydro-1H-benzazepine
142. 5-(N-Acetyl-N-methylamino)-1-[4-(3,5-dichlorobenzoylamino)benzoyl]-2,3,4,5-tetrahydro-1H-benzazepine
143. 5-Hydroxy-1-[4-(2-methylbenzoylamino)benzoyl]-2,3,4,5-tetrahydro-1H-benzazepine
144. 4-Dimethylamino-1-[3-methoxy-4-(2,3-dimethylbenzoylamino)benzoyl]-1,2,3,4-tetrahydroquinoline
145. 4-Dimethylaminomethyl-1-[4-(2-methylbenzoylamino)benzoyl]-1,2,3,4-tetrahydroquinoline
146. 4-Dimethylaminomethyl-1-[4-(3,5-dichlorobenzoylamino)benzoyl]-1,2,3,4-tetrahydroquinoline
147. 5-Methoxy-1-[4-(2-methylbenzoylamino)benzoyl]-2,3,4,5-tetrahydro-1H-benzazepine
148. 4-Methyl-1-[3-methyl-4-(2,4-dichlorobenzoylamino)benzoyl]-2,3,4,5-tetrahydro-1H-1,4-benzodiazepine
149. 5-Methoxy-1-[4-(2,4-dichlorobenzoylamino)benzoyl]-2,3,4,5-tetrahydro-1H-benzazepine
150. 4-Dimethylamino-1-[4-(2-chlorobenzoylamino)benzoyl]-2,3,4,5-tetrahydro-1H-benzazepine
151. 4-Acetyloxy-1-[4-(2-methylbenzoylamino)benzoyl]-1,2,3,4-tetrahydroquinoline
152. 5-Hydroxyimino-1-[4-(3,5-dichlorobenzoylamino)benzoyl]-2,3,4,5-tetrahydro-1H-benzazepine
153. 5-Acetyloxy-1-[4-(2-chlorobenzoylamino)benzoyl]-2,3,4,5-tetrahydro-1H-benzazepine
154. 5-Ethoxycarbonylmethoxy-1-[4-(2,4-dichlorobenzoylamino)benzoyl]-2,3,4,5-tetrahydro-1H-benzazepine
155. 4-Allylamino-1-[4-(3,5-dichlorobenzoylamino)benzoyl]-2,3,4,5-tetrahydro-1H-benzazepine
156. 5-Dimethylamino-1-[3-methoxy-4-(2,3,5-trichlorobenzoylamino)benzoyl]-2,3,4,5-tetrahydro-1H-benzazepine
157. 4-[4-(2-Methylbenzoylamino)benzoyl]-3,4-dihydro-2H-1,4-benzothiazine
158. 5-Dimethylamino-1-[2-chloro-4-(2-methylbenzoylamino)benzoyl]-2,3,4,5-tetrahydro-1H-benzazepine
159. 5-Dimethylamino-1-[4-(2-methylanilinocarbonyl)benzoyl]-2,3,4,5-tetrahydro-1H-benzazepine
160. 5-Ethoxycarbonylmethoxy-1-[4-(2-methylbenzoylamino)benzoyl]-2,3,4,5-tetrahydro-1H-benzazepine
161. 5-(4-dimethylaminobutoxy)-1-[4-(2-methylbenzoylamino)benzoyl]-2,3,4,5-tetrahydro-1H-benzazepine
162. 5-Carboxymethoxy-1-[4-(2-chlorobenzoylamino)benzoyl]-2,3,4,5-tetrahydro-1H-benzazepine
163. 5-Dimethylaminocarbonylmethoxy-1-[4-(2-methylbenzoylamino)benzoyl]-2,3,4,5-tetrahydro-1H-benzazepine
164. 5-Carbamoylmethoxy-1-[4-(2-chlorobenzoylamino)benzoyl]-2,3,4,5-tetrahydro-1H-benzazepine
165. 5-Dimethylamino-1-[3-ethoxy-4-(2-methylbenzoylamino)benzoyl]-2,3,4,5-tetrahydro-1H-benzazepine
166. 5-[4-(2-Methylbenzoylamino)benzoyl]-2,3,4,5-tetrahydro-1,5-benzothiazepine
167. 5-Amino-1-[4-(2-methylbenzoylamino)benzoyl]-2,3,4,5-tetrahydro-1H-benzazepine
168. 5-Dimethylamino-1-[3-hydroxy-4-[2-methylbenzoylamino)benzoyl]-2,3,4,5-tetrahydro-1H-benzazepine
169. 5-n-Propylamino-1-[4-(2,4-dichlorobenzoylamino)benzoyl]-2,3,4,5-tetrahydro-1H-benzazepine
170. 5-Dimethylamino-1-[3-benzyloxy-4-(2-methylbenzoylamino)benzoyl]-2,3,4,5-tetrahydro-1H-benzazepine
171. 5-[4-(2-Methylbenzoylamino)benzoyl]-2,3,4,5-tetrahydro-1,5-benzothiazepin-1-oxide
172. 5-[3-(Phthalimid-1-yl)-propoxy]-1-[4-(2-methylbenzoylamino)benzoyl]-2,3,4,5-tetrahydro-1H-benzazepine
173. 5-(3-Aminopropoxy)-1-[4-(2-methylbenzoylamino)benzoyl]-2,3,4,5-tetrahydro-1H-benzazepine
174. 5-(3-Acetylaminopropoxy)-1-[4-(2-methylbenzoylamino)benzoyl]-2,3,4,5-tetrahydro-1H-benzazepine
175. 5-Dimethylamino-1-[2-chloro-4-(2-t-butylbenzoylamino)benzoyl]-2,3,4,5-tetrahydro-1H-benzazepine
176. 5-Methylamino-1-[2-chloro-4-(2-chlorobenzoylamino)benzoyl]-2,3,4,5-tetrahydro-1H-benzazepine
177. 5-Dimethylamino-1-[2-methoxy-4-(2-chlorobenzoylamino)benzoyl]-2,3,4,5-tetrahydro-1H-benzazepine 178. 5-Hydroxy-1-[4-(3,5-dichlorobenzoylamino)benzoyl]-2,3,4,5-tetrahydro-1H-benzazepine
179. 5-Dimethylamino-1-[4-(2-methylbenzoylamino)benzoyl]-2,3,4,5-tetrahydro-1H-benzazepine
180. 5-Dimethylamino-1-[4-(2-chlorobenzoylamino)benzoyl]-2,3,4,5-tetrahydro-1H-benzazepine
181. 5-Methylamino-1-[4-(2-chlorobenzoylamino)benzoyl]-2,3,4,5-tetrahydro-1H-benzazepine
182. 5-Methylamino-1-[2-chloro-4-(2-methylbenzoylamino)benzoyl]-2,3,4,5-tetrahydro-1H-benzazepine
183. 5-Dimethylamino-1-[2-methoxy-4-(2-methylbenzoylamino)benzoyl]-2,3,4,5-tetrahydro-1H-benzazepine
184. 5-Dimethylamino-1-[2-chloro-4-(2-chlorobenzoylamino)benzoyl]-2,3,4,5-tetrahydro-1H-benzazepine
185. 5-Methylamino-1-[2-chloro-4-(2-methylbenzoylamino)benzoyl-2,3,4,5-tetrahydro-1H-benzazepine
186. 5-Cyclopropylamino-1-[2-chloro-4-(2,4-dichlorobenzoylamino)benzoyl]-2,3,4,5-tetrahydro-1H-benzazepine
187. 5-Dimethylaminocarbonyloxy-1-[4-(2-methylbenzoylamino)benzoyl]-2,3,4,5-tetrahydro-1H-benzazepine
188. 5-Dimethylamino-1-[4-(2-trifluoromethylbenzoylamino)benzoyl]-2,3,4,5-tetrahydro-1H-benzazepine
189. 5-Dimethylamino-1-[3-(2-chlorobenzoyloxy)-4-(2-chlorobenzoylamino)benzoyl]-2,3,4,5-tetrahydro-1H-benzazepine
190. 5-(N-Methyl-N-Allylamino)-1-[2-chloro-4-(2-methylbenzoylamino)benzoyl]-2,3,4,5-tetrahydro-1H-benzazepine
191. 5-Carbamoyloxy-1-[4-(2-methylbenzoylamino)benzoyl]-2,3,4,5-tetrahydro-1H-benzazepine
192. 1-[4-(2-Methylbenzoylamino)benzoyl]-1,2,3,5-tetrahydro-4,1-benzothiazepine
193. 4-Oxo-1-[4-(2-methylbenzoylamino)benzoyl]-2,3,4,5-tetrahydro-1H-benzazepine
194. 1-[4-(2-Methylbenzoylamino)benzoyl]-1,2,3,5-tetrahydro-4,1-benzothiazepine-1,1-dioxide
195. 5-Methylaminocarbonylmethoxy-1-[4-(2-chlorobenzoylamino)benzoyl]-2,3,4,5-tetrahydro-1H-benzazepine
196. 5-Methylaminocarbonyloxy-1-[4-(2-methylbenzoylamino)benzoyl]-2,3,4,5-tetrahyro-1H-benzazepine
197. 5-Dimethylamino-1-[2-dimethylamino-4-(2-methylbenzoylamino)benzoyl]-2,3,4,5-tetrahydro-1H-benzazepine
198. 5-Methylamino-1-[2-chloro-4-(2-trifluoromethylbenzoylamino)benzoyl]-2,3,4,5-tetrahydro-1H-benzazepine
199. 5-Cyclopropylamino-1-[2-chloro-4-(2-methylbenzoylamino)benzoyl]-2,3,4,5-tetrahydro-1H-benzazepine
200. 5-Cyclopropylamino-1-[2-chloro-4-(2-chlorobenzoylamino)benzoyl]-2,3,4,5-tetrahydro-1H-benzazepine
201. 5-Allylamino-1-[2-chloro-4-(2-methylbenzoylamino)benzoyl]-2,3,4,5-tetrahydro-1H-benzazepine
202. 5-(1-Piperidinyl)-1-[4-(2-chlorobenzoylamino)benzoyl]-2,3,4,5-tetrahydro-1H-benzazepine
203. 5-(4-Benzyl-1-piperazinyl)-1-[4-(2-chlorobenzoylamino)benzoyl]-2,3,4,5-tetrahydro-1H-benzazepine
204. 5-(1-Pyrrolidinyl)-1-[4-(2-chlorobenzoylamino)benzoyl]-2,3,4,5-tetrahydro-1H-benzazepine
205. 5-(4-Acetyl-1-piperazinyl)-1-[4-(2-chlorobenzoylamino)benzoyl]-2,3,4,5-tetrahydro-1H-benzazepine
206. 5-(4-Methyl-1-piperazinyl)-1-(4-(2-chlorobenzoylamino)benzoyl]-2,3,4,5-tetrahydro-1H-benzazepine
207. 1-[4-(2-Chlorobenzoylamino)benzoyl]-2,3-dihydro-1H-benzazepine
208. 5-Methyl-1-[4-(2-methylbenzoylamino)benzoyl]-2,3,4,5-tetrahydro-1H-benzazepine
209. 5-Methylidene-1-[4-(2-methylbenzoylamino)benzoyl]-2,3,4,5-tetrahydro-1H-benzazepine
210. 5-Hydroxy-1-[2-chloro-4-(2-methylbenzoylamino)benzoyl]-2,3,4,5-tetrahydro-1H-benzazepine
211. 5-(1-Morpholino)-1-[4-(2-chlorobenzoylamino)benzoyl]-2,3,4,5-tetrahydro-1H-benzazepine
212. 5-Dimethylamino-1-[4-(2-fluorobenzoylamino)benzoyl]-2,3,4,5-tetrahydro-1H-benzazepine
213. 5-Dimethylamino-1-[4-(2,4-difluorobenzoylamino)benzoyl]-2,3,4,5-tetrahydro-1H-benzazepine
214. 4-Hydroxy-1-[4-(2-methylbenzoylamino)benzoyl]-2,3,4,5-tetrahydro-1H-benzazepine
215. 5-Hydroxymethyl-1-[4-(2-methylbenzoylamino)benzoyl]-2,3,4,5-tetrahydro-1H-benzazepine
216. 5-Dimethylamino-4-hydroxy-1-[4-(2-chlorobenzoylamino)benzoyl]-2,3,4,5-tetrahydro-1H-benzazepine
217. 1-[4-(2-Methylbenzoylamino)benzoyl]-1,2-dihydroquinoline
218. 5-Dimethylamino-1-[2-methyl-4-(2-methylbenzoylamino)benzoyl]-2,3,4,5-tetrahydro-1H-benzazepine (the compound of Example 979)
219. 5-Dimethylamino-1-[2-methyl-4-(2-chlorobenzoylamino)benzoyl]-2,3,4,5-tetrahydro-1H-benzazepine
220. 5-Dimethylamino-1-[2-methyl-4-(2,4-dichlorobenzoylamino)benzoyl]-2,3,4,5-tetrahydro-1H-benzazepine
221. 5-Methylamino-1-{2-chloro-4-[2-(N-ethylanilino)acetylamino]benzoyl}-2,3,4,5-tetrahydro-1H-benzazepine
222. 5-Hydroxy-1-{2-chloro-4-[2-(N-ethylanilino)acetylamino]benzoyl}-2,3,4,5-tetrahydro-1H-benzazepine
223. 5-Dimethylamino-1-[2-fluoro-4-(2-chlorobenzoylamino)benzoyl]-2,3,4,5-tetrahydro-1H-benzazepine
224. 5-Methylamino-4-hydroxy-1-[2-chloro-4-(2-chlorobenzoylamino)benzoyl]-2,3,4,5-tetrahydro-1H-benzazepine.hydrochloride
225. 5-Hydroxymethyl-5-hydroxy-1-[2-chloro-4-(2-methylbenzoylamino)benzoyl]-2,3,4,5-tetrahydro-1H-benzazepine
226. 5-Dimethylamino-1-[2-fluoro-4-(2-methylbenzoylamino)benzoyl]-2,3,4,5-tetrahydro-1H-benzazepine 227. 5-Dimethylamino-1-[3-methyl-4-(2,4-dichlorobenzoylamino)benzoyl]-2,3,4,5-tetrahydro-1H-benzazepine 228. 5-(N-Methyl-N-ethylamino)-1-[4-(2-methylbenzoylamino)benzoyl]-2,3,4,5-tetrahydro-1H-benzazepine 229. 5-Ethylamino-1-[4-(2-methylbenzoylamino)benzoyl]-2,3,4,5-tetrahydro-1H-benzazepine 230. 5-Dimethylamino-1-[4-(3,5-difluorobenzoylamino)benzoyl]-2,3,4,5-tetrahydro-1H-benzazepine 231. 5-Acetyloxymethyl-1-[4-(2-methylbenzoylamino)benzoyl]-2,3,4,5-tetrahydro-1H-benzazepine 232. 5-Dimethylamino-1-[3-fluoro-4-(2-methylbenzoylamino)benzoyl]-2,3,4,5-tetrahydro-1H-benzazepine 233. 4,4-Dimethoxy-1-[4-(2-methylbenzoylamino)benzoyl]-2,3,4,5-tetrahydro-1H-benzazepine 234. 5-Acetyloxyimino-1-[4-(2-chlorobenzoylamino)benzoyl]-2,3,4,5-tetrahydro-1H-benzazepine 235. 5-Methylsulfonyloxymethyl-1-[4-(2-methylbenzoylamino)benzoyl]-2,3,4,5-tetrahydro-1H-benzazepine 236. 5,5-Epoxy-1-[4-(2-methylbenzoylamino)benzoyl]-2,3,4,5-tetrahydro-1H-benzazepine 237. 5-Hydroxymethyl-5-hydroxy-1-[4-(2-methylbenzoylamino)benzoyl]-2,3,4,5-tetrahydro-1H-benzazepine 238. 5-Hydroxy-1-[2-methoxy-4-(2-methylbenzoylamino)benzoyl]-2,3,4,5-tetrahydro-1H-benzazepine 239. 5-Dimethylamino-1-[4-(2-carbamoylmethoxybenzoylamino)benzoyl]-2,3,4,5-tetrahydro-1H-benzazepine 240. 5-Hydroxy-6-methyl-1-[2-chloro-4-(2-methylbenzoylamino)benzoyl]-2,3,4,5-tetrahydro-1H-benzazepine 241. 5-(2-Dimethylaminoethyl)amino-1-[2-chloro-4-(2-methylbenzoylamino)benzoyl]-2,3,4,5-tetrahydro-1H-benzazepine 242. 5-Hydroxymethyl-5-methylamino-1-[4-(2-methylbenzoylamino)benzoyl]-2,3,4,5-tetrahydro-1H-benzazepine 243. 5-Methylaminomethyl-5-hydroxy-1-[4-(2-methylbenzoylamino)benzoyl]-2,3,4,5-tetrahydro-1H-benzazepine 244. 5-Aminomethyl-1-[4-(2-methylbenzoylamino)benzoyl]-2,3,4,5-tetrahydro-1H-benzazepine 245. 5-[N-Methyl-N-(3-methoxy-2-hydroxypropyl)amino]-1-[4-(2-methylbenzoylamino)benzoyl]-2,3,4,5-tetrahydro-1H-benzazepine 246. 5-[N-Methyl-N-(3-diethylamino-2-hydroxypropyl)amino]-1-[4-(2-methylbenzoylamino)benzoyl]-2,3,4,5-tetrahydro-1H-benzazepine 247. 5-Dimethylamino-1-[3-methoxy-4-(2-methylbenzoylamino)benzoyl]-2,3,4,5-tetrahydro-1H-benzazepine 248. 5-Dimethylamino-1-[3-methoxy-4-(2,4-dichlorobenzoylamino)benzoyl]-2,3,4,5-tetrahydro-1H-benzazepine 249. 5-Dimethylamino-1-[4-(2-methylbenzoylamino)benzoyl]-2,3,4,5-tetrahydro-1H-benzazepine.hydrochloride 250. 5-Azidomethyl-1-[4-(2-methylbenzoylamino)benzoyl]-2,3,4,5-tetrahydro-1H-benzazepine 251. 7-[4-(2-Chlorobenzoylamino)benzoyl]-1-methyl-1,2,3,4a,5,6,7,11b-octahydro-3-oxo[1]benzazepino[4,5-b]-[1,4]oxazine 252. 5-Benzylamino-1-[4-(2-chlorobenzoylamino)benzoyl]-2,3,4,5-tetrahydro-1H-benzazepine 253. 5-Amino-1-[4-(2-chlorobenzoylamino)benzoyl]-2,3,4,5-tetrahydro-1H-benzazepine 254. 5-Dimethylamino-4-methyl-1-[4-(2-methylbenzoylamino)benzoyl]-2,3,4,5-tetrahydro-1H-benzazepine 255. 5-Acetylaminomethyl-1-[4-(2-methylbenzoylamino)benzoyl]-2,3,4,5-tetrahydro-1H-benzazepine 256. 5-Hydroxy-4-methyl-1-[4-(2-methylbenzoylamino)benzoyl]-2,3,4,5-tetrahydro-1H-benzazepine 257. 5-[2-(2-Pyridyl)ethylamino]-1-[4-(2-chlorobenzoylamino)benzoyl]-2,3,4,5-tetrahydro-1H-benzazepine 258. 5-(N-Methyl-N-methanesulfonylamino)-1-[4-(2-methylbenzoylamino)benzoyl]-2,3,4,5-tetrahydro-1H-benzazepine 259. 5-(N-Methyl-N-benozylamino)-1-[4-(2-methylbenzoylamino)benzoyl]-2,3,4,5-tetrahydro-1H-benzazepine 260. 5-Ethoxycarbonylamino-1-[4-(2-methylbenzoylamino)benzoyl]-2,3,4,5-tetrahydro-1H-benzazepine 261. 5-Methyl-5-hydroxy-1-[4-(2-methylbenzoylamino)benzoyl]-2,3,4,5-tetrahydro-1H-benzazepine 262. 5-(N-Methyl-N-ethoxycarbonylmethylamino)-1-[4-(2-methylbenzoylamino)benzoyl]-2,3,4,5-tetrahydro-1H-benzazepine 263. 5-Cyclopentylamino-1-[2-chloro-4-(2-methylbenzoylamino)benzoyl]-2,3,4,5-tetrahydro-1H-benzazepine 264. 5-[N-Methyl-N-(2,3-dihydroxypropyl)amino]-1-[4-(2-methylbenzoylamino)benzoyl]-2,3,4,5-tetrahydro-1H-benzazepine 265. 5-(N-Methyl-N-cyanomethylamino)-1-[4-(2-methylbenzoylamino)benzoyl]-2,3,4,5-tetrahydro-1H-benzazepine 266. 5-(N-Methyl-N-carbamoylmethylamino)-1-[4-(2-methylbenzoylamino)benzoyl]-2,3,4,5-tetrahydro-1H-benzazepine 267. 5-{N-Methyl-N-[3-(3,4,5,6-tetrahydro-2H-pyran-2-yloxy)propyl]amino}-1-[4-(2-methylbenzoylamino)benzoyl]-2,3,4,5-tetrahydro-1H-benzazepine 268. 5-Dimethylaminomethyl-1-[4-(2-methylbenzoylamino)benzoyl]-2,3,4,5-tetrahydro-1H-benzazepine 269. 5-Formylaminomethyl-1-[4-(2-methylbenzoylamino)benzoyl]-2,3,4,5-tetrahydro-1H-benzazepine 270. 5-[N-Methyl-N-(3-acetyloxypropyl)amino]-1-[4-(2-methylbenzoylamino)benzoyl]-2,3,4,5-tetrahydro-1H-benzazepine 271. 5-[N-Methyl-N-(3-hydroxypropyl)amino]-1-[4-(2-methylbenzoylamino)benzoyl]-2,3,4,5-tetrahydro-1H-benzazepine 272. Potassium {1-[2-chloro-4-(2-methylbenzoylamino)benzoyl]-2,3,4,5-tetrahydro-1H-benzazepin-5-yl}imino-o-sulfonate 273. 5-Dimethylamino-1-(4-benzoylaminobenzoyl)-2,3,4,5-tetrahydro-1H-benzazepine 274. 5-(1-Benzyl-4-piperidinyl)amino-1-[4-(2-methylbenzoylamino)benzoyl]-2,3,4,5-tetrahydro-1H-benzazepine 275. 5-(2-Dimethylaminoacetyloxy)-1-[4-(2-methylbenzoylamino)benzoyl]-2,3,4,5-tetrahydro-1H-benzazepine 276. 5-Dimethylamino-1-[4-(3-methoxybenzoylamino)benzoyl]-2,3,4,5-tetrahydro-1H-benzazepine 277. 5-[(4-Methyl-1-piperazinyl)carbonylmethoxy]-1-[4-(2-methylbenzoylamino)benzoyl]-2,3,4,5-tetrahydro-1H-benzazepine 278. 5-Morpholinocarbonylmethoxy-1-[4-(2-methylbenzoylamino)benzoyl]-2,3,4,5-tetrahydro-1H-benzazepine 279. 5-Thiomorpholinocarbonylmethoxy-1-[4-(2-methylbenzoylamino)benzoyl]-2,3,4,5-tetrahydro-1H-benzazepine 280. 5-Anilinocarbonylamino-1-[4-(2-methylbenzoylamino)benzoyl]-2,3,4,5-tetrahydro-1H-benzazepine 281. 5-(1-Oxothiomorpholino)carbonylmethoxy-1-[4-(2-methylbenzoylamino)benzoyl]-2,3,4,5-tetrahydro-1H-benzazepine 282. 5-Hydrazino-1-(4-(2-methylbenzoylamino)benzoyl]-2,3,4,5-tetrahydro-1H-benzazepine 283. 5-Methylaminocarbonylamino-1-[4-(2-methylbenzoylamino)benzoyl]-2,3,4,5-tetrahydro-1H-benzazepine 284. 5-[(2-α-Carbamoyl-1-pyrrolidinyl)carbonylmethoxy]-1-[4-(2-methylbenzoylamino)benzoyl]-2,3,4,5-tetrahydro-1H-benzazepine 285. 5-(Carbamoylmethylaminocarbonylmethoxy)-1-[4-(2-methylbenzoylamino)benzoyl]-2,3,4,5-tetrahydro-1H-benzazepine 286. 5-(1,1-Dioxothiomorpholino)carbonylmethoxy-1-[4-(2-methylbenzoylamino)benzoyl]-2,3,4,5-tetrahydro-1H-benzazepine 287. 7-Chloro-5-methylamino-1-[4-(2-methylbenzoylamino)benzoyl]-2,3,4,5-tetrahydro-1H-benzazepine 288. 5-[(4-Acetyl-1-piperazinyl)carbonylmethoxy]-1-[4-(2-methylbenzoylamino)benzoyl]-2,3,4,5-tetrahydro-1H-benzazepine 289. 5-Dimethylamino-1-[4-(3-nitrobenzoylamino)benzoyl]-2,3,4,5-tetrahydro-1H-benzazepine 290. 5-[(4-Pyridyl)methylaminocarbonylmethoxy]-1-[4-(2-methylbenzoylamino)benzoyl]-2,3,4,5-tetrahydro-1H-benzazepine 291. 5-[2-(Methylamino)acetylamino]-1-[4-(2-methylbenzoylamino)benzoyl]-2,3,4,5-tetrahydro-1H-benzazepine 292. 5-Dimethylamino-1-[4-(3-aminobenzoylamino)benzoyl]-2,3,4,5-tetrahydro-1H-benzazepine 293. 5-{[N-Methyl-N-(2-hydroxyethyl)amino]carbonylmethoxy}-1-[4-(2-methylbenzoylamino)benzoyl]-2,3,4,5-tetrahydro-1H-benzazepine 294. 5-Dimethylamino-1-[3-(2-diethylaminoethoxy)-4-(2-methylbenzoylamino)benzoyl]-2,3,4,5-tetrahydro-1H-benzazepine 295. 5-[N-Methyl-N-(dimethylaminocarbonylmethyl)amino]-1-[4-(2-methylbenzoylamino)benzoyl]-2,3,4,5-tetrahydro-1H-benzazepine 296. Potassium 2-[N-methyl-N-{1-[4-(2-methylbenzoylamino)benzoyl]-2,3,4,5-tetrahydro-1H-benzazepin-5-yl}amine]acetate 297. 5-{N-Methyl-N-[2-(1-imidazolyl)acetyl]amino}-1-[4-(2-methylbenzoylamino)benzoyl]-2,3,4,5-tetrahydro-1H-benzazepine 298. 5-Dimethylamino-1-[4-(2-dimethylaminobenzoylamino)benzoyl]-2,3,4,5-tetrahydro-1H-benzazepine 299. 5-[(2-Aminoacetyl)amino]-1-[4-(2-methylbenzoylamino)benzoyl]-2,3,4,5-tetrahydro-1H-benzazepine 300. 5-Dimethylamino-1-[4-(3-acetylaminobenzoylamino)benzoyl]-2,3,4,5-tetrahydro-1H-benzazepine 301. 5-(2-t-Butoxycarbonylaminoacetylamino)-1-[4-(2-methylbenzoylamino)benzoyl]-2,3,4,5-tetrahydro-1H-benzazepine 302. 5-Methylamino-7-chloro-1-[4-(2-chlorobenzoylamino)benzoyl]-2,3,4,5-tetrahydro-1H-benzazepine 303. 5-Dimethylamino-7-chloro-1-[4-(2-methylbenzoylamino)benzoyl]-2,3,4,5-tetrahydro-1H-benzazepine 304. 5-Dimethylamino-7-chloro-1-[4-(2-chlorobenzoylamino)benzoyl]-2,3,4,5-tetrahydro-1H-benzazepine 305. 5-Dimethylamino-1-[4-(phenylacetylamino)benzoyl]-2,3,4,5-tetrahydro-1H-benzazepine 306. 5-Dimethylamino-1-[4-(3-phenylpropionylamino)benzoyl]-2,3,4,5-tetrahydro-1H-benzazepine 307. 5-Methylamino-7-chloro-1-{4-[(N-ethylanilino)acetylamino]benzoyl}-2,3,4,5-tetrahydro-1H-benzazepine 308. 5-Dimethylamino-7-chloro-1-{4-[(N-ethylanilino)acetylamino]benzoyl}-2,3,4,5-tetrahydro-1H-benzazepine 309. 5-Dimethylamino-1-[4-(2-bromobenzoylamino)benzoyl]-2,3,4,5-tetrahydro-1H-benzazepine 310. 5-Cyclopropylamino-7-chloro-1-[4-(2-methylbenzoylamino)benzoyl]-2,3,4,5-tetrahydro-1H-benzazepine 311. 5-Cyclopropylamino-7-chloro-1-[4-(2-chlorobenzoylamino)benzoyl]-2,3,4,5-tetrahydro-1H-benzazepine 312. 5-hydroxy-1-{4-[2-(4-isopropylaminobutoxy)benzoylamino]benzoyl}-2,3,4,5-tetrahydro-1H-benzazepine 313. 5-Dimethylaminocarbonylmethoxy-1-{4-[(N-ethylanilino)acetylamino]benzoyl}-2,3,4,5-tetrahydro-1H-benzazepine 314. 5-(N-Methyl-N-ethylamino)-1-[2-chloro-4-(2-chlorobenzoylamino)benzoyl]-2,3,4,5-tetrahydro-1H-benzazepine 315. 5-Dimethylamino-1-{4-[(2-chloroanilino)acetylamino]benzoyl}-2,3,4,5-tetrahydro-1H-benzazepine 316. 5-Dimethylamino-1-{4-[(2-methylanilino)acetylamino]benzoyl}-2,3,4,5-tetrahydro-1H-benzazepine 317. 5-Dimethylamino-1-{4-[(N-methyl-2-methylanilino)acetylamino]benzoyl}-2,3,4,5-tetrahydro-1H-benzazepine 318. 5-Methylamino-9-chloro-1-[4-(2-methylbenzoylamino)benzoyl]-2,3,4,5-tetrahydro-1H-benzazepine 319. 5-Dimethylamino-1-[4-(phenoxyacetylamino)benzoyl]-2,3,4,5-tetrahydro-1H-benzazepine 320. 6-Methylamino-1-[4-(2-methylbenzoylamino)benzoyl]-1,2,3,4,5,6-hexahydrobenzazocine 321. 5-Methylamino-7-chloro-1-[3-methoxy-4-(2-chlorobenzoylamino)benzoyl]-2,3,4,5-tetrahydro-1H-benzazepine 322. 5-Cyclopropylamino-7-chloro-1-[3-methoxy-4-(2-chlorobenzoylamino)benzoyl]-2,3,4,5-tetrahydro-1H-benzazepine 323. 5-Methylamino-7-chloro-1-[3-methoxy-4-(2-methylbenzoylamino)benzoyl]-2,3,4,5-tetrahydro-1H-benzazepine

TABLE 10

| Test Comp. No. | IC$_{50}$ (µM) | Test Comp. No. | IC$_{50}$ (µM) |
|---|---|---|---|
| 26 | 0.071 | 78 | 0.10 |
| 27 | 0.095 | 88 | 0.34 |
| 28 | 0.056 | 90 | 0.38 |
| 29 | 0.15 | 114 | 0.011 |
| 30 | 0.15 | 115 | 0.012 |
| 32 | 0.30 | 116 | 0.04 |
| 33 | 0.092 | 117 | 0.22 |
| 36 | 0.41 | 119 | 0.049 |
| 46 | 0.40 | 120 | 0.29 |
| 56 | 0.025 | 121 | 0.45 |
| 57 | 0.46 | 124 | 0.15 |
| 58 | 0.40 | 125 | 0.091 |
| 59 | 0.31 | 130 | 0.023 |
| 60 | 0.18 | 143 | 0.15 |
| 62 | 0.098 | 147 | 0.28 |
| 63 | 0.14 | 161 | 0.14 |
| 64 | 0.069 | 163 | 0.22 |
| 67 | 0.34 | 164 | 0.15 |
| 68 | 0.013 | 172 | 0.26 |
| 69 | 0.066 | 173 | 0.15 |
| 70 | 0.041 | 174 | 0.14 |
| 71 | 0.18 | 187 | 0.45 |
| 72 | 0.12 | 188 | 0.47 |
| 74 | 0.10 | 192 | 0.054 |
| 75 | 0.069 | 193 | 0.17 |
| 76 | 0.042 | 195 | 0.17 |
| 77 | 0.085 | 196 | 0.40 |
| 207 | 0.16 | 284 | 0.29 |
| 208 | 0.11 | 285 | 0.18 |
| 209 | 0.074 | 286 | 0.40 |
| 214 | 0.27 | 287 | 0.064 |
| 215 | 0.13 | 288 | 0.26 |
| 222 | 0.096 | 290 | 0.21 |
| 231 | 0.16 | 293 | 0.19 |
| 235 | 0.088 | 298 | 0.29 |
| 236 | 0.16 | 302 | 0.071 |
| 238 | 0.39 | 303 | 0.19 |
| 244 | 0.23 | 304 | 0.21 |
| 250 | 0.19 | 307 | 0.024 |
| 252 | 0.36 | 308 | 0.11 |
| 255 | 0.046 | 309 | 0.43 |
| 256 | 0.049 | 310 | 0.065 |
| 266 | 0.29 | 311 | 0.078 |
| 269 | 0.48 | 312 | 0.056 |
| 274 | 0.11 | 313 | 0.032 |
| 275 | 0.18 | 315 | 0.38 |
| 277 | 0.23 | 316 | 0.47 |
| 278 | 0.30 | 321 | 0.059 |
| 279 | 0.15 | 322 | 0.044 |
| 280 | 0.47 | 323 | 0.064 |
| 281 | 0.18 | | |

Pharmacological Test

Experiment 2: V$_2$ receptor binding assay

Using rat kidney plasma membrane preparations prepared according to O. Hechter's method [cf: J. Bio. Chem., 253, 3211 (1978)], the plasma membrane (100000 dpm, 4×10$^{-10}$ M) of [$^3$H]-Arg-vasopressin and a test compound (0.6 mg, 10$^{-10}$–10$^{-5}$M) are incubated at 4° C. for 3 hours in 100 mM Tris-HCl buffer (pH: 8.0, 250 µl) containing 5 mM MgCl$_2$, 1 mM EDTA and 0.1% BSA. After incubation, the mixture is filtered using the glass filter (GF/F) so as to separate the membrane preparation combined with vasopressin and then washed twice with the buffer (5 ml). This glass filter is taken out and mixed with liquid scintillation cocktail. The amount of [$^3$H]-vasopressin combined with the membrane is measured by liquid scintillation counter and the rate of the inhibitory effect of the test compound is estimated according to the following equation.

$$\text{Rate of the inhibitory effect (\%)} = 100 - \frac{C_1 - B_1}{C_0 - B_1} \times 100$$

$C^1$: The amount of [$^3$H]-vasopressin combined with the membrane in the presence of the test compound (in prescribed amount).

$C^0$: The amount of [$^3$H]-vasopressin combined with the membrane in the absence of the test compound.

$B^1$: The amount of [$^3$H]-vasopressin combined with the membrane in the presence of the excess amount of vasopressin (10$^{-6}$M).

The results are expressed as IC$_{50}$ values, which is the concentration of the test compound required to achieve the inhibitory effect in the rate of 50%.

The results are shown the following Table 11.

TABLE 11

| Test Comp. No. | IC$_{50}$ (µM) | Test Comp. No. | IC$_{50}$ (µM) |
|---|---|---|---|
| 1 | 0.98 | 28 | 0.018 |
| 2 | 0.20 | 29 | 0.069 |
| 3 | 0.40 | 30 | 0.029 |
| 4 | 0.58 | 31 | 0.098 |
| 5 | 1.2 | 32 | 0.016 |
| 6 | 0.076 | 33 | 0.007 |
| 7 | 0.20 | 34 | 0.049 |
| 8 | 0.32 | 35 | 0.20 |
| 9 | 0.53 | 36 | 0.028 |
| 10 | 0.082 | 37 | 0.16 |
| 11 | 1.05 | 38 | 0.029 |
| 12 | 1.97 | 39 | 0.071 |
| 13 | 1.02 | 40 | 0.33 |
| 14 | 0.23 | 41 | 0.20 |
| 15 | 0.13 | 42 | 0.063 |
| 16 | 0.17 | 43 | 0.17 |
| 17 | 0.23 | 44 | 0.050 |
| 18 | 1.0 | 45 | 0.19 |
| 19 | 1.7 | 46 | 0.018 |
| 20 | 1.4 | 47 | 0.20 |
| 21 | 1 | 48 | 0.021 |
| 22 | 0.33 | 49 | 0.063 |
| 23 | 1.07 | 50 | 1.3 |
| 24 | 1.09 | 51 | 0.40 |
| 25 | 1.67 | 52 | 0.32 |
| 26 | 0.025 | 53 | 1.6 |
| 27 | 0.070 | 54 | 0.11 |
| 55 | 0.091 | 86 | 0.58 |
| 56 | 0.037 | 87 | 0.046 |
| 57 | 0.16 | 88 | 0.021 |
| 58 | 0.14 | 89 | 0.035 |
| 59 | 0.24 | 90 | 0.014 |
| 60 | 0.15 | 91 | 0.005 |
| 61 | 0.090 | 92 | 0.41 |
| 62 | 0.023 | 93 | 0.52 |
| 63 | 0.046 | 94 | 0.095 |
| 64 | 0.007 | 95 | 0.089 |
| 65 | 0.081 | 96 | 0.039 |
| 66 | 0.45 | 97 | 0.024 |
| 67 | 0.050 | 98 | 0.45 |
| 68 | 0.19 | 99 | 1.6 |

TABLE 11-continued

| Test Comp. No. | IC$_{50}$ (μM) | Test Comp. No. | IC$_{50}$ (μM) |
|---|---|---|---|
| 69 | 0.12 | 100 | 0.011 |
| 70 | 0.012 | 101 | 0.60 |
| 71 | 0.085 | 102 | 0.29 |
| 72 | 0.16 | 103 | 0.54 |
| 74 | 0.51 | 104 | 0.37 |
| 75 | 0.30 | 105 | 0.72 |
| 76 | 0.017 | 106 | 0.44 |
| 77 | 0.090 | 107 | 0.032 |
| 78 | 0.084 | 108 | 0.12 |
| 79 | 0.53 | 109 | 0.49 |
| 80 | 0.070 | 110 | 0.044 |
| 81 | 0.15 | 111 | 0.087 |
| 82 | 0.17 | 112 | 0.29 |
| 83 | 0.73 | 113 | 0.28 |
| 84 | 0.11 | 114 | 0.006 |
| 85 | 0.068 | 115 | 0.006 |
| 116 | 0.039 | 146 | 0.056 |
| 117 | 0.24 | 147 | 0.009 |
| 118 | 0.55 | 148 | 0.34 |
| 119 | 0.059 | 149 | 0.004 |
| 120 | 0.28 | 150 | 0.14 |
| 121 | 0.18 | 151 | 0.18 |
| 122 | 0.10 | 152 | 0.039 |
| 123 | 0.10 | 153 | 0.063 |
| 124 | 0.13 | 154 | 0.063 |
| 125 | 0.28 | 155 | 0.028 |
| 126 | 0.062 | 156 | 0.15 |
| 127 | 0.99 | 157 | 0.38 |
| 128 | 0.23 | 158 | 0.018 |
| 129 | 0.29 | 159 | 0.020 |
| 130 | 0.007 | 160 | 0.020 |
| 131 | 0.027 | 161 | 0.009 |
| 132 | 0.013 | 162 | 0.059 |
| 133 | 0.022 | 163 | 0.009 |
| 134 | 0.048 | 164 | 0.010 |
| 135 | 0.081 | 165 | 0.098 |
| 136 | 0.18 | 166 | 0.070 |
| 137 | 0.41 | 167 | 0.032 |
| 138 | 0.11 | 168 | 0.083 |
| 139 | 0.10 | 169 | 0.071 |
| 140 | 0.024 | 170 | 0.25 |
| 141 | 0.010 | 171 | 0.87 |
| 142 | 0.008 | 172 | 0.023 |
| 143 | 0.008 | 173 | 0.008 |
| 144 | 0.02 | 174 | 0.007 |
| 145 | 0.06 | 175 | 0.038 |
| 176 | 0.004 | 206 | 0.088 |
| 177 | 0.15 | 207 | 0.045 |
| 178 | 0.012 | 208 | 0.007 |
| 179 | 0.040 | 209 | 0.004 |
| 180 | 0.034 | 210 | 0.004 |
| 181 | 0.038 | 211 | 0.12 |
| 182 | 0.005 | 212 | 0.035 |
| 183 | 0.26 | 213 | 0.033 |
| 184 | 0.023 | 214 | 0.058 |
| 185 | 0.005 | 215 | 0.006 |
| 186 | 0.030 | 216 | 0.91 |
| 187 | 0.029 | 217 | 0.37 |
| 188 | 0.039 | 218 | 0.022 |
| 189 | 0.087 | 219 | 0.023 |
| 190 | 0.082 | 220 | 0.026 |
| 191 | 0.009 | 221 | 0.024 |
| 192 | 0.111 | 222 | 0.010 |
| 193 | 0.036 | 223 | 0.022 |
| 194 | 0.21 | 224 | 0.38 |
| 195 | 0.010 | 225 | 0.030 |
| 196 | 0.013 | 226 | 0.019 |
| 197 | 0.99 | 227 | 0.029 |
| 198 | 0.040 | 228 | 0.029 |
| 199 | 0.019 | 229 | 0.029 |
| 200 | 0.024 | 230 | 0.020 |
| 201 | 0.023 | 231 | 0.007 |
| 202 | 0.14 | 232 | 0.020 |
| 203 | 0.070 | 233 | 0.15 |
| 204 | 0.11 | 234 | 0.14 |
| 205 | 0.074 | 235 | 0.006 |
| 236 | 0.006 | 267 | 0.12 |
| 237 | 0.041 | 268 | 0.018 |
| 238 | 0.020 | 269 | 0.003 |
| 239 | 0.17 | 270 | 0.046 |
| 240 | 0.022 | 271 | 0.030 |
| 241 | 0.006 | 272 | 0.40 |
| 242 | 0.17 | 273 | 0.027 |
| 243 | 0.40 | 274 | 0.024 |
| 244 | 0.018 | 275 | 0.018 |
| 245 | 0.059 | 276 | 0.032 |
| 246 | 0.027 | 277 | 0.016 |
| 247 | 0.048 | 278 | 0.013 |
| 248 | 0.060 | 279 | 0.008 |
| 250 | 0.12 | 280 | 0.045 |
| 251 | 0.094 | 281 | 0.011 |
| 252 | 0.063 | 262 | 0.38 |
| 253 | 0.052 | 283 | 0.096 |
| 254 | 0.016 | 284 | 0.019 |
| 255 | 0.005 | 285 | 0.008 |
| 256 | 0.004 | 286 | 0.019 |
| 257 | 0.045 | 287 | 0.007 |
| 258 | 0.20 | 288 | 0.015 |
| 259 | 0.25 | 289 | 0.071 |
| 260 | 0.13 | 290 | 0.021 |
| 261 | 0.011 | 291 | 0.13 |
| 262 | 0.029 | 292 | 0.18 |
| 263 | 0.053 | 293 | 0.065 |
| 264 | 0.030 | 294 | 0.33 |
| 265 | 0.025 | 295 | 0.026 |
| 266 | 0.013 | 296 | 0.25 |
| 297 | 0.051 | 311 | 0.013 |
| 298 | 0.10 | 312 | 0.29 |
| 299 | 0.22 | 313 | 0.012 |
| 300 | 0.48 | 314 | 0.096 |
| 301 | 0.14 | 315 | 0.025 |
| 302 | 0.011 | 316 | 0.060 |
| 303 | 0.025 | 317 | 0.072 |
| 304 | 0.024 | 318 | 0.060 |
| 305 | 0.038 | 319 | 0.058 |
| 306 | 0.077 | 320 | 0.039 |
| 307 | 0.010 | 321 | 0.012 |
| 308 | 0.023 | 322 | 0.025 |
| 309 | 0.015 | 323 | 0.014 |
| 310 | 0.008 | | |

Experiment 3: Anti-antidiuretic activity (effect on endogenous ADH)

A test compound or solvent (dimethylformamide) is administered into a caudal vein of untreated, unrestrained SD rats (male, weight: 300–350 g) and the amount of urine, which is spontaneously excreted for a period of 2 hours thereafter, is collected and measured by using a metabolic gauge. During this measurement, the rats are allowed to take water and feed freely.

The amount of urine of control rats (solvent-treated group) is regarded as 100%, and the results are expressed as $ED_3$ value, which is the dose of the test compound to be required to excrete the urine by three times than that of the control rats. The results are shown in the following Table 12.

TABLE 12

| Test compound No. | $ED_3$ (mg/kg) |
|---|---|
| 6 | 10 |
| 33 | 1.9 |

TABLE 12-continued

| Test compound No. | ED$_3$ (mg/kg) |
|---|---|
| 178 | 4.2 |
| 249 | 0.4*[)] |

*[)]: Physicological saline solution was used as a solvent instead of dimethylformamide.

Using the suitable starting materials, the compounds of the following Table 13 are obtained in the same manner as in Examples 1 and 382.

TABLE 13

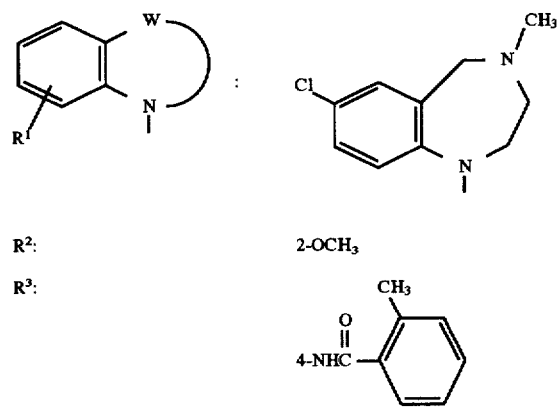

Example 1190

Structure:

R$^2$: 2-OCH$_3$

R$^3$:

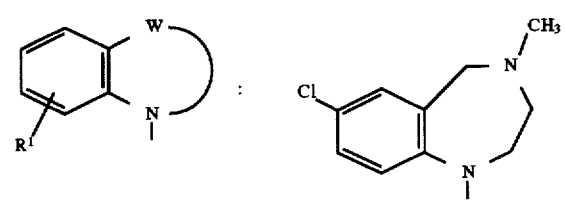

| Crystalline form: | White powder |
| Recrystallization solvent: | Dichloromethane/diethyl ether |
| Melting Point: | 210–213° C. |
| Form: | Free |

Example 1191

Structure:

R$^2$: 2-CH$_3$

TABLE 13-continued

R$^3$:

| Crystalline form: | White powder |
| Recrystallization solvent: | Dichloromethane/diethyl ether |
| Melting Point: | 184.5–186° C. |
| Form: | Free |

Example 1192

Structure:

R$^2$: H

R$^3$:

| Crystalline form: | White powder |
| Recrystallization solvent: | Dichloromethane/diethyl ether |
| Melting Point: | 201.5–202.5° C. |
| Form: | Free |

Example 1193

Structure:

R$^2$: 2-Cl

R$^3$:

| Crystalline form: | White powder |
| Recrystallization solvent: | Dichloromethane/diethyl ether |

TABLE 13-continued

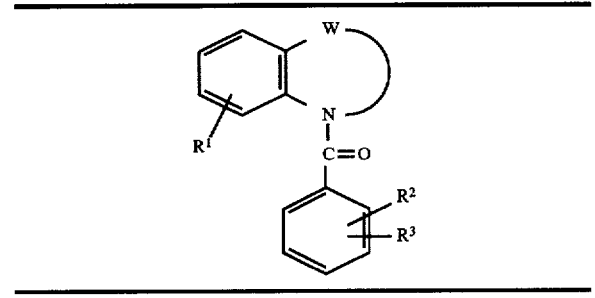

Melting Point: 159–162° C. (decomposed)
Form: Free

Example 1194

Structure

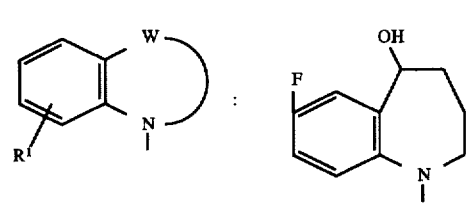

R²: 2-OCH₃

R³:

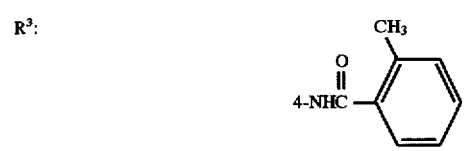

Crystalline form: White powder
Recrystallization solvent: diethyl ether/Dichloromethane
Melting Point: 237–240° C.
Form: Free Example 1195

Structure

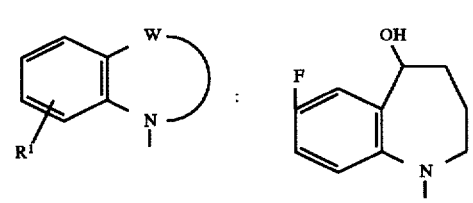

R²: 2-OCH₃

R³:

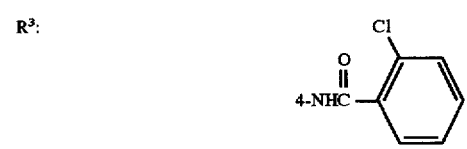

Crystalline form: White powder
Recrystallization solvent: diethyl ether/Dichloromethane
Melting Point: 269–272.5° C.
Form: Free TABLE 13-continued

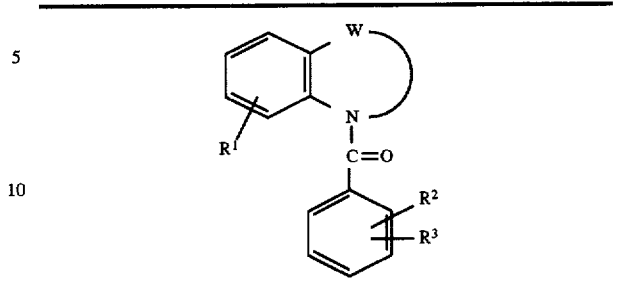

Example 1196

Structure

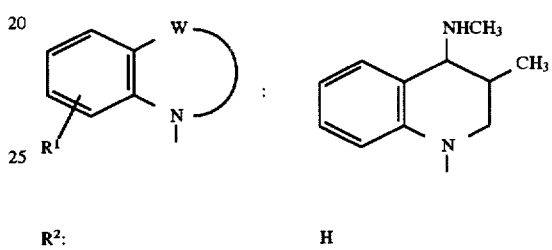

R²: H

R³:

Crystalline form: Colorless prisms
Recrystallization solvent: Ethanol/dichloromethane
Melting Point: 201–202° C.
Form: Free Example 1197

Structure

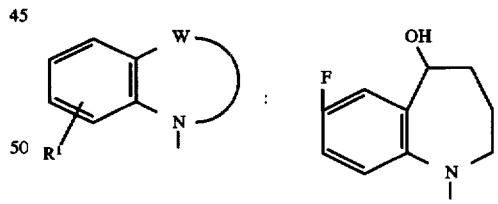

R²: 2-CH₃

R³:

Crystalline form: White powder
Recrystallization solvent: Methanol
Melting Point: 204–206° C.
Form: Free TABLE 13-continued

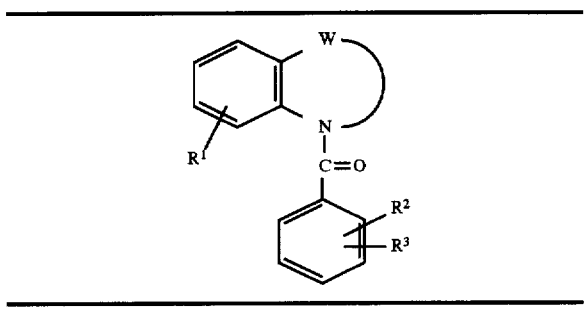

Example 1198

Structure

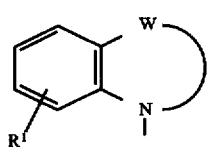

R²: 2-Cl

R³:
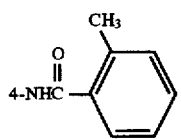

Crystalline form: Colorless amorphous
NMR analysis: 313)
Form: Free

Example 1199

Structure

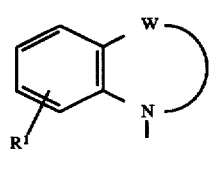

R²: 2-CH₃

R³:
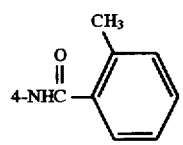

Crystalline form: Colorless amorphous
NMR analysis: 314)
Form: Free

TABLE 13-continued

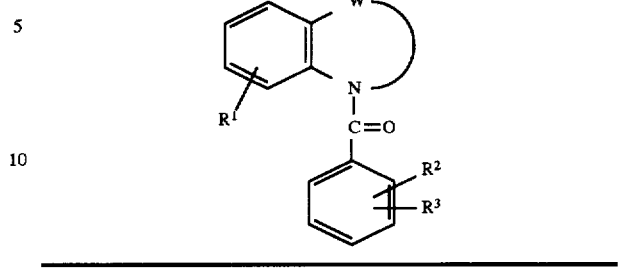

Example 1200

Structure

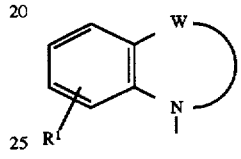

R²: 2-CH₃

R³:
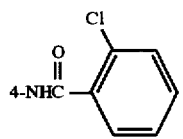

Crystalline form: Colorless amorphous
NMR analysis: 315)
Form: Free

Example 1201

Structure

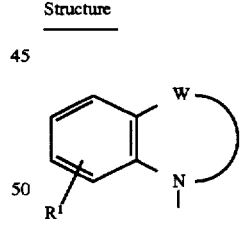

R²: 2-OCH₃

R³:
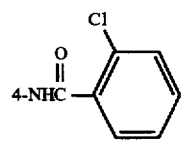

Crystalline form: Colorless amorphous
NMR analysis: 316)
Form: Free

TABLE 13-continued

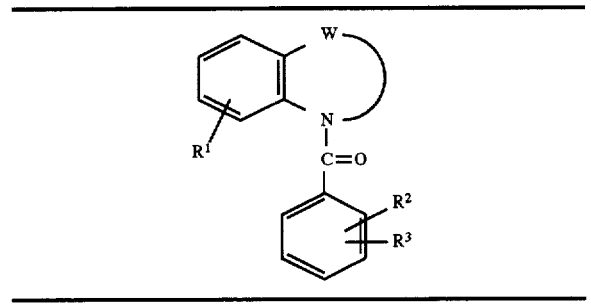

Example 1202

Structure

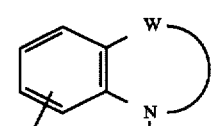 : 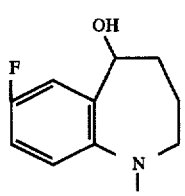

R²:  2-Cl

R³:

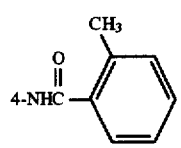

Crystalline form:  Colorless amorphous
NMR analysis:  317)
Form:  Free

Example 1203

Structure

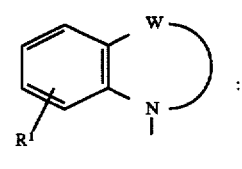 : 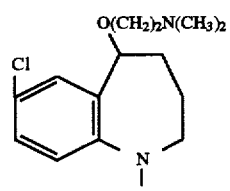

R²:  2-OCH₃

R³:

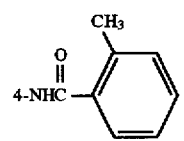

Crystalline form:  Light brown amorphous
NMR analysis:  318)
Form:  Hydrochloride TABLE 13-continued

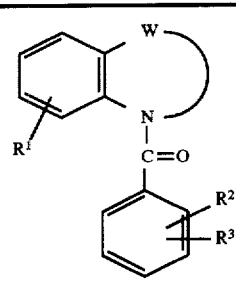

Example 1204

Structure

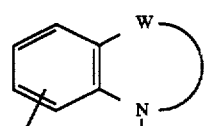 : 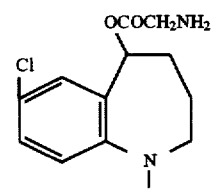

R²:  2-OCH₃

R³:

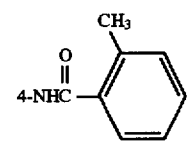

Crystalline form:  Colorless amorphous
NMR analysis:  319)
Form:  Free

Example 1205

Structure

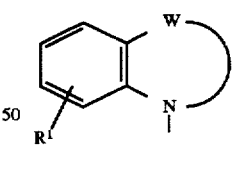 : 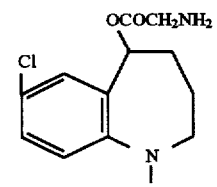

R²:  2-CH₃

R³:

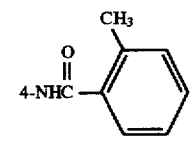

Crystalline form:  Colorless amorphous
NMR analysis:  320)
Form:  Hydrochloride

TABLE 13-continued

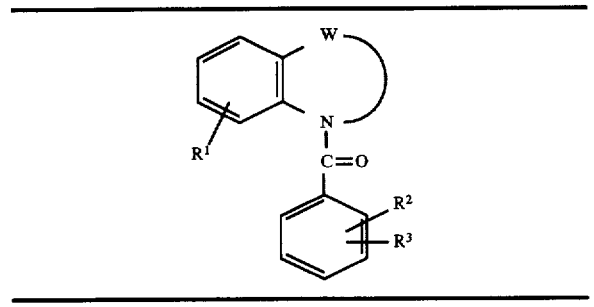

Example 1206

Structure

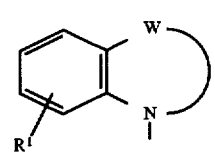 : 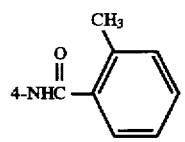

R²: 2-CH₃

R³:

(4-NHC(=O)-2-methylphenyl group)

Crystalline form: Colorless amorphous
NMR analysis: 321)
Form: Hydrochloride

Example 1207

Structure

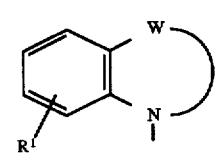 : 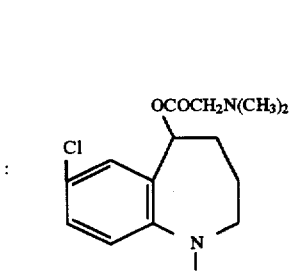

R²: 2-OCH₃

R³:

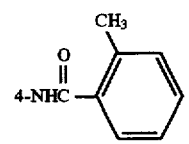

Crystalline form: Colorless amorphous
NMR analysis: 322)
Form: Free

TABLE 13-continued

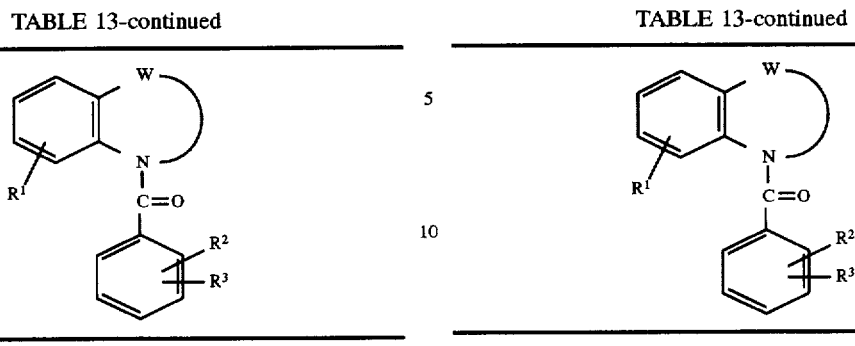

Example 1208

Structure

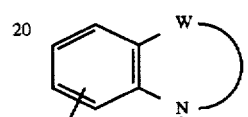 : 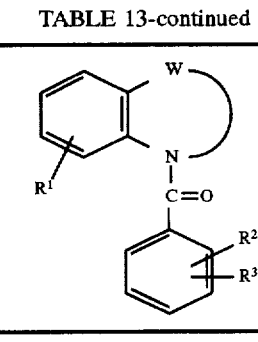

R²: 2-OCH₃

R³: 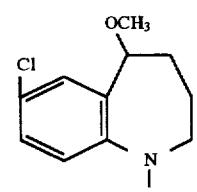

Crystalline form: Light yellow prisms
Recrystallization solvent: Ethyl acetate/n-hexane
Melting Point: 187–189° C.
Form: Free

Example 1209

Structure

: 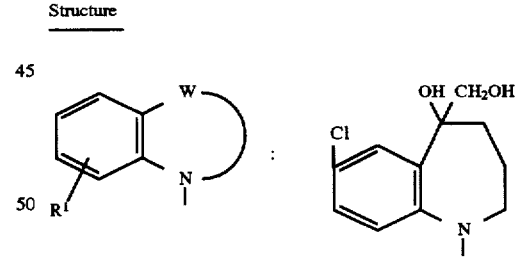

R²: H

R³: 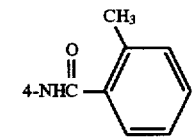

Crystalline form: White powder
Recrystallization solvent: Methanol/diethyl ether
Melting Point: 227–231° C.
Form: Free TABLE 13-continued

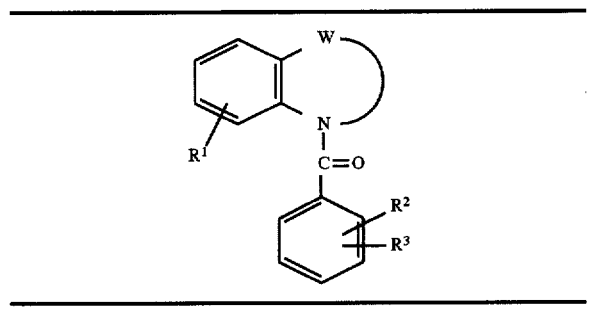

Example 1210

Structure

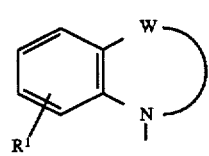 : 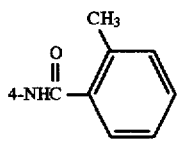

R²: 2-CH₃

R³: 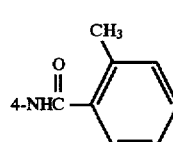

| | |
|---|---|
| Crystalline form: | White powder |
| Recrystallization solvent: | Methanol/diethyl ether |
| Melting Point: | 191–192° C. |
| Form: | Free |

Example 1211

Structure

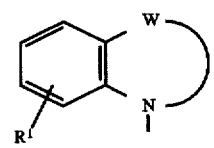 : 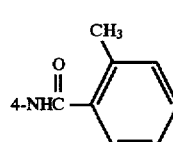

R²: 2-CH₃

R³: 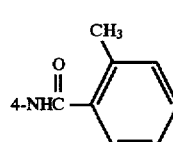

| | |
|---|---|
| Crystalline form: | Colorless amorphous |
| NMR analysis: | 323) |
| Form: | Free |

TABLE 13-continued

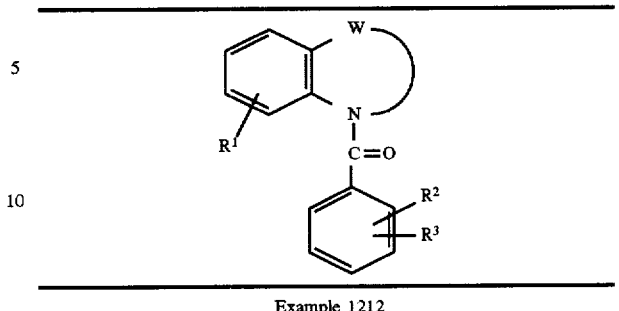

Example 1212

Structure

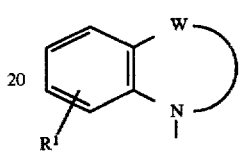 : 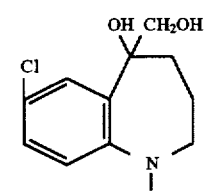

R²: 2-CH₃

R³: 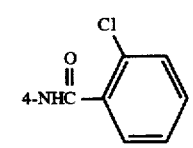

| | |
|---|---|
| Crystalline form: | Colorless amorphous |
| NMR analysis: | 324) |
| Form: | Free |

Example 1213

Structure

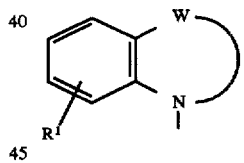 : 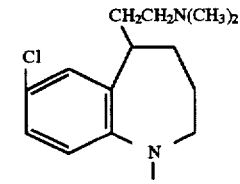

R²: 2-CH₃

R³: 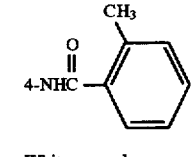

| | |
|---|---|
| Crystalline form: | White amorphous |
| NMR analysis: | 325) |
| Form: | Hydrochloride |

313) ¹H-NMR (CDCl₃) δ; 1.40–2.30 (4H, m), 2.36 (3H, s), 2.60–2.92 (2H, m), 4.35–5.18 (2H, m), 6.69–6.87 (1H, m), 6.87–7.04 (1H, m), 7.05–8.06 (8H, m), 8.25–8.60 (1H, m)

314) ¹H-NMR (CDCl₃) δ; 1.43–2.26 (4H, m), 2.38 (3H, s), 2.42 (3H, s), 2.61–2.91 (1H, m), 2.91–3.40 (1H, m), 4.49–5.08 (2H, m), 6.40–7.68 (10H, m), 7.68–7.93 (1H, m)

315) $^1$H-NMR (CDCl$_3$) δ; 1.32–2.25 (4H, m), 2.25–2.54 (3H, m), 2.59–3.42 (2H, m), 4.45–5.08 (2H, m), 6.40–7.80 (10H, m), 8.00–8.38 (1H, m)

316) $^1$H-NMR (CDCl$_3$) δ; 1.42–1.89 (2H, m), 1.90–2.30 (2H, m), 2.57–2.95 (2H, m), 3.36–3.64 (3H, m), 4.51–5.17 (2H, m), 6.52–7.80 (10H, m), 8.11–8.41 (1H, m)

317) $^1$H-NMR (CDCl$_3$) δ; 1.18–2.25 (4H, m), 2.25–2.59 (3H, m), 2.59–2.88 (1H, m), 2.88–4.32 (1H, m), 4.32–5.05 (2H, m), 6.44–8.08 (10H, m), 8.52–9.00 (1H, m)

318) $^1$H-NMR (DMSO-d$_6$) δ; 1.35–2.45 (7H, m), 2.6–3.0 (8H, m), 3.2–4.2 (6H, m), 4.45–4.85 (2H, m), 6.75–7.7 (11H, m)

319) $^1$H-NMR (CDCl$_3$) δ; 1.20–2.89, 3.22–4.33, 4.48–5.05, 5.75–6.32 [total 17H, m {2.45 (s)}], 6.52–7.78 (10H, m), 8.10–8.71 (1H, m)

320) $^1$H-NMR (DMSO-d$_6$) δ; 1.49–3.05 [11H, m {2.35 (s), 2.40 (s)}], 3.71–5.04 (3H, m), 5.28–5.88 (1H, m), 6.64–7.98 (10H, m), 8.58 (3H, brs), 10.32, 10.48 (total 1H, each s)

321) $^1$H-NMR (DMSO-d$_6$) δ; 1.50–3.70 [17H, m }2.36, 2.40 (each s), 2.87, 2.89, 2.94 (each s)}], 4.05–5.08 (3H, m), 5.90–6.28 (1H, m), 6.62–7.98 (10H, m), 10.36, 10.52 (total 1H, each brs), 10.94 (1H, brs)

322) $^1$H-NMR (CDCl$_3$) δ; 1.53–2.91 [14H, m {2.42, 2.47 (each s)}], 3.09–4.27 (5H, m), 4.70–5.12 (1H, m), 5.89–6.36 (1H, m), 6.57–7.94 (11H, m)

323) $^1$H-NMR (CDCl$_3$) δ; 1.32–2.23 (2H, m), 2.23–2.68 (7H, n), 2.68–3.84 (8H, m), 3.84–5.23 (4H, m), 6.47–7.88 (11H, m)

324) $^1$H-NMR (CDCl$_3$) δ; 1.45–2.32 (5H, m), 2.44 (3H, s), 2.63–3.21 (1H, m), 3.40–5.01 (4H, m), 6.28–7.93 (10H, m), 8.10–8.43 (1H, m)

325) $^1$H-NMR (DMSO-d$_6$) δ; 0.71–3.46, 4.15–4.44 [total 23H, 2.35 (s), 2.42 (s), 2.86 (s)], 6.71–7.88 (10H, m), 10.16–10.58 (2H, m)

What is claimed is:

1. A method for antagonizing vasopressin which comprises administering to a subject a therapeutically effective amount of a benzoheterocyclic compound of the formula:

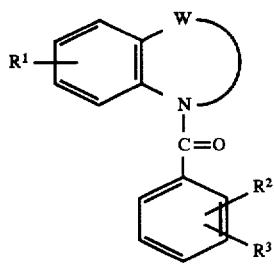

(I)

wherein $R^1$ is a hydrogen atom, a halogen atom, a C$_1$–C$_6$ alkyl, an amino having optionally a C$_1$–C$_6$ alkyl substituent, or a C$_1$–C$_6$ alkoxy, $R^2$ is a hydrogen atom, a halogen atom, a C$_1$–C$_6$ alkoxy, a phenyl-(C$_1$–C$_6$) alkoxy, hydroxy, a C$_1$–C$_6$ alkyl, an amino having optionally a C$_1$–C$_6$ alkyl substituent, a carbamoyl-substituted C$_1$–C$_6$ alkoxy, an amino-substituted C$_1$–C$_6$ alkoxy having optionally a C$_1$–C$_6$ alkyl substituent, or a benzoyloxy which has optionally a halogen substituent on the phenyl ring, $R^3$ is a group of the formula:

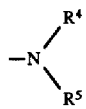

or a group of the formula:

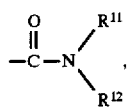

$R^4$ is a hydrogen atom, a benzoyl which has optionally a halogen substituent on the phenyl ring or a C$_1$–C$_6$ alkyl, $R^5$ is a group of the formula:

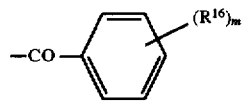

wherein $R^{16}$ is a halogen atom; a C$_1$–C$_6$ alkyl which has optionally a substituent selected from a halogen atom and hydroxy; hydroxy; a C$_1$–C$_6$ alkoxy; a C$_1$–C$_6$ alkanoyloxy; a C$_1$–C$_6$ alkylthio; a C$_1$–C$_6$ alkanoyl; carboxy; a C$_1$–C$_6$ alkoxycarbonyl; cyano; nitro; an amino which has optionally a substituent selected from a C$_1$–C$_6$ alkyl and a C$_1$–C$_6$ alkanoyl; phenyl; a C$_3$–C$_8$ cycloalkyl; a C$_2$–C$_6$ alkanoyloxy-substituted C$_1$–C$_6$ alkoxy; a carboxy-substituted C$_1$–C$_6$ alkoxy; a halogen-substituted C$_1$–C$_6$ alkoxy; a carbamoyl-substituted C$_1$–C$_6$ alkoxy; a hydroxy-substituted C$_1$–C$_6$ alkoxy; a C$_1$–C$_6$ alkoxycarbonyl-substituted C$_1$–C$_6$ alkoxy; a phthalimido-substituted C$_1$–C$_6$ alkoxy; an aminocarbonyl-(C$_1$–C$_6$) alkoxy having a C$_1$–C$_6$ alkyl substituent; or a group of the formula:

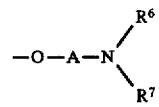

wherein A is a C$_1$–C$_6$ alkylene, and $R^6$ and $R^7$ are the same or different and are each a hydrogen atom, a C$_1$–C$_6$ alkyl having optionally a hydroxy substituent, a C$_1$–C$_6$ alkanoyl, or benzoyl, or $R^6$ and $R^7$ may bind together with the nitrogen atom to which they are bonded to form a 5- or 6-membered saturated heterocyclic group with or without being intervened with a nitrogen or oxygen atom wherein the heterocyclic group is one member selected from the group consisting of pyrrolidinyl, piperidinyl, piperazinyl and morpholino, and has optionally a substituent selected from piperidinyl and a C$_1$–C$_6$ alkyl; and m is an integer of 0 to 3, a phenyl-(C$_1$–C$_6$) alkoxycarbonyl, a C$_1$–C$_6$ alkanoyl, a phenyl-(C$_2$–C$_6$) alkanoyl, a C$_3$–C$_8$ cycloalkyl-(C$_2$–C$_6$) alkanoyl, a C$_3$–C$_8$ cycloalkylcarbonyl, tricyclo(3.3.1.1)decanylcarbonyl, naphthylcarbonyl, pyridylcarbonyl, furoyl, thenoyl, a phenoxy-(C$_2$–C$_6$) alkanoyl which phenyl ring has optionally 1 to 3 substituents selected from a C$_1$–C$_6$ alkyl, a C$_1$–C$_6$ alkoxy and an amino having optionally a C$_1$–C$_6$ alkanoyl substituent, a phthalimido-substituted C$_2$–C$_6$ alkanoyl, a C$_1$–C$_6$ alkoxycarbonyl- ($C_2$–$C_6$) alkanoyl, a carboxy-($C_2$–$C_6$) alkanoyl, a naphthyloxy-($C_2$–$C_6$) alkanoyl, a halogen-substituted $C_1$–$C_6$ alkanoyl, a group of the formula:

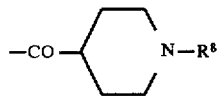

wherein $R^8$ is a hydrogen atom, a $C_1$–$C_6$ alkyl, a phenyl-($C_1$–$C_6$) alkoxycarbonyl, a carbamoyl-($C_1$–$C_6$) alkyl, an amino-($C_2$–$C_6$) alkanoyl having optionally a $C_1$–$C_6$ alkyl substituent, or a $C_1$–$C_6$ alkanoyl, an anilinocarbonyl which has optionally a $C_1$–$C_6$ alkyl substituent on the phenyl ring, phenoxycarbonyl, a phenylsulfonyl which has optionally a substituent selected from a halogen atom and a $C_1$–$C_6$ alkyl on the phenyl ring, quinolylsulfonyl, or a group of the formula:

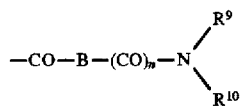

wherein B is a $C_1$–$C_6$ alkylene, n is an integer of 0 or 1, and $R^9$ and $R^{10}$ are the same or different and are each a hydrogen atom, a $C_1$–$C_6$ alkyl having optionally a hydroxy substituent, a $C_3$–$C_8$ cycloalkyl, a phenyl-($C_1$–$C_6$) alkyl, a $C_1$–$C_6$ alkanoyl, a $C_2$–$C_6$ alkenyl, a phenoxy-($C_1$–$C_6$) alkyl, a phenyl which has optionally 1 to 3 substituents selected from an amino-($C_1$–$C_6$) alkyl having optionally a $C_1$–$C_6$ alkanoyl substituent, a $C_1$–$C_6$ alkyl, a $C_1$–$C_6$ alkoxy and a halogen atom, a phthalimido-substituted $C_1$–$C_6$ alkyl, an amino-($C_1$–$C_6$) alkyl having optionally a $C_1$–$C_6$ alkanoyl substituent, a $C_2$–$C_6$ alkynyl, or an amino-($C_1$–$C_6$) alkyl having optionally a $C_1$–$C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1$–$C_6$ alkyl, a $C_1$–$C_6$ alkoxycarbonyl and piperidinyl, $R^{11}$ is a hydrogen atom or a $C_1$–$C_6$ alkyl, $R^{12}$ is a $C_3$–$C_8$ cycloalkyl, or a phenyl which has optionally 1 to 3 substituents selected from a $C_1$–$C_6$ alkoxy, a $C_1$–$C_6$ alkyl and a halogen atom, W is a group of the formula: —($CH_2$)$_p$— wherein p is an integer of 3 to 5, or a group of the formula: —CH=CH—($CH_2$)$_q$— wherein q is an integer of 1 to 3, and further said —($CH_2$)$_p$— group and said —CH=CH—($CH_2$)$_q$— group having optionally 1 to 3 substituents selected from a $C_1$–$C_6$ alkyl having optionally a hydroxy substituent, a $C_1$–$C_6$ alkoxycarbonyl, carboxy, hydroxy, oxo, a $C_1$–$C_6$ alkanoyloxy having optionally a halogen substituent, an amino-($C_1$–$C_6$) alkyl having optionally a substituent selected from a $C_1$–$C_6$ alkyl and a $C_1$–$C_6$ alkanoyl, a $C_1$–$C_6$ alkanoyloxy-substituted $C_1$–$C_6$ alkyl, a $C_1$–$C_6$ alkylsulfonyloxy-($C_1$–$C_6$) alkyl, an azido-($C_1$–$C_6$) alkyl, a group of the formula:

an aminocarbonyloxy having optionally a $C_1$–$C_6$ alkyl substituent, a $C_1$–$C_6$ alkoxy, a $C_1$–$C_6$ alkoxycarbonyl-substituted $C_1$–$C_6$ alkoxy, a carboxy-substituted $C_1$–$C_6$ alkoxy, an aminocarbonyl-($C_1$–$C_6$) alkoxy having optionally a $C_1$–$C_6$ alkyl substituent, an amino-($C_1$–$C_6$) alkoxy having optionally a substituent selected from a $C_1$–$C_6$ alkyl and a $C_1$–$C_6$ alkanoyl, a phthalimido-substituted $C_1$–$C_6$ alkoxy, hydroxy-imino, a $C_1$–$C_6$ alkanoyloxy-imino, a $C_1$–$C_6$ alkylidene, a halogen atom, azido, sulfoxyimino, a group of the formula:

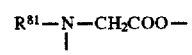

wherein $R^{81}$ is a hydrogen atom or a $C_1$–$C_6$ alkyl, hydrazino, pyrrolyl, an amino-($C_2$–$C_6$) alkanoyloxy having optionally a $C_1$–$C_6$ alkyl substituent, a group of the formula:

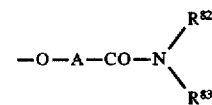

wherein A is as defined above in this claim, and $R^{82}$ and $R^{83}$ are the same or different and are each a hydrogen atom, a $C_1$–$C_6$ alkyl, a carbamoyl-substituted $C_1$–$C_6$ alkyl, a hydroxy-substituted $C_1$–$C_6$ alkyl, or a pyridyl-($C_1$–$C_6$) alkyl, or $R^{82}$ and $R^{83}$ may bind together with the nitrogen atom to which they are bonded to form a 5- or 6-membered saturated heterocyclic group with or without being intervened with a nitrogen, oxygen or sulfur atom wherein the heterocyclic group is one member selected from the group consisting of pyrrolidinyl, piperidinyl, piperazinyl, morpholino, and thiomorpholino, and has optionally a substituent selected from oxo, a $C_1$–$C_6$ alkyl, a $C_1$–$C_6$ alkanoyl, and carbamoyl, and a group of the formula:

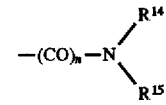

wherein n is as defined above in this claim, and $R^{14}$ and $R^{15}$ are the same or different and are each a hydrogen atom, a $C_1$–$C_6$ alkyl, a $C_2$–$C_6$ alkenyl, a $C_1$–$C_6$ alkanoyl, a $C_3$–$C_8$ cycloalkyl, an oxiranyl-substituted $C_1$–$C_6$ alkyl, a $C_1$–$C_6$ alkyl having 1 to 2 substituents selected from a $C_1$–$C_6$ alkoxy, hydroxy and an amino having optionally a $C_1$–$C_6$ alkyl substituent, a phenyl-($C_1$–$C_6$) alkyl, a pyridyl-($C_1$–$C_6$) alkyl, a $C_1$–$C_6$ alkylsulfonyl, benzoyl, a $C_1$–$C_6$ alkoxycarbonyl, anilinocarbonyl, an aminocarbonyl having optionally a $C_1$–$C_6$ alkyl substituent, a cyano-substituted $C_1$–$C_6$ alkyl, a $C_1$–$C_6$ alkoxycarbonyl-substituted $C_1$–$C_6$ alkyl, a carbamoyl-substituted $C_1$–$C_6$ alkyl, a carboxy-substituted $C_1$–$C_6$ alkyl, a tetrahydropyranyloxy-substituted $C_1$–$C_6$ alkyl, a $C_1$–$C_6$ alkanoyloxy-substituted $C_1$–$C_6$ alkyl, a piperidinyl having optionally a phenyl-($C_1$–$C_6$) alkyl substituent on the piperidine ring, a halogen substituted $C_1$–$C_6$ alkanoyl, an imidazolyl-substituted $C_2$–$C_6$ alkanoyl, an amino-($C_2$–$C_6$) alkanoyl having optionally a substituent selected from a $C_1$–$C_6$ alkyl and a $C_1$–$C_6$ alkoxycarbonyl, an aminocarbonyl-($C_1$–$C_6$) alkyl having optionally a $C_1$–$C_6$ alkyl substituent, or a phenyl-($C_1$–$C_6$) alkoxycarbonyl, or $R^{14}$ or $R^{15}$ may bind together with the nitrogen atom to which they are bonded to form a 5- or 6-membered saturated heterocyclic group with or without being intervened with a nitrogen or oxygen atom, wherein the heterocyclic group is one member selected from the group consisting of pyrrolidinyl, piperidinyl, piperazinyl, and morpholino, and may optionally have a substituent selected from a $C_1$–$C_6$ alkyl, a phenyl-($C_1$–$C_6$) alkyl or a $C_1$–$C_6$ alkanoyl, and a pharmaceutically acceptable salt thereof.

2. The method according to claim 1, wherein $R^1$ is a hydrogen atom.

3. The method according to claim 1, wherein $R^1$ is a halogen atom.

4. The method according to claim 1, wherein $R^1$ is a $C_1$–$C_6$ alkyl, an amino having optionally a $C_1$–$C_6$ alkyl substituent, or a $C_1$–$C_6$ alkoxy.

5. The method according to claim 2, wherein $R^2$ is a hydrogen atom.

6. The method according to claim 2, wherein $R^2$ is a halogen atom, a $C_1$–$C_6$ alkoxy, or a $C_1$–$C_6$ alkyl.

7. The method according to claim 2, wherein $R^2$ is a phenyl-($C_1$–$C_6$) alkoxy, hydroxy, an amino having optionally a $C_1$–$C_6$ alkyl substituent, a carbamoyl-substituted $C_1$–$C_6$ alkoxy, an amino-substituted $C_1$–$C_6$ alkoxy having optionally a $C_1$–$C_6$ alkyl substituent, or a benzoyloxy having optionally a halogen substituent on the phenyl ring.

8. The method according to claim 3, wherein $R^2$ is a hydrogen atom.

9. The method according to claim 3, wherein $R^2$ is a halogen atom, a $C_1$–$C_6$ alkoxy, or a $C_1$–$C_6$ alkyl.

10. The method according to claim 3, wherein $R^2$ is a phenyl-($C_1$–$C_6$) alkoxy, hydroxy, an amino having optionally a $C_1$–$C_6$ alkyl substituent, a carbamoyl-substituted $C_1$–$C_6$ alkoxy, an amino-substituted $C_1$–$C_6$ alkoxy having optionally a $C_1$–$C_6$ alkyl substituent, or a benzoyloxy having optionally a halogen substituent on the phenyl ring.

11. The method according to claim 4, wherein $R^2$ is a hydrogen atom.

12. The method according to claim 4, wherein $R^2$ is a halogen atom, a $C_1$–$C_6$ alkoxy, or a $C_1$–$C_6$ alkyl.

13. The method according to claim 4, wherein $R^2$ is a phenyl-($C_1$–$C_6$) alkoxy, hydroxy, an amino having optionally a $C_1$–$C_6$ alkyl substituent, a carbamoyl-substituted $C_1$–$C_6$ alkoxy, an amino-substituted $C_1$–$C_6$ alkoxy having optionally a $C_1$–$C_6$ alkyl substituent, or a benzoyloxy having optionally a halogen substituent on the phenyl ring.

14. The method according to claim 5, wherein $R^3$ is a group of the formula:

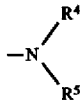

wherein $R^4$ and $R^5$ are as defined in claim 1.

15. The method according to claim 5, wherein $R^3$ is a group of the formula:

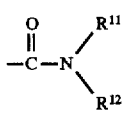

wherein $R^{11}$ and $R^{12}$ are as defined in claim 1.

16. The method according to claim 6, wherein $R^3$ is a group of the formula:

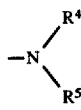

wherein $R^4$ and $R^5$ are as defined in claim 1.

17. The method according to claim 6, wherein $R^3$ is a group of the formula:

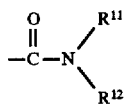

wherein $R^{11}$ and $R^{12}$ are as defined in claim 1.

18. The method according to claim 8, wherein $R^3$ is a group of the formula:

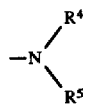

wherein $R^4$ and $R^5$ are as defined in claim 1.

19. The method according to claim 8, wherein $R^3$ is a group of the formula:

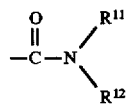

wherein $R^{11}$ and $R^{12}$ are as defined in claim 1.

20. The method according to claim 9, wherein $R^3$ is a group of the formula:

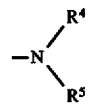

wherein $R^4$ and $R^5$ are as defined in claim 1.

21. The method according to claim 9, wherein $R^3$ is a group of the formula:

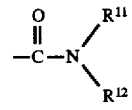

wherein $R^{11}$ and $R^{12}$ are as defined in claim 1.

22. The method according to claim 14, wherein $R^4$ is a hydrogen atom, and $R^5$ is a group of the formula:

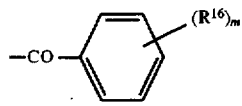

and $R^{16}$ and m are as defined in claim 1.

23. The method according to claim 14, wherein $R^4$ is a hydrogen atom and $R^5$ is a phenyl-($C_1$–$C_6$) alkoxycarbonyl, a $C_1$–$C_6$ alkanoyl, a phenyl($C_2$–$C_6$) alkanoyl, a $C_3$–$C_8$ cycloalkyl-($C_2$–$C_6$) alkanoyl, a $C_3$–$C_8$ cycloalkyl-carbonyl, tricyclo(3.3.1.1)decanylcarbonyl, naphthylcarbonyl, pyridylcarbonyl, furoyl, thenoyl, a phenoxy-($C_2$–$C_6$) alkanoyl which phenyl ring has optionally 1 to 3 substituents selected from a $C_1$–$C_6$ alkyl, a $C_1$–$C_6$ alkoxy and an amino having optionally a $C_1$–$C_6$ alkanoyl substituent, a phthalimido-substituted $C_2$–$C_6$ alkanoyl, a $C_1$–$C_6$ alkoxycarbonyl-($C_2$–$C_6$) alkanoyl, a carboxy-($C_2$–$C_6$) alkanoyl, a naphthyloxy-($C_2$–$C_6$) alkanoyl, a halogen-substituted $C_1$–$C_6$ alkanoyl, a group of the formula:

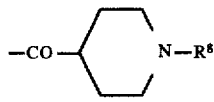

wherein $R^8$ is a hydrogen atom, a $C_1$–$C_6$ alkyl, a phenyl-($C_1$–$C_6$)alkoxycarbonyl, a carbamoyl-($C_1$–$C_6$) alkyl, an amino-($C_2$–$C_6$) alkanoyl having optionally a $C_1$–$C_6$ alkyl substituent, or a $C_1$–$C_6$ alkanoyl, an anilinocarbonyl which has optionally a $C_1$–$C_6$ alkyl substituent on the phenyl ring, phenoxycarbonyl, a phenylsulfonyl which has optionally a substituent selected from a halogen atom and a $C_1$–$C_6$ alkyl on the phenyl ring, quinolylsulfonyl, or a group of the formula:

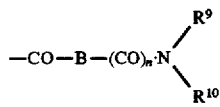

wherein B is a $C_1$–$C_6$ alkylene, n is an integer of 0 or 1, and $R^9$ and $R^{10}$ are the same or different and are each a hydrogen atom, a $C_1$–$C_6$ alkyl having optionally a hydroxy substituent, a $C_3$–$C_8$ cycloalkyl, a phenyl-($C_1$–$C_6$) alkyl, a $C_1$–$C_6$ alkanoyl, a $C_2$–$C_6$ alkenyl, a phenoxy-($C_1$–$C_6$) alkyl, a phenyl which has optionally 1 to 3 substituents selected from an amino-($C_1$–$C_6$) alkyl having optionally a $C_1$–$C_6$ alkanoyl substituent, a $C_1$–$C_6$ alkyl, a $C_1$–$C_6$ alkoxy and a halogen atom, a phthalimido-substituted $C_1$–$C_6$ alkyl, an amino-($C_1$–$C_6$) alkyl having optionally a $C_1$–$C_6$ alkanoyl substituent, a $C_2$–$C_6$ alkynyl, or an amino-($C_1$–$C_6$) alkyl having optionally a $C_1$–$C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1$–$C_6$ alkyl, a $C_1$–$C_6$ alkoxycarbonyl and piperidinyl.

24. The method according to claim 14, wherein $R^4$ is a $C_1$–$C_6$ alkyl.

25. The method according to claim 16, wherein $R^4$ is a hydrogen atom, and $R^5$ is a group of the formula:

wherein $R^{16}$ and m are as defined in claim 1.

26. The method according to claim 16, wherein $R^4$ is a hydrogen atom, and $R^5$ is a phenyl-($C_1$–$C_6$) alkoxycarbonyl, a $C_1$–$C_6$ alkanoyl, a phenyl-($C_2$–$C_6$) alkanoyl, a $C_3$–$C_8$ cycloalkyl-($C_2$–$C_6$) alkanoyl, a $C_3$–$C_8$ cycloalkylcarbonyl, tricyclo(3.3.1.1)decanylcarbonyl, naphthylcarbonyl, pyridylcarbonyl, furoyl, thenoyl, a phenoxy-($C_2$–$C_6$) alkanoyl which phenyl ring has optionally 1 to 3 substituents selected from a $C_1$–$C_6$ alkyl, a $C_1$–$C_6$ alkoxy and an amino having optionally a $C_1$–$C_6$ alkanoyl substituent, a phthalimido-substituted $C_2$–$C_6$ alkanoyl, a $C_1$–$C_6$ alkoxycarbonyl-($C_2$–$C_6$) alkanoyl, a carboxy-($C_2$–$C_6$) alkanoyl, a naphthyloxy-($C_2$–$C_6$) alkanoyl, a halogen-substituted $C_1$–$C_6$ alkanoyl, a group of the formula:

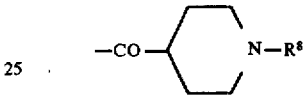

wherein $R^8$ is a hydrogen atom, a $C_1$–$C_6$ alkyl, a phenyl-($C_1$–$C_6$) alkoxycarbonyl, a carbamoyl-($C_1$–$C_6$) alkyl, an amino-($C_2$–$C_6$) alkanoyl having optionally a $C_1$–$C_6$ alkyl substituent, or a $C_1$–$C_6$ alkanoyl, an anilinocarbonyl which has optionally a $C_1$–$C_6$ alkyl substituent on the phenyl ring, phenoxycarbonyl, a phenylsulfonyl which has optionally a substituent selected from a halogen atom and a $C_1$–$C_6$ alkyl on the phenyl ring, quinolylsulfonyl, or a group of the formula:

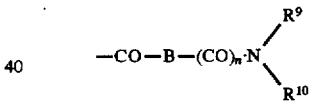

wherein B is a $C_1$–$C_6$ alkylene, n is an integer of 0 or 1, and $R^9$ and $R^{10}$ are the same or different and are each a hydrogen atom, a $C_1$–$C_6$ alkyl having optionally a hydroxy substituent, a $C_3$–$C_8$ cycloalkyl, a phenyl-($C_1$–$C_6$) alkyl, a $C_1$–$C_6$ alkanoyl, a $C_2$–$C_6$ alkenyl, a phenoxy-($C_1$–$C_6$) alkyl, a phenyl which has optionally 1 to 3 substituents selected from an amino-($C_1$–$C_6$) alkyl having optionally a $C_1$–$C_6$ alkanoyl substituent, a $C_1$–$C_6$ alkyl, a $C_1$–$C_6$ alkoxy and a halogen atom, a phthalimido-substituted $C_1$–$C_6$ alkyl, an amino-($C_1$–$C_6$) alkyl having optionally a $C_1$–$C_6$ alkanoyl substituent, a $C_2$–$C_6$ alkynyl, or an amino-($C_1$–$C_6$) alkyl having optionally a $C_1$–$C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1$–$C_6$ alkyl, a $C_1$–$C_6$ alkoxycarbonyl and piperidinyl.

27. The method according to claim 16, wherein $R^4$ is a $C_1$–$C_6$ alkyl.

28. The method according to claim 7, wherein $R^4$ is a hydrogen atom, and $R^5$ is a group of the formula:

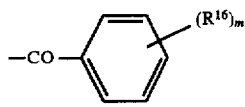

wherein $R^{16}$ and m are as defined in claim 1.

29. The method according to claim 7, wherein $R^4$ is a hydrogen atom, and $R^5$ is a phenyl-$(C_1-C_6)$ alkoxycarbonyl, a $C_1-C_6$ alkanoyl, a phenyl-$(C_2-C_6)$ alkanoyl, a $C_3-C_8$ cycloalkyl-$(C_2-C_6)$ alkanoyl, a $C_3-C_8$ cycloalkylcarbonyl, tricyclo(3.3.1.1)decanylcarbonyl, naphthylcarbonyl, pyridylcarbonyl, furoyl, thenoyl, a phenoxy-$(C_2-C_6)$ alkanoyl which phenyl ring has optionally 1 to 3 substituents selected from a $C_1-C_6$ alkyl, a $C_1-C_6$ alkoxy and an amino having optionally a $C_1-C_6$ alkanoyl substituent, a phthalimido-substituted $C_2-C_6$ alkanoyl, a $C_1-C_6$ alkoxycarbonyl-$(C_2-C_6)$ alkanoyl, a carboxy-$(C_2-C_6)$ alkanoyl, a naphthyloxy-$(C_2-C_6)$ alkanoyl, a halogen-substituted $C_1-C_6$ alkanoyl, a group of the formula:

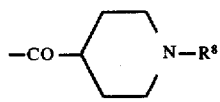

wherein $R^8$ is a hydrogen atom, a $C_1-C_6$ alkyl, a phenyl-$(C_1-C_6)$ alkoxycarbonyl, a carbamoyl-$(C_1-C_6)$ alkyl, an amino-$(C_2-C_6)$ alkanoyl having optionally a $C_1-C_6$ alkyl substituent, or a $C_1-C_6$ alkanoyl, an anilinocarbonyl which has optionally a $C_1-C_6$ alkyl substituent on the phenyl ring, phenoxycarbonyl, a phenylsulfonyl which has optionally a substituent selected from a halogen atom and a $C_1-C_6$ alkyl on the phenyl ring, quinolylsulfonyl, or a group of the formula:

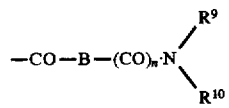

wherein B is a $C_1-C_6$ alkylene, n is an integer of 0 or 1, and $R^9$ and $R^{10}$ are the same or different and are each a hydrogen atom, a $C_1-C_6$ alkyl having optionally a hydroxy substituent, a $C_3-C_8$ cycloalkyl, a phenyl-$(C_1-C_6)$ alkyl, a $C_1-C_6$ alkanoyl, a $C_2-C_6$ alkenyl, a phenoxy-$(C_1-C_6)$ alkyl, a phenyl which has optionally 1 to 3 substituents selected from an amino-$(C_1-C_6)$ alkyl having optionally a $C_1-C_6$ alkanoyl substituent, a $C_1-C_6$ alkyl, a $C_1-C_6$ alkoxy and a halogen atom, a phthalimido-substituted $C_1-C_6$ alkyl, an amino-$(C_1-C_6)$ alkyl having optionally a $C_1-C_6$ alkanoyl substituent, a $C_2-C_6$ alkynyl, or an amino-$(C_1-C_6)$ alkyl having optionally a $C_1-C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1-C_6$ alkyl, a $C_1-C_6$ alkoxycarbonyl and piperidinyl.

30. The method according to claim 7, wherein $R^4$ is a $C_1-C_6$ alkyl.

31. The method according to claim 18, wherein $R^4$ is a hydrogen atom, $R^5$ is a group of the formula:

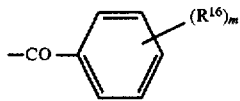

wherein $R^{16}$ and m are as defined in claim 1.

32. The method according to claim 18, wherein $R^4$ is a hydrogen atom, and $R^5$ is a phenyl-$(C_1-C_6)$ alkoxycarbonyl, a $C_1-C_6$ alkanoyl, a phenyl-$(C_2-C_6)$ alkanoyl, a $C_3-C_8$ cycloalkyl-$(C_2-C_6)$ alkanoyl, a $C_3-C_8$ cycloalkylcarbonyl, tricyclo(3.3.1.1)decanylcarbonyl, naphthylcarbonyl, pyridylcarbonyl, furoyl, thenoyl, a phenoxy-$(C_2-C_6)$ alkanoyl which phenyl ring has optionally 1 to 3 substituents selected from a $C_1-C_6$ alkyl, a $C_1-C_6$ alkoxy and an amino having optionally a $C_1-C_6$ alkanoyl substituent, a phthalimido-substituted $C_2-C_6$ alkanoyl, a $C_1-C_6$ alkoxycarbonyl-$(C_2-C_6)$ alkanoyl, a carboxy-$(C_2-C_6)$ alkanoyl, a naphthyloxy-$(C_2-C_6)$ alkanoyl, a halogen-substituted $(C_1-C_6)$ alkanoyl, a group of the formula:

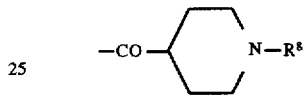

wherein $R^8$ is a hydrogen atom, a $C_1-C_6$ alkyl, a phenyl-$(C_1-C_6)$ alkoxycarbonyl, a carbamoyl-$(C_1-C_6)$ alkyl, an amino-$(C_2-C_6)$ alkanoyl having optionally a $C_1-C_6$ alkyl substituent, or a $C_1-C_6$ alkanoyl), an anilinocarbonyl which has optionally a $C_1-C_6$ alkyl substituent on the phenyl ring, phenoxycarbonyl, a phenylsulfonyl which has optionally a substituent selected from a halogen atom and a $C_1-C_6$ alkyl on the phenyl ring, quinolylsulfonyl, or a group of the formula:

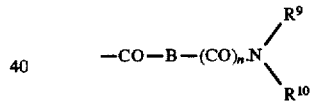

wherein B is a $C_1-C_6$ alkylene, n is an integer of 0 or 1, and $R^9$ and $R^{10}$ are the same or different and are each a hydrogen atom, a $C_1-C_6$ alkyl having optionally a hydroxy substituent, a $C_3-C_8$ cycloalkyl, a phenyl-$(C_1-C_6)$ alkyl, a $C_1-C_6$ alkanoyl, a $C_2-C_6$ alkenyl, a phenoxy-$(C_1-C_6)$ alkyl, a phenyl which has optionally 1 to 3 substituents selected from an amino-$(C_1-C_6)$ alkyl having optionally a $C_1-C_6$ alkanoyl substituent, a $C_1-C_6$ alkyl, a $C_1-C_6$ alkoxy and a halogen atom, a phthalimido-substituted $C_1-C_6$ alkyl, an amino-$(C_1-C_6)$ alkyl having optionally a $C_1-C_6$ alkanoyl substituent, a $C_2-C_6$ alkynyl, or an amino-$(C_1-C_6)$ alkyl having optionally a $C_1-C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1-C_6$ alkyl, a $C_1-C_6$ alkoxycarbonyl and piperidinyl.

33. The method according to claim 18, wherein $R^4$ is a $C_1-C_6$ alkyl.

34. The method according to claim 20, wherein $R^4$ is a hydrogen atom, and $R^5$ is a group of the formula:

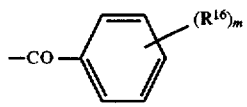

wherein $R^{16}$ and m are as defined in claim 1.

35. The method according to claim 20, wherein $R^4$ is a hydrogen atom, and $R^5$ is a phenyl-($C_1$–$C_6$) alkoxycarbonyl, a $C_1$–$C_6$ alkanoyl, a phenyl-($C_2$–$C_6$) alkanoyl, a $C_3$–$C_8$ cycloalkyl-($C_2$–$C_6$) alkanoyl, a $C_3$–$C_8$ cycloalkyl-carbonyl, tricyclo(3.3.1.1)decanylcarbonyl, naphthylcarbonyl, pyridylcarbonyl, furoyl, thenoyl, a phenoxy-($C_2$–$C_6$) alkanoyl which phenyl ring has optionally 1 to 3 substituents selected from a $C_1$–$C_6$ alkyl, a $C_1$–$C_6$ alkoxy and an amino having optionally a $C_1$–$C_6$ alkanoyl substituent, a phthalimido-substituted $C_2$–$C_6$ alkanoyl, a $C_1$–$C_6$ alkoxycarbonyl-($C_2$–$C_6$) alkanoyl, a carboxy-($C_2$–$C_6$) alkanoyl, a naphthyloxy-($C_2$–$C_6$) alkanoyl, a halogen-substituted $C_1$–$C_6$ alkanoyl, a group of the formula:

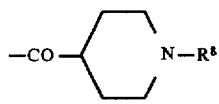

wherein $R^8$ is a hydrogen atom, a $C_1$–$C_6$ alkyl, a phenyl-($C_1$–$C_6$) alkoxycarbonyl, a carbamoyl-($C_1$–$C_6$) alkyl, an amino-($C_1$–$C_6$) alkanoyl having optionally a $C_1$–$C_6$ alkyl substituent, or a $C_1$–$C_6$ alkanoyl, an anilinocarbonyl which has optionally a $C_1$–$C_6$ alkyl substituent on the phenyl ring, phenoxycarbonyl, a phenylsulfonyl which has optionally a substituent selected from a halogen atom and a $C_1$–$C_6$ alkyl on the phenyl ring, quinolylsulfonyl, or a group of the formula:

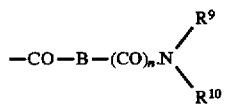

wherein B is a $C_1$–$C_6$ alkylene, n is an integer of 0 or 1, and $R^9$ and $R^{10}$ are the same or different and are each a hydrogen atom, a $C_1$–$C_6$ alkyl having optionally a hydroxy substituent, a $C_3$–$C_8$ cycloalkyl, a phenyl-($C_1$–$C_6$) alkyl, a $C_1$–$C_6$ alkanoyl, a $C_2$–$C_6$ alkenyl, a phenoxy-($C_1$–$C_6$) alkyl, a phenyl which has optionally 1 to 3 substituents selected from an amino-($C_1$–$C_6$) alkyl having optionally a $C_1$–$C_6$ alkanoyl substituent, a $C_1$–$C_6$ alkyl, a $C_1$–$C_6$ alkoxy and a halogen atom, a phthalimido-substituted $C_1$–$C_6$ alkyl, an amino-($C_1$–$C_6$) alkyl having optionally a $C_1$–$C_6$ alkanoyl substituent, a $C_2$–$C_6$ alkynyl, or an amino-($C_1$–$C_6$) alkyl having optionally a $C_1$–$C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1$–$C_6$ alkyl, a $C_1C_6$ alkoxycarbonyl and piperidinyl.

36. The method according to claim 20, wherein $R^4$ is a $C_1$–$C_6$ alkyl.

37. The method according to claim 10, wherein $R^4$ is a hydrogen atom, and $R^5$ is a group of the formula:

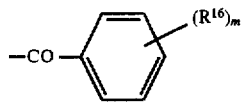

wherein $R^{16}$ and m are as defined in claim 1.

38. The method according to claim 10, wherein $R^4$ is a hydrogen atom, and $R^5$ is a phenyl-($C_1$–$C_6$) alkoxycarbonyl, a $C_1$–$C_6$ alkanoyl, a phenyl-($C_2$–$C_6$) alkanoyl, a $C_3$–$C_8$ cycloalkyl-($C_2$–$C_6$) alkanoyl, a $C_3$–$C_8$ cycloalkyl-carbonyl, tricyclo(3.3.1.1)decanylcarbonyl, naphthylcarbonyl, pyridylcarbonyl, furoyl, thenoyl, a phenoxy-($C_2$–$C_6$) alkanoyl which phenyl ring has optionally 1 to 3 substituents selected from a $C_1$–$C_6$ alkyl, a $C_1$–$C_6$ alkoxy and an amino having optionally a $C_1$–$C_6$ alkanoyl substituent, a phthalimido-substituted $C_2$–$C_6$ alkanoyl, a $C_1$–$C_6$ alkoxycarbonyl-($C_2$–$C_6$) alkanoyl, a carboxy-($C_2$–$C_6$) alkanoyl, a naphthyloxy-($C_2$–$C_6$) alkanoyl, a halogen-substituted $C_1$–$C_6$ alkanoyl, a group of the formula:

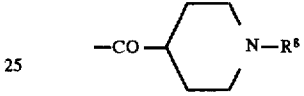

wherein $R^8$ is a hydrogen atom, a $C_1$–$C_6$ alkyl, a phenyl-($C_1$–$C_6$) alkoxycarbonyl, a carbamoyl-($C_1$–$C_6$) alkyl, an amino-($C_2$–$C_6$) alkanoyl having optionally a $C_1$–$C_6$ alkyl substituent, or a $C_1$–$C_6$ alkanoyl, an anilinocarbonyl which has optionally a $C_1$–$C_6$ alkyl substituent on the phenyl ring, phenoxycarbonyl, a phenylsulfonyl which has optionally a substituent selected from a halogen atom and a $C_1$–$C_6$ alkyl on the phenyl ring, quinolylsulfonyl, or a group of the formula:

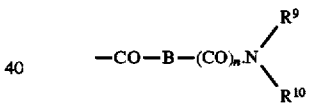

wherein B is a $C_1$–$C_6$ alkylene, n is an integer of 0 or 1, and $R^9$ and $R^{10}$ are the same or different and are each a hydrogen atom, a $C_1$–$C_6$ alkyl having optionally a hydroxy substituent, a $C_3$–$C_8$ cycloalkyl, a phenyl-($C_1$–$C_6$) alkyl, a $C_1$–$C_6$ alkanoyl, a $C_2$–$C_6$ alkenyl, a phenoxy-($C_1$–$C_6$) alkyl, a phenyl which has optionally 1 to 3 substituents selected from an amino-($C_1$–$C_6$) alkyl having optionally a $C_1$–$C_6$ alkanoyl substituent, a $C_1$–$C_6$ alkyl, a $C_1$–$C_6$ alkoxy and a halogen atom, a phthalimido-substituted $C_1$–$C_6$ alkyl, an amino-($C_1$–$C_6$) alkyl having optionally a $C_1$–$C_6$ alkanoyl substituent, a $C_2$–$C_6$ alkynyl, or an amino-($C_1$–$C_6$) alkyl having optionally a $C_1$–$C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1$–$C_6$ alkyl, a $C_1$–$C_6$ alkoxycarbonyl and piperidinyl.

39. The method according to claim 10, wherein $R^4$ is a $C_1$–$C_6$ alkyl.

40. The method according to claim 11, wherein $R^4$ is a hydrogen atom, and $R^5$ is a group of the formula:

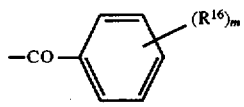

wherein $R^{16}$ and m are as defined in claim 1.

41. The method according to claim 11, wherein $R^4$ is a hydrogen atom, and $R^5$ is a phenyl-($C_1$–$C_6$) alkoxycarbonyl, a $C_1$–$C_6$ alkanoyl, a phenyl-($C_2$–$C_6$) alkanoyl, a $C_3$–$C_8$ cycloalkyl-($C_2$–$C_6$) alkanoyl, a $C_3$–$C_8$ cycloalkyl-carbonyl, tricyclo(3.3.1.1)decanylcarbonyl, naphthylcarbonyl, pyridylcarbonyl, furoyl, thenoyl, a phenoxy-($C_2$–$C_6$) alkanoyl which phenyl ring has optionally 1 to 3 substituents selected from a $C_1$–$C_6$ alkyl, a $C_1$–$C_6$ alkoxy and an amino having optionally a $C_1$–$C_6$ alkanoyl substituent, a phthalimido-substituted $C_2$–$C_6$ alkanoyl, a $C_1$–$C_6$ alkoxycarbonyl-($C_2$–$C_6$) alkanoyl, a carboxy-($C_2$–$C_6$) alkanoyl, a naphthyloxy-($C_2$–$C_6$) alkanoyl, a halogen-substituted $C_1$–$C_6$ alkanoyl, a group of the formula:

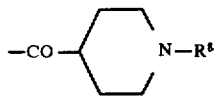

wherein $R^8$ is a hydrogen atom, a $C_1$–$C_6$ alkyl, a phenyl-($C_1$–$C_6$) alkoxycarbonyl, a carbamoyl-($C_1$–$C_6$) alkyl, an amino-($C_2$–$C_6$) alkanoyl having optionally a $C_1$–$C_6$ alkyl substituent, or a $C_1$–$C_6$ alkanoyl, an anilinocarbonyl which has optionally a $C_1$–$C_6$ alkyl substituent on the phenyl ring, phenoxycarbonyl, a phenylsulfonyl which has optionally a substituent selected from a halogen atom and a $C_1$–$C_6$ alkyl on the phenyl ring, quinolylsulfonyl, or a group of the formula:

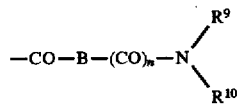

wherein B is a $C_1$–$C_6$ alkylene, n is an integer of 0 or 1, and $R^9$ and $R^{10}$ are the same or different and are each a hydrogen atom, a $C_1$–$C_6$ alkyl having optionally a hydroxy substituent, a $C_2$–$C_8$ cycloalkyl, a phenyl-($C_1$–$C_6$) alkyl, a $C_1$–$C_6$ alkanoyl, a $C_2$–$C_6$ alkenyl, a phenoxy-($C_1$–$C_6$) alkyl, a phenyl which has optionally 1 to 3 substituents selected from an amino-($C_1$–$C_6$) alkyl having optionally a $C_1$–$C_6$ alkanoyl substituent, a $C_1$–$C_6$ alkyl, a $C_1$–$C_6$ alkoxy and a halogen atom, a phthalimido-substituted $C_1$–$C_6$ alkyl, an amino-($C_1$–$C_6$) alkyl having optionally a $C_1$–$C_6$ alkanoyl substituent, a $C_2$–$C_6$ alkynyl, or an amino-($C_1$–$C_6$) alkyl having optionally a $C_1$–$C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1$–$C_6$ alkyl, a $C_1$–$C_6$ alkoxycarbonyl and piperidinyl.

42. The method according to claim 12, wherein $R^4$ is a $C_1$–$C_6$ alkyl.

43. The method according to claim 12, wherein $R^4$ is a hydrogen atom, and $R^5$ is a group of the formula:

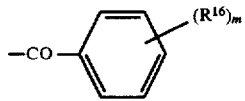

wherein $R^{16}$ and m are as defined in claim 1.

44. The method according to claim 12, wherein $R^4$ is a hydrogen atom, and $R^5$ is a phenyl-($C_1$–$C_6$) alkoxycarbonyl, a $C_1$–$C_6$ alkanoyl, a phenyl-($C_2$–$C_6$) alkanoyl, a $C_3$–$C_8$ cycloalkyl-($C_2$–$C_6$) alkanoyl, a $C_3$–$C_8$ cycloalkyl-carbonyl, tricyclo(3.3.1.1)decanylcarbonyl, naphthylcarbonyl, pyridylcarbonyl, furoyl, thenoyl, a phenoxy-($C_2$–$C_6$) alkanoyl which phenyl ring has optionally 1 to 3 substituents selected from a $C_1$–$C_6$ alkyl, a $C_1$–$C_6$ alkoxy and an amino having optionally a $C_1$–$C_6$ alkanoyl substituent, a phthalimido-substituted $C_2$–$C_6$ alkanoyl, a $C_1$–$C_6$ alkoxycarbonyl-($C_2$–$C_6$) alkanoyl, a carboxy-($C_2$–$C_6$) alkanoyl, a naphthyloxy-($C_2$–$C_6$) alkanoyl, a halogen-substituted $C_1$–$C_6$ alkanoyl, a group of the formula:

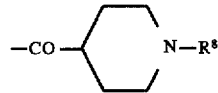

wherein $R^8$ is a hydrogen atom, a $C_1$–$C_6$ alkyl, a phenyl-($C_1$–$C_6$) alkoxycarbonyl, a carbamoyl-($C_1$–$C_6$) alkyl, an amino-($C_2$–$C_6$) alkanoyl having optionally a $C_1$–$C_6$ alkyl substituent, or a $C_1$–$C_6$ alkanoyl, an anilinocarbonyl which has optionally a $C_1$–$C_6$ alkyl substituent on the phenyl ring, phenoxycarbonyl, a phenylsulfonyl which has optionally a substituent selected from a halogen atom and a $C_1$–$C_6$ alkyl on the phenyl ring, quinolylsulfonyl, or a group of the formula:

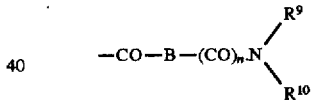

wherein B is a $C_1$–$C_6$ alkylene, n is an integer of 0 or 1, and $R^9$ and $R^{10}$ are the same or different and are each a hydrogen atom, a $C_1$–$C_6$ alkyl having optionally a hydroxy substituent, a $C_3$–$C_8$ cycloalkyl, a phenyl-($C_1$–$C_6$) alkyl, a $C_1$–$C_6$ alkanoyl, a $C_2$–$C_6$ alkenyl, a phenoxy-($C_1$–$C_6$) alkyl, a phenyl which has optionally 1 to 3 substituents selected from an amino-($C_1$–$C_6$) alkyl having optionally a $C_1$–$C_6$ alkanoyl substituent, a $C_1$–$C_6$ alkyl, a $C_1$–$C_6$ alkoxy and a halogen atom, a phthalimido-substituted $C_1$–$C_6$ alkyl, an amino-($C_1$–$C_6$) alkyl having optionally a $C_1$–$C_6$ alkanoyl substituent, a $C_2$–$C_6$ alkynyl, or an amino-($C_1$–$C_6$) alkyl having optionally a $C_1$–$C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1$–$C_6$ alkyl, a $C_1$–$C_6$ alkoxycarbonyl and piperidinyl.

45. The method according to claim 12, wherein $R^4$ is a $C_1$–$C_6$ alkyl.

46. The method according to claim 13, wherein $R^4$ is a hydrogen atom, and $R^5$ is a group of the formula:

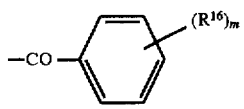

wherein $R^{16}$ and m are as defined in claim 1.

47. The method according to claim 13, wherein $R^4$ is a hydrogen atom, and $R^5$ is a phenyl-$(C_1$–$C_6)$ alkoxycarbonyl, a $C_1$–$C_6$ alkanoyl, a phenyl($C_2$–$C_6$) alkanoyl, a $C_3$–$C_8$ cycloalkyl-($C_2$–$C_6$) alkanoyl, a $C_3$–$C_8$ cycloalkylcarbonyl, tricyclo(3.3.1.1)decanylcarbonyl, naphthylcarbonyl, pyridylcarbonyl, furoyl, thenoyl, a phenoxy-($C_2$–$C_6$) alkanoyl which phenyl ring has optionally 1 to 3 substituents selected from a $C_1$–$C_6$ alkyl, a $C_1$–$C_6$ alkoxy and an amino having optionally a $C_1$–$C_6$ alkanoyl substituent, a phthalimido-substituted $C_2$–$C_6$ alkanoyl, a $C_1$–$C_6$ alkoxycarbonyl-($C_2$–$C_6$) alkanoyl, a carboxy-($C_2$–$C_6$) alkanoyl, a naphthyloxy-($C_2$–$C_6$) alkanoyl, a halogen-substituted $C_1$–$C_6$ alkanoyl, a group of the formula:

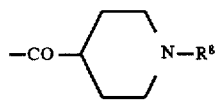

wherein $R^8$ is a hydrogen atom, a $C_1$–$C_6$alkyl, a phenyl-($C_1$–$C_6$) alkoxycarbonyl, a carbamoyl-($C_1$–$C_6$) alkyl, an amino-($C_2$–$C_6$) alkanoyl having optionally a $C_1$–$C_6$ alkyl substituent, or a $C_1$–$C_6$ alkanoyl, an anilinocarbonyl which has optionally a $C_1$–$C_6$ alkyl substituent on the phenyl ring, phenoxycarbonyl, a phenylsulfonyl which has optionally a substituent selected from a halogen atom and a $C_1$–$C_6$ alkyl on the phenyl ring, quinolylsulfonyl, or a group of the formula:

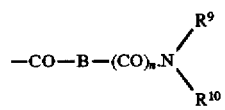

wherein B is a $C_1$–$C_6$ alkylene, n is an integer of 0 or 1, and $R^9$ and $R^{10}$ are the same or different and are each a hydrogen atom, a $C_1$–$C_6$ alkyl having optionally a hydroxy substituent, a $C_3$–$C_8$ cycloalkyl, a phenyl-($C_1$–$C_6$) alkyl, a $C_1$–$C_6$ alkanoyl, a $C_2$–$C_6$ alkenyl, a phenoxy-($C_1$–$C_6$) alkyl, a phenyl which has optionally 1 to 3 substituents selected from an amino-($C_1$–$C_6$) alkyl having optionally a $C_1$–$C_6$ alkanoyl substituent, a $C_1$–$C_6$ alkyl, a $C_1$–$C_6$ alkoxy and a halogen atom, a phthalimido-substituted $C_1$–$C_6$ alkyl, an amino-($C_1$–$C_6$) alkyl having optionally a $C_1$–$C_6$ alkanoyl substituent, a $C_2$–$C_6$ alkynyl, or an amino-($C_1$–$C_6$) alkyl having optionally a $C_1$–$C_6$ alkyl substituent, or $R^9$ and $R^{10}$ may bind together with the nitrogen atom to which they are bonded to form a 5- or 6-membered saturated heterocyclic group with or without being intervened with a nitrogen or an oxygen atom wherein the heterocyclic group is one member selected from the group consisting of pyrrolidinyl, piperidinyl, piperazinyl and morpholino, and has optionally a substituent selected from a $C_1$–$C_6$ alkyl, a $C_1$–$C_6$ alkoxycarbonyl and piperidinyl.

48. The method according to claim 13, wherein $R^4$ is a $C_1$–$C_6$ alkyl.

49. The method according to claim 22, wherein $R^{16}$ is a halogen atom, or a $C_1$–$C_6$ alkyl having optionally a substituent selected from a halogen atom and hydroxy.

50. The method according to claim 25, wherein $R^{16}$ is a halogen atom, or a $C_1$–$C_6$ alkyl having optionally a substituent selected from a halogen atom and hydroxy.

51. The method according to claim 31, wherein $R^{16}$ is a halogen atom, or a $C_1$–$C_6$ alkyl having optionally a substituent selected from a halogen atom and hydroxy.

52. The method according to claim 34, wherein $R^{16}$ is a halogen atom, or a $C_1$–$C_6$ alkyl having optionally a substituent selected from a halogen atom and hydroxy.

53. The method according to claim 1, wherein W is a group of the formula: —$(CH_2)_p$— wherein p is an integer of 3 to 5, and further said —$(CH_2)_p$— group has optionally 1 to 3 substituents selected from a $C_1$–$C_6$ alkyl having optionally a hydroxy substituent, a $C_1$–$C_6$ alkoxycarbonyl, carboxy, hydroxy, oxo, a $C_1$–$C_6$ alkanoyloxy having optionally a halogen substituent, an amino-($C_1$–$C_6$) alkyl having optionally a substituent selected from a $C_1$–$C_6$ alkyl and a $C_1$–$C_6$ alkanoyl, a $C_1$–$C_6$ alkanoyloxy-substituted $C_1$–$C_6$ alkyl, a $C_1$–$C_6$ alkylsulfonyloxy-($C_1$–$C_6$) alkyl, an azido-($C_1$–$C_6$) alkyl, a group of the formula:

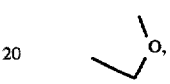

an aminocarbonyloxy having optionally a $C_1$–$C_6$ alkyl substituent, a $C_1$–$C_6$ alkoxy, a $C_1$–$C_6$ alkoxycarbonyl-substituted $C_1$–$C_6$ alkoxy, a carboxy-substituted C–$C_6$ alkoxy, an amino-carbonyl-($C_1$–$C_6$) alkoxy having optionally a $C_1$–$C_6$ alkyl substituent, an amino-($C_1$–$C_6$) alkoxy having optionally a substituent selected from a $C_1$–$C_6$ alkyl and a $C_1$–$C_6$ alkanoyl, a phthalimido-substituted $C_1$–$C_6$ alkoxy, hydroxyimino, a $C_1$–$C_6$ alkanoyloxy-imino, a $C_1$–$C_6$ alkylidene, a halogen atom, azido, sulfoxy-imino, a group of the formula:

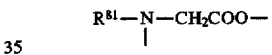

wherein $R^{81}$ is a hydrogen atom or a $C_1$–$C_6$ alkyl, hydrazino, pyrrolyl, an amino-($C_2$–$C_6$) alkanoyloxy having optionally a $C_1$–$C_6$ alkyl substituent, a group of the formula:

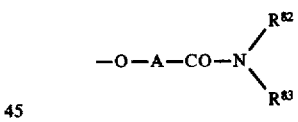

wherein A is as defined above, and $R^{82}$ and $R_{83}$ are the same or different and are each a hydrogen atom, a $C_1$–$C_6$ alkyl, a carbamoyl-substituted $C_1$–$C_6$ alkyl, a hydroxy-substituted $C_1$–$C_6$ alkyl, or a pyridyl-($C_1$–$C_6$) alkyl, or $R^{82}$ and $R^{83}$ may bind together with the nitrogen atom to which they are bonded to form a 5- or 6-membered saturated heterocyclic group with or without being intervened with a nitrogen, oxygen or sulfur atom wherein the heterocyclic group is one member selected from the group consisting of pyrrolidinyl, piperidinyl, piperazinyl, morpholino, and thiomorpholino, and has optionally a substituent selected from oxo, a $C_1$–$C_6$ alkyl, a $C_1$–$C_6$ alkanoyl, and carbamoyl, and a group of the formula:

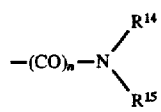

wherein n is as defined above, and $R^{14}$ and $R^{15}$ are the same or different and are each a hydrogen atom, a $C_1$–$C_6$ alkyl, a $C_2$–$C_6$ alkenyl, a $C_1$–$C_6$ alkanoyl, a $C_3$–$C_8$ cycloalkyl, an oxiranyl-substituted $C_1$–$C_6$ alkyl, a $C_1$–$C_6$ alkyl having 1 to 2 substituents selected from a $C_1$–$C_6$ alkoxy, hydroxy and an amino having optionally a $C_1$–$C_6$ alkyl substituent, a phenyl-($C_1$–$C_6$) alkyl, a pyridyl-($C_1$–$C_6$) alkyl, a $C_1$–$C_6$ alkylsulfonyl, benzoyl, a $C_1$–$C_6$ alkoxycarbonyl, anilinocarbonyl, an aminocarbonyl having optionally a $C_1$–$C_6$ alkyl substituent, a cyano-substituted $C_1$–$C_6$ alkyl, a $C_1$–$C_6$ alkoxycarbonyl-substituted $C_1$–$C_6$ alkyl, a carbamoyl-substituted $C_1$–$C_6$ alkyl, a carboxy-substituted $C_1$–$C_6$ alkyl, a tetrahydropyranyloxy-substituted $C_1$–$C_6$ alkyl, a $C_1$–$C_6$ alkanoyloxy-substituted $C_1$–$C_6$ alkyl, a piperidinyl having optionally a phenyl-($C_1$–$C_6$) alkyl substituent on the piperidine ring, a halogen-substituted $C_1$–$C_6$ alkanoyl, an imidazolyl-substituted $C_2$–$C_6$ alkanoyl, an amino-($C_2$–$C_6$) alkanoyl having optionally a substituent selected from a $C_1$–$C_6$ alkyl and a $C_1$–$C_6$ alkoxycarbonyl, an aminocarbonyl-($C_1$–$C_6$) alkyl having optionally a $C_1$–$C_6$ alkyl substituent, or a phenyl-($C_1$–$C_6$) alkoxycarbonyl, or $R^{14}$ or $R^{15}$ may bind together with the nitrogen atom to which they are bonded to form a 5- or 6-membered saturated heterocyclic group with or without being intervened with a nitrogen or oxygen atom, wherein the heterocyclic group is one member selected from the group consisting of pyrrolidinyl, piperidinyl, piperazinyl, and morpholino, and may optionally have a substituent selected from a $C_1$–$C_6$ alkyl, a phenyl-($C_1$–$C_6$) alkyl or a $C_1$–$C_6$ alkanoyl.

54. The method according to claim 1, wherein W is a group of the formula: —CH=CH—(CH$_2$)$_q$— wherein q is an integer of 1 to 3, and further said —CH=CH—(CH$_2$)$_q$— group has optionally 1 to 3 substituents selected from a $C_1$–$C_6$ alkyl having optionally a hydroxy substituent, a $C_1$–$C_6$ alkoxycarbonyl, carboxy, hydroxy, oxo, a $C_1$–$C_6$ alkanoyloxy having optionally a halogen substituent, an amino-($C_1$–$C_6$) alkyl having optionally substituent selected from a $C_1$–$C_6$ alkyl and a $C_1$–$C_6$ alkanoyl, a $C_1$–$C_6$ alkanoyloxy-substituted $C_1$–$C_6$ alkyl, a $C_1$–$C_6$ alkylsulfonyloxy -($C_1$–$C_6$) alkyl, an azido —($C_1$–$C_6$) alkyl, a group of the formula:

an aminocarbonyloxy having optionally a $C_1$–$C_6$ alkyl substituent, a $C_1$–$C_6$ alkoxy, a $C_1$–$C_6$ alkoxycarbonyl-substituted $C_1$–$C_6$ alkoxy, a carboxy-substituted $C_1$–$C_6$ alkoxy, an aminocarbonyl-($C_1$–$C_6$) alkoxy having optionally a $C_1$–$C_6$ alkyl substituent, an amino-($C_1$–$C_6$) alkoxy having optionally a substituent selected from a $C_1$–$C_6$ alkyl and a $C_1$–$C_6$ alkanoyl, a phthalimido-substituted $C_1$–$C_6$ alkoxy, hydroxyimino, a $C_1$–$C_6$ alkanoyloxy-imino, a $C_1$–$C_6$ alkylidene, a halogen atom, azido, sulfoxyimino, a group of the formula:

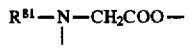

wherein $R^{18}$ is a hydrogen atom or a $C_1$–$C_6$ alkyl, hydrazino, pyrrolyl, an amino-($C_2$–$C_6$) alkanoyloxy having optionally a $C_1$–$C_6$ alkyl substituent, a group of the formula:

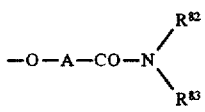

wherein A is as defined above, and $R^{82}$ and $R^{83}$ are the same or different and are each a hydrogen atom, a $C_1$–$C_6$ alkyl, a carbamoyl-substituted $C_1$–$C_6$ alkyl, a hydroxy-substituted $C_1$–$C_6$ alkyl, or a pyridyl-($C_1$–$C_6$) alkyl, or $R^{82}$ and $R^{83}$ may bind together with the nitrogen atom to which they are bonded to form a 5- or 6-membered saturated heterocyclic group with or without being intervened with a nitrogen, oxygen or sulfur atom wherein the heterocyclic group is one member selected from the group consisting of pyrrolidinyl, piperidinyl, piperazinyl, morpholino, and thiomorpholino, and has optionally a substituent selected from oxo, a $C_1$–$C_6$ alkyl, a $C_1$–$C_6$ alkanoyl, and carbamoyl, and a group of the formula:

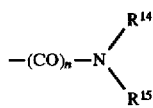

wherein n is as defined above, and $R^{14}$ and $R^{15}$ are the same or different and are each a hydrogen atom, a $C_1$–$C_6$ alkyl, a $C_2$–$C_6$ alkenyl, a $C_1$–$C_6$ alkanoyl, a $C_3$–$C_8$ cycloalkyl, an oxiranyl-substituted $C_1$–$C_6$ alkyl, a $C_1$–$C_6$ alkyl having 1 to 2 substituents selected from a $C_1$–$C_6$ alkoxy, hydroxy and an amino having optionally a $C_1$–$C_6$ alkyl substituent, a phenyl-($C_1$–$C_6$) alkyl, a pyridyl-($C_1$–$C_6$) alkyl, a $C_1$–$C_6$ alkylsulfonyl, benzoyl, a $C_1$–$C_6$ alkoxycarbonyl, anilinocarbonyl, an aminocarbonyl having optionally a $C_1$–$C_6$ alkyl substituent, a cyano-substituted $C_1$–$C_6$ alkyl, a $C_1$–$C_6$ alkoxycarbonyl-substituted $C_1$–$C_6$ alkyl, a carbamoyl-substituted $C_1$–$C_6$ alkyl, a carboxy-substituted $C_1$–$C_6$ alkyl, a tetrahydropyranyloxy-substituted $C_1$–$C_6$ alkyl, a $C_1$–$C_6$ alkanoyloxy-substituted $C_1$–$C_6$ alkyl, a piperidinyl having optionally a phenyl-($C_1$–$C_6$) alkyl substituent on the piperidine ring, a halogen-substituted $C_1$–$C_6$ alkanoyl, an imidazolyl-substituted $C_2$–$C_6$ alkanoyl, an amino-($C_2$–$C_6$) alkanoyl having optionally a substituent selected from a $C_1$–$C_6$ alkyl and a $C_1$–$C_6$ alkoxycarbonyl, an aminocarbonyl-($C_1$–$C_6$) alkyl having optionally a $C_1$–$C_6$ alkyl substituent, or a phenyl-($C_1$–$C_6$) alkoxycarbonyl, or $R^{14}$ or $R^{15}$ may bind together with the nitrogen atom to which they are bonded to form a 5- or 6-membered saturated heterocyclic group with or without being intervened with a nitrogen atom or an oxygen atom, wherein the heterocyclic group is one member selected from the group consisting of pyrrolidinyl, piperidinyl, piperazinyl, and morpholino, and may optionally have a substituent selected from a $C_1$–$C_6$ alkyl, a phenyl-($C_1$–$C_6$) alkyl or a $C_1$–$C_6$ alkanoyl.

55. The method according to claim 53, wherein W is a group of the formula: —(CH$_2$)$_p$— wherein p is an integer of 3 to 5, and said —(CH$_2$)$_p$— group has optionally 1 to 3 substituents selected from a $C_1$–$C_6$ alkyl having optionally a hydroxy substituent, a $C_1$–$C_6$ alkoxycarbonyl, carboxy, hydroxy, oxo, a $C_1$–$C_6$ alkanoyloxy having optionally a halogen substituent, an amino-($C_1$–$C_6$) alkyl having optionally a substituent selected from a $C_1$–$C_6$ alkyl and a $C_1$–$C_6$ alkanoyl, a $C_1$–$C_6$ alkanoyloxy-substituted $C_1$–$C_6$ alkyl, a $C_1$–$C_6$ alkylsulfonyloxy-($C_1$–$C_6$) alkyl, an azido -($C_1$–$C_6$) alkyl, a group of the formula:

937

an aminocarbonyloxy having optionally a $C_1$–$C_6$ alkyl substituent, a $C_1$–$C_6$ alkoxy, a $C_1$–$C_6$ alkoxycarbonyl-substituted $C_1$–$C_6$ alkoxy, a carboxy-substituted $C_1$–$C_6$ alkoxy, an aminocarbonyl-($C_1$–$C_6$) alkoxy having optionally a $C_1$–$C_6$ alkyl substituent, an amino-($C_1$–$C_6$) alkoxy having optionally a substituent selected from a $C_1$–$C_6$ alkyl and a $C_1$–$C_6$ alkanoyl, a phthalimido-substituted $C_1$–$C_6$ alkoxy, hydroxyimino, a $C_1$–$C_6$ alkanoyloxyimino, a $C_1$–$C_6$ alkylidene, a halogen atom, azido, sulfoxyimino, a group of the formula:

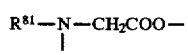

wherein $R^{81}$ is a hydrogen atom or a $C_1$–$C_6$ alkyl, hydrazino, pyrrolyl, an amino-($C_2$–$C_6$) alkanoyloxy having optionally a $C_1$–$C_6$ alkyl substituent, a group of the formula:

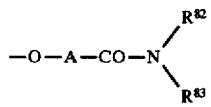

wherein A is as defined above, and $R^{82}$ and $R^{83}$ are the same or different and are each a hydrogen atom, a $C_1$–$C_6$ alkyl, a carbamoyl-substituted $C_1$–$C_6$ alkyl, a hydroxy-substituted $C_1$–$C_6$ alkyl, or a pyridyl-($C_1$–$C_6$) alkyl, or $R^{82}$ and $R^{83}$ may bind together with the nitrogen atom to which they are bonded to form a 5- or 6-membered saturated heterocyclic group with or without being intervened with a nitrogen, oxygen or sulfur atom wherein the heterocyclic group is one member selected from the group consisting of pyrrolidinyl, piperidinyl, piperazinyl, morpholino, and thiomorpholino, and has optionally a substituent selected from oxo, a $C_1$–$C_6$ alkyl, a $C_1$–$C_6$ alkanoyl, and carbamoyl, and a group of the formula:

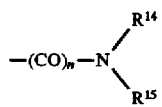

wherein n is as defined above, and $R^{14}$ and $R^{15}$ are the same or different and are each a hydrogen atom, a $C_1$–$C_6$ alkyl, a $C_2$–$C_6$ alkenyl, a $C_1$–$C_6$ alkanoyl, a $C_3$–$C_8$ cycloalkyl, an oxiranyl-substituted $C_1$–$C_6$ alkyl, a $C_1$–$C_6$ alkyl having 1 to 2 substituents selected from a $C_1$–$C_6$ alkoxy, hydroxy and an amino having optionally a $C_1$–$C_6$ alkyl substituent, a phenyl-($C_1$–$C_6$) alkyl, a pyridyl-($C_1$–$C_6$) alkyl, a $C_1$–$C_6$ alkylsulfonyl, benzoyl, a $C_1$–$C_6$ alkoxycarbonyl, anilinocarbonyl, an aminocarbonyl having optionally a $C_1$–$C_6$ alkyl substituent, a cyano-substituted $C_1$–$C_6$ alkyl, a $C_1$–$C_6$ alkoxycarbonyl-substituted $C_1$–$C_6$ alkyl, a carbamoyl-substituted $C_1$–$C_6$ alkyl, a carboxy-substituted $C_1$–$C_6$ alkyl, a tetrahydropyranyloxy-substituted $C_1$–$C_6$ alkyl, a $C_1$–$C_6$ alkanoyloxy-substituted $C_1$–$C_6$ alkyl, a piperidinyl having optionally a phenyl-($C_1$–$C_6$) alkyl substituent on the piperidine ring, a halogen-substituted $C_1$–$C_6$ alkanoyl, an imidazolyl-substituted $C_2$–$C_6$ alkanoyl, an amino-($C_2$–$C_6$) alkanoyl having optionally a substituent selected from a $C_1$–$C_6$ alkyl and a $C_1$–$C_6$ alkoxycarbonyl, an aminocarbonyl-($C_1$–$C_6$) alkyl having optionally a $C_1$–$C_6$ alkyl substituent, or a phenyl-($C_1$–$C_6$) alkoxycarbonyl, or

938

$R^{14}$ or $R^{15}$ may bind together with the nitrogen atom to which they are bonded to form a 5- or 6-membered saturated heterocyclic group with or without being intervened with a nitrogen or oxygen atom, wherein the heterocyclic group is one member selected from the group consisting of pyrrolidinyl, piperidinyl, piperazinyl, and morpholino, and may optionally have a substituent selected from a $C_1$–$C_6$ alkyl, a phenyl-($C_1$–$C_6$) alkyl or a $C_1$–$C_6$ alkanoyl.

56. The method according to claim 55, wherein p in the group of the formula: —$(CH_2)_p$— is 3 and the group has no substituent.

57. The method according to claim 55, wherein p in the group of the formula: —$(CH_2)_p$— is 3 and the group has a substituent of group of the formula:

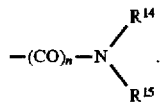

58. The method according to claim 55, wherein p in the group of the formula: —$(CH_2)_p$— is 4 and the group has no substituent.

59. The method according to claim 55, wherein p in the group of the formula: —$(CH_2)_p$— is 4 and the group has a substituent of a group of the formula:

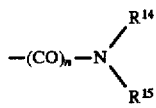

wherein $R^{14}$ and $R^{15}$ and n are as defined in claim 55.

60. The method according to claim 55, wherein p in the group of the formula: —$(CH_2)_p$— is 5.

61. The method according to claim 54, wherein q in the group of the formula: —CH=CH—$(CH_2)_q$— is 1.

62. The method according to claim 54, wherein q in the group of the formula: —CH=CH—$(CH_2)_q$— is 2.

63. The method according to claim 54, wherein q in the group of the formula: —CH=CH—$(CH_2)_q$— is 3.

64. The method according to claim 57 or 59, wherein n in the group of the formula:

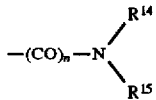

is 0, and $R^{14}$ and $R^{15}$ are the same or different and are each a hydrogen atom, a $C_1$–$C_6$ alkyl, or a $C_3$–$C_8$ cycloalkyl.

65. The method according to claim 62, wherein the heterocyclic group of the formula:

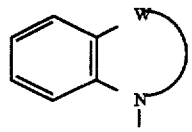

is 2,3,-dihydro-1 H-benzazepine.

66. The method according to claim 1, wherein the benzoheterocyclic compound is 5-dimethylamino-1-[4-(2-methylbenzoylamino)benzoyl]-2,3,4,5-tetrahydro-1H-benzazepine.

67. The method according to claim 1, wherein the benzoheterocyclic compound is 5-dimethylamino-1-[2-chloro-4-(2-methylbenzoylamino)benzoyl]-2,3,4,5-tetrahydro-1H-benzazepine.

68. The method according to claim 1, wherein the benzoheterocyclic compound is 5-methylamino-1-[2-chloro-4-(2-methylbenzoylamino)benzoyl]-2,3,4,5-tetrahydro-1H-benzazepine.

69. The method according to claim 1, wherein the benzoheterocyclic compound is 5-cyclopropylamino-1-[2-chloro-4-(2-methylbenzoylamino)benzoyl]-2,3,4,5-tetrahydro-1H-benzazepine.

70. The method according to claim 1, wherein the benzoheterocyclic compound is 5-cyclopropylamino-1-[2-chloro-4-(2-chlorobenzoylamino)benzoyl]-2,3,4,5-tetrahydro-1H-benzazepine.

71. The method according to claim 1, wherein the benzoheterocyclic compound is 5-dimethylamino-1-[2-methyl-4-(2-methylbenzoylamino)benzoyl]-2,3,4,5-tetrahydro-1H-benzazepine.

72. The method according to claim 1, wherein the benzoheterocyclic compound is 4-dimethylamino-1-[3-methoxy-4-(2-methylbenzoylamino)benzoyl]-1,2,3,4-tetrahydroquinoline.

73. The method according to claim 1, wherein the benzoheterocyclic compound is 7-chloro-5-methylamino-1-[4-(2-methylbenzoylamino)benzoyl]-2,3,4,5-tetrahydro-1H-benzazepine.

74. The method according to claim 1, wherein the benzoheterocyclic compound is 7-chloro-5-methylamino-1-[4-(2-chlorobenzoylamino)benzoyl]-2,3,4,5-tetrahydro-1H-benzazepine.

75. The method according to claim 1, wherein the benzoheterocyclic compound is 7-chloro-5-hydroxy-1-[2-methyl-4-(2-methylbenzoylamino)-benzoyl]-2,3,4,5-tetrahydro-1H-benzazepine.

76. The method according to claim 1, wherein the benzoheterocyclic compound is 7-chloro-5-hydroxy-1-[2-methoxy-4-(2-methylbenzoylamino)-benzoyl]-2,3,4,5-tetrahydro-1H-benzazepine.

77. The method according to claim 1, wherein the benzoheterocyclic compound is 7-fluoro-5-hydroxy-1-[2-chloro-4-(2-methylbenzoylamino)benzoyl]-2,3,4,5-tetrahydro-1H-benzazepine.

78. The method according to claim 1, wherein the benzoheterocyclic compound is 7-fluoro-5-hydroxymethyl-5-hydroxy-1-[2-chloro-4-(2-methylbenzoylamino)benzoyl]-2,3,4,5-tetrahydro-1H-benzazepine.

\* \* \* \* \*

UNITED STATES PATENT AND TRADEMARK OFFICE
CERTIFICATE OF CORRECTION

PATENT NO. : 5,753,677  Page 1 of 1
APPLICATION NO. : 08/474544
DATED : May 19, 1998
INVENTOR(S) : Hidenori Ogawa et al.

It is certified that error appears in the above-identified patent and that said Letters Patent is hereby corrected as shown below:

On the face of the patent, Related U.S. Application Data:
Division of Ser. No. 76,804, Jun. 10, 1993, Pat. No. 5,559,230, which is a division of Ser. No. 851,541, Mar. 13, 1992, Pat. No. 5,258,510, which is a Continuation-in-Part of Ser. No. 762,015, Jun. 19, 1991, abandoned, which is a national stage entry of PCT/JP90/01340, filed Oct. 18, 1990.

On the face of the patent, Foreign Application Priority Data:
Oct 20, 1989 [JP]   1-274338
Jul 09, 1990 [JP]   2-181858
Apr 19, 1991 [JP]   3-182066

In the first line of the Specification:
This is a divisional of application Ser. No. 08/076,804 filed Jun. 10, 1993, now U.S. Pat. No. 5,559,230, which is a divisional of application Ser. No. 07/851,541 filed Mar. 13, 1992, now U.S. Pat. No. 5,258,510, which is a Continuation-In-Part of application Ser. No. 07/762,015 filed Jun. 19, 1991, now abandoned, which is a national stage entry of PCT/JP90/01340, filed Oct. 18, 1990.

Signed and Sealed this

Twenty-seventh Day of February, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 5,753,677 | Page 1 of 1 |
| APPLICATION NO. | : 08/474544 | |
| DATED | : May 19, 1998 | |
| INVENTOR(S) | : Hidenori Ogawa et al. | |

It is certified that error appears in the above-identified patent and that said Letters Patent is hereby corrected as shown below:

Claim 1:
Column 923, lines 17-18, the reference to "and a pharmaceutically acceptable salt thereof" should be changed to --or a pharmaceutically acceptable salt thereof--.

Signed and Sealed this

Seventh Day of July, 2009

JOHN DOLL
*Acting Director of the United States Patent and Trademark Office*